(12) United States Patent
Reed et al.

(10) Patent No.: US 9,938,249 B2
(45) Date of Patent: Apr. 10, 2018

(54) ANTI-AMYLOID COMPOUNDS CONTAINING BENZOFURAZAN

(71) Applicant: Treventis Corporation, Bryn Mawr, PA (US)

(72) Inventors: Mark A. Reed, Oakville (CA); Thomas K. Wood, Santa Barbara, CA (US); Scott C. Banfield, Ellershouse (CA); Christopher J. Barden, Toronto (CA); Arun Yadav, Toronto (CA); Erhu Lu, Toronto (CA); Fan Wu, Toronto (CA)

(73) Assignee: Treventis Corporation, Bryn Mawr, PA (US)

( * ) Notice: Subject to any disclaimer, the term of this patent is extended or adjusted under 35 U.S.C. 154(b) by 0 days.

(21) Appl. No.: 15/118,310

(22) PCT Filed: Feb. 27, 2015

(86) PCT No.: PCT/US2015/017939
§ 371 (c)(1),
(2) Date: Aug. 11, 2016

(87) PCT Pub. No.: WO2015/131021
PCT Pub. Date: Sep. 3, 2015

(65) Prior Publication Data
US 2017/0174641 A1 Jun. 22, 2017

Related U.S. Application Data

(60) Provisional application No. 61/945,697, filed on Feb. 27, 2014.

(51) Int. Cl.
| | | |
|---|---|---|
| *C07D 271/12* | (2006.01) | |
| *C07D 417/14* | (2006.01) | |
| *C07D 413/12* | (2006.01) | |
| *C07D 413/04* | (2006.01) | |
| *C07D 413/14* | (2006.01) | |
| *C07D 417/12* | (2006.01) | |

(52) U.S. Cl.
CPC ......... *C07D 271/12* (2013.01); *C07D 413/04* (2013.01); *C07D 413/12* (2013.01); *C07D 413/14* (2013.01); *C07D 417/12* (2013.01); *C07D 417/14* (2013.01)

(58) Field of Classification Search
CPC .. C07D 271/12; C07D 417/14; C07D 413/12; C07D 413/04; C07D 413/14
See application file for complete search history.

(56) References Cited

U.S. PATENT DOCUMENTS

| | | | |
|---|---|---|---|
| 6,277,872 B1 | 8/2001 | Brenner et al. | |
| 9,328,078 B2 * | 5/2016 | Reed | E21B 36/001 |
| 2005/0026927 A1 | 2/2005 | Boettcher et al. | |
| 2005/0282818 A1 | 12/2005 | Ramesh et al. | |

FOREIGN PATENT DOCUMENTS

| | | |
|---|---|---|
| WO | WO 98/17652 A | 4/1998 |
| WO | WO2003/042208 | 5/2003 |
| WO | WO 03042208 A | 5/2003 |
| WO | WO2012/080727 | 6/2012 |
| WO | WO 2014031873 A2 * | 2/2014 |

OTHER PUBLICATIONS

Akama, KT, et al. 'beta-Amyloid Stimulation of Inducible Nitric-oxide Synthase in Astrocytes is Interleukin-1beta-and Tumor Necrosis Factor-alpha (TNFalpha)-dependent and Involves a TNFa Receptor-asociated Factor- and NFkappaB-inducing Kinase-dependent Signaling Mechanism'. The Journal of Biological Chemistry, 2000, vol. 275, No. 11, pp. 7918-1924; second column, last paragraph—p. 7921.
Butterfield, S et al. 'Chemical Strategies for Controlling Protein Folding and Elucidating the Molecular Mechanisms of Amyloid Formation and Toxicity'. Jounral of Molecular Biology, 2012, vol. 421, pp. 204-236; first column, first paragraph—p. 205.
International Search Report for International Application No. PCT/US15/017939 dated Jun. 1, 2015.

* cited by examiner

*Primary Examiner* — Matthew P Coughlin
(74) *Attorney, Agent, or Firm* — Davidson, Davidson & Kappel, LLC

(57) ABSTRACT

In general, among other things, compounds of Formula I are provided:

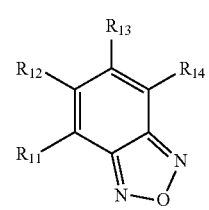

(I)

in which $R_{11}$ is e.g., 4-(pyrrolidin-1-yl)piperidin-1-yl, N-methyl-3-(pyrrolidin-1-yl)propan-1-amino, $N^1,N^1,N^3$-trimethylpropane-1,3-diamino, N,N-dimethylpiperidin-4-amino, 3-(pyrrolidin-1-ylmethyl)azetidin-1-yl, 3-(pyrrolidin-1-ylmethanon)azetidin-1-yl, or 3-(morpholin-1-ylmethyl)azetidin-1-yl; $R_{13}$ is, e.g., phenyl optionally substituted with one or more substituents; and $R_{12}$ and $R_{14}$ are each independently hydrogen or alkyl. Methods of treatment are also provided.

20 Claims, 8 Drawing Sheets

ANTI-AMYLOID COMPOUNDS CONTAINING BENZOFURAZAN

CROSS-REFERENCE TO RELATED APPLICATIONS

This application claims the benefit of U.S. Provisional Patent Application 61/945,697, filed Feb. 27, 2014, which is hereby incorporated by reference in its entirety.

BACKGROUND

The build-up of amyloid proteins in living tissue, a condition known as amyloidosis, is either the cause or a major factor in the pathology of many so-called amyloid diseases such as Alzheimer's Parkinson's, Huntington's, and prion diseases, including non-CNS disorders such as Type 2 diabetes mellitus. Historically, aggregations of protein were classified as amyloid if they displayed apple-green birefringence under polarized light when stained with the dyes Congo red or Thioflavin T (ThT) (Sipe and Cohen, 2000, J. Struct. Biol. 130:88-98). That definition of amyloid has been expanded in recent years to apply to any polypeptide which can polymerize in a cross-beta sheet conformation in vitro or in vivo, regardless of sequence (Xu, 2007, Amyloid 14:119-31). Certain types of amyloidosis may occur principally in the central nervous system, as with aggregation of beta-amyloid protein in Alzheimer's Disease, tau protein in progressive supranuclear palsy, alpha-synuclein in Parkinson's Disease, huntingtin protein in Huntington's Disease, and prion protein in Creutzfeldt-Jacob and other prion diseases. Other types of amyloidosis are systemic in nature, as with aggregation of transthyretin in senile systemic amyloidosis.

All of the above listed diseases are invariably fatal using current medical practice. In none of these diseases is there any known, widely accepted therapy or treatment that can halt and/or reverse the aggregation of amyloid deposits. As such there remains an urgent need for treatments.

SUMMARY

Anti-amyloid are disclosed herein that prevent or reduce the speed of oligomerization or aggregation of amyloid proteins. This effect is expected to have beneficial effects in diseases impacted by amyloidosis.

In general, in an aspect, compounds of Formula I, or a pharmaceutically acceptable salt thereof, are provided:

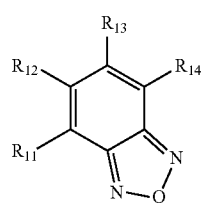

(I)

in which $R_{11}$ is selected from the group consisting of 4-(pyrrolidin-1-yl)piperidin-1-yl, N-methyl-3-(pyrrolidin-1-yl)propan-1-amino, $N^1,N^1,N^3$-trimethylpropane-1,3-diamino, N,N-dimethylpiperidin-4-amino, 3-(pyrrolidin-1-ylmethyl)azetidin-1-yl, 3-(pyrrolidin-1-ylmethanon)azetidin-1-yl, 3-(morpholin-1-ylmethyl)azetidin-1-yl, 3-(2-ethanolamino-N-methyl)azetidin-1-yl, 3-(morpholin-1-yl)pyrrolidin-1-yl, 3-(morpholin-1ylmethyl)pyrrolidin-1-yl, 4-(ethylamido)piperidin-1-yl, 3-(aminomethyl)azetidin-1-yl, 4-(morpholin-1-yl)piperidin-1-yl, 4-(morpholin-1-ylmethyl)piperidin-1-yl, 3-amidoazetidin-1-yl, 3-(propan-2-ol-2-yl)azetidin-1-yl, 3-(methylsulfonamide-N-methyl)azetidin-1-yl, 3-(methylamido-N-methyl)azetidin-1-yl, and 3-(methylamino-N-methyl)azetidin-1-yl; $R_{13}$ is selected from the group consisting of 3-(benzyloxy)-1-methylcyclobutan-1-ol-1-yl, oxazole optionally substituted with one or more of substituents A, oxadiazole optionally substituted with one or more of substituents A, phenyl optionally substituted with one or more of substituents A, thiophene optionally substituted with one or more of substituents A, thiazole optionally substituted with one or more of substituents A, furan optionally substituted with one or more of substituents A, pyrazole optionally substituted with one or more of substituents A, N-methylpyrazole optionally substituted with one or more of substituents A, 2-pyridine optionally substituted with one or more of substituents A, 3-pyridine optionally substituted with one or more of substituents A, and 4-pyridine optionally substituted with one or more of substituents A, where A is selected from the group consisting of alkyl, alkoxy, alkthiolyl, isopropyl, t-butyl, trifluoromethyl, chloro, cyano, $CF_3O$—, methanonyl, methylsulfonyl, trifluoromethylsulfonyl, amide (connected in either direction) optionally substituted with one or more alkyl, —$CH_2OH$, 1-ol-2,2,2-trifluoroethan-1-yl, oxetan-3-ol-3-yl, 2-ol-propan-2-yl, and cyclopropyl; and $R_{12}$ and $R_{14}$ are each independently hydrogen or alkyl.

In general, in an aspect, a compound according to the above formula or a pharmaceutically acceptable salt thereof is provided, in which $R_{11}$ is selected from the group consisting of 4-(pyrrolidin-1-yl)piperidin-1-yl, N-methyl-3-(pyrrolidin-1-yl)propan-1-amino, $N^1,N^1,N^3$-trimethylpropane-1,3-diamino, N,N-dimethylpiperidin-4-amino, 3-(pyrrolidin-1-ylmethyl)azetidin-1-yl, 3-(pyrrolidin-1-ylmethanon)azetidin-1-yl, and 3-(morpholin-1-ylmethyl)azetidin-1-yl; and $R_{13}$ is selected from the group consisting of phenyl optionally substituted with one or more of substituents A, thiophene optionally substituted with one or more of substituents A, thiazole optionally substituted with one or more of substituents A, furan optionally substituted with one or more of substituents A, pyrazole optionally substituted with one or more of substituents A, N-methylpyrazole optionally substituted with one or more of substituents A, 2-pyridine optionally substituted with one or more of substituents A, 3-pyridine optionally substituted with one or more of substituents A, and 4-pyridine optionally substituted with one or more of substituents A, where A is selected from the group consisting of alkyl, alkoxy, alkthiolyl, isopropyl, t-butyl, trifluoromethyl, chloro, cyano, $CF_3O$—, methanonyl, methylsulfonyl, trifluoromethylsulfonyl, amide (connected in either direction) optionally substituted with one or more alkyl, and —$CH_2OH$.

In general, in an aspect, a compound according to the above formula or a pharmaceutically acceptable salt thereof is provided, in which $R_{11}$ is selected from the group consisting of 3-(morpholin-1-ylmethyl)azetidin-1-yl, 3-(2-ethanolamino-N-methyl)azetidin-1-yl, 3-(morpholin-1-yl)pyrrolidin-1-yl, 3-(morpholin-1ylmethyl)pyrrolidin-1-yl, 4-(ethylamido)piperidin-1-yl, 3-(aminomethyl)azetidin-1-yl, 4-(morpholin-1-yl)piperidin-1-yl, 4-(morpholin-1-ylmethyl)piperidin-1-yl, 3-amidoazetidin-1-yl, 3-(propan-2-ol-2-yl)azetidin-1-yl, 3-(methylsulfonamide-N-methyl)azetidin-1-yl, 3-(methylamido-N-methyl)azetidin-1-yl, and 3-(methylamino-N-methyl)azetidin-1-yl; and $R_{13}$ is selected from the group consisting of 3-(benzyloxy)-1-methylcyclobutan-1-ol-1-yl, oxazole optionally substituted with one or more of substituents A, oxadiazole optionally substituted with one or more of substituents A, and 3-pyridine optionally substituted with one or more of substituents A, where A is selected from the group consisting of 1-ol-2,2,2-trifluoroethan-1-yl, oxetan-3-ol-3-yl, 2-ol-propan-2-yl, and cyclopropyl.

In general, in an aspect, a compound according to the above formula or a pharmaceutically acceptable salt thereof is provided, in which $R_{13}$ is selected from the group consisting of 5-(2-ol-propan-2-yl)oxadizol-3-yl, 4-(1-ol-2,2,2-trifluoroethan-1-yl)oxazol-5-yl, 4-(1-ol-2,2,2-trifluoroethan-1-yl)pyridin-2-yl, 4-(1-ol-2,2,2-trifluoroethan-1-yl)pyridin-3-yl, 4-(1-ol-2,2,2-trifluoroethan-1-yl)thiazol-2-yl, 4-(1-ol-2,2,2-trifluoroethan-1-yl)pyridin-6-yl, 2-(1-ol-2,2,2-trifluoroethan-1-yl)-pyridin-6-yl, 5-(1-ol-2,2,2-trifluoroethan-1-yl)oxazol-2-yl, 5-(1-ol-2,2,2-trifluoroethan-1-yl)oxazol-3-yl, 5-(1-ol-2,2,2-trifluoroethan-1-yl)thiophen-2-yl, 5-(1-ol-2,2,2-trifluoroethan-1-yl)thiophen-3-yl, 2-(1-ol-2,2,2-trifluoroethan-1-yl)pyridin-5-yl, 3-(1-ol-2,2,2-trifluoroethan-1-yl)pyridin-2-yl, 3-(1-ol-2,2,2-trifluoroethan-1-yl)pyridin-6-yl, and 2-(1-ol-2,2,2-trifluoroethan-1-yl)pyridin-3-yl.

In general, in an aspect, a compound according to the above formula or a pharmaceutically acceptable salt thereof is provided, in which $R_{11}$ is 3-(morpholin-1-ylmethyl)azetidin-1-yl and $R_{13}$ is selected from the group consisting of 2-(1-ol-2,2,2-trifluoroethan-1-yl)pyridin-3-yl and 5-(2-ol-propan-2-yl)oxadizol-3-yl.

In general, in an aspect, methods useful in the treatment of amyloidosis are provided. The methods include administering to a subject a therapeutic compound of the present invention which inhibits amyloid aggregation or oligomerization. The amyloidosis can be Alzheimer's disease, progressive supranuclear palsy, frontotemporal dementia, Parkinson's disease, Huntington's disease, prion disease, senile systemic amyloidosis, type 2 diabetes mellitus, or some other systemic or central nervous system amyloidosis.

In general, in an aspect, pharmaceutical compositions for treating amyloidosis are provided. The pharmaceutical compositions include a therapeutic compound of the present invention in an amount effective to inhibit amyloid aggregation, and a pharmaceutically acceptable excipient or vehicle. In some implementations the amount effective is between about 0.0003 to about 50 mg/kg of body weight of the person in need thereof.

In accordance with the above, the present invention is also directed to pharmaceutically acceptable salts, stereoisomers, polymorphs, metabolites, analogues, and pro-drugs of the compounds, and to any combination thereof.

With the foregoing and other advantages and features of the invention that will become hereafter apparent, the nature of the invention may be more clearly understood by reference to the following detailed description of the invention and the appended claims.

DESCRIPTION

Figure 1:
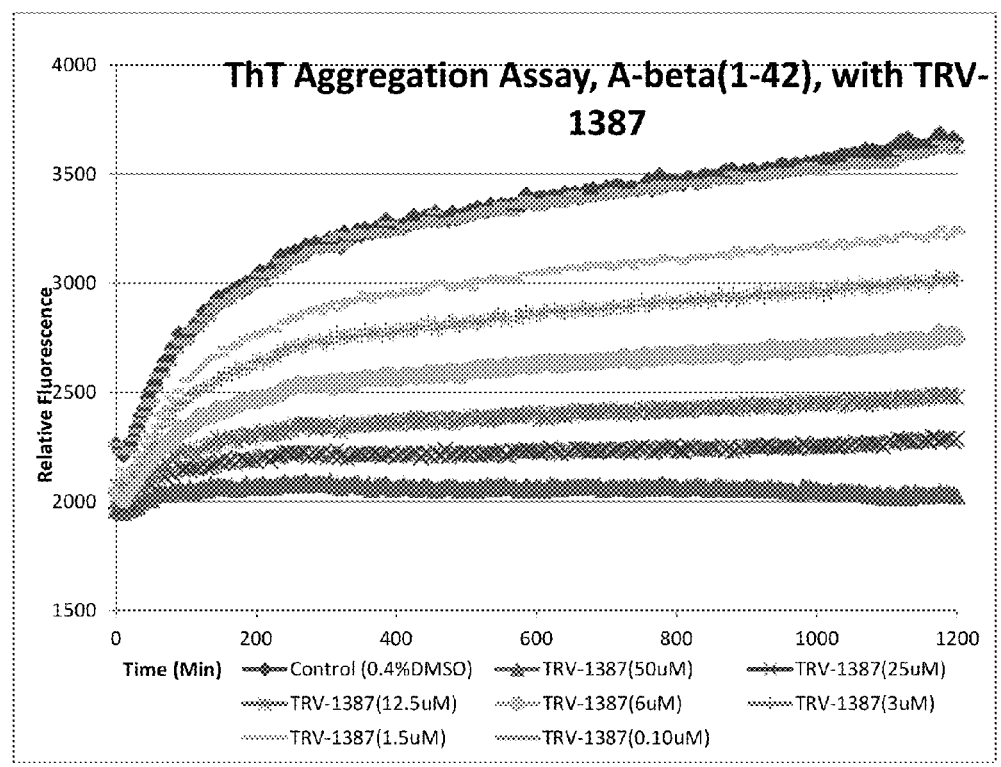
FIG. 1 shows a beta-amyloid aggregation assay for a compound described herein.

All patents, patent applications, and other publications referred to herein are hereby incorporated by reference in their entireties.

In one embodiment, compounds of Formula I, or a pharmaceutically acceptable salt thereof, are provided:

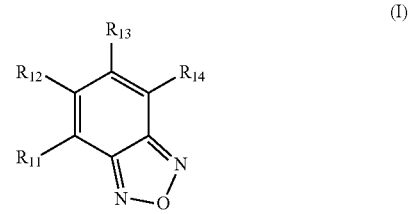

(I)

in which $R_{11}$ is selected from the group consisting of 4-(pyrrolidin-1-yl)piperidin-1-yl, N-methyl-3-(pyrrolidin-1-yl)propan-1-amino, $N^1,N^1,N^3$-trimethylpropane-1,3-diamino, N,N-dimethylpiperidin-4-amino, 3-(pyrrolidin-1-ylmethyl)azetidin-1-yl, 3-(pyrrolidin-1-ylmethanon)azetidin-1-yl, 3-(morpholin-1-ylmethyl)azetidin-1-yl, 3-(2-ethanolamino-N-methyl)azetidin-1-yl, 3-(morpholin-1-yl)pyrrolidin-1-yl, 3-(morpholin-1-ylmethyl)pyrrolidin-1-yl, 4-(ethylamido)piperidin-1-yl, 3-(aminomethyl)azetidin-1-yl, 4-(morpholin-1-yl)piperidin-1-yl, 4-(morpholin-1-ylmethyl)piperidin-1-yl, 3-amidoazetidin-1-yl, 3-(propan-2-ol-2-yl)azetidin-1-yl, 3-(methylsulfonamide-N-methyl)azetidin-1-yl, 3-(methylamido-N-methyl)azetidin-1-yl, and 3-(methylamino-N-methyl)azetidin-1-yl; $R_{13}$ is selected from the group consisting of 3-(benzyloxy)-1-methylcyclobutan-1-ol-1-yl, oxazole optionally substituted with one or more of substituents A, oxadiazole optionally substituted with one or more of substituents A, phenyl optionally substituted with one or more of substituents A, thiophene optionally substituted with one or more of substituents A, thiazole optionally substituted with one or more of substituents A, furan optionally substituted with one or more of substituents A, pyrazole optionally substituted with one or more of substituents A, N-methylpyrazole optionally substituted with one or more of substituents A, 2-pyridine optionally substituted with one or more of substituents A, 3-pyridine optionally substituted with one or more of substituents A, and 4-pyridine optionally substituted with one or more of substituents A, where A is selected from the group consisting of alkyl, alkoxy, alkthiolyl, isopropyl, t-butyl, trifluoromethyl, chloro, cyano, $CF_3O$—, methanonyl, methylsulfonyl, trifluoromethylsulfonyl, amide (connected in either direction) optionally substituted with one or more alkyl, —$CH_2OH$, 1-ol-2,2,2-trifluoroethan-1-yl, oxetan-3-ol-3-yl, 2-ol-propan-2-yl, and cyclopropyl; and $R_{12}$ and $R_{14}$ are each independently hydrogen or alkyl.

In one embodiment, compounds of Formula I, or a pharmaceutically acceptable salt thereof, are provided:

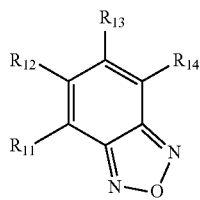

(I)

in which R$_{11}$ is selected from the group consisting of 4-(pyrrolidin-1-yl)piperidin-1-yl, N-methyl-3-(pyrrolidin-1-yl)propan-1-amino, N$^1$,N$^1$,N$^3$-trimethylpropane-1,3-diamino, N,N-dimethylpiperidin-4-amino, 3-(pyrrolidin-1-ylmethyl)azetidin-1-yl, 3-(pyrrolidin-1-ylmethanon)azetidin-1-yl, and 3-(morpholin-1-ylmethyl)azetidin-1-yl;

R$_{13}$ is selected from the group consisting of phenyl optionally substituted with one or more of substituents A, thiophene optionally substituted with one or more of substituents A, thiazole optionally substituted with one or more of substituents A, furan optionally substituted with one or more of substituents A, pyrazole optionally substituted with one or more of substituents A, N-methylpyrazole optionally substituted with one or more of substituents A, 2-pyridine optionally substituted with one or more of substituents A, 3-pyridine optionally substituted with one or more of substituents A, and 4-pyridine optionally substituted with one or more of substituents A, where A is selected from the group consisting of alkyl, alkoxy, alkthiolyl, isopropyl, t-butyl, trifluoromethyl, chloro, cyano, CF$_3$O—, methanonyl, methylsulfonyl, trifluoromethylsulfonyl, amide (connected in either direction) optionally substituted with one or more alkyl, and —CH$_2$OH; and R$_{12}$ and R$_{14}$ are each independently hydrogen or alkyl.

In one embodiment, compounds of Formula I, or a pharmaceutically acceptable salt thereof, are provided:

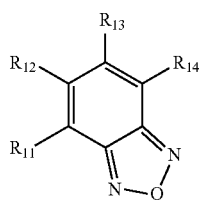

(I)

in which R$_{11}$ is selected from the group consisting of 3-(morpholin-1-ylmethyl)azetidin-1-yl, 3-(2-ethanolamino-N-methyl)azetidin-1-yl, 3-(morpholin-1-yl)pyrrolidin-1-yl, 3-(morpholin-1-ylmethyl)pyrrolidin-1-yl, 4-(ethylamido)piperidin-1-yl, 3-(aminomethyl)azetidin-1-yl, 4-(morpholin-1-yl)piperidin-1-yl, 4-(morpholin-1-ylmethyl)piperidin-1-yl, 3-amidoazetidin-1-yl, 3-(propan-2-ol-2-yl)azetidin-1-yl, 3-(methylsulfonamide-N-methyl)azetidin-1-yl, 3-(methylamido-N-methyl)azetidin-1-yl, and 3-(methylamino-N-methyl)azetidin-1-yl; R$_{12}$ and R$_{14}$ are each independently hydrogen or alkyl; and R$_{13}$ is selected from the group consisting of 3-(benzyloxy)-1-methylcyclobutan-1-ol-1-yl, oxazole optionally substituted with one or more of substituents A, oxadiazole optionally substituted with one or more of substituents A, and 3-pyridine optionally substituted with one or more of substituents A, where A is selected from the group consisting of 1-ol-2,2,2-trifluoroethan-1-yl, oxetan-3-ol-3-yl, 2-ol-propan-2-yl, and cyclopropyl.

In one embodiment, compounds of Formula I, or a pharmaceutically acceptable salt thereof, are provided:

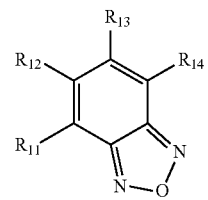

(I)

in which R$_{11}$ is selected from the group consisting of 3-(morpholin-1-ylmethyl)azetidin-1-yl, 3-(2-ethanolamino-N-methyl)azetidin-1-yl, 3-(morpholin-1-yl)pyrrolidin-1-yl, 4-(ethylamido)piperidin-1-yl, 3-(aminomethyl)azetidin-1-yl, 4-(morpholin-1-yl)piperidin-1-yl, 4-(morpholin-1-ylmethyl)piperidin-1-yl, 3-amidoazetidin-1-yl, 3-(propan-2-ol-2-yl)azetidin-1-yl, 3-(methylsulfonamide-N-methyl)azetidin-1-yl, 3-(methylamido-N-methyl)azetidin-1-yl, and 3-(methylamino-N-methyl)azetidin-1-yl; R$_{12}$ and R$_{14}$ are each independently hydrogen or alkyl; and R$_{13}$ is selected from the group consisting of 5-(2-ol-propan-2-yl)oxadizol-3-yl, 4-(1-ol-2,2,2-trifluoroethan-1-yl)oxazol-5-yl, 4-(1-ol-2,2,2-trifluoroethan-1-yl)pyridin-2-yl, 4-(1-ol-2,2,2-trifluoroethan-1-yl)pyridin-3-yl, 4-(1-ol-2,2,2-trifluoroethan-1-yl)thiazol-2-yl, 4-(1-ol-2,2,2-trifluoroethan-1-yl)pyridin-6-yl, 2-(1-ol-2,2,2-trifluoroethan-1-yl)-pyridin-6-yl, 5-(1-ol-2,2,2-trifluoroethan-1-yl)oxazol-2-yl, 5-(1-ol-2,2,2-trifluoroethan-1-yl)oxazol-3-yl, 5-(1-ol-2,2,2-trifluoroethan-1-yl)thiophen-2-yl, 5-(1-ol-2,2,2-trifluoroethan-1-yl)thiophen-3-yl, 2-(1-ol-2,2,2-trifluoroethan-1-yl)pyridin-5-yl, 3-(1-ol-2,2,2-trifluoroethan-1-yl)pyridin-2-yl, 3-(1-ol-2,2,2-trifluoroethan-1-yl)pyridin-6-yl, and 2-(1-ol-2,2,2-trifluoroethan-1-yl)pyridin-3-yl.

In one embodiment, compounds of Formula I, or a pharmaceutically acceptable salt thereof, are provided:

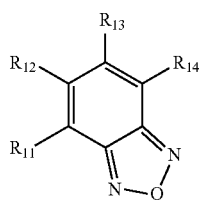

(I)

in which R$_{11}$ is 3-(morpholin-1-ylmethyl)azetidin-1-yl; R$_{12}$ and R$_{14}$ are each independently hydrogen or alkyl; and R$_{13}$ is selected from the group consisting of 2-(1-ol-2,2,2-trifluoroethan-1-yl)pyridin-3-yl and 5-(2-ol-propan-2-yl)oxadizol-3-yl.

In one embodiment, a method of treatment of an amyloid disease in a subject is provided, comprising administering a therapeutically effective amount of a compound of the present invention to the subject. In some embodiments, the amyloid disease is Alzheimer's disease. In some embodiments, the amyloid disease is Parkinson's disease. In some embodiments, the amyloid disease is Huntington's disease. In some embodiments, the amyloid disease is frontotemporal dementia. In some embodiments, the amyloid disease is progressive supranuclear palsy. In some embodiments, the amyloid disease is type 2 diabetes mellitus.

13. A method for treating a condition which is a member selected from loss of memory, loss of cognition and a combination thereof, said method comprising administering to a subject in need thereof a therapeutically effective amount of a compound of any of claims 1-5.

In one embodiment, a pharmaceutical composition is provided comprising a compound of the present invention and a pharmaceutically acceptable carrier.

In one embodiment, a method for treating a condition which is a member selected from loss of memory, loss of cognition and a combination thereof, said method comprising administering to a subject in need thereof a therapeutically effective amount of a compound disclosed herein. In some embodiments, said condition is associated with Alzheimer's disease. In some embodiments, said condition is associated with progressive supranuclear palsy. In some embodiments, the therapeutically effective amount is a total daily dose of from about 0.0003 to about 50 mg/kg of body weight of the subject.

It is believed that compounds of the present invention inhibit the aggregation of amyloid protein. Data supportive of this conclusion can be found in the Examples below.

Definitions

Unless otherwise defined, terms as used in the specification refer to the following definitions, as detailed below.

The terms "administration" or "administering" compound should be understood to mean providing a compound of the present invention to an individual in a form that can be introduced into that individual's body in an amount effective for prophylaxis, treatment, or diagnosis, as applicable. Such forms may include e.g., oral dosage forms, injectable dosage forms, transdermal dosage forms, inhalation dosage forms, and rectal dosage forms.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The term "alkthiolyl" as used herein means the analogous group containing sulfur rather than oxygen.

The term "alkyl" as used herein means a straight or branched chain hydrocarbon containing from 1 to 20 carbon atoms, preferably from 1 to 10 carbon atoms, more preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "carbonyl" as used herein means a —C(=O)— group.

The term "carboxy" as used herein means a —COOH group, which may be protected as an ester group: —COO-alkyl.

The term "fluoro" as used herein means —F.

The term "halo" or "halogen" as used herein means Cl, Br, I, or F.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein. Heteroaryl rings are connected to a parent molecular moiety through a carbon or nitrogen atom.

The terms "heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or atom; one, two, or three N atoms arranged in a suitable manner to provide an aromatic ring; or a ring wherein two carbon atoms in the ring are replaced with one O or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five membered rings containing one to four nitrogen atoms; and five membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3] oxadiazolyl, thiazolyl, thienyl, [1,2,3]triazinyl, [1,2,4]triazinyl, [1,3,5]triazinyl, [1,2,3]triazolyl, and [1,2,4]triazolyl.

Heteroaryl groups of the invention can be substituted with hydrogen or alkyl. Monocyclic heteroaryl or 5- or 6-membered heteroaryl rings are substituted with 0, 1, 2, 3, 4, or 5 substituents. Heteroaryl groups of the present invention may be present as tautomers.

The term "hydroxy" as used herein means an —OH group.

Unless otherwise indicated, the term "prodrug" encompasses pharmaceutically acceptable esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters of compounds disclosed herein. Examples of prodrugs include compounds that comprise a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Prodrugs of compounds disclosed herein are readily envisioned and prepared by those of ordinary skill in the art. See, e.g., Design of Prodrugs, Bundgaard, A. Ed., Elseview, 1985; Bundgaard, hours, "Design and Application of Prodrugs," A Textbook of Drug Design and Development, Krosgaard-Larsen and hours. Bundgaard, Ed., 1991, Chapter 5, p. 113-191; and Bundgaard, hours, Advanced Drug Delivery Review, 1992, 8, 1-38.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., Protective Groups in Organic Synthesis (3 rd ed., John Wiley & Sons: 1999); Larock, R. C., Comprehensive Organic Transformations (2 nd ed., John Wiley & Sons: 1999). Some examples include benzyl, diphenylmethyl, trityl, Cbz, Boc, Fmoc, methoxycarbonyl, ethoxycarbonyl, and pthalimido. Protecting groups include, for example, nitrogen protecting groups and hydroxy-protecting groups.

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

The compounds of the invention can be used in the form of pharmaceutically acceptable salts derived from inorganic or organic acids. Pharmaceutically acceptable salt(s) are well-known in the art. For clarity, the term "pharmaceutically acceptable salts" as used herein generally refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., Remington's Pharmaceutical Sciences, 18 th ed. (Mack Publishing, Easton Pa.: 1990) and Remington: The Science and Practice of Pharmacy, 19th ed. (Mack Publishing, Easton Pa.: 1995). The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

Certain compounds of the present invention may be isotopically labelled, e.g., with various isotopes of carbon, fluorine, or iodine, as applicable when the compound in question contains at least one such atom. In preferred embodiments, methods of diagnosis of the present invention comprise administration of such an isotopically labelled compound.

Certain compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Certain compounds of the present invention may exist as cis or trans isomers, wherein substituents on a ring may attach in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, for example, the two phrases "XOH, wherein X is pyridyl" and "XOH, wherein X is pyridine" are accorded the same meaning, and encompass the compounds pyridin-2-ol, pyridin-3-ol and pyridin-4-ol.

The term "pharmaceutically acceptable excipient", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

Unless otherwise indicated, the terms "prevent," "preventing" and "prevention" contemplate an action that occurs before a patient begins to suffer from the specified disease or disorder, which inhibits or reduces the severity of the disease or disorder or of one or more of its symptoms. The terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound is an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a "diagnostically effective amount" of a compound is an amount sufficient to diagnose a disease or condition. In general, administration of a compound for diagnostic purposes does not continue for as long as a therapeutic use of a compound, and could be administered only once if such is sufficient to produce the diagnosis.

Unless otherwise indicated, a "therapeutically effective amount" of a compound is an amount sufficient to treat a disease or condition, or one or more symptoms associated with the disease or condition. The appropriate amount depends upon, among other things, the stage of the disease or condition; the age of the patient; the weight of the patient; the bioavailability of the compound with respect to a target tissue; the concentration of compound required in vivo to result in a beneficial effect relative to control as measured by behavior, motor, biochemical, anatomical, or other readouts; or the concentration of compound required to result in a pharmacodynamic effect upon a target amyloid protein at the target tissue. In some embodiments, the disease is a neurologic disorder, the target amyloid protein is beta-amyloid protein, and the target tissue is brain. In some embodiments, the disease is a neurologic disorder, the target amyloid protein is tau protein, and the target tissue is brain. In some embodiments, the diseases is a neurologic disorder, both beta-amyloid and tau protein are target amyloid proteins, and the target tissue is brain. In some embodiments, the disease is a metabolic disorder such as Type 2 diabetes, the target amyloid protein is amylin, and the target tissue is pancreas. In the absence of clinical data, the concentration of compound required to result in a pharmacodynamic effect may be estimated in vitro by correlating the compound concentration required for reduction in oligomerization or aggregation in vitro as against a concentration of a target amyloid protein in vitro with the concentration of the target amyloid protein expected to be found in the target tissue, such that the required concentration in vivo is approximately equal to (in vitro compound concentration * in vivo amyloid concentration/in vitro amyloid concentration); from which the therapeutically effective amount can be further estimated based on animal-derived pharmacokinetic information such as bioavailability, blood-brain barrier penetrance, and protein binding.

The term "subject" is intended to include living organisms in which disease may occur. Examples of subjects include humans, monkeys, cows, sheep, goats, dogs, cats, mice, rats, and transgenic species thereof.

The term "substantially pure" means that the isolated material is at least 90% pure, preferably 95% pure, even more preferably 99% pure as assayed by analytical techniques known in the art.

The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration. Pharmaceutical compositions of the present invention suitable for oral administration can be presented as discrete dosage forms, e.g., tablets, chewable tablets, caplets, capsules, liquids, and flavored syrups. Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions. Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants. These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof. If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents. Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

An effective amount of one of the compounds of the invention can be employed in pure form or, where such forms exist, in pharmaceutically acceptable salt form. Alternatively, the compound can be administered as a pharmaceutical composition containing the compound of interest in combination with one or more pharmaceutically acceptable carriers. It will be understood, however, that the total daily usage of the compounds and compositions of the invention will be decided by the attending physician within the scope of sound medical judgment. The specific effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; the risk/benefit ratio; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of the present invention as administered to a human or lower animal may range from about 0.0003 to about 50 mg/kg of body weight. For purposes of oral administration, more preferable doses can be in the range of from about 0.0003 to about 5 mg/kg body weight. If desired, the effective daily dose can be divided into multiple doses for purposes of administration; consequently, single dose compositions may contain such amounts or submultiples thereof to make up the daily dose. For oral administration, the compositions of the invention are preferably provided in the form of tablets containing about 1.0, about 5.0, about 10.0, about 15.0, about 25.0, about 50.0, about 100, about 250, or about 500 milligrams of the active ingredient.

EXAMPLES

Synthetic Methods

Unless otherwise stated, compound IDs denoted by "TRV-" that contain chiral centers found in

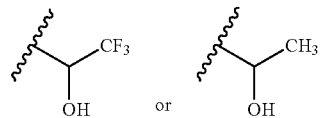

groups were synthesized and tested as racemic mixtures with respect to that respective chiral center. Compounds containing substituted pyrrolidines are intended to encompass both R and S enantiomers either as substantially entantiomerically pure, or as racemates.

The following synthetic schemes and written procedures were used to synthesize the compounds described herein:

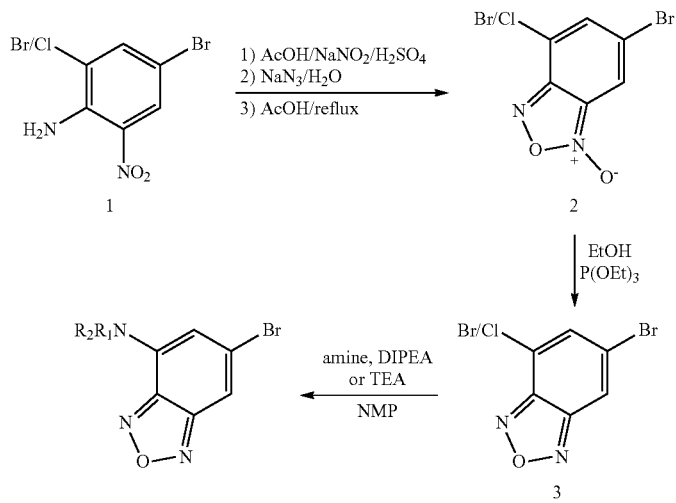

NR₁R₂ = benzylamine, pyrrolidine, N-methyl-1-phenylmethanamine, ethyl pyrrolidine-2-carboxylate, morpholine, 4- methylimidazole, 1-methylpiperazine, N-isopropylmethylamine, 2-methylpyrrolidine, piperidine, diethylamine, (2-methoxyetheryl)methylamine, N-methylethanamine, thiomorpholine, 4-(pyrrolidin-1-yl)piperidine, pyrazole, 4-methylpyrazole, 4-fluoro-N-methylbenzylamine, ethylamine, isoindoline, 3-hydroxyazetidine, azetidine, propargylamine, cyclopropylamine, 3-hydroxypyrrolidine, N-methyl-N-(2-pyridinylmethyl)amine, N-methyl-N-(3-pyridinylmethyl)amine, 4-methoxybenzylamine, 3,5-dimethoxybenzylamine, 3-azetidine carboxylic acid, azetidine, (S)-ethyl pyrrolidine-2-carboxylate, N-methyl-1-(thiazol-2-yl) methanamine

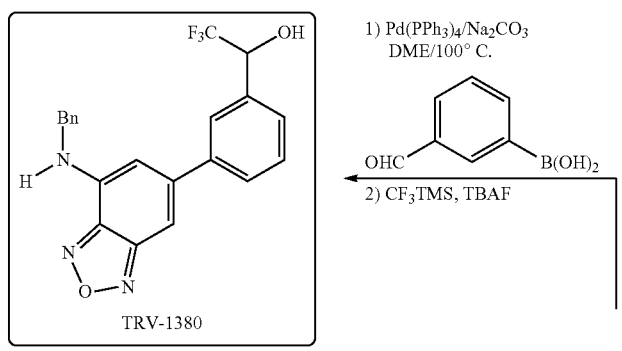

-continued
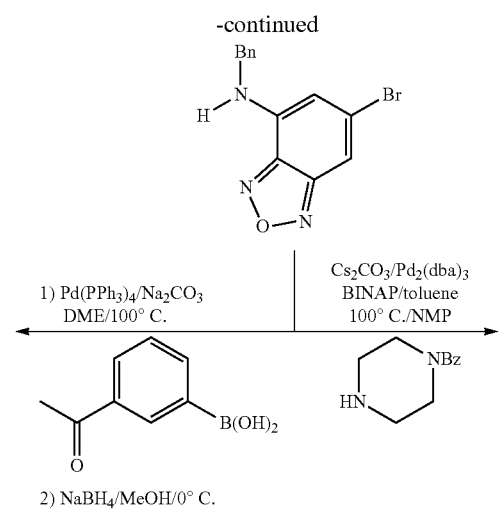
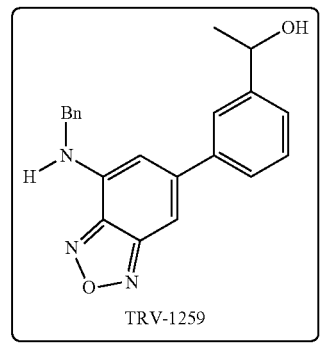
TRV-1259
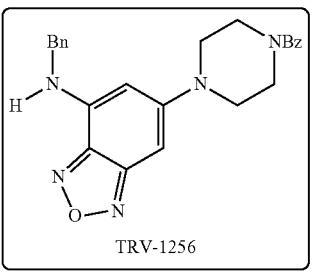
TRV-1256
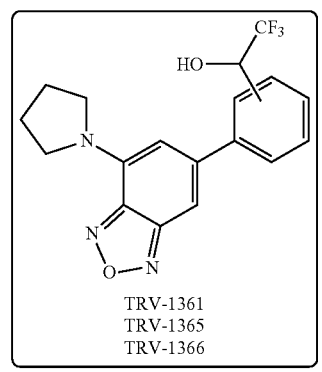
TRV-1361
TRV-1365
TRV-1366
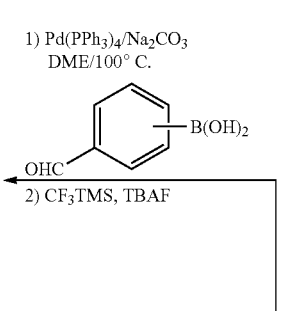
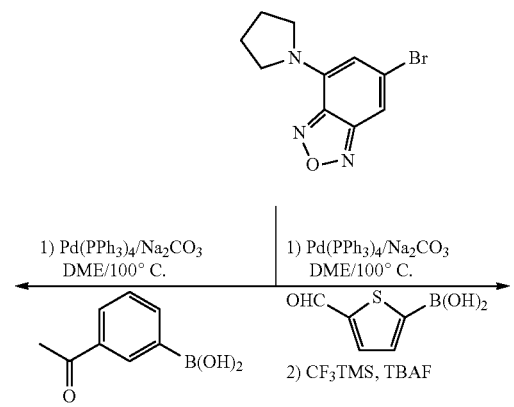
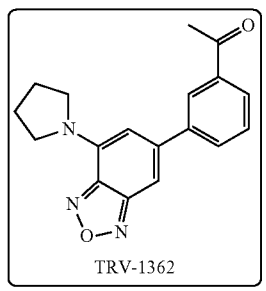
TRV-1362
TRV-1364
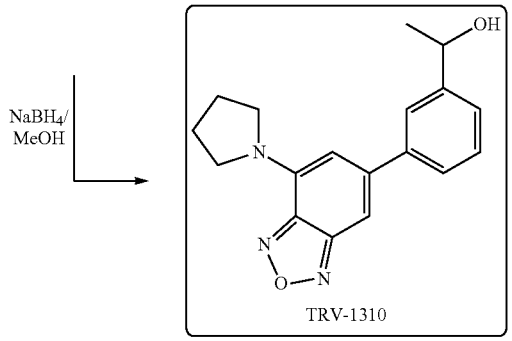
TRV-1310

-continued
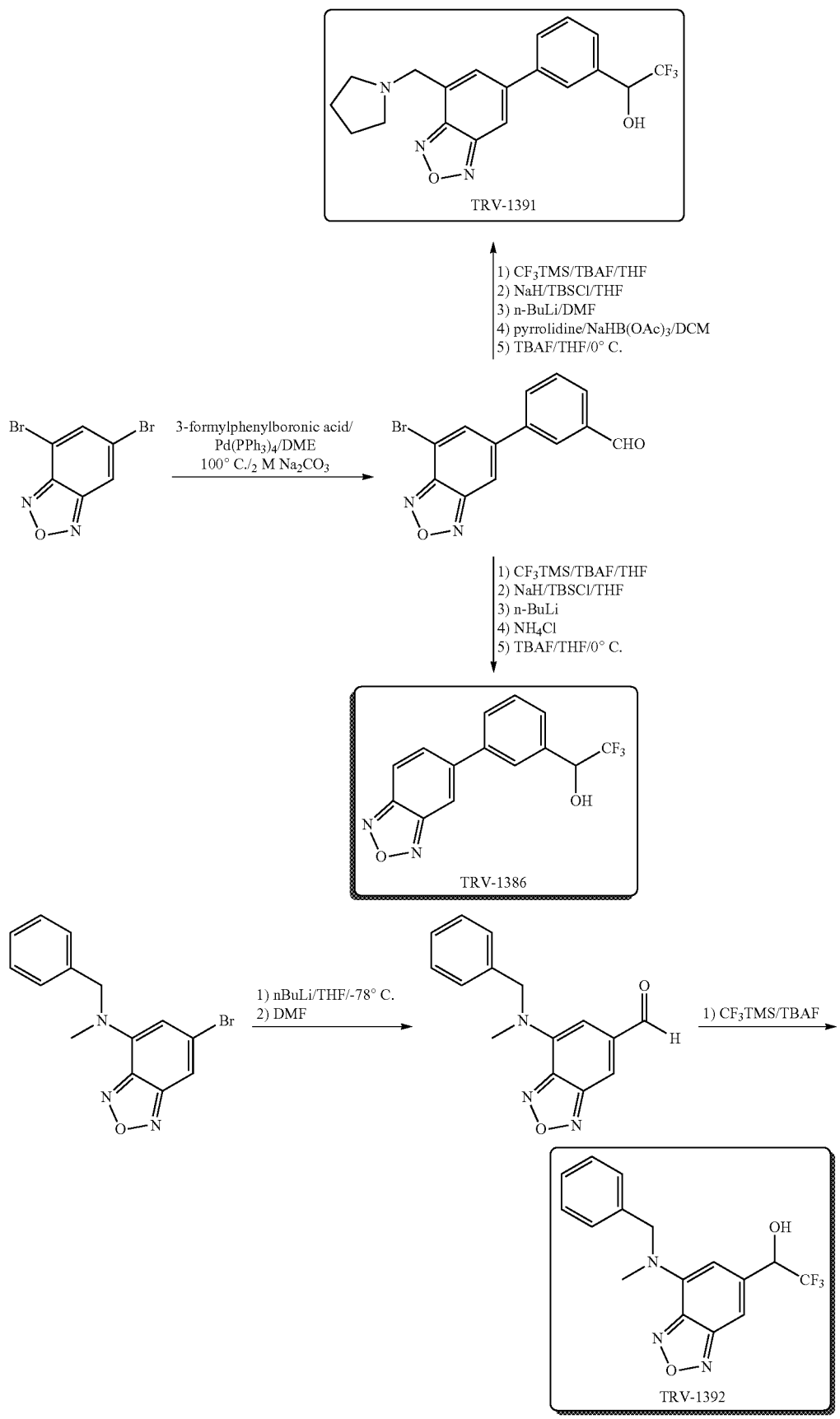

21 22
-continued
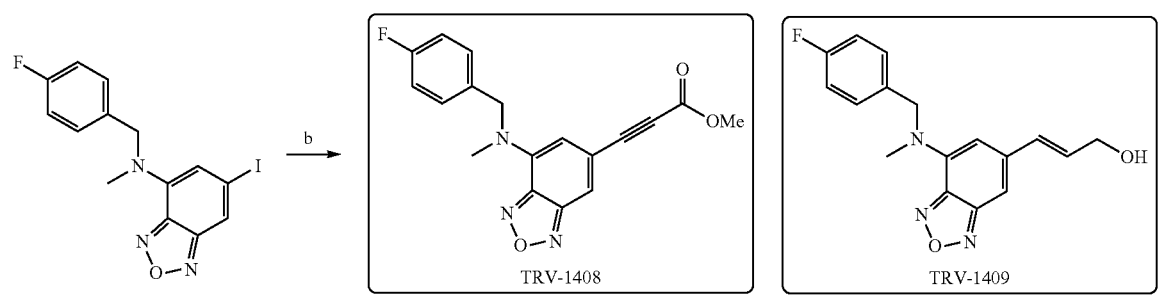
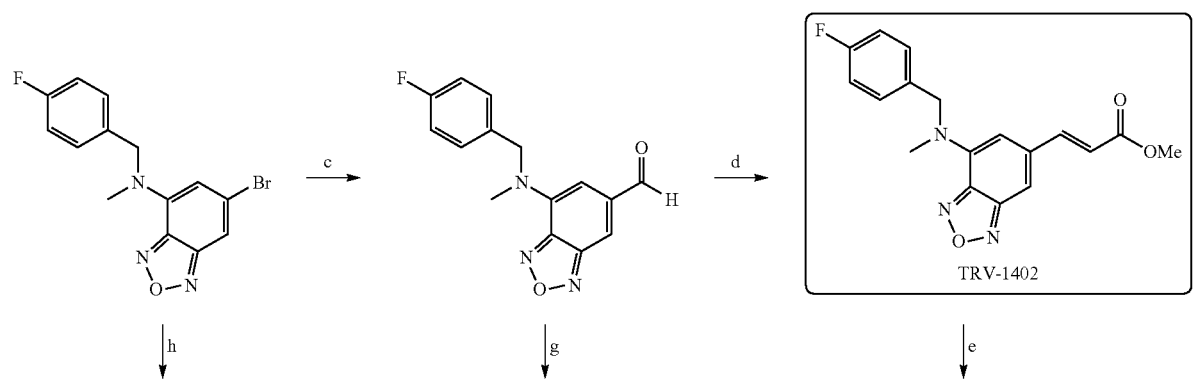
a) i) nBuLi, -78° C.; ii) I₂, THF, -78° C.; b) methyl propiolate, Pd(PPh₃)₂Cl₂, CuI, K₂CO₃, THF, 65° C.; c) i) nBuLi, -78° C.; ii) DMF; d) i) trimethylphosphonoacetate, NaH, THF, 0° C.; e) i) CF₃TMS, TBAF; f) DIBAL, DCM, -78° to -30° C.; g) CF₃TMS, TBAF; h) nBuLi, -78° C.; ii) methylchloroformate, THF, -78° C;
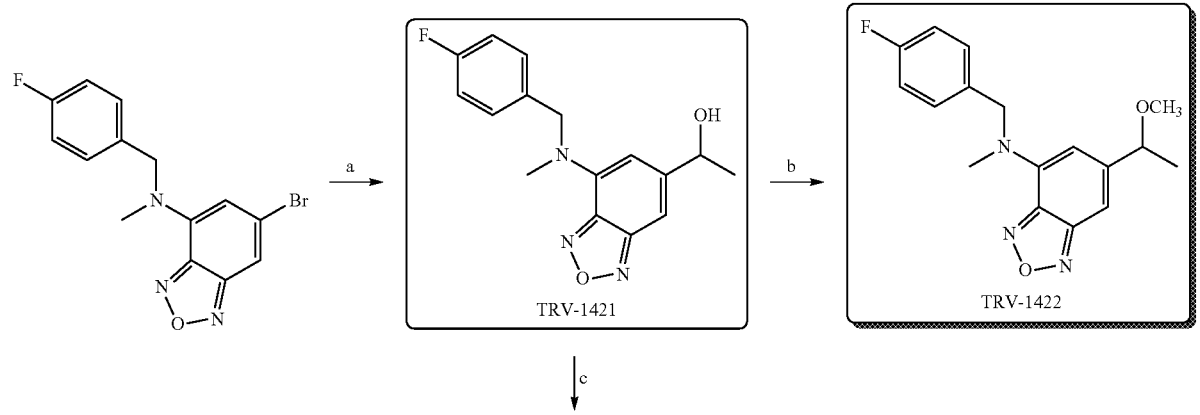

-continued
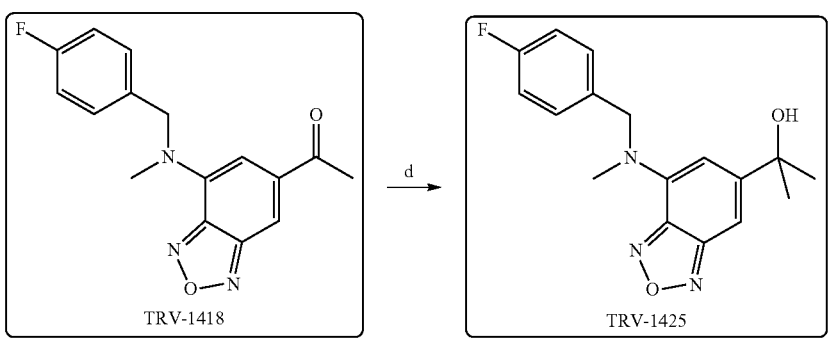
a) i) nBuLi/-78° C.; ii) acetaldehyde; b) NaH/THF/MeI; c) Dess-Martin/DCM; d) MeMgBr/THF/-78° C.
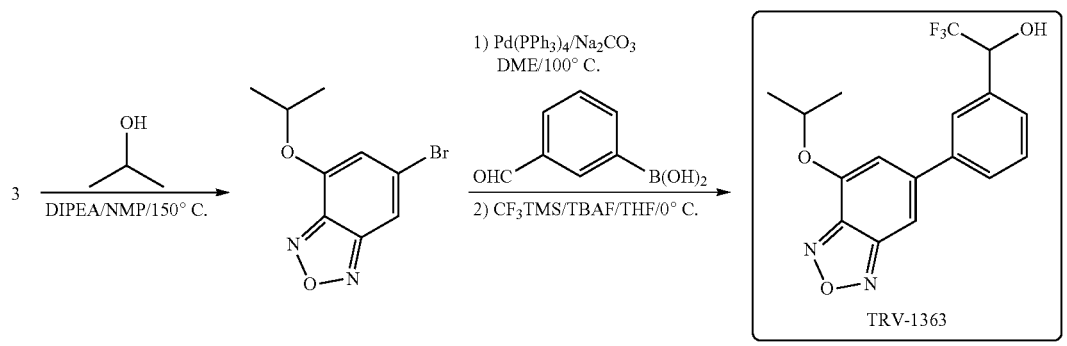
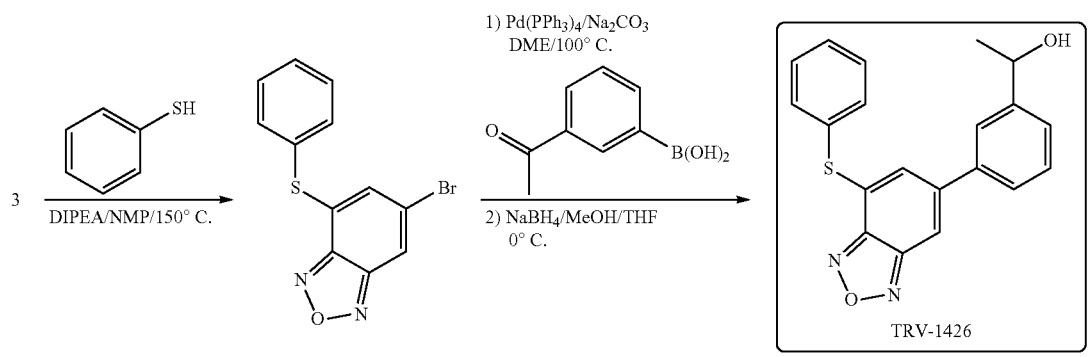
1p;2p
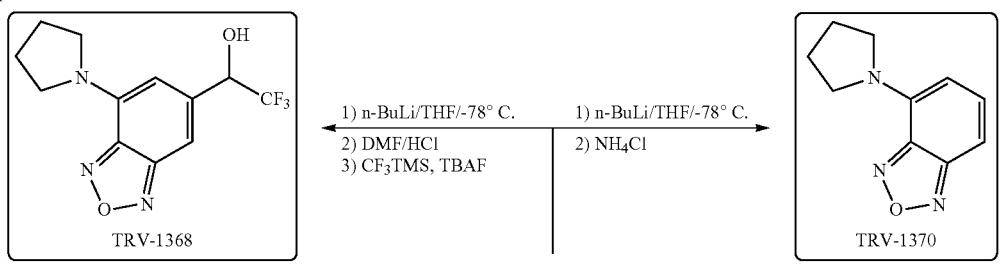

-continued
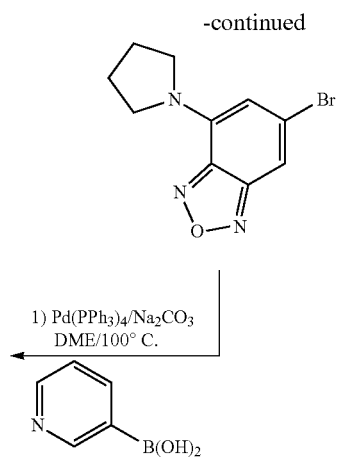
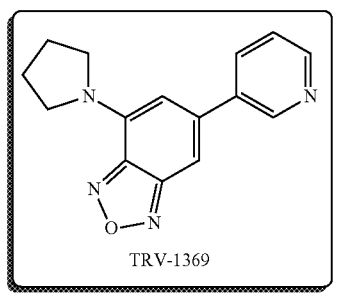
1) Pd(PPh₃)₄/Na₂CO₃
DME/100° C.
TRV-1369
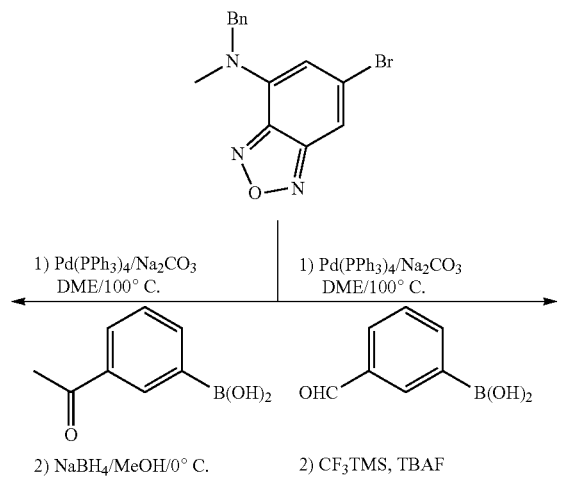
1) Pd(PPh₃)₄/Na₂CO₃
DME/100° C.
1) Pd(PPh₃)₄/Na₂CO₃
DME/100° C.
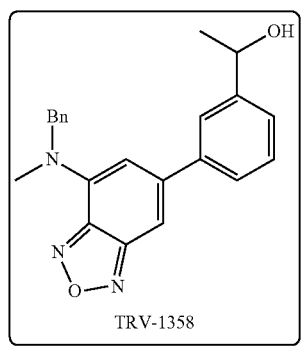
TRV-1358
2) NaBH₄/MeOH/0° C.
2) CF₃TMS, TBAF
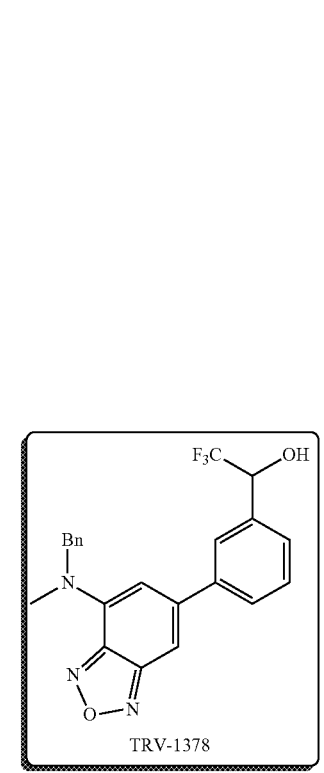
TRV-1378
1) NaH/THF 0° C.
2) MeI
TRV-1398
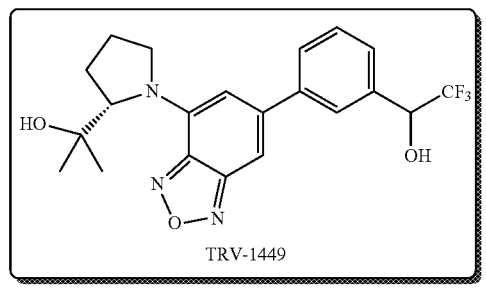
TRV-1449
1) 3-formylphenylboronic acid
Pd(PPh₃)₄/DME/100° C.
2 M Na₂CO₃
2) CF₃TMS/TBAF
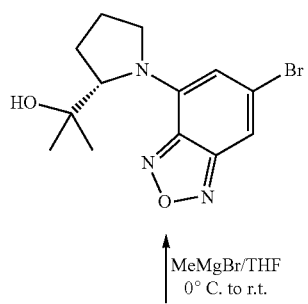
MeMgBr/THF
0° C. to r.t.

-continued
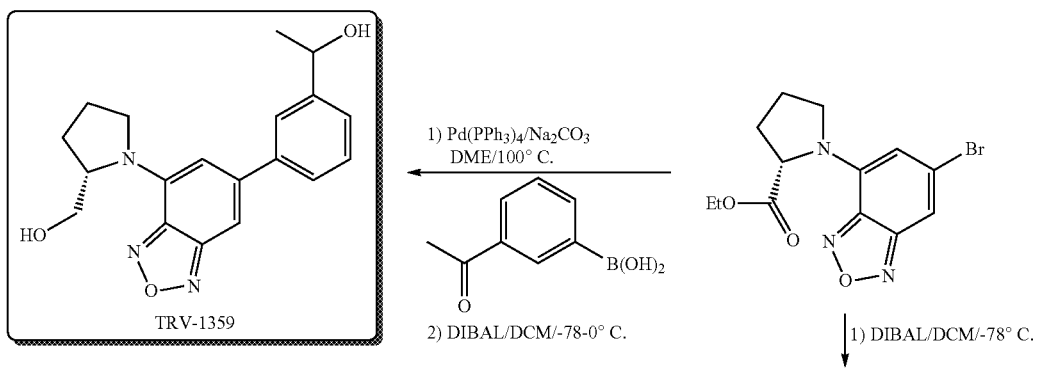
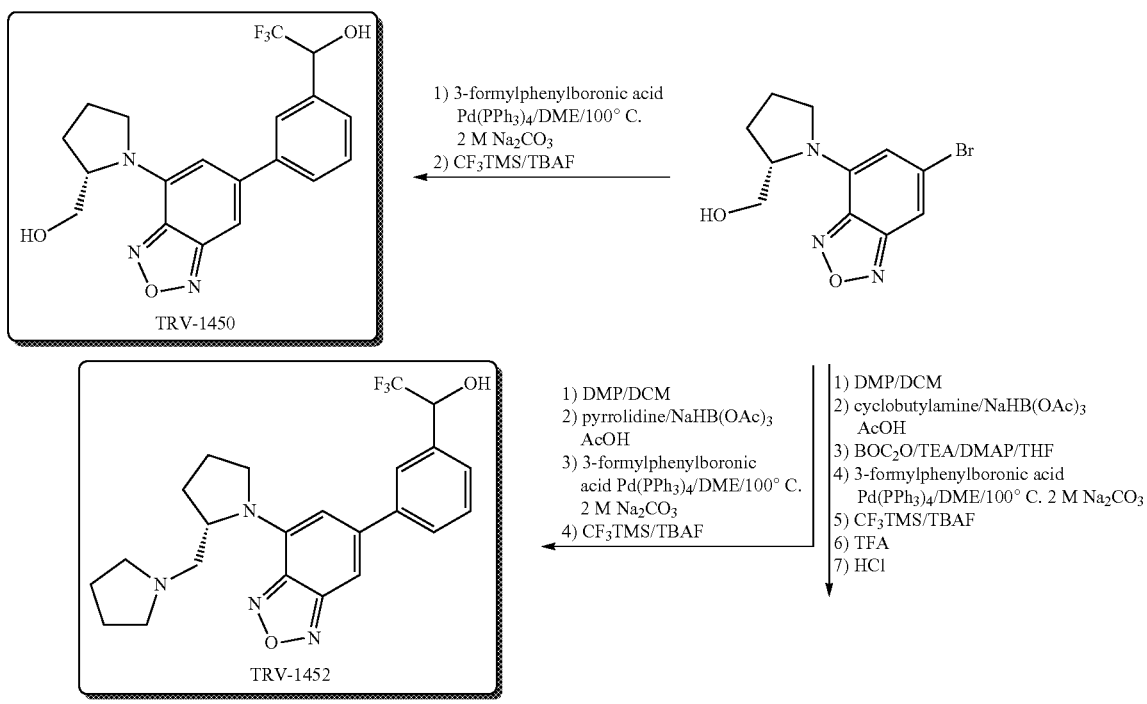
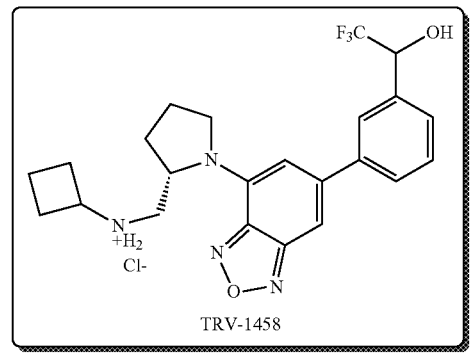

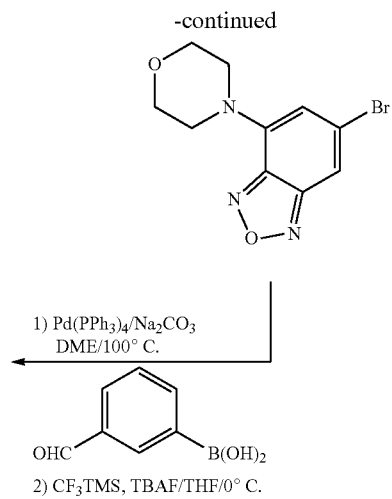
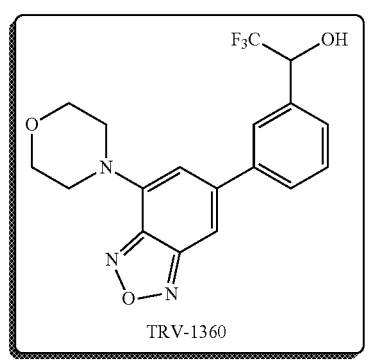
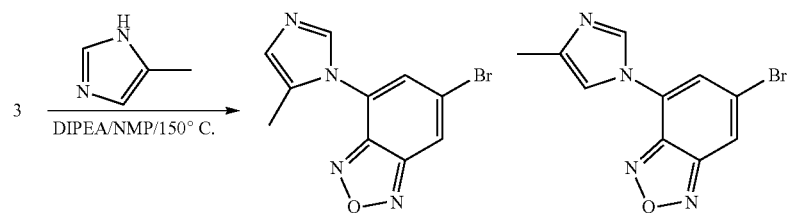
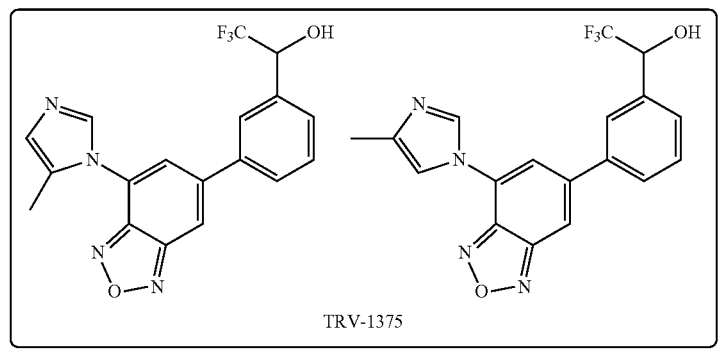
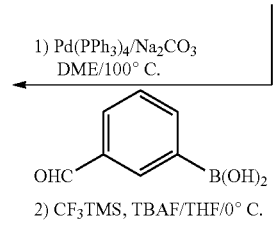

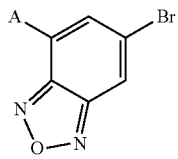

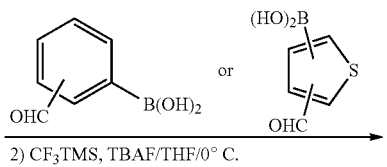

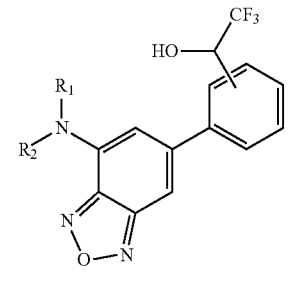

or

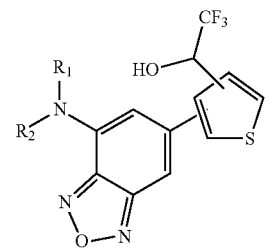

A (Amino group) = morpholine, 1-methylpiperazine, N-isopropylmethylamine, 2-methylpyrrolidine, piperidine, diethylamine, (2-methoxyethyl)methylamine, N-methylethanamine, thiomorpholine 4-(pyrrolidin-1-yl) piperidine, pyrazole, 4-methylpyrazole, 4-fluoro-N-methylbenzylamine, isoindoline, N-methyl propargylamine, N-methyl-N-(2-pyridinylmethyl)amine, N-methyl-N-(3-pyridinylmethyl)amine, azetidine, N-methyl-1-(thiazol-2-yl)methanamine, 1-(azetidin-3-ylmethyl)pyrrolidine; 4-(azetidin-3-ylmethyl)morpholine; N-methyl-3-(pyrrolidin-1-yl)propan-1-amine; N,4-dimethylpentan-1-amine; N,N-dimethylpiperidin-1-amine TRV-1360, 1376, 1377, 1379, 1381, 1382, 1383, 1384, 1385, 1387, 1388, 1389, 1390, 1401, 1404, 1412, 1413, 1432, 1459, 1463 - 1469, 1471, 1474, 1535, 1543

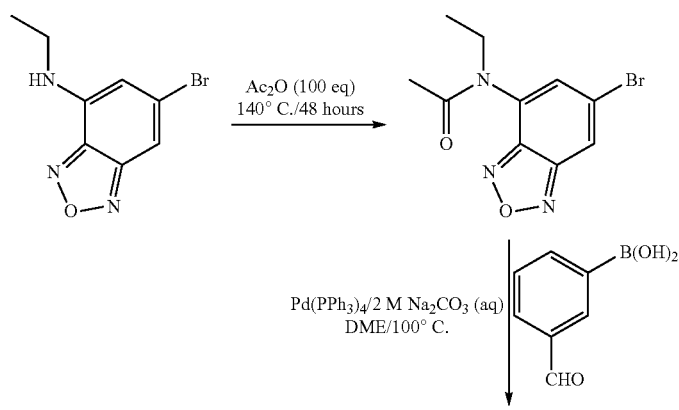

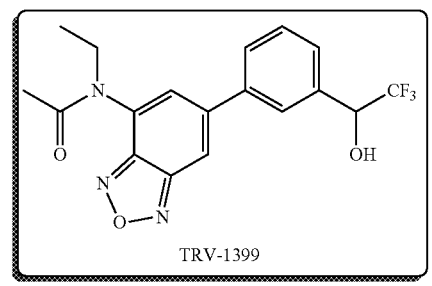

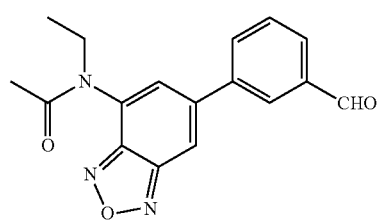

33 34
-continued
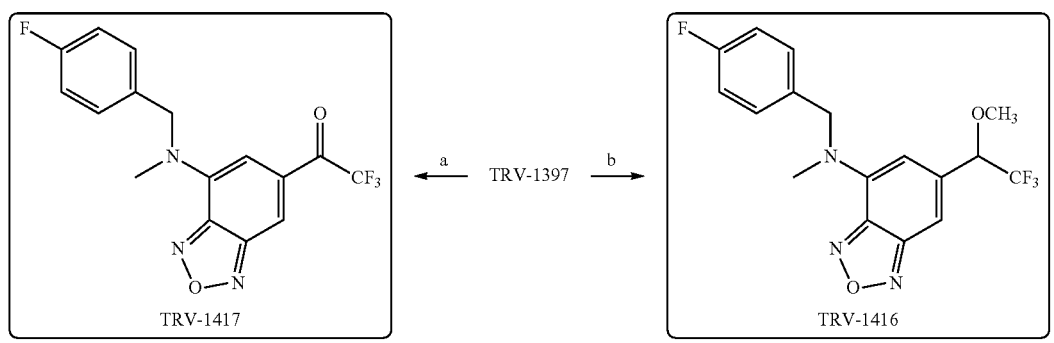
a) (COCl)$_2$/DMSO/TEA/DCM; b) NaH/THF/MeI
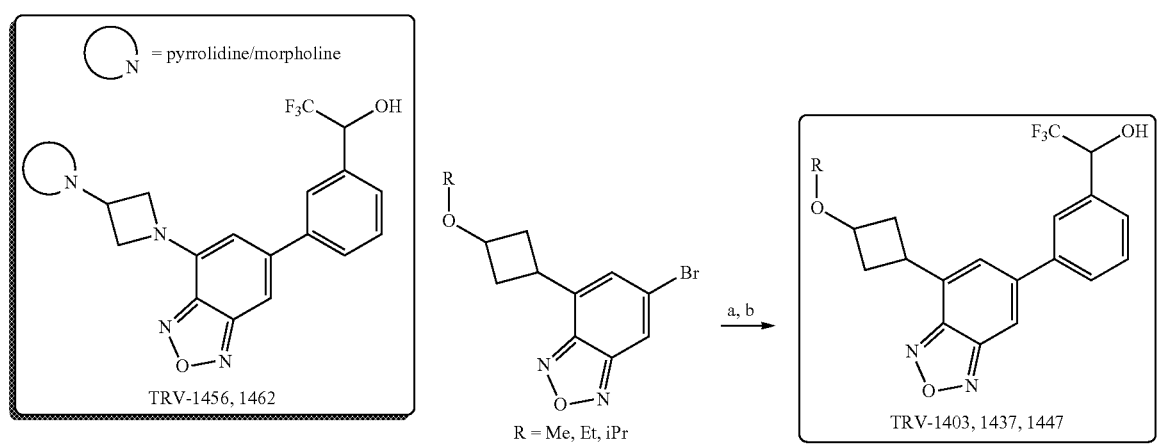
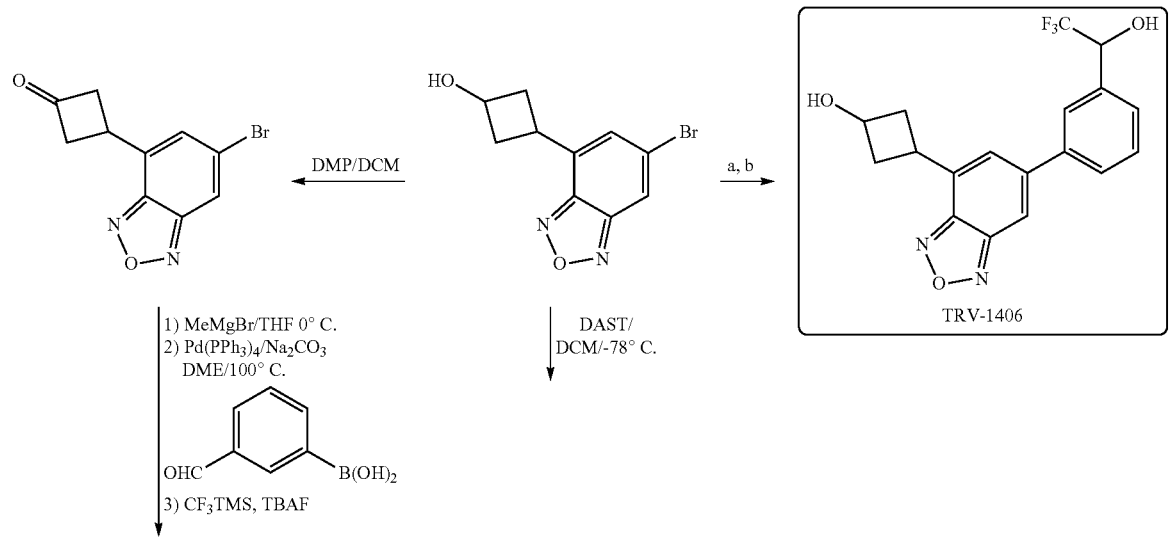

-continued
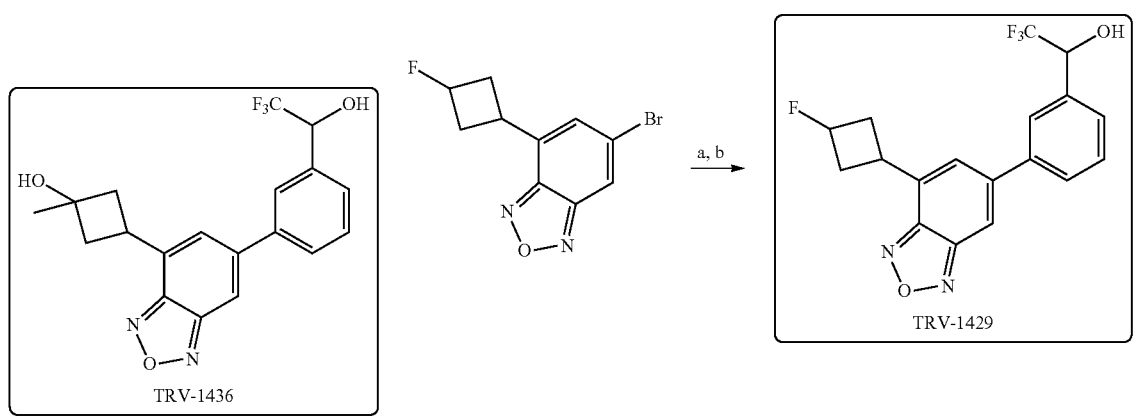
a) Pd(PPh₃)₄/Na₂CO₃ DME/100° C. 3-formylphenylboronic acid b) CF₃TMS/TBAF 0° C.
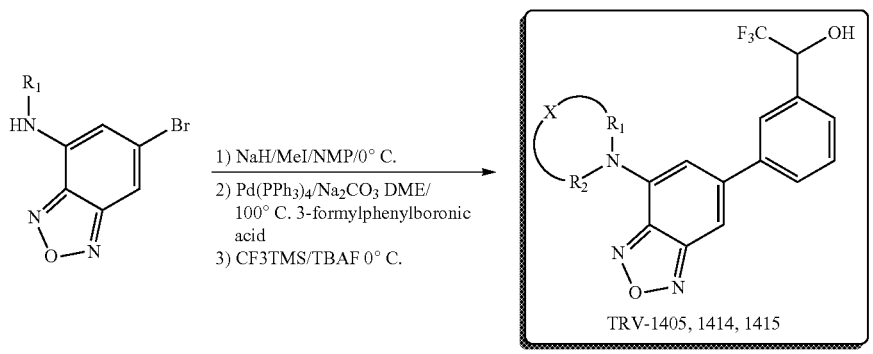
NR₁ = cyclopropylamine, 4-methoxybenzylamine, 3,5-dimethoxybenzylamine
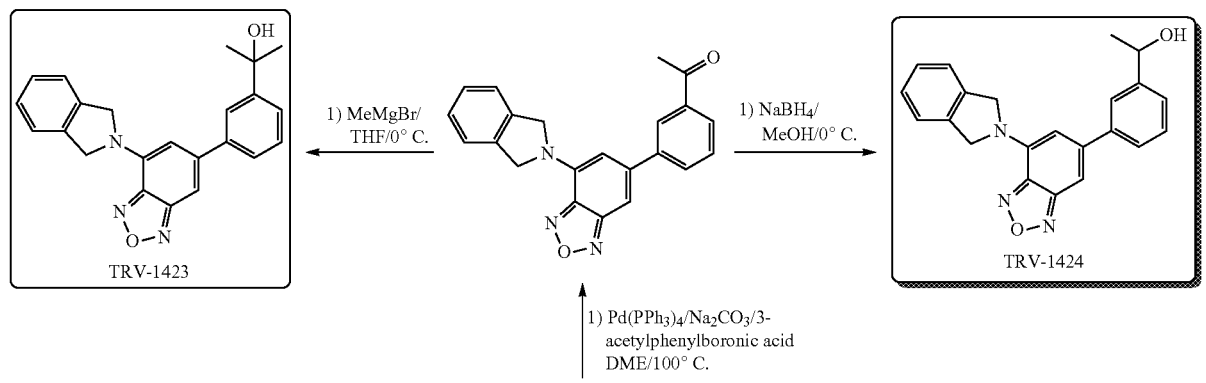

-continued
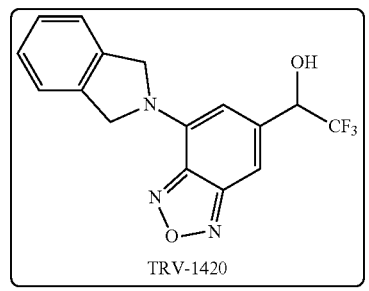
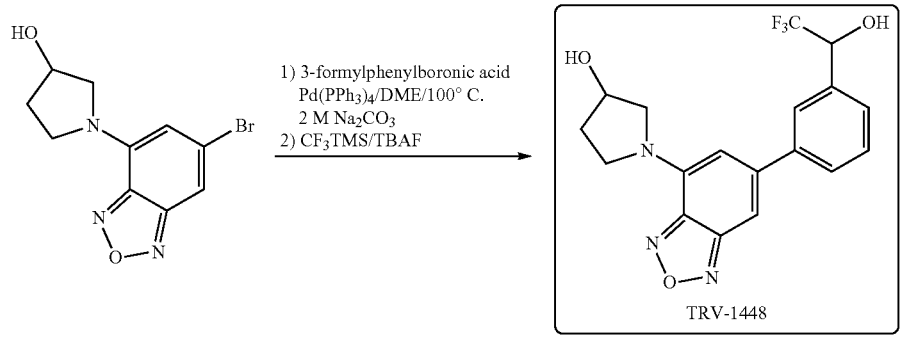
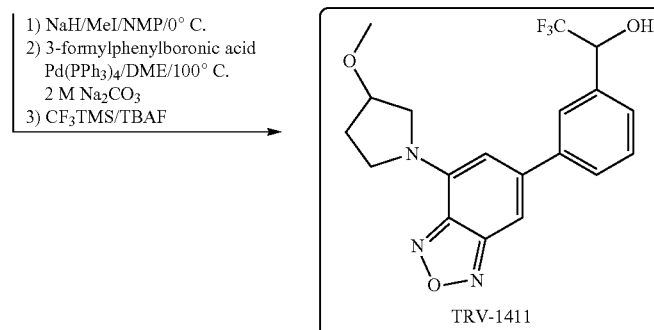
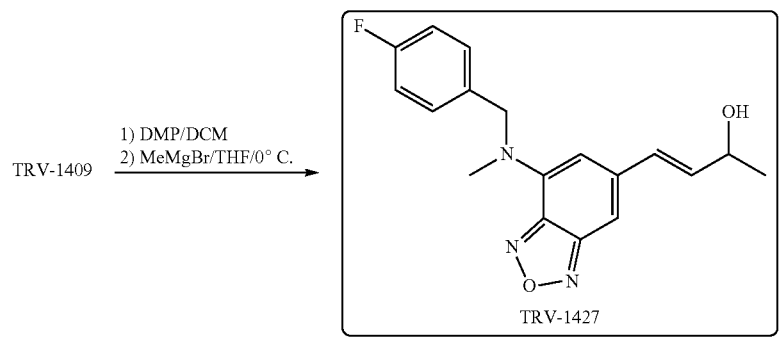
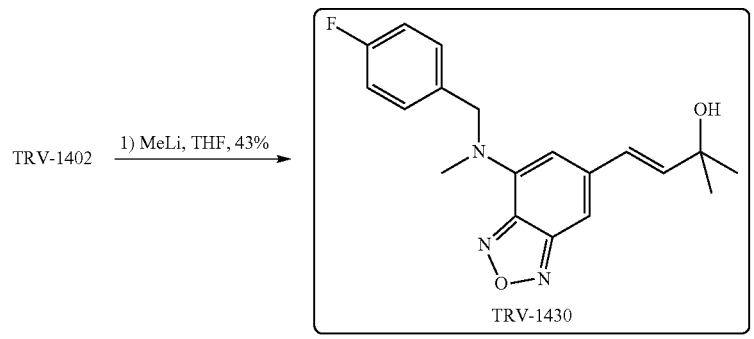

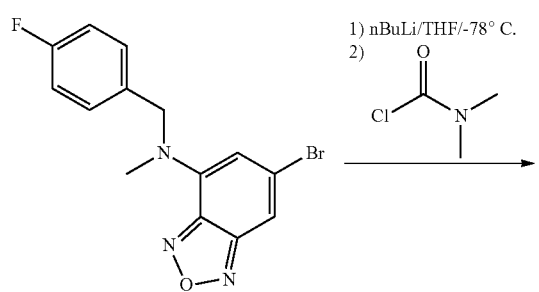 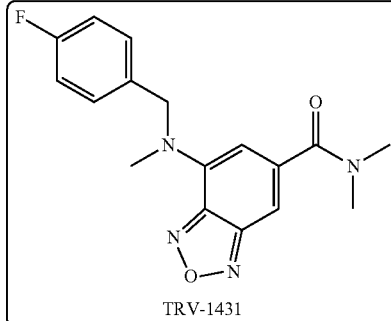
TRV-1431
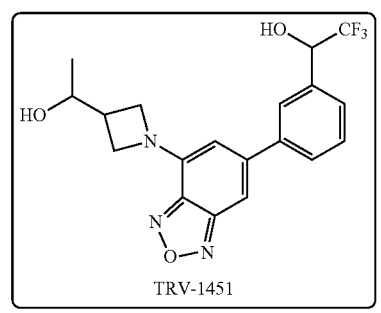
TRV-1451
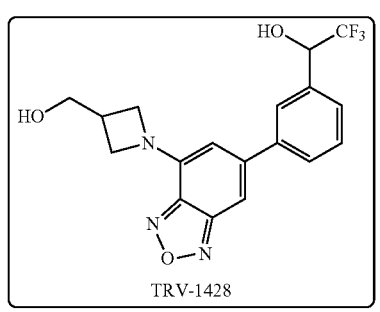
TRV-1428
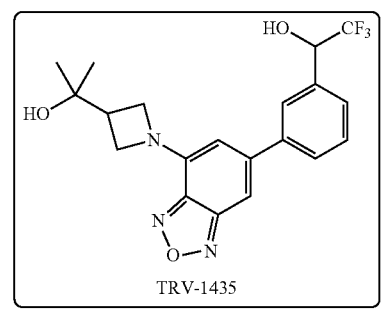
TRV-1435
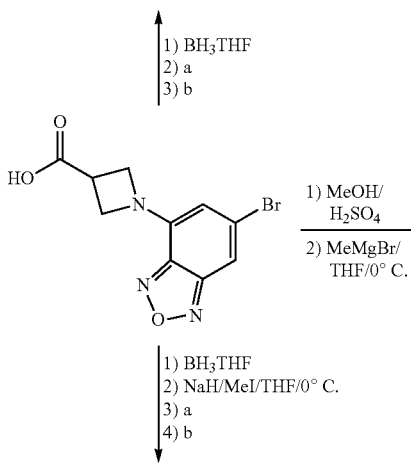
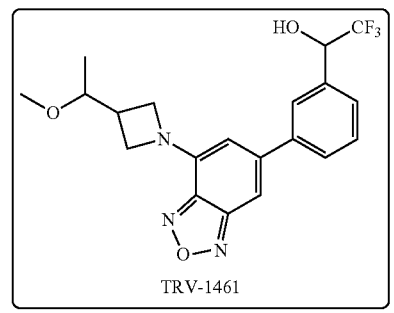
TRV-1461
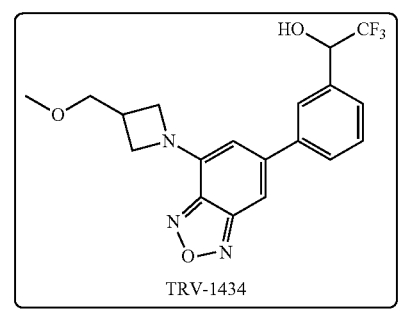
TRV-1434
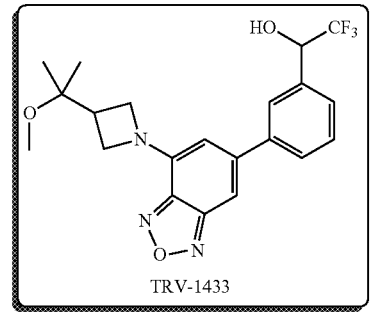
TRV-1433
a) 3-formylphenylboronic acid Pd(PPh₃)₄/DME/100° C. 2 M Na₂CO₃; b) CF₃TMS/TBAF

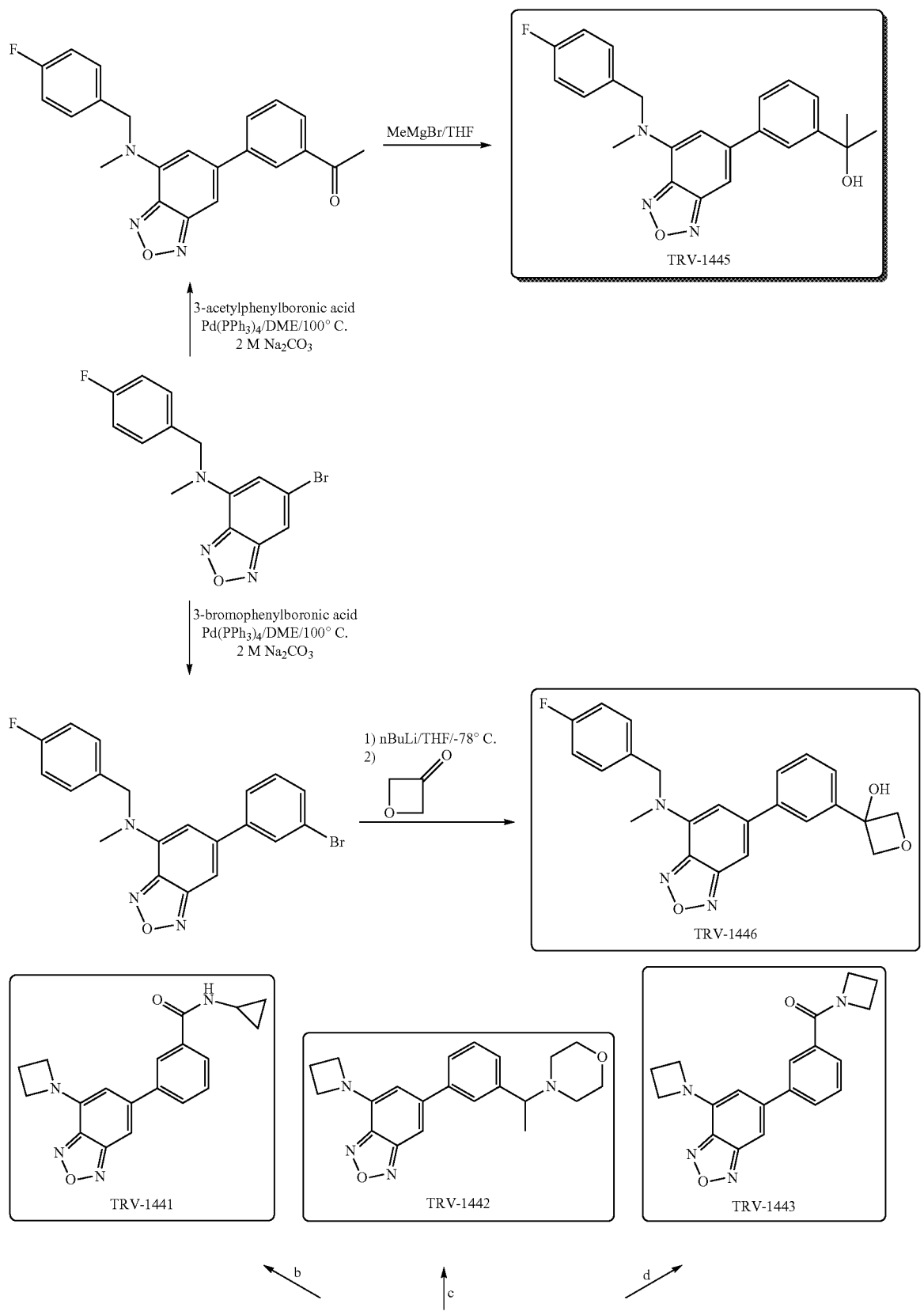

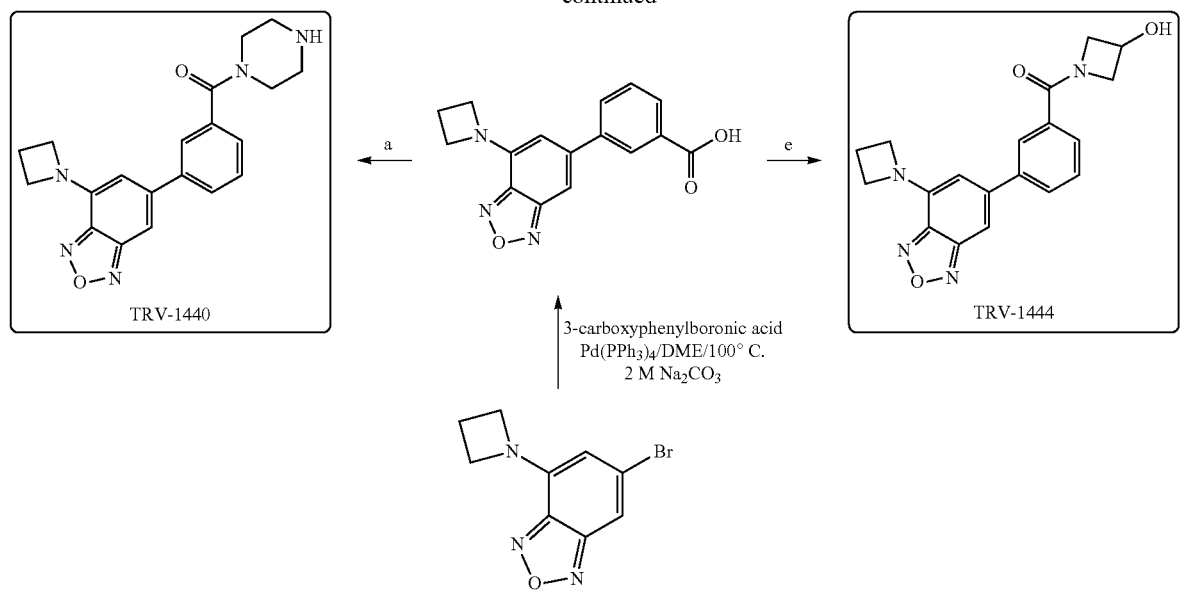
a) piperazine/HATU/DIPEA; b) cyclopropylamine/HATU/DIPEA; c) moprholine/HATU/DIPEA; d) azetidine hydrochloride/HATU/DIPEA; e) 3-hydroxyazetidine hydrochloride/HATU/DIPEA
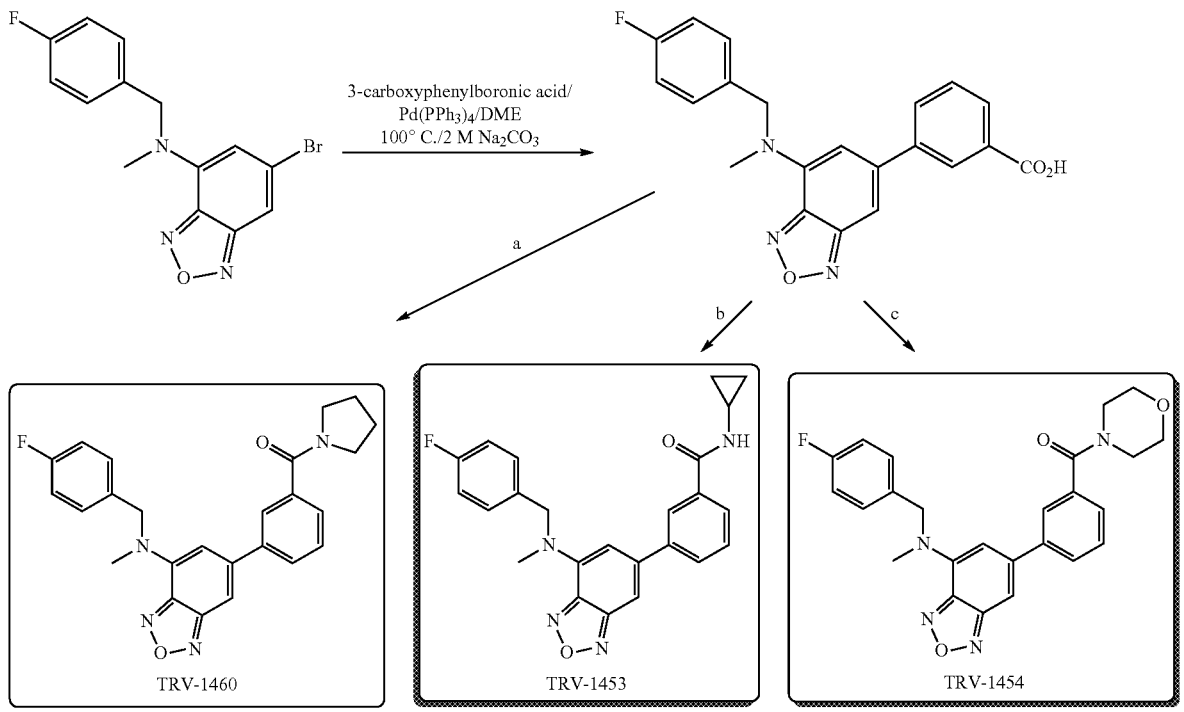
a) pyrrolidine/EtOAc/T3P/TEA; b) cyclopropylamine/EtOAc/T3P/TEA; c) morpholine/EtOAc/T3P/TEA
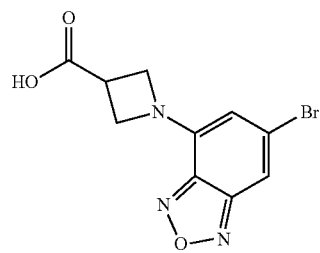
1) BH₃THF
2) DMP/DCM
3) morpholine/HATU/NMP
4) a
5) b
1) BH₃THF
2) DMP/DCM
3) pyrrolidine/HATU/NMP
4) a
5) b

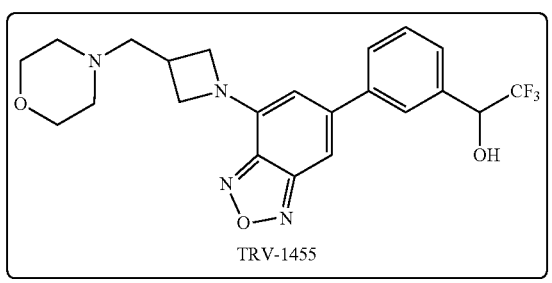
TRV-1455
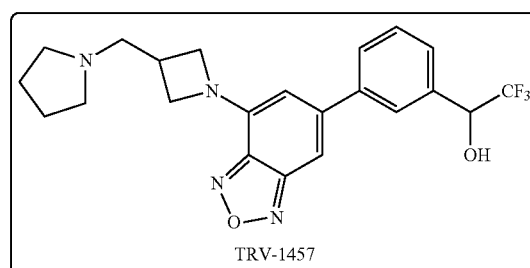
TRV-1457
a) 3-formylphenylboronic acid Pd(PPh$_3$)$_4$/DME/100° C. 2 M Na$_2$CO$_3$; b) CF$_3$TMS/TBAF
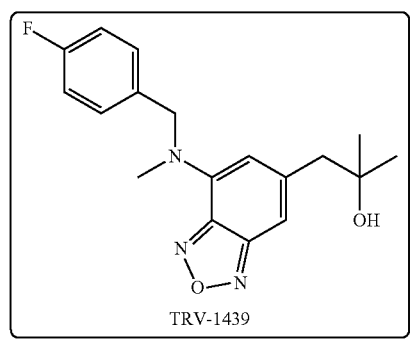
TRV-1439
↑ MeLi/THF  
-78° C.
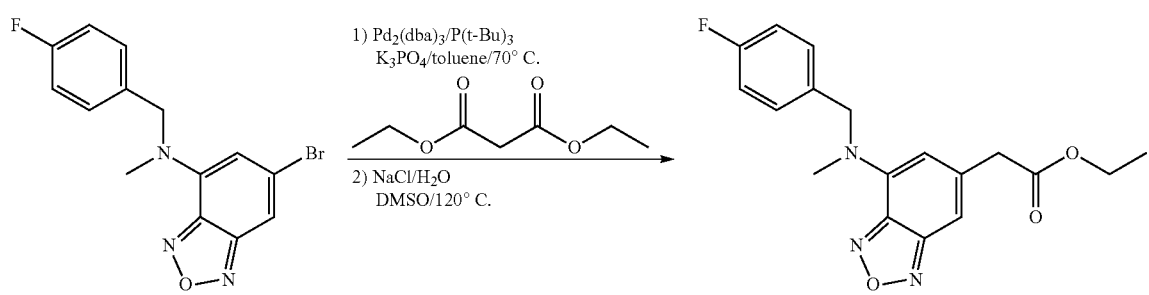
1) Pd$_2$(dba)$_3$/P(t-Bu)$_3$ K$_3$PO$_4$/toluene/70° C.  
2) NaCl/H$_2$O DMSO/120° C.
↓ DIBAL/DCM -78° C.
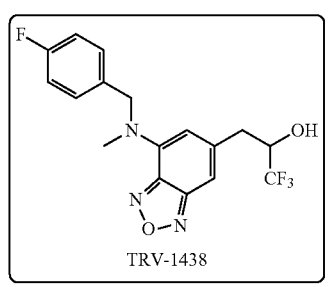
TRV-1438
← CF$_3$TMS/TBAF
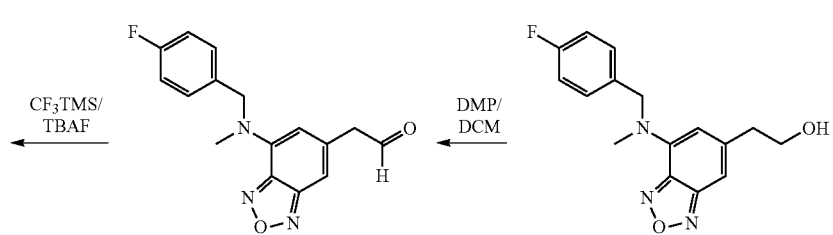
← DMP/DCM -continued
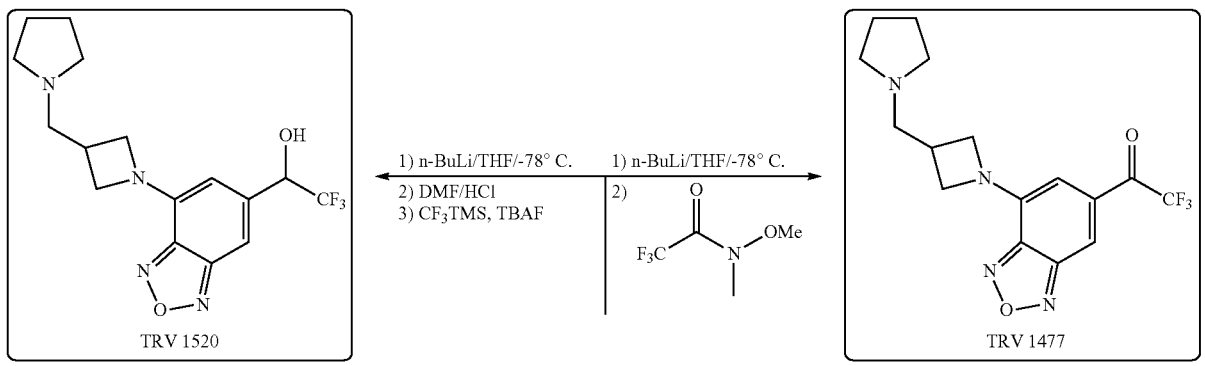
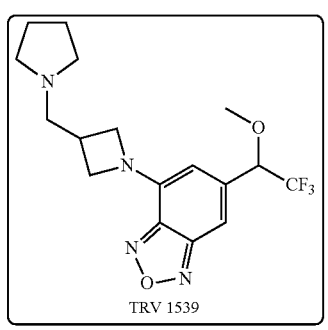
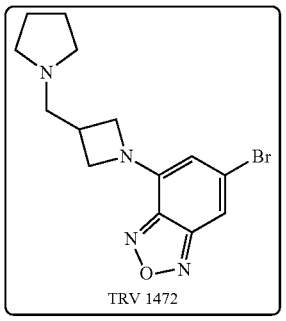
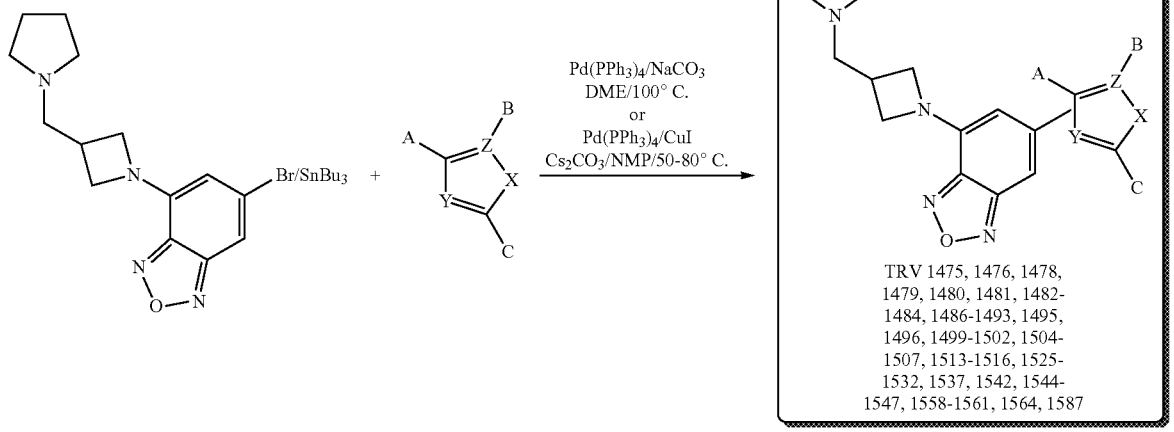
X, Y or Z = C, N, S, O, C≡C, C≡N
A, B or C = H, alkyl, Cl, Br, F, OMe, OPh, SO$_2$Me
C═O(CH$_3$), NHC═O(CH$_3$), CF$_3$CN, OCF$_3$, B(OH)$_2$
CH$_2$OH, C═ON(CH$_3$)$_2$, CH(OH)CF$_3$, —O(CH$_2$)O—

-continued
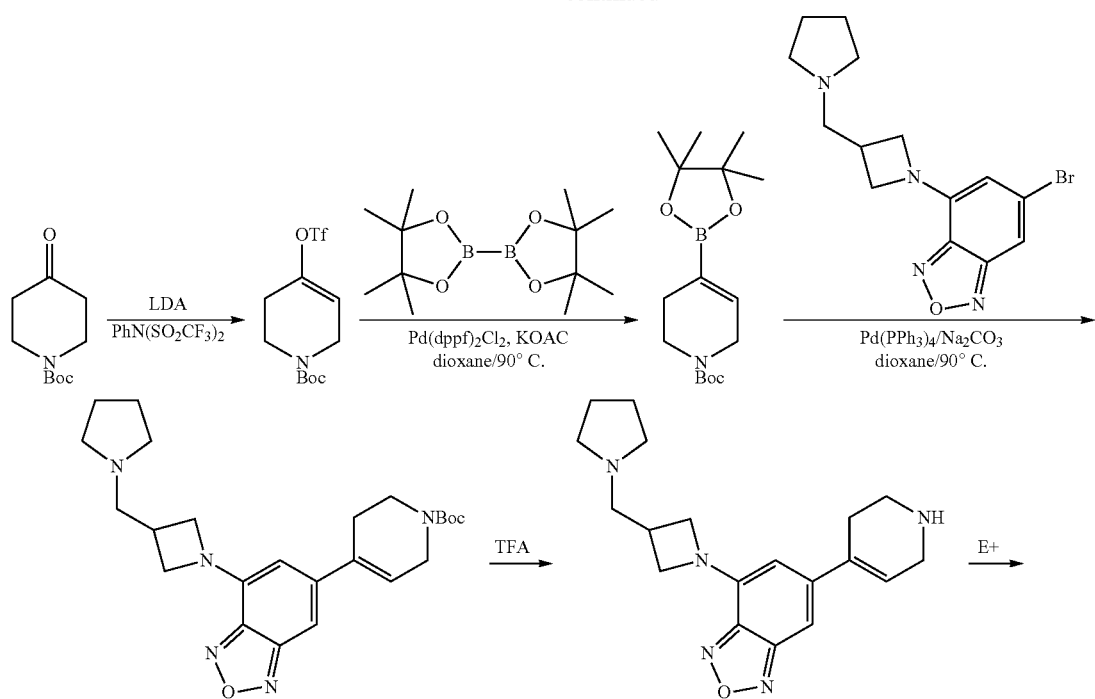
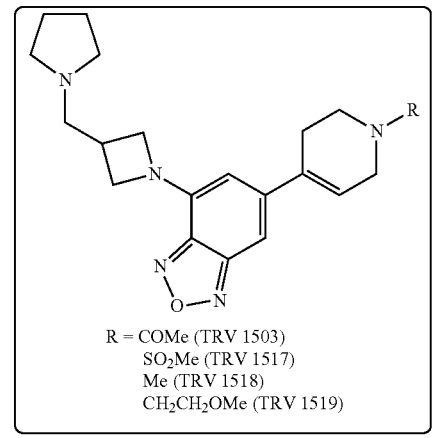
R = COMe (TRV 1503)
SO₂Me (TRV 1517)
Me (TRV 1518)
CH₂CH₂OMe (TRV 1519)
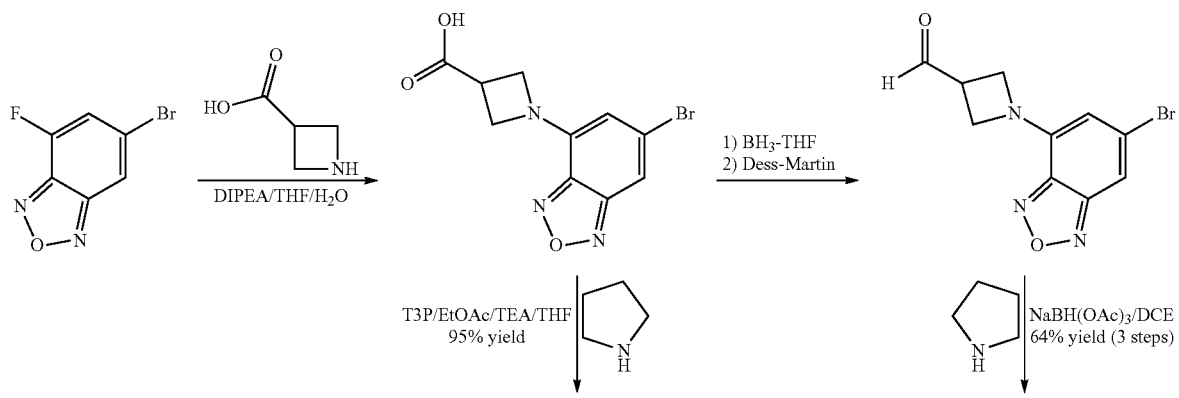

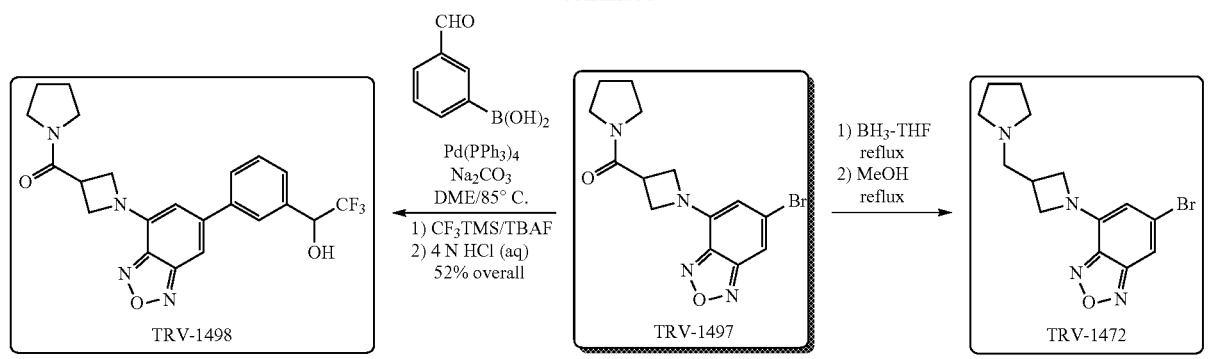
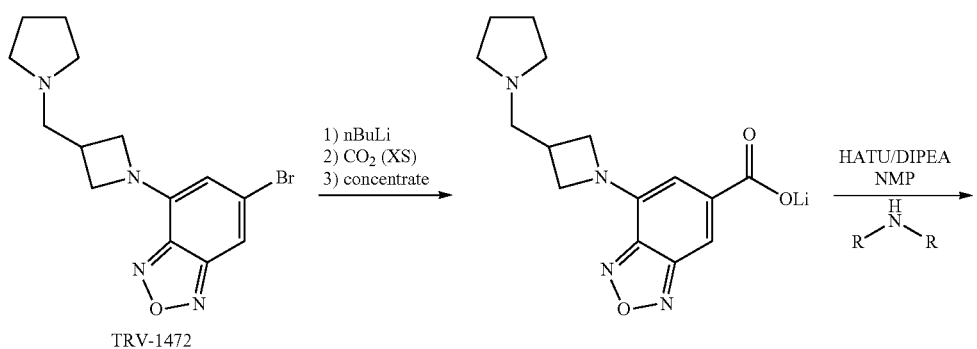
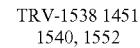

-continued
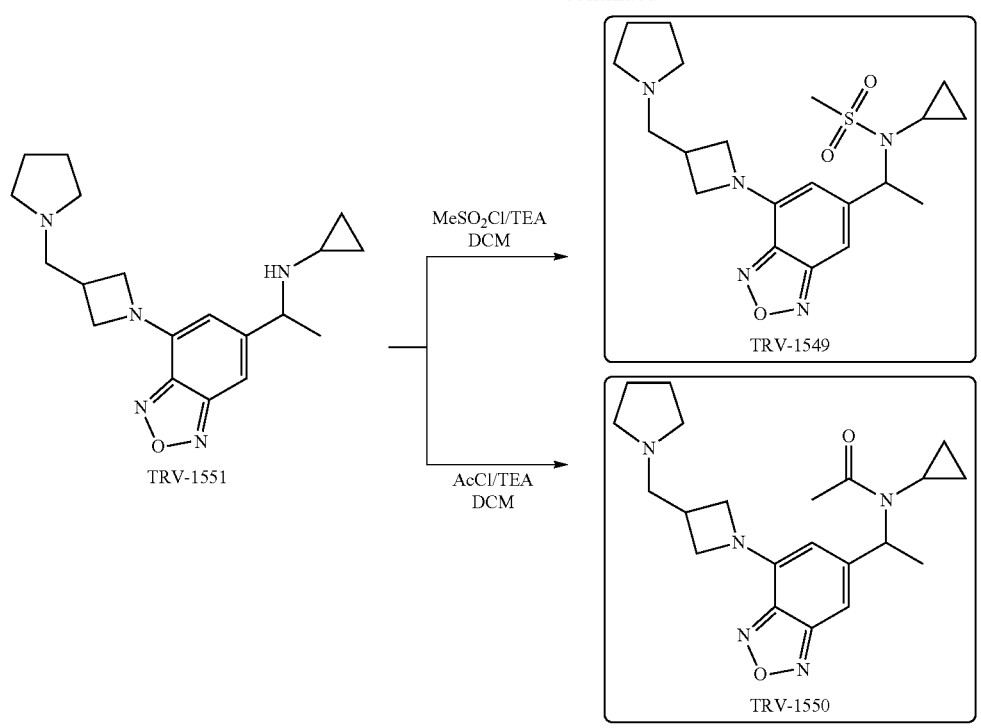
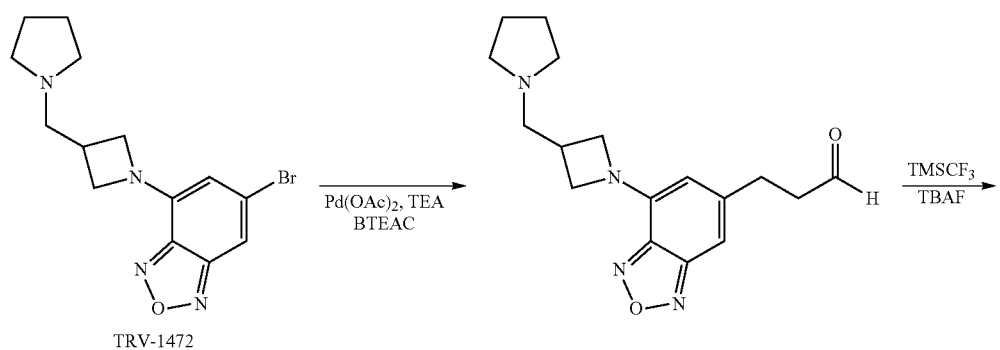
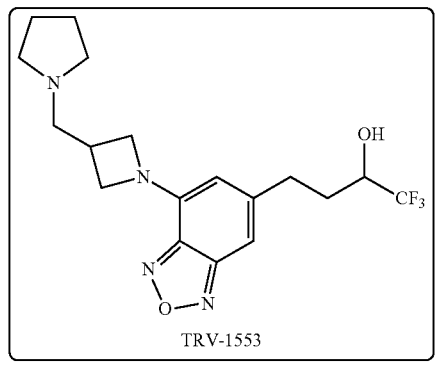

-continued
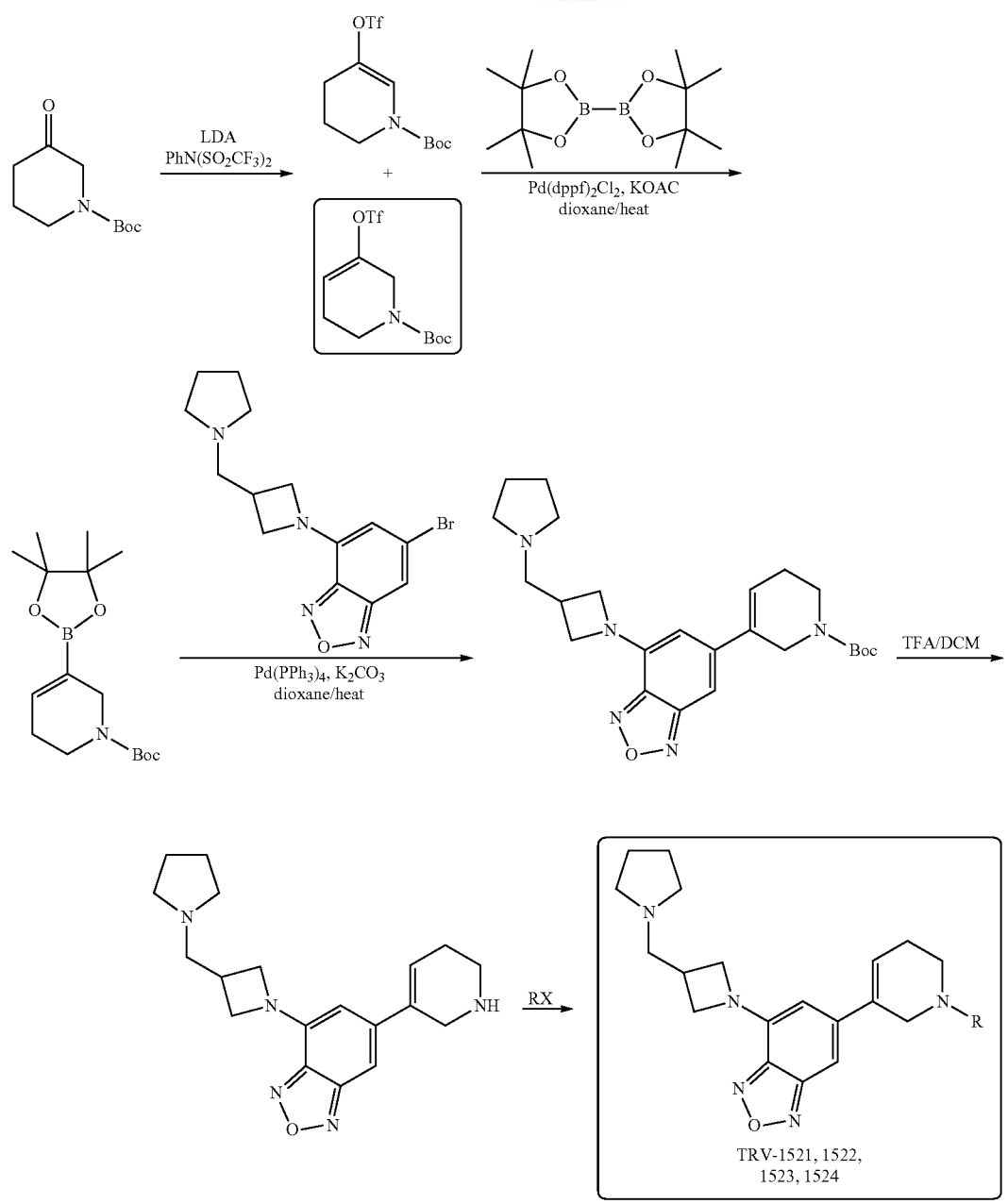
TRV-1521, 1522, 1523, 1524
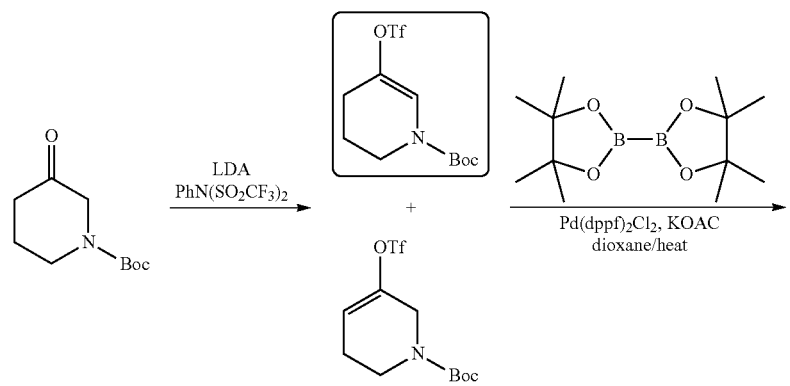

-continued
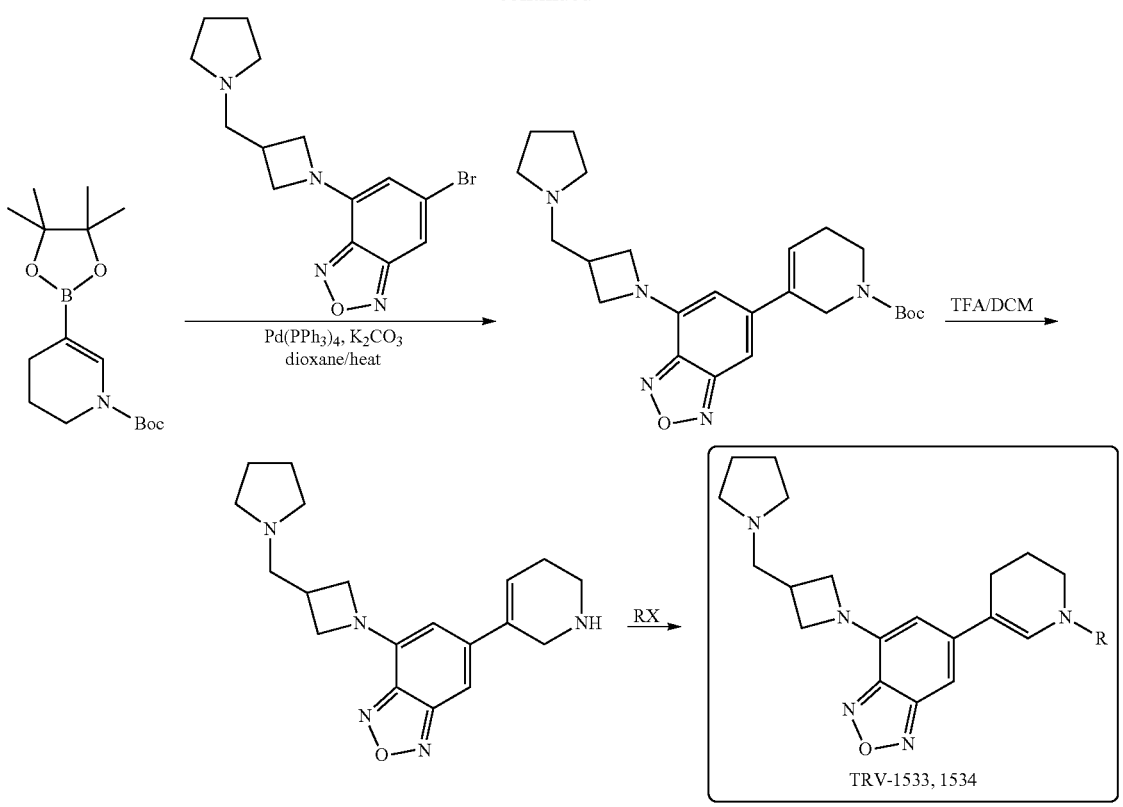
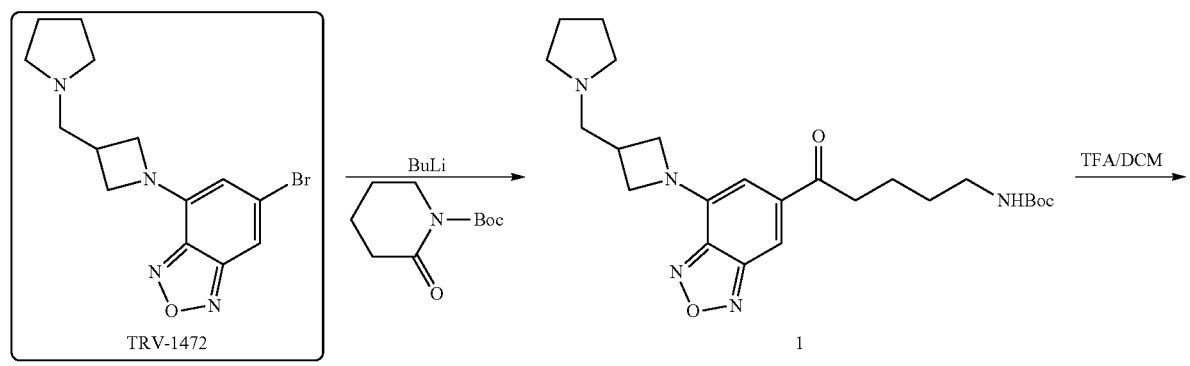
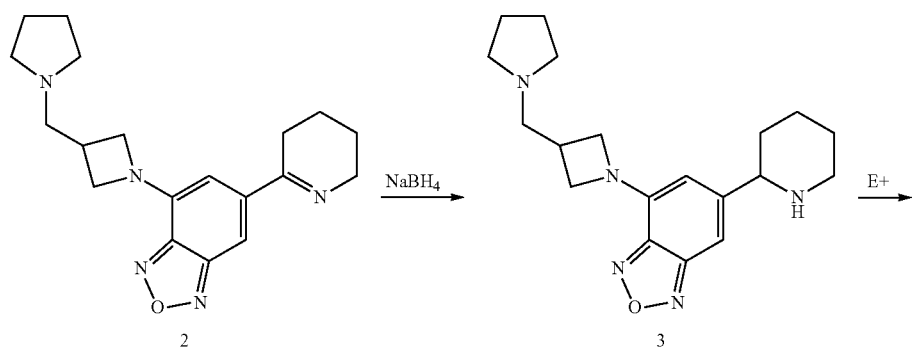

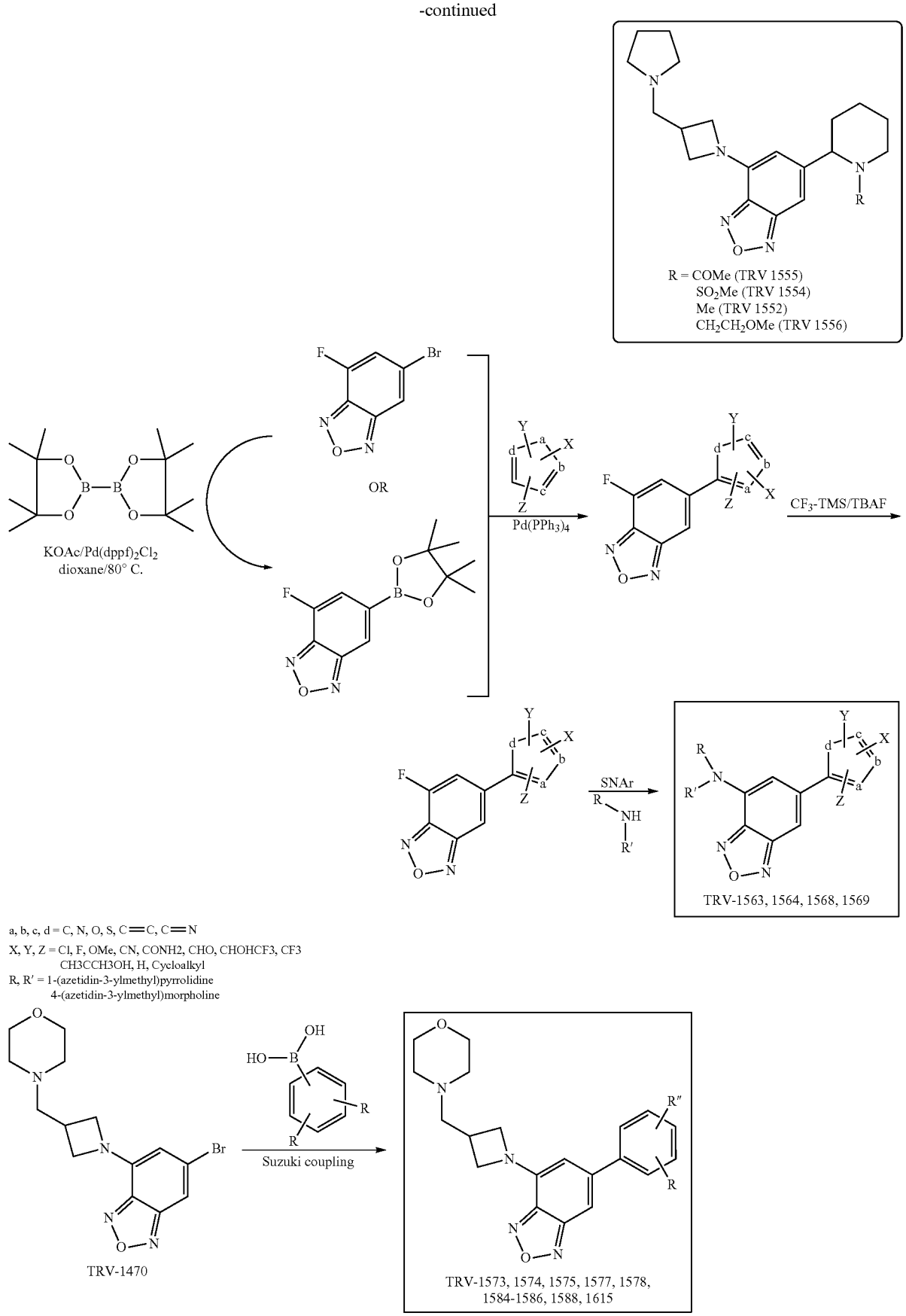

R, R″ = H, Cl, F, CN, OMe, CONH2,
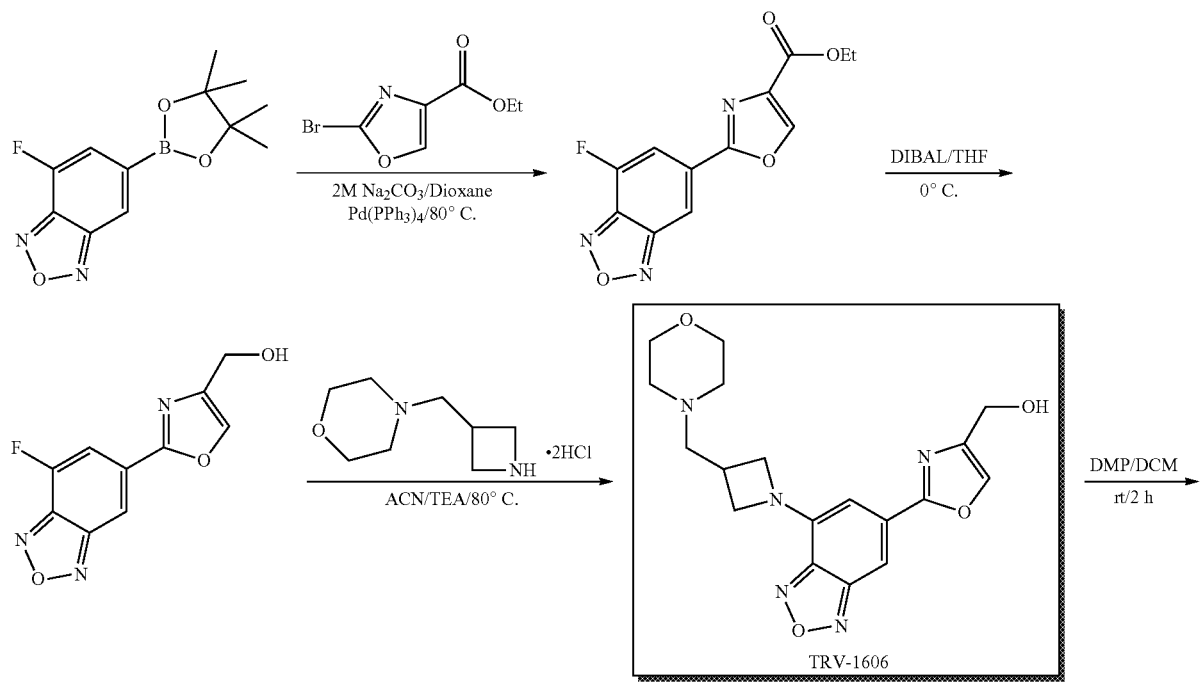
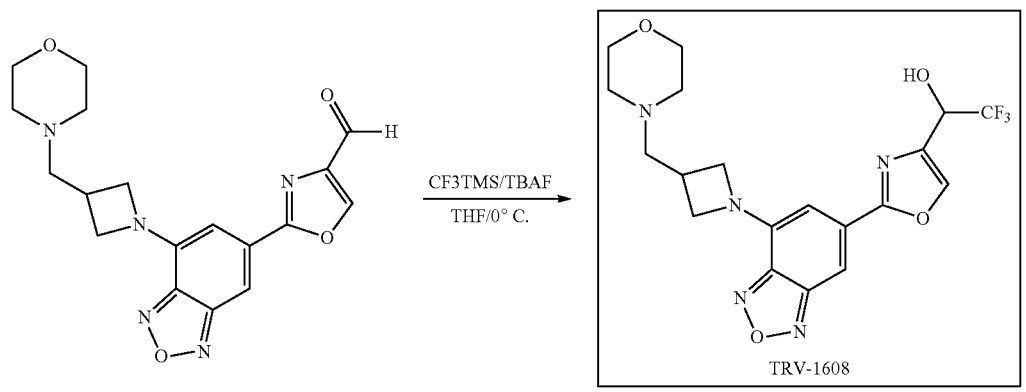
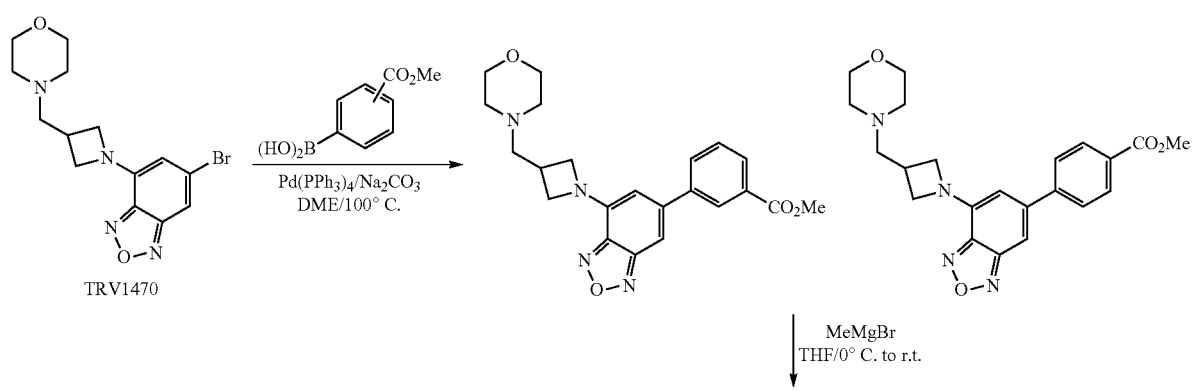

-continued
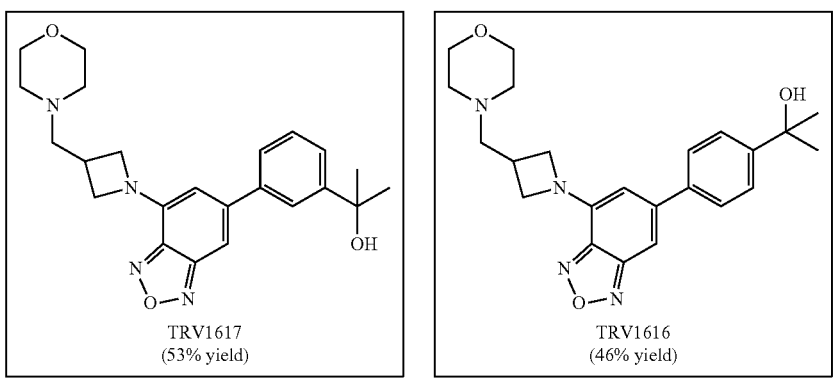
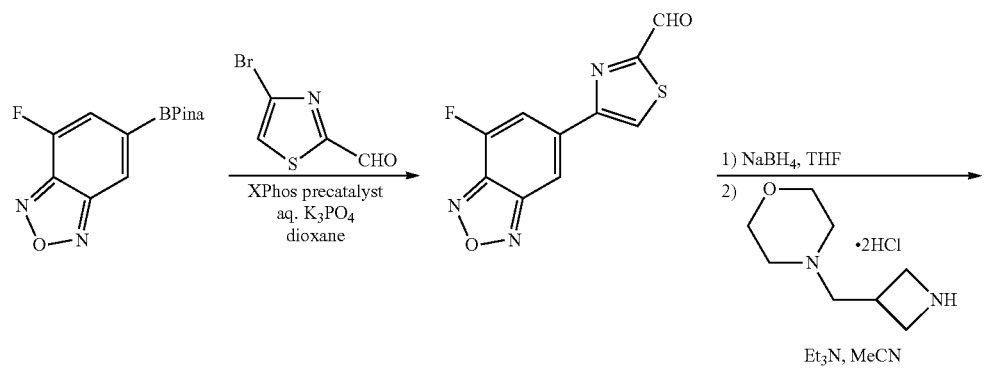
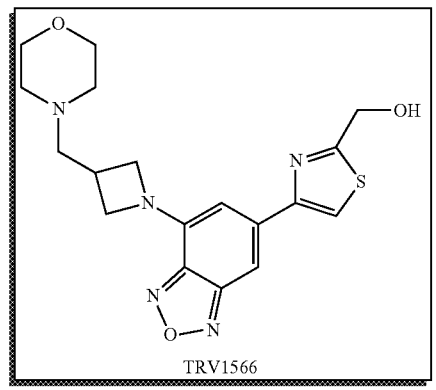
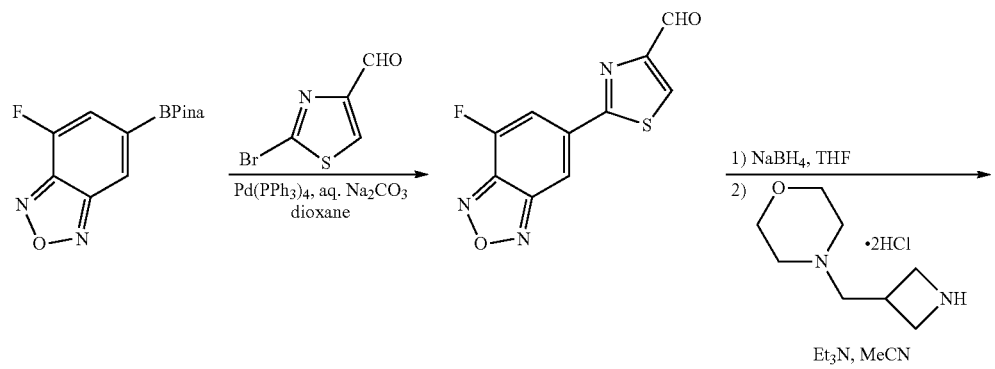

-continued
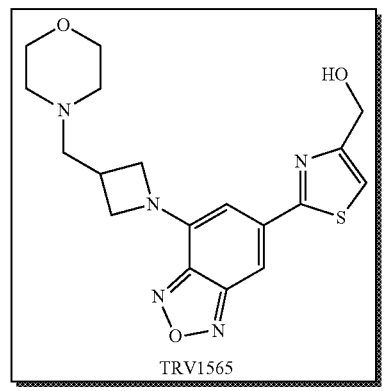
TRV1565
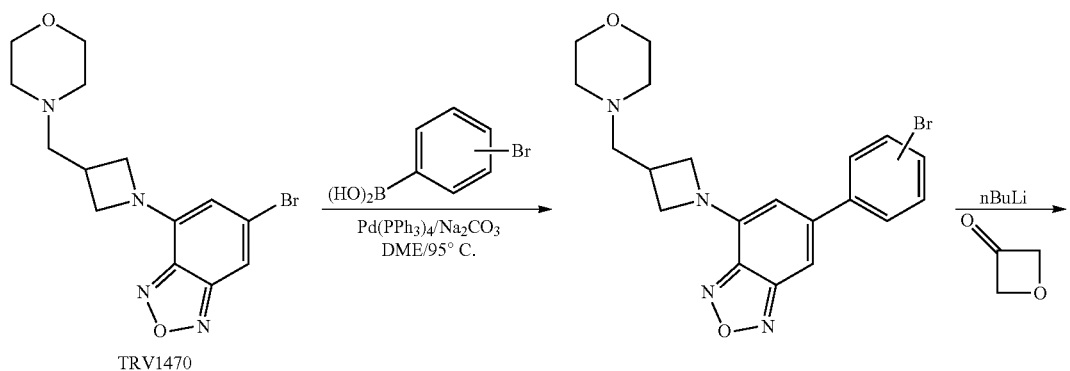
TRV1470
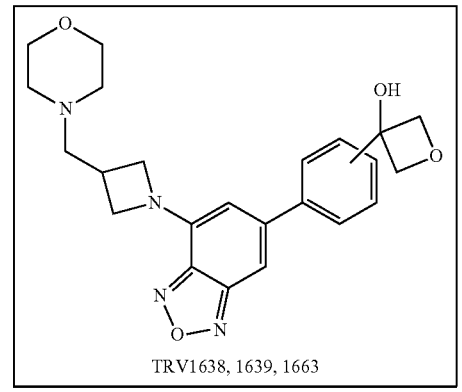
TRV1638, 1639, 1663
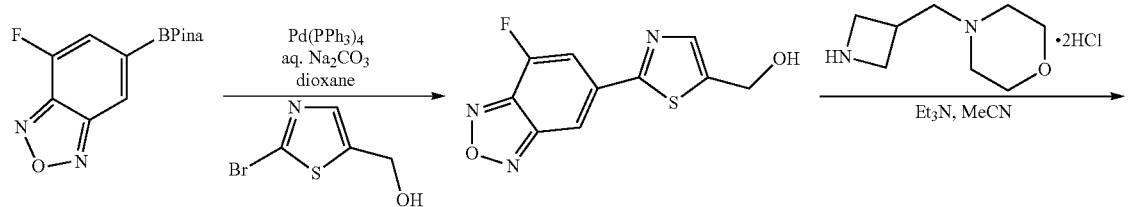

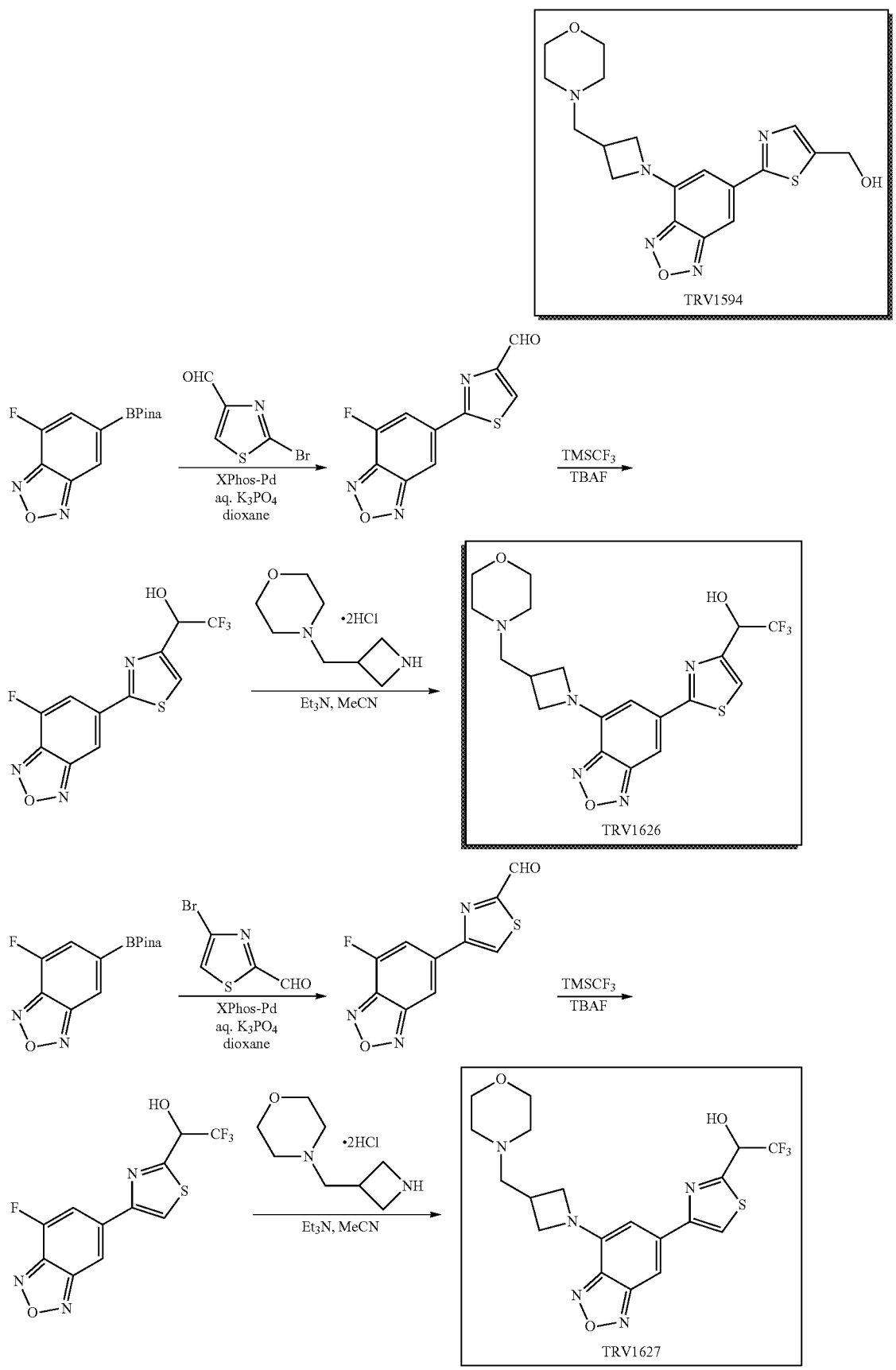
-continued

-continued
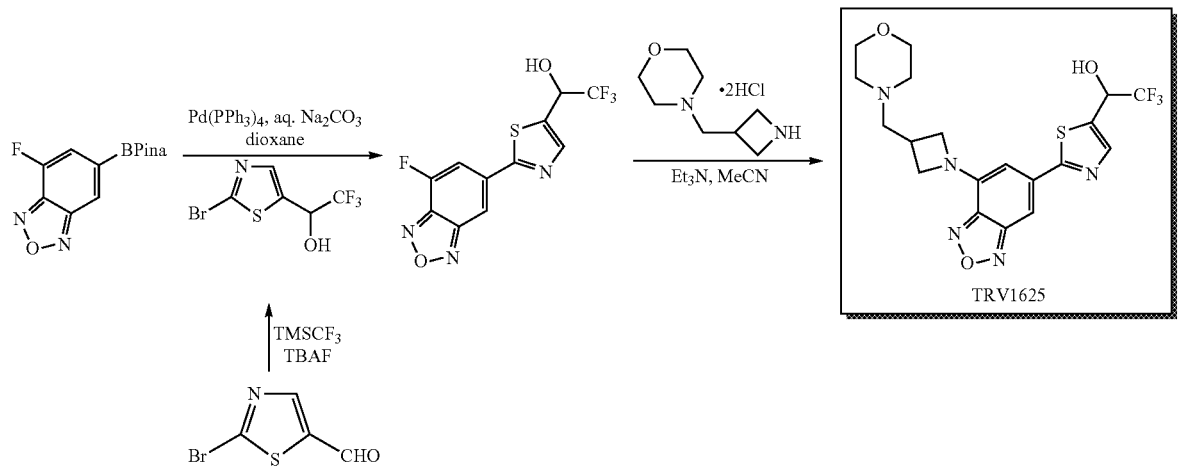
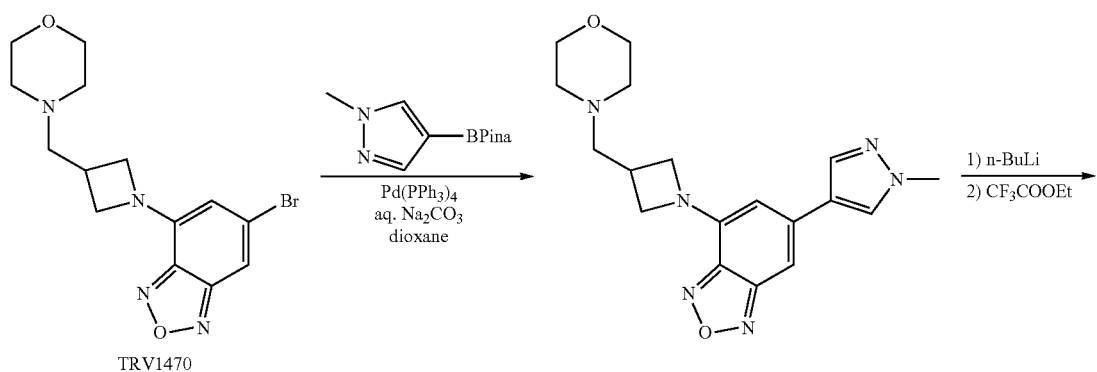
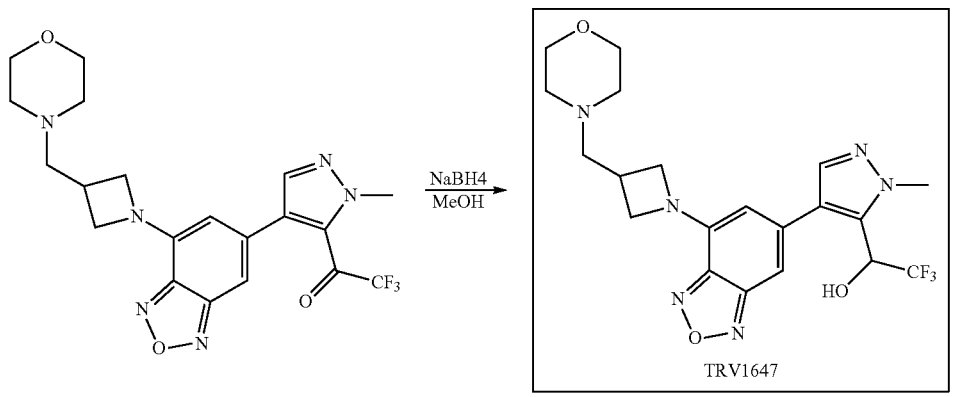
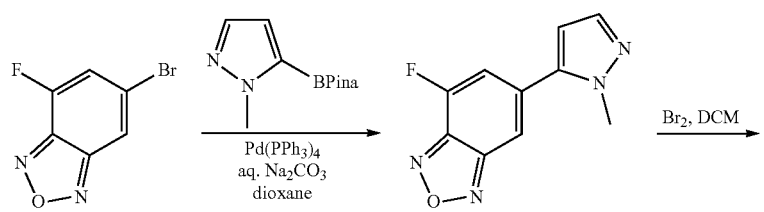

-continued
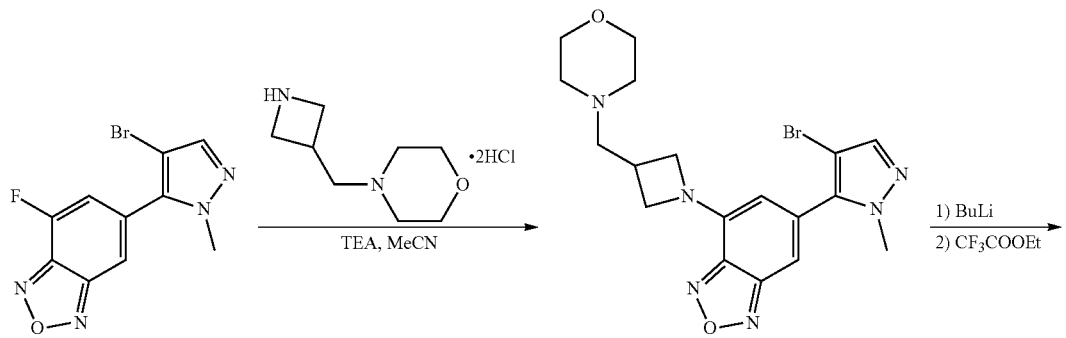
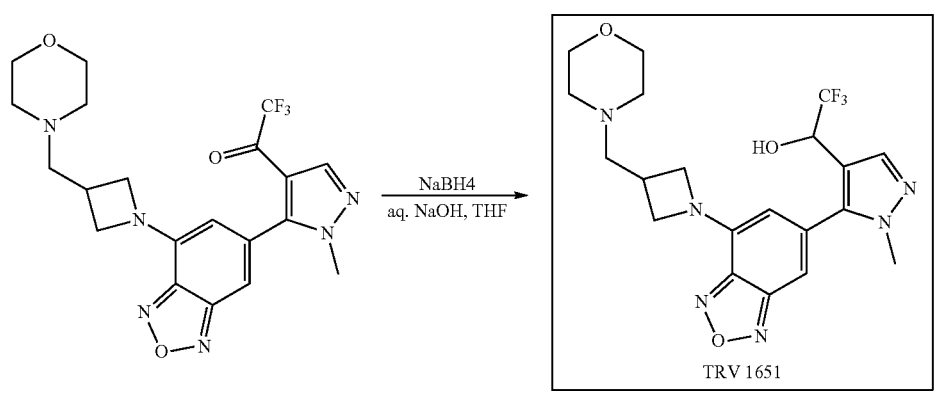
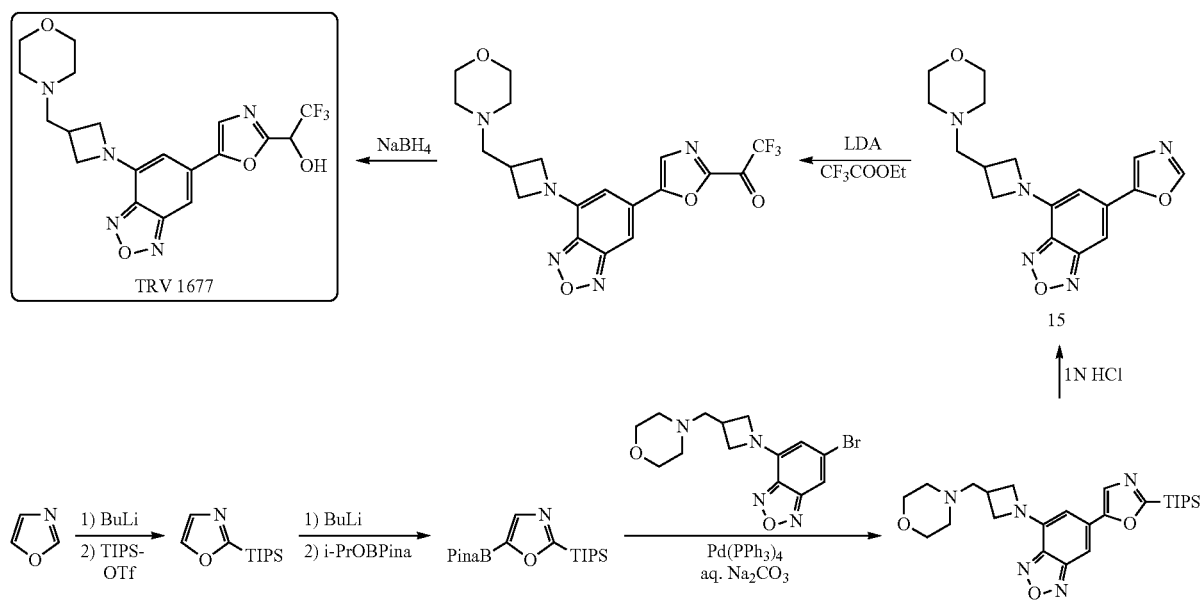
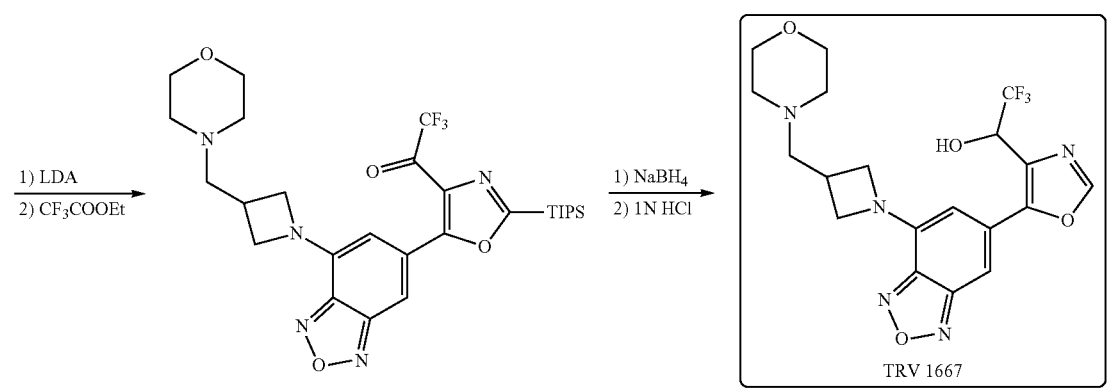

-continued
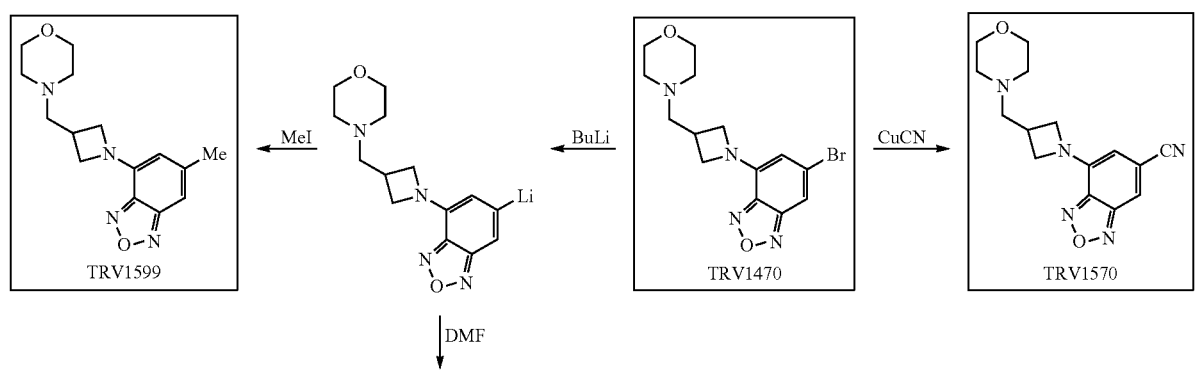
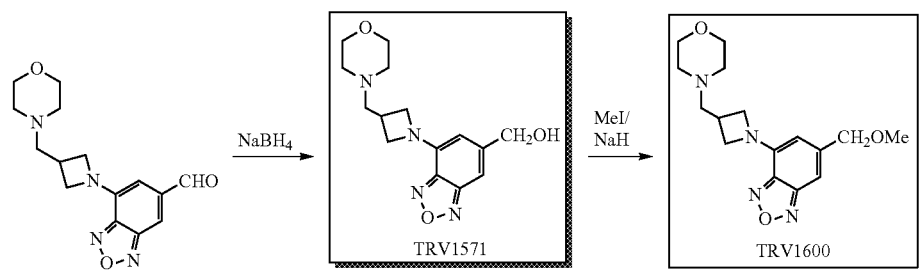
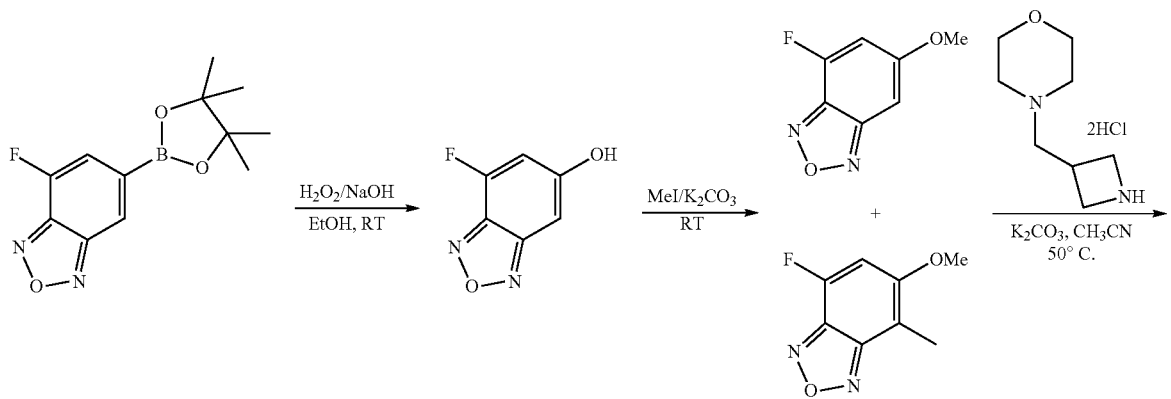

-continued
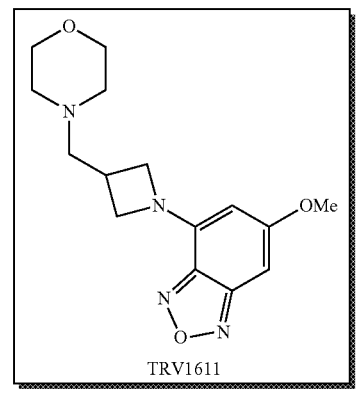
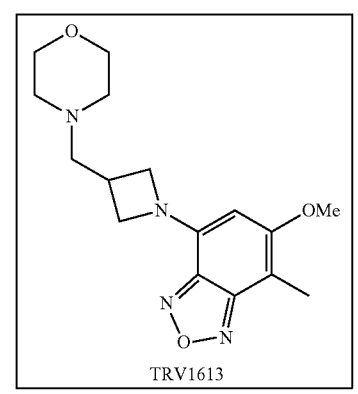
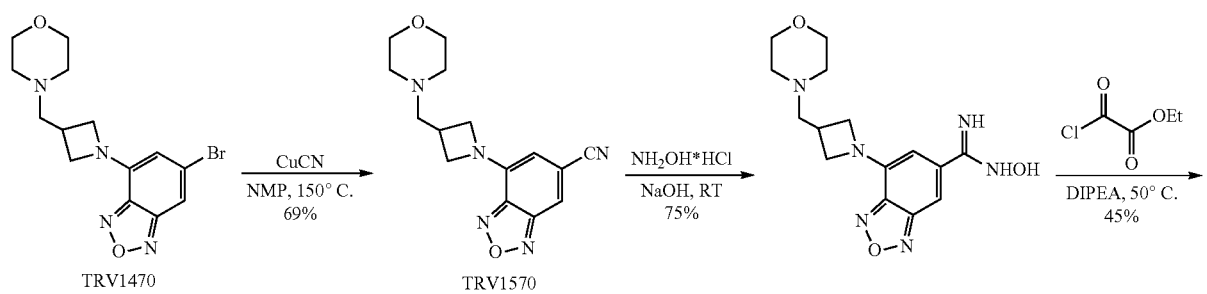
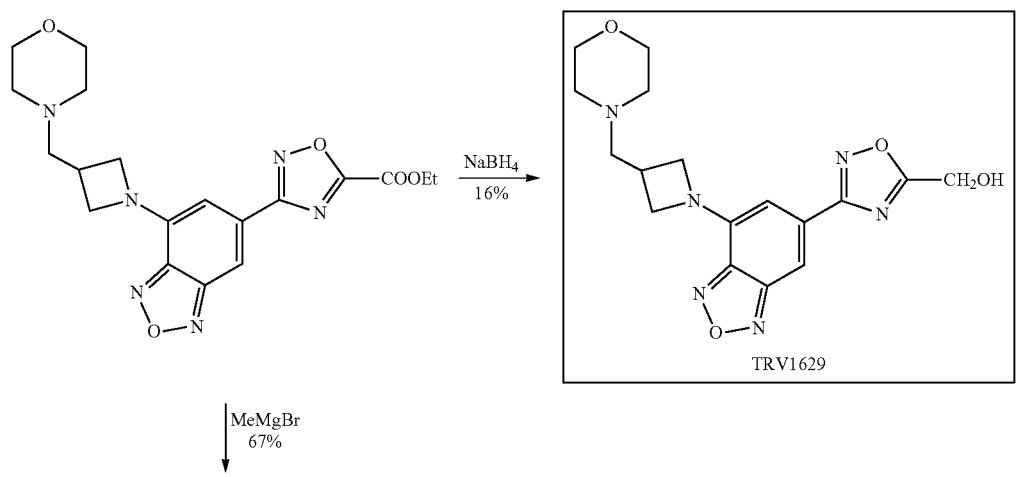

-continued
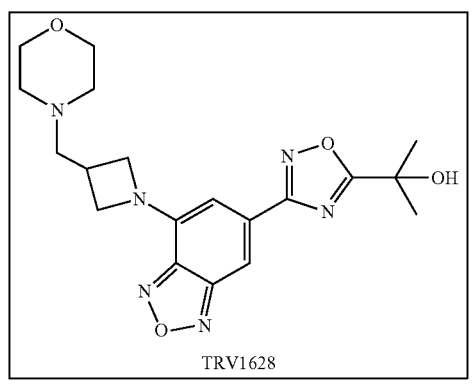
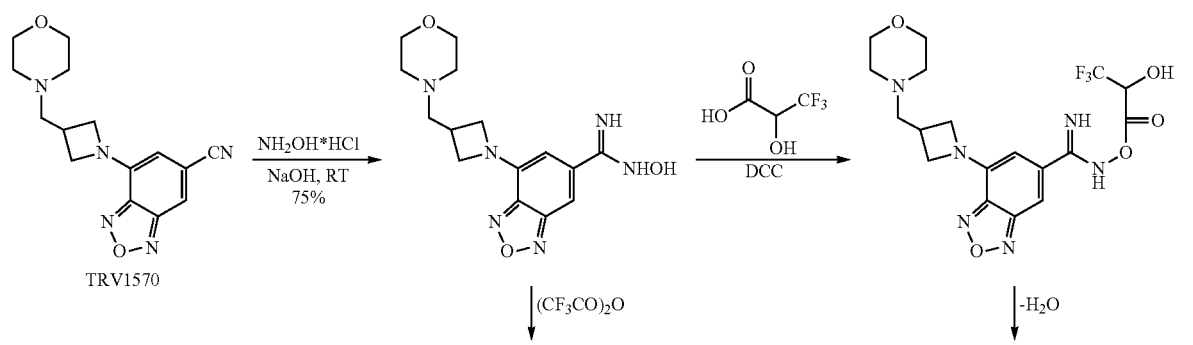
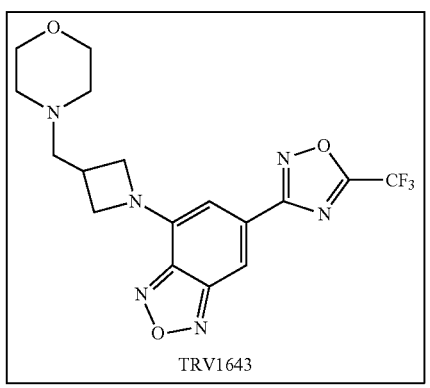
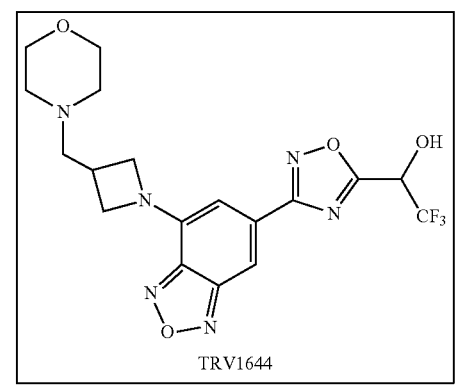
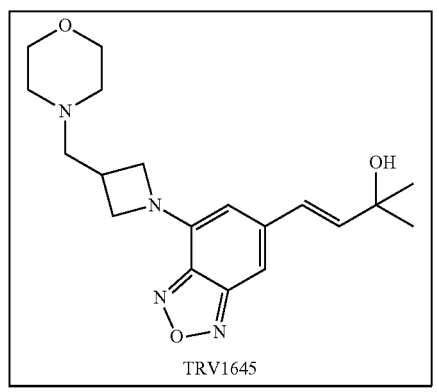
i. CH3MgBr
ii.
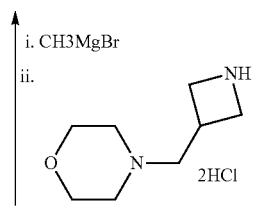

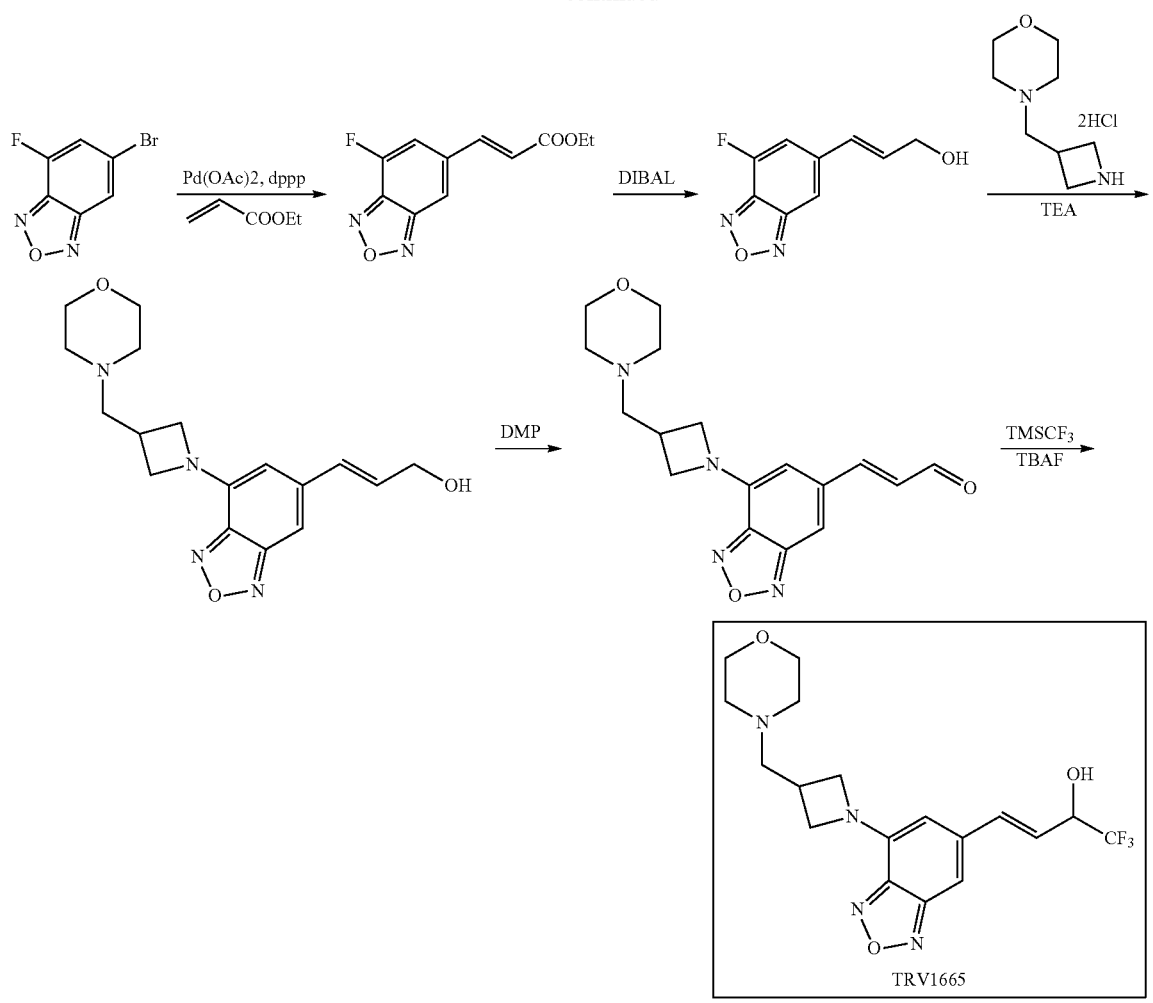
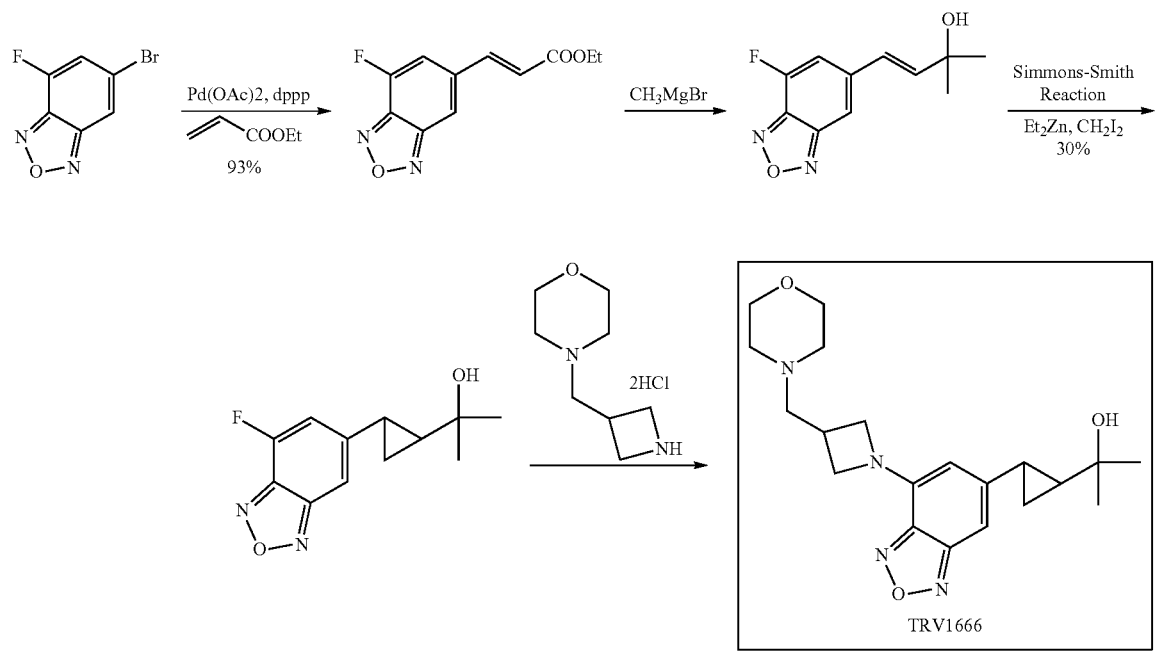

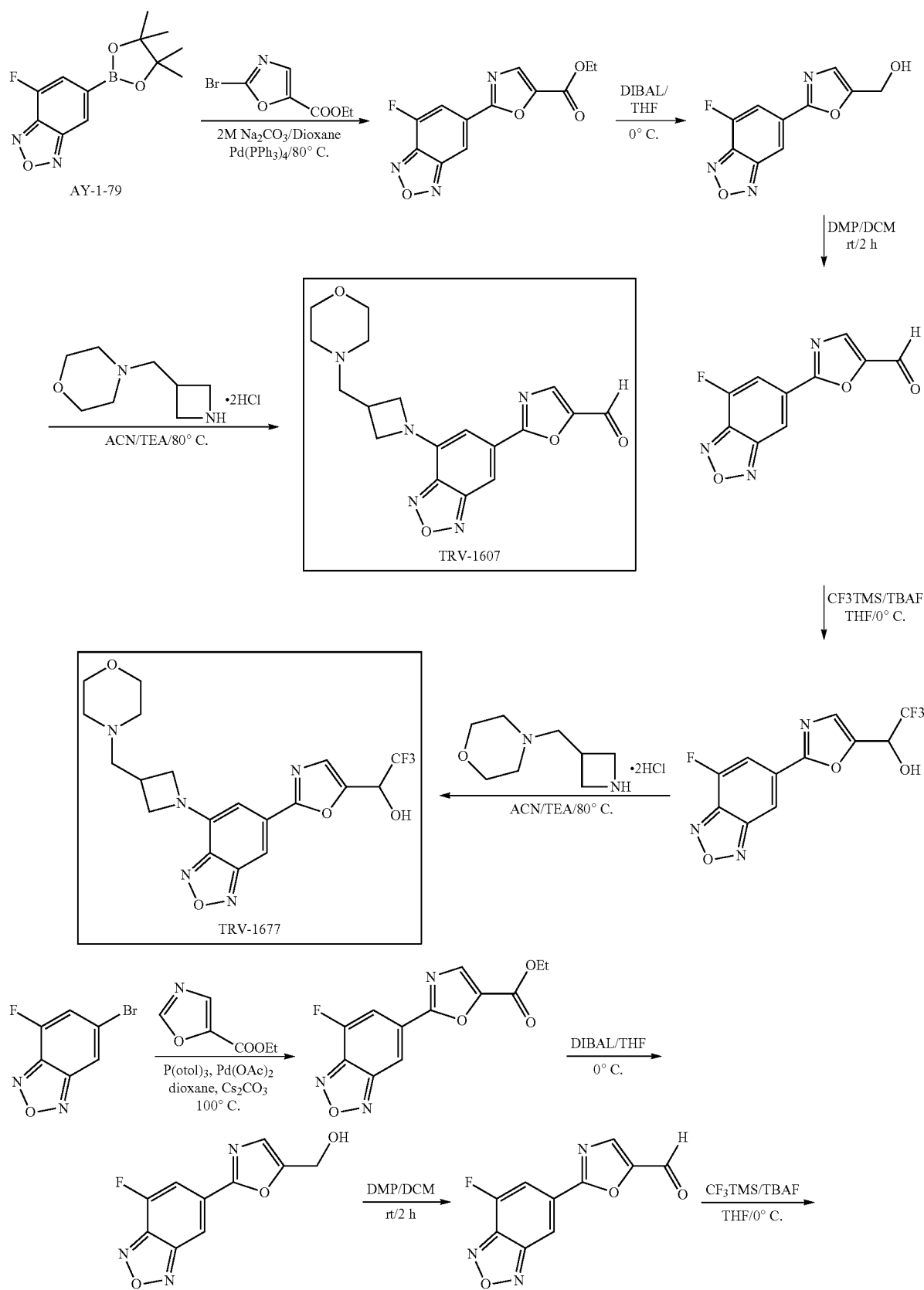

-continued
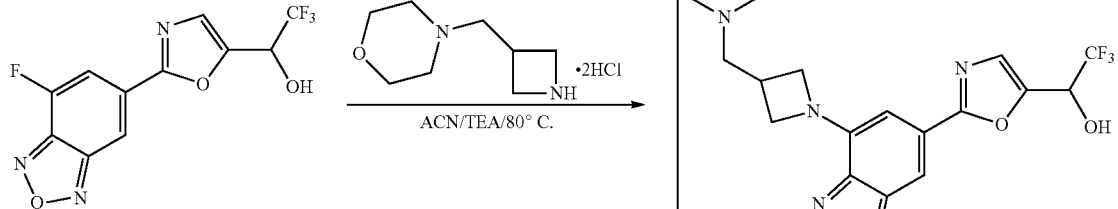
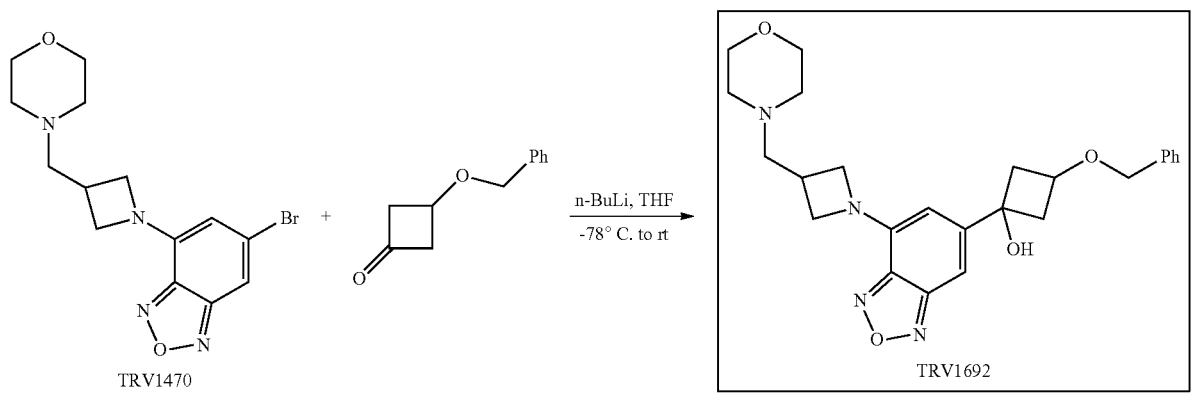
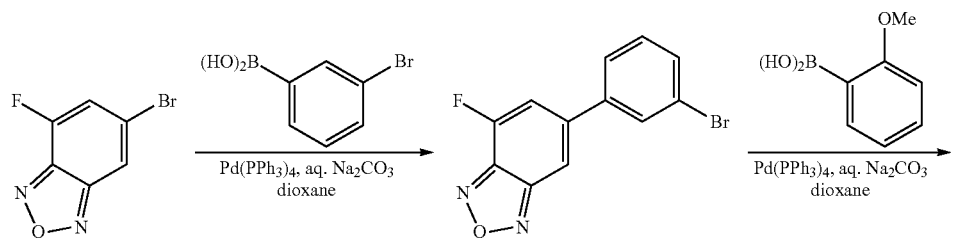
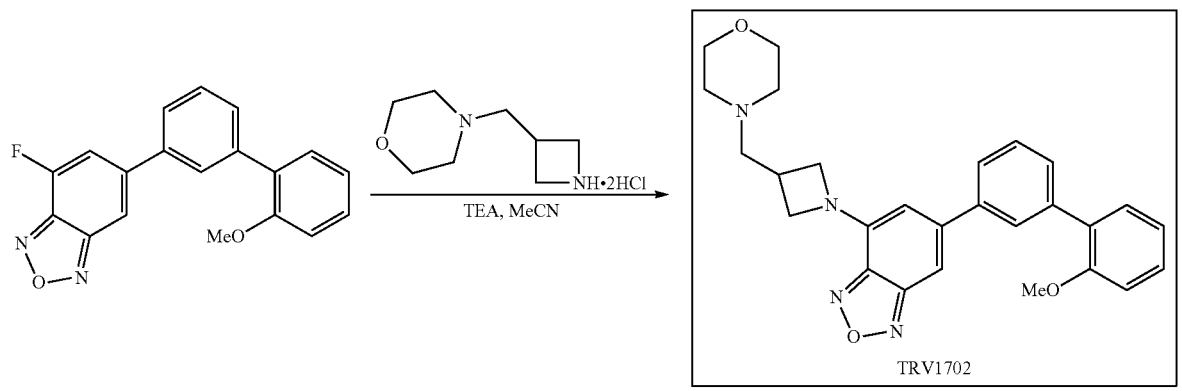

-continued
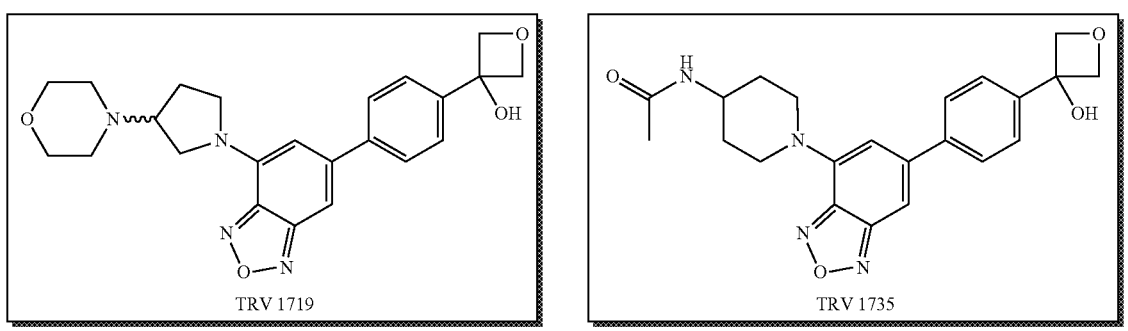
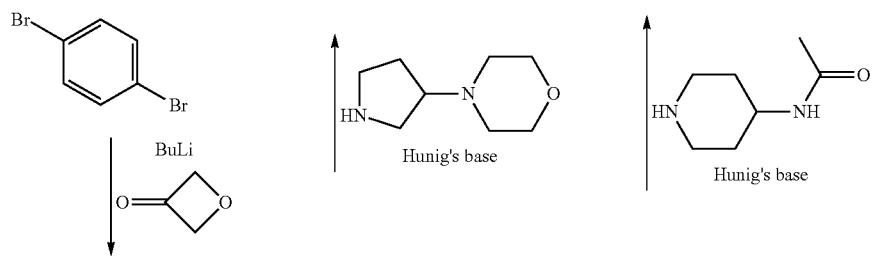
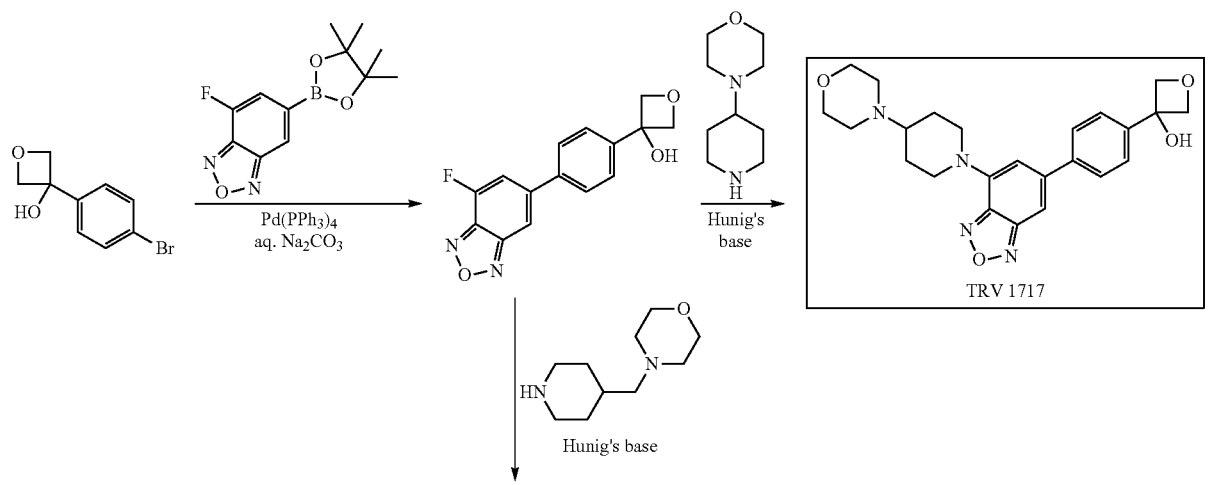
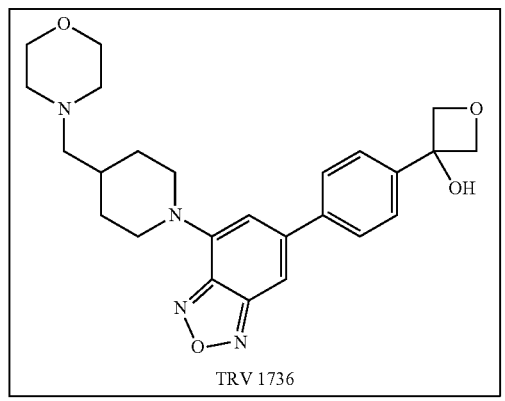

TRV1256

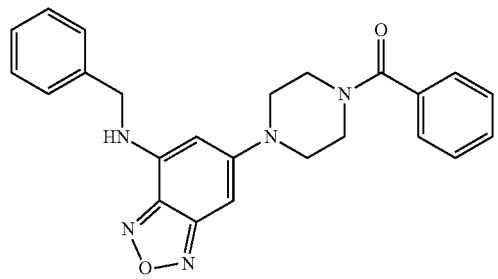

4,6-dibromobenzo[c][1,2,5]oxadiazole 4 (0.9678 g, 3.48 mmol) and benzylamine (1.9 mL, 17.4 mmol) were dissolved in DMSO (10.5 mL) under argon and stirred in a sealed tube for 3 days, after which time, the tube was heated to 60° C. for 12 hours. Upon cooling to room temperature, the reaction was diluted with water and extracted with EtOAc. The combined organic layers were washed with $H_2O$ (5x), 1 N HCl (aq), saturated $NaHCO_3$ (aq) and brine before drying with $Na_2SO_4$, filtering and concentrating. The dark solid was recrystallized from EtOH and the dark crystals were collected by filtration and dried to afford 0.4516 g (43% yield) of N-benzyl-6-bromobenzo[c][1,2,5]oxadiazol-4-amine. This material (0.1980 g, 0.651 mmol), benzoylpiperazine hydrochloride (0.1771 g, 0.781 mmol) and $Cs_2CO_3$ (0.6353 g, 1.95 mmol) were added to a tube. The tube was evacuated and purged with argon (3x). Toluene (2 mL) and NMP (1.2 mL) were then added to the tube and its contents were degassed for 15 minutes, at which point $Pd_2(dba)_3$ (0.0119 g, 0.0130 mmol) and BINAP (0.0162 g, 0.026 mmol) were quickly added, the tube was sealed and heated at 100° C. overnight. Upon cooling to room temperature, the reaction was diluted with water and extracted with EtOAc. The combined organic layers were washed with $H_2O$ (5x), 1 N HCl (aq), saturated $NaHCO_3$ (aq) and brine before drying with $Na_2SO_4$, filtering and concentrating. The crude material was purified via chromatography (40% EtOAc/Hexanes) to give 0.188 g (70% yield) of TRV-1256. $^1$H NMR (500 MHz, $CDCl_3$) δ=7.46-7.43 (m, 5H), 7.39-7.36 (m, 4H), 7.34-7.31 (m, 1H), 6.13 (d, J=1.0 Hz, 1H), 5.88 (s, 1H), 5.32 (t, J=5.5 Hz, 1H), 4.48 (d, J=5.5 Hz, 2H), 3.90 (br s, 2H), 3.58 (br s, 2H), 3.29 (br s, 2H), 3.15 (br s, 2H).

TRV-1259

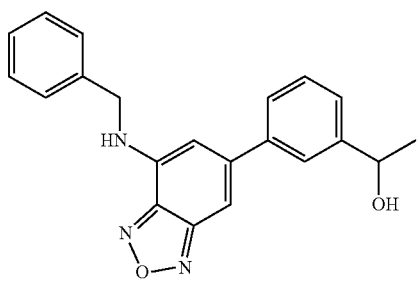

N-benzyl-6-bromobenzo[c][1,2,5]oxadiazol-4-amine (0.2235 g, 0.735 mmol) and 3-acetylbenzeneboronic acid (0.1566 g, 0.955 mmol) were added to a tube. The tube was evacuated and purged with argon (3x). 2 M $Na_2CO_3$ (1.1 mL, 2.21 mmol) and DME (1.6 mL) were added and the solution was degassed for 15 minutes. $Pd(PPh_3)_4$ (0.0425 g, 0.0368 mmol) was quickly added and the tube was heated at 100° C. overnight. Upon cooling to room temperature, the reaction was diluted with water and extracted with EtOAc. The combined organic layers were washed with $H_2O$ (5x), saturated $NaHCO_3$ (aq) and brine before drying with $Na_2SO_4$, filtering and concentrating. The crude material was dissolved in methanol (15 mL) and cooled to 0° C. $NaBH_4$ (0.0556 g, 1.47 mmol) was added and the mixture was stirred at 0° C. for 3 hours. The reaction mixture was quenched with saturated $NaHCO_3$. This thick mixture was diluted with water and extracted with DCM (5x). The extracts were then dried ($Na_2SO_4$), filtered and concentrated. The crude material was purified via chromatography (30% EtOAc/Hexane) to afford 0.1412 g (56% yield) of TRV-1259. $^1$H NMR (500 MHz, $CDCl_3$) δ=7.47 (s, 1H), 7.46-7.38 (m, 7H), 7.36-7.33 (m, 1H), 7.18 (s, 1H), 6.36 (s, 1H), 5.44 (t, J=5.5 Hz, 1H), 4.99-4.95 (m, 1H), 4.57 (d, J=5.5 Hz, 2H), 1.88 (d, J=3.5 Hz, 1H), 1.54 (d, J=7.0 Hz, 3H)

TRV-1310

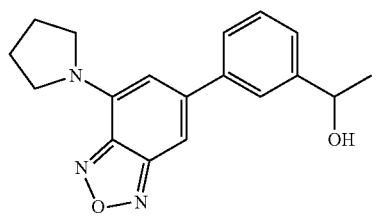

4,6-dibromobenzo[c][1,2,5]oxadiazole (0.3122 g, 1.12 mmol), pyrrolidine (0.10 mL, 1.12 mmol) and DIPEA (0.20 mL, 1.12 mmol) were dissolved in NMP (2 mL) under argon and stirred in a sealed tube at 100° C. overnight. Upon cooling to room temperature, the reaction was diluted with water and extracted with EtOAc. The combined organic layers were washed with $H_2O$ (5x), 1 N HCl(aq), saturated $NaHCO_3$ (aq) and brine before drying with $Na_2SO_4$, filtering and concentrating to give the crude 6-bromo-4-(pyrrolidin-1-yl)benzo[c][1,2,5]oxadiazole (0.2247 g, 75% yield). The crude material (0.1964 g, 0.73 mmol) and 3-acetylbenzeneboronic acid (0.1558 g, 0.95 mmol) were added to a tube. The tube was evacuated and purged with argon (3x). 2 M $Na_2CO_3$ (1.1 mL, 2.21 mmol) and DME (1.6 mL) were added and the solution was degassed for 15 minutes. $Pd(PPh_3)_4$ (0.0422 g, 0.0365 mmol) was quickly added and the tube was heated at 100° C. overnight. Upon cooling to room temperature, the reaction was diluted with water and extracted with EtOAc. The combined organic layers were washed with $H_2O$ (5x), saturated $NaHCO_3$ (aq) and brine before drying with $Na_2SO_4$, filtering and concentrating. The crude material was dissolved in methanol (12 mL) and cooled to 0° C. NaBH₄ (0.0552 g, 1.46 mmol) was added and the mixture was stirred at 0° C. for 3 hours. The reaction mixture was quenched with saturated NaHCO₃. This thick mixture was diluted with water and extracted with DCM (5×). The extracts were then dried (Na₂SO₄), filtered and concentrated. The crude material was purified via chromatography (30% EtOAc/Hexane) to afford 0.2029 g (90% yield, over 2 steps) of TRV-1310. ¹H NMR (CDCl₃) δ=7.65 (s, 1H), 7.55 (d, J=7.0 Hz, 1H), 7.47-7.42 (m, 2H), 7.07 (s, 1H), 6.11 (s, 1H), 5.00-4.99 (m, 1H), 3.81 (s, 4H), 2.12-2.09 (m, 4H), 1.92 (d, J=3.0 Hz, 1H), 1.56 (d, J=6.5 Hz, 3H).

TRV-1358

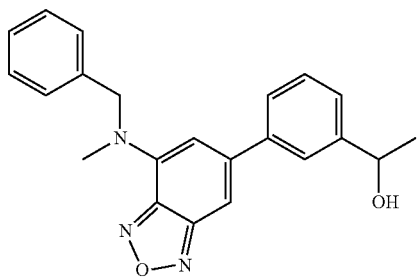

4,6-dibromobenzo[c][1,2,5]oxadiazole (0.5607 g, 2.0 mmol), N-methyl-1-phenylmethanamine (0.28 mL, 2.2 mmol) and DIPEA (0.52 mL, 3.0 mmol) were dissolved in NMP (3 mL) under argon and stirred in a sealed tube at 100° C. overnight. Upon cooling to room temperature, the reaction was diluted with water and extracted with EtOAc. The combined organic layers were washed with H₂O (5×), 1 N HCl (aq), saturated NaHCO₃ (aq) and brine before drying with Na₂SO₄, filtering and concentrating to give the crude material (N-benzyl-6-bromo-N-methylbenzo[c][1,2,5]oxadiazol-4-amine) as an oil. This crude material and 3-acetylbenzeneboronic acid (0.4263 g, 2.6 mmol) were added to a tube. The tube was evacuated and purged with argon (3×). 2 M Na₂CO₃ (3.0 mL, 6.0 mmol) and DME (4.5 mL) were added and the solution was degassed for 15 minutes. Pd(PPh₃)₄ (0.1156 g, 0.10 mmol) was quickly added and the tube was heated at 100° C. overnight. Upon cooling to room temperature, the reaction was diluted with water and extracted with EtOAc. The combined organic layers were washed with H₂O (5×), saturated NaHCO₃ (aq) and brine before drying with Na₂SO₄, filtering and concentrating. The crude material was dissolved in methanol (33 mL) and cooled to 0° C. NaBH₄ (0.1513 g, 4.0 mmol) was added and the mixture was stirred at 0° C. for 3 hours. The reaction mixture was quenched with saturated NaHCO₃. This thick mixture was diluted with water and extracted with DCM (5×). The extracts were then dried (Na₂SO₄), filtered and concentrated. The crude material was purified via chromatography (30% EtOAc/Hexane) to afford 0.4843 g (67% yield, over 3 steps) of TRV-1358 as yellow oil. ¹H NMR (CDCl₃, 500 MHz) δ=7.60 (s, 1H), 7.51 (dt, J=6.5, 2.0 Hz, 1H), 7.47-7.42 (m, 2H), 7.35-7.32 (m, 2H), 7.29-7.28 (m, 3H), 7.24 (s, 1H), 6.37 (s, 1H), 5.16 (s, 2H), 5.01-4.96 (m, 1H), 3.22 (s, 3H), 1.85 (d, J=3.5 Hz, 1H), 1.55 (d, J=6.5 Hz, 3H).

TRV-1359

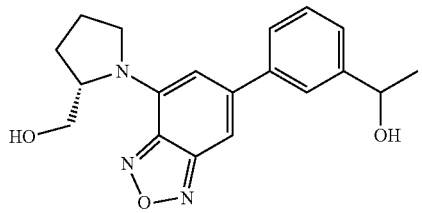

4,6-dibromobenzo[c][1,2,5]oxadiazole (0.3765 g, 1.35 mmol), ethyl pyrrolidine-2-carboxylate hydro chloride (0.2677 g, 1.49 mmol) and DIPEA (0.59 mL, 3.38 mmol) were dissolved in NMP (1.8 mL) under argon and stirred in a sealed tube at 100° C. overnight. Upon cooling to room temperature, the reaction was diluted with water and extracted with EtOAc. The combined organic layers were washed with H₂O (5×), 1 N HCl (aq), saturated NaHCO₃ (aq) and brine before drying with Na₂SO₄, filtering and concentrating to give 0.1756 g (38% yield) of crude material. This crude material and 3-acetylbenzeneboronic acid (0.1099 g, 0.67 mmol) were added to a tube. The tube was evacuated and purged with argon (3×). 2 M Na₂CO₃ (0.8 mL, 1.55 mmol) and DME (1.2 mL) were added and the solution was degassed for 15 minutes. Pd(PPh₃)₄ (0.0298 g, 0.0258 mmol) was quickly added and the tube was heated at 100° C. overnight. Upon cooling to room temperature, the reaction was diluted with water and extracted with EtOAc. The combined organic layers were washed with H₂O (5×), saturated NaHCO₃ (aq) and brine before drying with Na₂SO₄, filtering and concentrating. The crude material was then dissolved in DCM (0.3 mL) and toluene (1.6 mL) and this solution was cooled to 0° C. DIBAL (1.7 mL of a 1.0 M solution in hexane) was added dropwise and the reaction was allowed to stir overnight. Another 1.5 eq of DIBAL (0.8 mL) was added at 0° C. and the reaction was stirred for an additional 24 hours. The mixture was quenched with a saturated solution of sodium potassium tartrate and extracted with ethyl acetate. The combined extracts were washed with H₂O and brine, dried with Na₂SO₄, filtered and concentrated. The crude material was purified via 60% EtOAc/hexane column to afford 0.1224 (70% yield, 2 steps) of TRV-1359 as orange solid. ¹H NMR (CDCl₃, 500 MHz) δ=7.64 (s, 1H), 7.54 (dt, J=6.5, 2.0 Hz, 1H), 7.47-7.43 (m, 2H), 7.14 (s, 1H), 6.26 (s, 1H), 5.00-4.99 (br s, 1H), 4.74 (br s, 1H), 3.87-3.83 (m, 1H), 3.80-3.77 (m, 1H), 3.69-3.64 (m, 1H), 3.54-3.50 (m, 1H), 2.21-2.11 (m, 4H), 1.92-1.86 (m, 2H), 1.56 (d, J=6.5 Hz, 3H)

TRV-1360

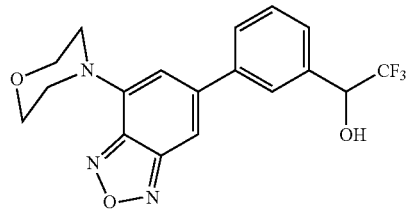

4,6-dibromobenzo[c][1,2,5]oxadiazole (0.5385 g, 1.94 mmol), morpholine (0.17 mL, 1.94 mmol) and DIPEA (0.34 mL, 1.94 mmol) were dissolved in NMP (2.5 mL) under argon and stirred in a sealed tube at 100° C. overnight. Upon cooling to room temperature, the reaction was diluted with water and extracted with EtOAc. The combined organic layers were washed with H₂O (5×), 1 N HCl (aq), saturated NaHCO₃ (aq) and brine before drying with Na₂SO₄, filtering and concentrating to give 0.5360 g (97% yield) of brown solid. This crude material (0.5002 g, 1.76 mmol) and 3-formylphenylboronic acid (0.3434 g, 2.29 mmol) were added to a tube. The tube was evacuated and purged with argon (3×). 2 M Na₂CO₃ (2.6 mL, 5.3 mmol) and DME (3.9 mL) were added and the solution was degassed for 15 minutes. Pd(PPh₃)₄ (0.1040 g, 0.09 mmol) was quickly added and the tube was heated at 100° C. overnight. Upon cooling to room temperature, the reaction was diluted with water and extracted with DCM. The combined organic layers were washed with H₂O (5×), saturated NaHCO₃ (aq) and brine before drying with Na₂SO₄, filtering and concentrating. This crude material was then dissolved in THF (1.8 mL) and cooled to 0° C. CF₃TMS (0.3003 g, 2.11 mmol) was added followed by TBAF (0.18 mL, 0.18 mmol) at 0° C. After the addition was complete, the ice bath was removed and the reaction was stirred at room temperature for several hours, at which point, an additional 2 eq of CF₃TMS (0.52 mL) was added along with 0.1 eq of TBAF (0.18 mL) at 0° C. Once again warmed to room temperature and stirred for 2 hours. To this mixture was then added TBAF (7.6 mL, 7.6 mmol) at 0° C. and the reaction was stirred overnight. The reaction was quenched with brine and extracted with EtOAc. The combined extracts were washed with H₂O (4×), brine, dried (Na₂SO₄), filtered and concentrated. Purification via flash chromatography (30% EtOAc/hexane) afford 0.2303 g (34% yield, over 3 steps) of TRV-1360 as yellow solid. ¹H NMR (CDCl₃, 500 MHz) δ=7.74 (s, 1H), 7.67-7.65 (m, 1H), 7.57-7.52 (m, 2H), 7.40 (s, 1H), 6.58 (s, 1H), 5.17-5.12 (m, 1H), 3.97 (t, J=5.0 Hz, 4H), 3.65 (t, J=5.0 Hz, 4H), 2.75 (d, J=4.5 Hz, 1H).

TRV-1361

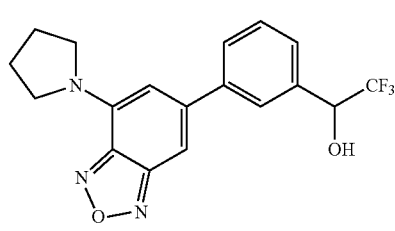

6-bromo-4-(pyrrolidin-1-yl)benzo[c][1,2,5]oxadiazole (0.4244 g, 1.58 mmol) and 3-formylphenylboronic acid (0.3149 g, 2.1 mmol) were added to a tube. The tube was evacuated and purged with argon (3×). 2 M Na₂CO₃ (2.4 mL, 4.7 mmol) and DME (3.6 mL) were added and the solution was degassed for 15 minutes. Pd(PPh₃)₄ (0.0924 g, 0.08 mmol) was quickly added and the tube was heated at 100° C. overnight. Upon cooling to room temperature, the reaction was diluted with water and extracted with ethyl acetate. The combined organic layers were washed with H₂O (5×), saturated NaHCO₃ (aq) and brine before drying with Na₂SO₄, filtering and concentrating. This crude material was then dissolved in THF (1.6 mL) and cooled to 0° C. CF₃TMS (0.2702 g, 1.9 mmol) was added followed by TBAF (0.16 mL, 0.16 mmol) at 0° C. After the addition was complete, the ice bath was removed and the reaction was stirred at room temperature for several hours, at which point, an additional 2 eq of CF₃TMS (0.47 mL) was added along with 0.1 eq of TBAF (0.16 mL) at 0° C. Once again warmed to room temperature and stirred for 2 hours. To this mixture was then added TBAF (7.0 mL, 7.0 mmol) at 0° C. and the reaction was stirred overnight. The reaction was quenched with brine and extracted with EtOAc. The combined extracts were washed with H₂O (4×), brine, dried (Na₂SO₄), filtered and concentrated. Purification via flash chromatography (20% EtOAc/hexane) afford 0.2749 g (48% yield, over 3 steps) of TRV-1361 as orange solid. ¹H NMR (CDCl₃, 500 MHz) δ=7.74 (s, 1H), 7.68 (dt, J=7.0, 1.5 Hz, 1H), 7.55-7.50 (m, 2H), 7.07 (s, 1H), 6.09 (s, 1H), 5.13 (q, J=6.5 Hz, 1H), 3.83-3.80 (m, 4H), 2.67 (brs, 1H), 2.14-2.09 (m, 4H).

TRV-1362

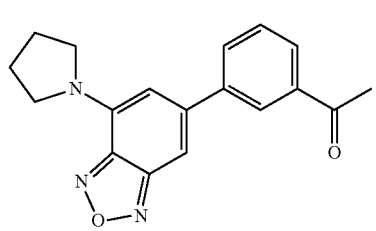

6-bromo-4-(pyrrolidin-1-yl)benzo[c][1,2,5]oxadiazole (0.1239 g, 0.46 mmol) and 3-acetylbenzeneboronic acid (0.0984 g, 0.60 mmol) were added to a tube. The tube was evacuated and purged with argon (3×). 2 M Na₂CO₃ (0.70 mL, 1.38 mmol) and DME (1.0 mL) were added and the solution was degassed for 15 minutes. Pd(PPh₃)₄ (0.0266 g, 0.023 mmol) was quickly added and the tube was heated at 100° C. overnight. Upon cooling to room temperature, the reaction was diluted with water and extracted with EtOAc. The combined organic layers were washed with H₂O (5×), saturated NaHCO₃ (aq) and brine before drying with Na₂SO₄, filtering and concentrating. The crude material was purified via flash chromatography (25% EtOAc/hexane) to afford 0.0391 g (28% yield) of TRV-1362 as orange solid. ¹H NMR (CDCl₃, 500 MHz) δ=8.22 (d, J=1.5 Hz, 1H), 8.00 (d, J=8.0 Hz, 1H), 7.84 (d, J=8.0 Hz, 1H), 7.57 (t, J=8.0 Hz, 1H), 7.09 (s, 1H), 6.10 (s, 1H), 3.82 (s, 4H), 2.68 (s, 3H), 2.13-2.11 (m, 4H).

TRV-1363

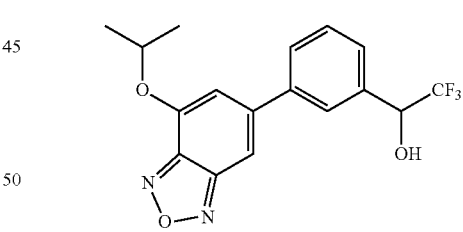

4,6-dibromobenzo[c][1,2,5]oxadiazole (1.00 g, 3.6 mmol) and isopropanol (0.31 mL, 4.0 mmol) were dissolved in THF (20 mL) under argon and cooled to −78° C. NaHMDS (4.0 mL of a 1.0 M solution in THF) was added dropwise and the reaction was stirred for 30 minutes at −78° C. The cooling bath was then removed and the reaction was stirred at room temperature for a few hours. The reaction was then cooled to 0° C. and quenched with saturated NH₄Cl (aq) solution. This suspension was extracted with DCM (3×). The combined extracts were washed with H₂O, brine, dried (Na₂SO₄), filtered and concentrated to afford 0.9407 g of crude black oil. This crude material (0.6702 g, 2.6 mmol) and 3-formylphenylboronic acid (0.5098 g, 3.4 mmol) were added to a tube. The tube was evacuated and purged with argon (3×). 2 M Na₂CO₃ (3.9 mL, 7.8 mmol) and DME (5.8 mL) were added and the solution was degassed for 15 minutes. Pd(PPh₃)₄ (0.1502 g, 0.13 mmol) was quickly added and the tube was heated at 100° C. overnight. Upon cooling to room temperature, the reaction was diluted with water and extracted with ethyl acetate. The combined organic layers were washed with H₂O (5×), saturated NaHCO₃ (aq) and brine before drying with Na₂SO₄, filtering and concentrating. This crude material was purified via flash chromatography (20% EtOAc/hexane) to afford 0.4836 g (66% yield) of the aldehyde. This aldehyde (0.6702 g, 2.6 mmol) was dissolved in THF (2.0 mL) and cooled to 0° C. CF₃TMS (0.23 mL, 1.56 mmol) was added followed by TBAF (0.1 mL, 0.1 mmol) at 0° C. After the addition was complete, the ice bath was removed and the reaction was stirred at room temperature for several hours. The mixture was then re-cooled to 0° C. and TBAF (2.8 mL, 2.8 mmol) was added to the reaction, which was stirred overnight. The reaction was quenched with brine and extracted with EtOAc. The combined extracts were washed with H₂O (4×), brine, dried (Na₂SO₄), filtered and concentrated. Purification via flash chromatography (25% EtOAc/hexane) afford 0.1468 g (53% yield, over 2 steps) of TRV-1363 as yellow oil. ¹H NMR (CDCl₃, 500 MHz) δ=7.74 (s, 1H), 7.66 (dt, J=7.0, 2.0 Hz, 1H), 7.58-7.54 (m, 2H), 7.48 (s, 1H), 6.78 (s, 1H), 5.17-5.13 (m, 1H), 4.99 (sept, J=6.0 Hz, 1H), 2.76 (d, J=4.5 Hz, 1H), 1.52 (d, J=6.0 Hz, 6H).

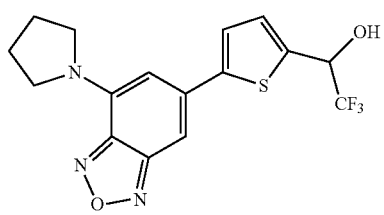

TRV-1364

6-bromo-4-(pyrrolidin-1-yl)benzo[c][1,2,5]oxadiazole (0.3898 g, 1.45 mmol) and 5-formyl-2-thienylboronic acid (0.2948 g, 1.89 mmol) were added to a tube. The tube was evacuated and purged with argon 3 times. Then 2M Na₂CO₃ (aq) (2.2 mL) and DME (3.3 mL) were added and the solution was degassed for 15 minutes. Pd(PPh₃)₄ (0.0844 g, 0.073 mmol) was added quickly, the tube was sealed and heated to 100° C. overnight. Upon cooling to room temperature, it was determined that the reaction was not complete. Another equivalent of 5-formyl-2-thienylboronic acid was added along with an additional 5 mol % of Pd(PPh₃)₄ and the mixture was heated overnight again. It was necessary to added more boronic acid and catalyst once again, and heated for an additional 24 hours. Upon cooling to room temperature, the mixture was diluted with water and EtOAc. The layers were separated and then the aqueous layer was back-extracted with EtOAc. The combined organic extracts were washed with water (3×), brine, dried (Na₂SO₄), filtered and concentrated. The crude material was taken up in THF (3 mL) and CF₃TMS (0.43 mL, 2.9 mmol) was added. This solution was cooled to 0° C. before adding TBAF (0.15 mL, 0.145 mmol). The mixture was stirred overnight and then an additional 2 eq of CF₃TMS and 0.1 eq of TBAF were added. After stirring for an additional 2 hours, the reaction was cooled to 0° C. and TBAF (8 mL, 8 mmol) was added. The mixture was stirred overnight before diluting with water. The aqueous layer was extracted with EtOAc (3×). The combined extracts were washed with brine, dried (Na₂SO₄), filtered and concentrated. The crude material was purified via column (15-20% EtOAc/hexane) to give 0.1043 g (19% yield, 3 steps) of TRV-1364 as orange solid. ¹H NMR (CDCl₃, 700 MHz) δ=7.35 (d, J=3.2 Hz, 1H), 7.19 (d, J=3.2 Hz, 1H), 7.13 (s, 1H), 6.10 (s, 1H), 5.31 (q, J=3.2 Hz, 1H), 3.80 (br s, 4H), 2.90 (br s, 1H), 2.11 (s, 4H).

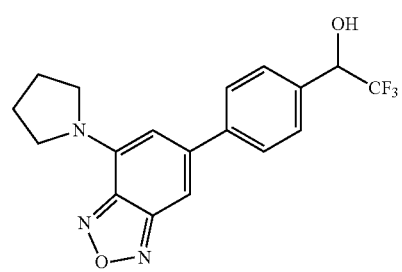

TRV-1365

6-bromo-4-(pyrrolidin-1-yl)benzo[c][1,2,5]oxadiazole (0.3948 g, 1.47 mmol) and 4-formylbenzeneboronic acid (0.2864 g, 1.91 mmol) were added to a tube. The tube was evacuated and purged with argon 3 times. Then 2M Na₂CO₃ (aq) (2.2 mL) and DME (3.3 mL) were added and the solution was degassed for 15 minutes. Pd(PPh₃)₄ (0.0855 g, 0.074 mmol) was added quickly, the tube was sealed and heated to 100° C. overnight. Upon cooling to room temperature, the mixture was diluted with water and EtOAc. The layers were separated and then the aqueous layer was back-extracted with EtOAc. The combined organic extracts were washed with water (3×), brine, dried (Na₂SO₄), filtered and concentrated. The crude material was taken up in THF (3 mL) and CF₃TMS (0.43 mL, 2.94 mmol) was added. This solution was cooled to 0° C. before adding TBAF (0.15 mL, 0.147 mmol). After stirring for 2 hours, the reaction was cooled to 0° C. and TBAF (5.1 mL, 5.1 mmol) was added. The mixture was stirred overnight before diluting with water. The aqueous layer was extracted with EtOAc (3×). The combined extracts were washed with brine, dried (Na₂SO₄), filtered and concentrated. The crude material was purified via column (15% EtOAc/hexane) to give 0.3795 g (71% yield, 3 steps) of TRV-1365 as orange solid. ¹H NMR (CDCl₃, 700 MHz) δ=7.68 (d, J=8.0 Hz, 2H), 7.58 (d, J=8.0 Hz, 2H), 7.07 (s, 1H), 6.10 (s, 1H), 5.11 (q, J=6.3 Hz, 1H), 3.81 (br s, 4H), 2.72 (br s, 1H), 2.13-2.09 (m, 4H).

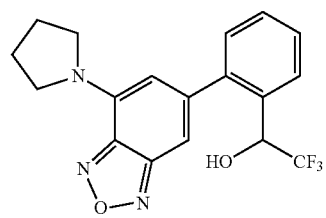

TRV-1366

6-bromo-4-(pyrrolidin-1-yl)benzo[c][1,2,5]oxadiazole (0.3856 g, 1.44 mmol) and 2-formylbenzeneboronic acid (0.2804 g, 1.87 mmol) were added to a tube. The tube was evacuated and purged with argon 3 times. Then 2M Na₂CO₃ (aq) (2.2 mL) and DME (3.3 mL) were added and the solution was degassed for 15 minutes. Pd(PPh₃)₄ (0.0832 g, 0.072 mmol) was added quickly, the tube was sealed and heated to 100° C. overnight. Upon cooling to room temperature, the mixture was diluted with water and EtOAc. The layers were separated and then the aqueous layer was back-extracted with EtOAc. The combined organic extracts were washed with water (3×), brine, dried (Na₂SO₄), filtered and concentrated. The crude material was taken up in THF (3 mL) and CF₃TMS (0.43 mL, 2.94 mmol) was added. This solution was cooled to 0° C. before adding TBAF (0.14 mL, 0.144 mmol). After stirring for 2 hours, the reaction was cooled to 0° C. and TBAF (5.0 mL, 5.0 mmol) was added. The mixture was stirred overnight before diluting with water. The aqueous layer was extracted with EtOAc (3×). The combined extracts were washed with brine, dried (Na₂SO₄), filtered and concentrated. The crude material was purified via column (10% EtOAc/hexane) to give 0.179 g (34% yield, 3 steps) of TRV-1366 as orange solid. ¹H NMR (CDCl₃, 500 MHz) δ=7.78 (d, J=8.0 Hz, 1H), 7.52-7.45 (m, 2H), 7.34 (d, J=7.5 Hz, 1H), 6.85 (s, 1H), 5.79 (s, 1H), 5.26 (q, J=6.5 Hz, 1H), 3.76 (br s, 4H), 2.55 (br s, 1H), 2.11-2.08 (m, 4H).

TRV-1368

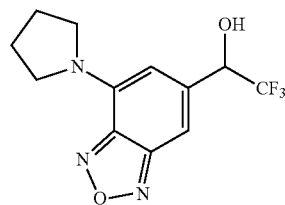

6-bromo-4-(pyrrolidin-1-yl)benzo[c][1,2,5]oxadiazole (0.7754 g, 2.89 mmol) was dissolved in THF and cooled to −78° C. nBuLi (1.6 mL of a 2.0 M solution in cyclohexane) was added dropwise and the mixture was allowed to stir for 30 minutes. At this point, to the solution which was stirring at −78° C. was added DMF (0.25 mL, 3.18 mmol) all at once at −78° C. The reaction was stirred for 30 minutes and then allowed to warm to room temperature. The reaction was then quenched with saturated NH₄Cl(aq), extracted with EtOAc. The combined organic layers were washed with water, brine, dried (Na₂SO₄), filtered and concentrated to afford 0.4779 g of crude aldehyde. This aldehyde (0.1352 g, 0.622 mmol) was dissolved in THF (2 mL) and treated with CF₃TMS (0.18 mL, 1.24 mmol). The solution was cooled to 0° C. and then TBAF (0.1 mL, 0.1 mmol) was added. After stirring for 2 hours, the mixture was re-cooled to 0° C. and TBAF (2.2 mL, 2.2 mmol) was added, the reaction was allowed to stir overnight. The mixture was then quenched with water and extracted with EtOAc. The combined extracts were washed with water, brine, dried (Na₂SO₄), filtered and concentrated. The crude material was purified via column (25% EtOAc/hexane) to afford 0.0201 g (11% yield) of TRV-1368 as red oil. ¹H NMR (CDCl₃, 700 MHz) δ=7.06 (s, 1H), 5.97 (s, 1H), 5.01 (q, J=6.3 Hz, 1H), 3.78 (br s, 4H), 2.74 (br s, 1H), 2.12-2.08 (m, 4H).

TRV-1369

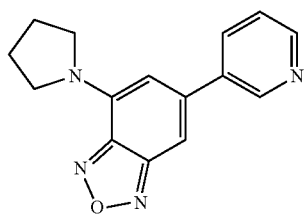

6-bromo-4-(pyrrolidin-1-yl)benzo[c][1,2,5]oxadiazole (0.5785 g, 2.16 mmol) and pyridine-3-boronic acid (0.3442 g, 2.8 mmol) were added to a tube. The tube was evacuated and purged with argon 3 times. Then 2M Na₂CO₃ (aq) (3.2 mL) and DME (4.8 mL) were added and the solution was degassed for 15 minutes. Pd(PPh₃)₄ (0.1248 g, 0.108 mmol) was added quickly, the tube was sealed and heated to 100° C. overnight. Upon cooling to room temperature, the mixture was diluted with water and EtOAc. The layers were separated and then the aqueous layer was back-extracted with EtOAc. The combined organic extracts were washed with water (3×), brine, dried (Na₂SO₄), filtered and concentrated. This crude material was purified via column (50% EtOAc/hexane) to afford 0.1902 g of contaminated material and 0.2624 g of pure material for a combined yield of 79% yield of TRV-1369 as orange solid. ¹H NMR (CDCl₃, 700 MHz) δ=8.90 (d, J=1.4 Hz, 1H), 8.65 (d, J=4.6 Hz, 1H), 7.93 (d, J=7.7 Hz, 1H), 7.39 (dd, J=7.7, 4.6 Hz, 1H), 7.07 (s, 1H), 6.05 (s, 1H), 3.82 (br s, 4H), 2.14-2.10 (m, 4H).

TRV-1370

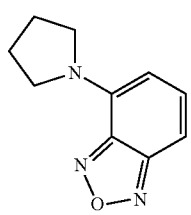

6-bromo-4-(pyrrolidin-1-yl)benzo[c][1,2,5]oxadiazole 1 (0.7754 g, 2.89 mmol) was dissolved in THF and cooled to −78° C. nBuLi (1.6 mL of a 2.0 M solution in cyclohexane) was added dropwise and the mixture was allowed to stir for 30 minutes. At this point, a 2.9 mL aliquot was taken and added dropwise to an ice-cold solution of saturated NH₄Cl (aq). After warming to room temperature, the mixture was extracted with EtOAc. The combined extracts were washed with water, brine, dried (Na₂SO₄), filtered and concentrated. This crude material was purified via column (5% EtOAc/hexane) to afford 0.0654 g (46% yield) of TRV-1370 as orange solid. ¹H NMR (CDCl₃, 500 MHz) δ=7.22 (dd, J=8.5, 8.0 Hz, 1H), 6.91 (d, J=8.5 Hz, 1H), 5.87 (d, J=8.0 Hz, 1H), 3.76-3.73 (m, 4H), 2.10-2.05 (m, 4H).

TRV-1375

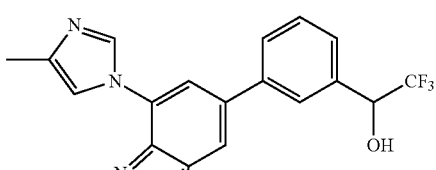

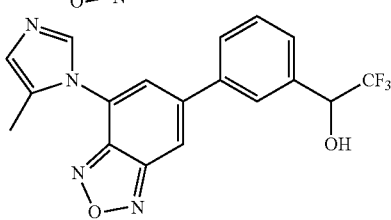

4,6-dibromobenzo[c][1,2,5]oxadiazole (1.0173 g, 3.66 mmol), 4-methylimidazole (0.3005 g, 3.66 mmol), NMP (5 mL) and DIPEA (0.64 mL, 3.66 mmol) was sealed in a tube and heated to 150° C. for 3 days. Upon cooling to room temperature, the mixture was diluted with water and EtOAc. The layers were separated and the aqueous layer was then back-extracted. The combined organic extracts were then washed with H$_2$O, 1 N HCl (aq), saturated NaHCO$_3$ (aq), H$_2$O (3×), brine and then dried (Na$_2$SO$_4$), filtered and concentrated. The crude material was purified via 35% EtOAc/Hexane column to afford 0.5295 g (52% yield) of the aniline. The aniline (0.2988 g, 1.07 mmol) and 3-formylbenzeneboronic acid (0.2084 g, 1.39 mmol) were sealed in a tube. The tube was evacuated and purged with argon (3 cycles). 2M Na$_2$CO$_3$ (1.6 mL, aq solution) was added along with DME (2.4 mL). The solution was degassed for 10 minutes and then Pd(PPh$_3$)$_4$ (0.0618 g, 0.0535 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. This crude material was then dissolved in THF (2 mL) and cooled in an ice bath. To this solution was added CF$_3$TMS (0.24 mL, 1.61 mmol) and then TBAF (0.1 mL, 1.0 M solution in THF). After 5 minutes, the ice bath was removed and the mixture was stirred for an additional 2 hours. The solution was then re-cooled to 0° C. and TBAF (3.2 mL, 3.2 mmol) was added, the mixture was allowed to warm to room temperature overnight. The mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. The crude material was purified via chromatography (5% MeOH/DCM) to afford 0.0616 g (15% yield, 3 steps) of TRV-1375 as a 1:1 mixture of regioisomers. $^1$H NMR (500 MHz, CDCl3) δ=8.353 (s, 1H), 8.350 (s, 1H), 7.89 (s, 1H), 7.88 (s, 1H), 7.85 (s, 2H), 7.71-7.69 (m, 2H), 7.65-7.63 (m, 2H), 7.61-7.56 (m, 4H), 7.48 (s, 2H), 5.20 (q, J=7.0 Hz, 2H), 5.07 (br s, 2H), 2.332 (s, 3H), 2.331 (s, 3H).

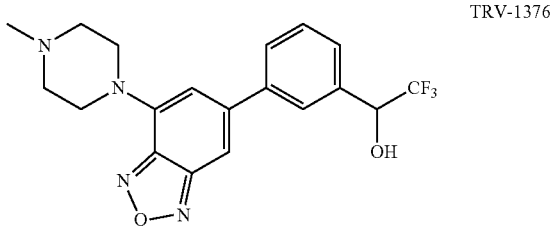 [SMILES: CN1CCN(c2cc(-c3cccc(C(O)C(F)(F)F)c3)cc3nonc23)CC1]

TRV-1376

4,6-dibromobenzo[c][1,2,5]oxadiazole (0.3327 g, 1.2 mmol), 1-methylpiperazine (0.13 mL, 1.2 mmol), NMP (2 mL) and DIPEA (0.21 mL, 1.2 mmol) was sealed in a tube and heated to 100° C. overnight. Upon cooling to room temperature, the mixture was diluted with water and EtOAc. The layers were separated and the aqueous layer was then back-extracted. The combined organic extracts were then washed with H$_2$O, 1 N HCl (aq), saturated NaHCO$_3$ (aq), H$_2$O (3×), brine and then dried (Na$_2$SO$_4$), filtered and concentrated. The crude aniline and 3-formylbenzeneboronic acid (0.2338 g, 1.56 mmol) were sealed in a tube. The tube was evacuated and purged with argon (3 cycles). 2M Na$_2$CO$_3$ (1.8 mL, aq solution) was added along with DME (2.7 mL). The solution was degassed for 10 minutes and then Pd(PPh$_3$)$_4$ (0.0693 g, 0.06 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. This crude material was then dissolved in THF (2.5 mL) and cooled in an ice bath. To this solution was added CF$_3$TMS (0.35 mL, 2.4 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.2 mL, 4.2 mmol) was added, the mixture was allowed to warm to room temperature overnight. The mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. The crude material was purified via chromatography (5% MeOH/DCM) to afford 0.1695 g (36% yield, 4 steps) of TRV-1376. $^1$H NMR (500 MHz, DMSO) δ=7.91 (s, 1H), 7.85-7.83 (m, 1H), 7.60-7.54 (m, 2H), 7.54 (s, 1H), 6.94 (d, J=6.0 Hz, 1H), 6.75 (s, 1H), 5.31-5.28 (m, 1H), 3.64 (t, J=5.0 Hz, 4H), 2.55 (t, J=5.0 Hz, 4H), 2.25 (s, 3H).

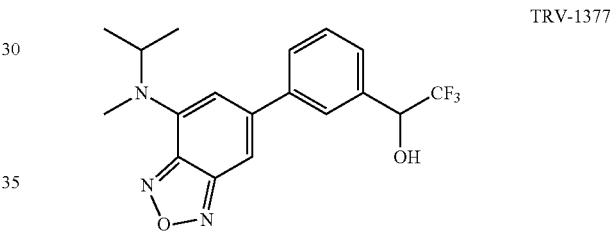

TRV-1377

4,6-dibromobenzo[c][1,2,5]oxadiazole (0.3113 g, 1.12 mmol), N-isopropylmethylamine (0.12 mL, 1.12 mmol), NMP (2 mL) and DIPEA (0.20 mL, 1.12 mmol) was sealed in a tube and heated to 100° C. overnight. Upon cooling to room temperature, the mixture was diluted with water and EtOAc. The layers were separated and the aqueous layer was then back-extracted. The combined organic extracts were then washed with H$_2$O, 1 N HCl (aq), saturated NaHCO$_3$ (aq), H$_2$O (3×), brine and then dried (Na$_2$SO$_4$), filtered and concentrated. The crude aniline and 3-formylbenzeneboronic acid (0.2189 g, 1.46 mmol) were sealed in a tube. The tube was evacuated and purged with argon (3 cycles). 2M Na$_2$CO$_3$ (1.7 mL, aq solution) was added along with DME (2.5 mL). The solution was degassed for 10 minutes and then Pd(PPh$_3$)$_4$ (0.0647 g, 0.056 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. This crude material was then dissolved in THF (2.5 mL) and cooled in an ice bath. To this solution was added CF$_3$TMS (0.33 mL, 2.24 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.0 mL, 4.0 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. The crude material was purified via chromatography (15% EtOAc/hexane) to afford 0.1283 g (31% yield, 4 steps) of TRV-1377. ¹H NMR (500 MHz, CDCl3) δ=7.74 (s, 1H), 7.68 (dt, J=5.0, 2.0 Hz, 1H), 7.55-7.51 (m, 2H), 7.18 (d, J=1.0 Hz, 1H), 6.30 (s, 1H), 5.24 (sept, J=6.5 Hz, 1H), 5.13 (q, J=6.5 Hz, 1H), 3.01 (s, 3H), 2.71 (br s, 1H), 1.30 (d, J=6.5 Hz, 6H).

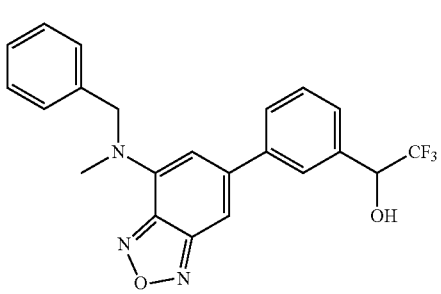

TRV-1378

N-benzyl-6-bromo-N-methylbenzo[c][1,2,5]oxadiazol-4-amine and 3-formylbenzeneboronic acid (0.2293 g, 1.53 mmol) were sealed in a tube. The tube was evacuated and purged with argon (3 cycles). 2M Na₂CO₃ (1.8 mL, aq solution) was added along with DME (2.6 mL). The solution was degassed for 10 minutes and then Pd(PPh₃)₄ (0.0682 g, 0.059 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H₂O (3×), brine and then dried (Na₂SO₄), filtered and concentrated. This crude material was then dissolved in THF (2.5 mL) and cooled in an ice bath. To this solution was added CF₃TMS (0.35 mL, 2.36 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.2 mL, 4.2 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. The crude material was purified via chromatography (15% EtOAc/hexane) to afford 0.2683 g (55% yield, 4 steps) of TRV-1378. ¹H NMR (500 MHz, CDCl3) δ=7.69 (s, 1H), 7.64 (dt, J=7.5, 1.5 Hz, 1H), 7.54-7.49 (m, 2H), 7.35-7.32 (m, 2H), 7.29-7.26 (m, 3H), 7.23 (d, J=1.0 Hz, 1H), 6.33 (s, 1H), 5.16 (s, 2H), 5.11 (q, J=6.5 Hz, 1H), 3.24 (s, 3H), 2.68 (s, 1H).

TRV-1379

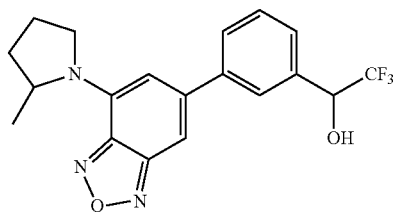

4,6-dibromobenzo[c][1,2,5]oxadiazole (0.3414 g, 1.23 mmol), 2-methylpyrrolidine (0.13 mL, 1.23 mmol), NMP (2 mL) and DIPEA (0.21 mL, 1.23 mmol) was sealed in a tube and heated to 100° C. overnight. Upon cooling to room temperature, the mixture was diluted with water and EtOAc. The layers were separated and the aqueous layer was then back-extracted. The combined organic extracts were then washed with H₂O, 1 N HCl (aq), saturated NaHCO₃ (aq), H₂O (3×), brine and then dried (Na₂SO₄), filtered and concentrated. The crude aniline and 3-formylbenzeneboronic acid (0.2398 g, 1.6 mmol) were sealed in a tube. The tube was evacuated and purged with argon (3 cycles). 2M Na₂CO₃ (1.9 mL, aq solution) was added along with DME (2.8 mL). The solution was degassed for 10 minutes and then Pd(PPh₃)₄ (0.0716 g, 0.062 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H₂O (3×), brine and then dried (Na₂SO₄), filtered and concentrated. This crude material was then dissolved in THF (2.5 mL) and cooled in an ice bath. To this solution was added CF₃TMS (0.36 mL, 2.46 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.3 mL, 4.3 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. The crude material was purified via chromatography (15% EtOAc/hexane) to afford 0.1319 g (28% yield, 4 steps) of TRV-1379, a 1:1:1:1 mixture of diastereomers due to the two chiral centers. ¹H NMR (500 MHz, CDCl3) δ=7.74 (s, 1H), 7.67 (dt, J=7.0, 2.0 Hz, 1H), 7.55-7.50 (m, 2H), 7.07 (s, 1H), 6.12 (s, 1H), 5.13 (q, J=6.5 Hz, 1H), 4.75-4.71 (m, 1H), 3.87-3.83 (m, 1H), 3.65-3.60 (m, 1H), 2.71 (br s, 1H), 2.24-2.08 (m, 3H), 1.85-1.81 (m, 1H), 1.29 (d, J=6.5 Hz, 3H).

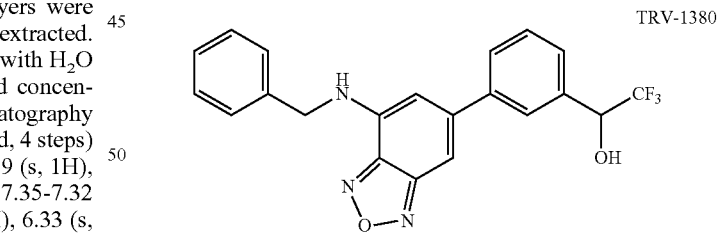

TRV-1380

N-benzyl-6-bromobenzo[c][1,2,5]oxadiazol-4-amine and 3-formylbenzeneboronic acid (0.2488 g, 1.66 mmol) were sealed in a tube. The tube was evacuated and purged with argon (3 cycles). 2M Na₂CO₃ (1.9 mL, aq solution) was added along with DME (2.9 mL). The solution was degassed for 10 minutes and then Pd(PPh₃)₄ (0.074 g, 0.064 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H₂O (3×), brine and then dried (Na₂SO₄), filtered and concentrated. This crude material was then dissolved in THF (3 mL) and cooled in an ice bath. To this solution was added CF₃TMS (0.28 mL, 1.92 mmol) and then TBAF (0.1 mL, 1.0 M solution in THF). After 5 minutes, the ice bath was removed and the mixture was stirred for an additional 2 hours. The solution was then re-cooled to 0° C. and TBAF (3.9 mL, 3.9 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. The crude material was purified via chromatography (15% EtOAc/hexane) to afford 0.0655 g (13% yield, 4 steps) of TRV-1380. ¹H NMR (500 MHz, CDCl3) δ=7.67 (s, 1H), 7.63 (dt, J=7.5, 1.5 Hz, 1H), 7.57-7.52 (m, 2H), 7.49-7.42 (m, 4H), 7.40-7.36 (m, 1H), 7.22 (d, J=1.0 Hz, 1H), 6.37 (s, 1H), 5.51 (t, J=5.0 Hz, 1H), 5.14 (q, J=6.5 Hz, 1H), 4.60 (d, J=5.0 Hz, 2H), 2.72 (br s, 1H).

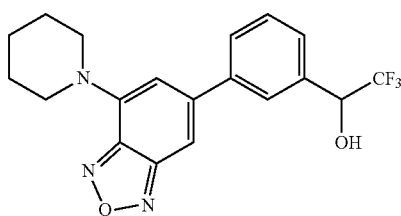

TRV-1381

4,6-dibromobenzo[c][1,2,5]oxadiazole (0.3095 g, 1.11 mmol), piperidine (0.11 mL, 1.11 mmol), NMP (2 mL) and DIPEA (0.19 mL, 1.11 mmol) were sealed in a tube and heated to 100° C. overnight. Upon cooling to room temperature, the mixture was diluted with water and EtOAc. The layers were separated and the aqueous layer was then back-extracted. The combined organic extracts were then washed with H₂O, 1 N HCl (aq), saturated NaHCO₃ (aq), H₂O (3×), brine and then dried (Na₂SO₄), filtered and concentrated. The crude aniline and 3-formylbenzeneboronic acid (0.2159 g, 1.44 mmol) were sealed in a tube. The tube was evacuated and purged with argon (3 cycles). 2M Na₂CO₃ (1.7 mL, aq solution) was added along with DME (2.5 mL). The solution was degassed for 10 minutes and then Pd(PPh₃)₄ (0.0647 g, 0.056 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H₂O (3×), brine and then dried (Na₂SO₄), filtered and concentrated. This crude material was then dissolved in THF (2.5 mL) and cooled in an ice bath. To this solution was added CF₃TMS (0.33 mL, 2.22 mmol) and then TBAF (0.1 mL, 1.0 M solution in THF). After 5 minutes, the ice bath was removed and the mixture was stirred for an additional 2 hours. The solution was then re-cooled to 0° C. and TBAF (3.9 mL, 3.9 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. The crude material was purified via chromatography (20% EtOAc/hexane) to afford 0.3097 g (74% yield, 4 steps) of TRV-1381. ¹H NMR (500 MHz, CDCl3) δ=7.73 (s, 1H), 7.67-7.66 (m, 1H), 7.57-7.51 (m, 2H), 7.30 (s, 1H), 6.53 (s, 1H), 5.14 (q, J=6.5 Hz, 1H), 3.65 (t, J=5.5 Hz, 4H), 2.70 (br s, 1H), 1.84-1.77 (m, 4H), 1.74-1.69 (m, 2H).

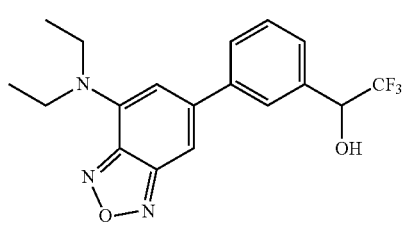

TRV-1382

4,6-dibromobenzo[c][1,2,5]oxadiazole (0.3340 g, 1.2 mmol), diethylamine (0.13 mL, 1.2 mmol), NMP (2 mL) and DIPEA (0.21 mL, 1.2 mmol) were sealed in a tube and heated to 100° C. overnight. Upon cooling to room temperature, the mixture was diluted with water and EtOAc. The layers were separated and the aqueous layer was then back-extracted. The combined organic extracts were then washed with H₂O, 1 N HCl (aq), saturated NaHCO₃ (aq), H₂O (3×), brine and then dried (Na₂SO₄), filtered and concentrated. The crude aniline and 3-formylbenzeneboronic acid (0.2338 g, 1.56 mmol) were sealed in a tube. The tube was evacuated and purged with argon (3 cycles). 2M Na₂CO₃ (1.8 mL, aq solution) was added along with DME (2.7 mL). The solution was degassed for 10 minutes and then Pd(PPh₃)₄ (0.0693 g, 0.06 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H₂O (3×), brine and then dried (Na₂SO₄), filtered and concentrated. This crude material was then dissolved in THF (2.5 mL) and cooled in an ice bath. To this solution was added CF₃TMS (0.35 mL, 2.4 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.2 mL, 4.2 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. The crude material was purified via chromatography (20% EtOAc/hexane) to afford 0.2184 g (50% yield, 4 steps) of TRV-1382. ¹H NMR (500 MHz, CDCl3) δ=7.73 (s, 1H), 7.65 (dt, J=7.0, 2.0 Hz, 1H), 7.55-7.51 (m, 2H), 7.11 (d, J=0.5 Hz, 1H), 6.25 (s, 1H), 5.13 (q, J=6.5 Hz, 1H), 3.81 (q, J=7.0 Hz, 4H), 2.76 (br s, 1H), 1.31 (t, J=7.0 Hz, 6H).

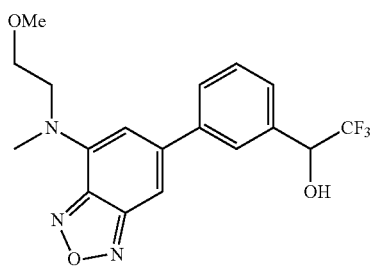

TRV-1383

4,6-dibromobenzo[c][1,2,5]oxadiazole (0.3322 g, 1.2 mmol), (2-methoxyethyl)methylamine (0.13 mL, 1.2 mmol), NMP (2 mL) and DIPEA (0.21 mL, 1.2 mmol) were sealed in a tube and heated to 100° C. overnight. Upon cooling to room temperature, the mixture was diluted with water and EtOAc. The layers were separated and the aqueous layer was then back-extracted. The combined organic extracts were then washed with $H_2O$, 1 N HCl (aq), saturated $NaHCO_3$ (aq), $H_2O$ (3×), brine and then dried ($Na_2SO_4$), filtered and concentrated. The crude aniline and 3-formylbenzeneboronic acid (0.2338 g, 1.56 mmol) were sealed in a tube. The tube was evacuated and purged with argon (3 cycles). 2M $Na_2CO_3$ (1.8 mL, aq solution) was added along with DME (2.7 mL). The solution was degassed for 10 minutes and then $Pd(PPh_3)_4$ (0.0693 g, 0.06 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was then dissolved in THF (2.5 mL) and cooled in an ice bath. To this solution was added $CF_3TMS$ (0.35 mL, 2.4 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.2 mL, 4.2 mmol) was added, the mixture was allowed to warm to room temperature overnight. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. The crude material was purified via chromatography (20% EtOAc/hexane) to afford 0.2514 g (55% yield, 4 steps) of TRV-1383. $^1$H NMR (500 MHz, CDCl3) δ=7.75 (s, 1H), 7.68 (dt, J=7.0, 2.0 Hz, 1H), 7.55-7.51 (m, 2H), 7.17 (d, J=1.0 Hz, 1H), 6.28 (s, 1H), 5.13 (q, J=7.0 Hz, 1H), 4.18 (t, J=5.5 Hz, 2H), 3.68 (t, J=5.5 Hz, 2H), 3.35 (s, 3H), 3.28 (s, 3H), 2.78 (br s, 1H).

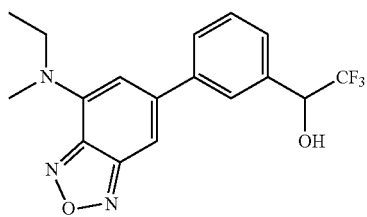

TRV-1384

4,6-dibromobenzo[c][1,2,5]oxadiazole (0.3327 g, 1.2 mmol), N-methylethanamine (0.10 mL, 1.2 mmol), NMP (2 mL) and DIPEA (0.21 mL, 1.2 mmol) were sealed in a tube and heated to 100° C. overnight. Upon cooling to room temperature, the mixture was diluted with water and EtOAc. The layers were separated and the aqueous layer was then back-extracted. The combined organic extracts were then washed with $H_2O$, 1 N HCl (aq), saturated $NaHCO_3$ (aq), $H_2O$ (3×), brine and then dried ($Na_2SO_4$), filtered and concentrated. The crude aniline and 3-formylbenzeneboronic acid (0.2338 g, 1.56 mmol) were sealed in a tube. The tube was evacuated and purged with argon (3 cycles). 2M $Na_2CO_3$ (1.8 mL, aq solution) was added along with DME (2.7 mL). The solution was degassed for 10 minutes and then $Pd(PPh_3)_4$ (0.0693 g, 0.06 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was then dissolved in THF (2.5 mL) and cooled in an ice bath. To this solution was added $CF_3TMS$ (0.35 mL, 2.4 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.2 mL, 4.2 mmol) was added, the mixture was allowed to warm to room temperature overnight. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. The crude material was purified via chromatography (20% EtOAc/hexane) to afford 0.2528 g (60% yield, 4 steps) of TRV-1384. $^1$H NMR (500 MHz, CDCl3) δ=7.74 (s, 1H), 7.66 (dt, J=7.0, 2.0 Hz, 1H), 7.55-7.50 (m, 2H), 7.15 (d, J=1.0 Hz, 1H), 6.23 (s, 1H), 5.13 (q, J=7.0 Hz, 1H), 4.00 (q, J=7.0 Hz, 2H), 3.22 (s, 3H), 2.78 (br s, 1H), 1.25 (t, J=7.0 Hz, 3H).

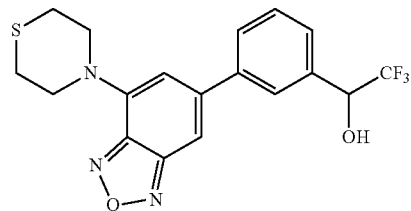

TRV-1385

4,6-dibromobenzo[c][1,2,5]oxadiazole (0.3373 g, 1.2 mmol), thiomorpholine (0.12 mL, 1.2 mmol), NMP (2 mL) and DIPEA (0.21 mL, 1.2 mmol) were sealed in a tube and heated to 100° C. overnight. Upon cooling to room temperature, the mixture was diluted with water and EtOAc. The layers were separated and the aqueous layer was then back-extracted. The combined organic extracts were then washed with $H_2O$, 1 N HCl (aq), saturated $NaHCO_3$ (aq), $H_2O$ (3×), brine and then dried ($Na_2SO_4$), filtered and concentrated. The crude aniline and 3-formylbenzeneboronic acid (0.2338 g, 1.56 mmol) were sealed in a tube. The tube was evacuated and purged with argon (3 cycles). 2M $Na_2CO_3$ (1.8 mL, aq solution) was added along with DME (2.7 mL). The solution was degassed for 10 minutes and then $Pd(PPh_3)_4$ (0.0693 g, 0.06 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was then dissolved in THF (2.5 mL) and cooled in an ice bath. To this solution was added $CF_3TMS$ (0.35 mL, 2.4 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.2 mL, 4.2 mmol) was added, the mixture was allowed to warm to room temperature overnight. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. The crude material was purified via chromatography (20% EtOAc/hexane) to afford 0.1863 g (39% yield, 4 steps) of TRV-1385. $^1H$ NMR (500 MHz, CDCl3) δ=7.73 (s, 1H), 7.65 (dt, J=7.0, 2.0 Hz, 1H), 7.57-7.52 (m, 2H), 7.34 (d, J=0.5 Hz, 1H), 6.55 (s, 1H), 5.14 (q, J=6.5 Hz, 1H), 4.06 (m, 4H), 2.86 (m, 4H), 2.76 (br s, 1H).

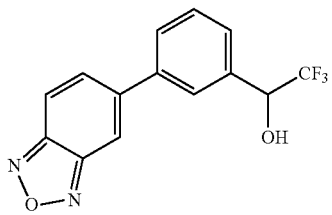

TRV-1386

4,6-dibromobenzo[c][1,2,5]oxadiazole (8.9 g, 32.0 mmol) and 3-formylbenzeneboronic acid (5.037 g, 33.6 mmol) were charged to a flask. The flask was evacuated and purged with argon (3 cycles). 2M $Na_2CO_3$ (48 mL, aq solution) was added along with DME (72 mL). The solution was degassed for 15 minutes and then $Pd(PPh_3)_4$ (1.85 g, 1.6 mmol) was added all at once. The flask was heated to 100° C. for 4 hours. After cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated to give 13.3 g of a yellow solid that was a mixture of the desired product, unreacted starting material, the wrong regioisomer and the his-coupled product. Purification of the crude material via chromatography (0, 5, 10, 15, 20% EtOAc/hexane gradient elution) afforded 1.9412 g (20% yield) of 3-(7-bromobenzo[c][1,2,5]oxadiazol-5-yl)benzaldehyde. This material (1.7903 g, 5.91 mmol) was then dissolved in THF (12 mL) and cooled in an ice bath. To this solution was added $CF_3TMS$ (1.75 mL, 11.8 mmol) and then TBAF (0.6 mL, 1.0 M solution in THF). After 5 minutes, the ice bath was removed and the mixture was stirred for an additional 2 hours. The solution was then re-cooled to 0° C. and TBAF (22 mL, 22 mmol) was added, the mixture was allowed to warm to room temperature overnight. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was dissolved in THF (15 mL) and cooled to 0° C. NaH (0.2836 g, 7.09 mmol) was added portion wise and the reaction was stirred for 10 minutes at 0° C. before warming to room temperature and stirring an additional 30 minutes. The solution was then re-cooled and TBSCl (1.336 g, 8.87 mmol) was added. The reaction was stirred overnight under argon. Cooled to 0° C. and quenched with saturated $NH_4Cl$ (aq) and then diluted with EtOAc. The layers were separated and the aqueous layer was then back-extracted. The combined organic extracts were then washed with $H_2O$ (3×), brine and then dried ($Na_2SO_4$), filtered and concentrated. The crude material was purified by chromatography (5% EtOAc/hexane) to afford 1.2744 g (44% yield, 3 steps) of the corresponding silyl ether as a brown solid. This material (0.2732 g, 0.56 mmol) was dissolved in THF (5 mL) and cooled to −78° C. nBuLi (0.31 mL, 2.0 M solution in cyclohexane, 0.62 mmol) was added dropwise and the solution was stirred for 30 minutes before quenching with saturated $NH_4Cl$ (aq) and allowed to warm to room temperature. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was dissolved in THF (10 mL) and cooled to 0° C. TBAF (1.2 mL, 1.0 M solution in THF) was added and the reaction was allowed to warm to room temperature overnight. The reaction was quenched with brine. The mixture was then diluted with water and EtOAc. The layers were separated and the aqueous layer was then back-extracted. The combined organic extracts were then washed with $H_2O$ (3×), brine and then dried ($Na_2SO_4$), filtered and concentrated. The crude material was purified via chromatography

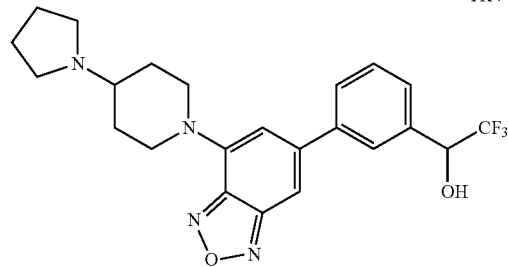

TRV-1387

4,6-dibromobenzo[c][1,2,5]oxadiazole (0.3832 g, 1.38 mmol), 4-(pyrrolidin-1-yl)piperidine (0.2127 g, 1.38 mmol), NMP (2 mL) and DIPEA (0.24 mL, 1.38 mmol) were sealed in a tube and heated to 100° C. overnight. Upon cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated. The crude aniline and 3-formylbenzeneboronic acid (0.2698 g, 1.8 mmol) were sealed in a tube. The tube was evacuated and purged with argon (3 cycles). 2M $Na_2CO_3$ (2.1 mL, aq solution) was added along with DME (3.1 mL). The solution was degassed for 10 minutes and then $Pd(PPh_3)_4$ (0.0797 g, 0.069 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was then dissolved in THF (2.8 mL) and cooled in an ice bath. To this solution was added $CF_3TMS$ (0.41 mL, 2.76 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.8 mL, 4.8 mmol) was added, the mixture was allowed to warm to room temperature overnight. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. The crude material was purified via chromatography (10% MeOH/DCM) to afford 0.1349 g (22% yield, 4 steps) of TRV-1387. $^1H$ NMR (500

MHz, CDCl3) δ=7.73 (s, 1H), 7.59 (d, J=7.5 Hz, 1H), 7.53-7.46 (m, 2H), 7.25 (s, 1H), 6.48 (s, 1H), 5.08 (q, J=6.5 Hz, 1H), 4.34-4.28 (m, 2H), 3.05-3.00 (m, 2H), 2.65 (br s, 4H), 2.30-2.27 (m, 1H), 2.06-2.03 (m, 2H), 1.84 (br s, 4H), 1.77-1.66 (m, 3H); $^1$H NMR (DMSO, 500 MHz) δ=7.91 (s, 1H), 7.83 (d, J=10 Hz, 1H), 7.59 (d, J=10 Hz, 1H), 7.55 (t, J=10 Hz, 1H), 7.50 (s, 1H), 6.97 (d, J=5 Hz, 1H), 6.73 (s, 1H), 5.31-5.26 (m, 1H), 4.20 (d, J=10 Hz, 2H), 3.16 (t, J=10 Hz, 2H), 2.52 (s, 4H), 2.26-2.22 (m, 1H), 2.00 (d, J=10 Hz, 2H), 1.67 (s, 4H), 1.63-1.56 (m, 2H).

TRV-1388

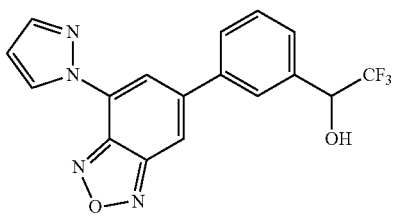

To a solution of 4,6-dibromobenzo[c][1,2,5]oxadiazole (0.3106 g, 1.12 mmol) and pyrazole (0.0837 g, 1.23 mmol) in THF at −78° C. was added NaHMDS (1.2 mL, 1.0 M solution in THF) dropwise. The solution was stirred for 30 minutes then warmed to room temperature. The solution was then degassed for 5 minutes before heating to 50° C. overnight. Upon cooling to room temperature, the reaction was quenched with saturated NH$_4$Cl (aq) and diluted with EtOAc. The layers were separated and the aqueous layer was then back-extracted. The combined organic extracts were then washed with H$_2$O (3×), brine and then dried (Na$_2$SO$_4$), filtered and concentrated. The crude aniline and 3-formyl-benzeneboronic acid (0.2189 g, 1.46 mmol) were sealed in a tube. The tube was evacuated and purged with argon (3 cycles). 2M Na$_2$CO$_3$ (1.7 mL, aq solution) was added along with DME (2.5 mL). The solution was degassed for 10 minutes and then Pd(PPh$_3$)$_4$ (0.0647 g, 0.056 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. This crude material was then dissolved in THF (2.5 mL) and cooled in an ice bath. To this solution was added CF$_3$TMS (0.33 mL, 2.24 mmol) and then TBAF (0.1 mL, 1.0 M solution in THF). After 5 minutes, the ice bath was removed and the mixture was stirred for an additional 2 hours. The solution was then re-cooled to 0° C. and TBAF (3.9 mL, 3.9 mmol) was added, the mixture was allowed to warm to room temperature overnight. The mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. The crude material was purified via chromatography (20% EtOAc/hexane) to afford 0.0342 g (8.5% yield, 4 steps) of TRV-1388. $^1$H NMR (500 MHz, CDCl3) δ=8.91 (d, J=2.5 Hz, 1H), 8.33 (d, J=1.5 Hz, 1H), 7.84-7.83 (m, 3H), 7.76 (dt, J=7.5, 1.5 Hz, 1H), 7.59-7.52 (m, 2H), 6.62-6.61 (m, 1H), 5.15-5.12 (m, 1H), 3.40 (d, J=4.0 Hz, 1H).

TRV-1389

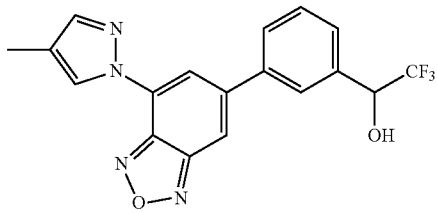

To a solution of 4,6-dibromobenzo[c][1,2,5]oxadiazole (0.3457 g, 1.24 mmol) and 4-methylpyrazole (0.11 mL, 1.37 mmol) in THF at −78° C. was added NaHMDS (1.3 mL, 1.0 M solution in THF) dropwise. The solution was stirred for 30 minutes then warmed to room temperature. The solution was then degassed for 5 minutes before heating to 50° C. overnight. Upon cooling to room temperature, the reaction was quenched with saturated NH$_4$Cl (aq) and diluted with EtOAc. The layers were separated and the aqueous layer was then back-extracted.

The combined organic extracts were then washed with H$_2$O (3×), brine and then dried (Na$_2$SO$_4$), filtered and concentrated. The crude aniline and 3-formylbenzeneboronic acid (0.2413 g, 1.61 mmol) were sealed in a tube. The tube was evacuated and purged with argon (3 cycles). 2M Na$_2$CO$_3$ (1.9 mL, aq solution) was added along with DME (2.8 mL). The solution was degassed for 10 minutes and then Pd(PPh$_3$)$_4$ (0.0716 g, 0.062 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. This crude material was then dissolved in THF (2.5 mL) and cooled in an ice bath. To this solution was added CF$_3$TMS (0.37 mL, 2.48 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.3 mL, 4.3 mmol) was added, the mixture was allowed to warm to room temperature overnight. The mixture was diluted with water and EtOAc. The layers were separated and the aqueous layer was then back-extracted. The combined organic extracts were then washed with H$_2$O (3×), brine and then dried (Na$_2$SO$_4$), filtered and concentrated. The crude material was purified via chromatography (20% EtOAc/hexane) to afford 0.0365 g (7.9% yield, 4 steps) of TRV-1389. $^1$H NMR (500 MHz, CDCl3) δ=8.68 (s, 1H), 8.28 (d, J=1.0 Hz, 1H), 7.84 (s, 1H), 7.81 (d, J=1.0 Hz, 1H), 7.76 (d, J=7.5 Hz, 1H), 7.66 (s, 1H), 7.60-7.54 (m, 2H), 5.16-5.14 (m, 1H), 3.06 (d, J=3.5 Hz, 1H), 2.23 (s, 3H).

TRV-1390

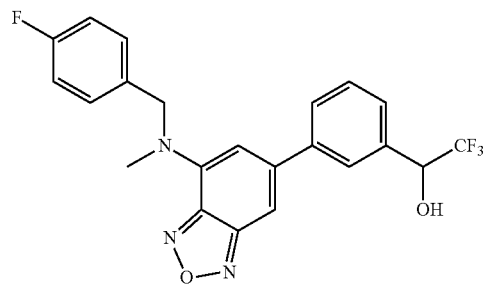

4,6-dibromobenzo[c][1,2,5]oxadiazole (0.3688 g, 1.33 mmol), 4-fluoro-N-methylbenzylamine (0.18 mL, 1.39 mmol), NMP (3 mL) and DIPEA (0.26 mL, 1.5 mmol) were sealed in a tube and heated to 100° C. overnight. Upon cooling to room temperature, the mixture was diluted with water and EtOAc. The layers were separated and the aqueous layer was then back-extracted. The combined organic extracts were then washed with $H_2O$, 1 N HCl (aq), saturated $NaHCO_3$ (aq), $H_2O$ (3×), brine and then dried ($Na_2SO_4$), filtered and concentrated to give 6-bromo-N-(4-fluorobenzyl)-N-methylbenzo[c][1,2,5]oxadiazol-4-amine. The crude aniline and 3-formylbenzeneboronic acid (0.2593 g, 1.73 mmol) were sealed in a tube. The tube was evacuated and purged with argon (3 cycles). 2M $Na_2CO_3$ (2.0 mL, aq solution) was added along with DME (3.0 mL). The solution was degassed for 10 minutes and then $Pd(PPh_3)_4$ (0.0768 g, 0.066 mmol) was added all at once. The tube was re-sealed and heated to 100° C. overnight. After cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was then dissolved in THF (4.0 mL) and cooled in an ice bath. To this solution was added $CF_3TMS$ (0.39 mL, 2.66 mmol) and then TBAF (0.1 mL, 1.0 M solution in THF). After 5 minutes, the ice bath was removed and the mixture was stirred for an additional 2 hours. The solution was then re-cooled to 0° C. and TBAF (4.7 mL, 4.7 mmol) was added, the mixture was allowed to warm to room temperature overnight. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. The crude material was purified via chromatography (15% EtOAc/hexane) to afford 0.2675 g (47% yield, 4 steps) of TRV-1390. $^1$H NMR (500 MHz, CDCl3) δ=7.70 (s, 1H), 7.64 (dt, J=7.0, 2.0 Hz, 1H), 7.55-7.50 (m, 2H), 7.27-7.24 (m, 3H), 7.04-7.00 (m, 2H), 6.34 (s, 1H), 5.12-5.10 (m, 3H), 3.19 (s, 3H), 2.71 (s, 1H).

TRV-1391

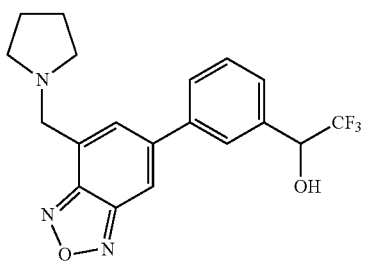

4,6-dibromobenzo[c][1,2,5]oxadiazole (8.9 g, 32.0 mmol) and 3-formylbenzeneboronic acid (5.037 g, 33.6 mmol) were charged to a flask. The flask was evacuated and purged with argon (3 cycles). 2M $Na_2CO_3$ (48 mL, aq solution) was added along with DME (72 mL). The solution was degassed for 15 minutes and then $Pd(PPh_3)_4$ (1.85 g, 1.6 mmol) was added all at once. The flask was heated to 100° C. for 4 hours. After cooling to room temperature, the mixture was diluted with water and EtOAc. The layers were separated and the aqueous layer was then back-extracted. The combined organic extracts were then washed with $H_2O$ (3×), brine and then dried ($Na_2SO_4$), filtered and concentrated to give 13.3 g of a yellow solid that was a mixture of the desired product, unreacted starting material, the wrong regioisomer, and the his-coupled product. Purification of the crude material via chromatography (0, 5, 10, 15, 20% EtOAc/hexane gradient elution) afforded 1.9412 g (20% yield) of 3-(7-bromobenzo[c][1,2,5]oxadiazol-5-yl)benzaldehyde. This material (1.7903 g, 5.91 mmol) was then dissolved in THF (12 mL) and cooled in an ice bath. To this solution was added $CF_3TMS$ (1.75 mL, 11.8 mmol) and then TBAF (0.6 mL, 1.0 M solution in THF). After 5 minutes, the ice bath was removed and the mixture was stirred for an additional 2 hours. The solution was then re-cooled to 0° C. and TBAF (22 mL, 22 mmol) was added, the mixture was allowed to warm to room temperature overnight. The mixture was diluted with water and EtOAc. The layers were separated and the aqueous layer was then back-extracted. The combined organic extracts were then washed with $H_2O$ (3×), brine and then dried ($Na_2SO_4$), filtered and concentrated. This crude material was dissolved in THF (15 mL) and cooled to 0° C. NaH (0.2836 g, 7.09 mmol) was added portion wise and the reaction was stirred for 10 minutes at 0° C. before warming to room temperature and stirring an additional 30 minutes. The solution was then re-cooled and TBSCl (1.336 g, 8.87 mmol) was added. The reaction was stirred overnight under argon. Cooled to 0° C. and quenched with saturated $NH_4Cl$ (aq) and then diluted with EtOAc. The layers were separated and the aqueous layer was then back-extracted. The combined organic extracts were then washed with $H_2O$ (3×), brine and then dried ($Na_2SO_4$), filtered and concentrated. The crude material was purified by chromatography (5% EtOAc/hexane) to afford 1.2744 g (44% yield, 3 steps) of brown solid. This solid (0.2647 g, 0.543 mmol) was dissolved in THF (5 mL) and cooled to −78° C. nBuLi (0.30 mL, 2.0 M solution in cyclohexane, 0.60 mmol) was added dropwise and the solution was stirred for 30 minutes before adding DMF (0.050 mL, 0.652 mmol). The mixture was slowly allowed to warm to room temperature. The solution was then re-cooled to 0° C. and quenched with saturated $NH_4Cl$ (aq). This mixture was extracted with EtOAc. The combined extracts were washed with water, brine, dried ($Na_2SO_4$), filtered and concentrated to give the crude aldehyde. The aldehyde was purified via flash chromatography (10% EtOAc/hexane) to give 0.0913 g (39% yield). This aldehyde was then dissolved in DCM (1 mL) and pyrrolidine (0.026 mL, 0.313 mmol) was added. To this mixture was then added $NaHB(OAc)_3$ (0.0886 g, 0.418 mmol) with vigorous stirring and the reaction was stirred overnight. The reaction was quenched with saturated $NaHCO_3$ (aq) and extracted with DCM. The combined extracts were washed with water, brine and then dried ($Na_2SO_4$), filtered and concentrated. This material was then redissolved in THF (2 mL) and cooled to 0° C. TBAF (0.42 mL, 1.0 M solution in THF) was added and the mixture was stirred overnight under argon. The reaction was quenched with brine and extracted with EtOAc. The combined extracts were washed with water, brine, dried ($Na_2SO_4$) filtered and concentrated. The crude material was purified via flash chromatography (5% MeOH/DCM) to afford 0.0181 g (23% yield) of TRV-1391. $^1$H NMR (CDCl3, 500 MHz) δ=7.84 (t, J=0.5 Hz, 1H), 7.78 (s, 1H), 7.72-7.70 (m, 2H), 7.58-7.54 (m, 2H), 5.15 (q, J=7.0 Hz, 1H), 4.12 (s, 2H), 2.69 (s, 4H), 1.86-1.84 (m, 4H).

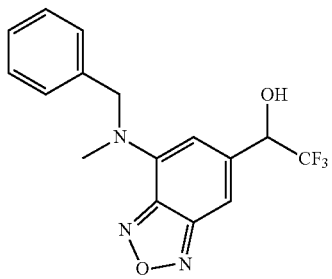

TRV-1392

N-benzyl-6-bromo-N-methylbenzo[c][1,2,5]oxadiazol-4-amine (0.3720 g, 1.17 mmol) was dissolved in THF (6 mL) under argon, and cooled to −78° C. nBuLi (0.65 mL, 2.0 M solution in cyclohexane) was added dropwise forming a deep red solution. This mixture was stirred for 30 minutes at −78° C. and then DMF (0.11 mL, 1.4 mmol) was added quickly. The mixture was allowed to slowly warm to room temperature. It was then re-cooled to 0° C. and quenched with saturated NH₄Cl (aq). This mixture was extracted with EtOAc. The combined extracts were washed with water, brine, dried (Na₂SO₄), filtered and concentrated to give the crude aldehyde. The aldehyde was purified via flash chromatography (10% EtOAc/hexane) to give 0.1737 g (56% yield) of the aldehyde 4. This material (0.1737 g, 0.546 mmol) was then dissolved in THF (2.0 mL) and cooled in an ice bath. To this solution was added CF₃TMS (0.16 mL, 1.09 mmol) and then TBAF (0.06 mL, 1.0 M solution in THF). After 5 minutes, the ice bath was removed and the mixture was stirred for an additional 2 hours. The solution was then re-cooled to 0° C. and TBAF (2.0 mL, 2.0 mmol) was added, the mixture was allowed to warm to room temperature overnight. The mixture was diluted with water and EtOAc. The layers were separated and the aqueous layer was then back-extracted. The combined dorganic extracts were then washed with H₂O (3×), brine and then dried (Na₂SO₄), filtered and concentrated. The crude material was purified via chromatography (15% EtOAc/hexane) to afford 0.1094 g (60% yield) of TRV-1392. ¹H NMR (500 MHz, CDCl3) δ=7.38-7.35 (m, 2H), 7.33-7.28 (m, 4H), 6.26 (s, 1H), 5.17 (s, 2H), 5.05 (q, J=6.5 Hz, 1H), 3.23 (s, 3H), 2.79 (br s, 1H).

TRV-1397

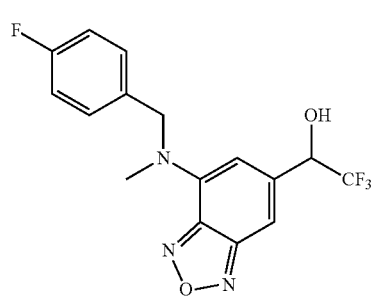

6-bromo-N-(4-fluorobenzyl)-N-methylbenzo[c][1,2,5]oxadiazol-4-amine (0.3753 g, 1.12 mmol) was dissolved in THF (6 mL) and cooled to −78° C. nBuLi (0.62 mL, 2.0 M solution in cyclohexane, 1.23 mmol) was added dropwise and the solution was stirred for 30 minutes before adding DMF (0.10 mL, 1.34 mmol). The mixture was stirred under argon at −78° C. After 3 hours, saturated NH₄Cl (aq) was added and then the mixture was allowed to warm to room temperature. This mixture was extracted with EtOAc. The combined extracts were washed with water, brine, dried (Na₂SO₄), filtered and concentrated to give the crude aldehyde. The aldehyde was purified via flash chromatography (10% EtOAc/hexane) to give 0.1846 g (58% yield). This material (0.1846 g, 0.647 mmol) was then dissolved in THF (3 mL) and cooled in an ice bath. To this solution was added CF₃TMS (0.19 mL, 1.3 mmol) and then TBAF (0.06 mL, 1.0 M solution in THF). After 5 minutes, the ice bath was removed and the mixture was stirred for an additional 2 hours. The solution was then re-cooled to 0° C. and TBAF (2.3 mL, 2.26 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. This material was purified via chromatography (20% EtOAc/hexane) to give 0.0794 g (34% yield) TRV-1397 as a red oil. ¹H NMR (500 MHz, CDCl3) δ=7.26 (s, 1H), 7.24-7.22 (m, 2H), 7.03-6.99 (m, 2H), 6.23 (s, 1H), 5.09 (s, 2H), 5.02 (q, J=7.0 Hz, 1H), 3.15 (s, 3H), 2.67 (br s, 1H).

TRV-1398

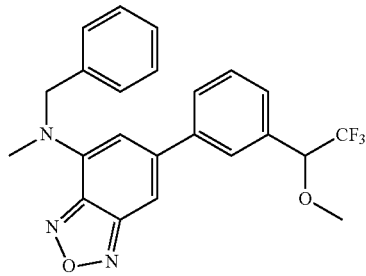

TRV-1378 (83 mg, 0.2 mmol) was dissolved in THF (2 mL) and added dropwise to a suspension of NaH (50 mg) stirring in THF (1 mL) at 0° C. Once the addition was complete the cold bath was removed and replaced with a room temperature water bath. After 5 min the reaction was cooled back to 0° C. and MeI (100 μL, 0.8 mmol) was added. The cold bath was left in place and the reaction was allowed to come to room temperature overnight. Following a standard workup and flash chromatography (9:1 Hex/EtOAc). the product was isolated as an orange solid (54 mg, 63% yield). ¹H NMR (500 MHz, CDCl₃) δ=7.68 (m, 2H), 7.54 (m, 2H), 7.37 (m, 2H), 7.32 (m, 4H), 6.38 (s, 1H), 5.20 (s, 2H0, 4.61 (q, J=7 Hz, 1H), 3.52 (s, 3H), 3.29 (s, 3H).

TRV-1399

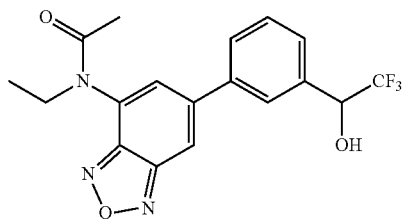

4,6-dibromobenzo[c][1,2,5]oxadiazole (0.9837 g, 3.53 mmol), ethylamine (0.29 mL, 3.53 mmol), NMP (5 mL) and DIPEA (0.61 mL, 3.53 mmol) were sealed in a tube and heated to 60° C. overnight. Upon cooling to room temperature, the mixture was diluted with water and EtOAc. The layers were separated and the aqueous layer was then back-extracted. The combined organic extracts were then washed with H₂O, 1 N HCl (aq), saturated NaHCO₃ (aq), H₂O (3×), brine and then dried (Na₂SO₄), filtered and concentrated. The crude material was purified via chromatography (3% EtOAc/hexane) to afford 0.3952 g (46% yield). This material (0.1298 g, 0.54 mmol) was dissolved in Ac₂O (5 mL) and heated to 140° C. for 48 hours. After cooling to room temperature the material was concentrated to afford 4 in 98% yield. This material (0.1499 g, 0.52 mmol) was added to a tube along with 3-formylbenzenboronic acid (0.1013 g, 0.676 mmol) and the tube was purged and evacuated with argon (3 times). Na₂CO₃ (1.6 mL, 3.12 mmol, 2 M aqueous solution) and DME (2.3 mL) were added and the solution was degassed for 10 minutes. Finally Pd(PPh₃)₄ (0.030 g, 0.026 mmol) was added, the tube was sealed and heated to 100° C. overnight. Upon cooling to room temperature, the mixture was diluted with EtOAc and water. The layers were separated and the aqueous layer was back-extracted with EtOAc (3×). The combined organic layers were washed with H₂O (4×), brine, dried (Na₂SO₄), filtered and concentrated to give a crude aldehyde 6. This aldehyde was then dissolved in THF (3 mL) and cooled in an ice bath. To this solution was added CF₃TMS (0.08 mL, 0.52 mmol) and then TBAF (0.05 mL, 1.0 M solution in THF). After 5 minutes, the ice bath was removed and the mixture was stirred for an additional 2 hours. The solution was then re-cooled to 0° C. and TBAF (1.3 mL, 1.3 mmol) was added, the mixture was allowed to warm to room temperature overnight. The mixture was diluted with water and EtOAc. The layers were separated and the aqueous layer was then back-extracted. The combined organic extracts were then washed with H₂O (3×), brine and then dried (Na₂SO₄), filtered and concentrated. This material was purified via chromatography (40% EtOAc/hexane) to give 0.0327 g (17% yield over 3 steps) of TRV-1399 as yellow solid. ¹H NMR (500 MHz, CDCl3) δ=7.98 (s, 1H), 7.78 (s, 1H), 7.68-7.67 (m, 1H), 7.61-7.57 (m, 2H), 7.52 (s, 1H), 5.19-5.14 (m, 1H), 3.97 (q, J=10 Hz, 2H), 3.33 (d, J=5 Hz, 1H), 2.02 (br s, 3H), 1.21 (t, J=10 Hz, 3H).

TRV-1400

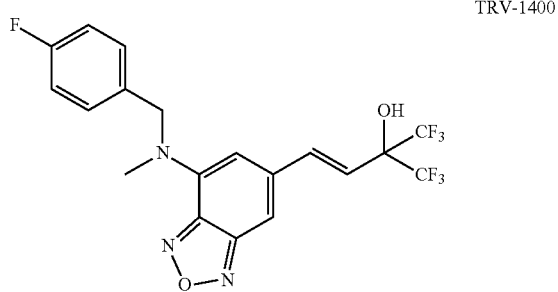 [SMILES: CN(Cc1ccc(F)cc1)c1cc(/C=C/C(O)(C(F)(F)F)C(F)(F)F)cc2nonc12]

CsF (0.0052 g, 0.034 mmol) was added to a mixture of TRV-1402 (0.1162 g, 0.34 mmol) and CF₃TMS (0.10 mL, 0.68 mmol) in THF (3 mL) at room temperature. This solution was stirred until 100% conversion of starting material m was obtained and then TBAF (1.2 mL, 1.0 M solution in THF) was added, this was stirred for an additional 16 hours. The reaction was quenched with brine and diluted with EtOAc and water. The layers were separated and the aqueous layer was back-extracted with EtOAc. The combined organic layers were washed with H₂O (3×), brine, dried (Na₂SO₄), filtered and concentrated. The crude material was purified via 10% EtOAc/hexane column and then again with a 5% EtOAc/hexane column to afford 0.020 g (13% yield) of TRV-1400 as orange solid. ¹H NMR (500 MHz, CDCl3) δ=7.24-7.21 (m, 2H), 7.17 (d, J=15 Hz, 1H), 7.16 (s, 1H), 7.03-6.99 (m, 2H), 6.23 (d, J=15 Hz, 1H), 6.18 (s, 1H), 5.11 (s, 2H), 3.30 (br s, 1H), 3.17 (s, 3H).

TRV-1401

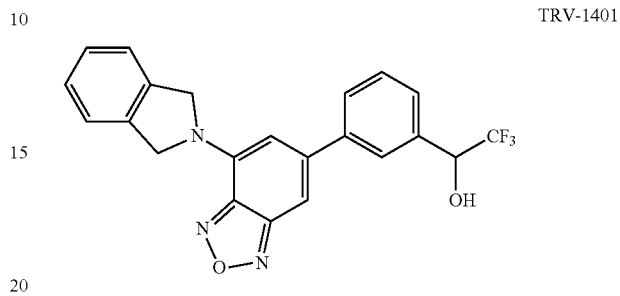

To a solution of 6-bromo-4-chlorobenzo[c][1,2,5]oxadiazole (372 mg, 1.6 mmol) in NMP (3 mL) in a 4 dram vial was added isoindoline (238 mg, 2 mmol) and triethylamine (400 µL, 2.9 mmol). A cap was tightly fitted and the reaction was heated at 85° C. O/N. The reaction was worked up by diluting with EtOAc (60 mL) and washing with 1M HCl (3×20 mL) and brine (1×20 mL). The organic phase was dried with MgSO₄ filtered and concentrated in vacuo. The crude material was purified by flash column chromatography (9:1 Hex/EtOAc) to give 208 mg (41% yield) of 6-bromo-4-(isoindolin-2-yl)benzo[c][1,2,5]oxadiazole. ¹H NMR (300 MHz, CDCl₃) δ=7.38 (m, 4H), 7.26 (s, 1H), 6.14 (s, 1H), 5.14 (s, 4H). To a solution of the afore mentioned material, (200 mg, 0.6 mmol) in DME (4 mL)/Na₂CO₃ (0.9 mL) was added 3-formyl-phenylboronic acid (134 mg, 0.9 mmol) and Pd(P(Ph)₃)₄ (35 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO₄ and concentrated in vacuo. The crude material was fused to SiO₂ (2 g) and purified by flash column chromatography (2:1 DCM/Hex) to give 190 mg (92% yield). ¹H NMR (500 MHz, CDCl₃) δ=10.18 (s, 1H), 8.24 (m, 1H), 7.99 (dm, J=8 Hz, 2H), 7.70 (t, J=7 Hz, 1H), 7.44 (m, 4H), 7.26 (s, 1H), 6.30 (s, 1H), 5.25 (s, 4H). To a stirring solution of the afore mentioned material, (190 mg, 0.55 mmol) and Rupert's reagent (150 mg, 1.1 mmol) in DCM (5 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH₄Cl, brine, and then dried with MgSO₄ and concentrated in vacuo. The crude material was passed through a plug of SiO₂ (DCM) and then purified by flash column chromatography (2:1 DCM/Hex). ¹H NMR (500 MHz, CDCl₃) δ=7.84 (s, 1H), 7.77 (dt, J=7 Hz, 2 Hz, 1H), 7.60 (m, 2H), 7.43 (m, 4H), 7.23 (s, 1H), 6.25 (s, 1H), 5.31 (s, 4H), 5.2 (m, 1H), 2.68 (s, 1H).

TRV-1402

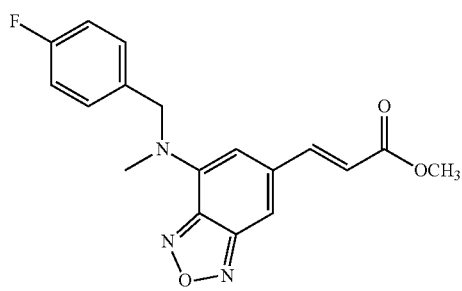

6-bromo-N-(4-fluorobenzyl)-N-methylbenzo[c][1,2,5]oxadiazol-4-amine (1.5615 g, 4.65 mmol) was dissolved in THF (45 mL) and cooled to −78° C. nBuLi (2.6 mL, 2.0 M solution of cyclohexane) was added dropwise and the solution was stirred for 30 minutes at −78° C. DMF (0.54 mL, 7.0 mmol) was added and the reaction was stirred at −78° C. for 3 hours. This reaction was then quenched with saturated NH$_4$Cl(aq) and allowed to slowly warm to room temperature. This mixture was extracted with EtOAc and the combined organic layers were washed with H$_2$O (3×), brine, dried (Na$_2$SO$_4$), filtered and concentrated to give the crude aldehyde. This material was purified via 10% EtOAc/hexane column to afford 0.7248 g (55% yield) of aldehyde. This aldehyde (0.5615 g, 1.97 mmol) in THF (5 mL) was added to a stirred suspension of NaH (0.104 g, 2.6 mmol) and trimethyl phosponoacetate (0.31 mL, 2.17 mmol) in THF (20 mL) at 0° C. After the addition was complete the mixture was stirred overnight while warming to room temperature. After re-cooling to 0° C. the reaction was quenched with saturated NH$_4$Cl (aq). This mixture was then extracted with EtOAc. The combined organic layers were washed with H$_2$O (3×), brine, dried (Na$_2$SO$_4$), filtered and concentrated. The crude material was purified via 20% EtOAc/hexane to give 0.5945 g (88% yield) of TRV-1402 as the trans-isomer. $^1$H NMR (500 MHz, CDCl3) δ=7.64 (d, J=15 Hz, 1H), 7.25 (s, 1H), 7.23-7.21 (m, 2H), 7.03-7.00 (m, 2H), 6.46 (d, J=15 Hz, 1H), 6.25 (s, 1H), 5.10 (s, 2H), 3.83 (s, 3H), 3.15 (s, 3H). 4.92 (m, 1H), 4.59 (m, 2H), 4.15 (m, 2H), 2.20 (d, J=6 Hz, 1H). To a stirring 0° C. solution of 1-(6-bromobenzo[c][1,2,5]oxadiazol-4-yl)azetidin-3-ol (480 mg, 2 mmol) in NMP (12 mL) was added MeI (1.4 g, 10 mmol) followed by NaH (200 mg, 8.5 mmol). With the cold bath in place the reaction was allowed to come to RT. After 16 hours the reaction was cautiously quenched with water, treated with saturated NH$_4$Cl and extracted into EtOAc (3×20 mL). The combined organics were washed with HCl (2M) followed by brine, dried with MgSO$_4$ and concentrated in vacuo. The material purified by dry suction chromatography (1:1 DCM/Hex) to give 46 mg (71% yield). $^1$H NMR (300 MHz, CDCl$_3$) δ=7.22 (d, J=1 Hz, 1H), 5.92 (s, br, 1H), 4.44 (m, 3H), 4.16 (m, 2H), 3.37 (s, 3H). To a solution of TKW-I-92 (406 mg, 1.43 mmol) in DME (7 mL)/Na$_2$CO$_3$ (2.1 mL) was added 3-formyl-phenylboronic acid (322 mg, 2.1 mmol) and Pd(P(Ph)$_3$)$_4$ (80 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO$_4$ and concentrated in vacuo. The crude material was purified by dry suction filtration (DCM) to give 411 mg of material. $^1$H NMR (500 MHz, CDCl$_3$) δ=10.11 (s, 1H), 8.12 (m, 1H), 7.93 (dm, J=8 Hz, 1H), 7.88 (dm, J=8 Hz, 1H), 7.65 (t, J=8 Hz, 1H), 7.21 (m, 1H), 6.08 (m, 1H), 4.56 (dd, J=10 Hz/5 Hz, 2H), 4.46 (m, 1H), 4.21 (dd, J=10 Hz/4 Hz, 2H), 3.39 (s, 3H). To a stirring solution of TKW-I-93 (411 mg, 1.33 mmol) and Rupert's reagent (378 mg, 2.7 mmol) in DCM (13 mL) at 0° C. was added TBAF (0.2 mL, 1 M THF, 0.2 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (DCM) to give 477 mg (94% yield). $^1$H NMR (500 MHz, CDCl$_3$) δ=7.72 (s, broad, 1H), 7.65 (dt, J=7 Hz/2 Hz, 2H), 7.51 (m, 2H), 7.17 (d, J=1 Hz, 1H), 6.06 (s, 1H), 5.12 (m, 1H), 4.53 (m, 2H), 4.45 (m, 1H), 4.18 (dm, J=10 Hz, 2H), 3.38 (s, 3H).

TRV-1403

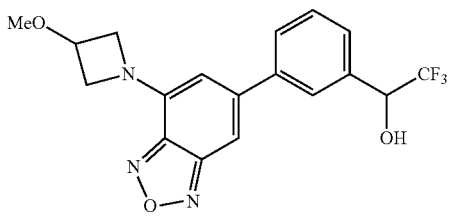

To a solution of 6-bromo-4-chlorobenzo[c][1,2,5]oxadiazole (353 mg, 1.5 mmol) in NMP (3 mL) in a 4 dram vial was added 3-hydroxyazetidine hydrochloride (180 mg, 1.65 mmol) and triethylamine (635 μL, 4.5 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO$_4$ filtered and concentrated in vacuo. The crude material was purified by flash column chromatography (DCM) to give 264 mg (65% yield) of 1-(6-bromobenzo[c][1,2,5]oxadiazol-4-yl)azetidin-3-ol. $^1$H NMR (300 MHz, CDCl$_3$) δ=7.23 (s, 1H), 5.95 (s, 1H),

TRV-1404

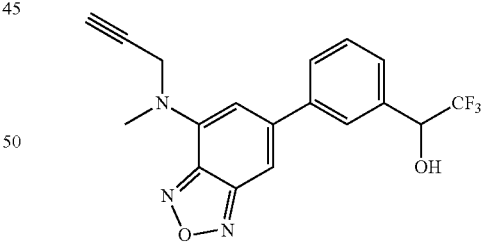

To a solution of 6-bromo-4-chlorobenzo[c][1,2,5]oxadiazole (355 mg, 1.52 mmol) in NMP (3 mL) in a 4 dram vial was added N-methyl propargylamine (92 mg, 1.67 mmol) and triethylamine (635 μL, 4.5 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO$_4$ filtered and concentrated in vacuo. Due to the volatile nature of the SM the crude material was only 50% converted. The mixture was used without further purification. $^1$H NMR (300 MHz, CDCl$_3$) δ=8.03 (s, 1H, SM), 7.55 (s, 1H, SM), 7.41 (s, 1H), 6.35 (s, 1H), 4.66 (s, 2H), 3.24 (s, 3H), 2.27 (s, 1H). To a solution of TKW-I-81 (180 mg, 0.7 mmol) in DME (3 mL)/Na₂CO₃ (1.0 mL) was added 3-formyl-phenylboronic acid (152 mg, 1.0 mmol) and Pd(P(Ph)₃)₄ (40 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO₄ and concentrated in vacuo. The crude material was purified by flash column chromatography (9:1 Hex/EtOAc) to give 58 mg of material. ¹H NMR (500 MHz, CDCl₃) δ=10.12 (s, 1H), 8.17 (m, 1H), 7.99 (dm, J=8 Hz, 1H), 7.96 (dm, J=8 Hz, 1H), 7.39 (s, 1H), 6.54 (s, 1H), 4.71 (s, 2H), 3.31 (s, 3H), 2.28 (s, 1H). To a stirring solution of TKW-I-87 (277 mg, 0.94 mmol) and Rupert's reagent (400 mg, 2.8 mmol) in DCM (10 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH₄Cl, brine, and then dried with MgSO₄ and concentrated in vacuo. The crude material was purified by flash column chromatography (50-80 DCM in Hex). ¹H NMR (300 MHz, CDCl₃) δ=7.76 (m, 1H), 7.69 (m, 1H), 7.55 (m, 2H), 7.34 (d, J=1 Hz, 1H), 6.55 (d, J=1 Hz, 1H), 5.14 (m, 1H), 4.68 (d, J=2 Hz, 2H), 3.30 (s, 3H), 2.69 (d, J=4 Hz, 1H), 2.29 (t, J=2 Hz, 1H).

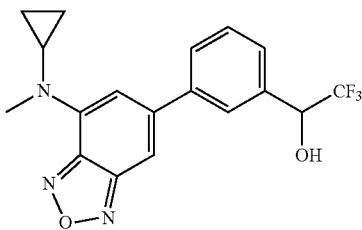

TRV-1405

To a solution of 6-bromo-4-chlorobenzo[c][1,2,5]oxadiazole (388 mg, 1.66 mmol) in NMP (3 mL) in a 4 dram vial was added cyclopropylamine (104 mg, 1.83 mmol) and triethylamine (694 μL, 4.9 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO₄ filtered and concentrated in vacuo. The crude material was purified by flash column chromatography (DCM) to give 264 mg (65% yield). ¹H NMR (500 MHz, CDCl₃) δ=7.32 (m, 1H), 6.60 (m, 1H), 5.46 (s, broad, 1H), 2.65 (m, 1H), 0.94 (m, 2H), 0.74 (m, 2H). To a solution of TKW-I-88 (214 mg, 0.8 mmol) in DME (3 mL)/Na₂CO₃ (1.0 mL) was added 3-formyl-phenylboronic acid (240 mg, 1.6 mmol) and Pd(P(Ph)₃)₄ (40 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO₄ and concentrated in vacuo. The crude material was fused to SiO₂ (3 g) and purified by flash column chromatography (9:1 Hex/EtOAc) to give 100 mg (42% yield) of material. ¹H NMR (300 MHz, CDCl₃) δ=10.13 (s, 1H), 8.19 (m, 1H), 7.94 (m, 2H), 7.69 (t, J=7 Hz, 1H), 7.32 (m, 1H), 6.83 (m, 1H), 3.57 (s, 3H), 2.77 (m, 1H), 1.01 (m, 2H), 0.76 (m, 2H). To a stirring solution of TKW-I-91 (277 mg, 0.94 mmol) and Rupert's reagent (400 mg, 2.8 mmol) in DCM (10 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH₄Cl, brine, and then dried with MgSO₄ and concentrated in vacuo. The crude material purified by flash column chromatography (10-15% EtOAc in Hex) to give 100 mg (80% yield). ¹H NMR (300 MHz, CDCl₃) δ=7.77 (s, 1H), 7.68 (m, 1H), 7.53 (m, 2H), 7.28 (m, 1H), 6.82 (d, J=1 Hz, 1H), 5.13 (m, 1H), 3.54 (s, 3H), 2.67 (m, 2H), 0.96 (m, 2H), 0.75 (m, 2H).

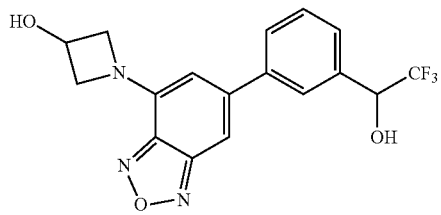

TRV-1406

To a solution of 1-(6-bromobenzo[c][1,2,5]oxadiazol-4-yl)azetidin-3-ol (260 mg, 0.9 mmol) in DME (6 mL)/Na₂CO₃ (1.5 mL) was added 3-formyl-phenylboronic acid (225 mg, 0.9 mmol) and Pd(P(Ph)₃)₄ (45 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO₄ and concentrated in vacuo to give 277 mg. The crude material was a single spot by TLC and used without further purification. ¹H NMR (300 MHz, CDCl₃) δ=10.12 (s, 1H), 8.14 (s, 1H), 7.98 (dm, J=7 Hz, 1H), 7.93 (dm, J=8 Hz, 1H), 7.70 (t, J=7 Hz, 1H), 7.24 (s, 1H), 6.11 (s, 1H), 4.95 (m, 1H), 4.63 (m, 2H), 4.19 (2H), 2.28 (m, 1H). To a stirring solution of aldehyde (277 mg, 0.94 mmol) and Rupert's reagent (400 mg, 2.8 mmol) in DCM (10 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH₄Cl, brine, and then dried with MgSO₄ and concentrated in vacuo. The crude material purified by flash column chromatography (40% EtOAc in Hex) to give 147 mg (42% yield) of TRV-1406. ¹H NMR (500 MHz, CDCl₃) δ=7.76 (s, 1H), 7.69 (dt, J=7 Hz, 2 Hz, 1H), 7.57 (m, 2H), 7.23 (s, 1H), 6.12 (s, 1H), 5.16 (q, J=6 Hz, 1H), 4.96 (m, 1H), 4.65 (dd, J=10 Hz/6 Hz, 2H), 4.20 (dd, J=10 Hz/6 Hz, 2H), 2.71 (s, broad, 1H), 2.22 (s, broad, 1H).

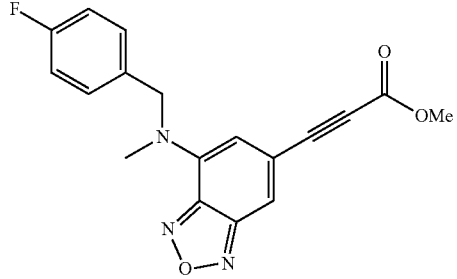

TRV-1408

6-bromo-N-(4-fluorobenzyl)-N-methylbenzo[c][1,2,5]oxadiazol-4-amine (0.2959 g, 0.88 mmol) was dissolved in THF (5 mL) and cooled to −78° C. nBuLi (0.51 mL, 1.01 mmol, 2.0 M solution in cyclohexane) was added dropwise and the solution was stirred for 20 minutes at −78° C. $I_2$ (1.3 mL, 1.0 M solution in THF) was added and the solution was allowed to slowly warm to 0° C. overnight. The reaction was quenched with saturated $NH_4Cl$ (aq) and extracted with EtOAc. The combined organic layers were washed with $H_2O$ (3×), brine, dried ($Na_2SO_4$), filtered and concentrated. The crude material was purified via 3% EtOAc/hexane column to provide 0.1381 g (41% yield, 89% c.p.) of aryl iodide 8. The aryl iodide (0.1332 g, 0.348 mmol) and methyl propiolate (0.12 mL, 1.39 mmol) were added to a tube. The tube was evacuated and purged with argon (3×). The $Pd(PPh_3)_2Cl_2$ (0.0122 g, 0.0174 mmol), CuI (0.0066 g, 0.0348 mmol) and $K_2CO_3$ (0.0962 g, 0.696 mmol) were added. The tube was sealed and heated to 65° C. overnight. Upon cooling to room temperature the mixture was diluted with water and EtOAc. The layers were separated and the aqueous layer was washed with $H_2O$ (3×), brine, dried ($Na_2SO_4$), filtered and concentrated. The crude material was purified via 10% EtOAc/hexane column to afford 0.0154 g (13% yield) of TRV-1408. $^1$H NMR (500 MHz, CDCl3) δ=7.42 (s, 1H), 7.21-7.18 (m, 2H), 7.03-7.00 (m, 2H), 6.17 (s, 1H), 5.11 (s, 2H), 3.86 (s, 3H), 3.13 (s, 3H).

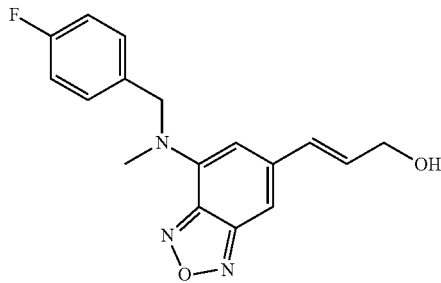

TRV-1409

To a stirred solution of TRV-1402 (0.5283 g, 1.55 mmol) in DCM (10 mL) at −78° C. was added DIBAL (3.6 mL, 1.0 M solution in hexane) dropwise. Once the addition was complete the reaction was warmed to −40° C. and stirred under argon until complete consumption of starting material. Quenched with a saturated solution of Rochelle's salt and stirred for 30 minutes. This mixture was extracted with EtOAc. The combined organic layers were washed with $H_2O$ (3×), brine, dried ($Na_2SO_4$), filtered and concentrated. The crude oil was purified via 50% EtOAc é hexane column to afford 0.3740 g (77% yield) of TRV-1409 as an orange oil. $^1$H NMR (500 MHz, CDCl3) δ=7.23-7.21 (m, 2H), 7.03 (s, 1H), 7.02-6.98 (m, 2H), 6.64 (d, J=15 Hz, 1H), 6.44 (dt, J=15, 5 Hz, 1H), 6.26 (s, 1H), 5.06 (s, 2H), 4.38 (dd, J=5 Hz, 2H), 3.11 (s, 3H).

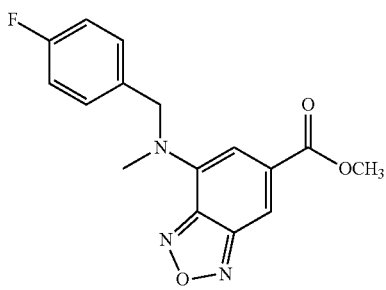

TRV-1410

6-bromo-N-(4-fluorobenzyl)-N-methylbenzo[c][1,2,5]oxadiazol-4-amine (0.1444 g, 0.43 mmol) was dissolved in THF (5 mL) and cooled to −78° C. nBuLi (0.23 mL, 0.45 mmol, 2.0 M solution of cyclohexane) was added dropwise and the mixture was stirred for 30 minutes. Methyl chloroformate (0.050 mL, 0.65 mmol) was then added and the reaction was allowed to slowly warm to room temperature. After re-cooling to 0° C. the reaction was quenched with saturated $NH_4Cl$ (aq). This mixture was then extracted with EtOAc. The combined organic layers were washed with $H_2O$ (3×), brine, dried ($Na_2SO_4$), filtered and concentrated. The crude material was purified via 15% EtOAc/hexane to afford 0.0234 g (17% yield) of TRV-1410. $^1$H NMR (500 MHz, CDCl3) δ=7.88 (d, J=5 Hz, 1H), 7.22-7.19 (m, 2H), 7.03-6.98 (m, 2H), 6.75 (s, 1H), 5.12 (s, 2H), 3.95 (s, 3H), 3.17 (s, 3H).

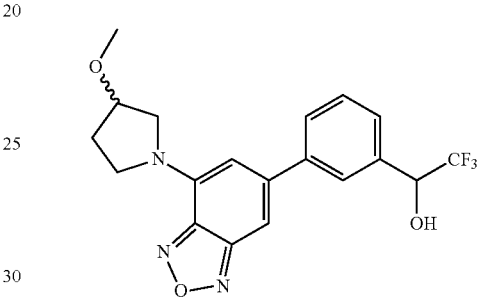

TRV-1411

To a solution of 6-bromo-4-chlorobenzo[c][1,2,5]oxadiazole (396 mg, 1.7 mmol) in NMP (3 mL) in a 4 dram vial was added 3-hydroxypyrrolidine hydrochloride (230 mg, 1.83 mmol) and triethylamine (710 µL, 5.1 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with $MgSO_4$ filtered and concentrated in vacuo. The crude aniline was used without further purification. To a stirring 0° C. solution of aniline (480 mg, 1.7 mmol) in NMP (10 mL) was added MeI (1.06 mL mg, 17 mmol) followed by NaH (200 mg, 8.5 mmol). With the cold bath in place the reaction was allowed to come to RT. After 16 hours the reaction was cautiously quenched with water, treated with saturated $NH_4Cl$ and extracted into EtOAc (3×20 mL). The combined organics were washed with HCl (2M) followed by brine, and then dried with $MgSO_4$ and concentrated in vacuo. The material obtained was used without further purification. To a solution of the afore mentioned ether (1.7 mmol) in DME (8 mL)/$Na_2CO_3$ (2.5 mL) was added 3-formyl-phenylboronic acid (382 mg, 2.6 mmol) and $Pd(P(Ph)_3)_4$ (80 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with $MgSO_4$ and concentrated in vacuo. The crude material was purified by flash chromatography (4:1 Hex/EtOAc) to give 415 mg of material. $^1$H NMR (500 MHz, $CDCl_3$) δ=10.11 (s, 1H), 8.15 (s, 1H), 7.91 (m, 2H), 7.64 (t, J=8 Hz, 1H), 7.14 (s, 1H), 6.14 (s, 1H), 4.94 (m, 1H), 3.95 (m, 4H), 3.41 (s, 3H), 2.17 (m, 2H). To a stirring solution of aldehyde (415 mg, 1.33 mmol) and Rupert's reagent (365 µL, 2.6 mmol) in DCM (10 mL) at 0° C. was added TBAF (0.2 mL, 1 M THF, 0.2 mmol). After 30 min at low temperature the cold bath was removed and the reaction was allowed to come to RT. After 3 hours an excess of TBAF was added and the reaction was diluted with DCM. The organic phases were washed with saturated NH₄Cl, brine, and then dried with MgSO₄ and concentrated in vacuo. The crude material was purified by flash column chromatography (10-30% EtOAc in Hex) to give 240 mg (48% yield) of TRV-1411, a 1:1:1:1 mixture of diastereomers due to the two chiral centers. $^1$H NMR (500 MHz, DMSO-D₆) δ=7.90 (s, 1H), 7.82 (dm, J=7 Hz, 1H), 7.53 (m, 2H), 7.29 (s, 1H), 6.93 (d, J=6 Hz, 1H), 6.29 (s, 1H), 5.28 (m, 1H), 4.18 (s, 1H), 3.87 (m, 3H), 3.77 (m, 1H), 2.15 (m, 2H).

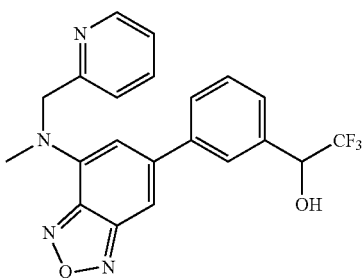

TRV-1412

To a solution of 6-bromo-4-chlorobenzo[c][1,2,5]oxadiazole (355 mg, 1.52 mmol) in NMP (3 mL) in a 4 dram vial was added N-methyl-N-(2-pyridinylmethyl)amine (204 mg, 1.67 mmol) and triethylamine (400 μL, 2.9 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO₄ filtered and concentrated in vacuo. The crude material was purified by flash column chromatography (4:1 Hex/EtOAc) to give 293 mg (60% yield) of aniline To a solution of this aniline (293 mg, 0.91 mmol) in DME (5 mL)/Na₂CO₃ (1.4 mL) was added 3-formyl-phenylboronic acid (202 mg, 1.4 mmol) and Pd(P(Ph)₃)₄ (50 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO₄ and concentrated in vacuo. The crude material was fused to SiO₂ (3 g) and purified by flash column chromatography (4:1 Hex/EtOAc) to give 280 mg of aldehyde. $^1$H NMR (500 MHz, CDCl₃) δ=10.01 (s, 1H), 8.60 (dm, J=4 Hz, 1H), 8.09 (t, J=2H, 1H), 7.93 (dt, J=7 Hz/2 Hz, 1H), 7.87 (dm, J=8 Hz, 1H), 7.64 (m, 2H), 7.28 (m, 2H), 7.20 (m, 1H), 6.39 (s, 1H), 5.28 (s, 2H), 3.37 (s, 3H). To a stirring solution of aldehyde (280 mg, 0.81 mmol) and Rupert's reagent (230 mg, 1.63 mmol) in DCM (10 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH₄Cl, brine, and then dried with MgSO₄ and concentrated in vacuo. The crude material was purified by flash column chromatography (10% EtOAc in Hex) to give 120 mg (35% yield) of TRV-1412. $^1$H NMR (500 MHz, DMSO-D₆) δ=8.51 (d, J=6 Hz, 1H), 7.87 (s, 1H), 7.80 (dm, J=8 Hz, 1H), 7.74 (td, J=8 Hz/2 Hz, 1H), 7.57 (m, 2H), 7.36 (s, 1H), 7.32 (d, J=8 Hz, 1H), 7.26 (m, 1H), 6.95 (d, J=5 Hz, 1H), 5.27 (m, 3H), 3.36 (s, 3H).

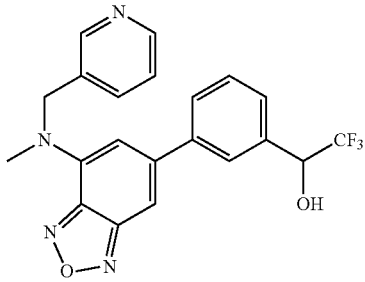

TRV-1413

To a solution of 6-bromo-4-chlorobenzo[c][1,2,5]oxadiazole (360 mg, 1.54 mmol) in NMP (3 mL) in a 4 dram vial was added N-methyl-N-(3-pyridinylmethyl)amine (207 mg, 1.69 mmol) and triethylamine (400 μL, 2.9 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO₄ filtered and concentrated in vacuo. The crude material was purified by flash column chromatography (5% EtOAc in DCM) to give 247 mg (50% yield) of aniline. $^1$H NMR (500 MHz, DMSO-D₆) δ=8.50 (d, J=2 Hz, 1H), 8.48 (dd, J=5 Hz/1 Hz, 1H), 7.64 (dm, J=8 Hz, 1H), 7.52 (d, J=1 Hz, 1H), 7.35 (dd, J=8 Hz/5 Hz, 1H), 6.35 (m, 1H), 5.17 (s, 2H), 3.21 (s, 3H). To a solution of aniline (247 mg, 0.77 mmol) in DME (4 mL)/Na₂CO₃ (1.1 mL) was added 3-formyl-phenylboronic acid (173 mg, 1.2 mmol) and Pd(P(Ph)₃)₄ (40 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO₄ and concentrated in vacuo to give 312 mg of crude aldehyde. To a stirring solution of aldehyde (0.77 mmol) and Rupert's reagent (400 mg, 2.8 mmol) in DCM (8 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH₄Cl, brine, dried with MgSO₄ and concentrated in vacuo. The crude material was purified by flash column chromatography (2% MeOH in DCM). $^1$H NMR (300 MHz, CDCl₃) δ=8.51 (m, 2H), 7.70-7.55 (m, 3H), 7.50-7.45 (m, 2H), 7.28 (m, 1H), 7.25 (m, 1H), 6.35 (s, 1H), 5.14 (m, 3H), 4.24 (s, broad, 1H), 3.19 (s, 3H).

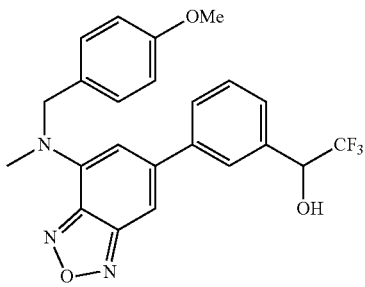

TRV-1414

To a solution of 6-bromo-4-chlorobenzo[c][1,2,5]oxadiazole (357 mg, 1.5 mmol) in NMP (3 mL) in a 4 dram vial was added 4-methoxybenzylamine (230 mg, 1.65 mmol) and triethylamine (400 μL, 2.9 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO$_4$ filtered and concentrated in vacuo. The crude aniline was used without further purification. To a stirring 0° C. solution of aniline (220 mg, 0.6 mmol) in NMP (5 mL) was added NaH (151 mg, 6.3 mmol). After the evolution of gas had ceased MeI (446 mg, 3.1 mmol) was added dropwise. With the cold bath in place the reaction was allowed to come to RT. After 16 hours the reaction was cautiously quenched with water, treated with saturated NH$_4$Cl and extracted into EtOAc (3×20 mL). The combined organics were washed with brine, dried with MgSO$_4$ and concentrated in vacuo. The aniline obtained was used without further purification. To a solution of aniline (0.6 mmol) in DME (4 mL)/Na$_2$CO$_3$ (1.0 mL) was added 3-formyl-phenylboronic acid (142 mg, 0.9 mmol) and Pd(P(Ph)$_3$)$_4$ (45 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO$_4$ and concentrated in vacuo to give 220 mg of crude material. $^1$H NMR (300 MHz, CDCl$_3$) δ=10.1 (s, 1H), 8.1 (s, 1H), 7.9 (m, 2H), 7.7 (m, 1H), 7.2 (m, 2H), 6.9 (d, J=6 Hz, 2H), 6.4 (m, 1H), 5.1 (s, 2H), 3.8 (s, 3H), 3.2 (s, 3H). To a stirring solution of aldehyde (220 mg, 0.59 mmol) and Rupert's reagent (168 mg, 1.2 mmol) in DCM (6 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (20% EtOAc in Hex). $^1$H NMR (300 MHz, CDCl$_3$) δ=7.7 (s, 1H), 7.6 (dt, J=7 Hz, 1 Hz, 1H), 7.5 (m, 2H), 7.19 (m, 3H), 6.8 (d, J=8 Hz, 2H), 6.3 (s, 1H), 5.1 (m, 1H), 5.0 (s, 2H), 3.8 (s, 3H), 3.2 (s, 3H).

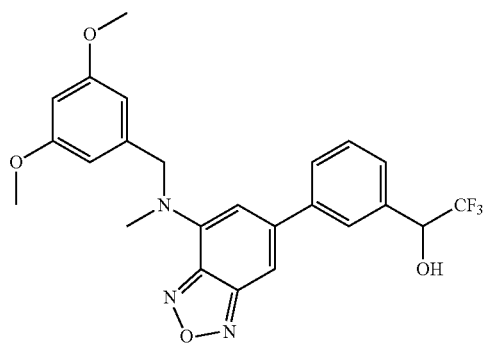

TRV-1415

To a solution of 6-bromo-4-chlorobenzo[c][1,2,5]oxadiazole (345 mg, 1.5 mmol) in NMP (3 mL) in a 4 dram vial was added 3,5-dimethoxybenzylamine (272 mg, 1.6 mmol) and triethylamine (600 μL, 4.3 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO$_4$ filtered and concentrated in vacuo. The crude material was used without further purification. To a stirring 0° C. solution of aniline (1.5 mmol) in NMP (5 mL) was added NaH (211 mg, 8.8 mmol). After the evolution of gas had ceased MeI (570 mg, 4 mmol) was added dropwise. With the cold bath in place the reaction was allowed to come to RT. After 16 hours the reaction was cautiously quenched with water, treated with saturated NH$_4$Cl and extracted into EtOAc (3×20 mL). The combined organics were washed with brine, dried with MgSO$_4$ and concentrated in vacuo. The crude material was fused to SiO$_2$ and flashed (10% EtOAc in Hex) to give 163 mg of material. To a solution of aniline (165 mg, 0.44 mmol) in DME (4 mL)/Na$_2$CO$_3$ (0.7 mL) was added 3-formyl-phenylboronic acid (98 mg, 0.9 mmol) and Pd(P(Ph)$_3$)$_4$ (40 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO$_4$ and concentrated in vacuo to give 277 mg. The crude material was used without further purification. To a stirring solution of aldehyde (277 mg, 0.4 mmol) and Rupert's reagent (125 mg, 0.8 mmol) in DCM (4 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material was fused to SiO$_2$ (3 g) purified by flash column chromatography (10-20% EtOAc in Hex). $^1$H NMR (500 MHz, CDCl$_3$) δ=7.7 (s, 1H), 7.6 (dt, 7 Hz, 1 Hz, 2H), 7.5 (m, 2H), 7.2 (s, 1H), 6.4 (m, 1H), 6.3 (m, 2H), 5.1 (m, 1H), 5.0 (s, 2H), 3.7 (s, 3H), 3.3 (s, 3H), 2.7 (s, broad, 1H)

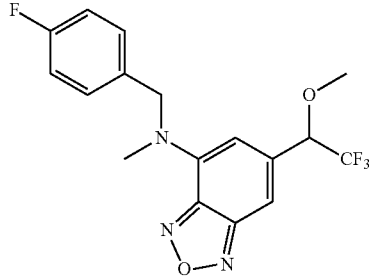

TRV-1416

TRV-1397 (0.0768 g, 0.22 mmol) was dissolved in THF (5 mL) and cooled to 0° C. NaH (0.0132 g, 0.33 mmol) was added and the suspension was stirred for 30 minutes. Iodomethane (0.03 mL, 0.44 mmol) was then added and the reaction was stirred overnight while warming to room temperature. The mixture was then re-cooled to 0° C. and quenched with saturated ammonium chloride. The mixture was extracted with EtOAc. The combined organic extracts were washed with water, brine, dried (Na$_2$SO$_4$), filtered and concentrated. The crude material was then purified via a 10% EtOAc/hexane column to afford 0.0259 g (32% yield) of TRV-1416 as orange oil. $^1$H NMR (500 MHz, CDCl3) δ=7.30-7.27 (m, 2H), 7.23 (s, 1H), 7.07-7.04 (m, 2H), 6.22 (s, 1H), 5.11 (s, 2H), 4.52 (q, J=5 Hz, 1H), 3.50 (s, 3H), 3.20 (s, 3H).

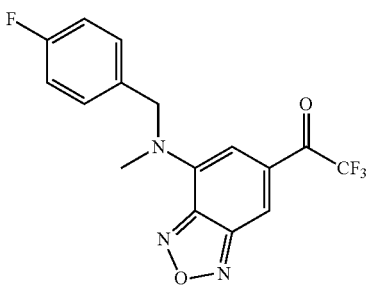

TRV-1417

To a solution of oxalyl chloride (0.032 mL, 0.37 mmol) in DCM (1 mL) at −78° C. was added a solution of DMSO (0.024 mL, 0.34 mmol) in DCM (1.1 mL). The solution was stirred for 5 minutes and then a solution of TRV-1397 (0.1097 g, 0.31 mmol) in DCM (1.0 mL) was added and the mixture was stirred an additional 15 minutes. TEA (0.22 mL, 1.55 mmol) was added in one portion, the reaction was stirred for 10 minutes at −78° C. and then allowed to warm to room temperature. The mixture was then diluted with water and ethyl acetate. The layers were separated and the aqueous layer was back-extracted. The combined organic layers were washed with brined, dried (Na$_2$SO$_4$), filtered and concentrated to give the crude trifluoroketone. This material was then purified via flash chromatography (30% EtOAc/hexane) to give 0.0356 g (32% yield) of TRV-1417 as orange oil. $^1$H NMR (500 MHz, CDCl3) δ=7.93 (s, 1H), 7.23-7.20 (m, 2H), 7.04-7.00 (m, 2H), 6.67 (s, 1H), 5.16 (s, 2H), 3.23 (s, 3H).

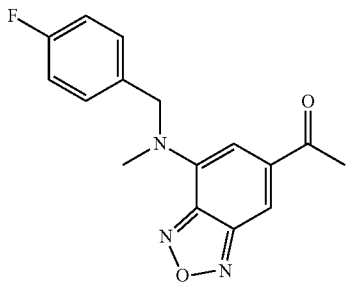

TRV-1418

TRV-1421 (0.3511 g, 1.17 mmol) was dissolved in DCM (50 mL) and Dess-Martin reagent (1.4845 g, 3.5 mmol) was added. The reaction was stirred for 40 minutes and then was quenched with saturated NaHCO$_3$ (aq) and excess Na$_2$S$_2$O$_3$. The mixture was stirred until all the solids dissolved and then was extracted several times with DCM. The combined organic extracts were washed with saturated NaHCO$_3$, dried (NA$_2$SO$_4$), filtered and concentrated. The crude material was purified via 10% EtOAc/hexane column to afford 0.2322 g (66% yield) of TRV-1418 as orange solid. $^1$H NMR (500 MHz, CDCl3) δ=7.74 (s, 1H), 7.22-7.19 (m, 2H), 7.02-6.97 (m, 2H), 6.74 (s, 1H), 3.17 (s, 3H), 2.65 (s, 3H).

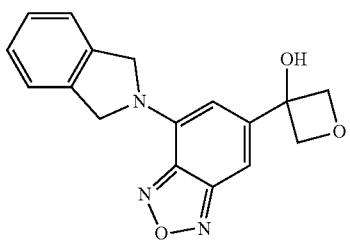

TRV-1419

To a stirring solution of 6-bromo-4-(isoindolin-2-yl)benzo[c][1,2,5]oxadiazole (158 mg, 0.3 mmol) in THF (5 mL) at −78° C. was added n-BuLi (0.25 mL, 2 M). After stirring for 30 min at low temperature oxatenanone (72 mg, 1 mmol) dissolved in THF (4 mL). The cold bath was removed and the reaction was allowed to come to RT and monitored by TLC. The reaction was worked up with dilute HCl and extracted into EtOAc (3×20 mL). The organic phase was dried with MgSO$_4$ and concentrated in vacuo. The crude material was fused to SiO$_2$ (3 g) and purified by flash column chromatography (DCM modified with MeOH) to give 40 mg of material. $^1$H NMR (300 MHz, DMSO-D$_6$) δ=7.5 (m, 2H), 7.4 (m, 2H), 7.2 (s, 1H), 6.6 (s, 1H) 6.5 (s, 1H), 6.5 (s, 1H), 5.1 (s, 4H), 4.8 (m, 4H).

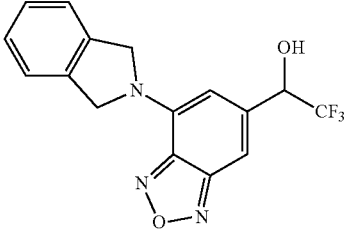

TRV-1420

To a stirring solution of 6-bromo-4-(isoindolin-2-yl)benzo[c][1,2,5]oxadiazole (98 mg, 0.3 mmol) in THF (3 mL) at −78° C. was added n-BuLi (0.15 mL, 2 M). After stirring for 30 min at low temperature dry DMF (0.5 mL) was added and the reaction was stirred for an additional hour before it was quenched with MeOH followed by HCl (4 M). The reaction was allowed to come to RT, diluted with water and extracted into DCM (3×20 mL). The organic phase was dried with MgSO$_4$ and concentrated in vacuo. The crude material was fused to SiO$_2$ (3 g) and purified by flash column chromatography (1:1 DCM/Hex) to give 71 mg of material. To a stirring solution of aldehyde (71 mg, 0.26 mmol) and Rupert's reagent (74 mg, 0.52 mmol) in DCM (3 mL) at 0° C. was added TBAF (0.1 mL, 1 M THF, 0.1 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material purified by flash column chromatography (DCM). $^1$H NMR (500 MHz, DMSO-D$_6$) δ=7.50 (m, 2H), 7.37 (m, 2H), 7.27 (s, 1H), 7.11 (d, J=5 Hz, 1H), 6.32 (s, 1H), 5.29 (m, 1H), 5.09 (s. 4H).

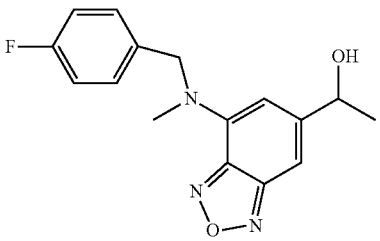

TRV-1421

6-bromo-N-(4-fluorobenzyl)-N-methylbenzo[c][1,2,5]oxadiazol-4-amine (0.8514 g, 2.53 mmol) was dissolved in THF (25 mL) and cooled to −78° C. nBuLi (1.3 mL, 2.0 M solution in cyclohexane) was added dropwise at −78° C. and the reaction was then stirred for 15-20 minutes. Acetaldehyde (0.21 mL, 3.8 mmol) were then added and the reaction was allowed to slowly warm to room temperature. The solution was re-cooled to 0° C. and quenched with saturated ammonium chloride. The mixture was extracted with EtOAc. The combined organic extracts were washed with water, brine, dried ($Na_2SO_4$), filtered and concentrated. The crude material was then purified via a 40% EtOAc/hexane column to produce 0.5340 g (70% yield) of TRV-1421 as orange oil. $^1$H NMR (500 MHz, CDCl3) δ=7.24-7.21 (m, 2H), 7.10 (s, 1H), 7.02-6.98 (m, 2H), 6.16 (s, 1H), 5.06 (s, 2H), 4.87 (q, J=5 Hz, 1H), 3.11 (s, 3H), 1.90 (s, 1H), 1.51 (d, J=5 Hz, 3H).

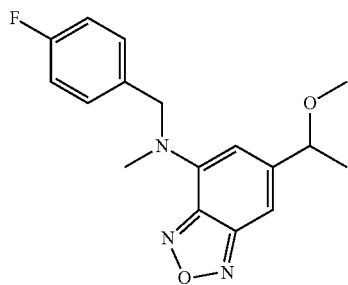

TRV-1422

TRV-1421 (0.1381 g, 0.458 mmol) was dissolved in THF (5 mL) and cooled to 0° C. NaH (0.0275 g, 0.687 mmol) was added and the suspension was stirred for 30 minutes. Iodomethane (0.06 mL, 0.916 mmol) was then added and the reaction was allowed to warm to room temperature. The solution was re-cooled to 0° C. and quenched with saturated ammonium chloride. The mixture was extracted with EtOAc. The combined organic extracts were washed with water, brine, dried ($Na_2SO_4$), filtered and concentrated. The crude material was then purified via a 10% EtOAc/hexane column to afford 0.1243 g (86% yield) of TRV-1422 as yellow oil. $^1$H NMR (500 MHz, CDCl3) δ=7.25-7.23 (m, 2H), 7.02 (s, 1H), 7.02-6.98 (m, 2H), 6.14 (s, 1H), 5.07 (d, J=15 Hz, 1H), 5.03 (d, J=15 Hz, 1H), 4.27 (q, J=5 Hz, 1H), 3.26 (s, 3H), 3.12 (s, 3H), 1.44 (d, J=5 Hz, 3H).

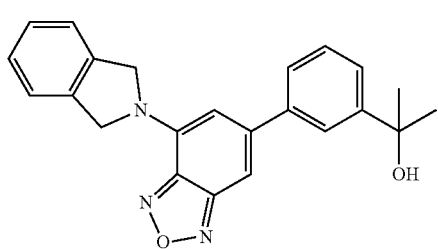

TRV-1423

To a solution of 6-bromo-4-(isoindolin-2-yl)benzo[c][1,2,5]oxadiazole (647 mg, 2.0 mmol) in DME (10 mL)/ $Na_2CO_3$ (3 mL) was added 3-acetyl-phenylboronic acid (500 mg, 0.9 mmol) and $Pd(P(Ph)_3)_4$ (90 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with $MgSO_4$ and concentrated in vacuo. The crude material was dissolved in DCM and eluted through a short $SiO_2$ plug to give 456 mg of material which was suitable for further reactions. $^1$H NMR (300 MHz, $CDCl_3$) δ=8.3 (m, 1H), 8.0 (d, J=8 Hz, 1H), 7.8 (d, J=8 Hz, 1H), 7.6 (t, J=8 Hz, 1H), 7.4 (m, 4H), 7.2 (s, 1H), 6.2 (s, 1H), 5.1 (s, 4H), 2.7 (s, 3H). To a stirring solution of ketone (222 mg, 0.6 mmol) dissolved in THF (4 mL) at 0° C. was added MeMgBr (0.9 mL, 0.9 mmol). After 30 minutes at low temperature the reaction was warmed to RT and quenched with dilute HCl and extracted into EtOAc (3×20 mL). The organic phase was dried with $MgSO_4$ and concentrated in vacuo. The crude material was purified by flash column chromatography (DCM). $^1$H NMR (300 MHz, $CDCl_3$) δ=7.8 (m, 1H), 7.5 (m, 2H), 7.4-7.3 (m, 5H), 7.2 (s, 1H), 5.1 (s, 4H), 1.0 (s, 1H), 1.6 (s, 6H).

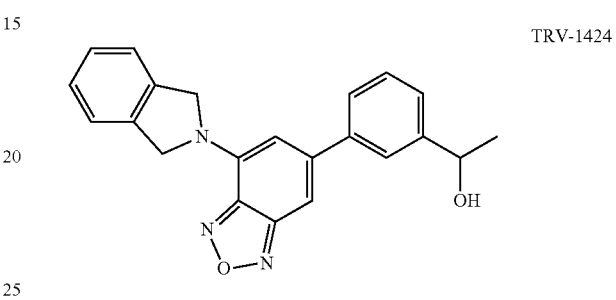

TRV-1424

To a solution of 6-bromo-4-(isoindolin-2-yl)benzo[c][1,2,5]oxadiazole (647 mg, 2.0 mmol) in DME (10 mL)/ $Na_2CO_3$ (3 mL) was added 3-acetyl-phenylboronic acid (500 mg, 0.9 mmol) and $Pd(P(Ph)_3)_4$ (90 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with $MgSO_4$ and concentrated in vacuo. The crude material was dissolved in DCM and eluted through a short $SiO_2$ plug to give 456 mg of material which was suitable for further reactions. $^1$H NMR (300 MHz, $CDCl_3$) δ=8.3 (m, 1H), 8.0 (d, J=8 Hz, 1H), 7.8 (d, J=8 Hz, 1H), 7.6 (t, J=8 Hz, 1H), 7.4 (m, 4H), 7.2 (s, 1H), 6.2 (s, 1H), 5.1 (s, 4H), 2.7 (s, 3H). To a stirring solution of ketone (230 mg, 0.65 mmol) dissolved in MeOH/THF at 0° C. was added $NaBH_4$ (80 mg, 2 mmol). Once the initial exothermic reaction had subsided the cold bath was removed and the reaction was allowed to come to RT. The reaction was stirred at RT for 1 hour and then poured onto water, after 30 min the reaction was acidified and extracted into EtOAc (3×20 mL). The organic phase was dried with $MgSO_4$ and concentrated in vacuo. The crude material was purified by flash column chromatography (DCM). $^1$H NMR (300 MHz, $CDCl_3$) δ=7.7 (s, 1H), 7.6 (dt, J=10 Hz, 1 Hz), 7.5-7.3 (m, 6H), 7.1 (s, 1H), 6.2 (s, 1H), 5.2 (s, 4H), 5.0 (m, 1H), 1.9 (m, 1h), 1.5 (d, J=6 Hz, 3H).

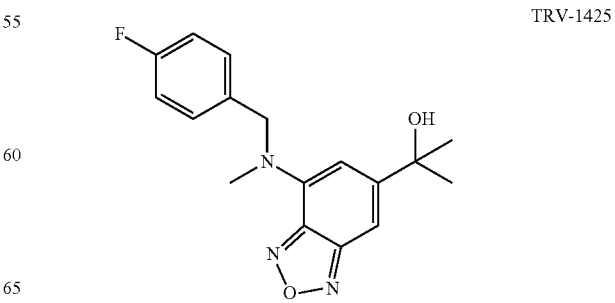

TRV-1425

TRV-1418 (0.1195 g, 0.399 mmol) was dissolved in THF (5 mL) and cooled to 0° C. MeMgBr (0.52 mL, 1.0 M solution in Bu$_2$O) was added dropwise and the reaction was stirred until complete by TLC. The solution was re-cooled to 0° C. and quenched with saturated ammonium chloride. The mixture was extracted with EtOAc. The combined organic extracts were washed with water, brine, dried (Na$_2$SO$_4$), filtered and concentrated. The crude material was then purified via two consecutive 30% EtOAc/hexane columns to afford 0.0626 g (50% yield) of TRV-1425 as an orange oil in approximately 90% cp. $^1$H NMR (500 MHz, CDCl3) δ=7.23-7.20 (m, 2H), 7.19 (s, 1H), 7.02-6.95 (m, 2H), 6.33 (s, 1H), 5.04 (s, 2H), 3.12 (s, 3H), 1.59 (s, 6H).

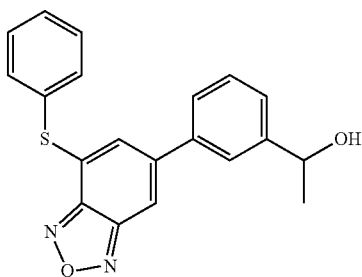

TRV-1426

To a solution of 6-bromo-4-chlorobenzo[c][1,2,5]oxadiazole (347 mg, 1.49 mmol) in NMP (3 mL) in a 4 dram vial was added benzenethiol (104 mg, 1.83 mmol) and triethylamine (400 µL, 2.8 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO$_4$ filtered and concentrated in vacuo. The crude material was purified by flash column chromatography (DCM) to give 264 mg (65% yield). $^1$H NMR (500 MHz, CDCl$_3$) δ=7.8 (m, 1H), 7.6 (m, 2H), 7.5 (m, 3H), 6.7 (m, 1H). To a solution of thioether (220 mg, 0.7 mmol) in DME (6 mL)/Na$_2$CO$_3$ (1.5 mL) was added 3-acetyl-phenylboronic acid (185 mg, 1.1 mmol) and Pd(P(Ph)$_3$)$_4$ (75 mg). The flask was then fitted with a reflux condenser, purged with argon and heated to 115° C. O/N. The reaction was worked up by diluting with 1 M NaOH (40 mL) and extracting with EtOAc (3×20 mL). The organic phase was washed with brine, dried with MgSO$_4$ and concentrated in vacuo. The crude material was purified by pushing through a SiO$_2$ plug with DCM. $^1$H NMR (500 MHz, CDCl$_3$) δ=8.0 (s, 1H), 7.9 (m, 1H), 7.7 (s, 1H), 7.6 (m, 3H), 7.5 (m, 1H), 7.5 (m, 3H), 7.1 (m, 1H), 2.6 (s, 3H). To a stirring solution of ketone dissolved in MeOH/THF at 0° C. was added NaBH$_4$ (80 mg, 2 mmol). Once the initial exothermic reaction had subsided the cold bath was removed and the reaction was allowed to come to RT. The reaction was stirred at RT for 1 hour and then poured onto water, after 30 min the reaction was acidified and extracted into EtOAc (3×20 mL). The organic phase was dried with MgSO$_4$ and concentrated in vacuo. The crude material was purified by flash column chromatography (DCM). $^1$H NMR (500 MHz, CDCl$_3$) δ=7.7 (d, J=1 Hz, 1H), 7.6 (m, 2H), 7.5-7.3 (m, 7H), 7.1 (d, J=1 Hz, 1H), 4.9 (m, 1H), 1.8 (d, J=3 Hz, 1H), 1.5 (d, J=6 Hz, 3H).

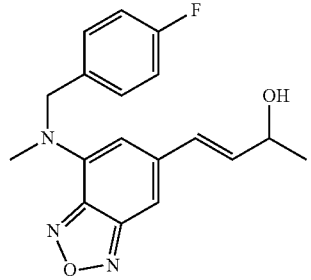

TRV-1427

TRV-1409 (0.2077 g, 0.663 mmol) was dissolved in DCM (37 mL) and then DMP (0.8436 g, 1.99 mmol) was added in one portion. The reaction was stirred for 3 hours and then quenched with saturated NaHCO$_3$ (aq) and excess Na$_2$S$_2$O$_3$. This mixture was stirred until all the solids dissolved and then extracted with DCM. The combined organic layers were dried (Na$_2$SO$_4$), filtered and concentrated to afford the crude aldehyde. Purification via flash chromatography (20% EtOAc/hexane) afforded 0.0556 g (27% yield) of the aldehyde 4. This aldehyde (0.0532 g, 0.171 mmol) was dissolved in THF (5 mL) and cooled to 0° C. MeMgBr (0.19 mL, 1.0 M solution in Et$_2$O) was added dropwise and the reaction was stirred until complete by TLC. The reaction was then quenched with NH$_4$Cl and extracted with EtOAc. The combined organic extracts were washed with water, brine, dried (Na$_2$SO$_4$), filtered and concentrated. The crude material was then purified with flash chromatography to afford 0.0262 g (47% yield) of TRV-1427 as orange oil. $^1$H NMR (500 MHz, CDCl3) δ=7.23-7.21 (m, 2H), 7.03-6.99 (m, 3H), 6.59 (d, J=15 Hz, 1H), 6.34 (dd, J=15, 5 Hz, 1H), 6.26 (s, 1H), 4.54 (m, 1H), 3.10 (s, 3H), 1.62 (d, J=5 Hz, 1H), 1.40 (d, J=10 Hz, 3H).

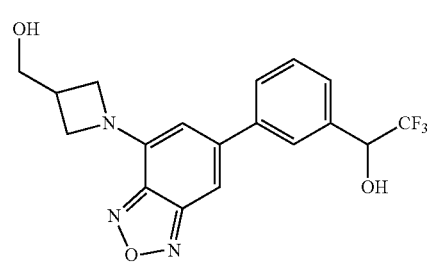

TRV-1428

In a sealed vial 4,6-dibromobenzo[c][1,2,5]oxadiazole (2.2 g, 8 mmol) was combined with, (888 mg, 8.8 mmol), Et$_3$N (3.3 mL, 24 mmol), and NMP (13 mL). The mixture was heated to 85° C. for 2 days. At this time the reaction was diluted with 1 M NaOH (150 mL) and the insoluble material was removed by filtration. The desired compound was precipitated by the addition of HCl (conc.) to the aqueous layer and isolated by vacuum filtration to give 1-(6-bromobenzo[c][1,2,5]oxadiazol-4-yl)azetidine-3-carboxylic acid (1.7 g), which was used without further purification. The acid (1.5 g, 5 mmol) was dissolved in THF (50 mL) and cooled to 0° C. To this was added BH$_3$-THF (10 mL, 10 mmol). The reaction was allowed to come to room temperature overnight. The next day the reaction was quenched with AcOH and extracted into EtOAc. The organic layer was washed with 1 M NaOH until the washings remained litmus blue and then concentrated in vacuo. The crude material was fused to SiO$_2$ and purified by flash column chromatography (3:2 Hex:EtOAc) to give 800 mg of (1-(6-bromobenzo[c][1,2,5]oxadiazol-4-yl)azetidin-3-yl)methanol (56% yield). $^1$H NMR (500 MHz, CDCl$_3$) δ=7.05 (s, 1H), 6.11 (s, 1H), 5.30 (s, 1H), 4.11 (t, J=8 Hz, 2H), 3.85 (m, 4H), 3.00 (m, 1H). To a solution of the afore mentioned alcohol (400 mg, 1.4 mmol) in DME (7 mL)/Na$_2$CO$_3$ (2.1 mL) was added 3-formyl-phenylboronic acid (315 mg, 2.1 mmol) and Pd(P(Ph)$_3$)$_4$ (50 mg). The flask was then fitted with a reflux condenser, purged with argon and heated to 115° C. O/N. The reaction was worked up by pouring into 1 M NaOH (150 mL) and isolating the resultant solids by vacuum filtration. The crude material was purified by plugging through SiO$_2$ (50% EtOAc in Hex) to give 350 mg of material which was used as is. To a stirring solution of aldehyde (400 mg, 1.4 mmol) and Rupert's reagent (483 mg, 3.3 mmol) in DCM (13 mL) at 0° C. was added TBAF (0.1 mL, 1 M THF, 0.2 mmol). After 30 min at low temperature the cold bath was removed and the reaction was allowed to come to RT. After stirring overnight an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (30% EtOAc in Hex) to give 150 mg (34% yield). $^1$H NMR (500 MHz, CDCl$_3$) δ=7.72-7.66 (m, 2H), 7.5 (m, 2H), 7.14 (s, 1H), 6.04 (s, 1H), 5.11 (m, 1H), 4.41 (t, J=8 Hz, 2H), 4.15 (dd, 2H), 3.93 (d, J=5 Hz, 2H), 3.06 1H), 2.82 (s, broad), 1.63 (s, broad).

TRV-1429

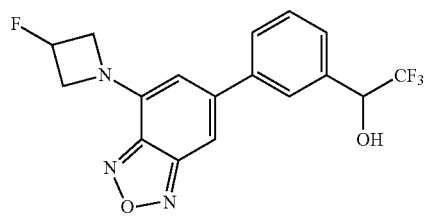

1-(6-bromobenzo[c][1,2,5]oxadiazol-4-yl)azetidin-3-ol (574 mg, 2.1 mmol) was dissolved in DCM (25 mL) and cooled to −78° C. and DAST (421 uL, 3.2 mmol) was added dropwise and the cold bath was removed. After 2 h at room temperature the reaction was cooled to 0° C. and quenched with MeOH. The reaction mixture was then diluted with water and extracted with DCM. The combined extracts were dried (MgSO$_4$) and concentrated in vacuo. The residue was purified by flash column chromatography (50% DCM in Hex) to give product as a yellow solid (160 mg, 27% yield). $^1$H NMR (500 MHz, CDCl$_3$) δ=7.27 (s, 1H), 5.96 (s, 1H), 5.51 (dm, $^2$J$_{HF}$=57 Hz, 1H), 4.56 (m, 2H), 4.42 (dm, $^3$J$_{HF}$=23 Hz, 2H). To a solution of aniline (330 mg, 1.2 mmol) in DME (7 mL)/Na$_2$CO$_3$ (1.8 mL) was added 3-formyl-phenylboronic acid (270 mg, 1.9 mmol) and Pd(P(Ph)$_3$)$_4$ (50 mg). The flask was then fitted with a reflux condenser, purged with argon and heated to 115° C. O/N. The reaction was worked up by pouring into 1 M NaOH (150 mL) and vacuum isolating the resultant solids. The crude material was purified by plugging through SiO$_2$ (20% EtOAc in Hex) and used without further purification. To a stirring solution of aldehyde (about 1.0 mmol) and Rupert's reagent (348 mg, 2.0 mmol) in DCM (13 mL) at 0° C. was added TBAF (0.1 mL, 1 M THF, 0.2 mmol). After 30 min at low temperature the cold bath was removed and the reaction was allowed to come to RT. After stirring overnight an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (25% EtOAc in Hex) to give 300 mg (80% yield). $^1$H NMR (500 MHz, CDCl$_3$) δ=7.72 (s, 1H), 7.66 (dm, J=10 Hz, 1H), 7.51 (m, 2H), 7.23 (s, 1H), 6.12 (s, 1H), 5.53 (dm, $^2$J$_{HF}$=56 Hz, 1H), 5.14 (m, 1H), 4.64 (m, 2H), 4.42 (ddm, J=23 Hz/10 Hz, 2H), 2.73 (s, 1H).

TRV-1430

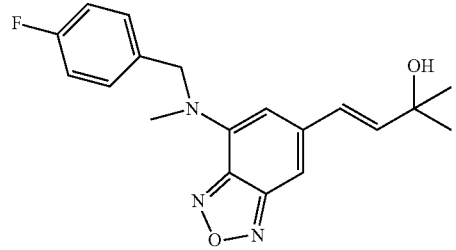

TRV-1402 (0.1992 g, 0.58 mmol) was dissolved in THF (10 mL) and cooled to −78° C. MeLi (0.80 mL, 1.6 M solution in Et$_2$O) was added dropwise and the reaction was allowed to warm to room temperature overnight. The mixture was then re-cooled to 0° C. and quenched with saturated ammonium chloride. This mixture was extracted three times with EtOAc. The combined organic extracts were washed with water, brine, dried (Na$_2$SO$_4$), filtered and concentrated to give the crude alcohol. This material was then purified via chromatography (30% EtOAc/hexane) to afford 0.0843 g (43% yield) of orange oil. $^1$H NMR (500 MHz, CDCl3) δ=7.23-7.21 (m, 2H), 7.03 (s, 1H), 7.02-6.98 (m, 2H), 6.61 (d, J=15 Hz, 1H), 6.42 (d, J=15 Hz, 1H), 6.25 (s, 1H), 5.08 (s, 2H), 3.10 (s, 3H), 1.45 (s, 6H).

TRV-1431

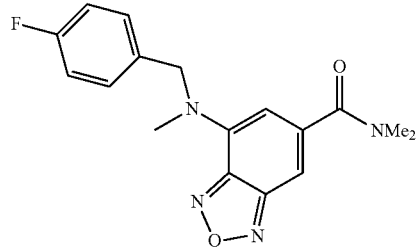

6-bromo-N-(4-fluorobenzyl)-N-methylbenzo[c][1,2,5]oxadiazol-4-amine (0.2771 g, 0.82 mmol) was dissolved in THF (10 mL) and cooled to −78° C. nBuLi (0.43 mL, 2.0 M solution in cyclohexane) was added dropwise and the mixture was stirred for 30 minutes before adding N,N-dimethylcarbamyl chloride (0.10 mL, 1.1 mmol) dropwise. The mixture was then allowed to warm to room temperature overnight. The mixture was then re-cooled to 0° C. and quenched with saturated ammonium chloride. This mixture was extracted three times with EtOAc. The combined organic extracts were washed with water, brine, dried (Na$_2$SO$_4$), filtered and concentrated to give the crude amide. Final purification of this material was with a 50% EtOAc/ hexane column to afford 16.6 mg (6.2% yield) of orange oil. $^1$H NMR (500 MHz, CDCl3) δ=7.23-7.20 (m, 2H), 7.08 (s, 1H), 7.03-6.99 (m, 2H), 6.12 (s, 1H), 5.11 (s, 2H), 3.14 (s, 3H), 3.12 (s, 3H), 3.01 (s, 3H).

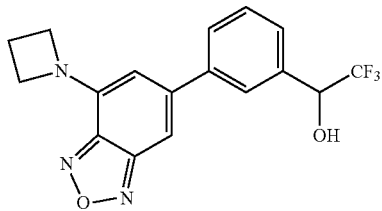

TRV-1432

In a sealed vial 4,6-dibromobenzo[c][1,2,5]oxadiazole (834 mg, 3 mmol) was combined with azetidine hydrochloride (309 mg, 3.3 mmol), Et$_3$N (1.25 mL, 9 mmol), and NMP (6 mL). The mixture was heated to 85° C. for 2 days. The crude material was precipitated by pouring the reaction mixture into water (150 mL). The crude material was plugged through SiO$_2$ (10% EtOAc in Hex) to give (540 mg) an orange solid which NMR showed to be a 2:1 mixture of starting material and 4-(azetidin-1-yl)-6-bromobenzo[c][1,2,5]oxadiazole. $^1$H NMR (500 MHz, CDCl$_3$) δ=7.05 (s, 1H), 5.85 (s, 1H), 4.33 (m, 4H), 2.53 (m, 2H). To a solution of 4-(azetidin-1-yl)-6-bromobenzo[c][1,2,5]oxadiazole (322 mg, 1.27 mmol) in DME (7 mL)/Na$_2$CO$_3$ (2.0 mL) was added 3-formyl-phenylboronic acid (286 mg, 1.9 mmol) and Pd(P(Ph)$_3$)$_4$ (50 mg). The flask was then fitted with a reflux condenser, purged with argon and heated to 115° C. O/N. The reaction was worked up by pouring into 1 M NaOH (150 mL) and vacuum isolating the resultant solids. The crude material was purified by plugging through SiO$_2$ (DCM) to give 280 mg of material which was used as is. To a stirring solution of the aldehyde (411 mg, 1.33 mmol) and Rupert's reagent (378 mg, 2.7 mmol) in DCM (13 mL) at 0° C. was added TBAF (0.2 mL, 1 M THF, 0.2 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (DCM) to give 477 mg (94% yield). $^1$H NMR (500 MHz, CDCl$_3$) δ=7.72 (s, 1h), 7.66 (m, 1H), 7.52 (m, 2H), 7.13 (s, 1H), 6.01 (s, 1H), 5.12 (q, J=7 Hz, 1H), 4.35 (t, J=8 Hz, 4H), 2.74 (s, br, 1H), 2.53 (p, J=7 Hz, 2H).

denser was fitted and the reaction gently refluxed for 24 h. At this time the reaction was diluted with EtOAc (200 mL) and extracted with water (3×100 mL). The crude material was fused to SiO$_2$ and purified by flash column chromatography (DCM) to give essentially a quantitative yield (2.08 mmol). The ester (650 mg, 2.08 mmol) was dissolved in THF (20 mL) and cooled to 0° C. To this was added MeMgBr (6 mL, 6 mmol). After 30 min at low temperature the reaction was brought to RT and followed by TLC. When the reaction was deemed complete the mixture was cooled back to 0° C. and cautiously quenched with aqueous NH$_4$Cl. The mixture was then extracted into EtOAc (3×100 mL), dried with MgSO$_4$ and concentrated in vacuo. The crude material was fused to SiO$_2$ and purified by flash column chromatography (20% Acetone in Hex) to give 474 mg of 2-(1-(6-bromobenzo[c][1,2,5]oxadiazol-4-yl)azetidin-3-yl) propan-2-ol (73% yield). $^1$H NMR (500 MHz, CDCl$_3$) δ=7.20 (s, 1H), 5.89 (s, 1H), 4.26 (m, 4H), 2.87 (m, 1H), 1.38 (s, 1H), 1.26 (s, 6H). To a stirring solution of the tertiary alcohol (223 mg, 0.71 mmol) dissolved in THF (10 mL) and cooled to 0° C. was added NaH (600 mg, 20 mmol). Once the initial bubbling had subsided MeI (1.14 g, 8 mmol) was added dropwise and the reaction mixture was left to come to RT. After 18 h the reaction was cooled back to 0° C. and NH$_4$Cl was cautiously added. The reaction mixture was extracted with EtOAc (3×50 mL), washed with brine, (1×50 mL) and concentrated in vacuo. The crude material was then purified by flash column chromatography (10% Acetone in Hex). To a solution of the ether (193 mg, 0.6 mmol) in DME (4 mL)/Na$_2$CO$_3$ (2M, 0.9 mL) was added 3-formyl-phenylboronic acid (133 mg, 0.9 mmol) and Pd(P(Ph)$_3$)$_4$ (40 mg). The flask was then fitted with a reflux condenser, purged with argon and heated to 110° C. O/N. The reaction was worked up by pouring into 1 M NaOH (150 mL) and vacuum isolating the resultant solids. The crude aldehyde was purified by plugging through SiO$_2$ (20% EtOAc in Hex) to give 184 mg of material which was used as is. To a stirring solution of aldehyde (400 mg, 1.4 mmol) and Rupert's reagent (483 mg, 3.3 mmol) in DCM (13 mL) at 0° C. was added TBAF (0.1 mL, 1 M THF, 0.2 mmol). After 30 min at low temperature the cold bath was removed and the reaction was allowed to come to RT. After stirring overnight an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (30% EtOAc in Hex) to give 90 mg (41% yield). $^1$H NMR (500 MHz, CDCl$_3$) δ=7.72 (s, 1H), 7.66 (m, 1H), 7.50 (m, 2H), 7.11 (s, 1H), 6.01 (s, 1H), 5.11 (m, 1H), 4.25 (m, 4H), 3.24 (s, 3H), 2.96 (m, 1H)

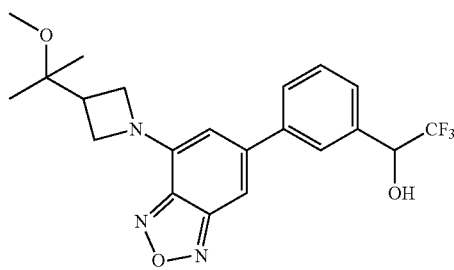

TRV-1433

1-(6-bromobenzo[c][1,2,5]oxadiazol-4-yl)azetidine-3-carboxylic acid (≈600 mg, 2 mmol) was dissolved in MeOH (100 mL) and H$_2$SO$_4$ (2 drops) were added. A reflux con-

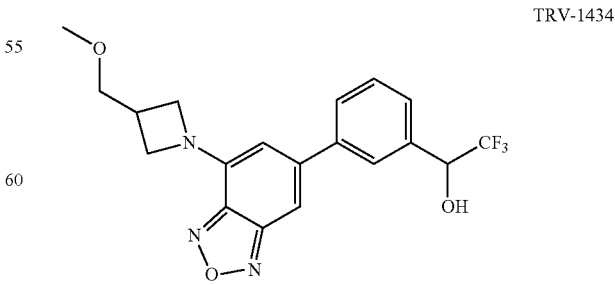

TRV-1434

To a stirring solution of (1-(6-bromobenzo[c][1,2,5]oxadiazol-4-yl)azetidin-3-yl)methanol (427 mg, 1.58 mmol)

dissolved in NMP (10 mL) and cooled to 0° C. was added NaH (758 mg, 20 mmol). Once the initial bubbling had subsided MeI (2.24 g, 10 mmol) was added dropwise and the reaction mixture was left to come to RT. After 18 h the reaction was cooled back to 0° C. and NH$_4$Cl was cautiously added. The reaction mixture was extracted with EtOAc (3×50 mL), washed with brine, (1×50 mL) and concentrated in vacuo. The crude material was then purified by flash column chromatography (10% EtOAc in Hex). $^1$H NMR (500 MHz, CDCl$_3$) δ=7.16 (s, 1H), 5.86 (s, 1H), 4.3 (m, 2H), 4.09 (m, 2H), 3.6 (d, J=6 Hz 2H), 3.40 (s, 3H), 3.08 (m, 1H). To a solution of the methyl ether (245 mg, 0.8 mmol) in DME (5 mL)/Na$_2$CO$_3$ (2M, 1.2.0 mL) was added 3-formyl-phenylboronic acid (184 mg, 1.9 mmol) and Pd(P(Ph)$_3$)$_4$ (40 mg). The flask was then fitted with a reflux condenser, purged with argon and heated to 110° C. O/N. The reaction was worked up by pouring into 1 M NaOH (150 mL) and vacuum isolating the resultant solids. The crude material was purified by plugging through SiO$_2$ (DCM) to give 214 mg of aldehyde which was used as is. $^1$H NMR (500 MHz, CDCl$_3$) δ=10.11 (s, 1H), 8.12 (s, 1H), 7.94 (d, J=8 Hz, 1H), 7.88 (d, J=8 Hz, 1H), 7.65 (t, J=8 Hz, 1H), 7.17 (s, 1H), 6.03 (s, 1H), 4.42 (m, 2H), 4.13 (m, 2H), 3.65 (d, J=6 Hz, 2H), 3.41 (s, 3H), 3.11 (m, 1H). To a stirring solution of the aldehyde (214 mg, 1.33 mmol) and Rupert's reagent (298 mg, 2.1 mmol) in DCM (13 mL) at 0° C. was added TBAF (0.2 mL, 1 M THF, 0.2 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (30% EtOAc in Hex) to give 150 mg (94% yield). $^1$H NMR (500 MHz, CDCl$_3$) δ=7.71 (m, 1H), 7.64 (m, 1H), 7.51 (m, 2H), 7.13 (s, 1H), 6.02 (s, 1H), 5.11 (m 1H), 4.38 (t, J=8 Hz, 2H), 4.11 (m, 2H), 3.64 (d, J=7 Hz, 2H), 3.41 (s, 3H), 3.09 (m, 1H).

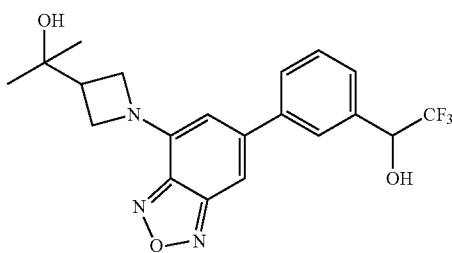

TRV-1435

1-(6-bromobenzo[c][1,2,5]oxadiazol-4-yl)azetidine-3-carboxylic acid (250 mg, 0.8 mmol) in DME (5 mL)/Na$_2$CO$_3$ (2M, 1.2 mL) was added 3-formyl-phenylboronic acid (181 mg, 1.2 mmol) and Pd(P(Ph)$_3$)$_4$ (50 mg). The flask was then fitted with a reflux condenser, purged with argon and heated to 110° C. O/N. The reaction was worked up by pouring into 1 M NaOH (150 mL) and vacuum isolating the resultant solids. The crude aldehyde was purified by plugging through SiO$_2$ (30% EtOAc in Hex) to give 211 mg of material which was used as is. To a stirring solution of aldehyde (211 mg, 0.63 mmol) and Rupert's reagent (266 mg, 1.88 mmol) in DCM (10 mL) at 0° C. was added TBAF (0.2 mL, 1 M THF, 0.2 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (20-40% EtOAc gradient in Hex) to give 70 mg (27% yield). $^1$H NMR (500 MHz, CDCl$_3$) δ=7.71 (s, 1H), 7.64 (m, 1H), 7.49 (m, 2H), 7.13 (s, 1H), 6.04 (s, 1H), 5.12 (s, br, 1H), 4.33 (t, J=8 Hz, 2H), 4.25 (m, 2H), 2.91 (m, 1H), 2.74 (d, J=4 Hz, 1H), 1.43 (s, 1H), 1.27 (s, 6H).

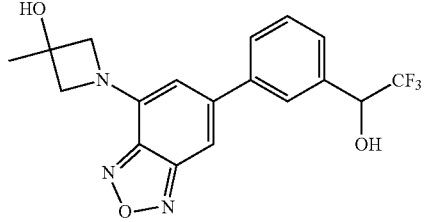

TRV-1436

To a stirring solution of 1-(6-bromobenzo[c][1,2,5]oxadiazol-4-yl)azetidin-3-ol (280 mg, 1.04 mmol) dissolved in DCM (10 mL) was added Dess-Martin reagent (571 mg, 1.3 mmol) dissolved in DCM (4 mL). After 1 hour the reaction had become turbid and a precipitate had formed. The material was poured in to 1 M NaOH and extracted with TBME, the resultant ketone was used as is. $^1$H NMR (500 MHz, CDCl$_3$) δ=7.40 (s, 1H), 6.13 (s, 1H), 5.10 (s, 4H). To a cooled 0° C. stirring solution of ketone (275 mg, 1.03 mmol) dissolved in THF (10 mL) was added MeMgBr (1M THF, 3 mL). The cold bath was left in place and the reaction was allowed to come to RT over 8 hours. At this time the mixture was re-cooled and quenched with NH$_4$Cl$_{(aq)}$ and extracted with EtOAc (3×20 mL), dried with MgSO$_4$ and concentrated in vacuo. The crude tertiary alcohol was passed through a plug of SiO$_2$ (DCM) to give a yellow solid. To a solution of tertiary alcohol (284 mg, 1 mmol) in DME (6 mL)/Na$_2$CO$_3$ (2M, 1.5 mL) was added 3-formyl-phenylboronic acid (225 mg, 1.5 mmol) and Pd(P(Ph)$_3$)$_4$ (40 mg). The flask was then fitted with a reflux condenser, purged with argon and heated to 110° C. O/N. The reaction was worked up by pouring into 1 M NaOH (150 mL) and vacuum isolating the resultant solids. The crude material was purified by plugging through SiO$_2$ (10-30% gradient EtOAc in Hex) to give 250 mg of aldehyde which was used as is. $^1$H NMR (500 MHz, CDCl$_3$) δ=10.11 (s, 1H), 8.11 (s, 1H), 7.92 (d, J=8 Hz, 1H), 7.87 (d, J=8 Hz, 1H), 7.65 (t, J=8 Hz, 1H), 7.21 (s, 1H), 6.09 (s, 1H), 4.30 (d, J=9 Hz, 2H), 4.24 (d, J=8 Hz, 2H), 2.19 (s, Br, 1H), 1.71 (s, 3H). To a stirring solution of aldehyde (250 mg, 0.81 mmol) and Rupert's reagent (344 mg, 2.4 mmol) in DCM (10 mL) at 0° C. was added TBAF (0.2 mL, 1 M THF, 0.2 mmol). After 30 min at low temperature the cold bath was removed and the reaction was allowed to come to RT. After 3 hours an excess of TBAF was added and the reaction was diluted with DCM. The organic phases were washed with saturated NH$_4$Cl, brine, and then dried with MgSO$_4$ and concentrated in vacuo. The crude material was purified by flash column chromatography (20-40% EtOAc gradient in Hex) to give 185 mg (60% yield). $^1$H NMR (500 MHz, CDCl$_3$) δ=7.71 (s, 1H), 7.64 (d, J=7 Hz, 1H), 7.51 (m, 2H), 7.18 (s, 1H), 6.08 (s, 1H), 5.12 (m, 1H), 4.29 (d, J=9 Hz, 2H), 4.22 (d, J=9 Hz, 2H), 2.71 (s, br, 1H). 2.10 (s, br, 1H), 1.70 (s, 3H).

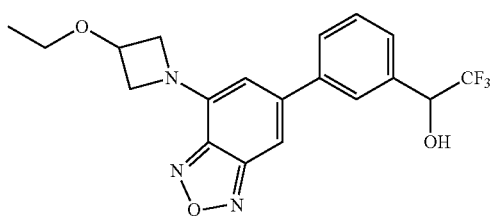

TRV-1437

1-(6-bromobenzo[c][1,2,5]oxadiazol-4-yl)azetidin-3-ol (0.500 g, 1.85 mmol) was dissolved in NMP (2 mL) and cooled to 0° C. NaH (0.096 g, 2.4 mmol) was then added portionwise and stirring was continued until all bubbling ceased, at which point ethyl iodide (0.16 mL, 2.0 mmol) was added. The reaction was allowed to warm to room temperature overnight. The mixture was then re-cooled to 0° C. and quenched with saturated NH$_4$Cl (aq). This mixture was then extracted with EtOAc. The combined organic layers were washed with water (2×) brine, dried (Na$_2$SO$_4$), filtered and concentrated to give a crude ethyl ether. This ether and 3-formylphenylboronic acid (0.2908 g, 1.94 mmol) were massed into a tube. The tube was evacuated and purged with argon (3×). DME (4.1 mL) and 2M Na$_2$CO$_3$ (2.8 mL, 5.6 mmol) were then added followed by Pd(PPh$_3$)$_4$ (0.1075 g, 0.093 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na$_2$SO$_4$), filtered and concentrated to give an oil. This crude oil was then dissolved in THF (5.6 mL) and cooled to 0° C. CF$_3$TMS (0.41 mL, 2.8 mmol) was added followed by TBAF (0.1 mL, 1.0 M solution in THF). The reaction was then stirred for 60 minutes before re-cooling to 0° C. TBAF (5.6 mL, 1.0 M solution in THF) was added and the reaction was allowed to warm to room temperature overnight. The mixture was quenched with brine and then extracted with EtOAc. The combined organic layers were washed with water (2×), brine, dried (Na$_2$SO$_4$), filtered and concentrated to give a crude oil. This material was purified via flash column chromatography (20% EtOAc/hexane) to afford 0.3755 g (51% yield over 3 steps) of TRV-1437. $^1$H NMR (CDCl3, 500 MHz) δ=7.72 (s, 1H), 7.66-7.64 (m, 1H), 7.55-7.50 (m, 2H), 7.17 (s, 1H), 6.06 (s, 1H), 5.14-5.11 (m, 1H), 4.56-4.54 (m, 3H), 4.18 (d, J=5 Hz, 2H), 3.54 (q, J=5 Hz, 2H), 2.67 (d, J=5 Hz, 1H), 1.26 (t, J=5 Hz, 3H).

cycles). To this vial was then added diethylmalonate (1.9 mL, 12.4 mmol), P(tBu)$_3$ (4 mL, 1.98 mmol) and toluene (18 mL) before adding Pd$_2$(dba)$_3$ (0.4542 g, 0.496 mmol) and K$_3$PO$_4$ (4.6063 g, 21.7 mmol). The tube was then sealed and heated to 100° C. for 16 hours. The reaction was then cooled and filtered through a plug of Celite and then concentrated. The residue was purified via flash chromatography (15% EtOAc/hexane) to afford 1.257 g (49% yield) of substituted malonate. This material (1.2572 g, 3.03 mmol) was dissolved in DMSO (30 mL) and NaCl (0.3536 g, 6.05 mmol) and H$_2$O (1.8 mL, 97 mmol) were then added. This mixture was heated to 150° C. for 8 hours. Upon cooling to room temperature the mixture was diluted with EtOAc and water. The organic layer was then washed with H$_2$O (6×), brine, dried (Na$_2$SO$_4$), filtered and concentrated to give the crude ethyl ester. This material was purified via flash chromatography (10% EtOAc/hexane) to afford 0.7641 g (73% yield) of orange solid. The ethyl ester (0.5873 g, 1.71 mmol) was then dissolved in DCM (20 mL) and cooled to −78° C. DIBAL (4.0 mL, 1.0 M solution in hexane) was added dropwise. The reaction was stirred at −78° C. for 5 minutes and then warmed to −30° C. After stirring at this temperature for 3 hours it was quenched with methanol and allowed to warm to room temperature. Water (5 mL) and Na$_2$SO$_4$ were added, the mixture was stirred for 30 minutes and then filtered to give a mixture of the aldehyde and alcohol. This mixture was taken up in DCM (50 mL) and then DMP (0.7253 g, 1.71 mmol) were added with vigorous stirring. After 60 minutes the reaction was quenched with saturated aqueous NaHCO$_3$ and excess Na$_2$S$_2$O$_3$, stirring was continued until all the solids dissolved. The mixture was then extracted with DCM. The combined organic layers were dried with Na$_2$SO$_4$, filtered and concentrated. The residue was then purified via flash chromatography (20% EtOAc/hexane) to afford 0.0726 g (14% yield, 2 steps) of aldehyde 9. This aldehyde (0.0726 g, 0.243 mmol) was dissolved in THF (5 mL) and cooled to 0° C. CF$_3$TMS (0.05 mL) was added followed by TBAF (0.03 mL, 1.0 M solution in THF). The mixture was stirred for 60 minutes and then TBAF (0.46 mL, 1.0 M solution in THF) was added and the reaction was stirred overnight. The reaction was then quenched with brine and extracted with EtOAc. The combined organic layers were washed with water (2×), brine, dried (Na$_2$SO$_4$), filtered and concentrated to give a crude oil. This material was purified via flash column chromatography (20% EtOAc/hexane) to afford 0.0349 g (39% yield) of TRV-1438. $^1$H NMR (CDCl3, 500 MHz) δ=7.23-7.21 (m, 2H), 7.03-6.99 (m, 3H), 6.01 (s, 1H), 5.08 (s, 2H), 4.23 (br s, 1H), 3.11 (s, 3H), 3.03 (dd, J=14, 2.5 Hz, 1H), 2.87 (dd, J=14, 10 Hz, 1H), 2.21 (s, 1H).

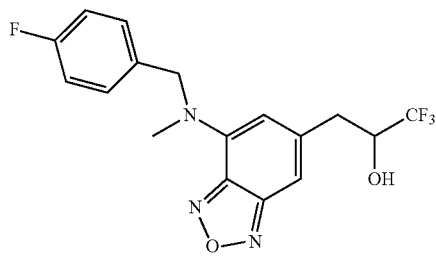

TRV-1438

6-bromo-N-(4-fluorobenzyl)-N-methylbenzo[c][1,2,5]oxadiazol-4-amine (2.085 g, 6.20 mmol) was added to a tube, which was then evacuated and purged with argon (3

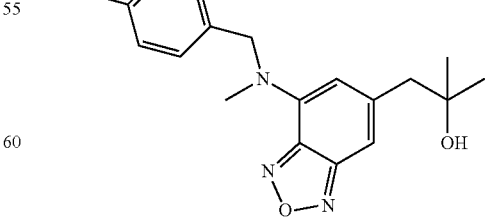

TRV-1439

6-bromo-N-(4-fluorobenzyl)-N-methylbenzo[c][1,2,5]oxadiazol-4-amine (2.085 g, 6.20 mmol) was added to a tube, which was then evacuated and purged with argon (3 cycles). To this vial was then added diethylmalonate (1.9 mL, 12.4 mmol), P(tBu)₃ (4 mL, 1.98 mmol) and toluene (18 mL) before adding Pd₂(dba)₃ (0.4542 g, 0.496 mmol) and K₃PO₄ (4.6063 g, 21.7 mmol). The tube was then sealed and heated to 100° C. for 16 hours. The reaction was then cooled and filtered through a plug of Celite and then concentrated. The residue was purified via flash chromatography (15% EtOAc/hexane) to afford 1.257 g (49% yield) of compound 2. This material (1.2572 g, 3.03 mmol) was dissolved in DMSO (30 mL) and NaCl (0.3536 g, 6.05 mmol) and H₂O (1.8 mL, 97 mmol) were then added. This mixture was heated to 150° C. for 8 hours. Upon cooling to room temperature the mixture was diluted with EtOAc and water. The organic layer was then washed with H₂O (6×), brine, dried (Na₂SO₄), filtered and concentrated to give the crude ethyl ester. This material was purified via flash chromatography (10% EtOAc/hexane) to afford 0.7641 g (73% yield) of orange solid. This material (0.1736 g, 0.506 mmol) was dissolved in THF (10 mL) and cooled to −78° C. MeLi (0.70 mL, 1.6 M solution in Et₂O) was added dropwise, and the reaction was allowed to slowly warm to room temperature. It was then re-cooled to 0° C. and quenched with ammonium chloride. This mixture was extracted with EtOAc and the combined organic extracts were washed with H₂O (3×), brine, dried (Na₂SO₄), filtered and concentrated to give a crude residue. The crude material was purified via flash chromatography (20% EtOAc/hexane) to afford 0.0288 g (17% yield) of the tertiary alcohol TRV-1439. ¹H NMR (CDCl3, 500 MHz) δ=7.24-7.21 (m, 2H), 7.05-6.99 (m, 2H), 6.94 (s, 1H), 6.08 (s, 1H), 5.02 (s, 2H), 3.11 (s, 3H), 2.76 (s, 2H), 1.40 (s, 1H), 1.27 (s, 6H).

TRV-1440

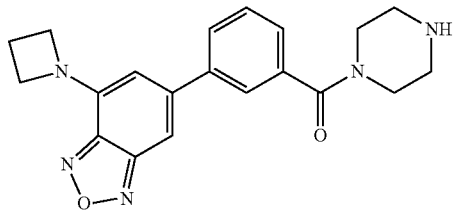

To a solution of 4-(azetidin-1-yl)-6-bromobenzo[c][1,2,5]oxadiazole (480 mg, 0.6 mmol) in DME (11 mL)/Na₂CO₃ (2M, 2.8 mL) was added 3-carboxy-phenylboronic acid (470 mg, 2.8 mmol) and Pd(P(Ph)₃)₄ (93 mg). The flask was then fitted with a reflux condenser, purged with argon and heated to 100° C. O/N. The reaction was worked up by pouring into 1 M HCl (150 mL) and vacuum isolating the resultant solids. The crude acid was purified by flash column chromatography (DCM 1% AcOH) to give 330 mg of material which was used as is. To a stirring solution of this acid (110 mg, 0.37 mmol) dissolved in NMP (2 mL) was added DIPEA (130 μL, 0.74 mmol) and piperazine (230 mg, 0.37 mmol). After the mixture was homogeneous HATU (140 mg, 0.37 mmol) was added and the reaction was left to stir. After 1 hour at RT the reaction was diluted with EtOAc (100 mL) and diluted with water. The crude material was purified by flash column chromatography (50-100% EtOAc in Hex) to give (20 mg) 14% yield. ¹H NMR (500 MHz, CDCl₃) δ=7.66 (m, 2H), 7.50 (t, J=8 Hz, 1H), 7.42 (d, J=8 Hz, 1H), 7.12 (s, 1H), 6.01 (s, 1H), 4.34 (t, J=7 Hz, 4H), 3.79 (s, broad, 2H), 3.43 (s, broad, 2H), 2.97 (s, broad, 2H), 2.82 (s, broad, 2H), 2.61 (s, 1H), 2.53 (p, J=7 Hz, 2H).

TRV-1441

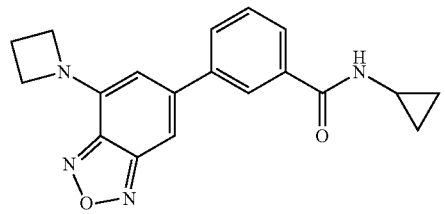

To a solution of 4-(azetidin-1-yl)-6-bromobenzo[c][1,2,5]oxadiazole (480 mg, 0.6 mmol) in DME (11 mL)/Na₂CO₃ (2M, 2.8 mL) was added 3-carboxy-phenylboronic acid (470 mg, 2.8 mmol) and Pd(P(Ph)₃)₄ (93 mg). The flask was then fitted with a reflux condenser, purged with argon and heated to 100° C. O/N. The reaction was worked up by pouring into 1 M HCl (150 mL) and vacuum isolating the resultant solids. The crude material was purified by flash column chromatography (DCM 1% AcOH) to give 330 mg of material which was used as is. To a stirring solution of this acid (165 mg, 0.56 mmol) dissolved in NMP (2 mL) was added DIPEA (300 μL, 1.7 mmol) and cyclopropylamine (55 mg, 0.59 mmol). After the mixture was homogeneous HATU (213 mg, 0.56 mmol) was added and the reaction was left to stir. After 1 hour at RT the reaction was diluted with EtOAc (100 mL) and diluted with water. The organic phase was washed with acid (1 M HCl, 1×100 mL), base (1M NaOH, 1×100 mL) and concentrated in vacuo. The crude material was purified by flash column chromatography (EtOAc) to give (120 mg) 64% yield. ¹H NMR (500 MHz, DMSO-D₆) δ=7.91 (m, 2H), 7.66 (d, J=8 Hz, 1H), 7.57 (t, J=8 Hz, 1H), 7.35 (s, 1H), 6.23 (s, 1H), 4.33 (m, 6H), 4.07 (t, J=7 Hz, 2H), 2.45 (p, J=7 Hz, 2H), 2.27 (p, J=7 Hz, 2H).

TRV-1442

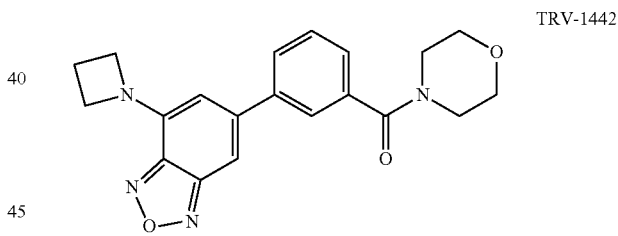

To a solution of 4-(azetidin-1-yl)-6-bromobenzo[c][1,2,5]oxadiazole (480 mg, 0.6 mmol) in DME (11 mL)/Na₂CO₃ (2M, 2.8 mL) was added 3-carboxy-phenylboronic acid (470 mg, 2.8 mmol) and Pd(P(Ph)₃)₄ (93 mg). The flask was then fitted with a reflux condenser, purged with argon and heated to 100° C. O/N. The reaction was worked up by pouring into 1 M HCl (150 mL) and vacuum isolating the resultant solids. The crude material was purified by flash column chromatography (DCM 1% AcOH) to give 330 mg of material which was used as is. To a stirring solution of this acid (110 mg, 0.37 mmol) dissolved in NMP (2 mL) was added DIPEA (130 μL, 0.74 mmol) and morpholine (32 μL, 0.37 mmol). After the mixture was homogeneous HATU (140 mg, 0.37 mmol) was added and the reaction was left to stir. After 1 hour at RT the reaction was diluted with EtOAc (100 mL) and diluted with water. The organic phase was washed with acid (1 M HCl, 1×100 mL), base (1M NaOH, 1×100 mL) and concentrated in vacuo. The crude material was purified by flash column chromatography (50-100% EtOAc in Hex) to give (40 mg) 29% yield. ¹H NMR (500 MHz, CDCl₃) δ=7.67 (m, 2H), 7.52 (t, J=8 Hz, 1H), 7.43 (d, J=7 Hz, 1H), 7.12 (s, 1H), 6.00 (s, 1H), 4.35 (t, J=7 Hz, 4H), 3.81 (m, br, 4H), 3.65 (m, br, 2H), 3.49 (m, br, 2H), 2.54 (p, J=7 Hz, 2H).

TRV-1443

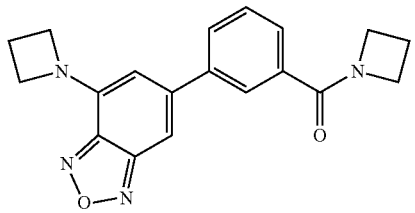

To a solution of 4-(azetidin-1-yl)-6-bromobenzo[c][1,2,5]oxadiazole (480 mg, 0.6 mmol) in DME (11 mL)/Na₂CO₃ (2M, 2.8 mL) was added 3-carboxy-phenylboronic acid (470 mg, 2.8 mmol) and Pd(P(Ph)₃)₄ (93 mg). The flask was then fitted with a reflux condenser, purged with argon and heated to 100° C. O/N. The reaction was worked up by pouring into 1 M HCl (150 mL) and vacuum isolating the resultant solids. The crude material was purified by flash column chromatography (DCM 1% AcOH) to give 330 mg of material which was used as is. To a stirring solution of this acid (165 mg, 0.56 mmol) dissolved in NMP (2 mL) was added DIPEA (300 µL, 1.7 mmol) and azetidine hydrochloride (55 mg, 0.59 mmol). After the mixture was homogeneous HATU (213 mg, 0.56 mmol) was added and the reaction was left to stir. After 1 hour at RT the reaction was diluted with EtOAc (100 mL) and diluted with water. The organic phase was washed with acid (1 M HCl, 1×100 mL), base (1M NaOH, 1×100 mL) and concentrated in vacuo. The crude material was purified by flash column chromatography (EtOAc) to give (120 mg) 64% yield. ¹H NMR (500 MHz, DMSO-D₆) δ=7.91 (m, 2H), 7.66 (d, J=8 Hz, 1H), 7.57 (t, J=8 Hz, 1H), 7.35 (s, 1H), 6.23 (s, 1H), 4.33 (m, 6H), 4.07 (t, J=7 Hz, 2H), 2.45 (p, J=7 Hz, 2H), 2.27 (p, J=7 Hz, 2H).

TRV-1444

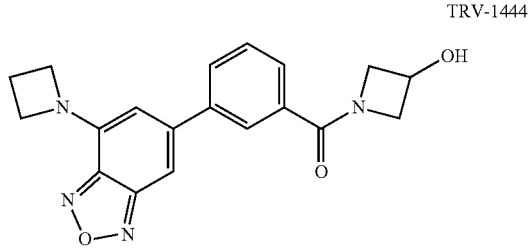 [SMILES: O=C(c1cccc(-c2cc(N3CCC3)c3nonc3c2)c1)N1CC(O)C1]

To a solution of 4-(azetidin-1-yl)-6-bromobenzo[c][1,2,5]oxadiazole (480 mg, 0.6 mmol) in DME (11 mL)/Na₂CO₃ (2M, 2.8 mL) was added 3-carboxy-phenylboronic acid (470 mg, 2.8 mmol) and Pd(P(Ph)₃)₄ (93 mg). The flask was then fitted with a reflux condenser, purged with argon and heated to 100° C. O/N. The reaction was worked up by pouring into 1 M HCl (150 mL) and vacuum isolating the resultant solids. The crude material was purified by flash column chromatography (DCM 1% AcOH) to give 330 mg of material which was used as is. To a stirring solution of this acid (165 mg, 0.56 mmol) dissolved in NMP (2 mL) was added DIPEA (300 µL, 1.7 mmol) and 3-hydroxyazetidine hydrochloride (64 mg, 0.59 mmol). After the mixture was homogeneous HATU (212 mg, 0.56 mmol) was added and the reaction was left to stir. After 1 hour at RT the reaction was diluted with EtOAc (100 mL) and diluted with water. The organic phase was washed with acid (1 M HCl, 1×100 mL), base (1M NaOH, 1×100 mL) and concentrated in vacuo. The crude material was purified by flash column chromatography (EtOAc) to give (60 mg) 30% yield. ¹H NMR (500 MHz, DMSO-D₆) δ=7.89 (m, 2H), 7.67 (d, J=8 Hz, 1H), 7.58 (t, J=8 Hz, 1H), 7.35 (s, 1H), 6.22 (s, 1H), 4.50 (m 2H), 4.29 (m, 5H), 4.08 (m, 1H), 3.80 (dd, J=10 Hz, 2 Hz, 1H), 2.45 (p, J=7 Hz, 2H).

TRV-1445

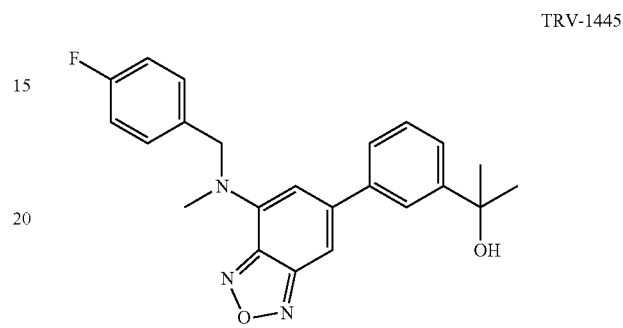

6-bromo-N-(4-fluorobenzyl)-N-methylbenzo[c][1,2,5]oxadiazol-4-amine (0.3010 g, 0.895 mmol) and 3-acetylphenylboronic acid (0.1542 g, 0.940 mmol) were massed into a tube. The tube was evacuated and purged with argon (3×). DME (2.1 mL) and 2M Na₂CO₃ (1.4 mL, 2.69 mmol) were then added followed by Pd(PPh₃)₄ (0.0518 g, 0.0448 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil was then dissolved in THF (10 mL) and cooled to 0° C. MeMgBr (1.2 mL, 1.0 M solution in Bu₂O) was added dropwise and then the reaction was allowed to slowly warm to room temperature overnight. The reaction was cooled to 0° C. and quenched with saturated ammonium chloride. This mixture was then extracted with EtOAc. The combined organic layers were washed with water (3×), brine, dried (Na₂SO₄), filtered and concentrated. The oil was purified via flash chromatography (20% EtOAc/hexane) to afford 0.0841 g (24% yield, 2 steps) of TRV-1445. ¹H NMR (CDCl3, 500 MHz) δ=7.75 (d, J=5 Hz, 1H), 7.54 (d, J=10 Hz, 1H), 7.49-7.43 (m, 2H), 7.25-7.24 (m, 3H), 7.02 (t, J=7 Hz, 2H), 6.38 (s, 1H), 5.11 (s, 2H), 3.18 (s, 3H), 1.78 (s, 1H), 1.64 (s, 6H).

TRV-1446

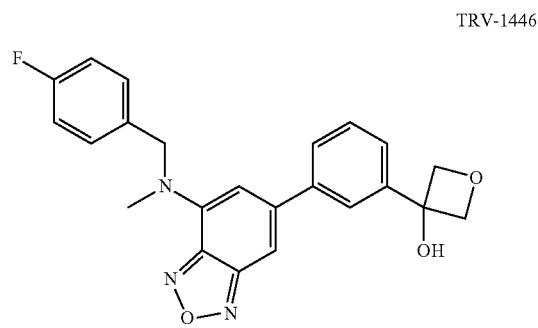 [SMILES: CN(Cc1ccc(F)cc1)c1cc(-c2cccc(C3(O)COC3)c2)cc2nonc12]

6-bromo-N-(4-fluorobenzyl)-N-methylbenzo[c][1,2,5]oxadiazol-4-amine (0.3207 g, 0.954 mmol) and 3-bromophenylboronic acid (0.164 g, 1.00 mmol) were massed into a tube. The tube was evacuated and purged with argon (3×). DME (2.1 mL) and 2M Na₂CO₃ (1.4 mL, 2.86 mmol) were then added followed by Pd(PPh₃)₄ (0.0551 g, 0.0477 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. The crude oil was purified via flash chromatography (5% EtOAc/hexane) to afford 0.3037 g (77% yield) of the corresponding aryl bromide. This aryl bromide (0.3037 g, 0.74 mmol) was dissolved in THF (7.5 mL) and cooled to −78° C. nBuLi (0.39 mL, 2.0 M solution in cyclohexane) was added drop wise. The solution was stirred for 30 minutes at this temperature and then oxetan-3-one (0.0692 g, 0.962 mmol) in THF (1 mL) was added drop wise. The solution was then stirred and allowed to warm to room temperature overnight. The reaction was cooled to 0° C. and quenched with saturated ammonium chloride. This mixture was extracted with EtOAc. The combined organic layers were washed with water (3×), brine, dried (Na₂SO₄), filtered and concentrated to a crude oil. The oil was then purified via flash chromatography (45% EtOAc/hexane) to afford 0.0587 g (19% yield) of TRV-1446. ¹H NMR (CDCl3, 500 MHz) δ=7.83 (s, 1H), 7.70 (d, J=5 Hz, 1H), 7.58 (d, J=5 Hz, 1H), 7.53 (t, J=10 Hz, 1H), 7.25-7.24 (m, 3H), 7.02 (t, J=10 Hz, 2H), 6.36 (s, 1H), 5.12 (s, 2H), 4.96 (s, 4H), 3.18 (s, 3H), 2.62 (s, 1H).

TRV-1447

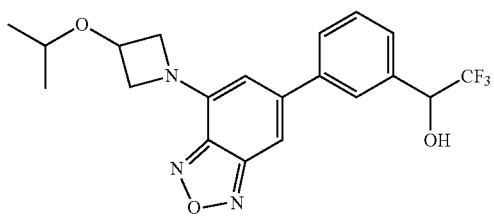

1-(6-bromobenzo[c][1,2,5]oxadiazol-4-yl)azetidin-3-ol (0.500 g, 1.85 mmol) was dissolved in NMP (2 mL) and cooled to 0° C. NaH (0.096 g, 2.4 mmol) was then added portion wise and stirring was continued until all bubbling ceased, at which point 2-bromopropane (0.19 mL, 2.0 mmol) was added. The reaction was allowed to warm to room temperature overnight. The mixture was then re-cooled to 0° C. and NaH (0.192 g, 4.8 mmol), 2-bromopropane (1.8 mL, 19 mmol) and NaI (1 eq) were added. The reaction was heated to 50° C. overnight. The mixture was then re-cooled to 0° C. and quenched with saturated NH₄Cl (aq). This mixture was then extracted with EtOAc. The combined organic layers were washed with water (2×) brine, dried (Na₂SO₄), filtered and concentrated to give the crude isopropyl ether. This ether (0.1942 g, 0.622 mmol) and 3-formylphenylboronic acid (0.0979 g, 1.94 mmol) were massed into a tube. The tube was evacuated and purged with argon (3×). DME (1.4 mL) and 2M Na₂CO₃ (0.93 mL, 1.87 mmol) were then added followed by Pd(PPh₃)₄ (0.0359 g, 0.0311 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil (0.1047 g, 0.31 mmol) was then dissolved in THF (1.0 mL) and cooled to 0° C. CF₃TMS (0.092 mL, 0.62 mmol) was added followed by TBAF (0.03 mL, 1.0 M solution in THF). The reaction was then stirred for 60 minutes before re-cooling to 0° C. TBAF (1.0 mL, 1.0 M solution in THF) was added and the reaction was allowed to warm to room temperature overnight. The mixture was quenched with brine and then extracted with EtOAc. The combined organic layers were washed with water (2×), brine, dried (Na₂SO₄), filtered and concentrated to give a crude oil. This material was purified via flash column chromatography (20% EtOAc/hexane) to afford 0.073 g (58% yield over 3 steps) of TRV-1447. ¹H NMR (CDCl3, 500 MHz) δ=7.71 (s, 1H), 7.65 (d, J=5 Hz, 1H), 7.54-7.50 (m, 2H), 7.16 (s, 1H), 6.06 (s, 1H), 5.13-5.12 (m, 1H), 4.60-4.55 (m, 3H), 4.16-4.14 (m, 2H), 3.70 (sept, J=5 Hz, 1H), 2.71 (s, 1H), 1.21 (d, J=5 Hz, 6H).

TRV-1448

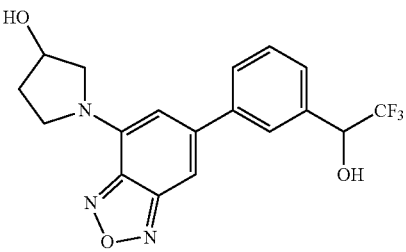

To a solution of 6-bromo-4-chlorobenzo[c][1,2,5]oxadiazole (396 mg, 1.7 mmol) in NMP (3 mL) in a 4 dram vial was added 3-hydroxypyrrolidine hydrochloride (230 mg, 1.83 mmol) and triethylamine (710 µL, 5.1 mmol). A cap was tightly fitted and the reaction was heated at 85° C. O/N. Reaction worked up by diluting with EtOAc (60 mL) and washing with 1M HCl (3×20 mL) and brine (1×20 mL). The organic phase was dried with MgSO₄ filtered and concentrated in vacuo. The crude aniline was used without further purification. To a solution of aniline (820 mg, 2.9 mmol) in DME (12 mL)/Na₂CO₃ (2M, 4.4 mL) was added 3-formylphenylboronic acid (645 mg, 4.3 mmol) and Pd(P(Ph)₃)₄ (110 mg). The flask was then fitted with a reflux condenser, purged with argon and heated to 110° C. O/N. The reaction was worked up by pouring into 1 M NaOH (150 mL) and vacuum isolating the resultant solids. The crude material was purified by plugging through SiO₂ (EtOAc) to give 680 mg of material which was used as is. ¹H NMR (500 MHz, CDCl₃) δ=10.11 (s, 1H), 8.12 (s, 1H), 7.94 (d, J=8 Hz, 1H), 7.88 (d, J=8 Hz, 1H), 7.65 (t, J=8 Hz, 1H), 7.17 (s, 1H), 6.03 (s, 1H), 4.42 (m, 2H), 4.13 (m, 2H), 3.65 (d, J=6 Hz, 2H), 3.41 (s, 3H), 3.11 (m, 1H). To a stirring solution of the aldehyde (680 mg, 2.2 mmol) and Rupert's reagent (937 mg, 6.6 mmol) in DCM (20 mL) at 0° C. was added TBAF (0.2 mL, 1 M THF, 0.2 mmol). After 30 min at low temperature the cold bath was removed and the reaction was allowed to come to RT. After 3 hours the reaction was concentrated in vacuo and the flask was charged with THF (20 mL). To this an excess of TBAF was added and the reaction was left to stir. Once the deprotection was complete EtOAc (100 mL) was added and the reaction was washed with saturated NH₄Cl, brine, and then dried with MgSO₄ and concentrated in vacuo. The crude material was purified by flash column chromatography (50% EtOAc in Hex) to give 380 mg (38% yield) of TRV-1448, a 1:1:1:1 mixture of diastereomers due to the two chiral centers. $^1$H NMR (500 MHz, CDCl$_3$) δ=7.73 (s, 1H), 7.66 (dt J=7 Hz, 2 Hz, 2H), 7.51 (m, 2H), 7.10 (s, 1H), 6.12 (s, 1H), 5.1 (m, 1H), 4.7 (s br, 1H), 3.96 (m, 4H), 2.81 (d, J=3 Hz, 1H), 2.20 (m, 2H), 1.75 (d, J=3 Hz, 1H).

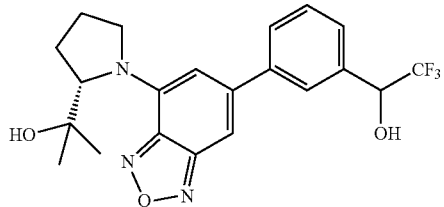

TRV-1449

4,6-dibromobenzo[c][1,2,5]oxadiazole (0.3765 g, 1.35 mmol), ethyl pyrrolidine-2-carboxylate hydro chloride (0.2677 g, 1.49 mmol) and DIPEA (0.59 mL, 3.38 mmol) were dissolved in NMP (1.8 mL) under argon and stirred in a sealed tube at 100° C. overnight. Upon cooling to room temperature, the reaction was diluted with water and extracted with EtOAc. The combined organic layers were washed with H$_2$O (5×), 1 N HCl (aq), saturated NaHCO$_3$ (aq) and brine before drying with Na$_2$SO$_4$, filtering and concentrating to give 0.1756 g (38% yield) of crude material. The aniline (0.4346 g, 1.28 mmol) was then dissolved in THF (12 mL) and cooled to 0° C. MeMgBr (3.2 mL, 1.0 M solution in Bu$_2$O) was added dropwise and the reaction was slowly allowed to warm to room temperature overnight. The reaction was quenched with NH$_4$Cl (aq) and then extracted with EtOAc. The combined organic layers were then washed with water (3×), brine, dried (Na$_2$SO$_4$), filtered and concentrated to give an oil. The oil was then purified via flash chromatography (15% EtOAc/hexane) to afford 0.1293 g (31% yield) of tertiary alcohol. The tertiary alcohol (0.1293 g, 0.316 mmol) and 3-formylphenylboronic acid (0.0624 g, 0.416 mmol) were massed into a tube. The tube was evacuated and purged with argon (3×). DME (1.0 mL) and 2M Na$_2$CO$_3$ (0.6 mL, 1.19 mmol) were then added followed by Pd(PPh$_3$)$_4$ (0.0229 g, 0.0198 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na$_2$SO$_4$), filtered and concentrated to give an oil. This crude oil was then dissolved in THF (3 mL) and cooled to 0° C. CF$_3$TMS (0.12 mL, 0.792 mmol) was added followed by TBAF (0.05 mL, 1.0 M solution in THF). The reaction was then stirred for 60 minutes before re-cooling to 0° C. TBAF (1.4 mL, 1.0 M solution in THF) was added and the reaction was allowed to warm to room temperature overnight. The mixture was quenched with brine and then extracted with EtOAc. The combined organic layers were washed with water (2×), brine, dried (Na$_2$SO$_4$), filtered and concentrated to give a crude oil. This material was purified via flash column chromatography (30% EtOAc/hexane) to afford 0.0748 g (45% yield over 2 steps) of TRV-1449. $^1$H NMR (CDCl3, 500 MHz) δ=7.73 (s, 1H), 7.67-7.65 (m, 1H), 7.54-7.49 (m, 2H), 7.14 (s, 1H), 6.46 (m, 1H), 5.12-5.10 (m, 1H), 4.92 (d, J=5 Hz, 1H), 3.99-3.95 (m, 1H), 3.73-3.68 (m, 1H), 2.83 (s, 1H), 2.77-2.21 (m, 1H), 2.11-2.02 (m, 3H), 1.82 (s, 1H), 1.31 (s, 3H), 1.24 (s, 3H).

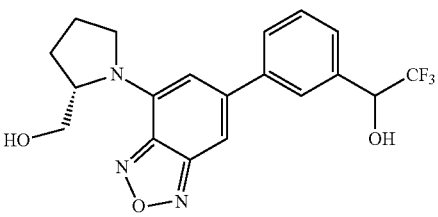

TRV-1450

4,6-dibromobenzo[c][1,2,5]oxadiazole (2.013 g, 7.24 mmol) and (S)-ethyl pyrrolidine-2-carboxylate hydrochloride salt (1.43 g, 7.96 mmol) were massed into a tube. The tube was evacuated and flushed with argon for three cycles. NMP (10 mL) and DIPEA (3.5 mL, 19.9 mmol) were then added and the tube was sealed and heated to 50° C. overnight. Upon cooling to room temperature the mixture was diluted with water and EtOAc. The layers were separated and the aqueous layer was back-extracted with EtOAc. The combined organic layers were then washed with water (5×), brine, dried (Na$_2$SO$_4$), filtered and concentrated to give an oil. The crude oil was then purified via flash column chromatography (15% EtOAc/hexane) to afford 0.6105 g (25% yield) of aniline. The aniline (1.696 g, 4.9 mmol) was dissolved in DCM (20 mL) and cooled to −78° C. DIBAL (12.5 mL, 1.0 M solution in hexanes) was added dropwise and then the reaction was allowed to warm to room temperature overnight. The reaction was quenched with MeOH and then Na$_2$SO$_4$ was added and the mixture was stirred for 30 minutes before filtering through Celite. The organic phase was diluted with EtOAc and water. The layers were separated and the organic layer was washed with H$_2$O (3×), brine, dried (Na$_2$SO$_4$), filtered and concentrated. The crude material was purified via chromatography (30% EtOAc/hexane) to give 1.294 g (87% yield) of the primary alcohol. This alcohol (0.2926 g, 0.98 mmol) and 3-formylphenylboronic acid (0.1544 g, 1.03 mmol) were massed into a tube. The tube was evacuated and purged with argon (3×). DME (2.2 mL) and 2M Na$_2$CO$_3$ (1.5 mL, 2.94 mmol) were then added followed by Pd(PPh$_3$)$_4$ (0.0566 g, 0.049 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na$_2$SO$_4$), filtered and concentrated to give an oil. This crude oil was then dissolved in THF (10 mL) and cooled to 0° C. CF$_3$TMS (0.29 mL, 1.96 mmol) was added followed by TBAF (0.1 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were was with water, brine, dried (Na$_2$SO$_4$), filtered and concentrated to give a crude oil. This material was purified via flash column chromatography (35% EtOAc/hexane) to afford 0.2158 g (56% yield, 2 steps) of TRV-1450. $^1$H NMR (DMSO, 500 MHz) δ=7.87 (s, 1H), 7.79 (d, J=5 Hz, 1H), 7.57-7.54 (m, 2H), 7.21 (s, 1H), 6.96 (d, J=5 Hz, 1H), 6.34 (t, J=5 Hz, 1H), 5.29-5.25 (m, 1H), 4.91-4.89

(m, 1H), 4.55 (br s, 1H), 3.82-3.81 (m, 1H), 3.58-3.57 (m, 3H), 2.12-2.11 (m, 2H), 2.02-1.97 (m, 2H).

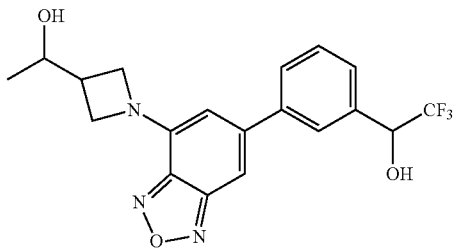

TRV-1451

1-(6-bromobenzo[c][1,2,5]oxadiazol-4-yl)azetidine-3-carboxylic acid (1.5 g, 5 mmol) was dissolved in THF (50 mL) and cooled to 0° C. To this was added $BH_3$-THF (10 mL, 10 mmol). The reaction was allowed to come to room temperature overnight. The next day the reaction was quenched with AcOH and extracted into EtOAc. The organic layer was washed with 1 M NaOH until the washings remained litmus blue and then concentrated in vacuo. The crude material was fused to $SiO_2$ and purified by flash column chromatography (3:2 Hex:EtOAc) to give 800 mg of primary alcohol (56% yield). $^1$H NMR (500 MHz, $CDCl_3$) δ=7.05 (s, 1H), 6.11 (s, 1H), 5.30 (s, 1H), 4.11 (t, J=8 Hz, 2H), 3.85 (m, 4H), 3.00 (m, 1H). To a stirring solution of the alcohol (500 mg, 1.76 mmol) in DCM (20 mL) was added Dess-Martin periodane (1.1 g, 2.64 mmol) and the solution was left to stir for 1 hour. At this time the reaction was diluted with EtOAc (100 mL) and washed with sodium carbonate (sat.). The organic layer was dried with $MgSO_4$, and concentrated in vacuo. The crude material was purified by plugging through $SiO_2$ (DCM) to give 420 mg (1.49 mmol, 84% yield) of aldehyde. $^1$H NMR (500 MHz, $CDCl_3$) δ=9.96 (d, J=2 Hz, 1H), 7.26 (s, 1H), 5.96 (s, 1H), 4.47 (m, 4H), 3.7 (m, 1H). To a 0° C. stirring solution of this aldehyde (420 mg, 1.5 mmol) in THF (10 mL) was added methylmagnesium bromide (1M, 1.8 mL). After 10 min at reduced temperature the cold bath was removed and the reaction was allowed to come to RT. After 1 hour the reaction was cooled back to 0° C. and saturated $NH_4Cl$ was cautiously added. The reaction mixture was then diluted with EtOAc (100 mL) and the phases were separated. The organic phase was washed with brine, dried with $MgSO_4$ and concentrated in vacuo. The crude material was fused to $SiO_2$ (4 g) and gradient flashed (0-2% MeOH in DCM) to give 380 mg (1.27 mmol, 85% yield) of the secondary alcohol. $^1$H NMR (500 MHz, $CDCl_3$) δ=7.18 (s, 1H), 5.898 (s, 1H), 4.36-4.08 (m, 5H), 2.85 (m, 1H), 1.25 (d, 3H). To a solution of this secondary alcohol (380 mg, 1.28 mmol) in DME (8 mL)/$Na_2CO_3$ (2M, 1.9 mL) was added 3-formyl-phenylboronic acid (286 mg, 1.9 mmol) and $Pd(P(Ph)_3)_4$ (70 mg). The flask was then fitted with a reflux condenser, purged with argon and heated to 85° C. O/N. The reaction was worked up by pouring into 1 M NaOH (150 mL) and vacuum isolating the resultant solids. The crude material was purified by plugging through $SiO_2$ (50% EtOAc in Hex) to give 356 mg of material which was used as is. $^1$H NMR (500 MHz, $CDCl_3$) δ=10.1 (s, 1H), 8.11 (s, 1H), 7.63 (d J=7 Hz, 1H), 7.88 (d, J=7 Hz, 1H), 7.65 (t, J=7 Hz, 1H), 7.17 (s, 1H), 6.05 (s, 1H), 4.40 (m, 2H), 4.27 (m, 1H), 4.15-4.05 (m, 2H), 2.87 (m, 1H), 1.26 (d, J=6 Hz, 3H). To a stirring solution of this aldehyde (356 mg, 1.1 mmol) and Rupert's reagent (488 µL, 3.3 mmol) in THF (3 mL) at 0° C. was added TBAF (0.2 mL, 1 M THF, 0.2 mmol). After 30 min at low temperature the cold bath was removed and the reaction was allowed to come to RT. After 3 hours the reaction was concentrated in vacuo and the flask was charged with THF (20 mL). To this an excess of TBAF was added and the reaction was left to stir. Once the deprotection was complete EtOAc (100 mL) was added and the reaction was washed with saturated $NH_4Cl$, brine, and then dried with $MgSO_4$ and concentrated in vacuo. The crude material was purified by flash column chromatography (20-40% EtOAc in Hex) to give 100 mg (23% yield) of TRV-1451, a 1:1:1:1 mixture of diastereomers due to the two chiral centers. $^1$H NMR (500 MHz, $CDCl_3$) δ=7.71 (s, 1H), 7.64 (m, 1H), 7.51 (m, 2H), 7.14 (s, 1H), 6.04 (s, 1H), 5.11 (m, 1H), 4.39 (m, 2H), 4.24 (m, 1H), 4.10 (m, 2H), 2.85 (m, 1H), 2.74 (m, 1H), 1.26 (d, J=6 Hz, 3H).

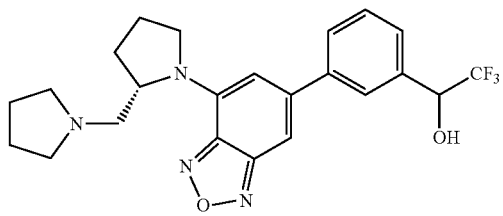

TRV-1452

4,6-dibromobenzo[c][1,2,5]oxadiazole (2.013 g, 7.24 mmol) and (S)-ethyl pyrrolidine-2-carboxylate hydrochloride salt (1.43 g, 7.96 mmol) were massed into a tube. The tube was evacuated and flushed with argon for three cycles. NMP (10 mL) and DIPEA (3.5 mL, 19.9 mmol) were then added and the tube was sealed and heated to 50° C. overnight. Upon cooling to room temperature the mixture was diluted with water and EtOAc. The layers were separated and the aqueous layer was back-extracted with EtOAc. The combined organic layers were then washed with water (5×), brine, dried ($Na_2SO_4$), filtered and concentrated to give an oil. The crude oil was then purified via flash column chromatography (15% EtOAc/hexane) to afford 0.6105 g (25% yield) of aniline. The aniline (1.696 g, 4.9 mmol) was dissolved in DCM (20 mL) and cooled to −78° C. DIBAL (12.5 mL, 1.0 M solution in hexanes) was added dropwise and then the reaction was allowed to warm to room temperature overnight. The reaction was quenched with MeOH and then $Na_2SO_4$ was added and the mixture was stirred for 30 minutes before filtering through Celite. The organic phase was diluted with EtOAc and water. The layers were separated and the organic layer was washed with $H_2O$ (3×), brine, dried ($Na_2SO_4$), filtered and concentrated. The crude material was purified via chromatography (30% EtOAc/hexane) to give 1.294 g (87% yield) of the primary alcohol. The primary alcohol (0.9956 g, 3.34 mmol) was dissolved in DCM (100 mL) and DMP (2.1249 g, 5.0 mmol) was added. The reaction was stirred for 2 hours and then it was quenched with saturated $NaHCO_3$ (aq) and excess $Na_2SO_4$ (8.0 g) was added and the mixture was stirred until all solids dissolved. This mixture was then extracted with DCM and the combined organic layer was dried ($Na_2SO_4$), filtered and concentrated. Purification (20% EtOAc/hexane column) afforded 0.6471 g (65% yield) of the aldehyde. This aldehyde (0.200 g, 0.675 mmol) and pyrrolidine (0.06 mL, 0.743 mmol) were dissolved in DCM (3.1 mL) and then treated with $NaBH(OAc)_3$ (0.2003 g, 0.945 mmol) and the mixture was stirred for 2 hours. The solution was cooled to 0° C. and quenched with 1N NaOH. This mixture was then extracted with EtOAc. The combined organic layers were washed with H₂O (3×), brine, dried (Na₂SO₄), filtered and concentrated to give the crude amine. This amine and 3-formylphenylboronic acid (0.1063 g, 0.709 mmol) were massed into a tube. The tube was evacuated and purged with argon (3×). DME (1.5 mL) and 2M Na₂CO₃ (1.0 mL, 2.0 mmol) were then added followed by Pd(PPh₃)₄ (0.0389 g, 0.033 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil was then dissolved in THF (3 mL) and cooled to 0° C. CF₃TMS (0.20 mL, 1.35 mmol) was added followed by TBAF (0.1 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were was with water, brine, dried (Na₂SO₄), filtered and concentrated to give a crude oil. This material was purified via flash column chromatography (5% MeOH/DCM) to afford 0.1537 g (51% yield) of TRV-1452. ¹H NMR (CDCl3, 500 MHz) δ=7.76-7.74 (m, 2H), 7.68-7.65 (m, 2H), 7.51-7.47 (m, 4H), 7.08 (s, 1H), 7.07 (s, 1H), 6.22 (s, 1H), 6.21 (s, 1H), 5.11-5.05 (m, 2H), 64.65 (br s, 1H), 4.52 (br s, 1H), 3.94-3.89 (m, 2H), 3.65-3.59 (m, 2H), 2.70-2.52 (m, 12H), 2.28-2.25 (m, 2H), 2.14-2.05 (m, 6H), 1.81 (br s, 8H).

TRV-1453

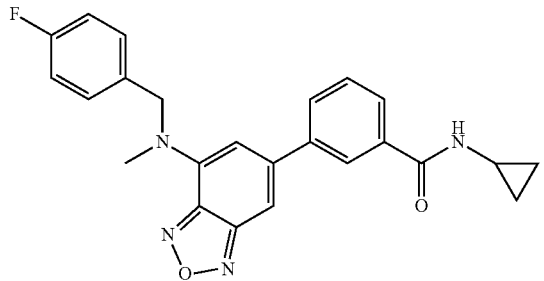

6-bromo-N-(4-fluorobenzyl)-N-methylbenzo[c][1,2,5]oxadiazol-4-amine (1.00 g, 2.97 mmol) and 3-carboxyphenylboronic acid (0.5176 g, 3.12 mmol) were massed into a tube. The tube was evacuated and purged with argon (3×). DME (8.9 mL) and 2M Na₂CO₃ (6.0 mL, 11.9 mmol) were then added followed by Pd(PPh₃)₄ (0.1733 g, 0.15 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give the crude material. This was purified via 5% MeOH/DCM column to afford 1.0873 g (97% yield, 90% chemical purity) of the acid. A mixture of the acid (0.200 g, 0.529 mmol), cyclopropylamine (0.04 mL, 0.529 mmol) and TEA (0.18 mL, 1.32 mmol) were stirred in EtOAc (6 mL) and cooled in an ice bath. The T3P solution (0.4040 g, 50% w/w in EtOAc) was added dropwise. Once the addition was complete the reaction was allowed to warm to room temperature. The reaction was then quenched with water and extracted with EtOAc. The combined organic layers were washed with water (3×), brine, dried (Na₂SO₄), filtered and concentrated. The crude material was then purified by chromatography (40% EtOAc/hexane) to give 0.1109 g (50% yield) of TRV-1453. ¹H NMR (CDCl3, 500 MHz) δ=8.01 (s, 1H), 7.72 (dd, J=8, 1.6 Hz, 2H), 7.51 (t, J=8 Hz, 1H), 7.26-7.23 (m, 3H), 7.02 (t, J=8 Hz, 2H), 6.35 (s, 1H), 6.32 (br s, 1H), 5.13 (s, 2H), 3.17 (s, 3H), 2.94-2.92 (m, 1H), 0.92-0.85 (m, 2H), 0.67-0.64 (m, 2H).

TRV-1454

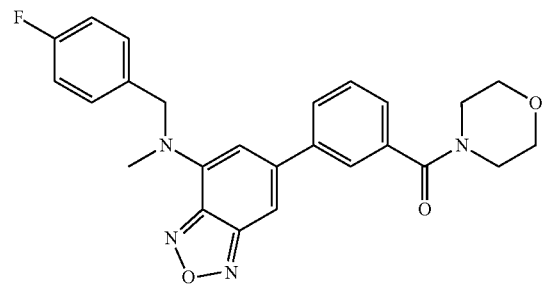

6-bromo-N-(4-fluorobenzyl)-N-methylbenzo[c][1,2,5]oxadiazol-4-amine (1.00 g, 2.97 mmol) and 3-carboxyphenylboronic acid (0.5176 g, 3.12 mmol) were massed into a tube. The tube was evacuated and purged with argon (3×). DME (8.9 mL) and 2M Na₂CO₃ (6.0 mL, 11.9 mmol) were then added followed by Pd(PPh₃)₄ (0.1733 g, 0.15 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give the crude material. This was purified via 5% MeOH/DCM column to afford 1.0873 g (97% yield, 90% chemical purity) of the acid. A mixture of the acid (0.200 g, 0.529 mmol), morpholine (0.05 mL, 0.529 mmol) and TEA (0.18 mL, 1.32 mmol) were stirred in EtOAc (6 mL) and cooled in an ice bath. The T3P solution (0.4040 g, 50% w/w in EtOAc) was added dropwise. Once the addition was complete the reaction was allowed to warm to room temperature. The reaction was then quenched with water and extracted with EtOAc. The combined organic layers were washed with water (3×), brine, dried (Na₂SO₄), filtered and concentrated. The crude material was then purified by chromatography (65% EtOAc/hexane) to give 0.1331 g (56% yield) of TRV-1454. ¹H NMR (CDCl3, 500 MHz) δ=7.67 (d, J=10 Hz, 1H), 7.64 (s, 1H), 7.52 (t, J=10 Hz, 1H), 7.44-7.41 (m, 2H), 7.26-7.23 (m, 2H), 7.02 (t, J=10 Hz, 2H), 6.33 (s, 1H), 5.13 (s, 2H), 3.81 (br s, 4H), 3.63 (br s, 2H), 3.48 (br s, 2H), 3.17 (s, 3H).

TRV-1455

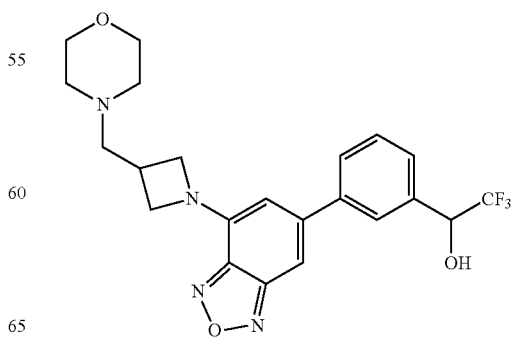

To a stirring solution of (1-(6-bromobenzo[c][1,2,5]oxadiazol-4-yl)azetidin-3-yl)methanol (500 mg, 1.76 mmol) in DCM (20 mL) was added Dess-Martin periodane (1.1 g, 2.64 mmol) and the solution was left to stir for 1 hour. At this time the reaction was diluted with EtOAc (100 mL) and washed with sodium carbonate (sat.). The organic layer was dried with MgSO$_4$, and concentrated in vacuo. The crude material was purified by plugging through SiO$_2$ (DCM) to give 420 mg (1.49 mmol, 84% yield) of aldehyde. $^1$H NMR (500 MHz, CDCl$_3$) δ=9.96 (d, J=2 Hz, 1H), 7.26 (s, 1H), 5.96 (s, 1H), 4.47 (m, 4H), 3.7 (m, 1H). To a stirring solution of this aldehyde (316 mg, 1.1 mmol) in DCM (5 mL) was added morpholine (105 μL, 1.21 mmol) followed by sodium triacetoxyborohydride (326 mg, 1.54 mmol). When the reaction was deemed complete (monitored by TLC), it was diluted with DCM (100 mL) and washed with water (50 mL), sodium hydroxide (1M, 50 mL), then dried with MgSO$_4$ and concentrated in vacuo to give 406 mg of amine. The material was used without further purification. $^1$H NMR (500 MHz, CDCl$_3$) δ=7.16 (s, 1H), 5.85 (s, 1H), 4.39 (m 2H), 3.97 (m, 2H), 3.70 (m, 4H), 3.05 (m, 1H), 2.68 (d, J=8 Hz, 2H), 2.45 (m, 4H). To a solution of this amine (406 mg, 1.15 mmol) in DME (7 mL)/Na$_2$CO$_3$ (2M, 1.7 mL) was added 3-formyl-phenylboronic acid (259 mg, 1.9 mmol) and Pd(P(Ph)$_3$)$_4$ (60 mg). The flask was then fitted with a reflux condenser, purged with argon and heated to 85° C. O/N. The reaction was worked up by pouring into 1 M NaOH (150 mL) and vacuum isolating the resultant solids. The crude material was purified by plugging through SiO$_2$ (50% Acetone in EtOAc) to give 380 mg (1 mmol, 85% yield) of aldehyde which was used as is. $^1$H NMR (500 MHz, CDCl$_3$) δ=10.1 (s, 1H), 8.13 (s, 1H), 7.93 (d, J=8 Hz, 1H), 7.89 (d, J=8 Hz, 1H), 7.66 (t, J=8 Hz, 1H), 7.18 (s, 1H), 6.05 (s, 1H), 4.46 (t, J=8 Hz, 2H), 4.04 (m, 2H), 3.72 (t, J=4 Hz, 4H), 3.10 (m, 1H), 2.72 (d, J=7 Hz, 2H), 2.47 (m, 4H). To a stirring solution of this aldehyde (380 mg, 1.0 mmol) and Rupert's reagent (220 μL, 1.5 mmol) in THF (3 mL) at 0° C. was added TBAF (0.2 mL, 1 M THF, 0.2 mmol). After 30 min at low temperature the cold bath was removed and the reaction was allowed to come to RT. After 3 hours the reaction was concentrated in vacuo and the flask was charged with THF (20 mL). To this an excess of TBAF was added and the reaction was left to stir. Once the deprotection was complete EtOAc (100 mL) was added and the reaction was washed with, brine, dried with MgSO$_4$ and concentrated in vacuo. The crude material was purified by flash column chromatography (80% EtOAc, 2% TEA, balance Hex) to give 100 mg (22% yield). $^1$H NMR (500 MHz, CDCl$_3$) δ=7.72 (s, 1H), 7.65 (dm, J=8 Hz, 1H), 7.52 (m, 2H), 7.15 (s, 1H), 6.03 (s, 1H), 5.13 (q, J=5 Hz, 1H), 4.44 (t, J=8 Hz, 2H), 4.01 (m, 2H), 3.72 (t, J=6 Hz, 4H), 3.09 (m, 1H), 2.92 (s, br, 1H), 2.71 (d, j=8 Hz, 2H), 2.47 (m, 4H).

To a stirring solution of 1-(6-bromobenzo[c][1,2,5]oxadiazol-4-yl)azetidin-3-ol (280 mg, 1.04 mmol) dissolved in DCM (10 mL) was added Dess-Martin reagent (Oakwood) (571 mg, 1.3 mmol) dissolved in DCM (4 mL). After 1 hour the reaction had become turbid and a precipitate had formed. The material was poured in to 1 M NaOH and extracted with TBME to give the corresponding ketone. $^1$H NMR (500 MHz, CDCl$_3$) δ=7.40 (s, 1H), 6.13 (s, 1H), 5.10 (s, 4H). To a stirring solution of the ketone (226 mg, 0.8 mmol) in DCM (4 mL) was added pyrrolidine (75 μL, 0.9 mmol), glacial acetic acid (45 μL, 0.9 mmol) and sodium triacetoxyborohydride (250 mg, 1.26 mmol). When the reaction was deemed complete (TLC) it was diluted with EtOAc (100 mL) and washed with sodium hydroxide (1M aq). The organic phase was then washed with brine, dried with MgSO$_4$ and concentrated in vacuo. The crude amine was purified by flash chromatography (EtOAc) to give 216 mg (0.7 mmol, 79% yield) of material. $^1$H NMR (500 MHz, CDCl$_3$) δ=7.18 (s, 1H), 5.89 (s, 1H), 4.28 (m, 2H), 4.21 (m, 2H), 3.53 (m, 1H), 2.57 (m, 4H), 1.58 (m, 4H). To a solution of this amine (216 mg, 0.7 mmol) in DME (4 mL)/Na$_2$CO$_3$ (2M, 1.05 mL) was added 3-formyl-phenylboronic acid (158 mg, 1.05 mmol) and Pd(P(Ph)$_3$)$_4$ (60 mg). The flask was then fitted with a reflux condenser, purged with argon and heated to 85° C. O/N. The reaction was worked up by pouring into 1 M NaOH (150 mL) and vacuum isolating the resultant solids. The crude material was purified by plugging through SiO$_2$ (EtOAc 1% MeOH) to give 212 mg of aldehyde which was used as is. $^1$H NMR (500 MHz, CDCl$_3$) δ=10.1 (s, 1H), 8.11 (s, 1H), 7.93 (d, J=8 Hz, 1H), 7.87 (d, J=8 Hz, 1H), 7.63 (m 1H), 7.17 (s, 1H), 6.05 (s, 1H), 4.43 (m, 2H), 4.24 (m, 2H), 3.53 (m, 1H), 2.58 (m, 4H), 1.85 (m, 4H). To a stirring solution of this aldehyde (212 mg, 0.6 mmol) and Rupert's reagent (266 μL, 1.8 mmol) in THF (3 mL) at 0° C. was added TBAF (0.2 mL, 1 M THF, 0.2 mmol).

After 30 min at low temperature the cold bath was removed and the reaction was allowed to come to RT. After 3 hours the reaction was concentrated in vacuo and the flask was charged with THF (20 mL). To this an excess of TBAF was added and the reaction was left to stir. Once the deprotection was complete EtOAc (100 mL) was added and the reaction was washed with saturated NH$_4$Cl, brine, and then dried with MgSO$_4$ and concentrated in vacuo. The crude material was purified by flash column chromatography (2% MeOH in DCM) to give 16 mg (6.2% yield). $^1$H NMR (500 MHz, DMSO) δ=7.89 (s, 1H), 7.81 (dm, J=8 Hz, 1H), 7.56 (m, 2H), 7.31 (s, 1H), 6.96 (d, J=6 Hz, 1H), 6.25 (s, 1H), 5.28 (m 1H), 4.38 (m, 2H), 4.16 (m, 2H), 3.52 (m, 1H), 2.51 (m, 4H), 1.73 (m, 4H).

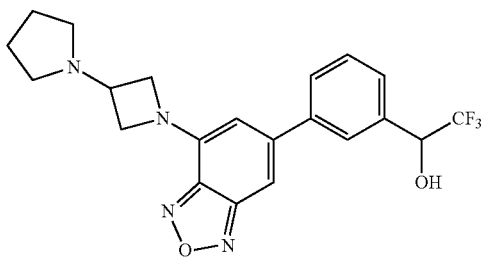

TRV-1456

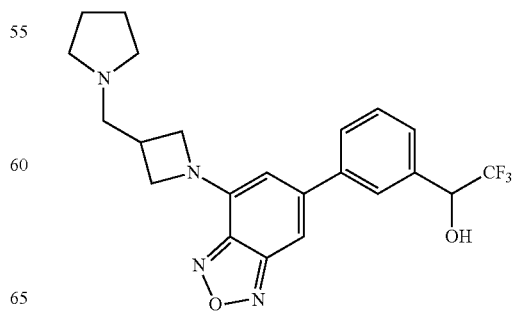

TRV-1457

To a stirring solution of (1-(6-bromobenzo[c][1,2,5]ox-adiazol-4-yl)azetidin-3-yl)methanol (500 mg, 1.76 mmol) in DCM (20 mL) was added Dess-Martin periodane (1.1 g, 2.64 mmol) and the solution was left to stir for 1 hour. At this time the reaction was diluted with EtOAc (100 mL) and washed with sodium carbonate (sat.). The organic layer was dried with MgSO$_4$, and concentrated in vacuo. The crude material was purified by plugging through SiO$_2$ (DCM) to give 420 mg (1.49 mmol, 84% yield) of aldehyde. $^1$H NMR (500 MHz, CDCl$_3$) δ=9.96 (d, J=2 Hz, 1H), 7.26 (s, 1H), 5.96 (s, 1H), 4.47 (m, 4H), 3.7 (m, 1H). To a stirring solution of this aldehyde (316 mg, 1.1 mmol) in DCM (5 mL) was added pyrrolidine (118 μL, 1.45 mmol) followed by sodium triacetoxyborohydride (385 mg, 1.82 mmol). When the reaction was deemed complete (monitored by TLC), it was diluted with DCM (100 mL) and washed with water (50 mL), sodium hydroxide (1M, 50 mL), then dried with MgSO$_4$ and concentrated in vacuo to give 425 mg. The material was used without further purification. $^1$H NMR (500 MHz, CDCl$_3$) δ=7.14 (s, 1H), 5.83 (s, 1H), 4.40 (m, 2H), 3.98 (m, 2H), 3.04 (m, 1H), 2.76 (d, J=8 Hz, 2H), 2.51 (m, 4H), 1.79 (m, 4H). To a solution of amine (425 mg, 1.26 mmol) in DME (8 mL)/Na$_2$CO$_3$ (2M, 1.9 mL) was added 3-formyl-phenylboronic acid (283 mg, 1.9 mmol) and Pd(P(Ph)$_3$)$_4$ (66 mg). The flask was then fitted with a reflux condenser, purged with argon and heated to 85° C. O/N. The reaction was worked up by pouring into 1 M NaOH (150 mL) and vacuum isolating the resultant solids. The crude material was purified by plugging through SiO$_2$ (50% Acetone in EtOAc) to give 274 mg (0.75 mmol, 75% yield) of aldehyde which was used as is. $^1$H NMR (500 MHz, CDCl$_3$) δ=10.10 (s, 1H), 8.12 (s, 1H), 7.93 (d, J=8 Hz, 1H), 7.89 (d, J=8 Hz, 1H), 7.65 (t, J=8 Hz, 1H), 717 (s, 1H), 6.03 (s, 1H), 4.48 (t, J=8 Hz, 2H), 4.05 (m, 2H), 3.10 (m, 1H), 2.81 (d, J=8 Hz, 2H), 2.54 (m, 4H), 1.80 (m, 4H). To a stirring solution of this aldehyde (274 mg, 0.75 mmol) and Rupert's reagent (166 μL, 1.1 mmol) in THF (3 mL) at 0° C. was added TBAF (0.1 mL, 1 M THF, 0.1 mmol). After 30 min at low temperature the cold bath was removed and the reaction was allowed to come to RT. After 3 hours the reaction was concentrated in vacuo and the flask was charged with THF (20 mL). To this an excess of TBAF was added and the reaction was left to stir. Once the deprotection was complete EtOAc (100 mL) was added and the reaction was washed with saturated NH$_4$Cl, brine, and then dried with MgSO$_4$ and concentrated in vacuo. The crude material was purified by flash column chromatography (50% EtOAc, 49% Hex, 1% TEA) to give 70 mg (22% yield). $^1$H NMR (500 MHz, DMSO-D$_6$) δ=7.88 (s, 1H), 7.81 (d, J=8 Hz, 1H), 7.59 (dm, J=7 Hz, 1H), 7.54 (t, J=8 Hz, 1H), 7.30 (s, 1H), 6.96 (d, J=5 Hz, 1H), 6.24 (s, 1H), 5.28 (m, 1H), 4.38 (m, 2H), 3.97 (m, 2H), 3.00 (m, 1H), 2.74 (d, J=7 Hz, 2H), 2.45 (m, 4H), 1.68 (m, 4H).

4,6-dibromobenzo[c][1,2,5]oxadiazole (2.013 g, 7.24 mmol) and (S)-ethyl pyrrolidine-2-carboxylate hydrochloride salt (1.43 g, 7.96 mmol) were massed into a tube. The tube was evacuated and flushed with argon for three cycles. NMP (10 mL) and DIPEA (3.5 mL, 19.9 mmol) were then added and the tube was sealed and heated to 50° C. overnight. Upon cooling to room temperature the mixture was diluted with water and EtOAc. The layers were separated and the aqueous layer was back-extracted with EtOAc. The combined organic layers were then washed with water (5×), brine, dried (Na$_2$SO$_4$), filtered and concentrated to give an oil. The crude oil was then purified via flash column chromatography (15% EtOAc/hexane) to afford 0.6105 g (25% yield) of aniline. The aniline (1.696 g, 4.9 mmol) was dissolved in DCM (20 mL) and cooled to −78° C. DIBAL (12.5 mL, 1.0 M solution in hexanes) was added dropwise and then the reaction was allowed to warm to room temperature overnight. The reaction was quenched with MeOH and then Na$_2$SO$_4$ was added and the mixture was stirred for 30 minutes before filtering through Celite. The organic phase was diluted with EtOAc and water. The layers were separated and the organic layer was washed with H$_2$O (3×), brine, dried (Na$_2$SO$_4$), filtered and concentrated. The crude material was purified via chromatography (30% EtOAc/hexane) to give 1.294 g (87% yield) of the primary alcohol. The primary alcohol (0.9956 g, 3.34 mmol) was dissolved in DCM (100 mL) and DMP (2.1249 g, 5.0 mmol) was added. The reaction was stirred for 2 hours and then it was quenched with saturated NaHCO$_3$ (aq) and excess Na$_2$SO$_4$ (8.0 g) was added and the mixture was stirred until all solids dissolved. This mixture was then extracted with DCM and the combined organic layer was dried (Na$_2$SO$_4$), filtered and concentrated. Purification (20% EtOAc/hexane column) afforded 0.6471 g (65% yield) of the aldehyde. This aldehyde (0.206 g, 0.696 mmol) and cyclobutylamine hydrolchloride (0.0794 g, 0.738 mmol) were dissolved in methanol (3 mL) and TEA (0.19 mL, 1.39 mmol) was added. This material was stirred for 24 hours and was then cooled to 0° C. To this mixture was then added NaBH$_4$ (0.0685 g, 1.81 mmol) portionwise. The mixture was stirred for 60 minutes and then was quenched with 1N NaOH (aq). The mixture was extracted with EtOAc (3×) and the combined organics were washed with H$_2$O (3×), brine, dried (Na$_2$SO$_4$), filtered and concentrated to give the crude amine To a solution of this amine in THF (5 mL) at 0° C. was added TEA (0.19 mL, 1.39 mmol), DMAP (a crystal) and then BOC$_2$O (0.1822 g, 0.835 mmol). The reaction was stirred at 0° C. while monitoring by TLC. It was then quenched with H$_2$O and extracted with EtOAc. The combined organics were washed with H$_2$O (3×), brine, dried (Na$_2$SO$_4$), filtered and concentrated to give the crude carbamate. This carbamate and 3-formylphenylboronic acid (0.1094 g, 0.73 mmol) were massed into a tube. The tube was evacuated and purged with argon (3×). DME (1.6 mL) and 2M Na$_2$CO$_3$ (1.1 mL, 2.09 mmol) were then added followed by Pd(PPh$_3$)$_4$ (0.0402 g, 0.0348 mmol). The tube was then sealed and heated to 80° C. overnight. Upon cooling to room temperature the mixture was diluted with water and EtOAc. The layers were separated and the aqueous layer was back-extracted with EtOAc. The combined organic layers were then washed with water (5×), brine, dried (Na$_2$SO$_4$), filtered and concentrated to give an oil. This crude oil was then dissolved in THF (4 mL) and cooled to 0° C. CF$_3$TMS (0.21 mL, 1.39 mmol) was added followed by TBAF (0.07 mL, 1.0 M solution in THF). The reaction was then stirred for 60 minutes before re-cooling to 0° C. and 4N HCl (aq) was added and stirred for 60 minutes. The mixture was diluted with water and EtOAc. The layers

TRV-1458

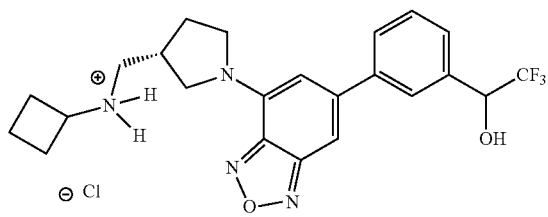

were separated and the aqueous layer was basified. The aqueous layer was then re-extracted with EtOAc. The combined organic layers were was with water, brine, dried (Na₂SO₄), filtered and concentrated to give the trifluorocarbinol, as a mixture of diastereomers. This crude material was then dissolved in DCM (15 mL) and cooled to 0° C. TFA (0.53 mL) was added and the mixture was stirred for 36 hours before quenching with saturated NaHCO₃(aq). This mixture was extracted with DCM (5×) and the combined organics were dried with NA₂SO₄, filtered and then concentrated. This crude material was purified via 5% MeOH/DCM column to afford 0.130 g of the free amine. This material was then dissolved in MeOH at 0° C. and treated with a large excess of methanolic HCl. The reaction mixture was stirred for 30 minutes and then concentrated to produce 0.081 g (24% yield, 8 steps) of TRV-1458. ¹H NMR (MeOD, 700 MHz) δ=7.83 (s, 1H), 7.74 (d, J=7.6 Hz, 1H), 7.56 (d, J=7.6 Hz, 1H), 7.52 (t, J=7.6 Hz, 1H), 7.26 (s, 1H), 6.43 (s, 1H), 5.16 (q, J=7.1 Hz, 1H), 3.87 (m, 1H), 3.78-3.77 (m, 1H), 3.52-3.50 (m, 1H), 3.30 (s, 2H), 3.25 (dd, J=12.5, 2.1 Hz, 1H), 3.05 (t, J=11.0 Hz, 1H), 2.36-2.20 (m, 9H), 1.99-1.90 (m, 2H).

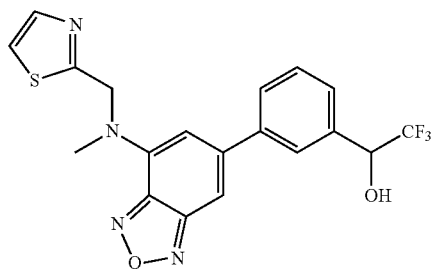

TRV-1459

4,6-dibromobenzo[c][1,2,5]oxadiazole (1.1509 g, 4.14 mmol) and N-methyl-1-(thiazol-2-yl)methanamine (4.97 mmol) were massed into a tube. The tube was evacuated and flushed with argon for three cycles. NMP (6 mL) and DIPEA (0.94 mL, 5.38 mmol) were then added and the tube was sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. The crude oil was then purified via flash column chromatography (30% EtOAc/hexane) to afford 0.1872 g (14% yield) of aniline. This aniline (0.1872 g, 0.58 mmol) and 3-formylphenylboronic acid (0.0899 g, 0.60 mmol) were massed into a tube. The tube was evacuated and purged with argon (3×). DME (1.5 mL) and 2M Na₂CO₃ (0.9 mL, 1.74 mmol) were then added followed by Pd(PPh₃)₄ (0.0335 g, 0.029 mmol). The tube was then sealed and heated to 85° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil was then dissolved in THF (4 mL) and cooled to 0° C. CF₃TMS (0.17 mL, 1.16 mmol) was added followed by TBAF (0.06 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were was with water, brine, dried (Na₂SO₄), filtered and concentrated to give a crude oil. This material was purified via flash column chromatography with step-gradient (100% DCM to 0.5% MeOH/DCM) to afford 0.0339 g (14% yield, 3 steps) of TRV-1459. ¹H NMR (CDCl3, 700 MHz) δ=7.77 (d, J=3.2 Hz, 1H), 7.73 (s, 1H), 7.66 (dt, J=7.2, 1.6 Hz, 1H), 7.55-7.51 (m, 2H), 7.31 (s, 1H), 7.30 (d, J=3.2 Hz, 1H), 6.46 (s, 1H), 5.46 (s, 2H), 5.13 (q, J=6.6 Hz, 1H), 3.32 (s, 3H).

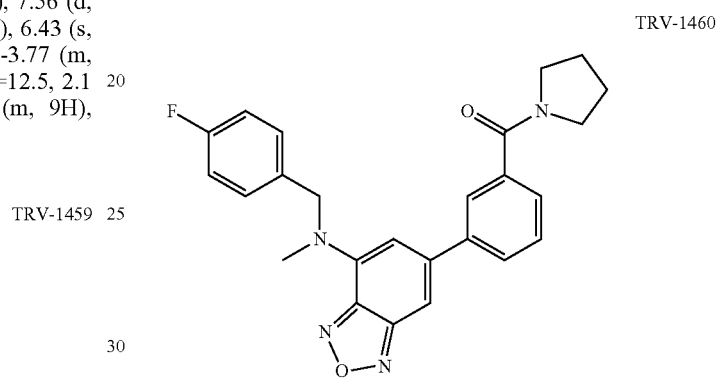

TRV-1460

6-bromo-N-(4-fluorobenzyl)-N-methylbenzo[c][1,2,5]oxadiazol-4-amine (1.00 g, 2.97 mmol) and 3-carboxyphenylboronic acid (0.5176 g, 3.12 mmol) were massed into a tube. The tube was evacuated and purged with argon (3×). DME (8.9 mL) and 2M Na₂CO₃ (6.0 mL, 11.9 mmol) were then added followed by Pd(PPh₃)₄ (0.1733 g, 0.15 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give the crude material. This was purified via 5% MeOH/DCM column to afford 1.0873 g (97% yield, 90% chemical purity) of the acid. A mixture of the acid (0.3774 g, 1.0 mmol), pyrrolidine (0.083 mL, 1.0 mmol) and TEA (0.35 mL, 2.5 mmol) were stirred in EtOAc (10 mL) and cooled in an ice bath. The T3P solution (0.7636 g, w/w in EtOAc) was added dropwise. Once the addition was complete the reaction was allowed to warm to room temperature. The reaction was then quenched with water and extracted with EtOAc. The combined organic layers were washed with water (3×), brine, dried (Na₂SO₄), filtered and concentrated. The crude material was then purified by two successive columns (75% EtOAc/hexane and then 70% EtOAc/hexane) to give 0.1436 g (33% yield, 96% c.p.) of TRV-1460. ¹H NMR (CDCl3, 500 MHz) δ=7.75 (s, 1H), 7.65 (d, J=10 Hz, 1H), 7.55 (d, J=10 Hz, 1H), 7.52-7.48 (m, 1H), 7.26-7.23 (m, 3H), 7.01 (t, J=10 Hz, 2H), 6.35 (s, 1H), 5.12 (s, 2H), 3.68 (t, J=5 Hz, 2H), 3.45 (t, J=5 Hz, 2H), 2.02-1.95 (m, 2H), 1.92-1.86 (m, 2H).

TRV-1461

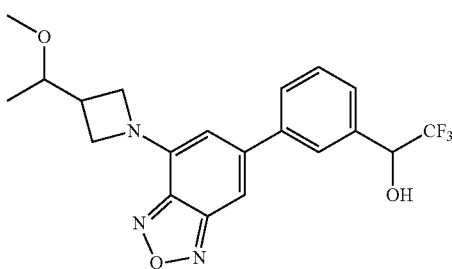

1-(6-bromobenzo[c][1,2,5]oxadiazol-4-yl)azetidine-3-carboxylic acid (1.5 g, 5 mmol) was dissolved in THF (50 mL) and cooled to 0° C. To this was added BH$_3$-THF (10 mL, 10 mmol). The reaction was allowed to come to room temperature overnight. The next day the reaction was quenched with AcOH and extracted into EtOAc. The organic layer was washed with 1 M NaOH until the washings remained litmus blue and then concentrated in vacuo. The crude material was fused to SiO$_2$ and purified by flash column chromatography (3:2 Hex:EtOAc) to give 800 mg of primary alcohol (56% yield). $^1$H NMR (500 MHz, CDCl$_3$) δ=7.05 (s, 1H), 6.11 (s, 1H), 5.30 (s, 1H), 4.11 (t, J=8 Hz, 2H), 3.85 (m, 4H), 3.00 (m, 1H). To a stirring solution of the alcohol (500 mg, 1.76 mmol) in DCM (20 mL) was added Dess-Martin periodane (1.1 g, 2.64 mmol) and the solution was left to stir for 1 hour. At this time the reaction was diluted with EtOAc (100 mL) and washed with sodium carbonate (sat.). The organic layer was dried with MgSO$_4$, and concentrated in vacuo. The crude material was purified by plugging through SiO$_2$ (DCM) to give 420 mg (1.49 mmol, 84% yield) of aldehyde. $^1$H NMR (500 MHz, CDCl$_3$) δ=9.96 (d, J=2 Hz, 1H), 7.26 (s, 1H), 5.96 (s, 1H), 4.47 (m, 4H), 3.7 (m, 1H). To a 0° C. stirring solution of this aldehyde (420 mg, 1.5 mmol) in THF (10 mL) was added methylmagnesium bromide (1M, 1.8 mL). After 10 min at reduced temperature the cold bath was removed and the reaction was allowed to come to RT. After 1 hour the reaction was cooled back to 0° C. and saturated NH$_4$Cl was cautiously added. The reaction mixture was then diluted with EtOAc (100 mL) and the phases were separated. The organic phase was washed with brine, dried with MgSO$_4$ and concentrated in vacuo. The crude material was fused to SiO$_2$ (4 g) and gradient flashed (0-2% MeOH in DCM) to give 380 mg (1.27 mmol, 85% yield) of secondary alcohol. To a solution of the secondary alcohol (approx. 190 mg, 0.65 mmol) dissolved in THF (5 mL) and cooled to 0° C. was added NaH 60% in oil (100 mg, 3 mmol). Once the initial bubbling had subsided MeI (200 µL, 3 mmol) was added dropwise the reaction mixture was left to come to RT. After 18 h the reaction was cooled back to 0° C. and NH$_4$Cl was cautiously added. The reaction mixture was extracted with EtOAc (3×50 mL), washed with brine (150 mL) and concentrated in vacuo. The crude material was purified by plugging through SiO$_2$ (80% DCM in Hex) to give 160 mg (78% yield) of methyl ether. To a solution of the methyl ether (160 mg, 0.5 mmol) in DME (4 mL)/Na$_2$CO$_3$ (2 M, 0.75 mL) was added 3-formyl-phenylboronic acid (113 mg, 1.5 mmol) and Pd(P(Ph)$_3$)$_4$ (40 mg). The flask was then fitted with a reflux condenser, purged with argon and heated to 85° C. O/N. The reaction was worked up by pouring into 1 M NaOH (150 mL) and vacuum isolating the resultant solids. The crude material was purified by plugging through SiO$_2$ (DCM/5% EtOAc) to give 150 mg of aldehyde which was used as is. To a stirring solution of the aldehyde (150 mg, 0.4 mmol) and Rupert's reagent (98 µL, 0.7 mmol) in THF (2 mL) at 0° C. was added TBAF (0.2 mL, 1 M THF, 0.2 mmol). After 30 min at low temperature the cold bath was removed and the reaction was allowed to come to RT. After 3 hours the reaction was concentrated in vacuo and the flask was charged with THF (20 mL). To this an excess of TBAF was added and the reaction was left to stir. Once the deprotection was complete EtOAc (100 mL) was added and the reaction was washed with saturated NH$_4$Cl, brine, and then dried with MgSO$_4$ and concentrated in vacuo. The crude material was purified by flash column chromatography (30% EtOAc in Hexane) to give 37 mg (23% yield) of TRV-1461, a 1:1:1:1 mixture of diastereomers due to the two chiral centers. $^1$H NMR (500 MHz, DMSO) δ=7.72 (s, 1H), 7.65 (d, J=7 Hz, 1H), 7.52 (m, 2H), 7.13 (s, 1H), 6.02 (s, 1H), 5.13 (m, 1H), 4.38 (m, 2H), 4.19 (m, 1H), 4.09 (m, 1H), 3.55 (p, J=6 Hz, 1H), 3.39 (s, 3H), 2.88 (m, 1H), 2.71 (s, br, 1H), 1.78 (d, J=6 Hz, 3H).

TRV-1462

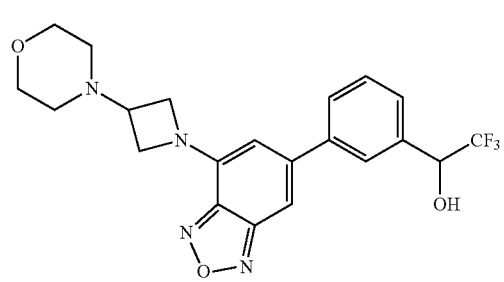

To a stirring solution of 1-(6-bromobenzo[c][1,2,5]oxadiazol-4-yl)azetidin-3-ol (730 mg, 2.7 mmol) dissolved in DCM (10 mL) was added Dess-Martin reagent (Oakwood) (1.26 g, 2.97 mmol) dissolved in DCM (10 mL). After 1 hour the reaction had become turbid and a precipitate had formed. The material was poured in to 1 M NaOH and extracted with TBME to give the corresponding ketone. $^1$H NMR (500 MHz, CDCl$_3$) δ=7.40 (s, 1H), 6.13 (s, 1H), 5.10 (s, 4H). To a stirring solution of the ketone (300 mg, 1.1 mmol) in DCM (4 mL) was added morpholine (160 µL, 1.23 mmol), glacial acetic acid (65 µL, 1.1 mmol) and sodium triacetoxyborohydride (360 mg, 1.68 mmol). When the reaction was deemed complete (TLC) it was diluted with EtOAc (100 mL) and washed with sodium hydroxide (1M aq). The organic phase was then washed with brine, dried with MgSO$_4$ and concentrated in vacuo. The crude amine was purified by flash chromatography (EtOAc) to give 470 mg (1.4 mmol, 52% yield) of material. To a solution of this amine (470 mg, 1.4 mmol) in DME (5 mL)/Na$_2$CO$_3$ (2M, 2 mL) was added 3-formyl-phenylboronic acid (180 mg, 1.05 mmol) and Pd(P(Ph)$_3$)$_4$ (80 mg). The flask was then fitted with a reflux condenser, purged with argon and heated to 85° C. O/N. The reaction was worked up by pouring into 1 M NaOH (150 mL) and vacuum isolating the resultant solids. The crude material was purified by plugging through SiO$_2$ (EtOAc 1% MeOH) to give 300 mg of aldehyde which was used as is. To a stirring solution of this aldehyde (300 mg, 0.8 mmol) and Rupert's reagent (240 µL, 1.6 mmol) in THF (3 mL) at 0° C. was added TBAF (0.2 mL, 1 M THF, 0.2 mmol). After 30 min at low temperature the cold bath was removed and the reaction was allowed to come to RT. After 3 hours the reaction was concentrated in vacuo and the flask was charged with THF (20 mL). To this an excess of TBAF was added and the reaction was left to stir. Once the deprotection was complete EtOAc (100 mL) was added and the reaction was washed with saturated NH₄Cl, brine, and then dried with MgSO₄ and concentrated in vacuo. The crude material was purified by flash column chromatography (2% MeOH in DCM) to give 40 mg (9% yield). ¹H NMR (500 MHz, DMSO) δ=7.71 (s, 1H), 7.63 (d, J=7 Hz, 1H), 7.51 (m, 2H), 7.16 (s, 1H), 6.06 (s, 1H), 5.13 (m, 1H), 4.41 (t, J=8 Hz, 2H), 4.18 (m, 2H), 3.77 (m, 4H), 3.42 (p, J=6 Hz, 1H), 2.87 (s, broad, 1H), 2.48 (m, 4H).

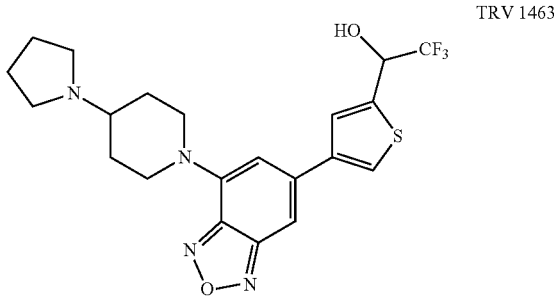 [SMILES: OC(c1cc(-c2cc(N3CCC(N4CCCC4)CC3)c3nonc3c2)cs1)C(F)(F)F]

TRV 1463

6-bromo-4-(4-(pyrrolidin-1-yl)piperidin-1-yl)benzo[c][1,2,5]oxadiazole (0.3366 g, 0.958 mmol) and 2-formylthiophene-4-boronic acid (0.1794 g, 1.15 mmol) were massed into a tube. The tube was evacuated and purged with argon (3×). DME (2.1 mL) and 2M Na₂CO₃ (1.4 mL, 2.87 mmol) were then added followed by Pd(PPh₃)₄ (0.0554 g, 0.048 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil was then dissolved in THF (5 mL) and cooled to 0° C. CF₃TMS (0.21 mL, 1.44 mmol) was added followed by TBAF (0.1 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na₂SO₄), filtered and concentrated to give a crude oil. This material was purified via flash column chromatography (5% MeOH/DCM) to afford 0.067 g (15% yield, 3 steps) of TRV-1463 as a yellow solid. ¹H NMR (DMSO, 700 MHz) δ=8.29 (d, J=1.0 Hz, 1H), 7.81 (s, 1H), 7.59 (s, 1H), 7.37 (d, J=6.0 Hz, 1H), 6.83 (s, 1H), 5.52-5.48 (m, 1H), 4.22 (br s, 2H), 3.13 (t, J=12 Hz, 2H), 2.59 (br s, 4H), 2.32-2.30 (m, 1H), 2.02-2.01 (m, 2H), 1.71 (s, 4H), 1.62-1.61 (m, 2H).

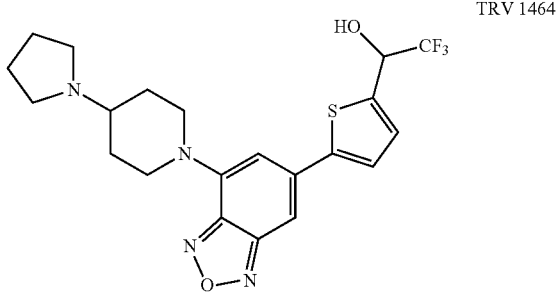 [SMILES: OC(c1ccc(-c2cc(N3CCC(N4CCCC4)CC3)c3nonc3c2)s1)C(F)(F)F]

TRV 1464

6-bromo-4-(4-(pyrrolidin-1-yl)piperidin-1-yl)benzo[c][1,2,5]oxadiazole (0.3368 g, 0.958 mmol) and 5-formyl-2-thienyl-boronic acid (0.1793 g, 1.15 mmol) were massed into a tube. The tube was evacuated and purged with argon (3×). DME (2.1 mL) and 2M Na₂CO₃ (1.4 mL, 2.87 mmol) were then added followed by Pd(PPh₃)₄ (0.0554 g, 0.048 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil was then dissolved in THF (5 mL) and cooled to 0° C. CF₃TMS (0.28 mL, 1.92 mmol) was added followed by TBAF (0.1 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na₂SO₄), filtered and concentrated to give a crude oil. This material was purified via flash column chromatography (10% MeOH/DCM). The purity after the first column was inadequate so the separation was repeated with a 5% MeOH/DCM column to afford 0.060 g (14% yield, 3 steps) of TRV-1464. ¹H NMR (DMSO, 700 MHz) δ=7.77 (d, J=5 Hz, 1H), 7.56 (s, 1H), 7.42 (d, J=5 Hz, 1H), 7.28 (d, J=5 Hz, 1H), 6.76 (s, 1H), 5.59-5.55 (m, 1H), 4.24 (d, J=10 Hz, 2H), 3.17 (d, J=10 Hz, 2H), 2.60 (br s, 4H), 2.37 (br s, 1H), 2.05-2.02 (m, 2H), 1.72 (br s, 4H), 1.64-1.62 (m, 2H).

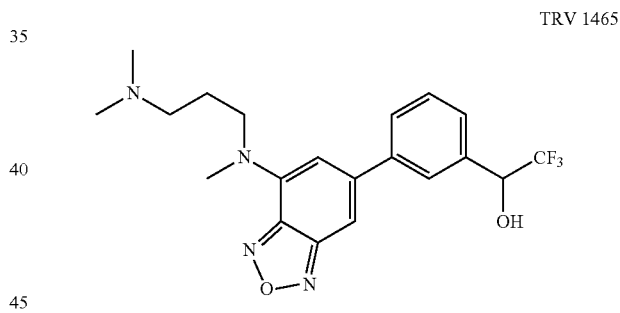

TRV 1465

A mixture of dibromobenzofurazan (0.500 g, 1.8 mmol), N1,N1,N3-trimethylpropane-1,3-diamine (0.28 mL, 1.9 mmol) and DIPEA (0.31 mL, 1.8 mmol) in NMP (2 mL) was heated to 100° C. overnight. After cooling to room temperature, the mixture was diluted with EtOAc and water. After the layers were separated, the aqueous layer was basified and extracted with EtOAc (3×). The combine organic layers were washed with water, brine, dried (MgSO₄), filtered and concentrated to give the crude aniline. This material was purified via 10% MeOH/DCM column to afford 0.3988 g of aniline. This aniline (0.3988 g, 1.27 mmol) and 3-formylphenylboronic acid (0.2488 g, 1.66 mmol) were massed into a tube. The tube was evacuated and purged with argon (3×). DME (2.8 mL) and 2M Na₂CO₃ (1.9 mL, 3.8 mmol) were then added followed by Pd(PPh₃)₄ (0.074 g, 0.064 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil was then dissolved in THF (5 mL) and cooled to 0° C. CF₃TMS (0.38 mL, 2.54 mmol) was added followed by TBAF (0.13 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na₂SO₄), filtered and concentrated to give a crude oil. This material was purified via flash column chromatography (10% MeOH/DCM) to afford 0.061 g (12% yield, 2 steps) of TRV-1465. ¹H NMR (DMSO, 500 MHz) δ=7.89 (s, 1H), 7.81 (d, J=10 Hz, 1H), 7.59-7.53 (m, 2H), 7.29 (s, 1H), 6.95 (d, J=5 Hz, 1H), 6.40 (s, 1H), 5.31-5.25 (m, 1H), 3.92 (t, J=10 Hz, 2H), 3.24 (s, 3H), 2.24 (t, J=10 Hz, 2H), 2.08 (s, 6H), 1.77-1.71 (m, 2H).

TRV 1466

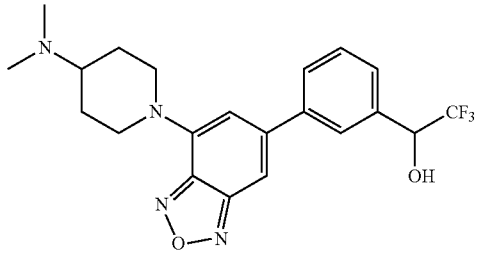

A mixture of dibromobenzofurazan (0.4669 g, 1.68 mmol), N,N-dimethylpiperidin-4-amine (0.2263 g, 1.76 mmol) and DIPEA (0.29 mL, 1.68 mmol) in NMP (3 mL) was heated to 95° C. overnight. After cooling to room temperature, the mixture was diluted with EtOAc and water. After the layers were separated, the aqueous layer was basified and extracted with EtOAc (3×). The combine organic layers were washed with water, brine, dried (MgSO₄), filtered and concentrated to give the crude aniline. This material was purified via 5% MeOH/DCM column to afford 0.2221 g of aniline. This aniline (0.2221 g, 0.68 mmol) and 3-formylphenylboronic acid (0.1334 g, 0.89 mmol) were massed into a tube. The tube was evacuated and purged with argon (3×). DME (3.0 mL) and 2M Na₂CO₃ (2.0 mL, 4 mmol) were then added followed by Pd(PPh₃)₄ (0.039 g, 0.034 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered and concentrated to give an oil. This crude oil was then dissolved in THF (5 mL) and cooled to 0° C. CF₃TMS (0.20 mL, 1.36 mmol) was added followed by TBAF (0.07 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na₂SO₄), filtered and concentrated to give a crude oil. This material was purified via flash column chromatography (10% MeOH/DCM) to afford 0.061 g (24% yield, 2 steps) of TRV-1466. ¹H NMR (DMSO, 700 MHz) δ=7.90 (s, 1H), 7.83 (d, J=7 Hz, 1H), 7.59 (d, J=7 Hz, 1H), 7.55 (t, J=7 Hz, 1H), 7.51 (d, J=3 Hz, 1H), 6.96 (d, J=3 Hz, 1H), 6.73 (s, 1H), 5.30-5.27 (m, 1H), 4.33 (d, J=7 Hz, 2H), 3.05 (t, J=14 Hz, 2H), 2.41-2.39 (m, 1H), 2.23 (s, 6H), 1.93 (d, J=14 Hz, 2H), 1.61-1.54 (m, 2H).

TRV 1467

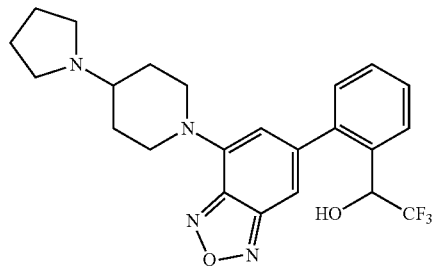

6-bromo-4-(4-(pyrrolidin-1-yl)piperidin-1-yl)benzo[c][1,2,5]oxadiazole (1 g, 2.8 mmol) and (2-formylphenyl)boronic acid (0.554 g, 3.6 mmol) were massed into a tube. The tube was evacuated and purged with argon (3×). DME (6 mL) and 2M Na₂CO₃ (4.2 mL, 8.4 mmol) were then added followed by Pd(PPh₃)₄ (0.160 g, 0.14 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered, concentrated and subjected to flash column chromatography (5% MeOH/DCM) to afford 0.95 g of 2-(7-(4-(pyrrolidin-1-yl)piperidin-1-yl)benzo[c][1,2,5]oxadiazol-5-yl)benzaldehyde. This aldehyde was then dissolved in THF (15 mL) and cooled to 0° C. CF₃TMS (0.738 mL, 5.06 mmol) was added followed by TBAF (0.25 mL, 1.0 M solution in THF). The cooling batch was removed and the reaction was stirred for 30 min. The reaction was then recooled and TBAF (0.30 mL, 1.0 M solution in THF) was added and the cooling bath removed. The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na₂SO₄), filtered and concentrated to give a crude oil. This material was purified via flash column chromatography (5% MeOH/DCM) to afford 0.550 g (44% yield, 2 steps) of TRV-1467 as a yellow solid. ¹H NMR (DMSO, 500 MHz) δ=7.72 (d, J=8.0 Hz, 1H), 7.58-7.48 (m, 2H), 7.36 (d, J=7.5 Hz, 1H), 7.15 (s, 1H) 6.91 (d, J=5 Hz, 1H), 6.33 (s, 1H), 5.13-5.11 (m, 1H), 4.16 (br s, 2H), 3.15-3.09 (m, 2H), 2.53-2.49 (m, 4H), 2.26 (br s, 1H), 1.99-1.97 (m, 2H), 1.68 (s, 4H), 1.59-1.57 (m, 2H).

TRV 1468

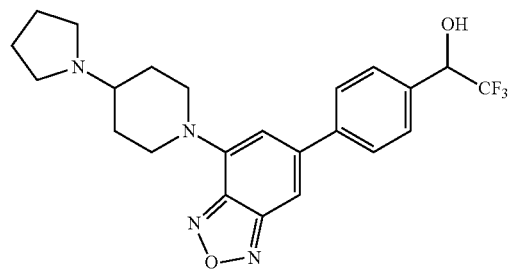

6-bromo-4-(4-(pyrrolidin-1-yl)piperidin-1-yl)benzo[c][1,2,5]oxadiazole (0.5 g, 1.4 mmol) and (2-formylphenyl)boronic acid (0.277 g, 1.8 mmol) were massed into a tube. The tube was evacuated and purged with argon (3×). DME (6 mL) and 2M Na₂CO₃ (4.2 mL, 8.4 mmol) were then added followed by Pd(PPh₃)₄ (0.080 g, 0.07 mmol). The tube was then sealed and heated to 100° C. overnight. Upon cooling to room temperature the mixture was diluted with water and EtOAc. The layers were separated and the aqueous layer was back-extracted with EtOAc. The combined organic layers were then washed with water (5×), brine, dried (Na₂SO₄), filtered, concentrated and subjected to flash column chromatography (5% MeOH/DCM) to afford 0.53 g of 4-(7-(4-(pyrrolidin-1-yl)piperidin-1-yl)benzo[c][1,2,5]oxadiazol-5-yl)benzaldehyde. This aldehyde was then dissolved in THF (5 mL) and cooled to 0° C. CF₃TMS (0.392 mL, 2.8 mmol) was added followed by TBAF (0.140 mL, 1.0 M solution in THF). The cooling batch was removed and the reaction was stirred for 30 min. The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na₂SO₄), filtered and concentrated to give a crude oil. This material was purified via flash column chromatography (5% MeOH/DCM) to afford 0.270 g (43% yield, 2 steps) of TRV-1468 as a yellow solid. ¹H NMR (DMSO, 500 MHz) δ=7.84 (d, J=8.0 Hz, 2H), 7.61 (d, J=8.0 Hz, 2H), 7.56 (s, 1H), 6.94 (d, J=5.5 Hz, 1H), 6.77 (s, 1H), 5.29-5.23 (m, 1H), 4.23 (br s, 2H), 2.49 (brs, 3H), 2.25 (br s, 1H), 2.01-1.99 (m, 2H) 1.69 (br s, 4H), 1.61-1.59 (m, 2H).

extracted with EtOAc. The combined organic layers were then washed with water (5×), brine, dried (Na₂SO₄), filtered and concentrated to give an oil. This crude oil was then dissolved in THF (5 mL) and cooled to 0° C. CF₃TMS (0.49 mL, 3.34 mmol) was added followed by TBAF (0.17 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na₂SO₄), filtered and concentrated to give a crude oil. This material was purified via flash column chromatography (5% MeOH/DCM with 6 mL NH₄OH) to afford 0.465 g (64% yield, 2 steps) of TRV-1469 as orange solid. ¹H NMR (DMSO, 700 MHz) δ=7.72 (s, 1H), 7.60 (d, J=7 Hz, 1H), 7.50 (d, J=7 Hz, 1H), 7.47 (t, J=7 Hz, 1H), 7.13 (d, J=3 Hz, 1H), 6.21 (s, 1H), 5.05 (q, J=7 Hz, 1H), 3.94 (t, J=7 Hz, 2H), 3.16 (s, 3H), 2.59 (br s, 6H), 1.95-1.91 (m, 2H), 1.81 (br s, 4H).

TRV-1470

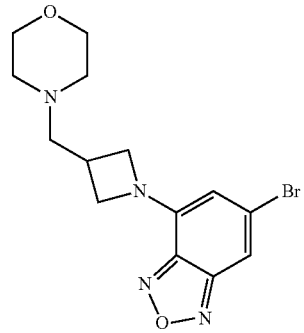

A mixture of 6-bromo-4-chlorobenzo[c][1,2,5]oxadiazole (3.1436 g, 13.4 mmol), 3-azetidinecarboxylic acid (1.76 g, 17.4 mmol) and DIPEA (7.0 mL, 40.2 mmol) in NMP (15 mL) was heated to 90° C. overnight. After cooling to room temperature, the mixture was diluted with EtOAc and 2N HCl. The layers were separated and the aqueous layer was back-extracted with EtOAc (3×). The combined organic layers were washed with water (3×), brine, dried (MgSO₄), filtered and concentrated to give the crude material. This material was then dissolved in EtOAc and extracted with 2 N NaOH (3×). The combined aqueous extracts were acidified to pH 1-2 with concentrated HCl. This suspension was then extracted with EtOAc (3×). The combined organic layers were then washed with water (3×), brine, dried (MgSO₄) filtered and concentrated to afford 3.0657 g of orange solid. This crude mixture (3.066 g, 10.3 mmol) was dissolved in THF and cooled to −10° C. with a MeOH/ice bath. A 1M solution of BH₃-THF in THF (21 mL, 21 mmol) was added dropwise, producing a bright red solution. The solution was stirred vigorously for 10 minutes and then allowed to warm to room temperature overnight. The reaction was quenched with the dropwise addition of 10 mL of AcOH/H₂O (1:1 v/v). After effervescence subsided, the mixture was concentrated to remove THF. The aqueous mixture was then basified with 2N NaOH and extracted with EtOAc (2×). The combined organic layers were washed with water, brine, dried (MgSO₄), filtered and concentrated. The material was purified via chromatography (40-50% EtOAc/hexane) to afford 1.942 g of the primary alcohol. This alcohol (0.9217 g, 3.2 mmol) was suspended in DCM (40

TRV 1469

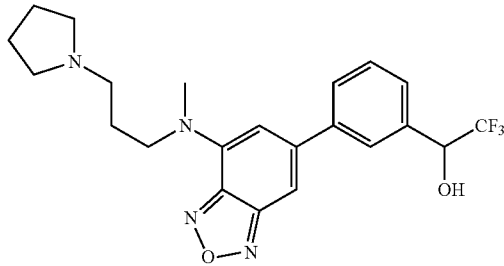

A mixture of 4,6-dibromobenzo[c][1,2,5]oxadiazole (1.6246 g, 5.8 mmol), N-methyl-3-(pyrrolidin-1-yl)propan-1-amine (approximately 7.6 mmol) and DIPEA (1.1 mL, 5.8 mmol) in NMP (6 mL) was heated to 90° C. overnight. After cooling to room temperature, the mixture was diluted with EtOAc and water. After the layers were separated, the aqueous layer was basified and extracted with EtOAc (3×). The combine organic layers were washed with water, brine, dried (MgSO₄), filtered and concentrated to give the crude aniline. This material was purified via 10% MeOH/DCM column to afford 0.5651 g of aniline. This aniline (0.5651 g, 1.67 mmol) and 3-formylphenylboronic acid (0.3253 g, 2.17 mmol) were massed into a tube. The tube was evacuated and purged with argon (3×). DME (3.7 mL) and 2M Na₂CO₃ (2.5 mL, 5 mmol) were then added followed by Pd(PPh₃)₄ (0.0965 g, 0.084 mmol). The tube was then sealed and heated to 100° C. overnight. Upon cooling to room temperature the mixture was diluted with water and EtOAc. The layers were separated and the aqueous layer was backmL) and then Dess-Martin reagent (1.789 g, 4.2 mmol) was added portion wise and the mixture was stirred for 2.5 hours. The reaction was then quenched with saturated NaHCO$_3$ (aq) and excess Na$_2$S$_2$O$_3$, stirring was continued until the solids dissolved. This mixture was then extracted with DCM (3×). The combined organic layers were washed with saturated NaHCO$_3$ (aq) and then dried with MgSO$_4$, before filtering and concentrating the solution. The crude aldehyde was then purified via chromatography (40% EtOAc/hexane) to provide 0.7704 g of aldehyde. The aldehyde (0.7411 g, 2.63 mmol) was dissolved in DCE (10 mL) and cooled in an ice bath. Morpholine (0.30 mL, 3.42 mmol) was added dropwise and the reaction was stirred for 5 minutes before NaBH(OAc)$_3$ was added portion wise, and the reaction was allowed to stir overnight. The reaction was quenched with saturated NaHCO$_3$ and then extracted with DCM. The combined organics were dried (MgSO$_4$), filtered and concentrated. The crude material was then purified via chromatography (80% EtOAc/hexane) to afford 0.7662 g TRV-1470. $^1$H NMR (CDCl$_3$, 700 MHz) δ=7.19 (s, 1H), 5.88 (s, 1H), 4.41 (br s, 2H), 4.00 (br s, 2H), 3.73 (br s, 4H), 3.09 (s, 1H), 2.71 (s, 2H), 2.48 (br s, 4H).

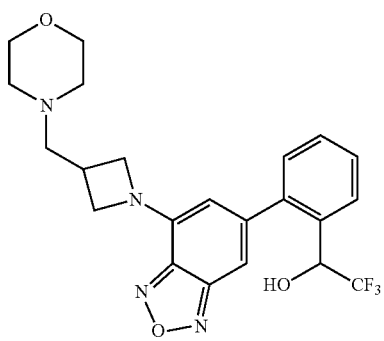

TRV 1471

TRV-1470 (0.4092 g, 1.16 mmol) and 3-formylphenylboronic acid (0.1829 g, 1.22 mmol) were massed into a tube. The tube was evacuated and purged with argon (3×). DME (2.6 mL) and 2M Na$_2$CO$_3$ (1.8 mL, 3.48 mmol) were then added followed by Pd(PPh$_3$)$_4$ (0.067 g, 0.058 mmol). The tube was then sealed and heated to 80° C. overnight. Upon cooling to room temperature the mixture was diluted with water and EtOAc. The layers were separated and the aqueous layer was back-extracted with EtOAc. The combined organic layers were then washed with water (5×), brine, dried (Na$_2$SO$_4$), filtered and concentrated to give an oil. This crude oil was then dissolved in THF (10 mL) and cooled to 0° C. CF$_3$TMS (0.34 mL, 2.32 mmol) was added followed by TBAF (0.12 mL, 1.0 M solution in THF). The reaction was then stirred for 60 minutes before re-cooling to 0° C. and 4N HCl (aq) was added and stirred for 60 minutes. The mixture was diluted with water and EtOAc. The layers were separated and the aqueous layer was basified. The aqueous layer was then re-extracted with EtOAc. The combined organic layers were washed with water, brine, dried (Na$_2$SO$_4$), filtered and concentrated to give a crude oil. This material was purified via flash column chromatography (3% of a 7 N NH$_3$ solution in MeOH/DCM) to afford 0.125 g of TRV 1471 (24% yield, 2 steps). $^1$H NMR (CDCl3, 700 MHz) δ=7.78 (d, J=7 Hz, 1H), 7.47 (t, J=7 Hz, 1H), 7.45 (t, J=7 Hz, 1H), 7.30 (d, J=1H), 6.90 (s, 1H), 5.73 (s, 1H), 5.21 (br s, 1H), 4.42-4.38 (m, 2H), 3.98 (br s, 2H), 3.71 (br s, 4H), 3.09-3.06 (m, 1H), 2.92 (s, 1H), 2.72 (d, J=7 Hz, 2H), 2.48 (br s, 4H).

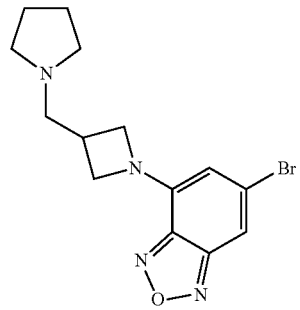

TRV-1472

(1-(6-bromobenzo[c][1,2,5]oxadiazol-4-yl)azetidin-3-yl) methanol (1.9573 g, 6.89 mmol) was suspended in DCM (85 mL) and Dess-Martin reagent (3.799 g, 8.9 mmol) was added all at once and stirred until complete consumption of starting material, approximately 90 minutes. The mixture was then cooled in an ice bath and saturated NaHCO$_3$ (aq) and Na$_2$S$_2$O$_3$ (4.2 g) were added and stirred until all the solids dissolved. The solution was then extracted with DCM (3×) and the combined organics were washed with saturated NaHCO$_3$ (aq), dried (MgSO$_4$), filtered and concentrated. The crude material was purified via column (20-100% EtOAc/hexane gradient) to afford 2.0355 g of aldehyde. The aldehyde was then dissolved in DCE (0.28 M solution) and cooled in an ice bath. Pyrrolidine (0.20 mL, 2.4 mmol) was added and stirred for 5 minutes, followed by the addition of NaHB(OAc)$_3$ (0.7630 g, 3.6 mmol) all at once. The mixture was allowed to warm to room temperature overnight. After cooling again in an ice bath, the reaction was quenched with saturated NaHCO$_3$ and stirred until effervescence stopped. This mixture was then extracted with DCM (3×). The combined organic layers were dried (MgSO$_4$), filtered and concentrated. Ultimately this crude material was purified via chromatography (63-69% MeCN/DCM gradient with 1% TEA additive) to afford TRV-1472. $^1$H NMR (CDCl3, 700 MHz) δ=7.18 (s, 1H), 5.88 (s, 1H), 4.44 (s, 2H), 4.03 (s, 2H), 3.13 (s, 1H), 2.87 (br s, 2H), 2.61 (br s, 4H), 1.86 (s, 4H).

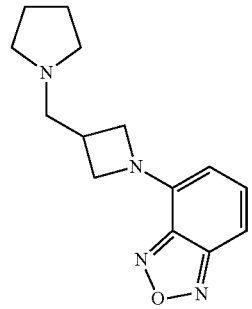

TRV 1473

TRV-1472 (0.1350 g, 0.40 mmol) was dissolved in THF (10 mL) under argon, and cooled to −78° C. nBuLi (0.23 mL, 2.0 M solution in cyclohexane) was added dropwise and the mixture was stirred for 20 minutes. Methanol (0.16 mL, 4 mmol) was added at −78° C. and the mixture was allowed to warm to 0° C. where it was quenched with saturated NH₄Cl(aq). This mixture was extracted with EtOAc (3×) and the combined organic layers were washed with H₂O, brine, dried (MgSO₄), filtered and concentrated. The crude material was purified via chromatography (10-100% EtOAc/Hexane gradient with 5% TEA additive) to afford 0.0585 g (57% yield) of TRV-1473 as orange oil. ¹H NMR (CDCl3, 700 MHz) δ=7.21 (dd, J=8.4, 7.7 Hz, 1H), 7.01 (d, J=8.4 Hz, 1H), 5.84 (d, J=7.7 Hz, 1H), 4.42 (t, J=7.7 Hz, 1H), 4.00 (s, 2H), 3.13 (br s, 1H), 2.90 (br s, 2H), 2.62 (br s, 4H), 1.88 (s, 4H).

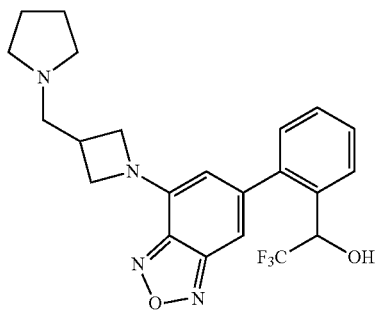

TRV-1474

TRV-1472 (0.2281 g, 0.68 mmol) and 2-formylbenzeneboronic acid (0.1070 g, 0.71 mmol) were sealed in a tube. The tube was evacuated and purged with argon (3 cycles). 2M Na₂CO₃ (1.0 mL, 2.0 M aq solution) was added along with DME (1.6 mL). The solution was degassed for 10 minutes and then Pd(PPh₃)₄ (0.0393 g, 0.0034 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude aldehyde was purified via chromatography (10-100% EtOAc/hexane gradient, 5% TEA additive) to afford 0.0753 g of pure material. The aldehyde was then dissolved in THF (5 mL) and cooled in an ice bath. To this solution was added CF₃TMS (61 µL, 0.415 mmol) and then TBAF (~20 µL, 1.0 M solution in THF). After 5 minutes, the ice bath was removed and the mixture was stirred until complete conversion of starting material, the mixture was cooled in an ice bath and quenched with 2N HCl(aq). After 30 minutes, the mixture was then made basic with 2N NaOH and extracted with EtOAc (3×). The combined organics were then washed with water, brine, dried (MgSO₄), filtered and concentrated. The crude material was then purified via chromatography (63% EtOAc/hexane with 5% TEA additive) to afford 0.0357 g (40% yield) of TRV-1474. ¹H NMR (CDCl3, 700 MHz) δ=7.80 (d, J=7.7 Hz, 1H), 7.49 (t, J=7.7 Hz, 1H), 7.43-7.41 (m, 1H), 7.29-7.27 (m, 1H), 6.93 (s, 1H), 5.78 (s, 1H), 5.24 (q, J=7.0 Hz, 1H), 4.47 (br s, 1H), 4.38 (s, 1H), 4.13 (br s, 1H), 4.02 (s, 1H), 3.15 (br s, 1H), 2.98 (br s, 2H), 2.74 (br s, 4H), 1.91 (br s, 4H).

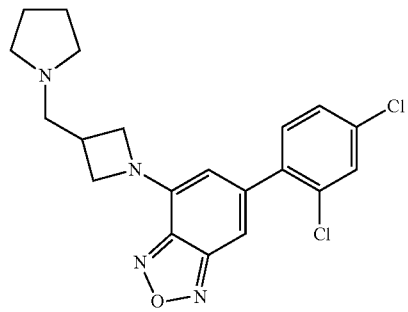

TRV-1475

TRV-1472 (0.2750 g, 0.82 mmol) and (2,4-dichlorophenyl)boronic acid (0.1643 g, 0.86 mmol) were sealed in a tube. The tube was evacuated and purged with argon (3 cycles). 2M Na₂CO₃ (1.2 mL, 2.0 M aq solution) was added along with DME (1.8 mL). The solution was degassed for 10 minutes and then Pd(PPh₃)₄ (0.0474 g, 0.041 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude aldehyde was purified via chromatography (10-100% EtOAc/hexane gradient, 5% TEA additive) to afford 0.1821 g (55% yield) of TRV-1475 as orange oil. ¹H NMR (CDCl3, 700 MHz) δ=7.51 (d, J=1.4 Hz, 1H), 7.33 (dd, J=1.4, 8.4 Hz, 1H), 7.31 (d, J=8.4 Hz, 1H), 6.99 (s, 1H), 5.85 (s, 1H), 4.48 (s, 2H), 4.06 (s, 2H), 3.19 (br s, 1H), 2.95 (br s, 2H), 2.64 (br s, 4H), 1.91 (br s, 4H).

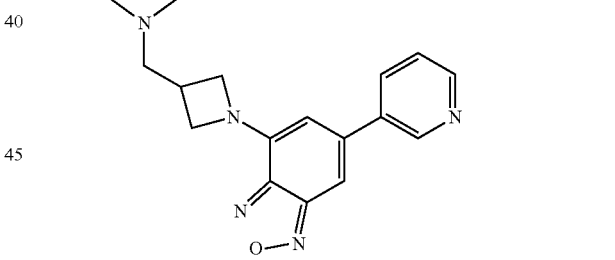

TRV-1476

TRV-1472 (0.2707 g, 0.80 mmol) and pyridin-3-ylboronic acid (0.1033 g, 0.84 mmol) were sealed in a tube. The tube was evacuated and purged with argon (3 cycles). 2M Na₂CO₃ (1.2 mL, 2.0 M aq solution) was added along with DME (1.8 mL). The solution was degassed for 10 minutes and then Pd(PPh₃)₄ (0.0462 g, 0.04 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude aldehyde was purified via chromatography (1-10% MeOH/DCM gradient, 1% TEA additive) to afford 0.106 g (40% yield) of TRV-1476 as orange oil. ¹H NMR (CDCl3, 700 MHz) δ=8.87 (d, J=2.1 Hz, 1H), 8.66 (dd, J=4.9, 2.1 Hz, 1H), 7.90 (dt, J=8.4, 2.1 Hz, 1H), 7.40 (dd, J=8.4, 4.9 Hz, 1H), 7.16 (s, 1H), 6.00 (s, 1H), 4.50 (s, 2H), 4.09 (s, 2H), 3.19 (br s, 1H), 2.93 (br s, 2H), 2.63 (br s, 4H), 1.89 (br s, 4H).

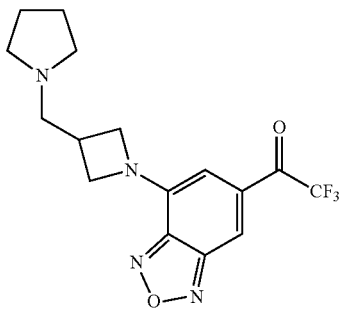

TRV-1477

TRV-1472 (0.3402, 1.0 mmol) was dissolved in THF (10 mL) and cooled to −78° C. under argon. nBuLi (0.60 mL, 1.16 mmol, 2.0 M solution in cyclohexane) was added dropwise and the resultant dark solution was stirred for 20 minutes before trifluoro Weinreb amide (0.16 mL, 1.26 mmol) was added. The mixture was allowed to stir overnight while warming to room temperature, it was then cooled to 0° C. and quenched with 2 N HCl (aq), stirring for 60 minutes. This mixture was then made basic with the dropwise addition of 2 N NaOH (aq) and then extracted with EtOAc. The combined organic layers were then washed with H₂O (3×), brine, dried (MgSO₄), filtered and concentrated. The material was purified via (10-100% EtOAc/hexane gradient and then a 1-10% MeOH/EtOAc gradient with 5% TEA additive the whole time) to afford 0.108 g (30% yield) of TRV-1477 as a mixture of the ketone and hydrated ketone. $^1$H NMR (CDCl3, 700 MHz) ketone: δ=7.77 (s, 1H), 6.28 (s, 1H), 4.47 (br s, 2H), 4.05 (br s, 2H), 3.13-3.06 (m, 1H), 2.81 (d, J=7.7 Hz, 2H), 2.54 (br s, 4H), 1.81-1.78 (m, 4H); hydrated ketone: δ=7.40 (s, 1H), 6.16 (s, 1H), 4.43-4.38 (m, 2H), 4.01-3.99 (m, 2H), (remaining peaks are overlapping with the ketone); $^1$H NMR (DMSO, 700 MHz) hydrated ketone: δ=7.85 (s, 2H), 7.27 (s, 1H), 6.14 (s, 1H), 4.32 (t, J=8.4 Hz, 2H), 3.88 (t, J=7.0 Hz, 2H), 3.03-2.95 (m, 1H), 2.69 (d, J=7.0 Hz, 2H), 2.44-2.43 (m, 4H), 1.68-1.66 (m, 4H); ketone: δ=7.83 (s, 1H), 6.25 (s, 1H), 4.42 (br s, 2H), 3.99 (br s, 2H), (remaining peaks are overlapping with hydrated ketone).

TRV-1478

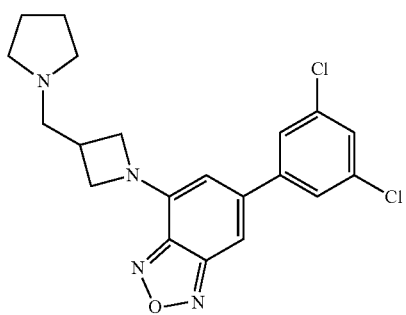

TRV-1472 (0.1584 g, 0.47 mmol) and (3,5-dichlorophenyl)boronic acid (0.0.0941 g, 0.49 mmol) were sealed in a tube. The tube was evacuated and purged with argon (3 cycles). 2M Na₂CO₃ (0.71 mL, 2.0 M aq solution) was added along with DME (1.1 mL). The solution was degassed for 10 minutes and then Pd(PPh₃)₄ (0.0272 g, 0.024 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude material was purified via chromatography (5% MeOH/DCM) to afford 0.0348 g (18% yield) of TRV-1478. $^1$H NMR (DMSO, 500 MHz) δ=7.87 (d, J=2.0 Hz, 2H), 7.69 (t, J=2.0 Hz, 1H), 7.45 (s, 1H), 6.28 (s, 1H), 4.38 (t, J=8.5 Hz, 2H), 3.99-3.96 (m, 2H), 3.03-2.94 (m, 1H), 2.71 (d, J=7.5 Hz, 2H), 2.46 (br s, 4H), 1.68 (br s, 4H).

TRV-1479

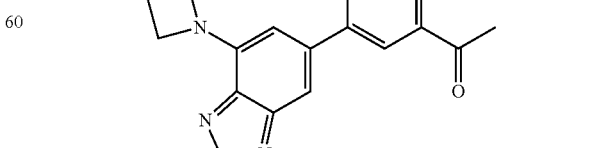

TRV-1472 (0.1987 g, 0.59 mmol) and 3-methylsulfonylphenylboronic acid (0.1240 g, 0.62 mmol) were sealed in a tube. The tube was evacuated and purged with argon (3 cycles). 2M Na₂CO₃ (0.9 mL, 2.0 M aq solution) was added along with DME (1.3 mL). The solution was degassed for 10 minutes and then Pd(PPh₃)₄ (0.034 g, 0.03 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude material was purified via chromatography (1-10% MeOH/DCM gradient) to afford 0.1103 g (45% yield) of TRV-1479. $^1$H NMR (CDCl3, 500 MHz) δ=8.17 (s, 1H), 7.99 (d, J=8.0 Hz, 1H), 7.89 (d, J=8.0 Hz, 1H), 7.68 (t, J=8.0 Hz, 1H), 7.17 (s, 1H), 6.01 (s, 1H), 4.51 (t, J=8.5 Hz, 2H), 4.11-4.09 (m, 2H), 3.22 (br s, 1H), 3.12 (s, 3H), 2.98 (br s, 2H), 2.75 (br s, 4H), 1.91 (br s, 4H).

TRV-1480

TRV-1472 (0.2075 g, 0.615 mmol) and 3-acetylbenzeneboronic acid (0.1059 g, 0.65 mmol) were sealed in a tube. The tube was evacuated and purged with argon (3 cycles). 2M $Na_2CO_3$ (0.92 mL, 2.0 M aq solution) was added along with DME (1.4 mL). The solution was degassed for 10 minutes and then $Pd(PPh_3)_4$ (0.036 g, 0.031 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with $H_2O$ (3×), brine and then dried ($Na_2SO_4$), filtered and concentrated. The crude material was purified via chromatography (0-10% MeOH/DCM gradient) to afford 0.1307 g (56% yield) of TRV-1480. $^1H$ NMR (CDCl3, 500 MHz) δ=8.19 (t, J=1.5 Hz, 1H), 7.99 (d, J=7.5 Hz, 1H), 7.81 (dd, J=7.5, 1.5 Hz, 1H), 7.57 (t, J=7.5 Hz, 1H), 7.16 (s, 1H), 6.04 (s, 1H), 4.48 (t, J=8.5 Hz, 2H), 4.07-4.04 (m, 2H), 3.15 (br s, 1H), 2.90 (br s, 2H), 2.67 (s, 3H), 2.64 (br s, 4H), 1.85 (br s, 4H).

TRV-1481

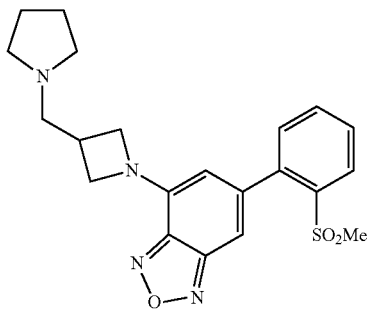

TRV-1472 (0.2009 g, 0.60 mmol) and 2-methylsulfonylphenylboronic acid (0.1260 g, 0.63 mmol) were sealed in a tube. The tube was evacuated and purged with argon (3 cycles). 2M $Na_2CO_3$ (0.9 mL, 2.0 M aq solution) was added along with DME (1.3 mL). The solution was degassed for 10 minutes and then $Pd(PPh_3)_4$ (0.034 g, 0.03 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with $H_2O$ (3×), brine and then dried ($Na_2SO_4$), filtered and concentrated. The crude material was purified via chromatography (0-100% EtOAc/hexane gradient with 5% TEA) to afford 0.0257 g (10% yield) of TRV-1481. $^1H$ NMR (CDCl3, 500 MHz) δ=8.21 (d, J=7.5 Hz, 1H), 7.68 (t, J=7.5 Hz, 1H), 7.62 (t, J=7.5 Hz, 1H), 7.39 (d, J=7.5 Hz, 1H), 6.98 (s, 1H), 5.93 (s, 1H), 4.48 (t, J=8.0 Hz, 2H), 4.07 (br s, 2H), 3.23 (br s, 1H), 3.05-3.01 (m, 2H), 2.91 (s, 3H), 2.77 (br s, 4H), 1.93 (br s, 4H).

TRV-1482

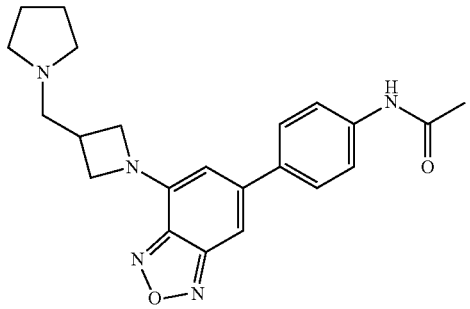

TRV-1472 (0.2039 g, 0.60 mmol) and (4-acetylaminophenyl)boronic acid (0.1128 g, 0.63 mmol) were sealed in a tube. The tube was evacuated and purged with argon (3 cycles). 2M $Na_2CO_3$ (0.9 mL, 2.0 M aq solution) was added along with DME (1.3 mL). The solution was degassed for 10 minutes and then $Pd(PPh_3)_4$ (0.036 g, 0.03 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with $H_2O$ (3×), brine and then dried ($Na_2SO_4$), filtered and concentrated. The crude material was purified via chromatography (0-10% MeOH/DCM gradient with 1% TEA) to afford 0.1350 g (57% yield) of TV-1482. $^1H$ NMR (CDCl3, 500 MHz) δ=7.61 (d, J=8.5 Hz, 2H), 7.55 (d, J=8.5 Hz, 2H), 7.47 (s, 1H), 7.11 (s, 1H), 6.04 (s, 1H), 4.46 (t, J=8.0 Hz, 2H), 4.06-4.04 (m, 2H), 3.19 (br s, 1H), 3.00 (br s, 2H), 2.77 (br s, 4H), 2.23 (s, 3H), 1.93 (br s, 4H).

TRV-1483

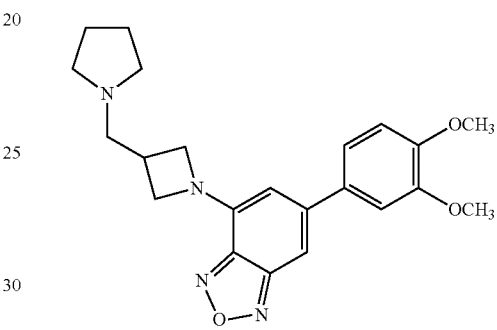

TRV-1472 (0.1910 g, 0.57 mmol) and 3,4-dimethoxybenzeneboronic acid (0.1092 g, 0.60 mmol) were sealed in a tube. The tube was evacuated and purged with argon (3 cycles). 2M $Na_2CO_3$ (0.90 mL, 2.0 M aq solution) was added along with DME (1.3 mL). The solution was degassed for 10 minutes and then $Pd(PPh_3)_4$ (0.034 g, 0.029 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with $H_2O$ (3×), brine and then dried ($Na_2SO_4$), filtered and concentrated. The crude material was purified via chromatography (0-8% MeOH/DCM) to afford 0.0471 g (21% yield) of TRV-1483. $^1H$ NMR (CDCl3, 500 MHz) δ=7.18 (dd, J=8.0, 2.0 Hz, 1H), 7.12 (d, J=2.0 Hz, 1H), 7.11 (s, 1H), 6.95 (d, J=8.0 Hz, 1H), 6.07 (s, 1H), 4.48 (t, J=8.0 Hz, 2H), 4.07 (t, J=6.0 Hz, 2H), 3.96 (s, 3H), 3.94 (s, 3H), 3.20 (br s, 1H), 2.98 (br s, 2H), 2.74 (br s, 4H), 1.92 (br s, 4H).

TRV-1484

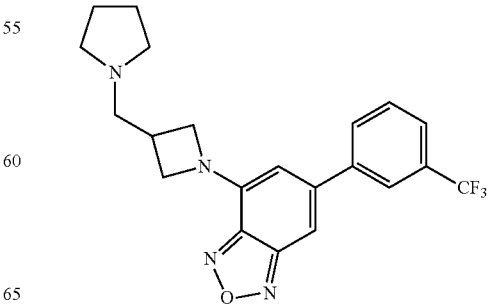

TRV-1472 (0.2297 g, 0.68 mmol) and 3-trifluorobenzeneboronic acid (0.1367 g, 0.72 mmol) were sealed in a tube. The tube was evacuated and purged with argon (3 cycles). 2M Na$_2$CO$_3$ (1.0 mL, 2.0 M aq solution) was added along with DME (1.5 mL). The solution was degassed for 10 minutes and then Pd(PPh$_3$)$_4$ (0.039 g, 0.034 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H$_2$O (3×), brine and then dried (Na$_2$SO$_4$), filtered and concentrated. The crude material was purified via chromatography (0-8% MeOH/DCM) to afford 0.0377 g (14% yield) of TRV-1484. $^1$H NMR (CDCl3, 500 MHz) δ=7.84 (s, 1H), 7.78 (d, J=7.5 Hz, 1H), 7.67 (d, J=7.5 Hz, 1H), 7.59 (t, J=7.5 Hz, 1H), 7.16 (s, 1H), 6.02 (s, 1H), 4.51 (t, J=8.0 Hz, 2H), 4.10 (t, J=6.0 Hz, 2H), 3.22 (br s, 1H), 3.00 (br s, 2H), 2.75 (br s, 4H), 1.92 (br s, 4H).

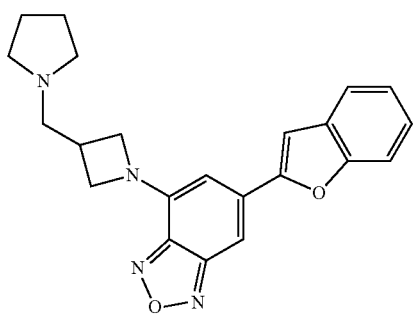

TRV-1485

TRV-1472 (0.2067 g, 0.61 mmol) and benzofuran-2-ylboronic acid (0.1042 g, 0.64 mmol) were sealed in a tube. The tube was evacuated and purged with argon (3 cycles). 2M Na$_2$CO$_3$ (0.92 mL, 2.0 M aq solution) was added along with DME (1.4 mL). The solution was degassed for 10 minutes and then Pd(PPh$_3$)$_4$ (0.035 g, 0.031 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H$_2$O (3×), brine and then dried (Na$_2$SO$_4$), filtered and concentrated. The crude material was purified via chromatography (0-8% MeOH/DCM) to afford 0.1032 g (45% yield) of TRV-1485. $^1$H NMR (CDCl3, 500 MHz) δ=7.62 (d, J=8.0 Hz, 1H), 7.56-7.54 (m, 2H), 7.37-7.33 (m, 1H), 7.28-7.25 (m, 1H), 7.15 (s, 1H), 6.26 (s, 1H), 4.50 (t, J=8.0 Hz, 2H), 4.08 (t, J=6.0 Hz, 2H), 3.16 (br s, 1H), 2.93 (br s, 2H), 2.67 (br s, 4H), 1.88 (br s, 4H).

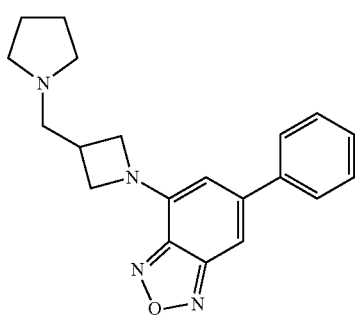

TRV-1486

TRV-1472 (0.2044 g, 0.61 mmol) and phenylboronic acid (0.0776 g, 0.63 mmol) were sealed in a tube. The tube was evacuated and purged with argon (3 cycles). 2M Na$_2$CO$_3$ (0.92 mL, 2.0 M aq solution) was added along with DME (1.4 mL). The solution was degassed for 10 minutes and then Pd(PPh$_3$)$_4$ (0.036 g, 0.031 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H$_2$O (3×), brine and then dried (Na$_2$SO$_4$), filtered and concentrated. The crude material was purified via chromatography (0-8% MeOH/DCM) to afford 0.0702 g (34% yield) of TRV-1486. $^1$H NMR (CDCl3, 500 MHz) δ=7.62 (d, J=7.0 Hz, 2H), 7.47 (t, J=7.0 Hz, 2H), 7.43 (d, J=7.0 Hz, 1H), 7.16 (s, 1H), 6.08 (s, 1H), 4.47 (t, J=8.0 Hz, 2H), 4.06-4.03 (m, 2H), 3.16 (br s, 1H), 2.94 (br s, 2H), 2.69 (br s, 4H), 1.88 (br s, 4H).

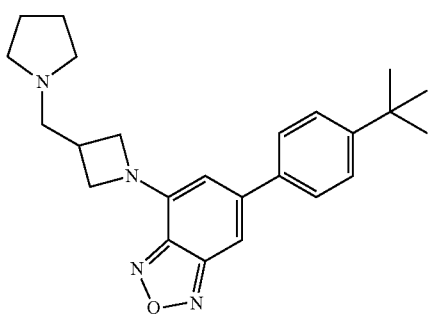

TRV 1487

A round-bottomed flask was charged with TRV-1472 (202 mg, 0.6 mmol), (4-(tert-butyl)phenyl) boronic acid (139 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 200 mg (85% yield) of TRV-1487 as a yellow solid. $^1$H NMR (500 MHz, CDCl$_3$) 1.42 (s, 4H), 1.95 (br, s, 4H), 2.76 (br, s, 4H), 3.01 (br, s, 2H), 3.23 (br, s, 1H), 4.08-4.11 (m, 2H), 4.52 (t, J=8.2, 2H), 6.16 (s, 1H), 7.21 (s, 1H), 7.55 (d, J=8.4, 2H), 7.62 (d, J=8.4, 2H).

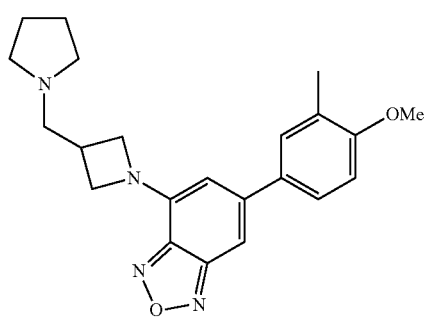

TRV-1488

A round-bottomed flask was charged with TRV-1472 (202 mg, 0.6 mmol), (4-methoxy-3-methylphenyl) boronic acid (130 mg, 0.78 mmol), and Pd(PPh₃)₄ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (2:5:100:500 MeOH/TEA/EtOAc/Hexane) to afford 190 mg (84% yield) of TRV-1488 as red oil. $^1$H NMR (500 MHz, CDCl3) 1.88 (t, 4H), 2.34 (s, 3H), 2.64 (br, s, 4H), 2.90 (d, J=7.4, 2H), 3.13-3.16 (m, 1H), 3.94 (s, 3H), 4.05-4.08 (m, 2H), 4.50 (t, J=8.2, 2H), 6.11 (s, 1H), 6.95 (d, J=8.4, 1H), 7.14 (s, 1H), 7.46 (s, 1H), 7.49 (d-d, J=8.4, J=2.2, 1H).

After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 165 mg (73% yield) of TRV-1490 as red oil. $^1$H NMR (500 MHz, CDCl₃) 1.88 (t, J=3.1, 4H), 2.48 (s, 3H), 2.64 (br, s, 4H), 2.90 (d, J=7.4, 2H), 3.15-3.18 (m, 1H), 4.06-4.09 (m, 2H), 4.51 (t, J=8.2, 2H), 6.03 (s, 1H), 7.15 (s, 1H), 7.36 (d, J=7.9, 1H), 7.45 (d-d, J=7.9, J=1.7, 1H), 7.64 (d, J=1.7, 1H).

TRV-1489

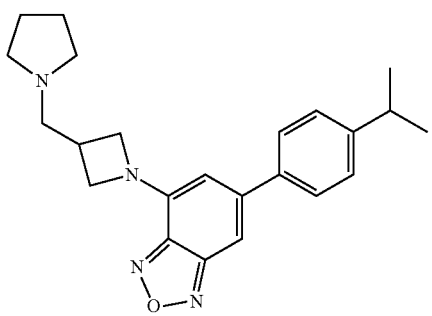

TRV-1491

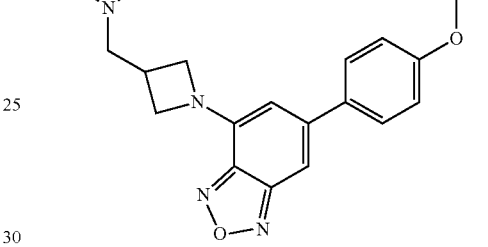

A round-bottomed flask was charged with TRV-1472 (202 mg, 0.6 mmol), (4-isopropylphenyl) boronic acid (128 mg, 0.78 mmol), and Pd(PPh₃)₄ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 165 mg (73% yield) of TRV-1489 as a yellow solid. $^1$H NMR (500 MHz, CDCl3) 1.35 (d, J=7.0, 6H), 1.88 (t, J=3.1, 4H), 2.63 (br, s, 4H), 2.89 (d, J=7.5, 2H), 3.01-3.05 (m, 1H), 3.12-3.18 (m, 1H), 4.05-4.08 (m, 2H), 4.50 (t, J=8.2, 2H), 6.13 (s, 1H), 7.19 (s, 1H), 7.38 (d, J=8.2, 2H), 7.60 (d, J=8.2, 2H).

A round-bottomed flask was charged with TRV-1472 (202 mg, 0.6 mmol), (4-phenoxyphenyl) boronic acid (167 mg, 0.78 mmol), and Pd(PPh₃)₄ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 215 mg (84% yield) of TRV-1491 as a red solid. $^1$H NMR (500 MHz, CDCl₃) 1.97 (br, s, 4H), 2.80 (br, s, 4H), 3.04 (br, s, 2H), 3.5 (br, s, 1H), 4.11-4.13 (m, 2H), 4.54 (t, J=8.2, 2H), 6.12 (s, 1H), 7.12-7.14 (m, 4H), 7.18 (s, 1H), 7.21 (t, J=7.5, 1H), 7.44 (t, J=7.8, 2H), 7.63 (d, J=8.6, 2H).

TRV-1490

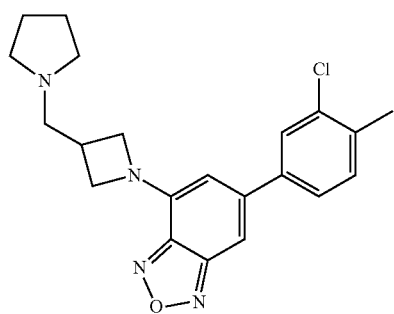

TRV-1492

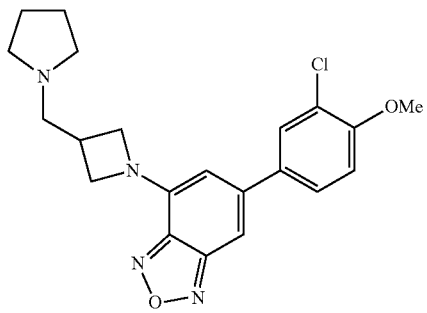

A round-bottomed flask was charged with TRV-1472 (202 mg, 0.6 mmol), (3-chloro-4-methylphenyl) boronic acid (133 mg, 0.78 mmol), and Pd(PPh₃)₄ (35 mg, 0.03 mmol).

A round-bottomed flask was charged with TRV-1472 (202 mg, 0.6 mmol), (4-phenoxyphenyl) boronic acid (145 mg, 0.78 mmol), and Pd(PPh₃)₄ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (2:5:100:500 MeOH/TEA/EtOAc/Hexane) to afford 178 mg (74% yield) of TRV-1492 as red oil. $^1$H NMR (500 MHz, CDCl$_3$) 1.98 (br, s, 4H), 2.83 (br, s, 4H), 3.06 (s, 2H), 3.27 (br, s, 1H), 4.02 (s, 3H), 4.12-4.14 (m, 2H), 4.4 (t, J=8.2, 2H), 6.06 (s, 1H), 7.06 (d, J=8.6, 1H), 7.15 (s, 1H), 7.55 (d-d, J=8.6, J=2.3, 1H), 7.69 (d, J=2.3, 1H).

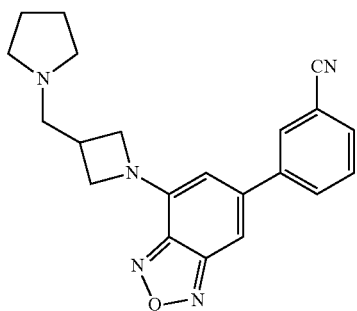

TRV-1493

A round-bottomed flask was charged with TRV-1472 (202 mg, 0.6 mmol), (3-cyanophenyl) boronic acid (115 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 6 h. After completion checked by TLC, 10 mL of water was added, and the reaction mixture was extracted with ethyl acetate. The organic phase was dried over anhydrous sodium sulphate and then concentrated. The residue was purified via flash column chromatography (2:5:100:500 MeOH/TEA/EtOAc/Hexane) to afford 159 mg (73% yield) of TRV-1493 as a red solid. $^1$H NMR (500 MHz, CDCl$_3$) 1.87-1.89 (br, s, 4H), 2.63 (br, s, 4H), 2.90 (d, J=7.5, 2H), 3.15-3.18 (m, 1H), 4.09-4.12 (m, 2H), 4.53 (t, J=8.3, 2H), 5.97 (s, 1H), 7.15 (s, 1H), 7.63 (t, J=7.8, 1H), 7.74 (d, J=7.7, 1H), 7.88 (d, J=7.9, 1H), 7.93 (s, 1H).

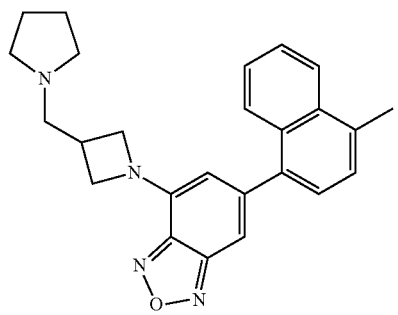

TRV-1494

A round-bottomed flask was charged with TRV-1472 (202 mg, 0.6 mmol), (4-methylnaphthalen-1-yl) boronic acid (145 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 204 mg (85% yield) of TRV-1494 as a red solid. $^1$H NMR (500 MHz, CDCl$_3$) 1.85-1.86 (m, 4H), 2.61 (br, s, 4H), 2.81 (s, 3H), 2.89 (d, J=7.4, 2H), 3.11-3.14 (m, 1H), 4.03-4.06 (m, 2H), 4.45-4.48 (m, 2H), 6.01 (s, 1H), 7.14 (s, 1H), 7.43 (s, 2H), 7.52 (t, J=7.3, J=7.9, 1H), 7.62 (t, J=7.7, J=7.4, 1H), 8.01 (d, J=7.4, 1H), 8.13 (d, J=7.5, 1H).

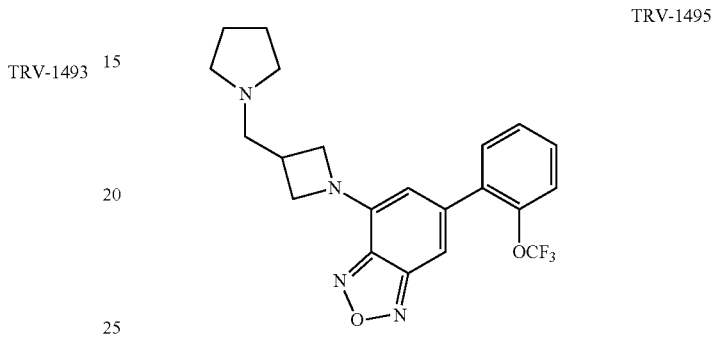

TRV-1495

A round-bottomed flask was charged with TRV-1472 (202 mg, 0.6 mmol), (2-(trifluoromethoxy) phenyl) boronic acid (161 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 211 mg (84% yield) of TRV-1495 as red oil. $^1$H NMR (500 MHz, CDCl$_3$) 2.06 (br, s, 4H), 2.97 (br, s, 4H), 3.19 (br, s, 2H), 3.37 (br, s, 1H), 4.12-4.14 (m, 2H), 4.53-4.56 (m, 2H), 6.01 (s, 1H), 7.15 (s, 1H), 7.42-7.46 (m, 2H), 7.49-7.51 (m, 2H).

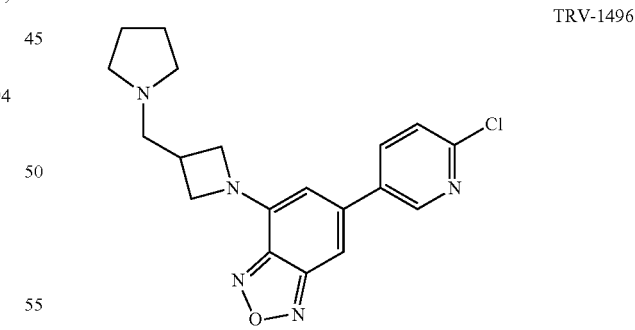

TRV-1496

A round-bottomed flask was charged with TRV-1472 (202 mg, 0.6 mmol), (6-chloropyridin-3-yl) boronic acid (161 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (6:5:100:500

MeOH/TEA/EtOAc/Hexane) to afford 167 mg (75% yield) of TRV-1496 as red oil. $^1$H NMR (500 MHz, CDCl$_3$) 1.92 (br, s, 4H), 2.17 (br, s, 4H), 2.97 (d, J=5.8, 2H), 3.21-3.22 (m, 1H), 4.13 (br, s, 2H), 4.53-4.54 (m, 2H), 5.97 (s, 1H), 7.16 (s, 1H), 7.49 (d, J=8.1, 1H), 7.92 (d, J=7.8, 1H), 8.69 (s, 1H).

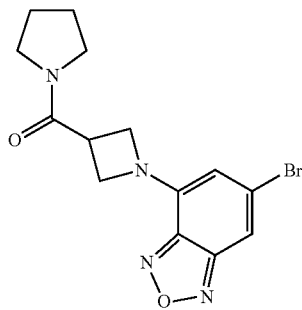

TRV-1497

A solution of 3-azeditinecarboxylic acid (3.4889 g, 34.5 mmol) in water (60 mL) was cooled in an ice bath and DIPEA (18 mL, 103.5 mmol) was added. The mixture was stirred for 5 minutes and then a solution of 6-bromo-4-fluorobenzo[c][1,2,5]oxadiazole 3 (7.4877 g, 34.5 mmol) in THF (60 mL) was added dropwise. The reaction was stirred for 30 minutes at 0° C., then it was removed from the ice bath and allowed to warm to room temperature overnight. The reaction was diluted with water and then basified with 2N NaOH (aq). The aqueous layer was then washed with DCM (3×) and then acidified with 2N HCl(aq). The resulting precipitate was collected by filtration to afford 4.8909 grams (48% yield) of a fine brown solid. A mixture of this material, pyrrolidine (1.36 mL, 16.4 mmol) and TEA (5.7 mL, 41 mmol) in THF (140 mL) was cooled in an ice bath. The solution of T3P (12.54 g, 19.7 mmol, 50 w/w solution in EtOAc) was added dropwise and then the reaction was allowed to warm to room temperature. The reaction was then diluted with water and extracted with EtOAc (3×). The combined organic layers were then washed with water (3×), brine, dried (MgSO$_4$), filtered and concentrated to afford 3.4558 g (60% yield, <95% c.p.). 85 mg of this material was purified via 3% MeOH/DCM column. This afforded approximately 60 mg (71% recovery) of a fine orange solid of TRV-1497. $^1$H NMR (500 MHz, DMSO) δ=7.40 (s, 1H), 6.10 (s, 1H), 4.45 (t, J=8.5 Hz, 2H), 4.35 (t, J=8.5 Hz, 2H), 3.86-3.81 (m, 1H), 3.35-3.30 (m, 4H), 1.90-1.85 (m, 2H), 1.81-1.75 (m, 2H).

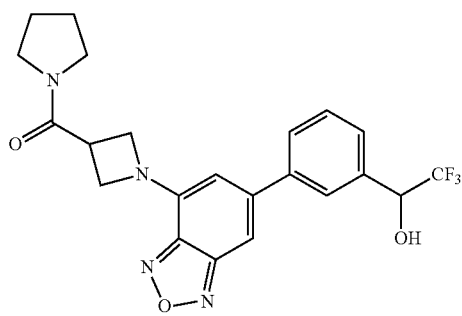

TRV-1498

TRV-1497 (0.4031 g, 1.15 mmol) and 3-formylbezeneboronic acid (0.1810 g, 1.21 mmol) were added to a tube and the tube was evacuated and purged with argon (3×). DME (2.8 mL) and Na$_2$CO$_3$ (1.7 mL, 3.4 mmol, 2 N aqueous solution) were added followed by Pd(PPh$_3$)$_4$ (0.069 g, 0.06 mmol). The tube was sealed and then heated to 85° C. overnight. The reaction was cooled and then diluted with EtOAc and water. The organic layer was washed with water (3×), brine, dried (MgSO$_4$), filtered and concentrated to give the crude aldehyde. This aldehyde was dissolved in THF (10 mL) and cooled in an ice bath. CF$_3$TMS (0.19 mL) was added and then the catalyst TBAF (0.1 mL, 1.0 M solution) was added. After 30 minutes the reaction was removed from the ice bath and allowed to warm to room temperature. Once complete by TLC, recooled to 0° C. and 2 N HCl(aq) was added, stirred for 40 minutes and then basified with 2N NaOH. This mixture was extracted with EtOAc. The combined extracts were washed with water (2×), brine, filtered and concentrated. The crude material was purified via chromatography (5% MeOH/DCM) to afford 0.261 g (51% yield) of TRV-1498 as an orange solid. $^1$H NMR (500 MHz, DMSO) δ=7.91 (s, 1H), 783 (d, J=7.5 Hz, 1H), 7.60 (d, J=7.5 Hz, 1H), 7.56 (t, J=7.5 Hz, 1H), 7.35 (s, 1H), 6.93 (d, J=5.5 Hz, 1H), 6.32 (s, 1H), 5.32-5.26 (m, 1H), 4.51-4.49 (m, 2H), 4.40 (t, J=7.0 Hz, 2H), 3.92-3.86 (m, 1H), 3.39 (t, J=6.5 Hz, 2H), 3.35 (t, J=6.5 Hz, 2H), 1.94-1.88 (m, 2H), 1.84-1.78 (m, 2H).

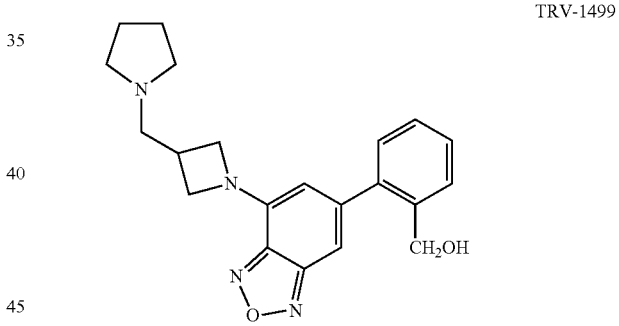

TRV-1499

A round-bottomed flask was charged with TRV-1472 (202 mg, 0.6 mmol), (2-(hydroxymethyl) phenyl) boronic acid (119 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 3 h. After completion checked by TLC, 10 mL of water was added, and the reaction mixture was extracted with ethyl acetate. The organic phase was dried over anhydrous sodium sulphate and then concentrated. The residue was purified via flash column chromatography (6:5: 100:500 MeOH/TEA/EtOAc/Hexane) to afford 142 mg (64% yield) of TRV-1499 as red oil. $^1$H NMR (400 MHz, CDCl$_3$) 1.78-1.81 (m, 4H), 1.83-1.87 (m, 1H), 2.51-2.55 (m, 4H), 2.81 (d, J=7.5, 2H), 3.02-3.09 (m, 1H), 3.97-4.01 (m, 2H), 4.42 (t, J=8.3, 2H), 4.67 (s, 2H), 5.84 (s, 1H), 6.95 (s, 1H), 7.32 (d-d, J=7.6, J=1.5, 1H), 7.38 (t-d, J=7.5, J=1.5, 1H), 7.45 (t-d, J=7.4, J=1.7, 1H), 7.59 (d, J=8.0, 1H).

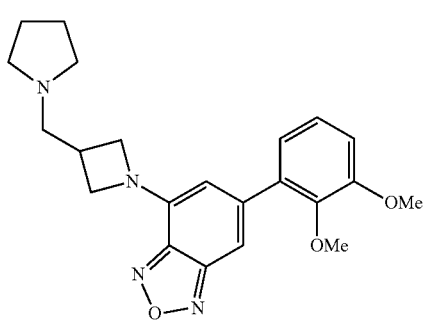

TRV-1500

A round-bottomed flask was charged with TRV-1472 (202 mg, 0.6 mmol), (2,3-dimethoxyphenyl) boronic acid (142 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 2 h. After completion checked by TLC, 10 mL of water was added, and the reaction mixture was extracted with ethyl acetate. The organic phase was dried over anhydrous sodium sulphate and then concentrated. The residue was purified via flash column chromatography (2:5:100:500 MeOH/TEA/EtOAc/Hexane) to afford 141 mg (72% yield) of TRV-1500 as red oil. $^1$H NMR (400 MHz, CDCl$_3$) 1.79-1.82 (m, 4H), 2.52-2.55 (m, 4H), 2.81 (d, J=7.5, 2H), 3.02-3.09 (m, 1H), 3.68 (s, 3H), 3.94 (s, 3H), 3.96-4.00 (m, 2H), 4.42 (t, J=8.3, 2H), 6.08 (s, 1H), 6.98-7.00 (m, 2H), 7.11-7.16 (m, 2H).

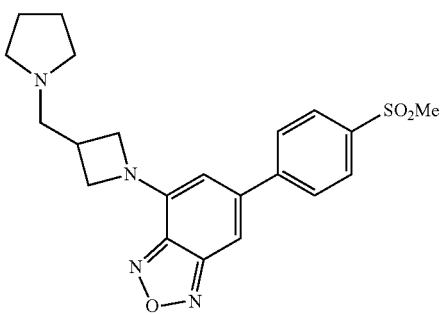

TRV-1501

A round-bottomed flask was charged with TRV-1472 (202 mg, 0.6 mmol), (4-(methylsulfonyl)phenyl) boronic acid (156 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (4:5:100:500 MeOH/TEA/EtOAc/Hexane) to afford 163 mg (66% yield) of TRV-1501 as a red solid. $^1$H NMR (400 MHz, CDCl$_3$) 1.79-1.83 (m, 4H), 2.53-2.57 (m, 4H), 2.83 (d, J=7.6, 2H), 3.09-3.13 (m, 1H), 4.04-4.08 (m, 2H), 4.49 (t, J=8.4, 2H), 5.98 (s, 1H), 7.16 (s, 1H), 7.81 (d, J=8.0, 2H), 8.05 (d, J=8.3, 1H).

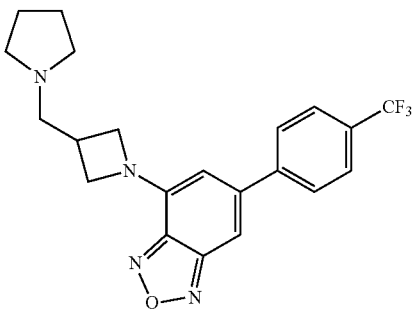

TRV-1502

A round-bottomed flask was charged with TRV-1472 (202 mg, 0.6 mmol), (4-(trifluoromethyl)phenyl) boronic acid (148 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 205 mg (85% yield) of TRV-1502 as a yellow solid. $^1$H NMR (400 MHz, CDCl$_3$) 1.80-1.83 (m, 4H), 2.53-2.57 (m, 4H), 2.83 (d, J=7.5, 2H), 3.07-3.13 (m, 1H), 4.03-4.07 (m, 2H), 4.48 (t, J=8.3, 2H), 6.00 (s, 1H), 7.16 (s, 1H), 7.73 (s, 4H).

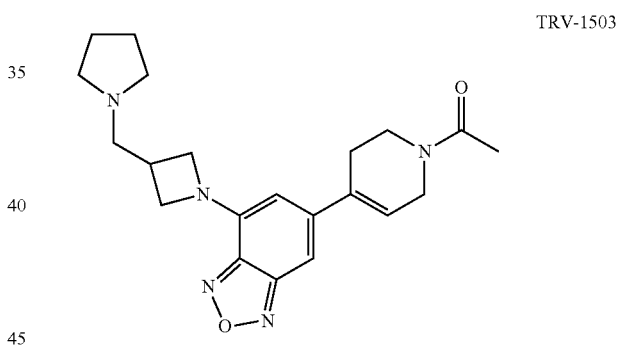

TRV-1503

LDA (6 ml, 12 mmol, 2 M solution in THF) was added dropwise to a stirred solution of 1-Boc-4-piperidone (1.99 g, 10 mmol) in THF (30 mL) at −78° C. under nitrogen atmosphere. After 20 minutes, a THF solution (10 ml) of N-phenyl-bis(trifluomethanesulfonimide) was added to the mixture at −78° C., and the viscous light yellow solution was stirred overnight and the temperature was allowed to warm to RT. The mixture was added 30 ml of hexanes and washed with brine. The organic layer was dried and concentrated.

tert-Butyl 4-(((trifluoromethyl)sulfonyl)oxy)-3,6-dihydropyridine-1(2H)-carboxylate (2.02 g, 61%) was obtained via chromatography (5:95 EtOAc/Hexane).

A round-bottomed flask was charged with tert-butyl 4-(((trifluoromethyl)sulfonyl)oxy)-3,6-dihydropyridine-1 (2H)-carboxylate (2.02 g, 6.1 mmol), bis(pinacolato)diboron (2.32 g, 9.15 mmol), Potassium acetate (1.79 g, 18.3 mmol), and PdCl$_2$(dppf) (223 mg, 0.31 mmol). After degassed, dioxane (15 mL) was added. The reaction mixture was heated to 90° C. for 2 h. After the reaction was completed, the mixture was cooled to rt. 40 mL of EtOAc was added, and the reaction mixture was washed with water for 3 times.

The organic phase was dried over anhydrous sodium sulphate and then concentrated. The residue was purified by flash chromatography (1:10 EtOAc/Hexane). 1.55 g (82%) of tert-butyl 4-(4,4,5,5-tetramethyl-1,3,2-dioxaborolan-2-yl)-3,6-dihydropyridine-1(2H)-carboxylate was obtained as a solid.

A round-bottomed flask was charged with TRV-1472 (1.422 g, 4.22 mmol), tert-butyl 4-(4,4,5,5-tetramethyl-1,3,2-dioxaborolan-2-yl)-3,6-dihydropyridine-1(2H)-carboxylate (1.500 g, 4.85 mmol), and Pd(PPh$_3$)$_4$ (195 mg, 0.169 mmol). After degassed, dioxane (12 mL) and aqueous sodium carbonate (6 mL, 2M) was added. The reaction mixture was heated to 90° C. for 2.5 h. After completion checked by TLC, 50 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 1.80 g (97% yield) of tert-butyl 4-(7-(3-(pyrrolidin-1-ylmethyl)azetidin-1-yl)benzo[c][1,2,5]oxadiazol-5-yl)-3,6-dihydropyridine-1(2H)-carboxylate.

tert-butyl 4-(7-(3-(pyrrolidin-1-ylmethyl)azetidin-1-yl)benzo[c][1,2,5]oxadiazol-5-yl)-3,6-dihydropyridine-1(2H)-carboxylate (1.80 g, 4.09 mmol) was stirred in the solution of DCM/CF$_3$COOH (2:1, 21 ml) for 1 hour at 0° C. After completion checked by TLC, the mixture was carefully neutralized with saturated K$_2$CO3 solution until no more gas gave out at 0° C. 50 ml of DCM was added to the solution and mixture was washed with water. The organic layer was dried over anhydrous sodium sulphate and then concentrated. The crude (4-(3-(pyrrolidin-1-ylmethyl)azetidin-1-yl)-6-(1,2,3,6-tetrahydropyridin-4-yl)benzo[c][1,2,5]oxadiazole) was used for the next step without further purification.

TEA (3.06 ml, 22 mmol) and acetic anhydride (1.04 ml, 11 mmol) were added dropwise to a solution of crude (4-(3-(pyrrolidin-1-ylmethyl)azetidin-1-yl)-6-(1,2,3,6-tetrahydropyridin-4-yl)benzo[c][1,2,5]oxadiazole) (250 mg, 0.735 mmol) in THF (10 ml) at rt respectively. The mixture was stirred for 3 hours. After completion checked by TLC, the reaction was quenched by Hexanes/H$_2$O (1:1, 50 ml). The mixture was washed with 2 N NaOH and brine. The organic layer was dried and concentrated. The residue was purified via chromatography (6:5:100:500 MeOH/TEA/EtOAc/Hexane) to afford TRV-1503 (210 mg 75%) as a yellow solid. $^1$H NMR (400 MHz, CDCl$_3$) 1.77-1.84 (m, 4H), 2.16 (s, 1.28H), 2.19 (s, 1.72H), 2.51-2.56 (m, 4H), 2.57-2.64 (m, 2H), 2.80 (d, J=7.5, 2H), 3.03-3.10 (m, 1H), 3.69 (t, J=5.6, 0.85H), 3.83 (t, J=5.8, 1.15H), 3.96-4.00 (m, 2H), 4.17 (d, J=3.0, 0.85H), 4.28 (d, J=2.4, 1.15H), 4.42 (t, J=7.7, 2H), 5.87 (s, 0.43H), 5.90 (s, 0.57H), 6.15 (s, 0.43H), 6.24 (s, 0.57H), 6.90 (s, 0.57H), 6.94 (s, 0.43H).

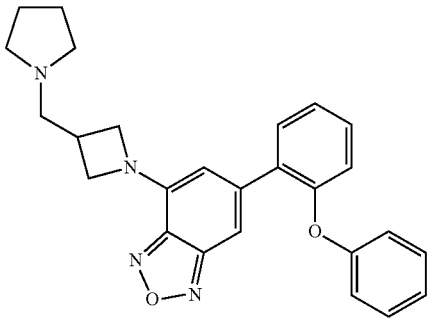

TRV 1504

A reaction vial was charged with TRV 1472 (0.19 g, 0.56 mmol), (2-phenoxyphenyl)boronic acid (0.14 g, 0.67 mmol), and Pd(PPh$_3$)$_4$ (0.032 g, 0.028 mmol). The vial was degassed and refilled with nitrogen. To the vial was added dioxane (5 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (2% of triethylamine and 2% of methanol in a 5:1 mixture solvent of hexane and ethyl acetate) to afford 0.20 g (84% yield) of TRV 1504 as a red solid. $^1$H NMR (CDCl$_3$, 400 MHz) δ=7.52 (dt, J$_1$=1.51 Hz, J$_2$=7.53 Hz, 1H), 7.38 (dt, J$_1$=1.75 Hz, J$_2$=7.80 Hz, 1H), 7.30 (t, J=8.54 Hz, 2H), 7.24 (t, J=7.53 Hz, 1H), 7.13 (s, 1H), 7.05 (t, J=7.40 Hz, 2H), 6.95 (d, J=7.53 Hz, 2H), 6.03 (s, 1H), 4.32 (t, J=8.16 Hz, 2H), 3.87 (dd, J$_1$=6.12 Hz, J$_2$=8.03 Hz, 2H), 3.01 (septet, J=7.28 Hz, 1H), 2.76 (d, J=7.28 Hz, 2H), 2.56-2.46 (m, 4H), 1.85-1.75 (m, 4H).

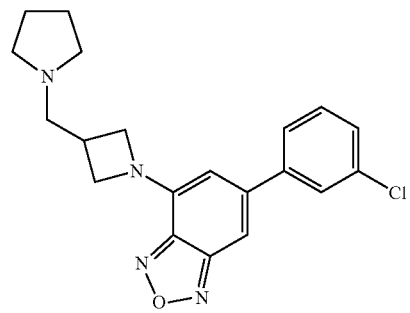

TRV 1505

A reaction vial was charged with TRV 1472 (0.16 g, 0.48 mmol), (3-chlorophenyl)boronic acid (0.10 g, 0.64 mmol), and Pd(PPh$_3$)$_4$ (0.028 g, 0.024 mmol). The vial was degassed and refilled with nitrogen. To the vial was added dioxane (5 mL) and aq. sodium carbonate (3 mL, 2.0 M, 6.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (2% of triethylamine and 2% of methanol in a 5:1 mixture solvent of hexane and ethyl acetate) to afford 0.15 g (85% yield) of TRV 1505 as red oil. $^1$H NMR (CDCl$_3$, 400 MHz) δ=7.60 (s, 1H), 7.52-7.48 (m, 1H), 7.43-7.38 (m, 2H), 7.13 (s, 1H), 6.99 (s, 1H), 4.48 (t, J=8.29 Hz, 2H), 4.04 (dd, J$_1$=5.90 Hz, J$_2$=8.66 Hz, 2H), 3.10 (septet, J=6.97 Hz, 1H), 2.82 (d, J=7.28 Hz, 2H), 2.59-2.51 (m, 4H), 1.86-1.78 (m, 4H).

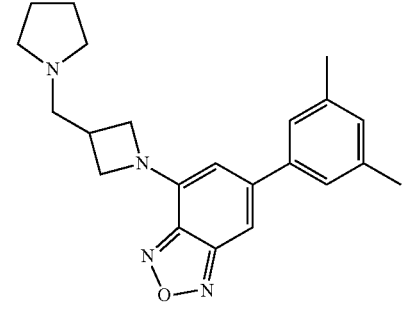

TRV 1506

A reaction vial was charged with TRV 1472 (0.25 g, 0.74 mmol), (3,5-dimethylphenyl)boronic acid (0.15 g, 1.00 mmol), and Pd(PPh$_3$)$_4$ (0.086 g, 0.074 mmol). The vial was degassed and refilled with nitrogen. To the vial was added dioxane (5 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (5% of triethylamine and 1.5% of methanol in a 5:1 mixture solvent of hexane and ethyl acetate) to afford 0.20 g (75% yield) of TRV 1506 as a yellow solid. $^1$H NMR (CDCl$_3$, 400 MHz) δ=7.24 (s, 2H), 7.14 (d, J=0.75 Hz, 1H), 7.07 (s, 1H), 6.07 (s, 1H), 4.46 (t, J=8.28 Hz, 2H), 4.02 (dd, J$_1$=5.65 Hz, J$_2$=8.41 Hz, 2H), 3.09 (septet, J=7.66 Hz, 1H), 2.82 (d, J=7.53 Hz, 2H), 2.59-2.51 (m, 4H), 2.41 (s, 6H), 1.86-1.77 (m, 4H).

TRV 1507

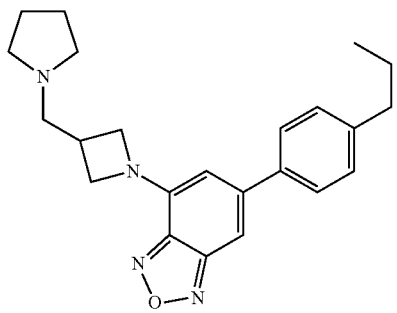

A reaction vial was charged with TRV 1472 (0.25 g, 0.74 mmol), (4-propylphenyl)boronic acid (0.16 g, 1.00 mmol), and Pd(PPh$_3$)$_4$ (0.086 g, 0.074 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (5% of triethylamine and 1.5% of methanol in a 5:1 mixture solvent of hexane and ethyl acetate) to afford 0.25 g (90% yield) of TRV 1507 as a yellow solid. $^1$H NMR (CDCl$_3$, 400 MHz) δ=7.55 (d, J=8.28 Hz, 2H), 7.29 (d, J=8.28 Hz, 2H), 7.15 (d, J=0.75 Hz, 1H), 6.08 (s, 1H), 4.46 (t, J=8.88 Hz, 2H), 4.02 (dd, J$_1$=5.65 Hz, J$_2$=8.41 Hz, 2H), 3.08 (septet, J=6.78 Hz, 1H), 2.82 (d, J=7.28 Hz, 2H), 2.66 (t, J=7.66 Hz, 2H), 2.59-2.50 (m, 4H), 1.87-1.78 (m, 4H), 1.70 (sextet, J=7.28 Hz, 2H), 0.99 (t, J=7.28 Hz, 3H).

TRV 1509

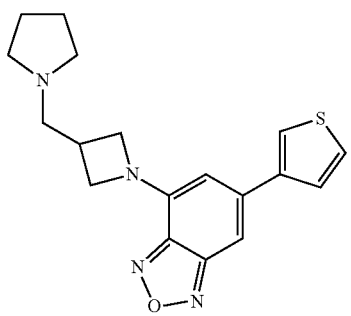

A reaction vial was charged with TRV 1472 (0.25 g, 0.74 mmol), thiophen-3-ylboronic acid (0.13 g, 1.00 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (5% of triethylamine and 1% of methanol in a 5:1 mixture solvent of hexane and ethyl acetate) to afford 0.20 g (79% yield) of TRV 1509 as an orange solid. $^1$H NMR (CDCl$_3$, 400 MHz) δ=7.58 (t, J=2.13 Hz, 1H), 7.43 (d, J=2.01 Hz, 2H), 7.19 (s, 1H), 6.09 (s, 1H), 4.46 (t, J=8.41 Hz, 2H), 4.03 (dd, J$_1$=5.90 Hz, J$_2$=8.46 Hz, 2H), 3.09 (septet, J=6.59 Hz, 1H), 2.82 (d, J=7.53 Hz, 2H), 2.62-2.48 (m, 4H), 1.89-1.76 (m, 4H).

TRV 1510

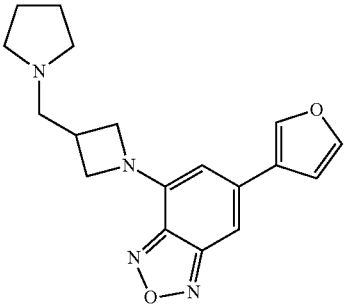

A reaction vial was charged with TRV 1472 (0.25 g, 0.74 mmol), furan-3-ylboronic acid (0.15 g, 1.30 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (5% of triethylamine and 1% of methanol in a 5:1 mixture solvent of hexane and ethyl acetate) to afford 0.18 g (75% yield) of TRV 1510 as an orange solid. $^1$H NMR (CDCl$_3$, 400 MHz) δ=7.81 (s, 1H), 7.52 (t, J=1.63 Hz, 1H), 7.08 (s, 1H), 6.75 (t, J=0.87 Hz, 1H), 5.94 (s, 1H), 4.45 (t, J=8.28 Hz, 2H), 4.01 (dd, J$_1$=5.77 Hz, J$_2$=8.54 Hz, 2H), 3.08 (septet, J=6.72 Hz, 1H), 2.81 (d, J=7.53 Hz, 2H), 2.59-2.51 (m, 4H), 1.87-1.77 (m, 4H).

TRV 1511

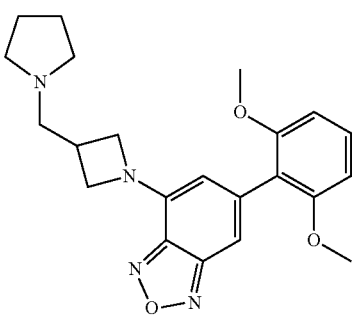

A reaction vial was charged with TRV 1472 (0.25 g, 0.74 mmol), (2,6-dimethoxyphenyl)boronic acid (0.18 g, 1.00 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (5% of triethylamine and 1% of methanol in a 5:1 mixture solvent of hexane and ethyl acetate) to afford 0.21 g (72% yield) of TRV 1511 as a yellow solid. $^1$H NMR (CDCl$_3$, 400 MHz) δ=7.33 (t, J=8.26 Hz, 1H), 6.99 (s, 1H), 6.68 (d, J=8.28 Hz, 1H), 5.82 (s, 1H), 4.39 (t, J=8.16 Hz, 2H), 3.96 (dd, J$_1$=5.65 Hz, J$_2$=8.41 Hz, 2H), 3.77 (s, 6H), 3.04 (septet, J=6.65 Hz, 1H), 2.79 (d, J=7.53 Hz, 2H), 2.58-2.48 (m, 4H), 1.85-1.75 (m, 4H).

A round-bottomed flask was charged with TRV-1472 (202 mg, 0.6 mmol), (2-(trifluoromethyl)phenyl) boronic acid (148 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (1:5:100:500 MeOH/TEA/EtOAc/Hexane) to afford 190 mg (79% yield) of TRV-1514 as orange oil. $^1$H NMR (400 MHz, CDCl$_3$) 1.78-1.82 (m, 4H), 2.52-2.55 (m, 4H), 2.81 (d, J=7.3, 2H), 3.03-3.10 (m, 1H), 3.98-4.02 (m, 2H), 4.42 (t, J=8.3, 2H), 5.77 (s, 1H), 6.93 (s, 1H), 7.39 (d, J=7.8, 1H), 7.52 (t, J=7.4, 1H), 7.60 (t, J=7.5, 1H), 7.77 (d, J=7.5, 1H).

TRV-1512

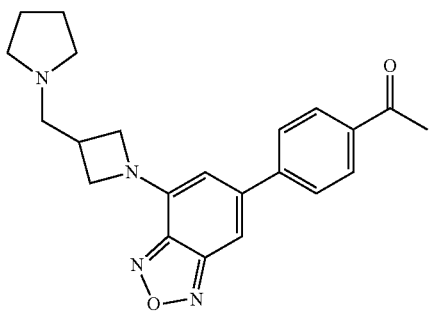

TRV-1515

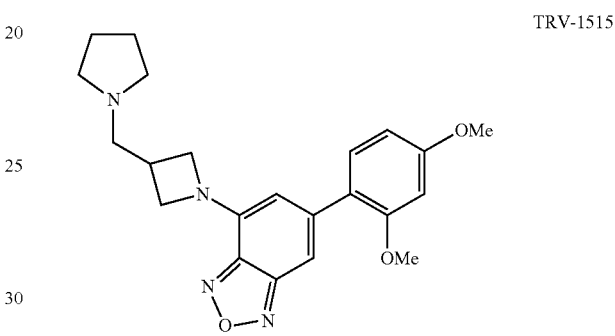

A round-bottomed flask was charged with TRV-1472 (202 mg, 0.6 mmol), (4-acetylphenyl) boronic acid (128 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 4 h. After completion checked by TLC, 10 mL of water was added, and the reaction mixture was extracted with ethyl acetate. The organic phase was dried over anhydrous sodium sulphate and then concentrated. The residue was purified via flash column chromatography (3:5:100:500 MeOH/TEA/EtOAc/Hexane) to afford 199 mg (88% yield) of TRV-1512 as a red solid. $^1$H NMR (400 MHz, CDCl$_3$) 1.80-1.83 (m, 4H), 2.53-2.56 (m, 4H), 2.67 (s, 3H), 2.82 (d, J=7.5, 2H), 3.07-3.13 (m, 1H), 4.03-4.07 (m, 2H), 4.48 (t, J=8.3, 2H), 6.03 (s, 1H), 7.19 (d, J=1.0, 1H), 7.70-7.73 (m, 2H), 8.04-8.07 (m, 2H).

A round-bottomed flask was charged with TRV-1472 (202 mg, 0.6 mmol), (2,4-dimethoxyphenyl) boronic acid (142 mg, 0.78 mmol), and Pd(PPh$_3$)$_4$ (35 mg, 0.03 mmol). After degassed, dioxane (5 mL) and aqueous sodium carbonate (2.5 mL, 2M) was added. The reaction mixture was heated to 90° C. for 2 h. After completion checked by TLC, 10 mL of water was added, and the reaction mixture was extracted with ethyl acetate. The organic phase was dried over anhydrous sodium sulphate and then concentrated. The residue was purified via flash column chromatography (2:5:100:500 MeOH/TEA/EtOAc/Hexane) to afford 190 mg (61% yield) of TRV-1515 as a yellow solid. $^1$H NMR (400 MHz, CDCl$_3$): 1.78-1.82 (m, 4H), 2.55 (s, br, 4H), 2.81 (d, J=7.3, 2H), 3.02-3.09 (m, 1H), 3.84 (s, 3H), 3.88 (s, 3H), 3.95-3.99 (m, 2H), 4.41 (t, J=8.2, 2H), 6.04 (s, 1H), 6.58-6.60 (m, 2H), 7.09 (s, 1H), 7.30-7.32 (m, 1H).

TRV-1514

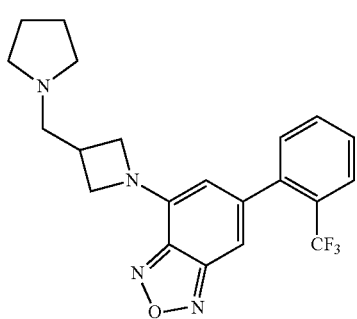

TRV-1516

A round-bottomed flask was charged with TRV-1472 (250 mg, 0.742 mmol), (4-(dimethylcarbamoyl)phenyl) boronic acid (172 mg, 0.89 mmol), and Pd(PPh$_3$)$_4$ (43 mg, 0.037 mmol). After degassed, dioxane (5 mL) and aqueous sodium carbonate (2.5 mL, 2M) was added. The reaction mixture was heated to 90° C. for 2.5 h. After completion checked by TLC, 10 mL of water was added, and the reaction mixture was extracted with ethyl acetate. The organic phase was dried over anhydrous sodium sulphate and then concentrated. The residue was purified via flash column chromatography (5:5:100:500 MeOH/TEA/EtOAc/Hexane) to afford 207 mg (85% yield) of TRV-1516 as a red solid. $^1$H NMR (400 MHz, CDCl$_3$): 1.80-1.84 (m, 4H), 2.54-2.56 (m, 4H), 2.82 (d, J=7.3, 2H), 3.05 (s, 3H), 3.07-3.13 (m, 1H), 3.16 (s, 3H), 4.02-4.06 (m, 2H), 4.47 (t, J=8.2, 2H), 6.03 (s, 1H), 7.15 (s, 1H), 7.27 (s, 1H), 7.53 (d, J=8.3, 1H), 7.66 (d, J=8.3, 2H).

TRV-1517

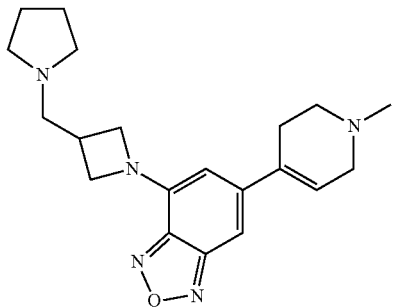

TEA (2.05 ml, 14.7 mmol) and methyl iodide (0.46 ml, 7.35 mmol) were added dropwise to a solution of crude (4-(3-(pyrrolidin-1-ylmethyl)azetidin-1-yl)-6-(1,2,3,6-tetrahydropyridin-4-yl)benzo[c][1,2,5]oxadiazole) (250 mg, 0.735 mmol) in DCM (10 ml) at rt respectively. The mixture was stirred for 5 hours. The reaction was quenched by EtOAc/H$_2$O (1:1, 50 ml). The mixture was washed with 2 N NaOH and brine. The organic layer was dried and concentrated. The residue was purified via chromatography (7:5:100:500 MeOH/TEA/EtOAc/Hexane) to afford Compound TRV-1517 (120 mg, 46%) as red oil. $^1$H NMR (400 MHz, CDCl$_3$): 1.79-1.83 (m, 4H), 2.43 (s, 3H), 2.52-2.55 (m, 4H), 2.58-2.63 (m, 2H), 2.67-2.71 (m, 2H), 2.79 (d, J=7.5, 2H), 3.02-3.09 (m, 1H), 3.13-3.17 (m, 2H), 3.94-3.98 (m, 2H), 4.40 (t, J=8.2, 2H), 5.95 (s, 1H), 6.22 (t, J=3.6, 1H), 6.95 (s, 1H).

TRV-1518

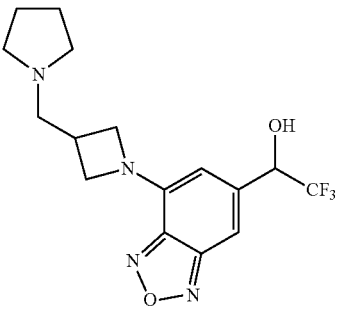

TEA (0.41 ml, 2.94 mmol) and Methanesulfonyl chloride (0.11 ml, 1.47 mmol) were added dropwise to a solution of crude (4-(3-(pyrrolidin-1-ylmethyl)azetidin-1-yl)-6-(1,2,3,6-tetrahydropyridin-4-yl)benzo[c][1,2,5]oxadiazole) (250 mg, 0.735 mmol) in DCM (10 ml) at rt respectively. The mixture was stirred for 5 hours. The reaction was quenched by EtOAc/H$_2$O (1:1, 50 ml). The mixture was washed with 2 N NaOH and brine. The organic layer was dried and concentrated. The residue was purified via chromatography (5:5:100:500 MeOH/TEA/EtOAc/Hexane) to afford Compound TRV-1518 (250 mg, 81%) as red solid. $^1$H NMR (400 MHz, CDCl3): 1.80-1.82 (m, 4H), 2.52-2.57 (m, 4H), 2.66-2.71 (m, 2H), 2.80 (d, J=7.3, 2H), 2.89 (s, 3H), 3.04-3.11 (m, 1H), 3.54 (t, J=5.6, 2H), 3.97-4.01 (m, 4H), 4.42 (t, J=8.2, 2H), 5.80 (s, 1H), 6.21 (s, br, 1H), 6.93 (s, 1H).

TRV-1519

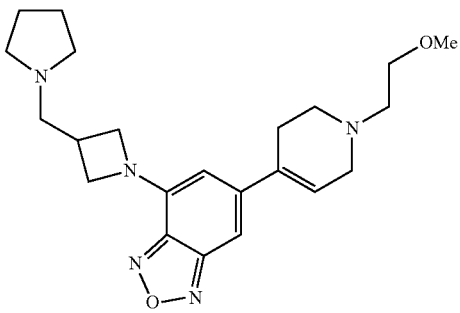

Potassium carbonate (203 mg, 1.47 mmol) and 2-bromoethyl methyl ether (0.316 ml, 3.3 mmol) were added dropwise to a solution of crude (4-(3-(pyrrolidin-1-ylmethyl)azetidin-1-yl)-6-(1,2,3,6-tetrahydropyridin-4-yl)benzo[c][1,2,5]oxadiazole) (250 mg, 0.735 mmol) in acetonitrile (10 ml) at rt respectively. The mixture was stirred overnight. The reaction was quenched by EtOAc/H$_2$O (1:1, 50 ml). The mixture was washed with 2 N NaOH and brine. The organic layer was dried and concentrated. The residue was purified via chromatography (5:5:100:500 MeOH/TEA/EtOAc/Hexane) to afford Compound TRV-1519 (180 mg, 61%) as red oil. $^1$H NMR (400 MHz, CDCl3): 1.78-1.82 (m, 4H), 2.52-2.55 (m, 4H), 2.60 (s, br, 2H), 2.73 (d, J=5.6, 2H), 2.77-2.80 (m, 4H), 3.02-3.08 (m, 1H), 3.26-3.29 (m, 2H), 3.58 (s, 3H), 3.60 (t, J=5.6, 2H), 3.94-3.97 (m, 2H), 4.40 (t, J=8.2, 2H), 5.95 (s, 1H), 6.21 (t, J=4.0, 1H), 6.93 (s, 1H).

TRV-1520

To a flame-dried 2-neck flask was added TRV-1472 (0.2336 g, 0.69 mmol). The flask was evacuated and purged with argon (3×). THF (9.2 mL) was added and the solution was cooled to −78° C. nBuLi (0.52 mL, 1.6 M solution in hexane) was added over 5 minutes, and the reaction was stirred for an additional 15 minutes. Neat DMF (0.08 mL)

was then added, stirred at −78° C. for 60 minutes. At this point, MeOH (1 mL) was added at −78° C. and the reaction was allowed to warm to room temperature. The mixture was diluted with water and EtOAc and the layers separated. The aqueous layer was back-extracted with EtOAc (3×). The combined organic layers were washed with water, brine, dried with MgSO₄, filtered and concentrated. The crude aldehyde was then dissolved in THF (10 mL) and cooled in an ice bath. CF₃TMS (0.20 mL, 1.38 mmol) was added followed by TBAF (70 μL). The reaction was stirred at 0° C. for 5 minutes and then warmed to room temperature. The reaction was complete after 90 minutes. Quenched with 10 mL of 2 N HCl, then diluted with EtOAc and water. The layers were separated and the aqueous layer was back-extracted with EtOAc (3×). The combined organic layers were washed with water, brine, dried with MgSO₄, filtered and concentrated. The crude material was purified with 10% MeOH/DCM column to afford 0.0525 g (21% yield) of TRV-1520. $^1$H NMR (500 MHz, DMSO) δ=7.22 (s, 1H), 7.04 (d, J=6 Hz, 1H), 6.06 (s, 1H), 5.23-5.18 (m, 1H), 4.33 (t, J=8 Hz, 2H), 3.91 (t, J=8 Hz, 2H), 3.02-2.97 (m, 1H), 2.76 (br s, 2H), 2.49-2.48 (m, 4H, overlapping with DMSO signal), 1.69 (s, 4H).

TRV-1521

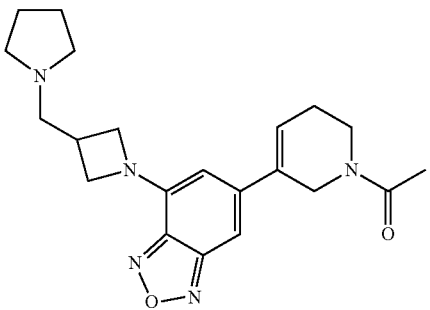

LDA (18 ml, 23 mmol, 2 M solution in THF) was added dropwise to a stirred solution of 1-Boc-3-piperidone (5.97 g, 30 mmol) in THF (80 mL) at −78° C. under nitrogen atmosphere. After 20 minutes, a THF solution (30 ml) of N-phenyl-bis(trifluomethanesulfonimide) was added to the mixture at −78° C., and the viscous light yellow solution was stirred overnight and the temperature was allowed to warm to RT. After addition of saturated NH₄Cl (80 ml), the mixture was diluted with water (100 ml). The mixture was added 150 ml of EtOAc and washed with brine. The organic layer was dried and concentrated. tert-Butyl 5-(((trifluoromethyl)sulfonyl)oxy)-3,4-dihydropyridine-1(2H)-carboxylate (4.02 g, 40.5%) and tert-butyl 5-(((trifluoromethyl)sulfonyl)oxy)-3,6-dihydropyridine-1(2H)-carboxylate (2.5 g, 25.2%) were obtained via chromatography (5:95 EtOAc/Hexane).

A round-bottomed flask was charged with tert-butyl 5-(((trifluoromethyl)sulfonyl)oxy)-3,6-dihydropyridine-1(2H)-carboxylate (2.5 g, 7.55 mmol), bis(pinacolato)diboron (2.88 g, 11.33 mmol), Potassium acetate (2.22 g, 22.7 mmol), and PdCl₂(dppf) (276 mg, 0.38 mmol). After degassed, dioxane (40 mL) was added. The reaction mixture was heated to 90° C. for 3 h. After the reaction was completed, the mixture was cooled to rt. 40 mL of EtOAc was added, and the reaction mixture was washed with water for 3 times. The organic phase was dried over anhydrous sodium sulphate and then concentrated. The residue was purified by flash chromatography (1:8:12 EtOAc/DCM/Hexane). 1.5 g (64.3%) of tert-butyl 5-(4,4,5,5-tetramethyl-1,3,2-dioxaborolan-2-yl)-3,6-dihydropyridine-1(2H)-carboxylate was obtained as a solid.

A round-bottomed flask was charged with TRV-1472 (1.36 g, 4.05 mmol), tert-butyl 5-(4,4,5,5-tetramethyl-1,3,2-dioxaborolan-2-yl)-3,6-dihydropyridine-1 (2H)-carboxylate (1.5 g, 4.85 mmol), and Pd(PPh₃)₄ (280 mg, 0.24 mmol). After degassed, dioxane (16 mL) and aqueous sodium carbonate (8 mL, 2M) were added. The reaction mixture was heated to 90° C. for 3 h. After completion checked by TLC, 20 mL of water was added, and the reaction mixture was extracted with ethyl acetate. The organic phase was dried over anhydrous sodium sulphate and then concentrated. The residue was purified by flash chromatography (1:5:100:500 MeOH/TEA/EtOAc/Hexane) to afford tert-butyl 5-(7-(3-(pyrrolidin-1-ylmethyl)azetidin-1-yl)benzo[c][1,2,5]oxadiazol-5-yl)-3,6-dihydropyridine-1(2H)-carboxylate (1.7 g, 94.4%).

tert-Butyl 5-(7-(3-(pyrrolidin-1-ylmethyl)azetidin-1-yl)benzo[c][1,2,5]oxadiazol-5-yl)-3,6-dihydropyridine-1(2H)-carboxylate (1.7 g, 3.86 mmol) was stirred in the solution of DCM/CF₃COOH (2:1, 21 ml) for 1 hour at 0° C. After completion checked by TLC, the mixture was carefully neutralized with saturated K₂CO₃ solution until no more gas gave out at 0° C. 15 ml of NaOH (2N) was added to the solution, and extracted with DCM (3×30 ml). The organic layer was dried over anhydrous sodium sulphate and then concentrated. The crude 4-(3-(pyrrolidin-1-ylmethyl)azetidin-1-yl)-6-(1,2,5,6-tetrahydropyridin-3-yl)benzo[c][1,2,5]oxadiazole was used for the next step without further purification.

TEA (1.02 ml, 7.35 mmol) and acetic anhydride (0.341 ml, 3.62 mmol) were added dropwise to a solution of crude 4-(3-(pyrrolidin-1-ylmethyl)azetidin-1-yl)-6-(1,2,5,6-tetrahydropyridin-3-yl)benzo[c][1,2,5]oxadiazole (250 mg, 0.735 mmol) in THF (10 ml) at rt respectively. The mixture was stirred for 3 hours. After completion checked by TLC, the reaction was quenched by Hexane/H₂O (1:1, 50 ml). The mixture was washed with 2 N NaOH and brine. The organic layer was dried and concentrated. The residue was purified via chromatography (6:5:100:500 MeOH/TEA/EtOAc/Hexane) to afford TRV-1521 (230 mg 82%) as a yellow solid. $^1$H NMR (400 MHz, CDCl3): 1.81 (s, br, 4H), 2.19 (s, 3H), 2.36-2.43 (m, 2H), 2.54 (s, br, 4H), 2.79-2.81 (m, 2H), 3.03-3.10 (m, 1H), 3.61 (t, J=5.8, 1.2H), 3.77 (t, J=5.8, 0.8H), 3.96-4.02 (m, 2H), 4.31-4.47 (m, 4H), 5.87 (s, 1H), 6.32-6.34 (m, 0.6H), 6.42-6.44 (m, 0.4H), 6.87 (s, 0.4H), 6.97 (s, 0.6H).

TRV-1522

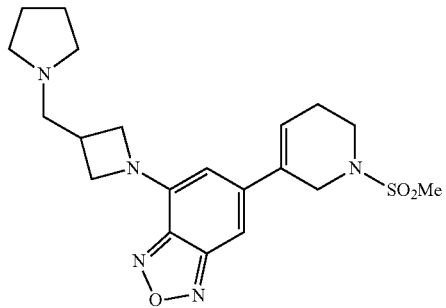

TEA (0.41 ml, 2.94 mmol) and Methanesulfonyl chloride (0.11 ml, 1.47 mmol) were added dropwise to a solution of crude 4-(3-(pyrrolidin-1-ylmethyl)azetidin-1-yl)-6-(1,2,5,6-tetrahydropyridin-3-yl)benzo[c][1,2,5]oxadiazole (250 mg, 0.735 mmol) in DCM (10 ml) at rt respectively. The mixture was stirred for 5 hours. The reaction was quenched by EtOAc/H₂O (1:1, 50 ml). The mixture was washed with 2 N NaOH and brine. The organic layer was dried and concentrated. The residue was purified via chromatography (6:5:100:500 MeOH/TEA/EtOAc/Hexane) to afford Compound TRV-1522 (240 mg, 78%) as a red solid. $^1$H NMR (400 MHz, CDCl3): 1.79-1.83 (m, 4H), 2.48-2.55 (m, 6H), 2.80 (d, J=7.3, 2H), 2.90 (s, 3H), 3.04-3.11 (m, 1H), 3.47 (t, J=5.8, 2H), 3.97-4.01 (m, 2H), 4.14-4.16 (m, 2H), 4.43 (t, J=8.2, 2H), 5.83 (s, 1H), 6.35-6.37 (m, 1H), 6.89 (s, 1H).

for another 3 h. The reaction was quenched by EtOAc/H₂O (1:1, 50 ml). The mixture was washed with 2 N NaOH and brine. The organic layer was dried and concentrated. The residue was purified via chromatography (4:5:100:500, MeOH/TEA/EtOAc/Hexane) to afford Compound TRV-1524 (150 mg, 48%) as red oil. $^1$H NMR (400 MHz, CDCl₃): 1.81-1.86 (m, 4H), 2.42-2.45 (m, 2H), 2.49 (s, 3H), 2.58-2.62 (m, 6H), 2.82 (d, J=7.3, 2H), 3.04-3.11 (m, 1H), 3.29-3.31 (m, 2H), 3.95-3.99 (m, 2H), 4.41 (t, J=8.2, 2H), 5.92 (s, 1H), 6.28-6.30 (m, 1H), 6.88 (s, 1H).

TRV-1523

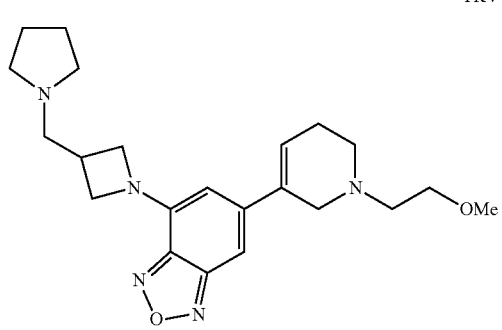

TRV 1525

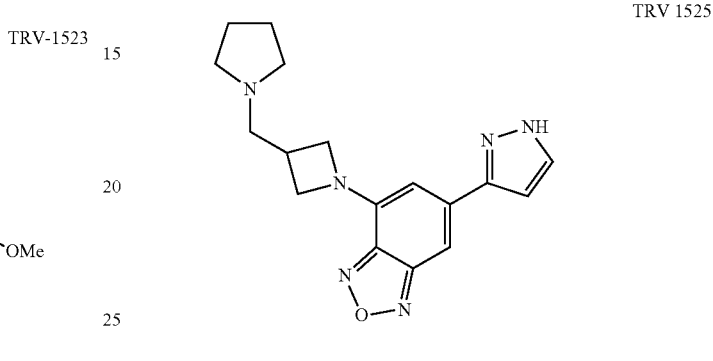

Potassium carbonate (507 mg, 3.68 mmol) and 2-bromoethyl methyl ether (0.316 ml, 3.3 mmol) were added dropwise to a solution of crude 4-(3-(pyrrolidin-1-ylmethyl)azetidin-1-yl)-6-(1,2,5,6-tetrahydropyridin-3-yl)benzo[c][1,2,5]oxadiazole (250 mg, 0.735 mmol) in acetonitrile (10 ml) at rt respectively. The mixture was stirred overnight. The reaction was quenched by EtOAc/H₂O (1:1, 50 ml). The mixture was washed with 2 N NaOH and brine. The organic layer was dried and concentrated. The residue was purified via chromatography chromatography (4:5:100:500 MeOH/TEA/EtOAc/Hexane) to afford Compound TRV-1523 (210 mg, 72%) as red oil. $^1$H NMR (400 MHz, CDCl3):_1.80-1.82 (m, 4H), 2.41-2.42 (m, 2H), 2.54 (s, br, 2H), 2.71 (d, J=5.6, 2H), 2.77-2.81 (m, 4H), 3.02-3.08 (m, 1H), 3.40-3.41 (m, 5H), 3.62 (t, J=5.6, 2H), 3.94-3.98 (m, 2H), 4.40 (t, J=8.0, 2H), 5.91 (s, 1H), 6.28 (s, br, 1H), 6.87 (s, 1H).

A reaction vial was charged with TRV 1472 (0.25 g, 0.74 mmol), (1H-pyrazol-3-yl)boronic acid (0.10 g, 0.90 mmol), and Pd(PPh₃)₄ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:hexane:EtOAc 5:3:75:15 to TEA:MeOH:hexane:EtOAc 5:8:75:15) to afford 0.050 g (21% yield) of TRV 1525 as a red solid. $^1$H NMR (DMSO, 400 MHz) δ=13.11 (broad, 1H), 8.43 (broad, 1H), 8.13 (broad, 1H), 7.31 (s, 1H), 6.32 (s, 1H), 4.34 (t, J=8.29 Hz, 2H), 3.92 (dd, J₁=5.53 Hz, J₂=8.54 Hz, 2H), 2.98 (septet, J=6.86 Hz, 1H), 2.71 (d, J=7.53 Hz, 2H), 2.53-2.37 (m, 4H), 1.76-1.62 (m, 4H).

TRV-1524

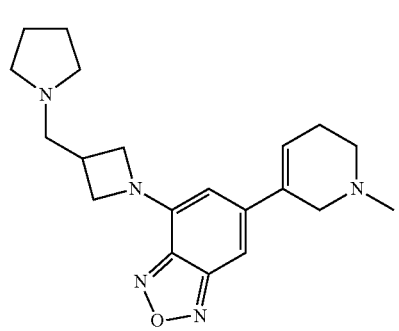

TRV 1526

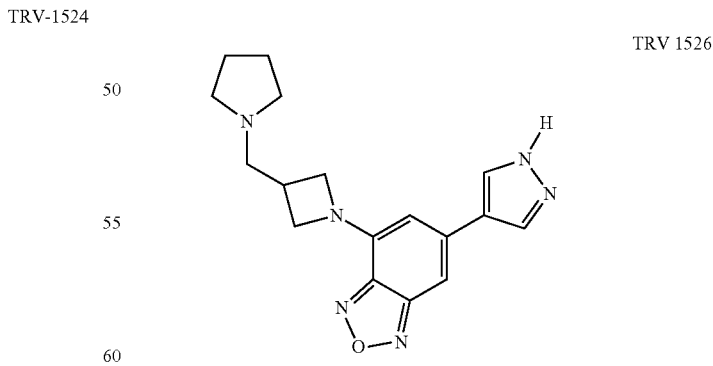

TEA (1.23 ml, 8.82 mmol) and methyl iodide (0.11 ml, 1.76 mmol) were added dropwise to a solution of crude 4-(3-(pyrrolidin-1-ylmethyl)azetidin-1-yl)-6-(1,2,5,6-tetrahydropyridin-3-yl)benzo[c][1,2,5]oxadiazole (300 mg, 0.882 mmol) in DCM (10 ml) at rt respectively. After the mixture was stirred for 2 hours, methyl iodide (0.11 ml, 1.76 mmol) was added to a solution, and the mixture was stirred A reaction vial was charged with TRV 1472 (0.25 g, 0.74 mmol), 4-(4,4,5,5-tetramethyl-1,3,2-dioxaborolan-2-yl)-1H-pyrazole (0.18 g, 0.90 mmol), and Pd(PPh₃)₄ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:hexane:EtOAc 5:3:75:15 to TEA:MeOH: hexane:EtOAc 5:10:75:15) to afford 0.080 g (33% yield) of TRV 1526 as a red solid. $^1$H NMR (CDCl$_3$, 400 MHz) δ=7.66 (d, J=2.51 Hz, 1H), 7.35 (s, 1H), 6.73 (d, J=2.26 Hz, 1H), 6.46 (s, 1H), 4.46 (t, J=8.28 Hz, 2H), 4.02 (dd, J$_1$=5.77 Hz, J$_2$=8.53 Hz, 2H), 3.08 (septet, J=6.99 Hz, 1H), 2.81 (d, J=7.28 Hz, 2H), 2.61-2.51 (m, 4H), 1.87-1.77 (m, 4H).

TRV 1527

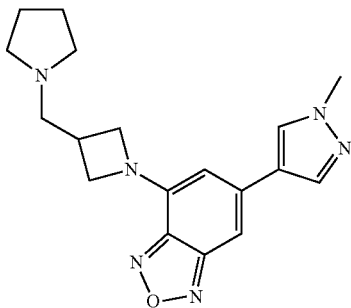

A reaction vial was charged with TRV 1472 (0.25 g, 0.74 mmol), 4-(4,4,5,5-tetramethyl-1,3,2-dioxaborolan-2-yl)-1H-pyrazole (0.18 g, 0.90 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:hexane:EtOAc 5:3:75:15 to TEA:MeOH: hexane:EtOAc 5:8:75:15) to afford 0.25 g (100% yield) of TRV 1527 as a red solid. $^1$H NMR (CDCl$_3$, 400 MHz) δ 7.81 (d, J=0.75 Hz, 1H), 7.70 (s, 1H), 7.05 (d, J=1.00 Hz, 1H), 5.95 (s, 1H), 4.44 (t, J=8.29 Hz, 2H), 4.01 (dd, J$_1$=5.65 Hz, J$_2$=8.66 Hz, 2H), 3.98 (s, 3H), 3.08 (septet, J=7.03 Hz, 1H), 2.81 (d, J=7.53 Hz, 2H), 2.62-2.49 (m, 4H), 1.88-1.76 (m, 4H).

TRV 1528

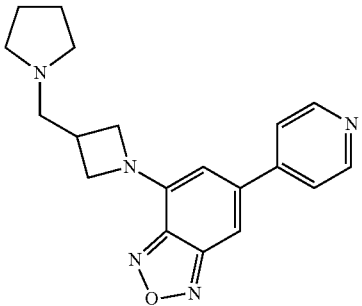

A reaction vial was charged with TRV 1472 (0.32 g, 0.95 mmol), pyridin-4-ylboronic acid (0.15 g, 1.20 mmol), and Pd(PPh$_3$)$_4$ (0.055 g, 0.048 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA: MeOH: hexane:EtOAc 1:1:15:3) to afford 0.26 g (82% yield) of TRV 1528 as a red solid. $^1$H NMR (CDCl$_3$, 400 MHz) δ=8.71 (dd, J$_1$=1.64 Hz, J$_2$=6.27 Hz, 1H), 7.52 (dd, J$_1$=1.26 Hz, J$_2$=6.27 Hz, 1H), 7.21 (s, 1H), 5.99 (s, 1H), 4.49 (t, J=8.28 Hz, 2H), 4.06 (dd, J$_1$=5.66 Hz, J$_2$=8.66 Hz, 2H), 3.10 (septet, J=6.99 Hz, 1H), 2.82 (d, J=7.53 Hz, 2H), 2.60-2.50 (m, 4H), 1.87-1.77 (m, 4H).

TRV 1529

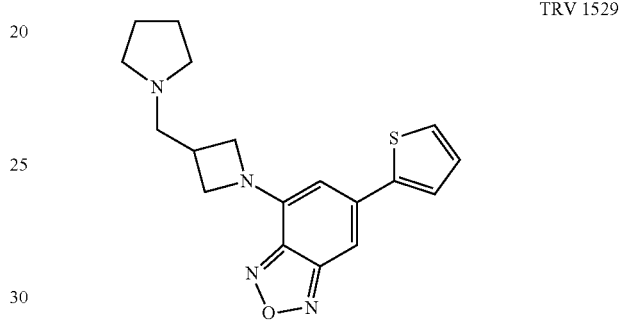

A reaction vial was charged with TRV 1472 (0.25 g, 0.74 mmol), thiophen-2-ylboronic acid (0.13 g, 1.00 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA: MeOH: hexane:EtOAc 5:1.2:75:15) to afford 0.21 g (83% yield) of TRV 1529 as a brown solid. δ=7.54 (dd, J$_1$=1.13 Hz, J$_2$=3.64 Hz, 1H), 7.38 (dd, J$_1$=1.13 Hz, J$_2$=5.15 Hz, 1H), 7.22 (d, J=1.00 Hz, 1H), 7.13 (dd, J$_1$=3.64 Hz, J$_2$=5.15 Hz, 1H), 6.10 (d, J=1.00 Hz, 1H), 4.47 (t, J=8.28 Hz, 2H), 4.03 (dd, J$_1$=5.65 Hz, J$_2$=8.66 Hz, 2H), 3.09 (septet, J=6.90 Hz, 1H), 2.82 (d, J=7.53 Hz, 2H), 2.60-2.53 (m, 4H), 1.87-1.77 (m, 4H).

TRV 1530

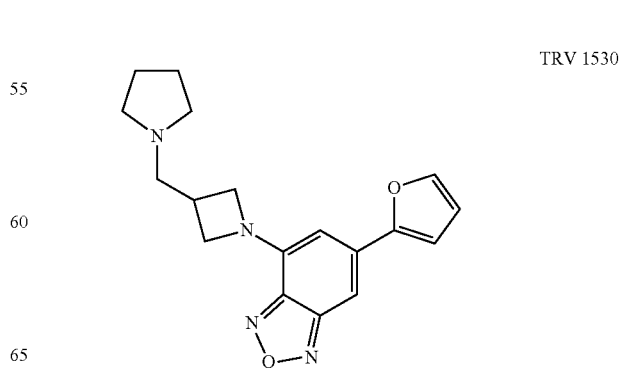

A reaction vial was charged with TRV 1472 (0.25 g, 0.74 mmol), furan-2-ylboronic acid (0.11 g, 1.00 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA:MeOH:hexane:EtOAc 5:1.2:75:15) to afford 0.18 g (75% yield) of TRV 1530 as an orange solid. $^1$H NMR (CDCl$_3$, 400 MHz) δ=7.54 (dd, J$_1$=0.75 Hz, J$_2$=1.76 Hz, 1H), 7.31 (s, 1H), 7.29 (dd, J$_1$=0.75 Hz, J$_2$=3.76 Hz, 1H), 6.53 (J$_1$=1.76 Hz, J$_2$=3.51 Hz, 1H), 6.13 (s, 1H), 4.45 (t, J=8.28 Hz, 2H), 4.02 (dd, J$_1$=5.77 Hz, J$_2$=8.53 Hz, 2H), 3.08 (septet, J=6.99 Hz, 1H), 2.81 (d, J=7.53 Hz, 2H), 2.61-2.49 (m, 4H), 1.88-1.76 (m, 4H).

TRV 1531

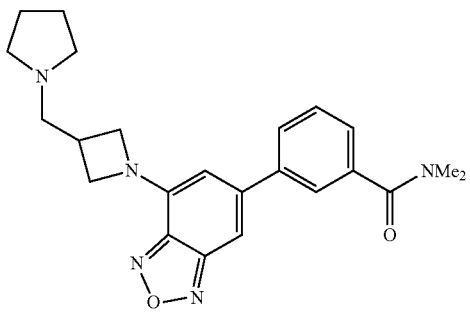

A reaction vial was charged with TRV 1472 (0.25 g, 0.74 mmol), (3-(dimethylcarbamoyl)phenyl)boronic acid (0.18 g, 0.91 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA:MeOH:hexane:EtOAc:DCM 5:4:60:20:20) to afford 0.24 g (80% yield) of TRV 1531 as a yellow solid. $^1$H NMR (CDCl$_3$, 400 MHz) δ=7.69-7.65 (m, 2H), 7.51 (dt, J$_1$=1.25 Hz, J$_2$=7.78 Hz, 1H), 7.46 (dt, J$_1$=1.25 Hz, J$_2$=7.53 Hz, 1H), 7.15 (s, 1H), 6.04 (s, 1H), 4.47 (t, J=8.28 Hz, 2H), 4.03 (dd, J$_1$=5.77 Hz, J$_2$=8.53 Hz, 2H), 3.16 (s, 3H), 3.09 (septet, J=6.78 Hz, 1H), 3.04 (s, 3H), 2.81 (d, J=7.53 Hz, 2H), 2.59-2.51 (m, 4H), 1.86-1.77 (m, 4H).

TRV 1532

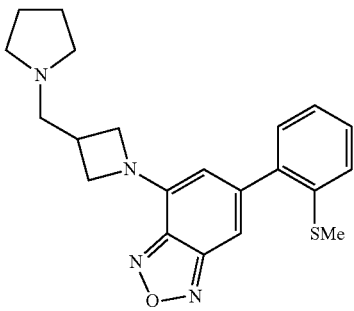

A reaction vial was charged with TRV 1472 (0.25 g, 0.74 mmol), (2-(methylthio)phenyl)boronic acid (0.11 g, 1.00 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA:MeOH:hexane:EtOAc 5:1:75:15) to afford 0.20 g (71% yield) of TRV 1532 as a yellow solid. $^1$H NMR (CDCl$_3$, 400 MHz) δ=7.39 (dt, J$_1$=2.01 Hz, J$_2$=7.66 Hz, 1H), 7.31 (d, J=7.78 Hz, 1H), 7.27 (dt, J$_1$=2.01 Hz, J$_2$=7.53 Hz, 1H), 7.23 (dt, J$_1$=1.00 Hz, J$_2$=7.03 Hz, 1H), 7.00 (s, 1H), 5.91 (s, 1H), 4.44 (t, J=8.29 Hz, 2H), 4.01 (dd, J$_1$=5.78 Hz, J$_2$=8.79 Hz, 2H), 3.06 (septet, J=6.78 Hz, 1H), 2.82 (d, J=7.53 Hz, 2H), 2.59-2.49 (m, 4H), 2.43 (s, 3H), 1.63-1.53 (m, 4H).

TRV-1533

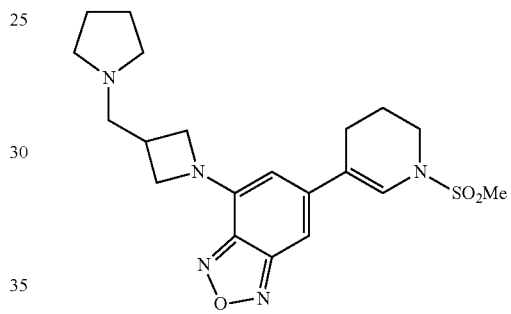

A round-bottomed flask was charged with tert-butyl 5-(((trifluoromethyl)sulfonyl)oxy)-3,4-dihydropyridine-1(2H)-carboxylate (4.02 g, 12.15 mmol), bis(pinacolato)diboron (4.63 g, 18.22 mmol), potassium acetate (3.57 g, 36.44 mmol), and PdCl$_2$(dppf) (445 mg, 0.61 mmol). After degassed, dioxane (60 mL) was added. The reaction mixture was heated to 90° C. for 3 h. After the reaction was completed, the mixture was cooled to rt. 40 mL of EtOAc was added, and the reaction mixture was washed with water for 3 times. The organic phase was dried over anhydrous sodium sulphate and then concentrated. The residue was purified by flash chromatography (1:19, EtOAc/Hexane). 2.27 g (60.5%) of tert-butyl 5-(4,4,5,5-tetramethyl-1,3,2-dioxaborolan-2-yl)-3,4-dihydropyridine-1 (2H)-carboxylate was obtained as a solid.

A round-bottomed flask was charged with TRV-1472 (2.06 g, 6.12 mmol), tert-butyl 5-(4,4,5,5-tetramethyl-1,3,2-dioxaborolan-2-yl)-3,4-dihydropyridine-1 (2H)-carboxylate (2.27 g, 7.35 mmol), and Pd(PPh$_3$)$_4$ (354 mg, 0.306 mmol). After degassed, dioxane (16 mL) and aqueous sodium carbonate (8 mL, 2M) were added. The reaction mixture was heated to 90° C. for 3 h. After completion checked by TLC, 20 mL of water was added, and the reaction mixture was extracted with ethyl acetate. The organic phase was dried over anhydrous sodium sulphate and then concentrated. The residue was purified by flash chromatography to afford tert-butyl 5-(7-(3-(pyrrolidin-1-ylmethyl)azetidin-1-yl)benzo[c][1,2,5]oxadiazol-5-yl)-3,4-dihydropyridine-1 (2H)-carboxylate (2.65 g, 98.4%). $^1$H NMR (400 MHz, CDCl$_3$): 1.55 (s, 9H), 1.79-1.83 (m, 4H), 1.96-2.02 (m, 2H), 2.47 (t, J=5.9, 2H), 2.54 (s, br, 4H), 2.78-2.82 (m, 2H), 3.02-3.09 (m, 1H), 3.63 (s, br, 2H), 3.94-3.97 (m, 2H), 4.40 (t, J=8.2, 2H), 5.90 (s, 0.44H), 6.03 (s, 0.6H), 6.86 (s, 1H), 7.43 (s, 0.4H), 7.66 (s, 0.6H).

tert-Butyl 5-(7-(3-(pyrrolidin-1-ylmethyl)azetidin-1-yl) benzo[c][1,2,5]oxadiazol-5-yl)-3,4-dihydropyridine-1(2H)-carboxylate (440 g, 1.0 mmol) was stirred in the solution of DCM/CF$_3$COOH (2:1, 6 ml) for 6 hour at 0° C. After completion checked by TLC, the mixture was carefully neutralized with saturated K$_2$CO$_3$ solution until no more gas gave out at 0° C. 15 ml of NaOH (2N) was added to the solution, and extracted with DCM (3×10 ml). The organic layer was dried over anhydrous sodium sulphate and then concentrated. The crude 4-(3-(pyrrolidin-1-ylmethyl)azetidin-1-yl)-6-(1,4,5,6-tetrahydropyridin-3-yl)benzo[c][1,2,5] oxadiazole was used for the next step without further purification.

TEA (1.39 ml, 10 mmol) and acetic anhydride (0.471 ml, 5 mmol) were added dropwise to a solution of 4-(3-(pyrrolidin-1-ylmethyl)azetidin-1-yl)-6-(1,4,5,6-tetrahydropyridin-3-yl)benzo[c][1,2,5]oxadiazole (crude, 1 mmol) in DCM (10 ml) at rt respectively. The mixture was stirred for 3 hours. After completion checked by TLC, the reaction was quenched by EtOAc/H$_2$O (1:1, 50 ml). The mixture was washed with 2 N NaOH and brine. The organic layer was dried and concentrated. The residue was purified via gradient elution (5:100:500, TEA/EtOAc/Hexane to 3:5:100:500 MeOH/TEA/EtOAc/Hexane) to afford TRV-1533 (65 mg, 17%) as a yellow solid. $^1$H NMR (400 MHz, CDCl$_3$): 1.79-1.83 (m, 4H), 1.96-2.02 (m, 1.1H), 2.04-2.10 (m, 0.9H), 2.26 (s, 1.35H), 2.31 (s, 1.65H), 2.50-2.55 (m, m, 6H), 2.79-2.82 (m, 2H), 3.02-3.11 (m, 1H), 3.66-3.69 (m, 0.9H), 3.76-3.78 (m, 1.1H), 3.96-4.01 (m, 2H), 4.42 (t, J=8.2, 2H), 5.84 (s, 0.55H), 6.02 (s, 0.45H), 6.90-6.91 (m, 1H), 7.15 (s, 0.55H), 7.93 (s, 0.45H).

TRV-1534

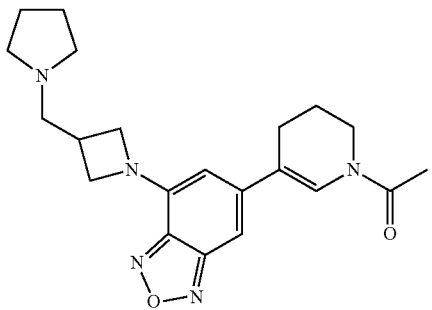

TEA (0.7 ml, 5 mmol) and Methanesulfonyl chloride (0.39 ml, 5 mmol) were added dropwise to a solution of 4-(3-(pyrrolidin-1-ylmethyl)azetidin-1-yl)-6-(1,4,5,6-tetrahydropyridin-3-yl)benzo[c][1,2,5]oxadiazole (crude, 1 mmol) in DCM (10 ml) at rt respectively. The mixture was stirred for 3 hours. The reaction was quenched by EtOAc/H$_2$O (1:1, 50 ml). The mixture was washed with 2 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford TRV-1534 (105 mg, 25%) as a red solid. $^1$H NMR (400 MHz, CDCl$_3$): 1.80-1.83 (m, 4H), 2.06-2.12 (m, 2H), 2.50-2.55 (m, 6H), 2.79 (d, J=7.5, 2H), 2.97 (s, 3H), 3.03-3.09 (m, 1H), 3.64 (t, J=5.5, 2H), 3.96-4.00 (m, 2H), 4.42 (t, J=8.2, 2H), 5.87 (s, 1H), 6.87 (s, 1H), 7.19 (s, 1H).

TRV 1535

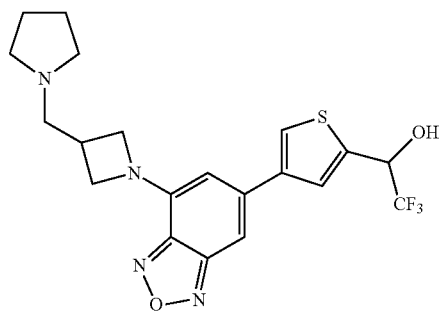

TRV-1472 (0.4 g, 1.15 mmol) and 2-formylthiophene-4-boronic acid (0.188 g, 1.21 mmol) were added to a tube and the tube was evacuated and purged with argon (3×). DME (2.8 mL) and Na$_2$CO$_3$ (1.7 mL, 3.4 mmol, 2 N aqueous solution) were added followed by Pd (PPh$_3$)$_4$ (0.069 g, 0.06 mmol). The tube was sealed and then heated to 85° C. overnight. The reaction was cooled and then diluted with EtOAc and water. The organic layer was washed with water (3×), brine, dried (MgSO$_4$), filtered and concentrated to give the crude aldehyde. Aldehyde was purified using column chromatography and was used in next step directly. Aldehyde 4-(7-(3-(pyrrolidin-1-ylmethyl)azetidin-1-yl)benzo[c][1,2,5]oxadiazol-5-yl)thiophene-2-carbaldehyde was dissolved in THF (10 mL) and cooled in an ice bath. CF$_3$TMS (0.19 mL) was added and then the catalyst TBAF (0.1 mL, 1.0 M solution) was added. After 30 minutes the reaction was removed from the ice bath and allowed to warm to room temperature. Once complete by TLC, recooled to 0° C. and 2 N HCl (aq) was added, stirred for 40 minutes and then basified with 2N NaOH. This mixture was extracted with EtOAc. The combined extracts were washed with water (2×), brine, filtered and concentrated. The crude material was purified via chromatography (hexane:ethylacetate:triethylamine:methanol, 5:1:0.3:0.1) to afford 0.210 mg (58%) of TRV 1535 as yellow solid. $^1$H NMR (500 MHz, CDCl3) δ 7.59(d, J=3.6 Hz, 1H), 7.49(s, 1H), 7.13(d, J=3.6 Hz, 1H), 5.97(s, 1H), 5.32-5.28 (m, 1H), 4.44-4.39 (m, 2H), 4.02-3.98 (m, 2H), 3.09-3.03(m, 1H), 2.81-2.83 (d, J=8 Hz, 2H), 2.58 (m, 4H), 1.85(m,4H).

TRV 1536

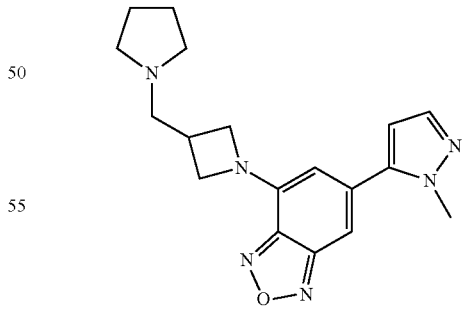

A reaction vial was charged with TRV 1472 (0.67 g, 2.00 mmol), 1-methyl-5-(4,4,5,5-tetramethyl-1,3,2-dioxaborolan-2-yl)-1H-pyrazole (0.50 g, 2.40 mmol), and Pd(PPh$_3$)$_4$ (0.12 g, 0.10 mmol). The vial was degassed and refilled with nitrogen. To the vial was added dioxane (6 mL) and aq. sodium carbonate (3 mL, 2.0 M, 6.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:hexane:EtOAc 5:1:75:15 to TEA:MeOH: hexane:EtOAc 5:5:75:15) to afford 0.67 g (99% yield) of TRV 1536 as a red solid. $^1$H NMR (CDCl$_3$, 400 MHz) δ=7.55 (d, J=2.00 Hz, 2H), 7.01 (d, J=0.76 Hz, 1H), 6.40 (d, J=2.01 Hz, 2H), 5.82 (s, 1H), 4.46 (t, J=8.29 Hz, 2H), 4.03 (dd, J$_1$=5.40 Hz, J$_2$=8.67 Hz, 2H), 3.97 (s, 3H), 3.09 (septet, J=7.09 Hz, 1H), 2.82 (d, J=7.53 Hz, 2H), 2.60-2.49 (m, 4H), 1.87-1.76 (m, 4H).

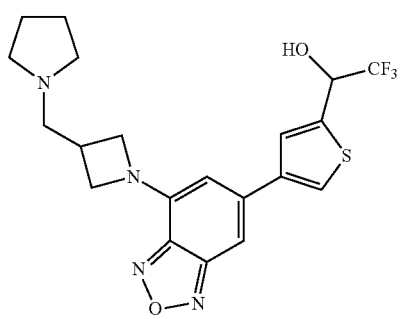

TRV 1537

A solution of 6-bromo-4-(3-(pyrrolidin-1-ylmethyl)azetidin-1-yl)benzo[c][1,2,5]oxadiazole (0.38 g, 1.13 mmol) in 6 mL of anhydrous THF was cooled to −78° C. under nitrogen. To the solution was added n-butyllithium (0.55 mL, 2.5 M, 1.38 mmol) dropwise. After complete addition, the reaction mixture was stirred for 30 minutes at the same temperature, and then tributyltin chloride (0.46 mL, 1.70 mmol) was added. The reaction was stirred for 1 h at −78° C. before quenched with methanol. The mixture was diluted with brine, extracted with ethyl acetate. The ethyl acetate phase was dried over anhydrous sodium sulfate and concentrated. The residue was purified by flash chromatography using gradient elution (TEA:hexane:EtOAc 2:100:0 to TEA:hexane:EtOAc 2:95:5) to afford 0.48 g (77% yield) of 4-(3-(Pyrrolidin-1-ylmethyl)azetidin-1-yl)-6-(tri-n-butylstannyl)benzo[c][1,2,5]oxadiazole as deep orange oil. $^1$H NMR (CDCl$_3$, 400 MHz) δ=7.14 (s, 1H), 5.89 (s, 1H), 4.40 (t, J=8.03 Hz, 2H), 3.96 (dd, J$_1$=5.77 Hz, J$_2$=8.28 Hz, 2H), 3.06 (septet, J=7.53 Hz, 1H), 2.81 (d, J=7.53 Hz, 2H), 2.61-2.49 (m, 4H), 1.88-1.76 (m, 4H), 1.61-1.51 (m, 6H), 1.35 (sextet, J=7.28 Hz, 6H), 1.09 (t, J=8.09 Hz, 6H), 0.91 (t, J=7.28 Hz, 9H).

A reaction vial was charged with 4-(3-(Pyrrolidin-1-ylmethyl)azetidin-1-yl)-6-(tri-n-butylstannyl)benzo[c][1,2,5]oxadiazole (0.33 g, 0.60 mmol), 1-(4-bromothiophen-2-yl)-2,2,2-trifluoroethan-1-ol (0.16 g, 0.60 mmol), Pd(PPh$_3$)$_4$ (0.035 g, 0.030 mmol), CuI (0.011 g, 0.06 mmol), and CsF (0.18 g, 1.20 mmol). The vial was degassed and refilled with nitrogen. To the vial was added DMF (4 mL). The reaction was re-degassed, refilled with nitrogen, sealed, and then heated to 50° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:hexane:EtOAc 5:1:75:15 to TEA: MeOH: hexane: EtOAc 5:5:75:15) to afford 0.080 g (31% yield) of TRV 1537 as a red solid. $^1$H NMR (CDCl$_3$, 400 MHz) δ=8.23 (d, J=1.51 Hz, 1H), 7.78 (s, 1H), 7.38 (s, 1H), 7.34 (d, J=5.52 Hz, 1H), 6.35 (s, 1H), 5.50 (pentet, J=6.52 Hz, 1H), 4.37 (t, J=8.03 Hz, 2H), 3.96 (dd, J$_1$=6.02 Hz, J$_2$=8.28 Hz, 2H), 2.99 (septet, J=7.53 Hz, 1H), 2.71 (d, J=7.53 Hz, 2H), 2.48-2.41 (m, 4H), 1.73-1.63 (m, 4H).

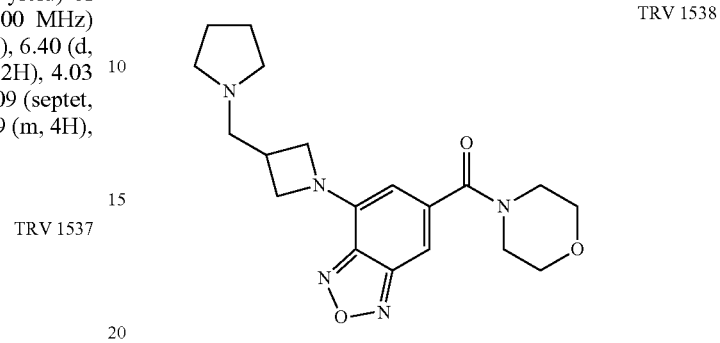

TRV 1538

TRV-1472 (2.0095 g, 5.96 mmol) was dissolved in THF (60 mL) and cooled to −78° C. nBuLi (4.5 mL, 1.6 M solution in hexane) was added dropwise over 10 minutes and stirred for an additional 10 minutes. CO$_2$ gas was bubbled through the reaction mixture via canula while gradually warming to room temperature. The reaction was then concentrated to give 2.12 grams of a dark solid. This material was then dissolved in NMP (70 mL) and then 20 mL aliquots of this mixture were used in the HATU coupling step. The lithium carboxylate 1 in NMP (20 mL, 0.6068 g of 1) was cooled to 0° C. and DIPEA (1.0 mL, 5.91 mmol) was added; followed by HATU (0.8239 g, 2.16 mmol). This mixture was stirred for 5 minutes before adding morpholine (0.52 mL, 5.91 mmol) and the reaction was stirred until complete by TLC. The reaction was diluted with brine and extracted with DCM (3×). The combined layers were dried with MgSO$_4$, filtered and concentrated. The crude residue was purified via chromatography, the first attempt was with 10% MeOH/DCM which failed to give >95% chemical purity. The purification was repeated with EtOAc:Hexane:TEA (6:4: 0.5) to afford 0.0803 g (11% yield) of TRV-1538 as a waxy solid. $^1$H NMR (500 MHz, DMSO) δ=7.06 (s, 1H), 5.88 (s, 1H), 4.34 (t, J=5 Hz, 2H), 3.92 (t, J=5 Hz, 2H), 3.65 (br s, 2H), 3.60 (br s, 2H), 3.54 (br s, 2H), 3.35 (br s, 2H), 3.03-2.95 (m, 1H), 2.70 (d, J=10 Hz, 2H), 2.44 (br s, 4H), 1.67 (br s, 4H).

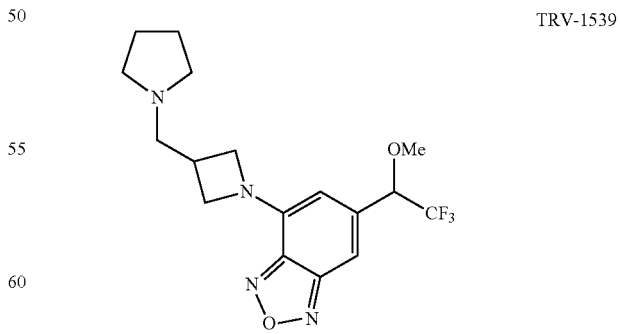

TRV-1539

TRV-1520 (0.3249 g, 0.91 mmol) was dissolved in NMP (10 mL) and was cooled in an ice bath. NaH (0.0401 g, 1.00 mmol, 60% in mineral oil) was added portion-wise and stirred for 20 minutes, after which time, iodomethane (0.056 mL, 0.91 mmol) was added to the reaction and the mixture was stirred overnight. The reaction was recooled to 0° C. and quenched with saturated ammonium chloride. The mixture was extracted with DCM (3×) and the combined organic layers were dried with $MgSO_4$, filtered and concentrated. The crude residue was purified via 8% MeOH/DCM and then again with EtOAC/Hexane/TEA (6:4:0.5) to afford 0.0602 g (18% yield) of TRV-1539. $^1H$ NMR (500 MHz, DMSO) δ=7.20 (s, 1H), 5.93 (s, 1H), 5.10 (q, J=7 Hz, 1H), 4.36-4.32 (m, 2H), 3.93-3.89 (m, 2H), 3.39 (s, 3H), 3.01-2.96 (m, 1H), 2.71 (d, J=5 Hz, 2H), 2.44 (br s, 4H), 1.70-1.64 (m, 4H).

TRV-1540

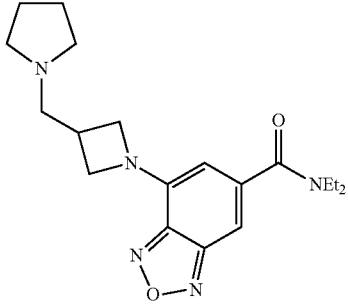

TRV-1472 (2.0095 g, 5.96 mmol) was dissolved in THF (60 mL) and cooled to −78° C. nBuLi (4.5 mL, 1.6 M solution in hexane) was added dropwise over 10 minutes and stirred for an additional 10 minutes. $CO_2$ gas was bubbled through the reaction mixture via canula while gradually warming to room temperature. The reaction was then concentrated to give 2.12 grams of a dark solid. This material was then dissolved in NMP (70 mL) and then 20 mL aliquots of this mixture were used in the HATU coupling step. The lithium carboxylate 1 in NMP (20 mL, 0.6068 g of 1) was cooled to 0° C. and DIPEA (1.0 mL, 5.91 mmol) was added; followed by HATU (0.8239 g, 2.16 mmol). This mixture was stirred for 5 minutes before adding diethylamine (1.0 mL, 5.91 mmol) and the reaction was stirred until complete by TLC. The reaction was diluted with brine and extracted with DCM (3×). The combined layers were dried with $MgSO_4$, filtered and concentrated. The crude residue was purified via chromatography, the first attempt was with EtOAc:Hexane:TEA (6:4:0.5) which failed to give >95% chemical purity. The purification was repeated with 10% MeOH/DCM to afford 0.0823 g (12% yield) of TRV-1540 as a waxy solid. $^1H$ NMR (500 MHz, DMSO) δ=6.99 (s, 1H), 5.81 (s, 1H), 4.35 (t, J=10 Hz, 2H), 3.93 (t, J=10 Hz, 2H), 3.42 (d, J=10 Hz, 2H), 3.21 (d, J=10 Hz, 2H), 3.00-2.97 (m, 1H), 2.72 (br s, 2H), 2.46 (br s, 4H), 1.68 (br s, 4H), 1.19-1.13 (m, 3H), 1.10-1.03 (m, 3H).

TRV-1541

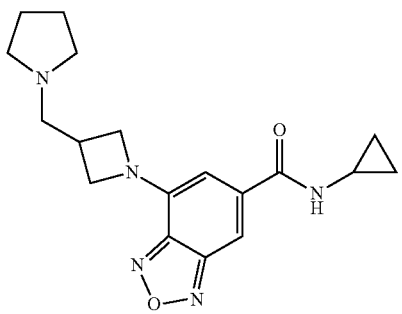

TRV-1472 (2.0095 g, 5.96 mmol) was dissolved in THF (60 mL) and cooled to −78° C. nBuLi (4.5 mL, 1.6 M solution in hexane) was added dropwise over 10 minutes and stirred for an additional 10 minutes. $CO_2$ gas was bubbled through the reaction mixture via canula while gradually warming to room temperature. The reaction was then concentrated to give 2.12 grams of a dark solid. This material was then dissolved in NMP (70 mL) and then 20 mL aliquots of this mixture were used in the HATU coupling step. The lithium carboxylate 1 in NMP (20 mL, 0.6068 g of 1) was cooled to 0° C. and DIPEA (1.0 mL, 5.91 mmol) was added; followed by HATU (0.8239 g, 2.16 mmol). This mixture was stirred for 5 minutes before adding cyclopropylamine (0.41 mL, 5.91 mmol) and the reaction was stirred until complete by TLC. The reaction was diluted with brine and extracted with DCM (3×). The combined layers were dried with $MgSO_4$, filtered and concentrated. The crude residue was purified via chromatography, the first attempt was with EtOAc:Hexane:TEA (6:4:0.5) which failed to give >95% chemical purity. The purification was repeated with 10% MeOH/DCM to afford 0.0459 g (6.8% yield) of TRV-1541 as a waxy solid. $^1H$ NMR (500 MHz, DMSO) δ=8.57 (d, J=5 Hz, 1H), 7.47 (s, 1H), 6.29 (s, 1H), 4.35 (t, J=10 Hz, 2H), 3.93 (t, J=10 Hz, 2H), 3.01-2.96 (m, 1H), 2.86-2.81 (m, 1H), 2.71 (d, J=10 Hz, 2H), 2.45 (br s, 4H), 1.68 (br s, 4H), 0.72-0.69 (m, 2H), 0.59-0.56 (m, 2H).

TRV 1542

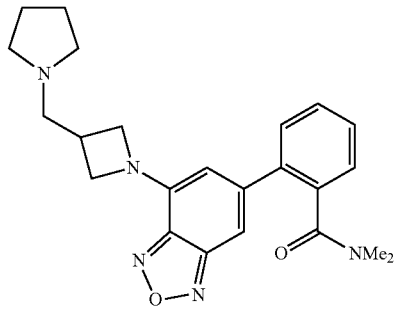

A reaction vial was charged with TRV 1472 (0.25 g, 0.74 mmol), (2-(dimethylcarbamoyl)phenyl)boronic acid (0.18 g, 0.91 mmol), and $Pd(PPh_3)_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA:MeOH:hexane:EtOAc 5:3:75:15) to afford 0.23 g (77% yield) of TRV 1542 as red oil. $^1H$ NMR ($CDCl_3$, 400 MHz) δ=7.52-7.38 (m, 4H), 7.02 (s, 1H), 5.98 (s, 1H), 4.42 (t, J=8.28 Hz, 2H), 3.99 (dd, $J_1$=5.65 Hz, $J_2$=8.41 Hz, 2H), 3.06 (septet, J=7.03 Hz, 1H), 2.94 (s, 3H), 2.79 (d, J=7.53 Hz, 2H), 2.65 (s, 3H), 2.58-2.46 (m, 4H), 1.86-1.72 (m, 4H).

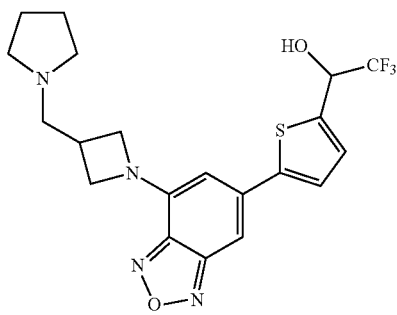

TRV 1543

TRV-1472 (0.4 g, 1.15 mmol) and 5-formylthiophene-2-boronic acid (0.188 g, 1.21 mmol) were added to a tube and the tube was evacuated and purged with argon (3×). DME (2.8 mL) and Na₂CO₃ (1.7 mL, 3.4 mmol, 2 N aqueous solution) were added followed by Pd (PPh₃)₄ (0.069 g, 0.06 mmol). The tube was sealed and then heated to 80° C. overnight. The reaction was cooled and then diluted with EtOAc and water. The organic layer was washed with water (3×), brine, dried (MgSO₄), filtered and concentrated to give the crude aldehyde. Aldehyde was purified using column chromatography and was used in next step directly. Aldehyde 2 was dissolved in THF (5 mL) and cooled in an ice bath. CF₃TMS (0.19 mL) was added and then the catalyst TBAF (0.1 mL, 1.0 M solution) was added. After 30 minutes the reaction was removed from the ice bath and allowed to warm to room temperature. Once complete by TLC, recooled to 0° C. and 2 N HCl (aq) was added, stirred for 40 minutes and then basified with 2N NaOH. This mixture was extracted with EtOAc. The combined extracts were washed with water (2×), brine, filtered and concentrated. The crude material was purified via chromatography (hexane:ethyl acetate:triethylamine:methanol, 5:1:0.3:0.1) to afford 40 mg (28%) of TRV 1543 as yellow solid. ¹H NMR (400 MHz, CDCl3) δ 7.33 (d, J=3.6 Hz, 1H), 7.20-7.20 (m, 2H), 5.99 (s, 1H), 5.31-5.25 (m, 1H), 4.45-4.40 (m, 2H), 4.02-3.99 (m, 2H), 3.09-3.03 (m, 1H), 2.83-2.81 (d, J=8 Hz, 2H), 2.57 (m, 4H), 1.83 (m, 4H).

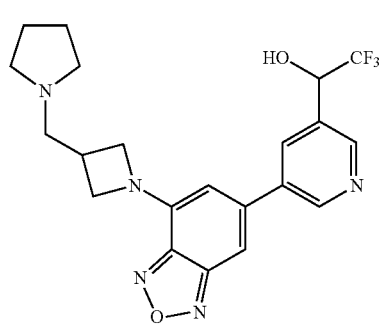

TRV 1544

4-(3-(pyrrolidin-1-ylmethyl)azetidin-1-yl)-6-(tributyl-stannyl)benzo[c][1,2,5]oxadiazole (0.4 g, 0.73 mmol), 1-(5-bromopyridin-3-yl)-2,2,2-trifluoroethan-1-ol (0.230 g, 0.9 mmol), CsF (0.45 g, 2.19 mmol), CuI (14 mg, 0.073 mmol), Pd(PPh3)4, (0.042 g, 0.0365 mmol) was charged in glass tube and sealed, it was then degassed and flushed with N₂. DMF (10 ml) was added and reaction mixture was heated at 45° C. overnight. After completion of reaction by TLC, the reaction was cooled and then diluted with EtOAc and water. The organic layer was washed with water (3×), brine, dried (MgSO₄), filtered and concentrated to give the crude product which was purified using column chromatography to give TRV-1544 (0.120 g, 42%). ¹H NMR (400 MHz, DMSO): δ 9.03(d, J=3.6 Hz, 1H), 8.75(s, 1H), 8.26(s, 1H), 7.41(s, 1H), 7.19(d, J=4.0 Hz, 1H), 6.26(s, 1H), 5.37-5.45(m,1H), 4.40 (m,2H), 3.99(m,2H), 2.97-3.04(m,1H), 2.72(d,J=8.0Hz, 2H), 2.45(s, 4H), 1.68(s,4H).

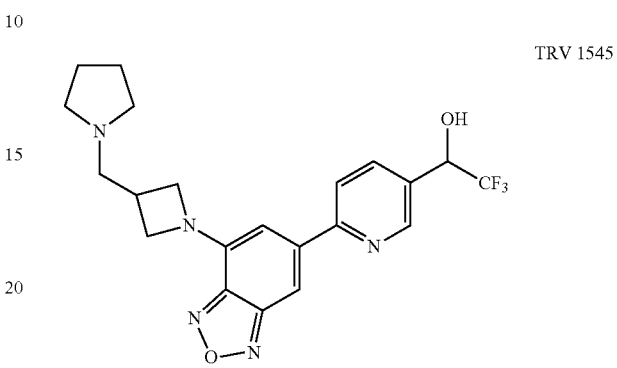

TRV 1545

4-(3-(pyrrolidin-1-ylmethyl)azetidin-1-yl)-6-(tributyl-stannyl)benzo[c][1,2,5]oxadiazole (0.4 g, 0.73 mmol), 1-(6-bromopyridin-3-yl)-2,2,2-trifluoroethan-1-ol (0.230 g, 0.9 mmol), CsF (0.45 g, 2.19 mmol), CuI (14 mg, 0.073 mmol), Pd(PPh3)4, (0.042 g, 0.0365 mmol) was charged in glass tube and sealed, it was then degassed and flushed with N2. DMF (10 ml) was added and reaction mixture was heated at 45° C. overnight. After completion of reaction by TLC, the reaction was cooled and then diluted with EtOAc and water. The organic layer was washed with water (3×), brine, dried (MgSO₄), filtered and concentrated to give the crude product which was purified using column chromatography to give TRV-1545 (0.108 g, 36%). ¹H NMR (400 MHz, DMSO): δ 8.80(s, 1H), 8.22(d, J=8.0 Hz, 1H), 8.03(d, J=8.0 Hz, 1H), 7.80(s, 1H), 7.14(s, 1H), 6.77(s, 1H), 5.40(m, 1H), 4.39(m, 2H), 3.96(m,2H), 3.0(m, 1H), 2.72(d, J=4.0Hz, 2H), 2.45(s, 4H), 1.68(s,4H).

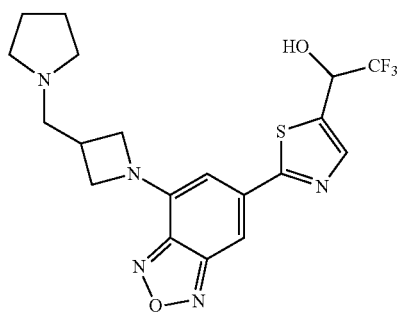

TRV 1546

A reaction vial was charged with 4-(3-(Pyrrolidin-1-ylmethyl)azetidin-1-yl)-6-(tri-n-butylstannyl)benzo[c][1,2,5]oxadiazole (0.33 g, 0.60 mmol), 1-(4-bromothiophen-2-yl)-2,2,2-trifluoroethan-1-ol (0.16 g, 0.60 mmol), Pd(PPh₃)₄ (0.035 g, 0.030 mmol), CuI (0.011 g, 0.06 mmol), and CsF (0.18 g, 1.20 mmol). The vial was degassed and refilled with nitrogen. To the vial was added DMF (4 mL). The reaction was re-degassed, refilled with nitrogen, sealed, and then heated to 50° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:hexane:EtOAc 5:1:75:15 to TEA:MeOH:hexane:EtOAc 5:5:75:15) to afford 0.14 g (42% yield) of 2-(7-(3-(pyrrolidin-1-ylmethyl)azetidin-1-yl)benzo[c][1,2,5]oxadiazol-5-yl)thiazole-5-carbaldehyde as a yellow solid.

2-(7-(Pyrrolidin-1-ylmethyl)azetidin-1-yl)benzo[c][1,2,5]oxadiazol-5-yl)thiazole-5-carbaldehyde (0.14 g, 0.38 mmol) was dissolved in THF (5 mL) and cooled to 0° C. $CF_3TMS$ (0.085 mL, 0.57 mmol) was added followed by TBAF (0.050 mL, 1.0 M solution in THF, 0.050 mmol). The reaction was then stirred for 60 minutes before re-cooling to 0° C. and 4N HCl (aq) was added and stirred for 60 minutes, and then basified with 3N aq. NaOH and extracted with EtOAc. The organic layer was dried over anhydrous $Na_2SO_4$, filtered and concentrated. The residue was purified by flash chromatography using gradient elution (TEA:MeOH:hexane:EtOAc 5:1:75:15 to TEA:MeOH:hexane:EtOAc 5:5:75:15) to afford 0.090 g (54% yield) of TRV 1546 as a red solid. $^1$H NMR (CDCl$_3$, 400 MHz) δ=8.54 (s, 1H), 7.48 (s, 1H), 6.42 (s, 1H), 5.20 (q, J=6.53 Hz, 1H), 4.49 (t, J=8.28 Hz, 2H), 4.30 (broad, 1H), 4.11-4.03 (m, 2H), 3.10 (septet, J=7.19 Hz, 1H), 2.82 (d, J=7.28 Hz, 2H), 2.60-2.50 (m, 4H), 1.87-1.77 (m, 4H).

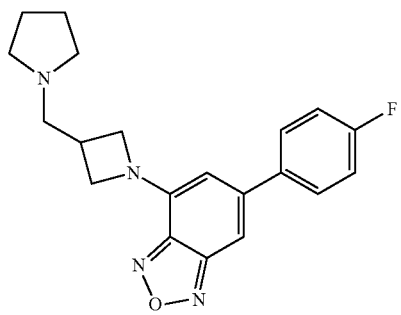

TRV 1547

A reaction vial was charged with TRV 1472 (0.25 g, 0.74 mmol), (4-fluorophenyl)boronic acid (0.14 g, 1.00 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA:MeOH:hexane:EtOAc 5:1:75:15) to afford 0.20 g (77% yield) of TRV 1547 as red oil. $^1$H NMR (CDCl$_3$, 400 MHz) δ=7.63-7.56 (m, 2H), 7.20-7.13 (m, 2H), 7.10 (s, 1H), 6.00 (s, 1H), 4.47 (t, J=8.28 Hz, 2H), 4.03 (dd, J$_1$=5.77 Hz, J$_2$=8.53 Hz, 2H), 3.09 (septet, J=6.65 Hz, 1H), 2.82 (d, J=7.53 Hz, 2H), 2.60-2.50 (m, 4H), 1.86-1.77 (m, 4H).

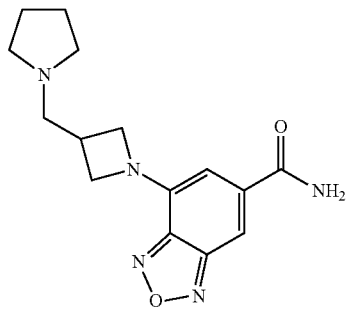

TRV 1548

Methyl 7-(3-(pyrrolidin-1-ylmethyl)azetidin-1-yl)benzo[c][1,2,5]oxadiazole-5-carboxylate (0.2146 g, 0.68 mmol) was dissolved in methanol (2 mL) and 7N NH$_3$ in methanol (12 mL) was added to the tube. The tube was sealed and heated to 50° C. for 48 hours behind a blast shield. The mixture was then concentrated to afford the crude amide. The crude amide was purified via chromatography (10% MeOH/DCM with NH$_4$OH layer) to produce 0.1439 g (70% yield) of TRV-1548 $^1$H NMR (500 MHz, DMSO) δ=8.10 (s, 1H), 7.58 (s, 1H), 7.57 (s, 1H), 6.36 (s, 1H), 4.35 (t, J=10 Hz, 2H), 3.92 (q, J=5 Hz, 2H), 3.02-2.94 (m, 1H), 2.70 (d, J=10 Hz, 2H), 2.44 (br s, 4H), 1.68-1.65 (m, 4H).

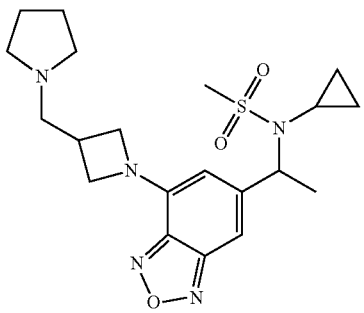

TRV 1549

TRV-1551 (0.1830 g, 0.54 mmol) was dissolved in DCM (10 mL) and cooled to 0° C. TEA (0.75 mL, 5.4 mmol) was added followed by the dropwise addition of MeSO$_2$Cl (0.21 mL, 2.7 mmol). The reaction was allowed to warm to room temperature and stirred until complete by TLC. The reaction was then concentrated and the residue was made basic by the addition of 2N NaOH(aq). This basic residue was then extracted with DCM (3×). The combined organic layers were washed with water, brine, dried (MgSO$_4$), filtered and concentrated to afford the crude amide. The material was purified via chromatography EtOAC:hexane:TEA (9:1:0.5) to afford 0.1417 g (63% yield) of TRV-1549. $^1$H NMR (500 MHz, CDCl3) δ=6.98 (s, 1H), 5.95 (s, 1H), 5.17 (q, J=10 Hz, 1H), 4.39 (q, J=10 Hz, 2H), 3.99-3.95 (m, 2H), 3.05 (br s, 1H), 2.97 (s, 3H), 2.81 (br s, 2H), 2.54 (br s, 4H), 2.30-2.26 (m, 1H), 1.81 (br s, 4H), 1.73 (d, J=10 Hz, 3H), 1.02-0.96 (m, 1H), 0.81-0.75 (m, 1H), 0.57-0.52 (m, 2H).

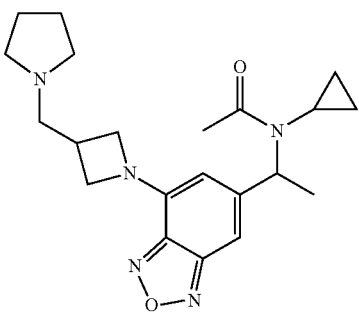

TRV-1550

TRV-1551 (0.2133 g, 0.62 mmol) was dissolved in DCM (10 mL) and cooled to 0° C. TEA (0.86 mL, 6.2 mmol) was added followed by the dropwise addition of AcCl (0.22 mL, 3.1 mmol). The reaction was allowed to warm to room temperature and stirred until complete by TLC. The reaction was then concentrated and the residue was made basic by the addition of 2N NaOH(aq). This basic residue was then extracted with DCM (3×). The combined organic layers were washed with water, brine, dried ($MgSO_4$), filtered and concentrated to afford the crude amide. The material was purified via chromatography EtOAC:hexane:TEA (9:1:0.5) to afford 0.1858 g (78% yield) of TRV-1550. $^1$H NMR (500 MHz, CDCl3) δ=6.87 (s, 1H), 5.70 (s, 1H), 5.68-5.67 (m, 1H), 4.37 (t, J=10 Hz, 1H), 4.32 (t, J=10 Hz, 1H), 3.95-3.89 (m, 2H), 3.05-2.97 (m, 1H), 2.78-2.73 (m, 2H), 2.56-2.52 (m, 5H), 2031 (s, 3H), 1.79 (s, 4H), 1.67 (d, J=10 Hz, 3H), 0.82-0.75 (m, 1H), 0.69-0.60 (m, 3H).

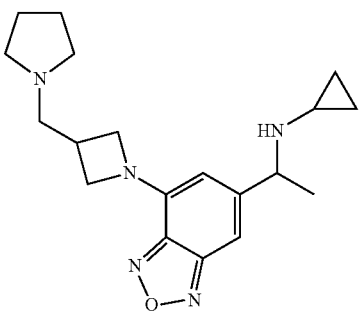

TRV-1551

TRV-1472 (1.7789 g, 5.28 mmol) was dissolved in toluene (25 mL) in a tube and Tributyl(1-ethoxyvinyl)tin (2.4789 g, 6.86 mmol) were added. The solution was degassed for 10 minutes by bubbling argon through the solution. $Pd(PPh_3)_4$ (0.6125 g, 0.53 mmol) was then added, the tube was sealed and the mixture was heated at 110° C. for 16 hours. An aliquot for $^1$H NMR indicated the reaction had reached 100% conversion. The material was filtered through Celite and then concentrated. The residue was dissolved in DCM and washed with aqueous KF solution, resulting in a precipitate. This material was removed by filtration. The organic layer was then washed with water, brine, dried ($MgSO_4$), filtered and concentrated. The crude material was partially dissolved in THF (80 mL) and EtOH (6 mL) was added to achieve complete solution. The solution was then cooled to 0° C. and 2N HCl(aq) (11 mL) was added dropwise. Stirred at 0° C. for 5 minutes before removing the ice bath. Stirred until complete by TLC (60 minutes) and then concentrated to remove the THF. The residue was cooled to 0° C. and then made basic with 2N NaOH (aq). This basic mixture was extracted with DCM (3×) and the combined organics were washed with water, brine, dried ($MgSO_4$), filtered and concentrated to afford the crude ketone 8. This ketone was then dissolved in methanol (50 mL) and cyclopropyl amine (0.76 mL, 11 mmol) and $Ti(OiPr)_4$ (2.1 mL, 6.9 mmol) were added producing a brown precipitate. This mixture was then cooled in an ice bath and $NaBH_4$ (0.2989 g, 7.9 mmol) was added portionwise and then stirred until complete by TLC. The reaction was then quenched with the addition of $NH_4Cl$ and then diluted with EtOAc. The layers were separated and the aqueous layer was back-extracted with EtOAc. The combined organic layers were washed with water, brine, dried ($MgSO_4$) filtered and concentrated. The crude amine was purified via chromatography (10% MeOH/DCM) to afford 0.8689 g (48% yield from TRV-1472) of TRV-1551. $^1$H NMR (500 MHz, DMSO) δ=6.99 (s, 1H), 6.09 (s, 1H), 4.29 (t, J=10 Hz, 2H), 3.86 (t, J=10 Hz, 2H), 3.73 (s, 1H), 3.00-2.91 (m, 1H), 2.75 (s, 1H), 2.69 (d, J=10 Hz, 2H), 2.44 (s, 4H), 1.88-1.84 (m, 1H), 1.70-1.64 (m, 4H), 1.23 (d, J=5 Hz, 3H), 0.29-0.19 (m, 4H).

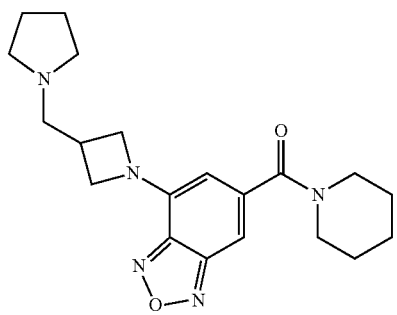

TRV-1552

TRV-1472 (0.7014 g, 2.08 mmol) was dissolved in THF (20 mL) and cooled to −78° C. nBuLi (1.8 mL, 1.6 M solution in hexane) was added dropwise over 10 minutes and stirred for an additional 10 minutes. $CO_2$ gas was bubbled through the reaction mixture via cannula while gradually warming to room temperature. The reaction was then concentrated to give 800 mg of a dark solid. This material was then dissolved in NMP (30 mL) and then 15 mL aliquots of this mixture were used in the HATU coupling step. The lithium carboxylate 1 in NMP (15 mL, 1.04 mmol of 1) was cooled to 0° C. and DIPEA (0.54 mL, 3.12 mmol) was added; followed by HATU (0.4349 g, 1.14 mmol). This mixture was stirred for 5 minutes before adding piperidine (0.31 mL, 3.13 mmol) and the reaction was stirred until complete by TLC. The reaction was diluted with brine and extracted with DCM (3×). The combined layers were dried with $MgSO_4$, filtered and concentrated. The crude residue was purified via chromatography, the first attempt was with EtOAc:Hexane:TEA (6:4:0.5) which failed to give >95% chemical purity. The purification was repeated with 10% MeOH/DCM to afford 0.081 g (21% yield) of TRV-1552 as a waxy solid. $^1$H NMR (500 MHz, DMSO) δ=7.00 (s, 1H), 5.84 (s, 1H), 4.34 (t, J=10 Hz, 2H), 3.92 (t, J=10 Hz, 2H), 3.56 (br s, 2H), 3.29-3.24 (m, 2H), 2.98-2.97 (m, 1H), 2.72 (br s, 2H), 2.49 (overlapping with DMSO signal, br s, 4H), 1.68 (s, 4H), 1.61-1.59 (m, 2H), 1.56 (s, 2H), 1.46 (s, 2H).

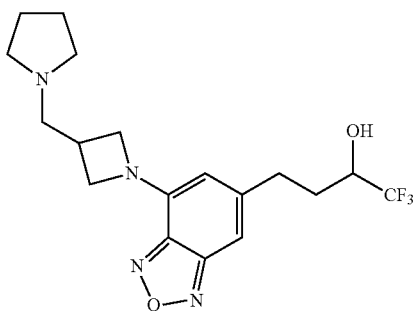

TRV-1553

A round-bottomed flask was charged with TRV-1472 (600 mg, 1.78 mmol), benzyltriethylammonium (406 mg, 1.78 mmol) and Pd(OAc)$_2$ (40 mg, 0.178 mmol). The flask was purged with nitrogen for several times, and then dry DMF (8 ml) allyl alcohol (0.181 ml, 2.67 mmol) and TEA (2.47 ml, 17.8 mmol) were added to the mixture separately. The resulting mixture was then heated to 55-60° C., and checked with TLC. After the reaction was completed, 50 ml of EtOAc was added to the mixture. The mixture was washed with brine for 3 times. The organic layer was dried and concentrated. 3-(7-(3-(pyrrolidin-1-ylmethyl)azetidin-1-yl)benzo[c][1,2,5]oxadiazol-5-yl)propanal (340 mg, 60.7%) was obtained via gradient elution (5:100:500, TEA/EtOAc/Hexane to 4:5:100:500 MeOH/TEA/EtOAc/Hexane). $^1$H NMR (400 MHz, CDCl$_3$): 1.78-1.83 (m, 4H), 2.52 (s, br, 4H), 2.78-2.84 (m, 4H), 2.91-2.94 (m, 2H), 3.01-3.07 (m, 1H), 3.95-3.97 (m, 2H), 4.38 (t, J=8.2, 2H), 5.63 (s, 1H), 6.77 (s, 1H), 9.85 (s, 1H).

The above aldehyde (250 mg, 0.79 mmol) was cool to 0° C. in dry THF solution (6 ml) under nitrogen atmosphere. TMSCF$_3$ (140 ul, 0.95 mmol) and TBAF (0.08 ml, 0.08 mmol, 1M solution) were added slowly to the mixture separately. The colour was changed from red to purple and back to red during the addition. The solution was stirred for 2 hours at 0° C. After completion checked by TLC, the mixture was added with 5 ml of water and stirred for 1 h. This mixture was added with 50 ml of EtOAc and washed with 1 N NaOH and brine. The organic layer was dried over anhydrous sodium sulphate and then concentrated. The product (TRV-1553, 220 mg, 72.6%) was obtained via gradient elution (5:100:500, TEA/EtOAc/Hexane to 4:5:100:500 MeOH/TEA/EtOAc/Hexane). $^1$H NMR (400 MHz, CDCl$_3$): 1.85 (s, br, 4H), 1.92-2.08 (m, 2H), 2.54 (s, br, 4H), 2.70-2.78 (m, 1H), 2.80 (d, J=7.6, 2H), 2.86-2.93 (m, 1H), 3.02-3.09 (m, 1H), 3.92-3.97 (m, 3H), 4.40 (t, J=8.2, 2H), 5.67 (s, 1H), 6.82 (s, 1H).

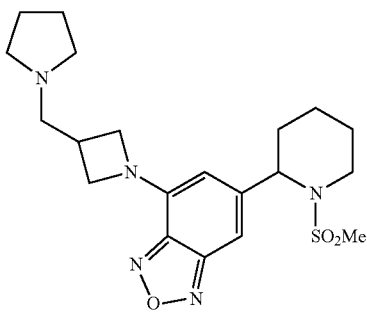

TRV-1554 n-BuLi (0.96 ml, 2.4 mmol, 4 M solution) was added dropwise to a stirred solution of TRV-1472 (674 mg, 2 mmol) in THF (10 mL) at −78° C. under nitrogen atmosphere. After 20 minutes, a THF solution (5 ml) of 1-Boc-2-piperidone (440 mg, 2.2 mmol) was added to the mixture at −78° C., and the black solution was stirred for 1 hour and the quench with MeOH. After addition of EtOAc (50 ml), the mixture was washed with 1 N NaOH and brine. The organic layer was dried and concentrated. tert-butyl (5-oxo-5-(7-(3-(pyrrolidin-1-ylmethyl)azetidin-1-yl)benzo[c][1,2,5]oxadiazol-5-yl)pentyl) carbamate (360 mg, 39.3%) was obtained via gradient elution (5:100:500, TEA/EtOAc/Hexane to 2:5:100:500 MeOH/TEA/EtOAc/Hexane). $^1$H NMR (400 MHz, CDCl$_3$): 1.45 (s, 9H), 1.56-1.60 (m, 2H), 1.74-1.82 (m, 6H), 2.53 (s, br, 4H), 2.79 (d, J=7.6, 2H), 3.00-3.09 (m, 3H), 3.17-3.20 (m, 2H), 4.00-4.04 (m, 2H), 4.45 (t, J=8.2, 2H), 4.63 (s, br, 1H), 6.34 (s, 1H), 7.61 (s, 1H).

tert-Butyl (5-oxo-5-(7-(3-(pyrrolidin-1-ylmethyl)azetidin-1-yl)benzo[c][1,2,5]oxadiazol-5-yl)pentyl) carbamate (280 mg, 1.0 mmol) was stirred in the solution of DCM/CF$_3$COOH (2:1, 3 ml) for 1 hour at 0° C. After completion checked by TLC, the mixture was carefully neutralized with saturated K$_2$CO$_3$ solution until no more gas gave out at 0° C. 15 ml of NaOH (2N) was added to the solution, and extracted with DCM (3×10 ml). The organic layer was dried over anhydrous sodium sulphate and then concentrated. The residue (4-(3-(pyrrolidin-1-ylmethyl)azetidin-1-yl)-6-(3,4,5,6-tetrahydropyridin-2-yl)benzo[c][1,2,5]oxadiazole) was used for the next step without further purification. NaBH$_4$ (114 mg, 1.83 mmol) was added to the solution of stirred in the solution of 4-(3-(pyrrolidin-1-ylmethyl)azetidin-1-yl)-6-(3,4,5,6-tetrahydropyridin-2-yl)benzo[c][1,2,5]oxadiazole (210 mg, 0.61 mmol) in MeOH (8 ml) for 2 hour at rt. After completion checked by TLC, the mixture was concentrated. 15 ml of NaOH (2N) was added to the residue, and extracted with DCM (3×10 ml). The organic layer was dried over anhydrous sodium sulphate and then concentrated. The residue (compound 3) was used for the next step without further purification. TEA (0.51 ml, 3.66 mmol) and methanesulfonyl chloride (0.14 ml, 1.83 mmol) were added dropwise to a solution of 6-(piperidin-2-yl)-4-(3-(pyrrolidin-1-ylmethyl)azetidin-1-yl)benzo[c][1,2,5]oxadiazole (crude, 0.61 mmol) in DCM (10 ml) at rt respectively. The mixture was stirred for 3 hours. After completion checked by TLC, the reaction was quenched by EtOAc/H$_2$O (1:1, 50 ml). The mixture was washed with 2 N NaOH and brine. The organic layer was dried and concentrated. The residue was purified via gradient elution (5:100:500, TEA/EtOAc/Hexane to 4:5:100:500 MeOH/TEA/EtOAc/Hexane) to afford Compound TRV-1554 (192 mg 75%) as yellow solid. $^1$H NMR (400 MHz, CDCl$_3$): 1.56-1.76 (m, 4H), 1.81 (s, br, 4H), 1.95-2.02 (m, 1H), 2.34 (d, J=8.0, 1H), 2.54 (s, br, 4H), 2.80 (d, J=7.6, 2H), 2.9 (s, 3H), 3.02-3.16 (m, 2H), 3.85 (d, J=7.2, 1H), 3.97-4.00 (m, 2H), 4.39-4.43 (m, 2H), 5.01 (d, J=4.8, 1H), 5.88 (s, 1H), 7.00 (s, 1H).

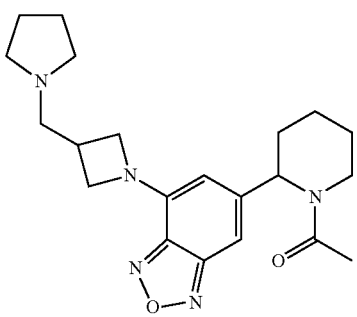

TRV-1555

TEA (0.81 ml, 5.84 mmol) and acetic anhydride (0.276 ml, 2.92 mmol) were added to a solution of 6-(piperidin-2-yl)-4-(3-(pyrrolidin-1-ylmethyl)azetidin-1-yl)benzo[c][1,2,5]oxadiazole (200 mg, 0.584 mmol) in DCM (10 ml) at rt respectively. The mixture was stirred for 2 hours. After completion checked by TLC, the reaction was quenched by EtOAc/H$_2$O (1:1, 50 ml). The mixture was washed with 2 N NaOH and brine. The organic layer was dried and concentrated. The residue was purified via gradient elution (5:100:500, TEA/EtOAc/Hexane to 3:5:100:500 MeOH/TEA/EtOAc/Hexane) to afford TRV-1555 (205 mg 91%) as yellow solid. $^1$H NMR (400 MHz, CDCl$_3$): 1.52-1.89 (m, 9H), 2.13-2.34 (m, 4H), 2.53 (s, br, 4H), 2.73-2.80 (m, 2.31H), 3.04-3.12 (m, 1.69H), 3.69-3.72 (m, 0.69H), 3.95 (s, br, 2H), 4.34-4.41 (m, 2H), 4.63-4.65 (m, 0.31H), 4.95 (s, br, 0.31H), 5.61-5.67 (m, 1H), 5.88 (s, 0.69H), 6.88 (s, 1H).

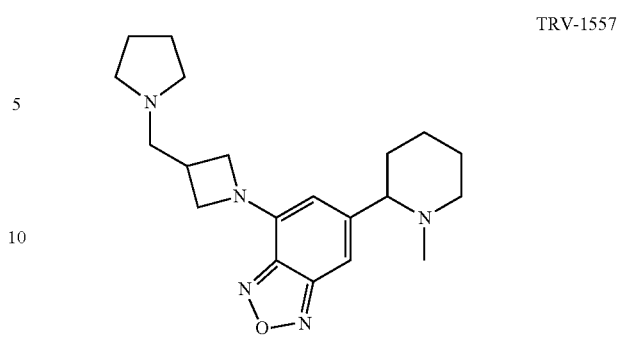

TRV-1557 n-BuLi (0.48 ml, 2.5 M, 1.2 mmol) was added dropwise to a solution of 6-(piperidin-2-yl)-4-(3-(pyrrolidin-1-ylmethyl)azetidin-1-yl)benzo[c][1,2,5]oxadiazole (342 mg, 1.0 mmol) in THF (10 ml) at −78° C. After the mixture was stirred for 5 minutes, methyl iodide (0.125 ml, 2.0 mmol) was added to a solution, and the mixture was stirred for 1 h at −78° C. The reaction was quenched by EtOAc/H$_2$O (1:1, 50 ml). The mixture was washed with 2 N NaOH and brine. The organic layer was dried and concentrated. The residue was purified via gradient elution (5:100:500, TEA/EtOAc/Hexane to 4:5:100:500 MeOH/TEA/EtOAc/Hexane) to afford TRV-1557 (156 mg, 44%) as red oil. $^1$H NMR (400 MHz, CDCl$_3$): 1.31-1.41 (m, 1H), 1.55-1.72 (m, 4H), 1.77-1.82 (m, 5H), 2.03-2.13 (m, 4H), 2.54 (s, br, 4H), 2.75-2.81 (m, 3H), 3.00-3.08 (m, 2H), 3.94-4.00 (m, 2H), 4.39-4.44 (m, 2H), 5.99 (s, 1H), 6.90 (s, 1H).

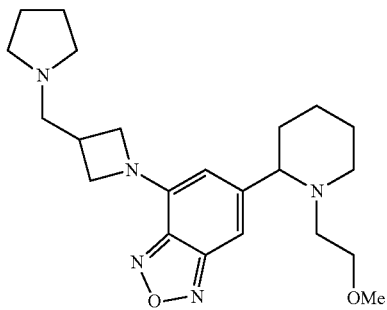

TRV-1556

Potassium carbonate (828 mg, 6 mmol) and 2-bromo-ethyl methyl ether (0.432 ml, 4.5 mmol) were added to a solution of 6-(piperidin-2-yl)-4-(3-(pyrrolidin-1-ylmethyl)azetidin-1-yl)benzo[c][1,2,5]oxadiazole (513 mg, 1.5 mmol) in acetonitrile (10 ml) respectively. Then the mixture was heated to 50° C. for overnight, another batch of 2-bromo-ethyl methyl ether (0.144 ml, 1.5 mmol) was added and heated for 8 h at 50° C. The reaction was quenched by EtOAc/H$_2$O (1:1, 50 ml). The mixture was washed with 2 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford TRV-1556 (280 mg, 46%) as red oil. $^1$H NMR (400 MHz, CDCl$_3$): 1.31-1.42 (m, 1H), 1.59-1.82 (m, 9H), 2.09-2.18 (m, 2H), 2.54 (s, br, 4H), 2.71-2.78 (m, 1H), 2.80 (d, J=7.6, 2H), 3.03-3.07 (m, 2H), 3.23 (d, J=7.6, 1H), 3.28 (s, 3H), 3.34-3.39 (m, 1H), 3.46-3.52 (m, 1H), 3.95-3.99 (m, 2H), 4.41 (q, J=8.0, J=6.0, 2H), 6.04 (s, 1H), 6.91 (s, 1H).

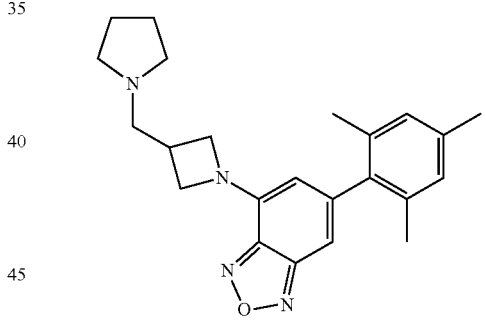

TRV 1558

A reaction vial was charged with TRV 1472 (0.25 g, 0.74 mmol), (2,4,6-trimethylphenyl)boronic acid (0.16 g, 1.00 mmol), and Pd(PPh$_3$)$_4$ (0.043 g, 0.037 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA:MeOH:hexane:EtOAc 5:1:75:15) to afford 0.21 g (75% yield) of TRV 1558 as red oil. $^1$H NMR (CDCl$_3$, 400 MHz) δ=6.96 (d, J=0.50 Hz, 2H), 6.79 (d, J=0.75 Hz, 1H), 5.62 (s, 1H), 4.40 (t, J=8.28 Hz, 2H), 3.97 (dd, J$_1$=5.90 Hz, J$_2$=8.16 Hz, 2H), 3.05 (septet, J=7.06 Hz, 1H), 2.82 (d, J=7.53 Hz, 2H), 2.58-2.49 (m, 4H), 2.35 (s, 3H), 2.10 (s, 6H), 1.85-1.76 (m, 4H).

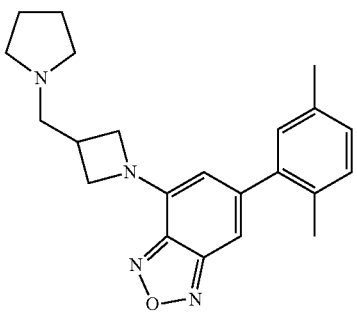

TRV 1559

A reaction vial was charged with TRV 1472 (0.16 g, 0.47 mmol), (2,5-dimethylphenyl)boronic acid (0.085 g, 0.57 mmol), and Pd(PPh$_3$)$_4$ (0.030 g, 0.026 mmol). The vial was degassed and refilled with nitrogen. To the vial was added dioxane (4 mL) and aq. sodium carbonate (2 mL, 2.0 M, 4.0 mmol). The reaction was re-degassed, refilled with nitrogen, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (TEA:MeOH:hexane:EtOAc 5:1:75:15) to afford 0.17 g (100% yield) of TRV 1559 as red oil. $^1$H NMR (CDCl$_3$, 400 MHz) δ=7.18 (d, J=7.78 Hz, 1H), 7.12 (d, J=7.78 Hz, 1H), 7.09 (s, 1H), 6.90 (d, J=0.75 Hz, 1H), 5.79 (s, 1H), 4.42 (t, J=8.28 Hz, 2H), 3.99 (dd, J$_1$=5.77 Hz, J$_2$=8.53 Hz, 2H), 3.06 (septet, J=7.15 Hz, 1H), 2.81 (d, J=7.28 Hz, 2H), 2.60-2.48 (m, 4H), 2.37 (s, 3H), 2.27 (s, 3H), 1.87-1.75 (m, 4H).

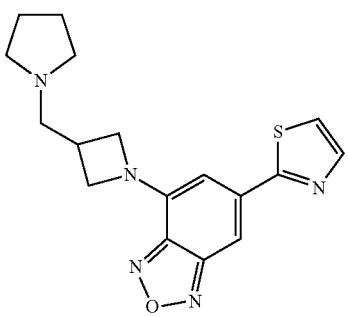

TRV 1560

A reaction vial was charged with 4-(3-(Pyrrolidin-1-ylmethyl)azetidin-1-yl)-6-(tri-n-butylstannyl)benzo[c][1,2,5]oxadiazole (0.33 g, 0.60 mmol), 2-bromothiazole (0.081 mL, 0.90 mmol), Pd(PPh$_3$)$_4$ (0.035 g, 0.030 mmol), CuI (0.011 g, 0.06 mmol), and CsF (0.18 g, 1.20 mmol). The vial was degassed and refilled with nitrogen. To the vial was added NMP (4 mL). The reaction was re-degassed, refilled with nitrogen, sealed, and then heated to 50° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA: MeOH: hexane: EtOAc 5:0:75:15 to TEA:MeOH:hexane:EtOAc 5:3:75:15) to afford 0.086 g (42% yield) of TRV 1560 as a red solid. $^1$H NMR (CDCl$_3$, 400 MHz) δ=7.93 (d, J=3.26 Hz, 1H), 7.56 (s, 1H), 7.44 (d, J=3.26 Hz, 1H), 6.56 (s, 1H), 4.50 (t, J=8.53 Hz, 2H), 4.07 (dd, J$_1$=6.02 Hz, J$_2$=8.53 Hz, 2H), 3.09 (septet, J=7.53 Hz, 1H), 2.81 (d, J=7.28 Hz, 2H), 2.58-2.50 (m, 4H), 1.85-1.77 (m, 4H).

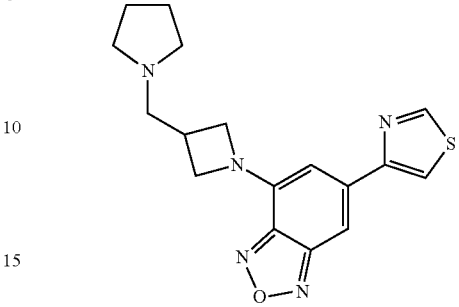

TRV 1561

A reaction vial was charged with 4-(3-(Pyrrolidin-1-ylmethyl)azetidin-1-yl)-6-(tri-n-butylstannyl)benzo[c][1,2,5]oxadiazole (0.41 g, 0.75 mmol), 4-bromothiazole (0.10 mL, 1.13 mmol), Pd(PPh$_3$)$_4$ (0.043 g, 0.037 mmol), CuI (0.014 g, 0.076 mmol), and CsF (0.28 g, 1.86 mmol). The vial was degassed and refilled with nitrogen. To the vial was added DMF (4 mL). The reaction was re-degassed, refilled with nitrogen, sealed, and then heated to 50° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:hexane:EtOAc 5:0:75:15 to TEA:MeOH:hexane:EtOAc 5:3:75:15) to afford 0.11 g (43% yield) of TRV 1561 as a red solid. $^1$H NMR (CDCl$_3$, 400 MHz) δ=8.91 (d, J=2.01 Hz, 1H), 7.68 (d, J=2.01 Hz, 1H), 7.59 (s, 1H), 6.44 (s, 1H), 4.48 (t, J=8.28 Hz, 2H), 4.05 (dd, J$_1$=5.77 Hz, J$_2$=8.53 Hz, 2H), 3.09 (septet, J=7.00 Hz, 1H), 2.81 (d, J=7.28 Hz, 2H), 2.59-2.49 (m, 4H), 1.85-1.75 (m, 4H).

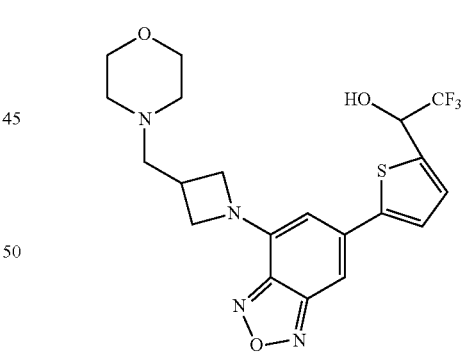

TRV 1562

6-bromo-4-fluorobenzo[c][1,2,5]oxadiazole (0.427 g, 2.0 mmol) and 5-formylthiophene-2-boronic acid (0.340 g, 2.2 mmol) were added to a glass tube and the tube was evacuated and purged with argon (3×). DME (2.8 mL) and Na$_2$CO$_3$ (3.0 mL, 6 mmol, 2 N aqueous solution) were added followed by Pd (PPh$_3$)$_4$ (0.115 g, 0.1 mmol). The tube was sealed and then heated to 80° C. overnight. The reaction was cooled and then diluted with EtOAc and water. The organic layer was washed with water (3×), brine, dried (MgSO$_4$), filtered and concentrated to give 5-(7-fluorobenzo[c][1,2,5] oxadiazol-5-yl)thiophene-2-carbaldehyde which was purified using column chromatography and used in next step.

5-(7-fluorobenzo[c][1,2,5]oxadiazol-5-yl)thiophene-2-carbaldehyde (0.2 g) was dissolved in THF (5 mL) and cooled in an ice bath. CF$_3$TMS (0.19 mL) was added and then the catalyst TBAF (0.1 mL, 1.0 M solution) was added. After 30 minutes the reaction was removed from the ice bath and allowed to warm to room temperature.

Once complete by TLC, recooled to 0° C. and 2 N HCl (aq) was added, stirred for 40 minutes and then basified with 2N NaOH. This mixture was extracted with EtOAc. The combined extracts were washed with water (2×), brine, filtered and concentrated. The crude material was purified via chromatography (hexane:ethyl acetate, 80:20) to afford 0.2 mg (80%) of 2, 2, 2-trifluoro-1-(5-(7-fluorobenzo[c][1,2,5]oxadiazol-5-yl)thiophen-2-yl)ethan-1-ol as yellow solid. $^1$H NMR (400 MHz, CDCl3) δ 7.82 (s1H), 7.42 (d, J=4.0 Hz,1H), 7.39 (d, J=8.0 Hz, 1H), 7.26 (d, J=4.0 Hz, 1H), 5.33-5.38 (m, 1H), 2.88 (d, J=8.0 Hz, 1H).

2, 2, 2-trifluoro-1-(5-(7-fluorobenzo[c][1,2,5]oxadiazol-5-yl)thiophen-2-yl)ethan-1-ol (0.172 g, 0.54 mmol) and 4-(azetidin-3-ylmethyl)morpholine hydrochloride salt (0.185 g, 0.81 mmol) were dissolved in Acetonitrile (5 ml) at room temperature, triethylamine (0.3 ml, 2.16 mmol) was added and mixture was heated at 80° C. for 2 h. After completion of reaction by TLC it was quenched with Na2CO3 (2M) and extracted with EtOAC to give 2,2,2-trifluoro-1-(5-(7-(3-(morpholinomethyl)azetidin-1-yl)benzo[c][1,2,5]oxadiazol-5-yl)thiophen-2-yl)ethan-1-ol TRV1562. $^1$H NMR (DMSO, 700 MHz) δ=7.77 (d, J=5 Hz, 1H), 7.56 (s, 1H), 7.42 (d, J=5 Hz, 1H), 7.28 (d, J=5 Hz, 1H), 6.76 (s, 1H), 5.59-5.55 (m, 1H), 4.38 (m,2H), 3.96 (m,2H), 3.54 (m,4H), 3.08 (m,1H), 2.64 (d, J=8.0 Hz, 2H), 2.39 (m,4H)

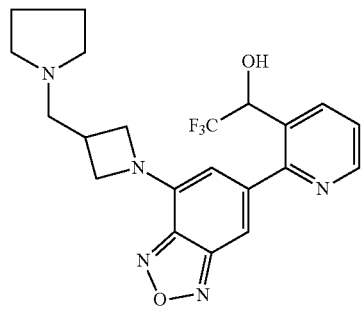

TRV1564

2,2,2-trifluoro-1-(2-(7-fluorobenzo[c][1,2,5]oxadiazol-5-yl)pyridin-3-yl)ethan-1-ol (0.1, 0.32 mmol) and 1-(azetidin-3-ylmethyl)pyrrolidine hydrochloride salt (0.102 g, 0.48 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give 2, 2, 2-trifluoro-1-(2-(7-(3-(pyrrolidin-1-ylmethyl)azetidin-1-yl) benzo[c][1,2,5]oxadiazol-5-yl) pyridin-3-yl) ethan-1-ol TRV1564. Purification was done on ISCO flash chromatography system using dichloromethane:methanol (95:5) as solvent to obtain the title Compound (0.103 g, 78%) as orange color solid. 1H NMR (DMSO-d6, 400 MHz): δ 8.70(d, J=4.0 Hz,1H), 8.13(d,J=8.0Hz,1H), 7.60(m,1H), 7.12(s,1H), 7.04(s,1H), 5.93(s,1H), 5.27(m,1H), 4.37(m,2H), 3.94(m,2H), 3.02(m, 1H), 2.72(d, J=8.0Hz, 2H), 2.43(m,4H), 1.67(m,4H).

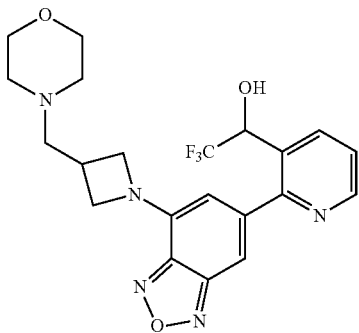

TRV1563

2,2,2-trifluoro-1-(2-(7-fluorobenzo[c][1,2,5]oxadiazol-5-yl)pyridin-3-yl)ethan-1-ol (0.1, 0.32 mmol) and 4-(azetidin-3-ylmethyl)morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give 2,2,2-trifluoro-1-(2-(7-(3-(morpholinomethyl)azetidin-1-yl) benzo[c][1,2,5]oxadiazol-5-yl)pyridin-3-yl)ethan-1-ol TRV-1563. Purification was done on ISCO flash chromatography system using dichloromethane:methanol (95:5) as solvent to obtain the title Compound (0.105 g, 80%) as orange color solid. 1H NMR (DMSO-d6, 400 MHz): δ 8.70(d, J=4.0 Hz, 1H), 8.13(d, J=8.0 Hz, 1H), 7.60(m,1H), 7.12(s,1H), 7.05(s,1H), 5.93(s,1H), 5.28(m,1H), 4.37(m,2H), 3.94(m,2H), 3.56(m,4H), 3.05(m,1H), 2.63(d, J=8.0 Hz, 2H), 2.37(m,4H).

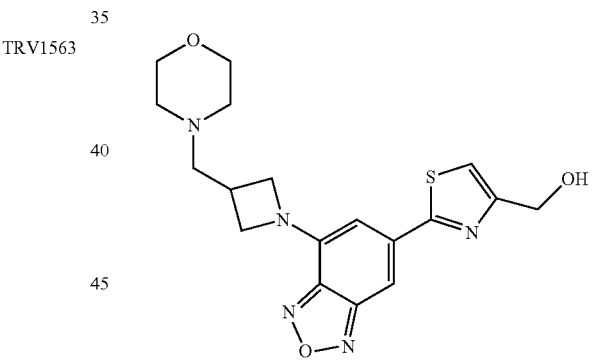

TRV 1565

A reaction vial was charged with 4-fluoro-6-(4,4,5,5-tetramethyl-1,3,2-dioxaborolan-2-yl)benzo[c][1,2,5]oxadiazole (0.33 g, 1.25 mmol), 2-bromothiazole-4-carbaldehyde (0.19 g, 1.00 mmol), Pd(PPh$_3$)$_4$ (0.058 g, 0.050 mmol). The vial was degassed and refilled with nitrogen. To the vial was added dioxane (4 mL) and aq. Na$_2$CO$_3$ (2 mL, 2.0 M, 5.0 mmol). The reaction vial was re-degassed, refilled with nitrogen, sealed, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (EtOAc:Hex 0:100 to 10:90) to afford 0.13 g (51% yield) of 2-(7-fluorobenzo[c][1,2,5]oxadiazol-5-yl)thiazole-4-carbaldehyde as a colorless solid. To a solution of 2-(7-fluorobenzo[c][1,2,5]oxadiazol-5-yl)thiazole-4-carbaldehyde (0.13 g, 0.51 mmol) in THF (5 mL) was added sodium borohydride (0.15 g, 4.07 mmol). The reaction mixture was stirred at rt until it was complete. The reaction was cooled in an ice-water bath, quenched with saturated ammonium chloride, and extracted with ethyl acetate. The ethyl acetate phase was dried over anhydrous sodium sulfate and concentrated. The residue was purified by flash chromatography using gradient elution (EtOAc:Hex 0:100 to 20:80) to afford 0.070 g (53% yield) of (2-(7-fluorobenzo[c][1,2,5]oxadiazol-5-yl)thiazol-4-yl)methanol as a colorless solid.

To a solution of (2-(7-fluorobenzo[c][1,2,5]oxadiazol-5-yl)thiazol-4-yl)methanol (0.070 g, 0.27 mmol) in acetonitrile (5 mL) was added 1-(azetidin-3-ylmethyl)morpholine dihydrochloride (0.093 g, 0.41 mmol) followed by TEA (0.14 mL, 1.03 mmol). The reaction was then heated to 50° C. until the reaction was complete. The mixture was diluted with water and extracted with ethyl acetate. The ethyl acetate phase was dried over anhydrous sodium sulfate and concentrated. The residue was purified by flash chromatography using gradient elution (TEA:MeOH:EtOAc:Hex 5:0:25:75 to 5:10:25:75) to afford 0.086 g (80% yield) of TRV 1565 as a red solid. $^1$H NMR (CDCl$_3$, 400 MHz) δ=7.55 (s, 1H), 7.30 (s, 1H), 6.31 (s, 1H), 4.87 (s, 2H), 4.48 (t, J=8.28 Hz, 2H), 4.07 (dd, J$_1$=5.52 Hz, J$_2$=8.53 Hz, 2H), 3.74 (t, J=4.65 Hz, 4H), 3.10 (septet, J=6.65 Hz, 1H), 2.72 (d, J=7.28 Hz, 2H), 2.49 (t, J=4.39 Hz, 4H), 2.40 (broad, 1H).

3-ylmethyl) morpholine dihydrochloride (0.17 g, 0.74 mmol) followed by TEA (0.26 mL, 1.87 mmol). The reaction was then heated to 50° C. until the reaction was complete. The mixture was diluted with water and extracted with ethyl acetate. The ethyl acetate phase was dried over anhydrous sodium sulfate and concentrated. The residue was purified by flash chromatography using gradient elution (TEA:MeOH:EtOAc:Hex 5:1:25:75 to 5:10:25:75) to afford 0.15 g (66% yield for two steps) TRV1566 as a red solid. $^1$H NMR (CDCl$_3$, 400 MHz) δ=7.60 (s, 1H), 7.55 (s, 1H), 6.37 (s, 1H), 5.04 (s, 2H), 4.45 (t, J=8.16 Hz, 2H), 4.07 (dd, J$_1$=5.52 Hz, J$_2$=8.28 Hz, 2H), 3.74 (t, J=4.65 Hz, 4H), 3.09 (septet, J=6.86 Hz, 1H), 2.78 (broad, 1H), 2.72 (d, J=7.53 Hz, 2H), 2.39 (t, J=4.39 Hz, 4H).

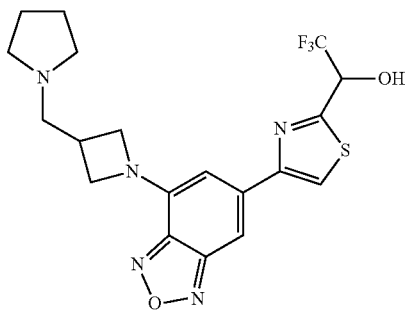

TRV 1567

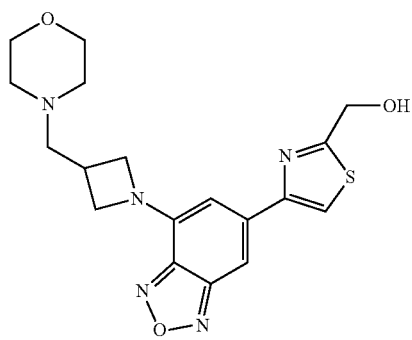

TRV 1566

A reaction vial was charged with 4-fluoro-6-(4,4,5,5-tetramethyl-1,3,2-dioxaborolan-2-yl)benzo[c][1,2,5]oxadiazole (0.33 g, 1.25 mmol), 4-bromothiazole-2-carbaldehyde (0.19 g, 1.00 mmol), chloro(2-dicyclohexylphosphino-2',4',6'-triisopropyl-1,1'-biphenyl) [2-(2'-amino-1,1'-biphenyl)]palladium(II) (0.016 g, 0.020 mmol). The vial was degassed and refilled with nitrogen. To the vial was added dioxane (3 mL) and aq. K$_3$PO$_4$ (3 mL, 0.68 M, 2.0 mmol). The reaction vial was re-degassed, refilled with nitrogen, sealed, and then heated to 80° C. overnight. The mixture was diluted with water, and extracted with ethyl acetate. The ethyl acetate phase was dried over anhydrous sodium sulfate and concentrated. The residue was purified by flash chromatography using gradient elution (EtOAc:Hex 0:100 to 10:90) to afford 0.15 g (59% yield) of 4-(7-fluorobenzo[c][1,2,5]oxadiazol-5-yl)thiazole-2-carbaldehyde as a colorless solid.

To a solution of 4-(7-fluorobenzo[c][1,2,5]oxadiazol-5-yl)thiazole-2-carbaldehyde (0.15 g, 0.59 mmol) in THF (5 mL) was added sodium borohydride (0.067 g, 1.77 mmol). The reaction mixture was stirred at rt until it was complete. The reaction was cooled in an ice-water bath, quenched with saturated ammonium chloride, and extracted with ethyl acetate. The ethyl acetate phase was dried over anhydrous sodium sulfate and concentrated. The residue was dissolved in acetonitrile (5 mL). To the solution was added 1-(azetidin- A reaction vial was charged with 4-fluoro-6-(4,4,5,5-tetramethyl-1,3,2-dioxaborolan-2-yl)benzo[c][1,2,5]oxadiazole (0.29 g, 1.08 mmol), 1-(4-bromothiazol-2-yl)-2,2,2-trifluoroethan-1-ol (0.22 g, 0.83 mmol), Pd(PPh$_3$)$_4$ (0.048 g, 0.042 mmol). The vial was degassed and refilled with nitrogen. To the vial was added dioxane (4 mL) and aq. Na$_2$CO$_3$ (2 mL, 2.0 M, 5.0 mmol). The reaction vial was re-degassed, refilled with nitrogen, sealed, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (EtOAc:Hex 0:100 to 15:85) to afford 0.050 g (19% yield) of 2,2,2-trifluoro-1-(4-(7-fluorobenzo[c][1,2,5]oxadiazol-5-yl)thiazol-2-yl)ethan-1-ol as a colorless solid.

To a solution of 2,2,2-trifluoro-1-(4-(7-fluorobenzo[c][1,2,5]oxadiazol-5-yl)thiazol-2-yl)ethan-1-ol (0.050 g, 0.16 mmol) in acetonitrile (5 mL) was added 1-(azetidin-3-ylmethyl)pyrrolidine dihydrochloride (0.050 g, 0.24 mmol) followed by TEA (0.09 mL, 0.62 mmol). The reaction was then heated to 50° C. until the reaction was complete. The mixture was diluted with water and extracted with ethyl acetate. The ethyl acetate phase was dried over anhydrous sodium sulfate and concentrated. The residue was purified by flash chromatography using gradient elution (TEA:MeOH:EtOAc:Hex 5:1:25:75 to 5:5:25:75) to afford 0.050 g (72% yield) TRV 1567 as a yellow solid. $^1$H NMR (CDCl$_3$, 400 MHz) δ=7.73 (s, 1H), 7.58 (s, 1H), 6.29 (s, 1H), 5.38 (q, J=7.27 Hz, 1H), 4.47 (t, J=8.28 Hz, 2H), 4.07-4.00 (m, 2H), 3.09 (septet, J=7.03 Hz, 1H), 2.83 (d, J=7.28 Hz, 2H), 2.61-2.52 (m, 4H), 1.87-1.78 (m, 4H).

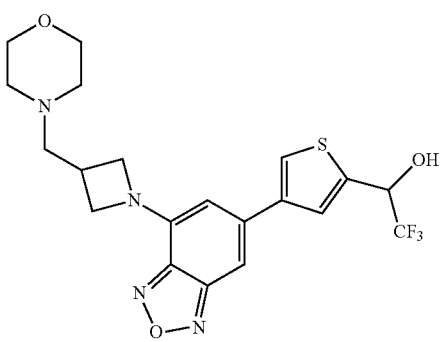

TRV 1568

2, 2, 2-trifluoro-1-(4-(7-fluorobenzo[c][1,2,5]oxadiazol-5-yl)thiophen-2-yl)ethan-1-ol (0.1, 0.31 mmol) and 4-(azetidin-3-ylmethyl)morpholine hydrochloride salt (0.108 g, 0.47 mmol) were dissolved in Acetonitrile (5 ml) at room temperature, triethylamine (0.18 ml, 1.25 mmol) was added and mixture was heated at 80° C. for 2 h. After completion of reaction by TLC it was quenched with Na2CO3 (2M) and extracted with EtOAC to give 2, 2, 2-trifluoro-1-(4-(7-(3-(morpholinomethyl)azetidin-1-yl) benzo[c][1,2,5]oxadiazol-5-yl) thiophen-2-yl) ethan-1-ol TRV 1568. Purification was done on ISCO flash Chromatography system using dichloromethane:methanol (95:5) solvent system to obtain the title Compound (0.118 g, 83%) as orange color solid. $^1$H NMR (DMSO-d6, 400 MHz): δ 8.23(s, 1H), 7.78(s, 1H), 7.38(s, 1H), 7.35(d, J=8.0 Hz, 1H), 6.36 (s,1H), 5.50(m,1H), 4.37(m,2H), 3.95(m,2H), 3.57(m,4H), 3.06(m,1H), 2.64(d, J=8.0 Hz, 2H), 2.39(m, 2H).

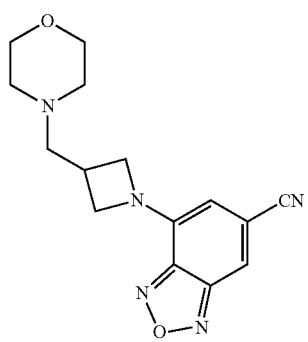

TRV 1570

CuCN (594 mg, 6.6 mmol) and TRV1470 (1.06 g, 3.0 mmol) were added to dry NMP (8 ml). The vial was purged with nitrogen for several times. The mixture was heated to 150° C. and stirred for 10 hours. After completion checked by TLC, the reaction was quenched with aqueous ammonia hydroxide (5 ml), and EtOAc (50 ml) was added to the solution. The mixture was washed with 1 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford 7-(3-(morpholinomethyl)azetidin-1-yl) benzo[c][1,2,5]oxadiazole-5-carbonitrile TRV1570 (708 mg, 79%) as a red solid. $^1$H NMR (400 MHz, CDCl$_3$): 2.44-2.49 (m, 4H), 2.72 (d, J=7.6, 2H), 3.08-3.15 (m, 1H), 3.69-3.76 (m, 4H), 4.05-4.11 (m, 2H), 4.45-4.49 (m, 2H), 5.83 (s, 1H), 7.40 (s, 1H).

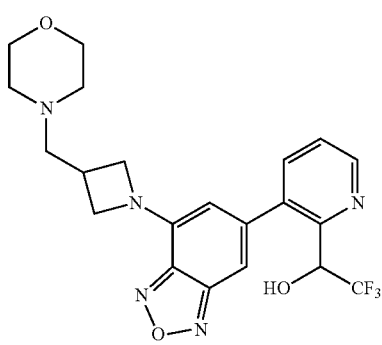

TRV 1569

2,2,2-trifluoro-1-(2-(7-fluorobenzo[c][1,2,5]oxadiazol-5-yl)pyridin-3-yl)ethan-1-ol (0.1, 0.32 mmol) and 4-(azetidin-3-ylmethyl)morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give 2, 2, 2-trifluoro-1-(3-(7-(3-(morpholinomethyl)azetidin-1-yl) benzo[c][1,2,5]oxadiazol-5-yl) pyridin-2-yl) ethan-1-ol TRV1569. Purification was done on ISCO flash chromatography system using dichloromethane:methanol (95:5) as solvent to obtain the title Compound (0.105 g, 80%) as orange color solid. 1H NMR (DMSO-d6, 400MHz): δ 8.72(d, J=4.0Hz, 1H), 7.73 (d, J=8.0Hz, 1H), 7.48 (m, 1H), 6.93(s, 1H), 5.67(s, 1H), 5.33(m, 1H), 4.98(d, J=8.0 Hz, 1H), 4.43(m,2H), 4.02(m, 2H), 3.72(m,4H), 3.10(m,1H), 2.73(d, J=4.0Hz, 2H), 2.48 (m, 4H).

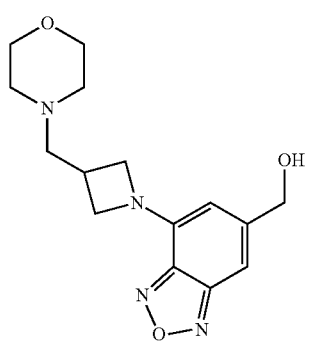

TRV 1571 n-BuLi (2.22 ml, 2.5 M, 5.56 mmol) was added dropwise to a solution of TRV1470 (1.51 mg, 4.28 mmol) in THF (20 ml) at −78° C. under nitrogen atmosphere. After the mixture was stirred for 10 minutes, DMF (0.46 ml, 6.0 mmol) was added to a solution, and the mixture was stirred for 1 h at −78° C. The reaction was quenched by MeOH (1 ml), and EtOAc (50 ml) was added to the solution. The mixture was washed with 1 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford 7-(3-(morpholinomethyl)azetidin-1-yl)benzo[c][1,2,5]oxadiazole-5-carbaldehyde (980 mg, 76%) as red solid.

NaBH$_4$ (370 mg, 9.73 mmol) was added to a solution of 7-(3-(morpholinomethyl)azetidin-1-yl) benzo[c][1,2,5]oxadiazole-5-carbaldehyde (980 mg, 3.24 mmol) in MeOH (10 ml) at room temperature. After the mixture was stirred for 1 hour, the reaction was quenched by EtOAc/H$_2$O (1:1, 50 ml). The mixture was washed with 1 N NaOH and brine. The organic layer was dried and concentrated. The residue was purified via gradient elution (5:100:500, TEA/EtOAc/Hexane to 10:5:100:500 MeOH/TEA/EtOAc/Hexane) to afford (7-(3-(morpholinomethyl)azetidin-1-yl)benzo[c][1,2,5]oxadiazol-5-yl)methanol TRV1571 (560 mg, 56%) as a yellow solid. $^1$H NMR (400 MHz, CDCl$_3$): 1.94 (s, br, 1H), 2.46-2.48 (m, 4H), 2.70 (d, J=7.6, 2H), 3.03-3.10 (m, 1H), 3.72-3.74 (m, 4H), 3.95-3.98 (m, 2H), 4.39 (t, J=8.2, 2H), 4.68 (s, 2H), 5.81 (s, 1H), 7.01 (s, 1H).

TRV 1572

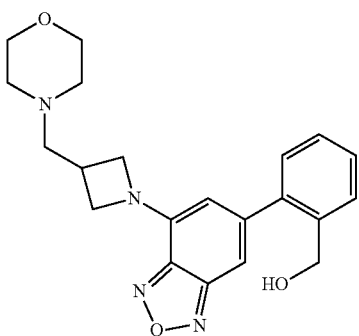

A reaction vial was charged with 6-bromo-4-(3-(morpholinomethyl)azetidin-1-yl)benzo[c][1,2,5]oxadiazole (1.20 g, 3.40 mmol), (2-formylphenyl)boronic acid (0.76 g, 5.07 mmol), Pd(PPh$_3$)$_4$ (0.20 g, 0.17 mmol). After degassed and refilled with nitrogen, the vial was charged with dioxane (15 mL) and aq. Na$_2$CO$_3$ (6 mL, 2.0 M, 12.0 mmol). The reaction vial was further re-degassed, refilled with nitrogen, sealed, and then heated to 100° C. until the reaction was complete. The mixture was diluted with water, added 5 mL of 2N NaOH, and extracted with ethyl acetate. The ethyl acetate phase was dried over anhydrous sodium sulfate and concentrated. The residue was purified by flash chromatography using gradient elution (TEA:MeOH:EtOAc:Hex 5:0:15:75 to 5:2:15:75) to afford 0.93 g (73% yield) of 2-(7-(3-(morpholinomethyl)azetidin-1-yl)benzo[c][1,2,5]oxadiazol-5-yl)benzaldehyde as a yellow semi-solid.

A solution of 2-(7-(3-(morpholinomethyl)azetidin-1-yl)benzo[c][1,2,5]oxadiazol-5-yl)benzaldehyde (0.20 g, 0.53 mmol) in THF (5 mL) was cooled in an ice-water bath. To the cooled solution was added sodium borohydride (0.060 g, 1.60 mmol) in portion. The reaction mixture was stirred until it was complete, then quenched with 1N aq. HCl, basified with 1N NaOH, and then extracted with ethyl acetate. The ethyl acetate phase was dried over anhydrous sodium sulfate and concentrated. The residue was purified by flash chromatography using gradient elution (TEA:MeOH:EtOAc:Hex 5:0:25:75 to 5:5:25:75) to afford 0.12 g (60% yield) of the TRV1572 as red oil. $^1$H NMR (CDCl$_3$, 400 MHz) δ=7.59 (d, J=7.53 Hz, 1H), 7.45 (dt, J$_1$=1.25 Hz, J$_2$=7.53 Hz, 1H), 7.39 (dt, J$_1$=1.25 Hz, J$_2$=7.53 Hz, 1H), 7.33 (dd, J$_1$=1.51 Hz, J$_2$=7.53 Hz, 1H), 6.97 (s, 1H), 5.86 (s, 1H), 4.68 (d, J=4.27 Hz, 2H), 4.41 (t, J=8.28 Hz, 2H), 3.99 (dd, J$_1$=5.77 Hz, J$_2$=8.53 Hz, 2H), 3.72 (t, J=4.65 Hz, 4H), 3.07 (septet, J=6.59 Hz, 1H), 2.72 (d, J=7.53 Hz, 2H), 2.47 (t, J=4.39 Hz, 4H), 1.67 (broad, 1H).

TRV 1573

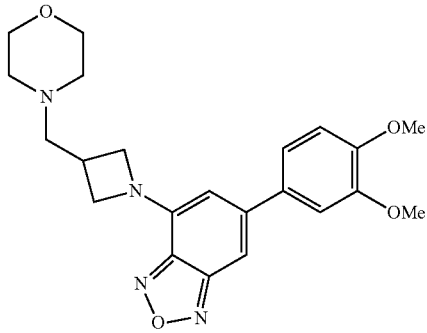

TRV1470 (0.250 g, 0.7 mmol) and 3, 4-dimethoxybenzeneboronic acid (0.155 g, 0.85 mmol) were sealed in a tube. The tube was evacuated and purged with argon (3 cycles). 2M Na$_2$CO$_3$ (1.2 mL, 2.0 M aq solution) was added along with Dioxane (5 mL). The solution was degassed for 10 minutes and then Pd(PPh$_3$)$_4$ (0.041 g, 0.035 mmol) was added all at once. The tube was re-sealed and heated to 80° C. overnight. After cooling to room temperature, the mixture was diluted with water and EtOAc. The layers were separated and the aqueous layer was then back-extracted. The combine organic extracts were then washed with H$_2$O (3×), brine and then dried (Na$_2$SO$_4$), filtered and concentrated. The crude material was purified via chromatography on ISCO (3% MeOH/DCM) to afford 0.238 g (82% yield) of 6-(3, 4-dimethoxyphenyl)-4-(3-(morpholinomethyl)azetidin-1-yl) benzo[c][1,2,5]oxadiazole TRV1573. $^1$H NMR (CDCl3, 500 MHz) δ=7.22 (dd, J=4.0 Hz, 1H), 7.14 (d, J=2.0 Hz, 1H), 7.12 (s, 1H), 6.98 (d, J=8.0 Hz, 1H), 6.06 (s, 1H), 4.47 (t, J=8.0 Hz, 2H), 4.07 (m, 2H), 3.98 (s, 3H), 3.96 (s, 3H), 3.74 (m, 4H), 3.10-3.06 (m, 1H), 2.74 (d, J=8.0 Hz, 2H), 2.49 (m, 4H).

TRV 1574

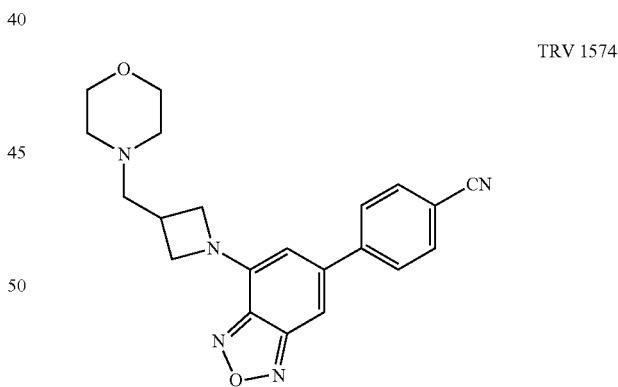

A round-bottomed flask was charged with TRV1470 (250 mg, 0.7 mmol), (4-cyanophenyl) boronic acid (125 mg, 0.85 mmol), and Pd (PPh$_3$)$_4$ (42 mg, 0.035 mmol). After degassed, dioxane (5 mL) and aqueous sodium carbonate (1.5 mL, 2M) was added. The reaction mixture was heated to 80° C. for 3 h. After completion checked by TLC, 10 mL of water was added, and the reaction mixture was extracted with ethyl acetate. The organic phase was dried over anhydrous sodium sulphate and then concentrated. The residue was purified on ISCO column chromatography system (2:5:100:500 MeOH/TEA/EtOAc/Hexane) to afford 219 mg (83% yield) of 4-(7-(3-(morpholinomethyl)azetidin-1-yl)

benzo[c][1,2,5]oxadiazol-5-yl)benzonitrile TRV1574 as a red solid. ¹H NMR (400 MHz, CDCl₃): δ 7.78(d, J=8.0Hz, 2H), 7.73(d, J=8.0Hz,2H), 7.16(s,1H), 5.97(s,1H), 4.49(t, J=8.0Hz,2H), 4.07(t,J=8.0Hz,2H), 3.74(m,4H), 3.15(m,1H), 2.74(d, J=8.0Hz,2H), 2.48(m,4H).

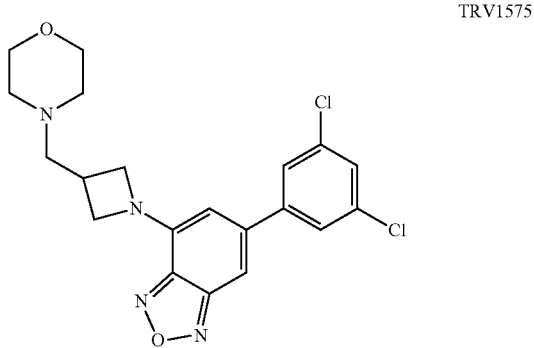 [SMILES: Clc1cc(Cl)cc(-c2cc(N3CC(CN4CCOCC4)C3)c3nonc3c2)c1]

TRV1575

TRV-1470 (0.250 g, 0.7 mmol) and (3, 5-dichlorophenyl) boronic acid (0.162 g, 0.85 mmol) were sealed in a tube. The tube was evacuated and purged with argon (3 cycles). 2M Na₂CO₃ (1.2 mL, 2.0 M aq solution) was added along with Dioxane (5 mL). The solution was degassed for 10 minutes and then Pd (PPh₃)₄ (0.041 g, 0.035 mmol) was added all at once. The tube was re-sealed and heated to 80° C. for 3 h. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude material was purified via chromatography on ISCO (2% MeOH/DCM) to afford 0.255 g (86% yield) of 6-(3, 5-dichlorophenyl)-4-(3-(morpholinomethyl)azetidin-1-yl) benzo[c][1,2,5]oxadiazole TRV1575. ¹H NMR (CDCl3, 400 MHz) δ=7.48 (m, 2H), 7.42 (m, 1H), 7.11 (s, 1H), 5.99 (s, 1H), 4.49 (t, J=8.0 Hz, 2H), 4.06-4.03 (m, 2H), 3.74 (m,4H), 3.14-3.08 (m, 1H), 2.74 (d, J=8.0 Hz, 2H), 2.49 (m, 4H).

TRV1576

3-(7-fluorobenzo[c][1,2,5]oxadiazol-5-yl)benzamide (0.102 g, 0.4 mmol) and 4-(azetidin-3-ylmethyl)morpholine hydrochloride salt (0.137 g, 0.6 mmol) were dissolved in NMP (5 ml) at room temperature, triethylamine (0.22 ml, 1.6 mmol) was added and mixture was heated at 80° C. for 2 h. After completion of reaction by TLC it was quenched with Na2CO3 (2M) and extracted with EtOAC to give 3-(7-(3-(morpholinomethyl) zetidin-1-yl) benzo[c][1,2,5]oxadiazol-5-yl) benzamide TRV1576. Purification was done on ISCO flash Chromatography system using dichloromethane: methanol (95:5) solvent system to obtain the title Compound (0.128 g, 80%) as orange color solid. ¹H NMR (DMSO-d6, 400MHz): δ 8.22(s, 1H), 8.16(s, 1H), 7.94(s, 1H), 7.92(s, 1H), 7.59(t, J=8.0 Hz, 1H), 7.51(s,1H), 7.41(s,1H), 6.31 (s,1H), 4.40(t, J=8.0 Hz, 2H), 3.98(m,2H), 3.58(m,4H), 3.09-3.02(m,1H), 2.63(d, J=4.0 Hz, 2H), 2.38 (m,2H).

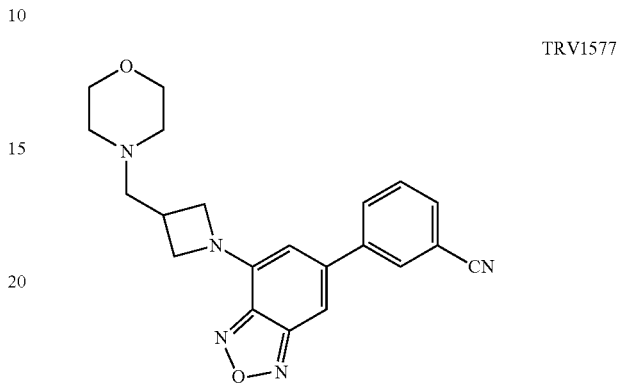

TRV1577

A round-bottomed flask was charged with TRV-1470 (250 mg, 0.7 mmol), (3-cyanophenyl) boronic acid (125 mg, 0.85 mmol), and Pd(PPh₃)₄ (42 mg, 0.035 mmol). After degassed, dioxane (5 mL) and aqueous sodium carbonate (1.5 mL, 2M) was added. The reaction mixture was heated to 80° C. for 3 h. After completion checked by TLC, 10 mL of water was added, and the reaction mixture was extracted with ethyl acetate. The organic phase was dried over anhydrous sodium sulphate and then concentrated. The residue was purified on ISCO column chromatography system (2:5:100:500 MeOH/TEA/EtOAc/Hexane) to afford 250 mg (94% yield) of 3-(7-(3-(morpholinomethyl) azetidin-1-yl) benzo[c][1,2,5] oxadiazol-5-yl)benzonitrile TRV1577 as a red solid. ¹H NMR (400 MHz, CDCl₃): δ 7.90(s,1H), 7.87(d, J=8.0Hz, 1H), 7.73(d,J=8.0Hz,1H), 7.61(t, J=8.0Hz,1H), 7.13(s,1H), 5.95(s,1H), 4.49(t, J=8.0Hz,2H), 4.07(t, =8.0Hz,2H), 3.74 (m,4H), 3.12(m,1H), 2.74(d, J=4.0Hz,2H), 2.50(m,4H),

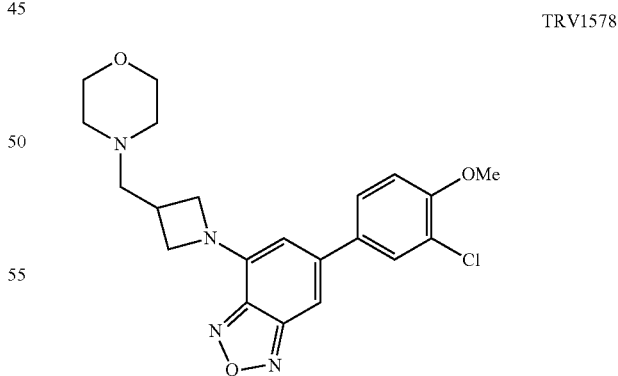

TRV1578

TRV1470 (0.250 g, 0.7 mmol) and (3-chloro-4-methoxyphenyl) boronic acid (0.158 g, 0.85 mmol) were sealed in a tube. The tube was evacuated and purged with argon (3 cycles). 2M Na₂CO₃ (1.2 mL, 2.0 M aq solution) was added along with Dioxane (5 mL). The solution was degassed for 10 minutes and then Pd (PPh₃)₄ (0.041 g, 0.035 mmol) was added all at once. The tube was re-sealed and heated to 80°

C. for 3 h. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude material was purified via chromatography on ISCO (2% MeOH/DCM) to afford 0.225 g (78% yield) of 6-(3-chloro-4-methoxyphenyl)-4-(3-(morpholinomethyl) azetidin-1-yl) benzo[c][1,2,5]oxadiazole TRV1578. $^1$H NMR (CDCl₃, 400 MHz) δ=7.65(d, J=4.0 Hz,1H), 7.52-7.49(dd,J=4.0Hz,1H), 7.09(s, 1H), 7.03(d, J=8 Hz,1H), 5.99 (s, 1H), 4.47(t, J=8.0 Hz, 2H), 4.04-4.01(m, 2H), 3.97(s,3H), 3.74(m,4H), 3.13-3.06 (m, 1H), 2.74 (d, J=8.0 Hz, 2H), 2.49 (m, 4H).

TRV1579

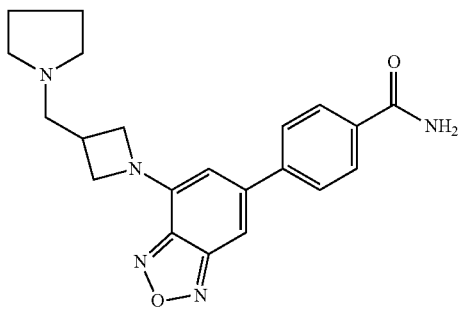

4-(7-fluorobenzo[c][1,2,5]oxadiazol-5-yl)benzamide (0.102 g, 0.4 mmol) and 1-(azetidin-3-yl methyl) pyrrolidinehydrochloride salt (0.128 g, 0.6 mmol) were dissolved in NMP (5 ml) at room temperature, triethylamine (0.22 ml, 1.6 mmol) was added and mixture was heated at 80° C. for 2 h. After completion of reaction by TLC it was quenched with Na2CO3 (2M) and extracted with EtOAC to give 4-(7-(3-(pyrrolidin-1-ylmethyl)azetidin-1-yl) benzo[c][1,2,5]oxadiazol-5-yl)benzamide TRV1579. Purification was done on ISCO flash Chromatography system using dichloromethane:methanol (95:5) solvent system to obtain the title Compound (0.110 g, 73%) as orange color solid. 1H NMR (DMSO-d6, 400MHz): δ 8.08(bs, 1H), 7.99(d, J=8.0 Hz, 2H), 7.88(d, J=8.0 Hz, 2H), 7.46(bs,1H), 7.40(s,1H), 6.30 (s,1H), 4.41(t,J=8.0 Hz, 2H), 4.0(t,J=8.0Hz,2H), 3.04-2.99 (m,1H), 2.80(m,2H), 2.40(m,2H), 1.69(m,4H).

TRV1580

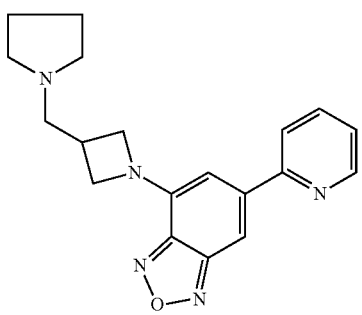

A reaction vial was charged with 4-(3-(Pyrrolidin-1-ylmethyl)azetidin-1-yl)-6-(tri-n-butylstannyl)benzo[c][1,2,5]oxadiazole (0.25 g, 0.74 mmol), 2-bromopyridine (0.90 mmol), Pd(PPh₃)₄ (35 mg, 0.030 mmol), CuI (11.4 mg, 0.06 mmol), and Cs₂CO₃ (182 mg, 1.20 mmol). The vial was degassed and refilled with nitrogen. To the vial was added NMP (4 mL). The reaction was re-degassed, refilled with nitrogen, sealed, and then heated to 50° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography (Combi-Flash RF200 system) to get 6-(Pyridin-2-yl)-4-(3-(pyrrolidin-1-ylmethyl)azetidin-1-yl)benzo[c][1,2,5] oxadiazole TRV1580. $^1$H NMR (CDCl₃, 400 MHz) δ=8.73 (d, J=4.52 Hz, 1H), 7.83-7.78 (m, 2H), 7.52 (s, 1H), 7.35-7.30 (m, 1H), 6.65 (s, 1H), 4.50 (t, J=8.28 Hz, 2H), 4.07 (dd, J₁=5.90 Hz, J₂=8.41 Hz, 2H), 3.09 (septet, J=6.90 Hz, 1H), 2.81 (d, J=7.28 Hz, 2H), 2.58-2.50 (m, 4H), 1.85-1.77 (m, 4H).

TRV1584

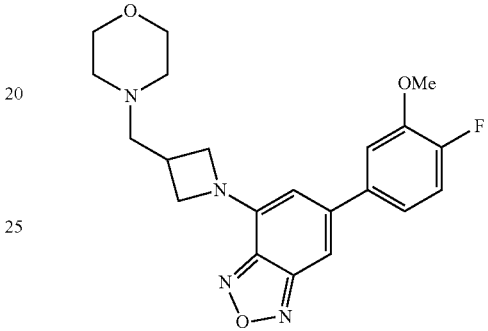

TRV1470 (0.250 g, 0.7 mmol) and (4-fluoro-3-methoxyphenyl) boronic acid (0.145 g, 0.85 mmol) were sealed in a tube. The tube was evacuated and purged with argon (3 cycles). 2M Na₂CO₃ (1.2 mL, 2.0 M aq solution) was added along with Dioxane (5 mL). The solution was degassed for 10 minutes and then Pd (PPh₃)₄ (0.041 g, 0.035 mmol) was added all at once. The tube was re-sealed and heated to 80° C. for 3 h. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude material was purified via chromatography on ISCO (2% MeOH/DCM) to afford 0.248 g (88% yield) of 6-(4-fluoro-3-methoxyphenyl)-4-(3-(morpholinomethyl) azetidin-1-yl) benzo[c][1,2,5]oxadiazole TRV1584. $^1$H NMR (CDCl3, 400 MHz) δ=7.20-7.15(m, 3H), 7.10(s,1H), 5.99 (s, 1H), 4.47 (t, J=8.0 Hz, 2H), 4.04-4.01(m, 2H), 3.98(s,3H), 3.74(m,4H), 3.13-3.07 (m, 1H), 2.74 (d, J=8.0 Hz, 2H), 2.48 (m, 4H).

TRV1585

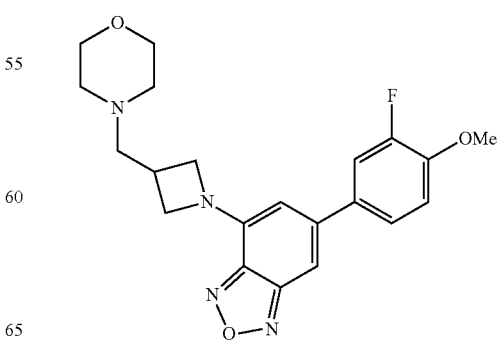

TRV1470 (0.250 g, 0.7 mmol) and (3-fluoro-4-methoxyphenyl) boronic acid (0.145 g, 0.85 mmol) were sealed in a tube. The tube was evacuated and purged with argon (3 cycles). 2M $Na_2CO_3$ (1.2 mL, 2.0 M aq solution) was added along with Dioxane (5 mL). The solution was degassed for 10 minutes and then Pd $(PPh_3)_4$ (0.041 g, 0.035 mmol) was added all at once. The tube was re-sealed and heated to 80° C. for 3 h. After cooling to room temperature, the mixture was diluted with water and EtOAc. The layers were separated and the aqueous layer was then back-extracted. The combine organic extracts were then washed with $H_2O$ (3×), brine and then dried ($Na_2SO_4$), filtered and concentrated. The crude material was purified via chromatography on ISCO (2% MeOH/DCM) to afford 0.260 g (92% yield) of 6-(3-fluoro-4-methoxyphenyl)-4-(3-(morpholinomethyl) azetidin-1-yl) benzo[c][1,2,5]oxadiazole TRV1585. $^1$H NMR (CDCl3, 400 MHz) δ=7.38-7.36(m,2H), 7.10(s,1H), 7.07-7.03(t, J=8 Hz,1H), 5.99 (s, 1H), 4.46 (t, J=8.0 Hz, 2H), 4.04-4.02(m, 2H), 3.96(s,3H), 3.75(m,4H), 3.13-3.06 (m, 1H), 2.73 (d, J=8.0 Hz, 2H), 2.49 (m, 4H).

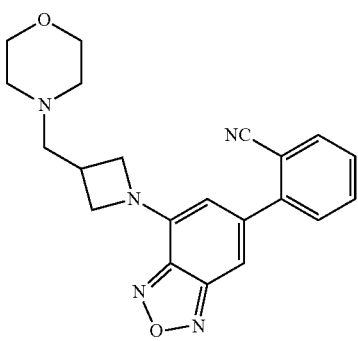

TRV1586

A round-bottomed flask was charged with TRV1470 (250 mg, 0.7 mmol), (2-cyanophenyl) boronic acid (125 mg, 0.85 mmol), and Pd $(PPh_3)_4$ (42 mg, 0.035 mmol). After degassed, dioxane (5 mL) and aqueous sodium carbonate (1.5 mL, 2M) was added. The reaction mixture was heated to 80° C. for 6 h. After completion checked by TLC, 10 mL of water was added, and the reaction mixture was extracted with ethyl acetate. The organic phase was dried over anhydrous sodium sulphate and then concentrated. The residue was purified on ISCO column chromatography system (2:5:100:500 MeOH/TEA/EtOAc/Hexane) to afford 150 mg (57% yield) of 2-(7-(3-(morpholinomethyl)azetidin-1-yl) benzo[c][1,2,5]oxadiazol-5-yl)benzonitrile TRV1586 as a red solid. $^1$H NMR (400 MHz, CDCl$_3$): δ 7.84(t, J=8.0 Hz, 1H), 7.71(t, J=8.0 Hz, 1H), 7.49-7.59(m, 2H), 7.10(s,1H), 5.96(s,1H), 4.49(t,J=8.0Hz,2H), 4.07(t, J=8.0Hz, 2H), 3.74 (m,4H), 3.12(m,1H), 2.74(d, J=8.0Hz,2H), 2.48(m,4H).

4-(3-(pyrrolidin-1-ylmethyl)azetidin-1-yl)-6-(tributylstannyl)benzo[c][1,2,5]oxadiazole (0.4 g, 0.73 mmol), 1-(2-bromopyridin-4-yl)-2,2,2-trifluoroethan-1-ol (0.230 g, 0.9 mmol), CsF (0.45 g, 2.19 mmol), CuI (14 mg, 0.073 mmol), Pd(PPh3)4, (0.042 g, 0.0365 mmol) was charged in glass tube and sealed, it was then degassed and flushed with N2. DMF (10 ml) was added and reaction mixture was heated at 45° C. overnight. After completion of reaction by TLC, the reaction was cooled and then diluted with EtOAc and water. The organic layer was washed with water (3×), brine, dried (MgSO$_4$), filtered and concentrated to give the crude product which was purified using column chromatography to give 2,2,2-trifluoro-1-(2-(7-(3-(pyrrolidin-1-ylmethyl)azetidin-1-yl) benzo[c][1,2,5]oxadiazol-5-yl) pyridin-4-yl)ethan-1-ol TRV1587 (0.08 g, 26%). $^1$H NMR (400 MHz, CDCl3): δ 8.74(d,J=4.0Hz,1H), 7.86(s,1H), 7.47(s,1H), 7.43(d, J=4.0Hz,1H), 6.39(s,1H), 5.09(m,1H), 4.42(m,2H), 3.99(m, 2H), 3.05(m,1H), 2.83(d,J=8.0Hz,2H), 2.57(m,4H), 1.84(m, 4H).

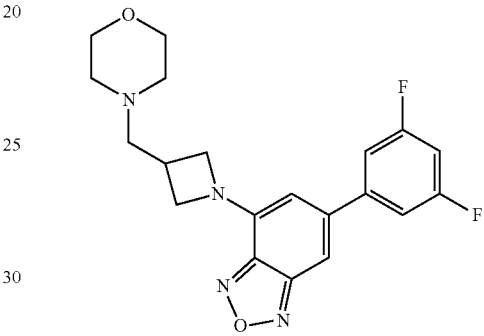

TRV1588

TRV1470 (0.250 g, 0.7 mmol) and (3, 5-difluorophenyl) boronic acid (0.135 g, 0.85 mmol) were sealed in a tube. The tube was evacuated and purged with argon (3 cycles). 2M $Na_2CO_3$ (1.2 mL, 2.0 M aq solution) was added along with Dioxane (5 mL). The solution was degassed for 10 minutes and then Pd $(PPh_3)_4$ (0.041 g, 0.035 mmol) was added all at once. The tube was re-sealed and heated to 80° C. for 3 h. After cooling to room temperature, the mixture was diluted with water and EtOAc. The layers were separated and the aqueous layer was then back-extracted. The combine organic extracts were then washed with $H_2O$ (3×), brine and then dried ($Na_2SO_4$), filtered and concentrated. The crude material was purified via chromatography on ISCO (2% MeOH/DCM) to afford 0.240 g (88% yield) of 6-(3, 5-difluorophenyl)-4-(3-(morpholinomethyl)azetidin-1-yl) benzo [c][1,2,5]oxadiazole TRV1588. $^1$H NMR (CDCl$_3$, 400 MHz) δ=7.15-7.13 (m, 3H), 6.89(t, J=8.0Hz,1H), 5.94 (s, 1H), 4.48 (t, J=8.0 Hz, 2H), 4.06-4.02(m, 2H), 3.74(m,4H), 3.14-3.08 (m, 1H), 2.74 (d, J=8.0 Hz, 2H), 2.49 (m, 4H).

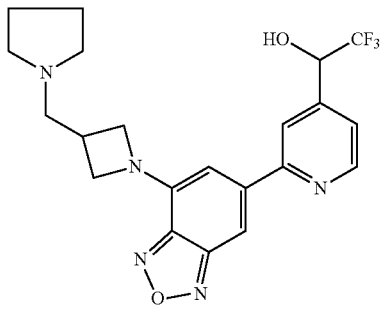

TRV1587

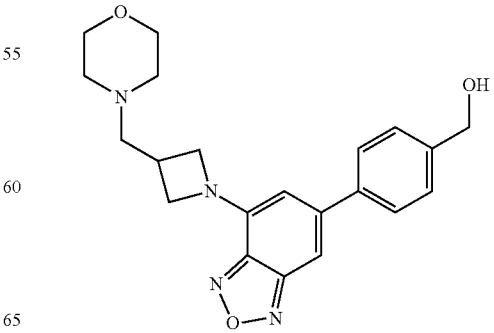

TRV1592

TRV-1470 (0.5571 g, 1.58 mmol) and 4-formylphenylboronic acid (0.2606 g, 1.74 mmol) were weighed into a tube. The tube was evacuated and purged with argon (3×). DME (3.5 mL) and aqueous $Na_2CO_3$ (2.4 mL, 2N aq solution) was added to the tube. The tube was degassed for 5 minutes by bubbling argon gas through the solution. $Pd(PPh_3)_4$ (0.0924 g, 0.08 mmol) was added all at once, the tube was sealed and heated to 95° C. for 4 hours. The reaction was then cooled to room temperature and diluted with DCM and water. The layers were separated and the aqueous layer was back-extracted with DCM (2×). The combined organic layers were washed with water, dried ($MgSO_4$), filtered and concentrated to give a crude brown solid. This crude material was purified via flash chromatography (60% EtOAc/hexane with 5% TEA additive) to afford 0.5709 g (95% yield) of aldehyde 3 as an orange solid. Aldehyde 3 (0.2852 g, 0.75 mmol) was dissolved in a mixture of MeOH (12.5 mL) and THF (5 mL) and then cooled in an ice bath. $NaBH_4$ (0.0567 g, 1.5 mmol) was then added all at once, and the mixture was stirred overnight while warming to room temperature. The reaction was then recooled to 0° C. and quenched with saturated ammonium chloride. The aqueous mixture was then made basic with 2N NaOH (aq) before extracting with DCM. The combined organic extracts were dried ($MgSO_4$), filtered and concentrated to give the crude benzyl alcohol. This material was purified via flash chromatography (5% MeOH/DCM) to afford 0.1551 g (54% yield) of TRV1592 as an orange solid. $^1$H NMR (500 MHz, DMSO) δ=7.74 (d, J=8 Hz, 2H), 7.42 (d, J=8 Hz, 2H), 7.30 (s, 1H), 6.27 (s, 1H), 5.24 (t, J=5.5 Hz, 1H), 4.55 (d, J=5.5 Hz, 2H), 4.37 (t, J=8.5 Hz, 2H), 3.97-3.94 (m, 2H), 3.57 (t, J=4.5 Hz, 4H), 3.09-3.01 (m, 1H), 2.63 (d, J=7.5 Hz, 2H), 2.38 (br s, 4H).

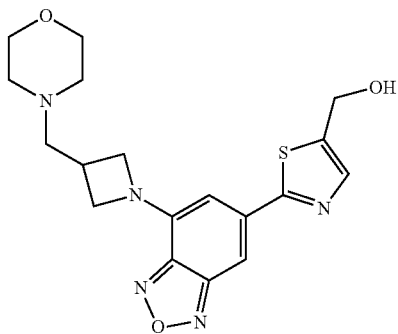

TRV1594

A reaction vial was charged with 4-fluoro-6-(4,4,5,5-tetramethyl-1,3,2-dioxaborolan-2-yl)benzo[c][1,2,5]oxadiazole (0.40 g, 1.50 mmol), (2-bromothiazol-5-yl)methanol (0.23 g, 1.19 mmol), $Pd(PPh_3)_4$ (0.068 g, 0.059 mmol). After degassed and refilled with nitrogen, the vial was charged with dioxane (4 mL) and aq. $Na_2CO_3$ (2 mL, 2.0 M, 5.0 mmol). The reaction vial was further re-degassed, refilled with nitrogen, sealed, and then heated to 100° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (EtOAc:Hex 0:100 to 15:85) to afford 0.20 g (68% yield) of (2-(7-fluorobenzo[c][1,2,5]oxadiazol-5-yl)thiazol-5-yl)methanol as a colorless solid.

To a solution of (2-(7-fluorobenzo[c][1,2,5]oxadiazol-5-yl)thiazol-5-yl)methanol (0.20 g, 0.80 mmol) in acetonitrile (5 mL) was added 1-(azetidin-3-ylmethyl)pyrrolidine dihydrochloride (0.28 g, 1.20 mmol) followed by TEA (0.42 mL, 3.00 mmol). The reaction was then heated to 50° C. until the reaction was complete. The mixture was diluted with water and extracted with ethyl acetate. The ethyl acetate phase was dried over anhydrous sodium sulfate and concentrated. The residue was purified by flash chromatography using gradient elution (TEA:MeOH:EtOAc:Hex 5:0:25:75 to 5:10:25:75) to afford 0.050 g (72% yield) of TRV1594 as an orange solid. $^1$H NMR (DMSO, 400 MHz) δ=7.82 (s, 1H), 7.59 (s, 1H), 6.51 (s, 1H), 5.72 (t, J=5.65 Hz, 1H), 4.74 (d, J=5.52 Hz, 2H), 4.39 (t, J=8.28 Hz, 2H), 4.00-3.91 (m, 2H), 3.57 (t, J=74.52 Hz, 4H), 3.06 (septet, J=6.71 Hz, 1H), 2.63 (d, J=7.53 Hz, 2H), 2.42-2.34 (m, 4H).

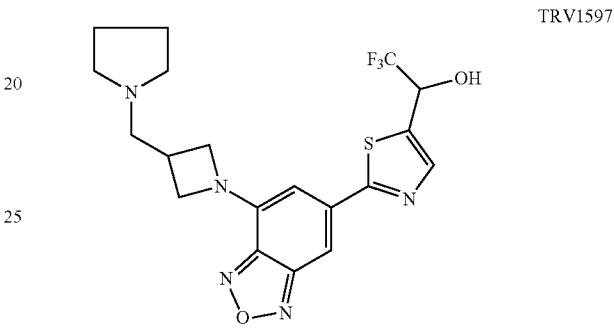

TRV1597

A reaction vial was charged with 4-fluoro-6-(4,4,5,5-tetramethyl-1,3,2-dioxaborolan-2-yl)benzo[c][1,2,5]oxadiazole (0.16 g, 0.61 mmol), 1-(2-bromothiazol-5-yl)-2,2,2-trifluoroethan-1-ol (0.16 g, 0.61 mmol), $Pd(PPh_3)_4$ (35 mg, 0.030 mmol). The vial was degassed and refilled with nitrogen. To the vial was added dioxane (4 mL) and aq. $Na_2CO_3$ (2 mL, 2.0 M, 4.0 mmol). The reaction vial was re-degassed, refilled with nitrogen, sealed, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (EtOAc:Hex 0:100 to 15:85) to afford 0.082 g (42% yield) of 2,2,2-trifluoro-1-(2-(7-fluorobenzo[c][1,2,5]oxadiazol-5-yl)thiazol-5-yl)ethan-1-ol as a colorless solid.

To a solution of 2,2,2-trifluoro-1-(2-(7-fluorobenzo[c][1,2,5]oxadiazol-5-yl)thiazol-5-yl)ethan-1-ol (0.082 g, 0.26 mmol) in acetonitrile (5 mL) was added 1-(azetidin-3-ylmethyl)pyrrolidine dihydrochloride (0.082 g, 0.39 mmol) followed by TEA (0.14 mL, 1.0 mmol). The reaction was then heated to 50° C. until the reaction was complete. The mixture was diluted with water and extracted with ethyl acetate. The ethyl acetate phase was dried over anhydrous sodium sulfate and concentrated. The residue was purified by flash chromatography using gradient elution (TEA:MeOH:EtOAc:Hex 5:1:25:75 to 5:10:25:75) to afford 0.10 g (88% yield) of TRV1597 as a yellow solid. $^1$H NMR (DMSO, 400 MHz) δ=8.06 (s, 1H), 7.67 (s, 1H), 7.54 (d, J=5.77 Hz, 1H), 6.51 (s, 1H), 5.74 (pentet, J=6.40 Hz, 1H), 4.41 (t, J=8.28 Hz, 2H), 3.98 (dd, $J_1$=5.77 Hz, $J_2$=8.28 Hz, 2H), 3.00 (septet, J=6.71 Hz, 1H), 2.72 (d, J=7.53 Hz, 2H), 2.48-2.38 (m, 4H), 1.74-1.61 (m, 4H).

TRV1598

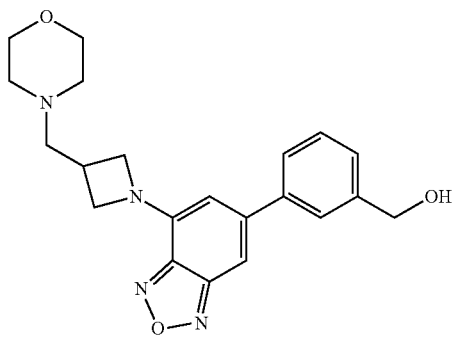

A reaction vial was charged with 6-bromo-4-(3-(morpholinomethyl)azetidin-1-yl)benzo[c][1,2,5]oxadiazole (1.20 g, 3.40 mmol), (3-formylphenyl)boronic acid (0.63 g, 4.25 mmol), Pd(PPh₃)₄ (0.20 g, 0.17 mmol). After degassed and refilled with nitrogen, the vial was charged with dioxane (10 mL) and aq. Na₂CO₃ (6 mL, 2.0 M, 12.0 mmol). The reaction vial was further re-degassed, refilled with nitrogen, sealed, and then heated to 100° C. until the reaction was complete. The mixture was diluted with water, added 5 mL of 2N NaOH, and extracted with ethyl acetate. The ethyl acetate phase was dried over anhydrous sodium sulfate and concentrated. The residue was purified by flash chromatography using gradient elution (TEA:MeOH:EtOAc:Hex 5:0:15:75 to 5:2:15:75) to afford 1.20 g (93% yield) of 3-(7-(3-(morpholinomethyl)azetidin-1-yl)benzo[c][1,2,5]oxadiazol-5-yl)benzaldehyde as red oil.

A solution of 3-(7-(3-(morpholinomethyl)azetidin-1-yl)benzo[c][1,2,5]oxadiazol-5-yl)benzaldehyde (0.26 g, 0.69 mmol) in THF (5 mL) was cooled in an ice-water bath. To the cooled solution was added sodium borohydride (0.040 g dissolved in 2 mL of 1N aq. NaOH, 1.06 mmol) slowly. The reaction mixture was stirred until it was complete, then quenched with 1N aq. HCl, basified with 1N NaOH, and then extracted with ethyl acetate. The ethyl acetate phase was dried over anhydrous sodium sulfate and concentrated. The residue was purified by flash chromatography using gradient elution (TEA:MeOH:EtOAc:Hex 5:0:25:75 to 5:5:25:75) to afford 0.086 g (80% yield) of TRV1598 as a brown solid. ¹H NMR (CDCl₃, 400 MHz) δ=7.64 (s, 1H), 7.56 (d, J=7.53 Hz, 1H), 7.47 (t, J=7.53 Hz, 1H), 7.43 (d, J=7.53 Hz, 1H), 7.16 (s, 1H), 6.07 (s, 1H), 4.80 (s, 2H), 4.44 (t, J=8.16 Hz, 2H), 4.02 (dd, J₁=5.52 Hz, J₂=8.53 Hz, 2H), 3.73 (t, J=4.65 Hz, 4H), 3.09 (septet, J=6.59 Hz, 1H), 2.72 (d, J=7.53 Hz, 2H), 2.47 (t, J=4.27 Hz, 4H), 1.90 (broad, 1H).

n-BuLi (0.64 ml, 2.5 M, 1.6 mmol) was added dropwise to a solution of TRV1470 (435 mg, 1.23 mmol) in THF (10 ml) at −78° C. under nitrogen atmosphere. After the mixture was stirred for 10 minutes, methyl iodide (0.153 ml, 2.46 mmol) was added to a solution, and the mixture was stirred for 1 h at −78° C. The reaction was quenched by MeOH (1 ml), and EtOAc (50 ml) was added to the solution. The mixture was washed with 1 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford 6-methyl-4-(3-(morpholinomethyl)azetidin-1-yl) benzo[c][1,2,5]oxadiazole TRV1599 (205 mg, 57%) as a red solid. ¹H NMR (400 MHz, CDCl₃): 2.35 (s, 1H), 2.46-2.49 (m, 4H), 2.70 (d, J=7.6, 2H), 3.02-3.09 (m, 1H), 3.72-3.74 (m, 4H), 3.94 (d-d, J=5.6, J=8.4, 2H), 4.37 (t, J=8.2, 2H), 5.68 (s, 1H), 6.79 (s, 1H).

TRV1600

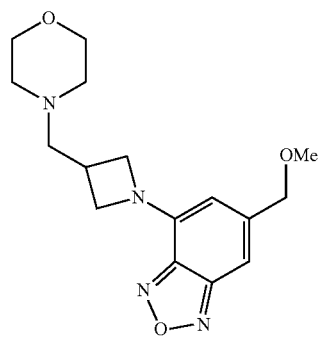

NaH (52 mg, 1.32 mmol) was added to a solution of TRV1571 (200 mg, 0.658 mmol) in THF (10 ml) at 0° C. Then methyl iodide (0.122 ml, 3.0 mmol) was added to a solution, and the mixture was stirred for 5 h from 0° C. to room temperature. After the completion, the reaction was quenched by EtOAc/H₂O (1:1, 50 ml). The mixture was washed with 1 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford 6-(methoxymethyl)-4-(3-(morpholinomethyl)azetidin-1-yl)benzo[c][1,2,5]oxadiazole TRV1600 (170 mg, 81%) as a yellow solid. ¹H NMR (400 MHz, CDCl₃): 2.46-2.48 (m, 4H), 2.70 (d, J=7.6, 2H), 3.03-3.09 (m, 1H), 3.44 (s, 3H), 3.72-3.74 (m, 4H), 3.97 (d-d, J=5.6, J=8.3, 2H), 4.38-4.42 (m, 4H), 5.83 (s, 1H), 6.97 (s, 1H).

TRV1599

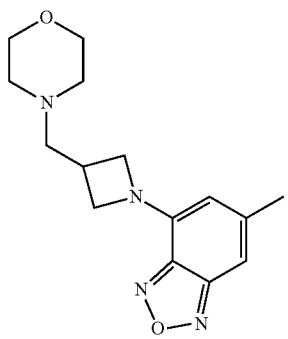

TRV1606

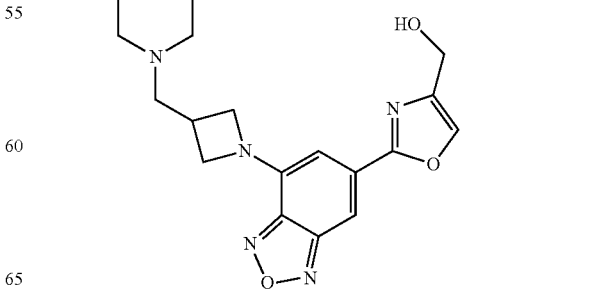

(2-(7-fluorobenzo[c][1,2,5]oxadiazol-5-yl)oxazol-4-yl) methanol (0.150 g, 0.64 mmol) and 4-(azetidin-3-ylmethyl) morpholine hydrochloride salt (0.218 g, 0.95 mmol) were dissolved in acetonitrile (5 ml) at room temperature, triethylamine (0.3 ml, 1.92 mmol) was added and mixture was heated at 80° C. for 2 h. After completion of reaction by TLC it was quenched with Na2CO3 (2M) and extracted with EtOAC to give (2-(7-(3-(morpholinomethyl) azetidin-1-yl) benzo[c][1,2,5]oxadiazol-5-yl)oxazol-4-yl)methanol TRV1606. Purification was done on ISCO flash chromatography using dichloromethane:methanol (95:5) solvent system to obtain TRV 1606 (0.210 g, 86%) as orange color solid. 1H NMR (CDCl3, 400MHz): δ 7.72 (s,1H), 7.67(s, 1H), 6.52(s,1H), 4.71(s,2H), 4.48(t,J=8.0Hz,2H), 4.06 (t, J=4.0,8.0Hz,2H), 3.75(m,4H), 3.11(m,1H), 2.73(d, J=8.0Hz, 2H), 2.48(m,4H)

TRV1607

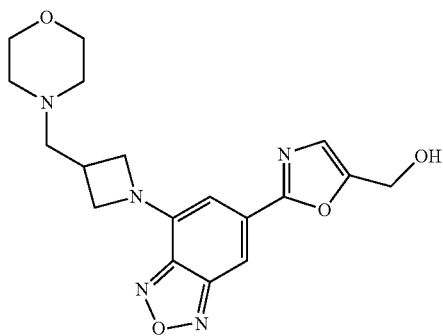

(2-(7-fluorobenzo[c][1,2,5]oxadiazol-5-yl)oxazol-5-yl) methanol (0.236 g, 1.0 mmol) and 4-(azetidin-3-ylmethyl) morpholine hydrochloride salt (0.343 g, 1.5 mmol) were dissolved in acetonitrile (5 ml) at room temperature, triethylamine (0.4 ml, 3.0 mmol) was added and mixture was heated at 80° C. for 6 h. After completion of reaction by TLC it was quenched with Na2CO3 (2M) and extracted with EtOAC to give crude product. Purification was done on ISCO flash Chromatography system using dichloromethane:methanol (95:5) solvent system to obtain (2-(7-(3-(morpholinomethyl)azetidin-1-yl) benzo[c][1,2,5]oxadiazol-5-yl)oxazol-5-yl)methanol TRV1607 (0.260 g, 70%) as orange color solid. 1H NMR (CDCl3, 400MHz): δ 7.65 (s,1H), 7.18(s,1H), 6.48(s,1H), 4.79(s,2H), 4.47(t,J=8.0Hz,2H), 4.05(t,J=8.0Hz,2H), 3.75(m,4H), 3.12(m,1H), 2.73(d, J=8.0Hz,2H), 2.48(m,4H).

TRV1608

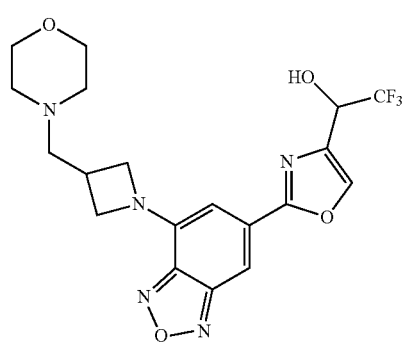

2-(7-(3-(morpholinomethyl)azetidin-1-yl) benzo[c][1,2,5]oxadiazol-5-yl) oxazole-4-carbaldehyde (0.08 g, 0.217 mmol) was dissolved in THF (5 mL) and cooled in an ice bath. CF3TMS (0.062 g, 0.434 mmol) was added and then the catalyst TBAF (0.05 mL, 1.0 M solution in THF) was added. After 30 minutes the reaction was removed from the ice bath and allowed to warm to room temperature. Once complete by TLC, recooled to 0° C. and 2 N HCl (aq) was added, stirred for 40 minutes and then basified with 2N NaOH. This mixture was extracted with EtOAc. The combined extracts were washed with water (2×), brine, filtered and concentrated. The crude material was purified via chromatography (hexane:ethyl acetate:MeOH:Et3N, 5:1:0.3:0.3) to afford 0.07 mg (75%) of 2,2,2-trifluoro-1-(2-(7-(3-(morpholinomethyl)azetidin-1-yl)benzo[c][1,2,5]oxadiazol-5-yl) oxazol-4-yl)ethan-1-ol TRV 1608 as red solid. 1H NMR (CDCl3, 400 MHz): δ 7.85(s,1H), 7.69(s,1H), 6.50(s,1H), 5.16(m,1H), 4.51(t,J=8.0Hz,2H), 4.09(t,J=8.0Hz,2H), 3.75 (m,4H), 3.15(m,1H), 2.74(d,J=4.0Hz,2H), 2.49(m,4H).

TRV1609

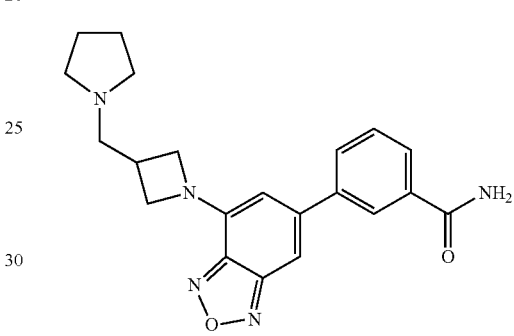

3-(7-fluorobenzo[c][1,2,5]oxadiazol-5-yl)benzamide (0.102 g, 0.4 mmol) and 1-(azetidin-3-ylmethyl) pyrrolidine hydrochloride salt (0.128 g, 0.6 mmol) were dissolved in NMP (5 ml) at room temperature, triethylamine (0.22 ml, 1.6 mmol) was added and mixture was heated at 80° C. for 2 h. After completion of reaction by TLC it was quenched with Na2CO3 (2M) and extracted with EtOAC to give crude product. Purification was done on ISCO flash chromatography system using dichloromethane:methanol (90:10) solvent system to obtain 3-(7-(3-(pyrrolidin-1-ylmethyl)azetidin-1-yl) benzo[c][1,2,5]oxadiazol-5-yl)benzamide TRV1609 (0.118 g, 78%) as orange color solid. 1H NMR (DMSO-d6, 400MHz): δ 8.22(s,1H), 8.16(s,1H), 7.94(m,2H), 7.60(t, J=8.0 Hz,1H), 7.51(s,1H), 7.41(s,1H), 6.32(s,1H), 4.42(t, J=8.0Hz, 2H), 4.0(t,J=8.0Hz,2H), 3.02(m,1H), 2.73(d, J=8.0Hz,2H), 2.45 (m,4H), 1.68(m,4H).

TRV1610

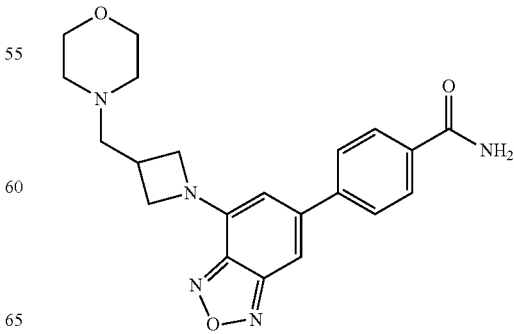

4-(7-fluorobenzo[c][1,2,5]oxadiazol-5-yl) benzamide (0.102 g, 0.4 mmol) and 4-(azetidin-3-ylmethyl) morpholine hydrochloride salt (0.137 g, 0.6 mmol) were dissolved in NMP (5 ml) at room temperature, triethylamine (0.22 ml, 1.6 mmol) was added and mixture was heated at 80° C. for 2 h. After completion of reaction by TLC it was quenched with Na2CO3 (2M) and extracted with EtOAC to give crude. Purification was done on ISCO flash Chromatography system using dichloromethane:methanol (95:5) solvent system to obtain 4-(7-(3-(morpholinomethyl)azetidin-1-yl) benzo[c][1,2,5]oxadiazol-5-yl)benzamide TRV1610 (0.068 g, 51%) as yellow solid. $^1$H NMR (DMSO-d6, 400MHz): δ 8.08(s,1H), 7.99(s,1H), 7.97(s,1H), 7.89(s,1H), 7.87(s,1H), 7.46(s,1H), 7.41(s,1H), 6.31(s,1H), 4.41(t,J=8.0Hz,2H), 3.99(m,2H), 3.58 (m,4H), 308(m,1H), 2.64(d,J=8.0Hz,2H), 2.39(m,4H).

TRV1611

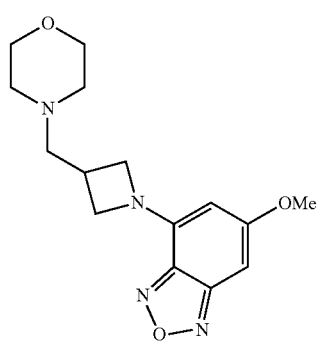

H$_2$O$_2$ (30% in H$_2$O, 2.65 ml) was added dropwise to a solution of 4-fluoro-6-(4,4,5,5-tetramethyl-1,3,2-dioxaborolan-2-yl)benzo[c][1,2,5]oxadiazole (700 mg, 2.65 mmol) and NaOH (1 N, 2.65 ml) in EtOH (10 ml) at room temperature. After the mixture was stirred for 20 minutes, the reaction was quench with HCl (1 N) and pH was adjusted to 2. The reaction mixture was concentrated, and 20 ml of EtOAc was added to the residue. The mixture was then washed with brine. The organic layer was dried and concentrated. The residue was purified via gradient elution (1:10, EtOAc/Hexane to 1:5 EtOAc/Hexane) to afford 7-fluorobenzo[c][1,2,5]oxadiazol-5-ol (330 mg, 81%) as a pale yellow solid.

MeI (0.25 ml, 4 mmol) was added to a suspension solution of 7-fluorobenzo[c][1,2,5]oxadiazol-5-ol (154 mg, 1.0 mmol) and K$_2$CO$_3$ (276 mg, 2.0 mmol) in MeCN (10 ml) at room temperature. After the mixture was stirred overnight, the reaction was concentrated to dry. The residue was added another batch of K$_2$CO$_3$ (518 mg, 3.75 mmol), 4-(azetidin-3-ylmethyl) morpholine 2HCl salt (344 mg, 1.5 mmol) and 10 ml of MeCN. The mixture was heated to 55° C. for 6 hours. After the mixture was cooled to room temperature, EtOAc (30 ml) was added to the solution. The mixture was washed with brine. The organic layer was dried and concentrated. The residue was purified via gradient elution (2:100:500, TEA/EtOAc/Hexane to 3:2:100:500 MeOH/TEA/EtOAc/Hexane) to afford 6-methoxy-4-(3-(morpholinomethyl)azetidin-1-yl)benzo[c][1,2,5]oxadiazole TRV1611 (210 mg, 69%) as a yellow solid. $^1$H NMR (400 MHz, CDCl$_3$): 2.44-2.46 (m, 4H), 2.68 (d, J=7.5, 2H), 2.98-3.06 (m, 1H), 3.69-3.72 (m, 4H), 3.84 (s, 3H), 3.89 (d-d, J=5.5, J=8.3, 2H), 4.33 (t, J=8.2, 2H), 5.51 (d, J=1.3, 1H), 6.20 (d, J=1.8, 1H). and 5-methoxy-4-methyl-7-(3-(morpholinomethyl)azetidin-1-yl)benzo[c][1,2,5]oxadiazole TRV1613 (45 mg, 14%) as a red solid. $^1$H NMR (400 MHz, CDCl3): 2.32 (s, 3H), 2.46-2.48 (m, 4H), 2.70 (d, J=7.5, 2H), 3.03-3.09 (m, 1H), 3.72-3.74 (m, 4H), 3.90 (s, 3H), 3.93 (d-d, J=5.5, J=8.0, 2H), 4.36 (t, J=8.0, 2H), 5.73 (s, 1H).

TRV1612

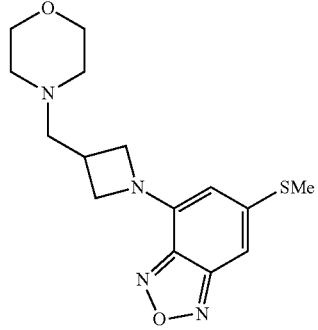

n-BuLi (1.0 ml, 2.5 M, 2.5 mmol) was added dropwise to a solution of TRV1470 (706 mg, 2.0 mmol) in THF (20 ml) at −78° C. under nitrogen atmosphere. After the mixture was stirred for 10 minutes, dimethyl disulfide (0.233 ml, 2.5 mmol) was added to a solution, and the mixture was stirred for 1 h at −78° C. The reaction was quenched by MeOH (1 ml), and EtOAc (50 ml) was added to the solution. The mixture was washed with 1 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford 6-(methylthio)-4-(3-(morpholinomethyl)azetidin-1-yl) benzo[c][1,2,5]oxadiazole TRV1612 (550 mg, 86%) as a red brown solid. $^1$H NMR (400 MHz, CDCl$_3$): 2.46-2.49 (m, 4H), 2.53 (s, 3H), 2.69 (d, J=7.5, 2H), 3.02-3.09 (m, 1H), 3.72-3.74 (m, 4H), 3.95 (d-d, J=5.5, J=8.4, 2H), 4.38 (t, J=8.2, 2H), 5.66 (s, 1H), 6.61 (s, 1H).

TRV1613

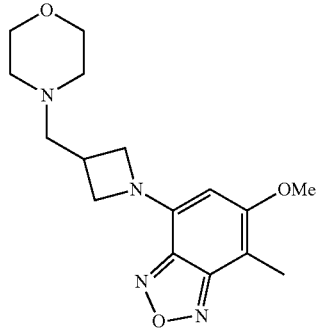

For experimental details see [00822] and [00823]

TRV1615

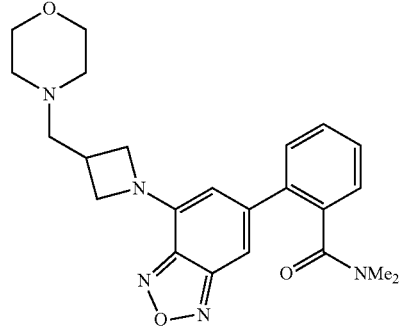

A reaction vial was charged with 6-bromo-4-(3-(morpholinomethyl)azetidin-1-yl)benzo[c][1,2,5]oxadiazole (0.44 g, 1.25 mmol), (2-(dimethylcarbamoyl)phenyl)boronic acid (0.30 g, 1.55 mmol), Pd(PPh$_3$)$_4$ (0.072 g, 0.063 mmol). After degassed and refilled with nitrogen, the vial was charged with dioxane (7.5 mL) and aq. Na$_2$CO$_3$ (3 mL, 2.0 M, 6.0 mmol). The reaction vial was further re-degassed, refilled with nitrogen, sealed, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (TEA:MeOH:EtOAc:Hex 2:0:15:75 to 2:5:15:75) to afford 0.52 g (100% yield) of TRV1615 as an orange solid. $^1$H NMR (CDCl$_3$, 400 MHz) δ=7.52-7.37 (m, 4H), 7.03 (s, 1H), 6.01 (s, 1H), 4.40 (t, J=8.16 Hz, 2H), 3.98 (dd, J$_1$=5.65 Hz, J$_2$=8.41 Hz, 2H), 3.72 (t, J=4.65 Hz, 4H), 3.06 (septet, J=6.65 Hz, 1H), 2.94 (s, 3H), 2.70 (d, J=7.53 Hz, 2H), 2.65 (s, 3H), 2.46 (t, J=4.27 Hz, 4H).

TRV1616

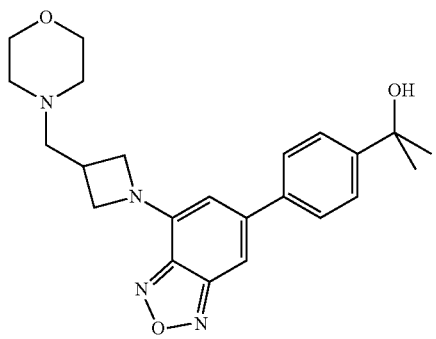

TRV1470 (0.4179 g, 1.18 mmol) and (4-(methoxycarbonyl) phenyl) boronic acid (0.2772 g, 1.54 mmol) were massed into a tube. The tube was evacuated and purged with argon (3×). DME (2.7 mL) and aqueous Na$_2$CO$_3$ (1.8 mL, 2N aq solution) was added to the tube. The tube was degassed for 5 minutes by bubbling argon gas through the solution. Pd (PPh$_3$)$_4$ (0.069 g, 0.06 mmol) was added all at once, the tube was sealed and heated to 95° C. for 16 hours. The reaction was then cooled to room temperature and diluted with DCM and water. The layers were separated and the aqueous layer was back-extracted with DCM (2×). The combined organic layers were washed with water, dried (MgSO$_4$), filtered and concentrated to give a crude brown solid. This crude material was purified via flash chromatography (60% EtOAc/hexane with 5% TEA additive) to afford 0.4752 g (99% yield) methyl ester 5. This material was dissolved in THF (15 mL) and cooled to 0° C. MeMgBr (1.2 mL, 3.0 M solution in Et$_2$O) was added dropwise and the reaction was allowed to warm to room temperature overnight. The reaction was then recooled and quenched with saturated ammonium chloride. This was extracted with EtOAc (3×) and the combined organic layers were washed with water, brine, dried (MgSO$_4$), filtered and concentrated to give the crude alcohol. The crude material was purified via chromatography (60% EtOAc/hexane with 5% TEA additive) to afford 0.2202 g (46% yield) of TRV1616. $^1$H NMR (500 MHz, DMSO) δ=7.70 (d, J=8.5 Hz, 2H), 7.56 (d, J=8.5 Hz, 2H), 7.29 (s, 1H), 6.26 (s, 1H), 5.06 (s, 1H), 4.37 (t, J=8.0 Hz, 2H), 3.97-3.94 (m, 2H), 3.57 (t, J=4.5 Hz, 4H), 3.09-3.01 (m, 1H), 2.62 (d, J=7.5 Hz, 2H), 2.38 (br s, 4H), 1.45 (s, 6H).

TRV1617

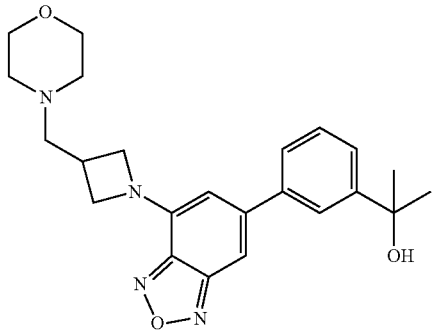

TRV1470 (0.4044 g, 1.14 mmol) and (3-(methoxycarbonyl) phenyl) boronic acid (0.2664 g, 1.48 mmol) were massed into a tube. The tube was evacuated and purged with argon (3×). DME (2.6 mL) and aqueous Na$_2$CO$_3$ (1.7 mL, 2N aq solution) was added to the tube. The tube was degassed for 5 minutes by bubbling argon gas through the solution. Pd (PPh$_3$)$_4$ (0.069 g, 0.06 mmol) was added all at once, the tube was sealed and heated to 95° C. for 16 hours. The reaction was then cooled to room temperature and diluted with DCM and water. The layers were separated and the aqueous layer was back-extracted with DCM (2×). The combined organic layers were washed with water, dried (MgSO$_4$), filtered and concentrated to give a crude brown solid. This crude material was purified via flash chromatography (70% EtOAc/hexane with 5% TEA additive) to afford 0.4769 g (99% yield) methyl ester. This material was dissolved in THF (15 mL) and cooled to 0° C. MeMgBr (1.2 mL, 3.0 M solution in Et$_2$O) was added dropwise and the reaction was allowed to warm to room temperature overnight. The reaction was then recooled and quenched with saturated ammonium chloride. This was extracted with EtOAc (3×) and the combined organic layers were washed with water, brine, dried (MgSO$_4$), filtered and concentrated to give the crude alcohol. The crude material was purified via chromatography (60% EtOAc/hexane with 5% TEA additive) to afford 0.2507 g (53% yield) of TRV1617. $^1$H NMR (500 MHz, DMSO) δ=7.82 (s, 1H), 7.57 (d, J=8.0 Hz, 1H), 7.53 (d, J=8.0 Hz, 1H), 7.41 (t, J=8.0 Hz, 1H), 7.27 (s, 1H), 6.23 (s, 1H), 5.08 (s, 1H), 4.38 (t, J=8.0 Hz, 2H), 3.97-3.94 (m, 2H), 3.57 (t, J=4.5 Hz, 4H), 3.10-3.01 (m, 1H), 2.63 (d, J=7.5 Hz, 2H), 2.38 (br s, 4H), 1.48 (s, 6H).

TRV1618

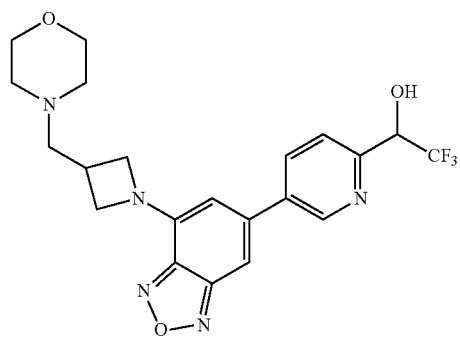

2,2,2-trifluoro-1-(5-(7-fluorobenzo[c][1,2,5]oxadiazol-5-yl)pyridin-2-yl)ethan-1-ol (0.1, 0.32 mmol) and 4-(azetidin-3-ylmethyl) morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give crude TRV-1618. Purification was done on ISCO flash chromatography system using dichloromethane:methanol (95:5) as solvent to obtain 2,2, 2-trifluoro-1-(5-(7-(3-(morpholinomethyl)azetidin-1-yl)benzo[c][1,2,5]oxadiazol-5-yl)pyridin-2-yl)ethan-1-ol TRV1618 (0.115 g, 85%) as orange color solid. $^1$H NMR (DMSO-d6, 400MHz): δ 9.0 (s,1H), 8.32(dd, J=4.0Hz, 1H), 7.74(d, J=8.0Hz, 1H), 7.47 (m, 1H), 7.15(d,J=8.0Hz,1H), 6.33(s,1H), 5.24(m, 1H), 4.41(t,J=8.0Hz,2H), 3.98(t, J=8.0Hz,2H), 3.57(m,4H), 3.10(m,1H), 2.64(d, J=4.0 Hz, 2H), 2.38(m, 4H).

2,2,2-trifluoro-1-(2-(7-fluorobenzo[c][1,2,5]oxadiazol-5-yl)pyridin-4-yl)ethan-1-ol (0.1, 0.32 mmol) and 4-(azetidin-3-ylmethyl) morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give crude TRV-1569. Purification was done on ISCO flash chromatography system using dichloromethane:methanol (95:5) as solvent to obtain 2,2, 2-trifluoro-1-(2-(7-(3-(morpholinomethyl)azetidin-1-yl)benzo[c][1,2,5]oxadiazol-5-yl)pyridin-4-yl)ethan-1-ol TRV1620 (0.110 g, 82%) as orange color solid. $^1$H NMR (DMSO-d6, 400MHz): δ 8.78 (d, J=4.0Hz, 1H), 8.23(s,1H), 7.75(s, 1H), 7.58(d, J=4.0Hz, 1H), 7.23(d, J=4.0Hz, 1H), 6.74(s, 1H), 5.39(m, 1H), 4.42(t,J=8.0Hz,2H), 3.99(t, J=8.0Hz,2H), 3.58(m,4H), 3.09(m,1H), 2.65(d, J=4.0Hz, 2H), 2.39(m, 4H).

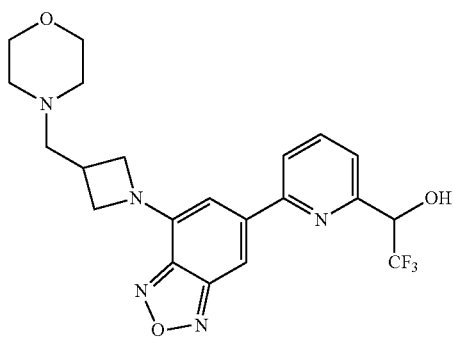

TRV1619

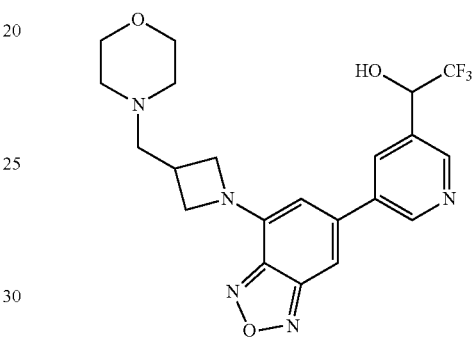

TRV1621

2,2,2-trifluoro-1-(6-(7-fluorobenzo[c][1,2,5]oxadiazol-5-yl)pyridin-2-yl)ethan-1-ol (0.1, 0.32 mmol) and 4-(azetidin-3-ylmethyl) morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give crude TRV-1569. Purification was done on ISCO flash chromatography system using dichloromethane:methanol (95:5) as solvent to obtain 2,2, 2-trifluoro-1-(6-(7-(3-(morpholinomethyl)azetidin-1-yl)benzo[c][1,2,5]oxadiazol-5-yl)pyridin-2-yl)ethan-1-ol TRV1619 (0.105 g, 80%) as orange color solid. $^1$H NMR (DMSO-d6, 400MHz): δ 8.18(d,J=8.0Hz, 1H), 8.06(t, J=8.0Hz, 1H), 7.84(s, 1H), 7.68(d,J=8.0Hz, 1H), 7.12(d, J=4.0Hz,1H), 6.78(s, 1H), 5.33(m, 1H), 4.38(t, J=8.0 Hz, 2H), 3.97(t, J=8.0Hz, 2H), 3.58(m,4H), 3.10(m,1H), 2.64(d, J=4.0Hz, 2H), 2.38(m, 4H).

2,2,2-trifluoro-1-(5-(7-fluorobenzo[c][1,2,5]oxadiazol-5-yl)pyridin-3-yl)ethan-1-ol (0.1, 0.32 mmol) and 4-(azetidin-3-ylmethyl) morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give crude TRV-1569. Purification was done on ISCO flash chromatography system using dichloromethane:methanol (95:5) as solvent to obtain 2,2, 2-trifluoro-1-(5-(7-(3-(morpholinomethyl)azetidin-1-yl)benzo[c][1,2,5]oxadiazol-5-yl)pyridin-3-yl)ethan-1-ol TRV-1621 (0.099 g, 75%) as orange color solid. $^1$H NMR (DMSO-d6, 400MHz): δ 9.04(d, J=4.0Hz, 1H), 8.75(s, 1H), 8.26(s,1H), 7.42(s,1H) 7.21(d,J=8.0Hz,1H), 6.27(s, 1H), 5.43(m, 1H), 4.98(d, J=8.0 Hz, 1H), 4.43(t,J=8.0Hz,2H), 4.01(t,J=8.0Hz,2H), 3.57(m,4H), 3.11(m,1H), 2.64(d, J=4.0Hz, 2H), 2.39(m, 4H).

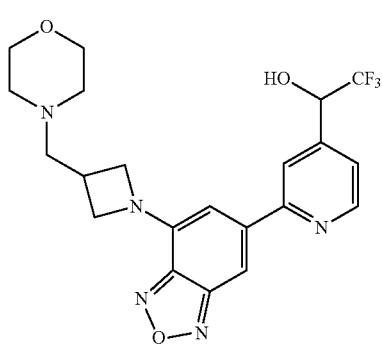

TRV1620

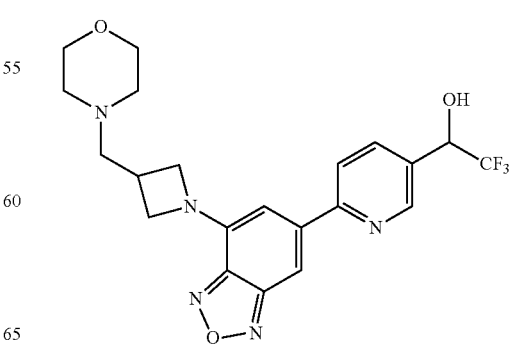

TRV1622

2,2,2-trifluoro-1-(6-(7-fluorobenzo[c][1,2,5]oxadiazol-5-yl)pyridin-3-yl)ethan-1-ol (0.1, 0.32 mmol) and 4-(azetidin-3-ylmethyl) morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na2CO3 (2M) and extracted with EtOAC to give crude TRV-1569. Purification was done on ISCO flash chromatography system using dichloromethane:methanol (95:5) as solvent to obtain 2,2,2-trifluoro-1-(6-(7-(3-(morpholinomethyl)azetidin-1-yl)benzo[c][1,2,5]oxadiazol-5-yl)pyridin-3-yl)ethan-1-ol TRV1622 (0.095 g, 73%) as orange color solid. $^1$H NMR (DMSO-d6, 400MHz): δ 8.80(s, 1H), 8.22(d,J=8.0Hz,1H), 8.03(d,J=8.0Hz,1H), 7.81(s, 1H), 7.19(s, 1H), 6.77(s, 1H), 5.41(m, 1H), 4.43(m,2H), 4.02(m,2H), 3.96(m,4H), 3.10(m, 1H), 2.64(d, J=4.0Hz, 2H), 2.38(m, 4H).

TRV1625

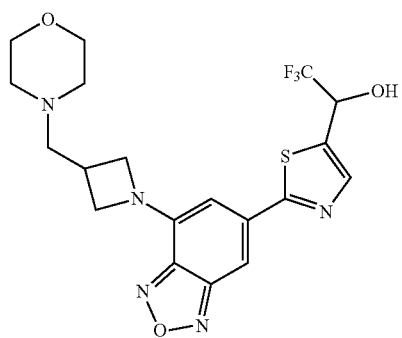

A reaction vial was charged with 4-fluoro-6-(4,4,5,5-tetramethyl-1,3,2-dioxaborolan-2-yl)benzo[c][1,2,5]oxadiazole (0.35 g, 1.34 mmol), 1-(2-bromothiazol-5-yl)-2,2,2-trifluoroethan-1-ol (0.28 g, 1.07 mmol), Pd(PPh$_3$)$_4$ (0.090 g, 0.080 mmol). After degassed and refilled with nitrogen, the vial was charged with dioxane (5 mL) and aq. Na$_2$CO$_3$ (3 mL, 2.0 M, 6.0 mmol). The reaction vial was further re-degassed, refilled with nitrogen, sealed, and then heated to 90° C. until the reaction was complete. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (EtOAc:Hex 0:100 to 20:80) to afford 0.20 g (60% yield) of 2,2,2-trifluoro-1-(2-(7-fluorobenzo[c][1,2,5]oxadiazol-5-yl)thiazol-5-yl)ethan-1-ol as a colorless solid.

2,2,2-Trifluoro-1-(2-(7-fluorobenzo[c][1,2,5]oxadiazol-5-yl)thiazol-5-yl)ethan-1-ol (0.20 g, 0.64 mmol) obtained above and 4-(azetidin-3-ylmethyl)morpholine dihydrochloride (0.23 g, 1.00 mmol) was suspended in MeCN (5 mL). To the suspension was added TEA (0.35 mL, 2.55 mmol). The resultant solution was heated to 50° C. overnight, cooled to room temperature, diluted with ethyl acetate, and washed with brine. The organic phase was dried over anhydrous sodium sulfate and concentrated. The residue was purified by flash chromatography using gradient elution (MeOH:DCM 0:100 to 5:95) to afford 0.25 g (86% yield) of TRV1625 as an orange solid. $^1$H NMR (CDCl$_3$, 400 MHz) δ=8.06 (s, 1H), 7.67 (s, 1H), 7.55 (d, J=5.77 Hz, 1H), 6.51 (s, 1H), 5.74 (pentet, J=6.60 Hz, 1H), 4.40 (t, J=8.15 Hz, 2H), 3.97 (t, J=6.90 Hz, 2H), 3.57 (t, J=4.27 Hz, 4H), 3.07 (septet, J=6.65 Hz, 1H), 2.63 (d, J=7.53 Hz, 2H), 2.44-2.33 (m, 4H).

TRV1626

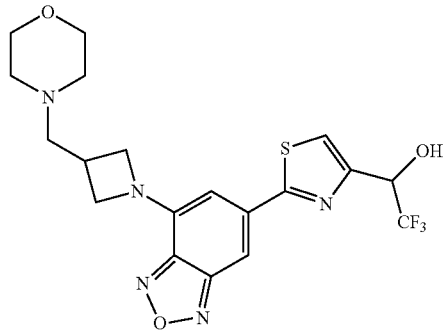

A reaction vial was charged with 4-fluoro-6-(4,4,5,5-tetramethyl-1,3,2-dioxaborolan-2-yl)benzo[c][1,2,5]oxadiazole (0.29 g, 1.10 mmol), 2-bromothiazole-4-carbaldehyde (0.19 g, 1.00 mmol), XPhos Pd G2 (0.024 g, 0.030 mmol). The vial was degassed and refilled with nitrogen. To the vial was added dioxane (3 mL) and aq. K$_3$PO$_4$ (3.3 mL, 0.62 M, 2.05 mmol). The reaction vial was re-degassed, refilled with nitrogen, sealed, and then heated to 60° C. for 24 h. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (EtOAc:Hex 0:100 to 20:80) to afford 0.120 g (48% yield) of 2-(7-fluorobenzo[c][1,2,5]oxadiazol-5-yl)thiazole-4-carbaldehyde as a colorless solid.

2-(7-Fluorobenzo[c][1,2,5]oxadiazol-5-yl) thiazole-4-carbaldehyde (0.22 g, 0.88 mmol) and trimethyl (trifluoromethyl) silane (0.20 mL, 1.30 mmol) was dissolved in anhydrous THF (7.5 mL). The solution was cooled in an ice-water bath before TBAF (0.080 mL, 1M, 0.080 mmol) was dropwise added. The resultant dark solution was stirred at ice-water bath temperature until it was complete, and then quenched with 2N aq. HCl. The reaction mixture was warmed to room temperature, stirred for 0.5 h, then diluted with water, and extracted with ethyl acetate. The ethyl acetate phase was dried over anhydrous sodium sulfate and concentrated. The residue was purified by flash chromatography using gradient elution (EtOAc:DCM:Hex 0:30:50 to 20:30:50) to afford 0.060 g (21% yield) of 2, 2, 2-trifluoro-1-(2-(7-fluorobenzo[c][1,2,5]oxadiazol-5-yl) thiazol-4-yl) ethan-1-ol as a white solid.

To a solution of 2,2,2-trifluoro-1-(2-(7-fluorobenzo[c][1,2,5]oxadiazol-5-yl)thiazol-4-yl)ethan-1-ol (0.060 g, 0.19 mmol) in acetonitrile (5 mL) was added 1-(azetidin-3-ylmethyl)morpholine dihydrochloride (0.060 g, 0.26 mmol) followed by TEA (0.10 mL, 0.72 mmol). The reaction was then heated to 50° C. until the reaction was complete. The mixture was diluted with water and extracted with ethyl acetate. The ethyl acetate phase was dried over anhydrous sodium sulfate and concentrated. The residue was purified by flash chromatography using gradient elution (MeOH:DCM 0:100 to 5:100) to afford 0.065 g (76% yield) of TRV1626 as an orange solid. $^1$H NMR (DMSO, 400 MHz) δ=7.98 (s, 1H), 7.66 (s, 1H), 7.09 (d, J=6.27 Hz, 1H), 6.49 (s, 1H), 5.40 (pentet, J=6.90 Hz, 1H), 4.41 (t, J=8.15 Hz, 2H), 3.98 (dd, J$_1$=6.02 Hz, J$_2$=8.03 Hz, 2H), 3.57 (t, J=4.40 Hz, 4H), 3.07 (septet, J=6.65 Hz, 1H), 2.64 (d, J=7.53 Hz, 2H), 2.44-2.34 (m, 4H).

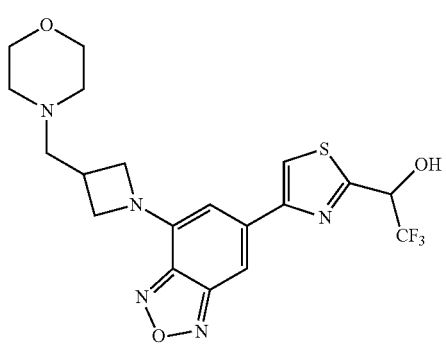

TRV1627

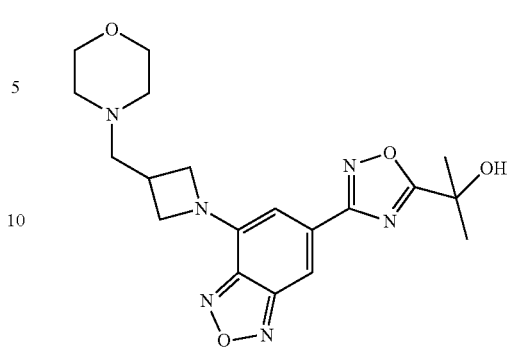

TRV1628

A reaction vial was charged with 4-fluoro-6-(4,4,5,5-tetramethyl-1,3,2-dioxaborolan-2-yl)benzo[c][1,2,5]oxadiazole (0.58 g, 2.20 mmol), 4-bromothiazole-2-carbaldehyde (0.38 g, 2.00 mmol), XPhos Pd G2 (0.047 g, 0.060 mmol). The vial was degassed and refilled with nitrogen. To the vial was added dioxane (6.5 mL) and aq. $K_3PO_4$ (6.5 mL, 0.62 M, 4.00 mmol). The reaction vial was re-degassed, refilled with nitrogen, sealed, and then heated to 60° C. for 24 h. The mixture was diluted with water, added 3 mL of 2N NaOH, and extracted with ethyl acetate. The ethyl acetate phase was dried over anhydrous sodium sulfate and concentrated. The residue was purified by flash chromatography using gradient elution (EtOAc:Hex 0:100 to 10:90) to afford 0.36 g (72% yield) of 4-(7-fluorobenzo[c][1,2,5]oxadiazol-5-yl) thiazole-2-carbaldehyde as a colorless solid.

4-(7-Fluorobenzo[c][1,2,5]oxadiazol-5-yl)thiazole-2-carbaldehyde (0.36 g, 1.44 mmol) and trimethyl(trifluoromethyl)silane (0.35 mL, 2.28 mmol) was dissolved in anhydrous THF (10 mL). The solution was cooled in an ice-water bath before TBAF (0.15 mL, 1M, 0.15 mmol) was dropwise added. The resultant dark solution was stirred at ice-water bath temperature until it was complete, and then quenched with 2N aq. HCl. The reaction mixture was warmed to room temperature, stirred for 0.5 h, then diluted with water, and extracted with ethyl acetate. The ethyl acetate phase was dried over anhydrous sodium sulfate and concentrated. The residue was purified by flash chromatography using gradient elution (EtOAc:DCM:Hex 0:30:50 to 20:30:50) to afford 0.050 g (11% yield) of 2, 2, 2-trifluoro-1-(4-(7-fluorobenzo[c][1,2,5]oxadiazol-5-yl)thiazol-2-yl)ethan-1-ol as a white solid.

To a solution of 2,2,2-trifluoro-1-(4-(7-fluorobenzo[c][1,2,5]oxadiazol-5-yl)thiazol-2-yl)ethan-1-ol (0.050 g, 0.16 mmol) in acetonitrile (5 mL) was added 1-(azetidin-3-ylmethyl)morpholine dihydrochloride (0.045 g, 0.20 mmol) followed by TEA (0.080 mL, 0.58 mmol). The reaction was then heated to 50° C. until the reaction was complete. The mixture was diluted with water and extracted with ethyl acetate. The ethyl acetate phase was dried over anhydrous sodium sulfate and concentrated. The residue was purified by flash chromatography using gradient elution (MeOH: DCM 0:100 to 5:100) to afford 0.060 g (84% yield) of TRV1627 as an orange solid. $^1$H NMR (DMSO, 400 MHz) δ=8.57 (s, 1H), 7.94 (d, J=6.02 Hz, 1H), 7.65 (s, 1H), 6.60 (s, 1H), 5.67 (pentet, J=6.65 Hz, 1H), 4.38 (t, J=7.78 Hz, 2H), 3.96 (dd, $J_1$=6.27 Hz, $J_2$=8.03 Hz, 2H), 3.58 (t, J=4.15 Hz, 4H), 3.07 (septet, J=6.75 Hz, 1H), 2.64 (d, J=7.53 Hz, 2H), 2.44-2.34 (m, 4H).

CuCN (594 mg, 6.6 mmol) and TRV1470 (1.06 g, 3.0 mmol) were added to dry NMP (8 ml). The vial was purged with nitrogen for several times. The mixture was heated to 150° C. and stirred for 10 hours. After completion checked by TLC, the reaction was quenched with aqueous ammonia hydroxide (5 ml), and EtOAc (50 ml) was added to the solution. The mixture was washed with 1 N NaOH and brine. The organic layer was dried and concentrated. The residue was purified via gradient elution (5:100:500, TEA/EtOAc/Hexane to 2:5:100:500 MeOH/TEA/EtOAc/Hexane) to afford TRV-1570 (708 mg, 79%) as a red solid.

Hydroxylamine hydrochloride (167 mg, 2.4 mmol) and sodium hydroxide (96 mg, 2.4 mmol) were added to a solution of TRV-1570 (598 mg, 2 mmol) in methanol at room temperature. The reaction mixture was stirred for two days at room temperature. Solvent was evaporated and the residue was used for the next step without purification.

N,N-Diisopropylethylamine (0.9 mL, 5.2 mol) was added to N-hydroxy-7-(3-(morpholinomethyl)azetidin-1-yl)benzo[c][1,2,5]oxadiazole-5-carboximidamide (664 mg, 2.0 mol) in DMF (15 mL) at room temperature under nitrogen. The mixture was cooled to 0° C. and ethyl oxalyl chloride (0.29 mL, 2.6 mmol) added dropwise. After stirring at 0° C. for 10 min, the mixture was warmed to room temperature and then to 50° C. and stirred for 3 h. The mixture was diluted with EtOAc (50 mL) and washed with brine (3×50 mL). The solution was dried ($Na_2SO_4$) and evaporated in vacuo. The residue was purified via gradient elution (2:100:500, TEA/EtOAc/Hexane to 2:2:100:500 MeOH/TEA/EtOAc/Hexane) to afford ethyl 3-(7-(3-(morpholinomethyl)azetidin-1-yl)benzo[c][1,2,5]oxadiazol-5-yl)-1,2,4-oxadiazole-5-carboxylate (397 mg, 48%) as red oil.

MeMgBr (0.50 ml, 1.5 mmol) was added to a solution of ethyl 3-(7-(3-(morpholinomethyl) azetidin-1-yl)benzo[c][1,2,5]oxadiazol-5-yl)-1,2,4-oxadiazole-5-carboxylate (200 mg, 0.48 mmol) THF (10 ml) at 0° C. After the mixture was stirred 2 h, the reaction was quenched by EtOAc/$H_2O$ (1:1, 50 ml). The mixture was washed with brine. The organic layer was dried and concentrated. The residue was purified via gradient elution (2:100:500, TEA/EtOAc/Hexane to 3:2:100:500 MeOH/TEA/EtOAc/Hexane) to afford TRV1628 (130 mg, 67%) as a red solid. $^1$H NMR (400 MHz, CDCl3): 1.71 (s, 6H), 2.47-2.49 (m, 4H), 2.72 (d, J=7.5, 2H), 3.05-3.11 (m, 1H), 3.72-3.75 (m, 4H), 4.04 (d-d, J=5.5, J=8.5, 2H), 4.46 (t, J=8.3, 2H), 6.44 (s, 1H), 7.81 (s, 1H).

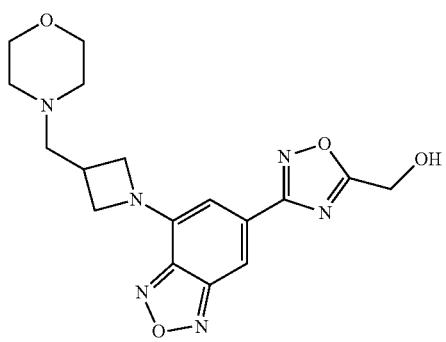

TRV1629

NaBH₄ (46 mg, 1.21 mmol) was added to a solution of ethyl 3-(7-(3-(morpholinomethyl)azetidin-1-yl)benzo[c][1,2,5]oxadiazol-5-yl)-1,2,4-oxadiazole-5-carboxylate (250 mg, 0.604 mmol) in THF (10 ml) at 0° C. After the mixture was stirred 2 h, the reaction was quenched by EtOAc/H₂O (1:1, 50 ml). The mixture was washed with brine. The organic layer was dried and concentrated. The residue was purified via gradient elution (2:100:500, TEA/EtOAc/Hexane to 3:2:100:500 MeOH/TEA/EtOAc/Hexane) to afford 3-(7-(3-(morpholinomethyl)azetidin-1-yl)benzo[c][1,2,5]oxadiazol-5-yl)-1,2,4-oxadiazol-5-yl)methanol TRV1629 (40 mg, 18%) as a red solid. ¹H NMR (400 MHz, CDCl3): 2.48-2.50 (m, 4H), 2.73 (d, J=7.3, 2H), 3.06-3.11 (m, 1H), 3.73-3.75 (m, 4H), 4.03 (d-d, J=5.6, J=8.4, 2H), 4.46 (t, J=8.3, 2H), 4.99 (s, 2H), 6.44 (s, 1H), 7.79 (s, 1H).

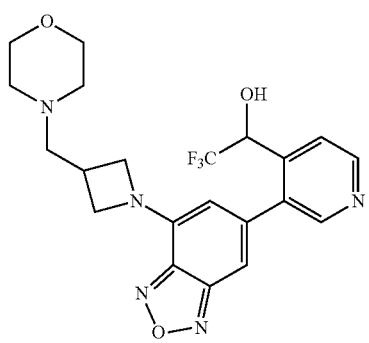

TRV1636

2,2,2-trifluoro-1-(3-(7-fluorobenzo[c][1,2,5]oxadiazol-5-yl)pyridin-2-yl)ethan-1-ol (0.1 g, 0.32 mmol) and 4-(azetidin-3-ylmethyl) morpholine hydrochloride salt (0.110 g, 0.47 mmol) were dissolved in Acetonitrile (5 ml) at room temperature, triethylamine (0.18 ml, 1.28 mmol) was added and mixture was heated at 80° C. for 2 h. After completion of reaction by TLC it was quenched with Na₂CO₃ (2M) and extracted with EtOAC to give crude product. Purification was done on ISCO flash chromatography system using dichloromethane:methanol (95:5) as solvent to obtain 2, 2, 2-trifluoro-1-(3-(7-(3-(morpholinomethyl)azetidin-1-yl) benzo[c][1,2,5]oxadiazol-5-yl) pyridin-4-yl) ethan-1-ol TRV1636 (0.080 g, 75%) as orange color solid. ¹H NMR (DMSO-d6, 400MHz): δ 8.74(d,J=8.0 Hz,1H), 8.57(s,1H), 7.70(d, J=8.0 Hz, 1H), 7.19(d, J=8.0 Hz, 1H), 7.03(s, 1H), 5.85(s,1H), 5.24(m, 1H), 4.40(m,2H), 3.95(m,2H), 3.56 (m,4H), 3.09(m, 1H), 2.64(d, J=8.0 Hz, 2H), 2.37(m, 4H).

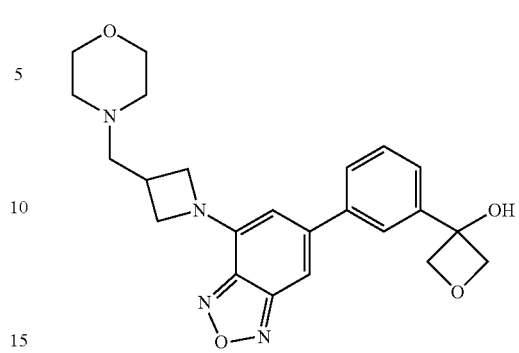

TRV1638

TRV1470 (0.4197 g, 1.19 mmol) and 3-bromophenylboronic acid (0.2510 g, 1.25 mmol) were sealed in a tube. The tube was evacuated and purged with argon (3 cycles). 2M Na₂CO₃ (1.8 mL, 2.0 M aq solution) was added along with DME (2.7 mL). Then Pd(PPh₃)₄ (0.0690 g, 0.059 mmol) was added all at once. The tube was re-sealed and heated to 95° C. for 5 hours. After cooling to room temperature, the mixture was diluted with water and EtOAc. The layers were separated and the aqueous layer was then back-extracted. The combine organic extracts were then washed with H₂O (3×), brine and then dried (Na₂SO₄), filtered and concentrated. The crude material was purified via chromatography (50% EtOAc/hexane+5% TEA) to afford 0.3918 g (75% yield) of arylbromide 2. The arylbromide (0.3881 g, 0.90 mmol) was dissolved in THF (10 mL) and cooled to −78° C. nBuLi (0.74 mL, 1.6 M solution in hexane) was added dropwise over 5 minutes. The reaction was allowed to stir for 15 minutes and then a solution of 3-oxetanone (0.1042 g, 1.45 mmol) in THF (1 mL) was added dropwise. The reaction was then stirred overnight while slowly warming to room temperature. Recooled in an ice bath and quenched with saturated ammonium chloride and then diluted with EtOAc. The layers were separated and the aqueous layer was back-extracted with EtOAc (3×). the combined layers were then washed with water (2×), brine, dried (MgSO₄), filtered and concentrated. The crude material was ultimately purified with column chromatography (70% EtOAc/hexane+5% TEA) to afford TRV1638 (0.1406 g, 37% yield). ¹H NMR (DMSO, 500 MHz) δ=7.90 (s, 1H), 7.69 (d, J=7.5 Hz, 2H), 7.52 (t, J=7.5 Hz, 1H), 7.32 (s, 1H), 6.41 (s, 1H), 6.25 (s, 1H), 4.81-4.77 (m, 4H), 4.38 (t, J=8.5 Hz, 2H), 3.98-3.95 (m, 2H), 3.57 (t, J=4.5 Hz, 4H), 3.09-3.01 (m, 1H), 2.64 (d, J=7.5 Hz, 2H), 2.38 (br s, 4H).

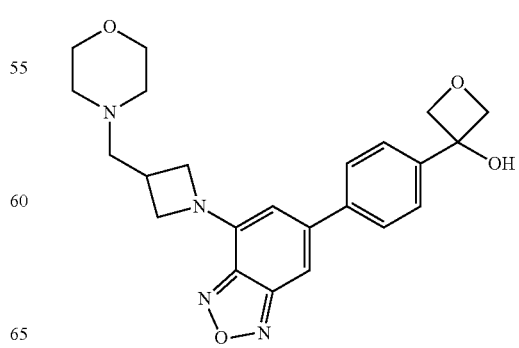

TRV1639

TRV1470 (0.4054 g, 1.15 mmol) and 4-bromophenylboronic acid (0.2430 g, 1.21 mmol) were sealed in a tube. The tube was evacuated and purged with argon (3 cycles). 2M Na$_2$CO$_3$ (1.8 mL, 2.0 M aq solution) was added along with DME (2.7 mL). Then Pd(PPh$_3$)$_4$ (0.0670 g, 0.058 mmol) was added all at once. The tube was re-sealed and heated to 95° C. for 5 hours. After cooling to room temperature, the mixture was diluted with water and EtOAc. The layers were separated and the aqueous layer was then back-extracted. The combine organic extracts were then washed with H$_2$O (3×), brine and then dried (Na$_2$SO$_4$), filtered and concentrated. The crude material was purified via chromatography (40% EtOAc/hexane+5% TEA) to afford 0.3273 g (66% yield) of arylbromide 1. The arylbromide (0.3054 g, 0.71 mmol) was dissolved in THF (10 mL) and cooled to −78° C. nBuLi (0.50 mL, 1.6 M solution in hexane) was added dropwise over 5 minutes. The reaction was allowed to stir for 15 minutes and then a solution of 3-oxetanone (0.0793 g, 1.1 mmol) in THF (1 mL) was added dropwise. The reaction was then stirred overnight while slowly warming to room temperature. Recooled in an ice bath and quenched with saturated ammonium chloride and then diluted with EtOAc. The layers were separated and the aqueous layer was back-extracted with EtOAc (3×). The combined layers were then washed with water (2×), brine, dried (MgSO$_4$), filtered and concentrated. The crude material was ultimately purified with column chromatography (85% EtOAc/hexane+5% TEA) to afford TRV1639 (0.1084 g, 36% yield). $^1$H NMR (DMSO, 500 MHz) δ=7.82 (d, J=8.0 Hz, 2H), 7.71 (d, J=8.0 Hz, 2H), 7.33 (s, 1H), 6.42 (s, 1H), 6.28 (s, 1H), 4.80 (d, J=6.5 Hz, 2H), 4.71 (d, J=6.5 Hz, 2H), 4.38 (t, J=8.0 Hz, 2H), 3.97 (t, J=8.0 Hz, 2H), 3.57 (t, J=4.5 Hz, 4H) 3.09-3.01 (m, 1H), 2.63 (d, J=7.5 Hz, 2H), 2.38 (br s, 4H).

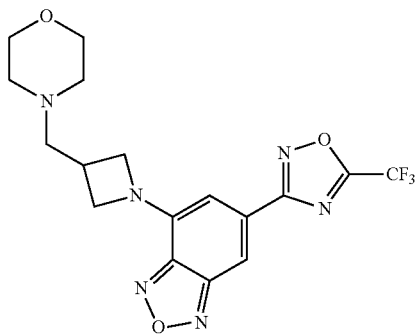

TRV1643

Diisopropylethylamine (1.043 ml, 6.0 mmol) and trifluoroacetic anhydrous (0.42 ml, 3.0 mmol) were added separately to a solution of N-hydroxy-7-(3-(morpholinomethyl) azetidin-1-yl) benzo[c][1,2,5]oxadiazole-5-carboximidamide (500 mg, 1.50 mmol) in THF (20 ml) and DMF (30 ml) at room temperature. After the mixture was stirred 2 h, the reaction was added with EtOAc (60 ml). The mixture was washed with brine. The organic layer was dried and concentrated. The residue was purified via gradient elution (5:100:500, TEA/EtOAc/Hexane to 3:5:100:500 MeOH/TEA/EtOAc/Hexane) to afford 4-(3-(morpholinomethyl) azetidin-1-yl)-6-(5-(trifluoromethyl)-1,2,4-oxadiazol-3-yl) benzo[c][1,2,5]oxadiazole TRV1643 (350 mg, 57%) as a red solid. $^1$H NMR (400 MHz, CDCl$_3$): 2.48-2.50 (m, 4H), 2.73 (d, J=7.5, 2H), 3.07-3.16 (m, 1H), 3.73-3.75 (m, 4H), 4.09 (d-d, J=5.3, J=8.5, 2H), 4.51 (t, J=8.2, 2H), 6.45 (s, 1H), 7.88 (s, 1H).

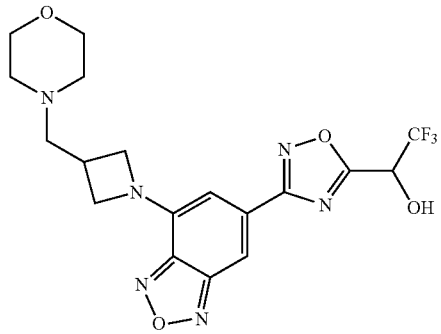

TRV1644

DCC (618 mg, 3.0 mmol) was added to a solution of N-hydroxy-7-(3-(morpholinomethyl) azetidin-1-yl) benzo[c][1,2,5]oxadiazole-5-carboximidamide (500 mg, 1.5 mmol) and 3,3,3-trifluoro-lactic acid (432 mg, 3.0 mmol) in THF (20 ml) and DMF (30 ml) at room temperature. After the mixture was stirred 3 h, the reaction was heated to 70° C. for overnight. One more equivalent of DCC (309 mg, 1.5 mmol) and 3, 3, 3-trifluoro-lactic acid (216 mg, 1.5 mmol) were added to the reaction mixture and the reaction was stirred for 8 hours at this temperature. The reaction was added with EtOAc (60 ml). The mixture was washed with brine. The organic layer was dried and concentrated. The residue was purified via gradient elution (1:99, MeOH/DCM to 3:97, MeOH/DCM) to afford 2,2,2-trifluoro-1-(3-(7-(3-(morpholinomethyl)azetidin-1-yl)benzo[c][1,2,5]oxadiazol-5-yl)-1,2,4-oxadiazol-5-yl) ethan-1-ol TRV1644 (350 mg, 53%) as an orange solid. $^1$H NMR (400 MHz, CDCl$_3$): 2.50-2.52 (m, 4H), 2.74 (d, J=7.5, 2H), 3.07-3.14 (m, 1H), 3.74-3.77 (m, 4H), 4.05 (d-d, J=5.5, J=8.5, 2H), 4.47 (t, J=8.3, 2H), 5.43 (q, J=5.9, 1H), 6.41 (s, 1H), 7.82 (s, 1H).

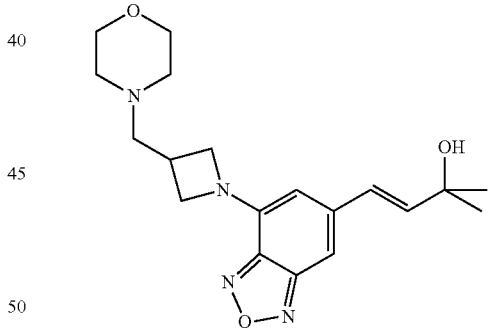

TRV1645

A round-bottomed flask was charged with 6-bromo-4-fluorobenzo[c][1,2,5]oxadiazole (3.255 g, 15.0 mmol), dppp (371 mg, 0.9 mmol) and Pd(OAc)$_2$ (101 mg, 0.45 mmol). The flask was purged with nitrogen for several times, and then dry DMF (30 ml), ethyl acrylate (4.9 ml, 45.0 mmol) and TEA (6.26 ml, 45 mmol) were added to the mixture separately.

The resulting mixture was then heated to 80° C. After the reaction was completed for 2 h, 100 ml of EtOAc was added to the mixture. The mixture was washed with brine for 3 times. The organic layer was dried and concentrated. The residue was purified via gradient elution (2:95, EtOAc/Hexane to 6:85 EtOAc/Hexane) to afford ethyl (E)-3-(7-fluorobenzo[c][1,2,5]oxadiazol-5-yl) acrylate (3.3 g, 93%) as an orange solid.

MeMgBr (10 mg, 30 mmol) was added to a solution of afford ethyl (E)-3-(7-fluorobenzo[c][1,2,5]oxadiazol-5-yl) acrylate (1.652 g, 7.0 mmol) in THF (35 ml) at −5° C. After the mixture was stirred 4 h, the reaction was quenched by 3 ml of MeOH. EtOAc (80 ml) was added to the mixture. The mixture was washed with saturated NH$_4$Cl and brine. The organic layer was dried and concentrated. The residue was purified via gradient elution (5:95, EtOAc/Hexane to 15:85 EtOAc/Hexane) to afford (E)-4-(7-fluorobenzo[c][1,2,5]oxadiazol-5-yl)-2-methylbut-3-en-2-ol (1.0 g, 64%) as a light yellow solid.

TEA (0.50 ml, 3.6 mmol) was added to a solution of (E)-4-(7-fluorobenzo[c][1,2,5]oxadiazol-5-yl)-2-methylbut-3-en-2-ol (200 mg, 0.90 mmol) and 4-(azetidin-3-ylmethyl) morpholine 2HCl salt (309 mg, 1.35 mmol) in MeCN (10 ml). The mixture was heated to 70° C. for 36 hours. After the mixture was cooled to room temperature, EtOAc (30 ml) was added to the solution. The mixture was washed with brine. The organic layer was dried and concentrated. The residue was purified via gradient elution (2:100:500, TEA/EtOAc/Hexane to 4:2:100:500 MeOH/TEA/EtOAc/Hexane) to afford (E)-2-methyl-4-(7-(3-(morpholinomethyl) azetidin-1-yl)benzo[c][1,2,5]oxadiazol-5-yl)but-3-en-2-ol TRV1645 (230 mg, 72%) as a yellow solid. $^1$H NMR (400 MHz, CDCl3): 1.46 (s, 6H), 2.47-2.49 (m, 4H), 2.71 (d, J=7.3, 2H), 3.05-3.11 (m, 1H), 3.72-3.75 (m, 4H), 3.97 (d-d, J=5.8, J=8.2, 2H), 4.41 (t, J=8.2, 2H), 5.96 (s, 1H), 5.43 (d, J=16.1, 1H), 6.59 (d, J=16.1, 1H), 6.92 (s, 1H).

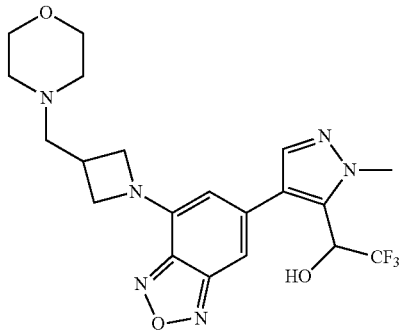

TRV1647

A reaction vial was charged with 6-bromo-4-(3-(morpholinomethyl)azetidin-1-yl)benzo[c][1,2,5]oxadiazole (0.71 g, 2.00 mmol), 1-methyl-4-(3,3,4,4-tetramethylborolan-1-yl)-1H-pyrazole (0.47 g, 2.30 mmol), Pd(PPh$_3$)$_4$ (0.070 g, 0.061 mmol). After degassed and refilled with argon, dioxane (6 mL) and aq. Na$_2$CO$_3$ (4.0 mL, 2.0 M, 8.0 mmol) was added. The reaction vial was further re-degassed, refilled with argon, sealed, and then heated to 90° C. until the reaction was complete. The mixture was diluted with water, added 3 mL of 2N NaOH, and extracted with ethyl acetate. The organic phase was dried over anhydrous sodium sulfate and concentrated. The residue was purified by flash chromatography using gradient elution (MeOH:TEA:EtOAc:Hex 0:2:25:75 to 5:2:25:75) to afford 0.70 g 6-(1-methyl-1H-pyrazol-4-yl)-4-(3-(morpholinomethyl)azetidin-1-yl) benzo[c][1,2,5]oxadiazole as an orange solid (99% of yield).

A reaction vial was charged with 6-(1-Methyl-1H-pyrazol-4-yl)-4-(3-(morpholinomethyl) azetidin-1-yl) benzo[c][1,2,5]oxadiazole (0.29 g, 0.82 mmol). After degassed and refilled with argon, THF (5 mL) was added. The resultant solution was cooled to −78° C. in a dry ice bath. n-BuLi (0.40 mL, 2.5 M, 1.00 mmol) was added dropwise. After stirred for 1 h −78° C., ethyl 2, 2, 2-trifluoroacetate (0.36 mL, 3.00 mmol) was added. The reaction was stirred at −78° C. for 2 h before quenched with methanol. The mixture was diluted with water, and extracted with ethyl acetate. The ethyl acetate phase was dried over anhydrous sodium sulfate and concentrated. The residue was purified by flash chromatography using gradient elution (MeOH:TEA:EtOAc:Hex 0:2:25:75 to 5:2:25:75) to afford 0.20 g (55% yield) of 2,2,2-trifluoro-1-(1-methyl-4-(7-(3-(morpholinomethyl) azetidin-1-yl)benzo[c][1,2,5]oxadiazol-5-yl)-1H-pyrazol-5-yl)ethan-1-one as an orange solid.

A solution of 2,2,2-trifluoro-1-(1-methyl-4-(7-(3-(morpholinomethyl)azetidin-1-yl)benzo[c][1,2,5]oxadiazol-5-yl)-1H-pyrazol-5-yl)ethan-1-one (0.050 g, 0.16 mmol) in methanol (5 mL) was cooled in an ice-water bath. Sodium borohydride (0.025 g, 0.66 mmol) was added. The reaction mixture was warmed to rt, and stirred until it was complete. The reaction was quenched with 1N aq. HCl, diluted with water, basified with aq. NaOH, and extracted with ethyl acetate. The ethyl acetate phase was dried over anhydrous sodium sulfate and concentrated. The residue was purified by flash chromatography using gradient elution (MeOH:TEA:EtOAc:Hex 0:2:25:75 to 5:2:25:75) to afford 0.18 g (90% yield) of TRV1647 as an orange solid. $^1$H NMR (CDCl$_3$, 400 MHz) δ=7.55 (s, 1H), 6.83 (s, 1H), 5.70 (s, 1H), 5.44 (q, J=7.27 Hz, 1H), 5.08 (broad, 1H), 4.34 (t, J=8.03 Hz, 1H), 4.27 (t, J=8.16 Hz, 1H), 4.14 (s, 3H), 3.96-3.86 (m, 2H), 3.71 (t, J=4.52 Hz, 4H), 3.01 (septet, J=6.90 Hz, 1H), 2.68 (d, J=7.53 Hz, 2H), 2.45 (t, J=4.27 Hz, 4H).

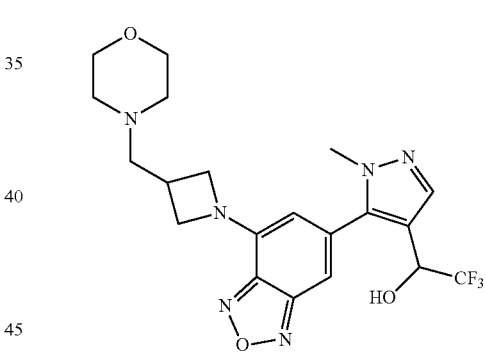

TRV1651

A reaction vial was charged with 6-bromo-4-fluorobenzo [c][1,2,5]oxadiazole (0.65 g, 3.00 mmol), 1-methyl-5-(3,3,4,4-tetramethylborolan-1-yl)-1H-pyrazole (0.72 g, 3.46 mmol), Pd(PPh$_3$)$_4$ (0.10 g, 0.090 mmol). After degassed and refilled with argon, dioxane (8 mL) and aq. Na$_2$CO$_3$ (6.0 mL, 2.0 M, 12.0 mmol) was added. The reaction vial was further re-degassed, refilled with argon, sealed, and then heated to 90° C. until the reaction was complete. The mixture was diluted with water, and extracted with ethyl acetate. The organic phase was dried over anhydrous sodium sulfate and concentrated. The residue was purified by flash chromatography using gradient elution (EtOAc:Hex:DCM 0:50:30 to 8:50:30) to afford 0.45 g of 4-fluoro-6-(1-methyl-1H-pyrazol-5-yl) benzo[c][1,2,5]oxadiazole (69% of yield) as a colorless solid.

A solution of 4-fluoro-6-(1-methyl-1H-pyrazol-5-yl) benzo[c][1,2,5]oxadiazole (0.23 g, 1.04 mmol) in DCM (5.0 mL) was cooled in an ice-water bath. Bromine (0.65 mL, 2.0 M in DCM, 1.30 mmol) was added slowly. The reaction mixture was slowly warmed to room temperature and stirred until it was complete. The reaction was concentrated and the crude product was used directly in the next step without further purification.

A solution of 6-(4-bromo-1-methyl-1H-pyrazol-5-yl)-4-fluorobenzo[c][1,2,5]oxadiazole (0.42 g, 1.41 mmol) in acetonitrile (10 mL) was added 1-(azetidin-3-ylmethyl)morpholine dihydrochloride (0.40 g, 1.75 mmol) followed by TEA (1.10 mL, 7.91 mmol). The reaction was then heated to 50° C. until the reaction was complete. The mixture was diluted with water and extracted with ethyl acetate. The ethyl acetate phase was dried over anhydrous sodium sulfate and concentrated. The residue was used directly in the next step without further purification.

A reaction vial was charged with 6-(4-bromo-1-methyl-1H-pyrazol-5-yl)-4-(3-(morpholinomethyl)azetidin-1-yl) benzo[c][1,2,5]oxadiazole (0.11 g, 0.25 mmol). After degassed and refilled with argon, THF (3 mL) was added. The resultant solution was cooled to −78° C. in a dry ice bath. n-BuLi (0.13 mL, 2.5 M, 0.31 mmol) was added dropwise. After stirred for 1 h −78° C., ethyl 2, 2, 2-trifluoroacetate (0.12 mL, 1.00 mmol) was added. The reaction was stirred at −78° C. for 2 h before quenched with methanol. The mixture was diluted with water, and extracted with ethyl acetate. The ethyl acetate phase was dried over anhydrous sodium sulfate and concentrated. The residue was purified by flash chromatography using gradient elution (MeOH:TEA:EtOAc:Hex 0:2:25:75 to 5:2:25:75) to afford 0.040 g of 2,2,2-trifluoro-1-(1-methyl-5-(7-(3-(morpholinomethyl)azetidin-1-yl)benzo[c][1,2,5]oxadiazol-5-yl)-1H-pyrazol-4-yl)ethan-1-one.

A solution of 2, 2, 2-trifluoro-1-(1-methyl-5-(7-(3-(morpholinomethyl)azetidin-1-yl) benzo[c][1,2,5]oxadiazol-5-yl)-1H-pyrazol-4-yl) ethan-1-one (0.13 g, 0.28 mmol) in THF (5 mL) was cooled in an ice-water bath. Sodium borohydride (0.016 g, 0.42 mmol) in aq. NaOH (0.80 mL, 1 M, 0.80 mmol) was added. The reaction mixture was stirred at ice-water bath temperature until it was complete. The reaction was diluted with ethyl acetate and washed with brine. The ethyl acetate phase was dried over anhydrous sodium sulfate and concentrated. The residue was purified by flash chromatography using gradient elution (MeOH:DCM 0:100 to 5:95) to afford 0.11 g (88% yield) of TRV1651 as an orange solid. ¹H NMR (CDCl₃, 400 MHz) δ=7.75 (s, 1H), 6.98 (s, 1H), 5.68 (s, 1H), 4.84 (q, J=7.03 Hz, 1H), 4.54-4.44 (m, 2H), 4.08-3.98 (m, 2H), 3.86-3.82 (m, 3H), 3.76-3.70 (m, 4H), 3.11 (septet, J=6.53 Hz, 1H), 2.74 (d, J=7.28 Hz, 2H), 2.52-2.45 (m, 4H).

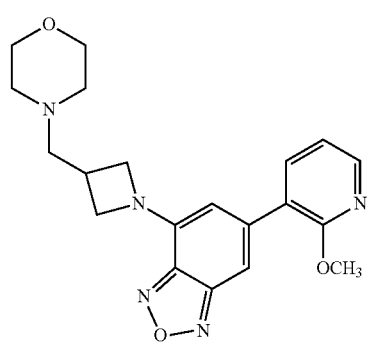

TRV1658

6-(2-methoxypyridin-3-yl)-4-fluorobenzo[c][1,2,5]oxadiazole (0.150 g, 0.612 mmol) and 4-(azetidin-3-yl methyl) morpholine hydrochloride salt (0.140 g, 0.612 mmol) were dissolved in Acetonitrile (5 ml) at room temperature, triethylamine (0.3 ml, 1.85 mmol) was added and mixture was heated at 50° C. overnight. After completion of reaction by TLC it was quenched with Na2CO3 (2M) and extracted with EtOAC to give crude product. Purification was done on ISCO flash chromatography system using dichloromethane:methanol (95:5) as solvent to obtain 6-(2-methoxypyridin-3-yl)-4-(3-(morpholinomethyl)azetidin-1-yl) benzo[c][1,2,5]oxadiazole TRV1658 (0.208 g, 90%) as red color solid. ¹H NMR (CDCl₃, 400MHz): δ 8.23 (d, J=4.0 Hz, 1H), 7.68 (d, J=8.0 Hz, 1H) 7.14(s, 1H), 7.02(m, 1H), 6.02(s, 1H), 4.44(t, J=8.0 Hz,2H), 4.05(s,3H), 3.98(m,2H), 3.74(m,4H), 3.11(m, 1H), 2.73(d, J=8.0 Hz, 2H), 2.48(m,4H)

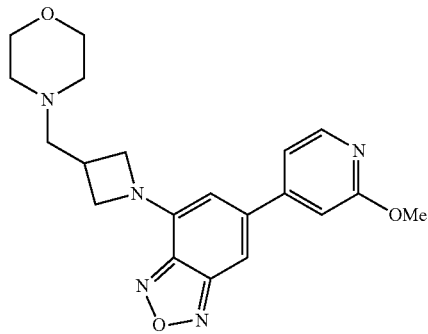

TRV1659

6-(2-methoxypyridin-4-yl)-4-fluorobenzo[c][1,2,5]oxadiazole (0.150 g, 0.612 mmol) and 4-(azetidin-3-yl methyl) morpholine hydrochloride salt (0.140 g, 0.612 mmol) were dissolved in Acetonitrile (5 ml) at room temperature, triethylamine (0.3 ml, 1.85 mmol) was added and mixture was heated at 50° C. overnight. After completion of reaction by TLC it was quenched with Na2CO3 (2M) and extracted with EtOAC to give crude product. Purification was done on ISCO flash chromatography system using dichloromethane:methanol (95:5) as solvent to obtain 6-(2-methoxypyridin-4-yl)-4-(3-(morpholinomethyl)azetidin-1-yl) benzo[c][1,2,5]oxadiazole TRV1659 (0.2180 g, 92%) as red color solid. ¹H NMR (CDCl₃, 400MHz): δ 8.26 (d, J=8.0 Hz, 1H), 7.20(s, 1H), 7.12(d, J=8.0 Hz, 1H), 6.96(s, 1H), 5.99(s, 1H), 4.47(t, J=8.0 Hz,2H), 4.05(m,2H), 4.01(s,3H), 3.74(m,4H), 3.14(m,1H), 2.73(d, J=4.0 Hz, 2H), 2.48(m, 4H).

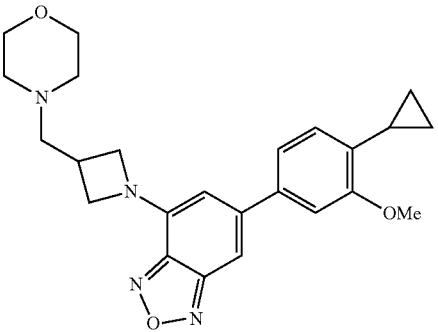

TRV1660

6-(4-cyclopropyl-3-methoxyphenyl)-4-fluorobenzo[c][1,2,5]oxadiazole (0.142 g, 0.5 mmol) and 4-(azetidin-3-ylmethyl) morpholine hydrochloride salt (0.114 g, 0.5 mmol) were dissolved in Acetonitrile (5 ml) at room temperature, triethylamine (0.2 ml, 1.5 mmol) was added and mixture was heated at 50° C. overnight. After completion of reaction by TLC it was quenched with Na2CO3 (2M) and extracted with EtOAC to give crude product.

Purification was done on ISCO flash chromatography system using dichloromethane:methanol (95:5) as solvent to obtain 6-(4-cyclopropyl-3-methoxyphenyl)-4-(3-(morpholinomethyl)azetidin-1-yl) benzo[c][1,2,5]oxadiazole TRV1660 (0.1780 g, 85%) as orange color solid. $^1$H NMR (CDCl$_3$,400 MHz): δ 7.30(s,1H), 7.08(s,1H), 7.05(d, J=8.0 Hz, 1H), 7.0(s, 1H), 5.96(s,1H), 4.42(t,J=8.0 Hz,2H), 3.99 (m,2H), 3.85(s,3H), 3.74(m,4H), 3.10(m,1H), 2.72(d, J=8.0 Hz, 2H), 2.47(m, 4H) 1.85(m,1H), 1.51(m,2H), 1.26 (m, 2H).

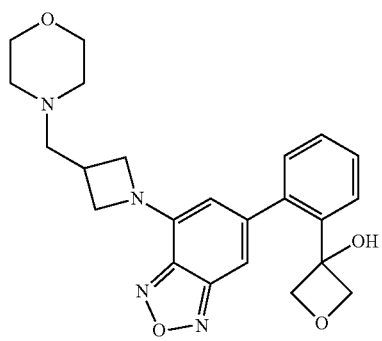

TRV1663

TRV1470 (0.4480 g, 1.27 mmol) and 2-bromophenylboronic acid (0.2678 g, 1.33 mmol) were sealed in a tube. The tube was evacuated and purged with argon (3 cycles). 2M Na$_2$CO$_3$ (1.9 mL, 2.0 M aq solution) was added along with DME (2.8 mL). Then Pd (PPh$_3$)$_4$ (0.0734 g, 0.064 mmol) was added all at once. The tube was re-sealed and heated to 95° C. for 5 hours. After cooling to room temperature, the mixture was diluted with water and EtOAc. The layers were separated and the aqueous layer was then back-extracted. The combine organic extracts were then washed with H$_2$O (3×), brine and then dried (Na$_2$SO$_4$), filtered and concentrated. The crude material was purified via chromatography (40% EtOAc/hexane+5% TEA) to afford 0.4642 g (85% yield) of arylbromide. This arylbromide (0.4642 g, 1.08 mmol) was dissolved in THF (10 mL) and cooled to −78° C. nBuLi (0.90 mL, 1.6 M solution in hexane) was added dropwise over 5 minutes. The reaction was allowed to stir for 15 minutes and then a solution of 3-oxetanone (0.1247 g, 1.73 mmol) in THF (1 mL) was added dropwise. The reaction was then stirred overnight while slowly warming to room temperature. Recooled in an ice bath and quenched with saturated ammonium chloride and then diluted with EtOAc. The layers were separated and the aqueous layer was back-extracted with EtOAc (3×). The combined layers were then washed with water (2×), brine, dried (MgSO$_4$), filtered and concentrated. The crude material was purified with column chromatography (85% EtOAc/hexane+5% TEA) to afford TRV1663 (0.3337 g, 73% yield). $^1$H NMR (DMSO, 500 MHz) δ=7.46-7.38 (m, 3H), 7.30 (d, J=7.5 Hz, 1H), 7.19 (s, 1H), 6.61 (br s, 1H), 6.15 (s, 1H), 4.62 (d, J=7.0 Hz, 2H), 4.41 (d, J=7.0 Hz, 2H), 4.34 (t, J=8.0 Hz, 2H), 3.94-3.91 (m, 2H), 3.57 (t, J=4.5 Hz, 4H), 3.07-3.01 (m, 1H), 2.63 (d, J=7.5 Hz, 2H), 2.38 (br s, 4H).

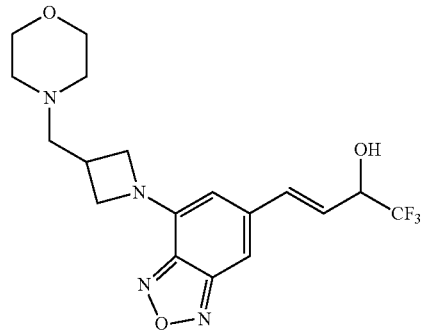

TRV1665

DIBAl (25.76 ml, 25.76 mmol) was added to a solution of afford ethyl (E)-3-(7-fluorobenzo[c][1,2,5]oxadiazol-5-yl) acrylate (1.52 g, 6.44 mmol) in THF (35 ml) at −5° C. After the mixture was stirred overnight at room temperature, the reaction was quenched by 3 ml of MeOH. EtOAc (40 ml) was added to the mixture. The mixture was washed with 1 N HCl and brine. The organic layer was dried and concentrated. The residue was purified via gradient elution (10:90, EtOAc/Hexane to 15:85 EtOAc/Hexane) to afford (E)-3-(7-fluorobenzo[c][1,2,5]oxadiazol-5-yl)prop-2-en-1-ol (340 mg, 28%) as a light yellow solid.

TEA (0.98 ml, 7.08 mmol) was added to a solution of (E)-3-(7-fluorobenzo[c][1,2,5]oxadiazol-5-yl)prop-2-en-1-ol (340 mg, 1.77 mmol) and 4-(azetidin-3-ylmethyl)morpholine 2HCl salt (608 mg, 2.66 mmol) in MeCN (10 ml). The mixture was heated to 70° C. for 48 hours. After the mixture was cooled to room temperature, EtOAc (30 ml) was added to the solution. The mixture was washed with brine. The organic layer was dried and concentrated. The residue was purified via gradient elution (2:100:500, TEA/ EtOAc/Hexane to 4:2:100:500 MeOH/TEA/EtOAc/ Hexane) to afford (E)-3-(7-(3-(morpholinomethyl)azetidin-1-yl)benzo[c][1,2,5]oxadiazol-5-yl)prop-2-en-1-ol (450 mg, 77%) as a yellow solid.

Dess-Martin periodinane (694 mg, 1.64 mmol) was added to a solution of (E)-3-(7-(3-(morpholinomethyl)azetidin-1-yl) benzo[c][1,2,5]oxadiazol-5-yl)prop-2-en-1-ol (450 mg, 1.36 mmol) in DCM (15 ml) at room temperature. After the mixture was stirred 1 h, the reaction was quenched by saturated Sodium thiosulfate (10 ml). The mixture was washed with saturated sodium bicarbonate and brine. The organic layer was dried and concentrated. The residue was purified via gradient elution (2:100:500, TEA/EtOAc/ Hexane to 3:2:100:500 MeOH/TEA/EtOAc/Hexane) to afford (E)-3-(7-(3-(morpholinomethyl) azetidin-1-yl) benzo [c][1,2,5]oxadiazol-5-yl)acrylaldehyde (360 mg, 81%) as an orange solid.

(E)-3-(7-(3-(morpholinomethyl)azetidin-1-yl)benzo[c][1, 2,5]oxadiazol-5-yl)acrylaldehyde (360 mg, 1.1 mmol) was cool to 0° C. in dry THF solution (10 ml) under nitrogen atmosphere. TMSCF$_3$ (0.195 ml, 1.32 mmol) and TBAF (0.22 ml, 0.22 mmol, 1M solution) were added slowly to the mixture separately. The solution was stirred for 2 hour at 0° C. After completion checked by TLC, the mixture was added with 5 ml of water. This mixture was added with 50 ml of EtOAc and washed with brine. The organic layer was dried over anhydrous sodium sulphate and then concentrated. The residue was purified via gradient elution (2:100:500, TEA/ EtOAc/Hexane to 4:2:100:500 MeOH/TEA/EtOAc/ Hexane) to afford (E)-1,1,1-trifluoro-4-(7-(3-(morpholinomethyl)azetidin-1-yl)benzo[c][1,2,5]oxadiazol-5-yl)but- 3-en-2-ol (280 mg, 64%) TRV1665 as an orange solid. ¹H NMR (400 MHz, CDCl3): 2.48-2.50 (m, 4H), 2.72 (d, J=7.5, 2H), 3.06-3.12 (m, 1H), 3.73-3.75 (m, 4H), 3.99 (d-d, J=5.6, J=8.2, 2H), 4.42 (t, J=8.2, 2H), 4.67-4.74 (m, 1H), 5.92 (s, 1H), 6.26 (d-d, J=6.0, J=16.1, 1H), 6.86 (d, J=16.1, 1H), 6.98 (s, 1H).

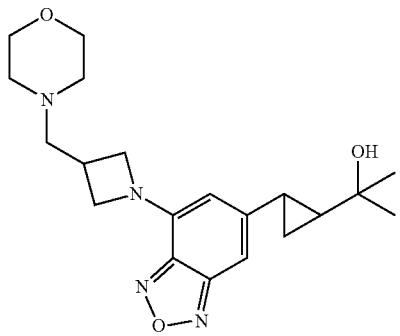

TRV1666

A 250-mL, one-necked, round-bottomed flask was charged with 45 mL of dry dichloromethane and 1.60 mL (15.0 mmol) of 1,2-dimethoxyethane (DME). The solution was cooled to −30° C. and 1.50 mL (15.0 mmol) of diethylzinc is added. To this stirred solution was added 2.40 mL (30.0 mmol) of diiodomethane over a 20 min period while maintaining the temperature between −20° C. and −30° C. After the addition was complete, the resulting clear solution was stirred for 1 hour at −10° C. A solution of 500 mg (2.25 mmol) of (E)-4-(7-fluorobenzo[c][1,2,5]oxadiazol-5-yl)-2-methylbut-3-en-2-ol in 10 mL of dichloromethane was added via cannula under argon. The reaction mixture is allowed to warm to room temperature and stirred for 24 hours. After completion checked by TLC, the mixture was added with 5 ml of water. This mixture was washed with 1 M HCl and brine. The organic layer was dried over anhydrous sodium sulphate and then concentrated. The residue was purified via gradient elution (10:90, EtOAc/Hexane to 20:80 EtOAc/Hexane) to afford 2-(2-(7-fluorobenzo[c][1,2,5]oxadiazol-5-yl)cyclopropyl)propan-2-ol (120 mg, 23%).

TEA (0.28 ml, 2.0 mmol) was added to a solution of 24247-fluorobenzo[c][1,2,5]oxadiazol-5-yl)cyclopropyl)propan-2-ol (120 mg, 0.51 mmol) and 4-(azetidin-3-ylmethyl)morpholine 2HCl salt (175 mg, 0.76 mmol) in MeCN (10 ml). The mixture was heated to 70° C. for 30 hours. After the mixture was cooled to room temperature, EtOAc (30 ml) was added to the solution. The mixture was washed with brine. The organic layer was dried and concentrated. The residue was purified via gradient elution (2:25:75, TEA/EtOAc/Hexane to 4:2:25:75 MeOH/TEA/EtOAc/Hexane) to afford 2-(2-(7-(3-(morpholinomethyl)azetidin-1-yl)benzo[c][1,2,5]oxadiazol-5-yl)cyclopropyl)propan-2-ol TRV1666 (150 mg, 79%) as a yellow solid. ¹H NMR (400 MHz, CDCl₃): ¹H NMR (400 MHz, CDCl₃): 0.93-0.98 (m, 1H), 1.07-1.24 (m, 1H), 1.32 (s, 6H), 1.42-1.47 (m, 1H), 1.92-1.97 (m, 1H), 2.47 (s, br, 4H), 2.70 (d, J=7.3, 2H), 3.01-3.08 (m, 1H), 3.72-3.74 (m, 4H), 3.92-3.95 (m, 2H), 4.36 (t, J=8.0, 2H), 5.59 (s, 1H), 6.67 (s, 1H).

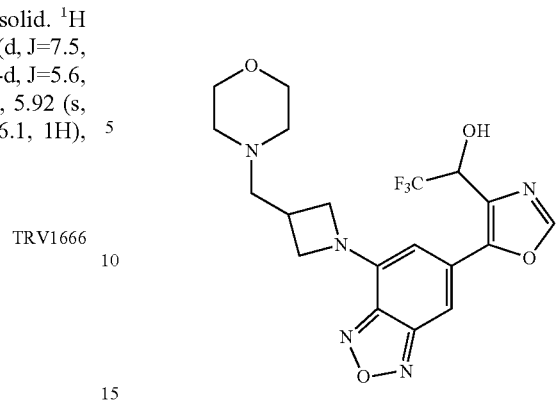

TRV1667

Oxazole (0.50 mL, 7.60 mmol) was dissolved in anhydrous THF (20 mL). The solution was cooled in a dry ice/acetone bath. To the solution was dropwise added n-BuLi (3.5 mL, 2.5 M, 8.8 mmol). After complete addition, the solution was aged for 1 h at −78° C., and then trimethylsilyl triflate (3.0 mL, 11.2 mmol) was added. The reaction mixture was naturally warmed to room temperature, quenched with saturated ammonium chloride, and extracted with ethyl acetate. The organic layer was dried over anhydrous sodium sulfate and concentrated. The residue was purified by flash chromatography using gradient elution (EtOAc:Hex 0:100 to 5:95) to give 1.36 g of 2-triisopropylsilyloxazole (79%).

2-Triisopropylsilyloxazole (0.45 g, 2.0 mmol) was dissolved in anhydrous THF (10 mL). The solution was cooled in a dry ice/acetone bath. To the solution was dropwise added n-BuLi (1.0 mL, 2.5 M, 2.5 mmol). After complete addition, the solution was aged for 1 h at −78° C., and then 2-isopropoxy-4, 4, 5, 5-tetramethyl-1, 3, 2-dioxaborolane (0.6 mL, 2.94 mmol) was added. The reaction mixture was naturally warmed to room temperature, quenched with saturated ammonium chloride, and extracted with ethyl acetate. The organic layer was dried over anhydrous sodium sulfate and concentrated. The residue was used directly used in the next step with further purification.

A reaction vial was charged with 5-(4,4,5,5-tetramethyl-1,3,2-dioxaborolan-2-yl)-2-(triisopropylsilyl)oxazole above, 6-bromo-4-(3-(morpholinomethyl)azetidin-1-yl) benzo[c][1,2,5]oxadiazole (0.70 g, 2.0 mmol), Pd(PPh₃)₄ (0.070 g, 0.060 mmol). After degassed and refilled with nitrogen, the vial was charged with dioxane (7.5 mL) and aq. Na₂CO₃ (4.0 mL, 2.0 M, 8.0 mmol). The reaction vial was further re-degassed, refilled with nitrogen, sealed, and then heated to 95° C. until the reaction was complete. The mixture was diluted with water, extracted with ethyl acetate. The ethyl acetate phase was dried over anhydrous sodium sulfate and concentrated. The residue was purified by flash chromatography using gradient elution (MeOH:TEA:EtOAc:Hex 0:2:25:75 to 1.5:2:25:75) to afford 0.60 g (61% yield for two steps) of 4-(3-(morpholinomethyl)azetidin-1-yl)-6-(2-(triisopropylsilyl) oxazol-5-yl) benzo[c][1,2,5]oxadiazole as a red solid.

4-(3-(morpholinomethyl)azetidin-1-yl)-6-(2-(triisopropylsilyl) oxazol-5-yl) benzo[c][1,2,5]oxadiazole (0.48 g, 0.97 mmol) was dissolved in anhydrous THF (7.5 mL). The solution was cooled in a dry ice/acetone bath. To the solution was dropwise added LDA (0.65 mL, 2.0 M, 1.30 mmol). After complete addition, the solution was aged for 1 h at −78° C., and then ethyl trifluoroacetate (0.24 mL, 2.0 mmol) was added. The reaction mixture was naturally warmed to room temperature, quenched with saturated ammonium chloride, and extracted with ethyl acetate. The organic layer was dried over anhydrous sodium sulfate and concentrated. The residue was purified by flash chromatography using gradient elution (TEA:EtOAc:Hex 0.5:10:90 to 0.5:80:20) to afford 0.26 g of the product as a red solid.

2,2,2-Trifluoro-1-(5-(7-(3-(morpholinomethyl)azetidin-1-yl)benzo[c][1,2,5]oxadiazol-5-yl)-2-(triisopropylsilyl)oxazol-4-yl)ethan-1-one (0.26 g, 0.44 mmol) was dissolved in THF (5 mL). The solution was cooled in an ice-water bath. Sodium borohydride (0.025 g, 0.66 mmol) in 0.5 mL of 0.5 N aqueous NaOH was added. The solution was stirred for 10 min, and then warmed to room temperature. The reaction was stirred until complete. The reaction mixture was cooled in an ice-water bath, quenched with 1N aqueous HCl, stirred for 1 h, basified with saturated sodium bicarbonate, and then extracted with ethyl acetate. The ethyl acetate phase was dried over anhydrous sodium sulfate and concentrated. The residue was purified by flash chromatography using gradient elution (MeOH:TEA:EtOAc:Hex 0:2:25:75 to 5:2:25:75) to afford 0.20 g of TRV1667 as a yellow solid. $^1$H NMR (CDCl$_3$, 400 MHz) δ=8.03 (s, 1H), 7.24 (s, 1H), 6.01 (s, 1H), 5.27 (q, J=6.19 Hz, 1H), 4.46 (t, J=7.53 Hz, 2H), 4.05 (t, J=6.78 Hz, 2H), 3.79 (broad, 1H), 3.74 (t, J=4.52 Hz, 4H), 3.12 (septet, J=6.90 Hz, 1H), 2.73 (t, J=7.53 Hz, 2H), 2.49 (t, J=4.14 Hz, 4H).

TRV1670

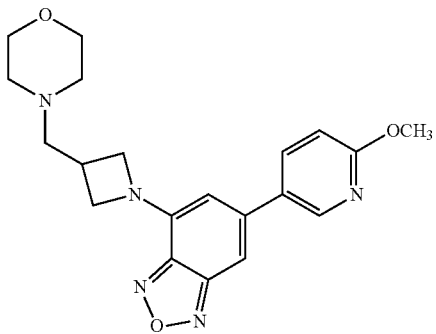

6-(6-methoxypyridin-3-yl)-4-fluorobenzo[c][1,2,5]oxadiazole (0.150 g, 0.612 mmol) and 4-(azetidin-3-yl methyl) morpholine hydrochloride salt (0.140 g, 0.612 mmol) were dissolved in Acetonitrile (5 ml) at room temperature, triethylamine (0.3 ml, 1.85 mmol) was added and mixture was heated at 80° C. overnight. After completion of reaction by TLC it was quenched with Na2CO3 (2M) and extracted with EtOAC to give crude product. Purification was done on ISCO flash chromatography system using dichloromethane:methanol (95:5) as solvent to obtain 6-(6-methoxypyridin-3-yl)-4-(3-(morpholinomethyl)azetidin-1-yl) benzo[c][1,2,5]oxadiazole TRV1670 (0.218 g, 93%) as red color solid. $^1$H NMR (CDCl$_3$, 400 MHz): δ 8.45 (d, J=4.0 Hz, 1H), 7.84(d, J=4.0 Hz, 1H), 7.82(d, J=4.0 Hz, 1H), 7.10(s, 1H), 6.86(d, J=8.0 Hz, 1H), 5.98(s, 1H), 4.47 (t, J=8.0 Hz,2H), 4.04(m, 2H), 4.01(s,3H), 3.75(m,4H), 3.13(m,1H), 2.74(d, J=8.0 Hz, 2H), 2.48(m,4H).

TRV1677

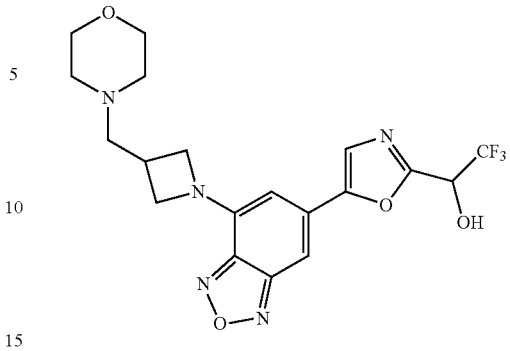

Oxazole (0.50 mL, 7.60 mmol) was dissolved in anhydrous THF (20 mL). The solution was cooled in a dry ice/acetone bath. To the solution was dropwise added n-BuLi (3.5 mL, 2.5 M, 8.8 mmol). After complete addition, the solution was aged for 1 h at −78° C., and then trimethylsilyl triflate (3.0 mL, 11.2 mmol) was added. The reaction mixture was naturally warmed to room temperature, quenched with saturated ammonium chloride, and extracted with ethyl acetate. The organic layer was dried over anhydrous sodium sulfate and concentrated. The residue was purified by flash chromatography using gradient elution (EtOAc:Hex 0:100 to 5:95) to give 1.36 g of 2-triisopropylsilyloxazole (79%).

2-Triisopropylsilyloxazole (0.45 g, 2.0 mmol) was dissolved in anhydrous THF (10 mL). The solution was cooled in a dry ice/acetone bath. To the solution was dropwise added n-BuLi (1.0 mL, 2.5 M, 2.5 mmol). After complete addition, the solution was aged for 1 h at −78° C., and then 2-isopropoxy-4, 4, 5, 5-tetramethyl-1, 3, 2-dioxaborolane (0.6 mL, 2.94 mmol) was added. The reaction mixture was naturally warmed to room temperature, quenched with saturated ammonium chloride, and extracted with ethyl acetate. The organic layer was dried over anhydrous sodium sulfate and concentrated. The residue was used directly used in the next step with further purification.

A reaction vial was charged with 5-(4,4,5,5-tetramethyl-1,3,2-dioxaborolan-2-yl)-2-(triisopropylsilyl)oxazole above, 6-bromo-4-(3-(morpholinomethyl)azetidin-1-yl) benzo[c][1,2,5]oxadiazole (0.76 g, 2.0 mmol), Pd(PPh$_3$)$_4$ (0.070 g, 0.060 mmol). After degassed and refilled with nitrogen, the vial was charged with dioxane (7.5 mL) and aq. Na$_2$CO$_3$ (4.0 mL, 2.0 M, 8.0 mmol). The reaction vial was further re-degassed, refilled with nitrogen, sealed, and then heated to 95° C. until the reaction was complete. The mixture was cooled to rt, worked up with 1N HCl, stirred for 1 h, and then extracted with ethyl acetate. The ethyl acetate phase was dried over anhydrous sodium sulfate and concentrated. The residue was purified by flash chromatography using gradient elution (MeOH:TEA:EtOAc:Hex 0:2:25:75 to 7.5:2:25:75) to afford 0.55 g (62% yield for two steps) of 4-(3-(morpholinomethyl)azetidin-1-yl)-6-(oxazol-5-yl) benzo[c][1,2,5]oxadiazole as a red solid.

4-(3-(morpholinomethyl)azetidin-1-yl)-6-(oxazol-5-yl) benzo[c][1,2,5]oxadiazole (0.36 g, 1.06 mmol) was dissolved in anhydrous THF (7.5 mL). The solution was cooled in a dry ice/acetone bath. To the solution was dropwise added LDA (1.60 mL, 2.0 M, 3.20 mmol). After complete addition, the solution was aged for 1 h at −78° C., and then ethyl trifluoroacetate (0.54 mL, 4.54 mmol) was added. The reaction mixture was naturally warmed to room temperature, quenched with water, and re-cooled in an ice-water bath before sodium borohydride (0.17 g, 4.54 mmol) was added. The solution was stirred for 10 min, and then warmed to room temperature and stirred until complete. The reaction mixture was cooled in an ice-water bath, quenched with 1N aqueous HCl, stirred for 1 h, basified with saturated sodium bicarbonate, and then extracted with ethyl acetate. The ethyl acetate phase was dried over anhydrous sodium sulfate and concentrated. The residue was purified by flash chromatography using gradient elution (MeOH:TEA:EtOAc:Hex 0:2:25:75 to 7.5:2:25:75) to afford 0.27 g (a yield of 58%) of TRV 1677 as an orange solid. $^1$H NMR (CDCl$_3$, 400 MHz) δ=8.07 (s, 1H), 7.58 (d, J=7.03 Hz, 1H), 7.33 (s, 1H), 6.32 (s, 1H), 5.62-5.52 (m, 1H), 4.38 (t, J=8.28 Hz, 2H), 4.03-3.88 (m, 2H), 3.58 (t, J=8.28 Hz, 4H), 3.07 (septet, J=6.78 Hz, 1H), 2.63 (t, J=7.53 Hz, 2H), 2.43-2.34 (m, 4H).

TRV1686

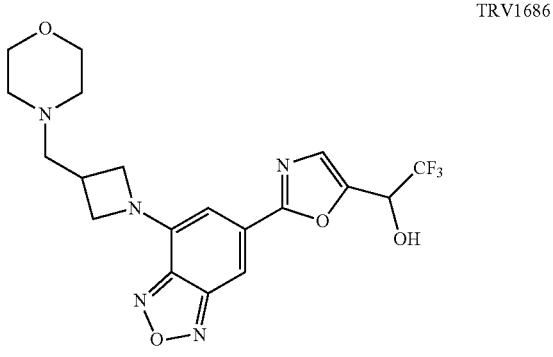 [SMILES: OC(c1cnc(-c2cc(N3CC(CN4CCOCC4)C3)c3nonc3c2)o1)C(F)(F)F]

2,2,2-trifluoro-1-(2-(7-fluorobenzo[c][1,2,5]oxadiazol-5-yl)oxazol-5-yl)ethan-1-ol (0.152 g, 0.5 mmol) and 4-(azetidin-3-ylmethyl) morpholine hydrochloride salt (0.114 g, 0.5 mmol) were dissolved in Acetonitrile (5 ml) at room temperature, triethylamine (0.2 ml, 1.5 mmol) was added and mixture was heated at 50° C. overnight. After completion of reaction by TLC it was quenched with Na2CO3 (2M) and extracted with EtOAC to give crude TRV-1660. Purification was done on ISCO flash chromatography system using dichloromethane:methanol (95:5) as solvent to obtain 2, 2, 2-trifluoro-1-(2-(7-(3-(morpholinomethyl) azetidin-1-yl) benzo[c][1,2,5]oxadiazol-5-yl) oxazol-5-yl) ethan-1-ol TRV1686 (0.1400 g, 68%) as orange color solid. $^1$H NMR (DMSO, 400 MHz): δ 7.59(s,1H), 7.53(s,1H), 7.36(d, J=4.0 Hz,1H), 6.45(s,1H), 5.57(m,1H), 4.41(t, J=8.0 Hz, 2H), 3.98(m,2H), 3.57(m,4H), 3.08(m,1H), 2.65(d, J=8.0 Hz,2H), 2.38(m,4H).

TRV1692

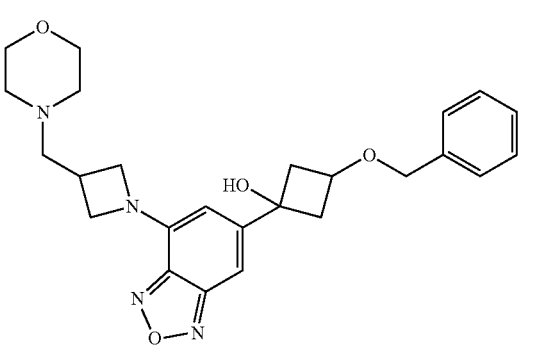

6-bromo-4-(3-(morpholinomethyl)azetidin-1-yl)benzo[c][1,2,5]oxadiazole (0.353 g, 1.0 mmol) was dissolved in dry THF (5 ml) and cooled to −78° C. under argon atm. 2.5M n-BuLi (0.48 ml, 1.2 mmol) was added drop wise and mixture was allowed to stir for 20 min at −78° C. 3-(benzyloxy)cyclobutan-1-one was then added to reaction mixture and was stirred for additional 30 min and brought to rt followed by stirring for another 30 min then it was quenched with ammonium chloride and extracted with dichloromethane. Evaporation of solvent gave crude product which was purified on ISCO. to get Synthesis of 3-(benzyloxy)-1-(7-(3-(morpholinomethyl)azetidin-1-yl) benzo[c][1,2,5]oxadiazol-5-yl) cyclobutan-1-ol TRV1692 (47%). $^1$H NMR (CDCl$_3$, 400MHz): δ 7.36(m,5H), 7.01(s,1H), 5.98(s,1H), 4.49(s,2H), 4.40(t, J=8.0 Hz, 2H), 3.98(m,2H), 3.94(m,1H), 3.73 (m, 4H), 3.08 (m, 1H), 2.94(m,2H), 2.71(d, J=8.0 Hz,2H), 2.47(m,6H).

TRV1717

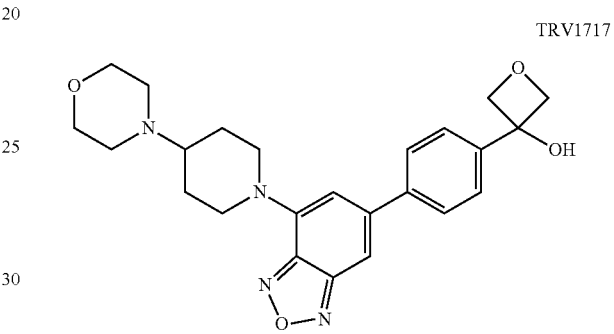

1, 4-Dibromobenzene (4.72 g, 20.00 mmol) was dissolved in anhydrous THF (50 mL) under argon. The solution was cooled to −78° C. and n-BuLi (2.5 M, 8.8 mL, 20.5 mmol) was dropwise added. The solution was stirred at −78° C. for 0.5 h before oxetan-3-one (1.2 mL, 20.5 mmol) was added. The solution was stirred at −78° C. for 1 h, then quenched with saturated aqueous ammonium chloride, and extracted with ethyl acetate. The organic layer was washed with brine, dried with anhydrous sodium sulfate, and then concentrated. The residue was purified by flash chromatography using gradient elution (EtOAc:Hex 10:90 to 50:50) to afford 3.94 g of 3-(4-bromophenyl) oxetan-3-ol as a white solid (86% yield).

A reaction vial was charged with 3-(4-bromophenyl) oxetan-3-ol (1.72 g, 7.5 mmol), 4-fluoro-6-(4,4,5,5-tetramethyl-1,3,2-dioxaborolan-2-yl)benzo[c][1,2,5]oxadiazole (2.28 g, 8.64 mmol), Pd(PPh$_3$)$_4$ (0.26 g, 0.23 mmol). After degassed and refilled with nitrogen, the vial was charged with dioxane (15 mL) and aq. Na$_2$CO$_3$ (10.0 mL, 2.0 M, 20.0 mmol). The reaction vial was further re-degassed, refilled with nitrogen, sealed, and then heated to 95° C. until it was complete. The mixture was cooled to rt, diluted with water, and then extracted with ethyl acetate. The ethyl acetate phase was dried over anhydrous sodium sulfate and concentrated. The residue was purified by flash chromatography using gradient elution (EtOAc:Hex 10:90 to 50:50) to afford 1.95 g (91% of yield) of 34447-fluorobenzo[c][1,2,5]oxadiazol-5-yl)phenyl)oxetan-3-ol as a white solid.

3-(4-(7-Fluorobenzo[c][1,2,5]oxadiazol-5-yl)phenyl)oxetan-3-ol (0.43 g, 1.50 mmol), 4-(piperidin-4-yl)morpholine (0.30 g, 1.80 mmol), Hunig's base (0.78 mL, 4.49 mmol) in MeCN (10 mL) was heated to 80° C. overnight. The reaction mixture was cooled to rt, diluted with water, and then extracted with ethyl acetate. The organic phase was dried over anhydrous sodium sulfate and concentrated. The residue was purified by flash chromatography using gradient elution (MeOH:TEA:EtOAC:Hex:0:2:25:75 to 5:2:25:75) to afford a total of 0.63 g (96% of yield) of TRV1717 as an orange solid. $^1$H NMR (CDCl$_3$, 400 MHz) δ=7.75 (d, J=8.53 Hz, 2H), 7.69 (d, J=8.53 Hz, 2H), 7.35 (s, 1H), 6.59 (s, 1H), 4.98 (d, J=7.03 Hz, 2H), 4.96 (d, J=7.03 Hz, 2H), 4.43 (d, J=12.80 Hz, 2H), 3.76 (t, J=4.65 Hz, 4H), 3.05 (dt, J$_1$=1.76 Hz, J$_2$=12.30 Hz, 2H), 2.71 (broad, 1H), 2.62 (t, J=4.52 Hz, 4H), 2.49 (tt, J$_1$=1.76 Hz, J$_2$=11.04 Hz, 1H), 2.05 (d, J=12.80 Hz, 2H), 1.78 (dq, J$_1$=3.51 Hz, J$_2$=12.05 Hz, 2H).

TRV1719

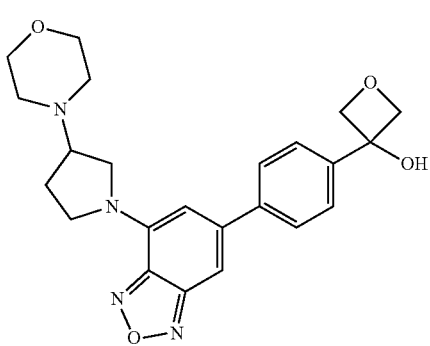

3-(4-(7-Fluorobenzo[c][1,2,5]oxadiazol-5-yl) phenyl)oxetan-3-ol (0.29 g, 1.00 mmol), 4-(pyrrolidin-3-yl) morpholine (0.19 g, 1.20 mmol), Hunig's base (0.52 mL, 3.00 mmol) in MeCN (7.5 mL) was heated to 80° C. overnight. The reaction mixture was cooled to rt, diluted with water, and then extracted with ethyl acetate. The organic phase was dried over anhydrous sodium sulfate and concentrated. The residue was purified by flash chromatography using gradient elution (MeOH:TEA:THF:Hex: 0:2:25:75 to 5:2:25:75) to afford a total of 0.36 g (85% of yield) of TRV1719 as an orange solid. $^1$H NMR (DMSO, 400 MHz) δ=7.84 (d, J=8.53 Hz, 2H), 7.71 (d, J=8.53 Hz, 2H), 7.26 (s, 1H), 6.46 (s, 1H), 6.33 (s, 1H), 4.81 (d, J=6.53 Hz, 2H), 4.71 (d, J=6.53 Hz, 2H), 4.05-3.92 (m, 2H), 3.75 (q, J=9.20 Hz, 1H), 3.61 (t, J=4.40 Hz, 4H), 3.52 (t, J=9.29 Hz, 1H), 3.00 (pentet, J=7.91 Hz, 1H), 2.55-2.45 (m, 4H, overlap with DMSO peaks), 2.31-2.22 (m, 1H), 1.91 (pentet, J=9.98 Hz, 1H).

TRV1735

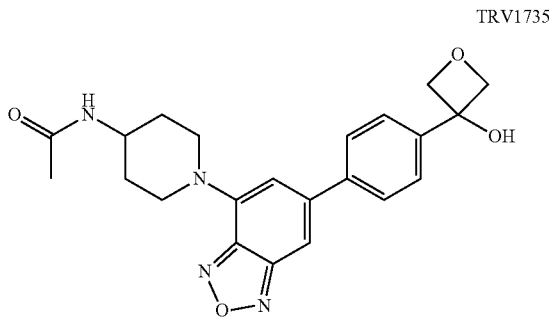 [SMILES: CC(=O)NC1CCN(c2cc(-c3ccc(C4(O)COC4)cc3)cc3nonc23)CC1]

1,4-Dibromobenzene (4.72 g, 20.00 mmol) was dissolved in anhydrous THF (50 mL) under argon. The solution was cooled to −78° C. and n-BuLi (2.5 M, 8.8 mL, 20.5 mmol) was dropwise added. The solution was stirred at −78° C. for 0.5 h before oxetan-3-one (1.2 mL, 20.5 mmol) was added. The solution was stirred at −78° C. for 1 h, then quenched with saturated aqueous ammonium chloride, and extracted with ethyl acetate. The organic layer was washed with brine, dried with anhydrous sodium sulfate, and then concentrated. The residue was purified by flash chromatography using gradient elution (EtOAc:Hex 10:90 to 50:50) to afford 3.94 g of 3-(4-bromophenyl)oxetan-3-ol as a white solid (86% yield).

A reaction vial was charged with 3-(4-bromophenyl)oxetan-3-ol (1.72 g, 7.5 mmol), 4-fluoro-6-(4,4,5,5-tetramethyl-1,3,2-dioxaborolan-2-yl)benzo[c][1,2,5]oxadiazole (2.28 g, 8.64 mmol), Pd(PPh$_3$)$_4$ (0.26 g, 0.23 mmol). After degassed and refilled with nitrogen, the vial was charged with dioxane (15 mL) and aq. Na$_2$CO$_3$ (10.0 mL, 2.0 M, 20.0 mmol). The reaction vial was further re-degassed, refilled with nitrogen, sealed, and then heated to 95° C. until it was complete. The mixture was cooled to rt, diluted with water, and then extracted with ethyl acetate. The ethyl acetate phase was dried over anhydrous sodium sulfate and concentrated. The residue was purified by flash chromatography using gradient elution (EtOAc:Hex 10:90 to 50:50) to afford 1.95 g (91% of yield) of 34447-fluorobenzo[c][1,2,5]oxadiazol-5-yl)phenyeoxetan-3-ol as a white solid.

3-(4-(7-Fluorobenzo[c][1,2,5]oxadiazol-5-yl)phenyl)oxetan-3-ol (0.29 g, 1.00 mmol), N-(4-piperidinyl)acetamide hydrochloride (0.22 g, 1.25 mmol), Hunig's base (0.80 mL, 4.60 mmol) in MeCN (7.5 mL) was heated to 100° C. for 48 h. The reaction mixture was cooled to rt, diluted with water, and then extracted with ethyl acetate. The organic phase was dried over anhydrous sodium sulfate and concentrated. The residue was purified by flash chromatography using gradient elution (MeOH:TEA:THF:Hex: 0:2:25:75 to 7.5:2:25:75) to afford a total of 0.25 g (82% of yield) of TRV1735 as a yellow solid. $^1$H NMR (DMSO, 400 MHz) δ=7.89 (d, J=7.78 Hz, 1H), 7.86 (d, J=8.28 Hz, 2H), 7.73 (d, J=8.28 Hz, 2H), 7.56 (s, 1H), 6.80 (s, 1H), 6.47 (s, 1H), 4.81 (d, J=6.78 Hz, 2H), 4.71 (d, J=6.53 Hz, 2H), 4.31-4.21 (m, 2H), 3.90-3.78 (m, 1H), 3.24-3.11 (m, 2H), 1.96-1.86 (s, 2H), 1.80 (s, 3H), 1.63-1.49 (m, 2H).

TRV1736

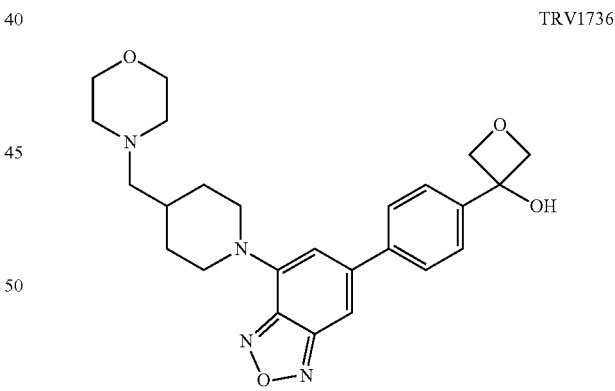

3-(4-(7-Fluorobenzo[c][1,2,5]oxadiazol-5-yl)phenyl)oxetan-3-ol (0.21 g, 0.75 mmol), 4-(piperidin-4-ylmethyl)morpholine dihydrochloride (0.26 g, 1.00 mmol), Hunig's base (0.80 mL, 4.60 mmol) in MeCN (7.5 mL) was heated to 100° C. for 48 h. The reaction mixture was cooled to rt, diluted with water, and then extracted with ethyl acetate. The organic phase was dried over anhydrous sodium sulfate and concentrated. The residue was purified by flash chromatography using gradient elution (MeOH:TEA:THF:Hex:0:2:25:75 to 5:2:25:75) to afford a total of 0.30 g (88% of yield) of TRV1736 as an orange solid. $^1$H NMR (DMSO, 400 MHz) δ=7.85 (d, J=8.28 Hz, 2H), 7.73 (d, J=8.28 Hz, 2H), 7.53 (s, 1H), 6.76 (s, 1H), 6.47 (s, 1H), 4.81 (d, J=6.53 Hz, 2H), 4.71 (d, J=6.53 Hz, 2H), 4.38-4.28 (m, 2H), 3.57 (t, J=4.40 Hz, 4H), 3.02 (t, J=12.30 Hz, 2H), 2.43-2.25 (m, 4H), 2.18 (d, J=6.78 Hz, 2H), 1.92-1.77 (m, 3H), 1.37-1.25 (m, 2H).

Biological Data

The following methodologies were used:

Preparation of Aβ$_{40}$ Stock Solutions

Aβ$_{40}$ (1.0 mg) was pre-treated in a 1.5 mL microfuge tube with HFIP (1 mL) and sonicated for 20 min to disassemble any pre-formed Aβ aggregates. The HFIP was removed with a stream of argon and the Aβ dissolved in Tris base (5.8 mL, 20 mM, pH ~10). The pH was adjusted to 7.4 with concentrated HCl (~10 μL) and the solution filtered using a syringe filter (0.2 μm) before being used.

Aβ$_{42}$ and tau proteins were prepared in an analogous manner as in the procedure above.

ThT Aβ Aggregation Assay

The kinetic ThT assay for Aβ aggregation is similar to that of Chalifour et al (Chalifour et al, 2003, J. Biol. Chem. 278:34874-81). Briefly, pre-treated Aβ$_{40}$ or Aβ$_{42}$ (40 μM in 20 mM Tris, pH 7.4) was diluted with an equal volume of 8 μM Thioflavin T (ThT) in Tris (20 mM, pH 7.4, 300 mM NaCl). Aliquots of Aβ/ThT (200 μL) were added to wells of a black polystyrene 96-well plate, followed by 2 μL of a compound in DMSO (variable concentration), or DMSO alone (controls). Incubations were performed in triplicate and were taken to contain 20 μM Aβ, various concentration of compound in 20 mM Tris, pH 7.4, 150 mM NaCl, 1% DMSO. Plates were covered with clear polystyrene lids and incubated at 37° C. in a Tecan Genios microplate reader.

ThS Tau Aggregation Assay

The kinetic ThS assay for tau aggregation generally follows the above procedure, except that Thioflavin S (ThS) is used in place of ThT and tau protein is used in place of Aβ.

Analysis of ThT and ThS Aggregation Assays

Figure 2:
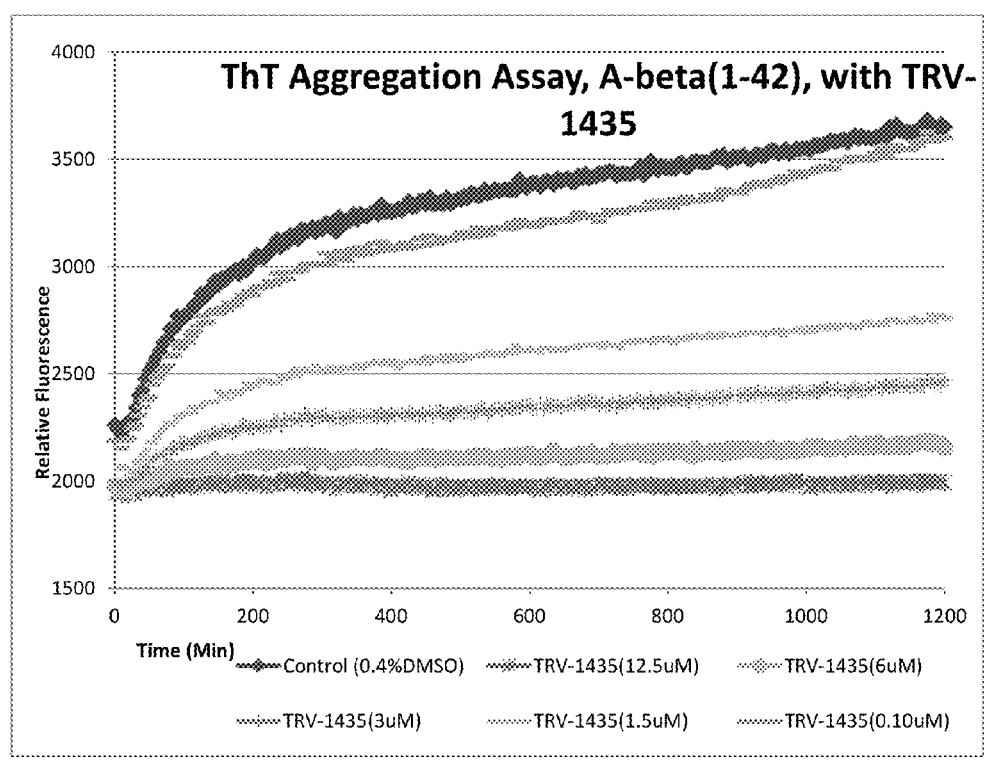
FIG. 2 shows a beta-amyloid aggregation assay for a compound described herein.
Figure 3:
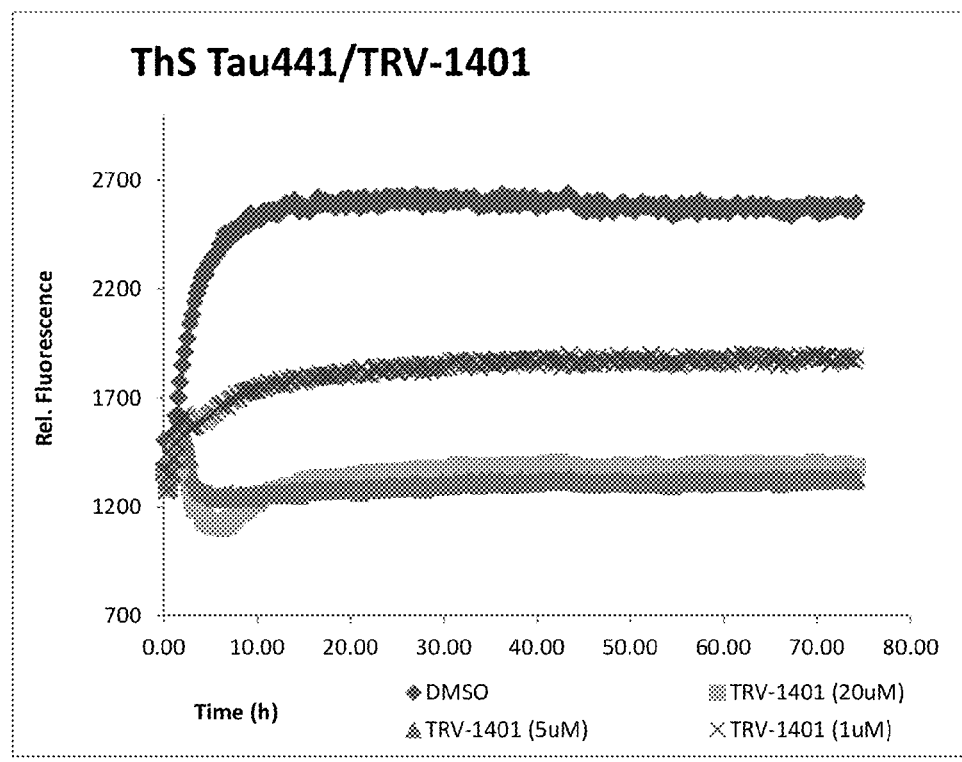
FIG. 3 shows a tau aggregation assay for a compound described herein.
Figure 4:
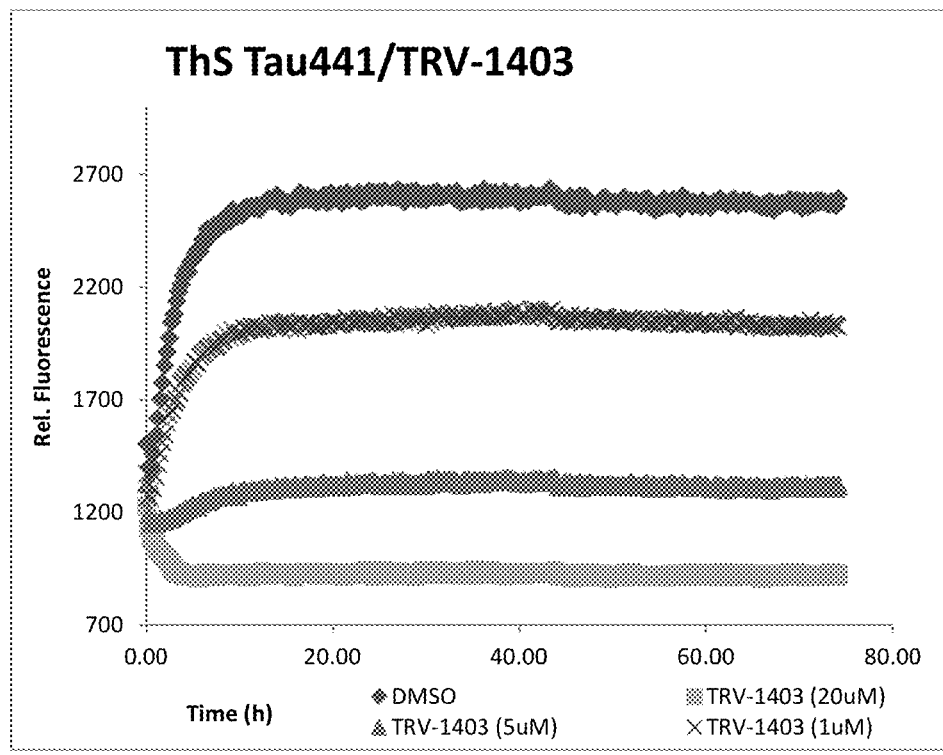
FIG. 4 shows a tau aggregation assay for a compound described herein.
Figure 5:
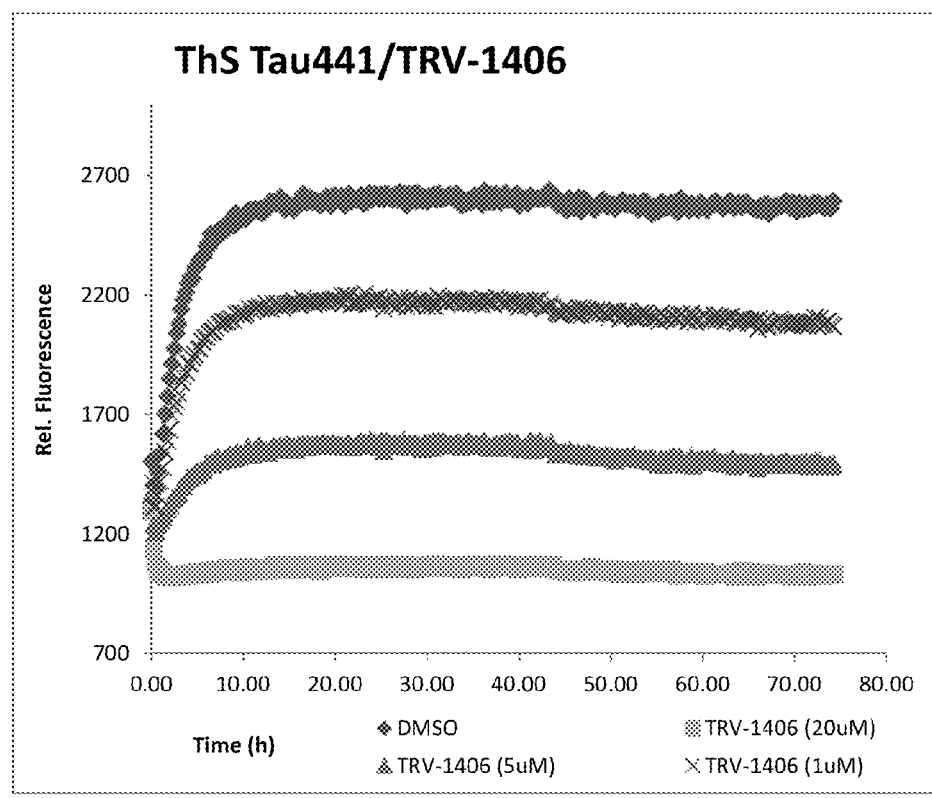
FIG. 5 shows a tau aggregation assay for a compound described herein.
Figure 6:
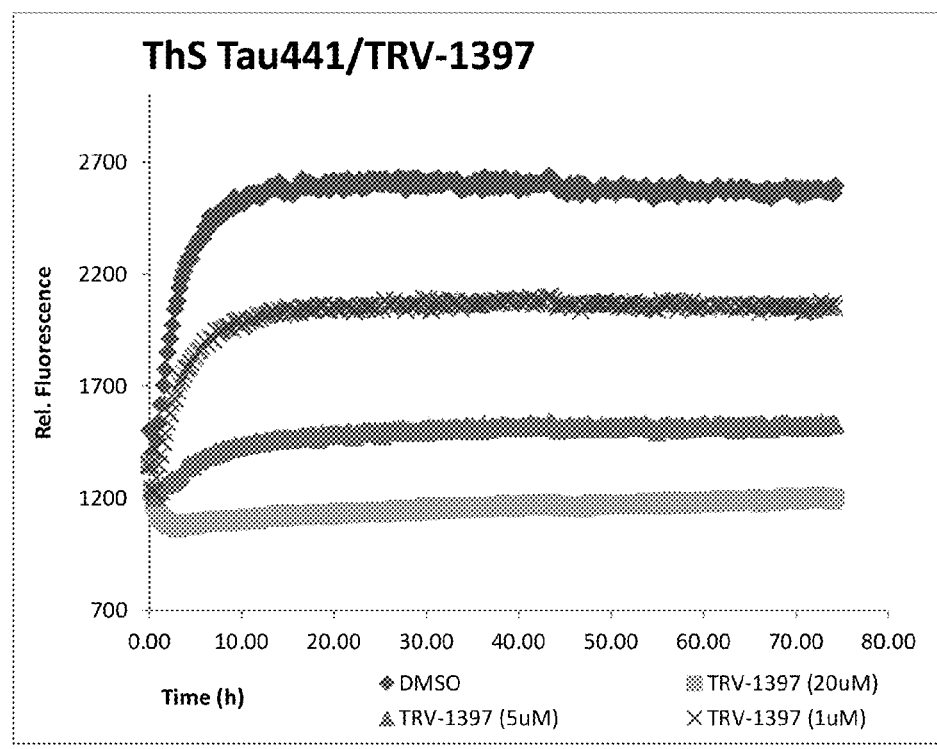
FIG. 6 shows a tau aggregation assay for a compound described herein.
Figure 7:
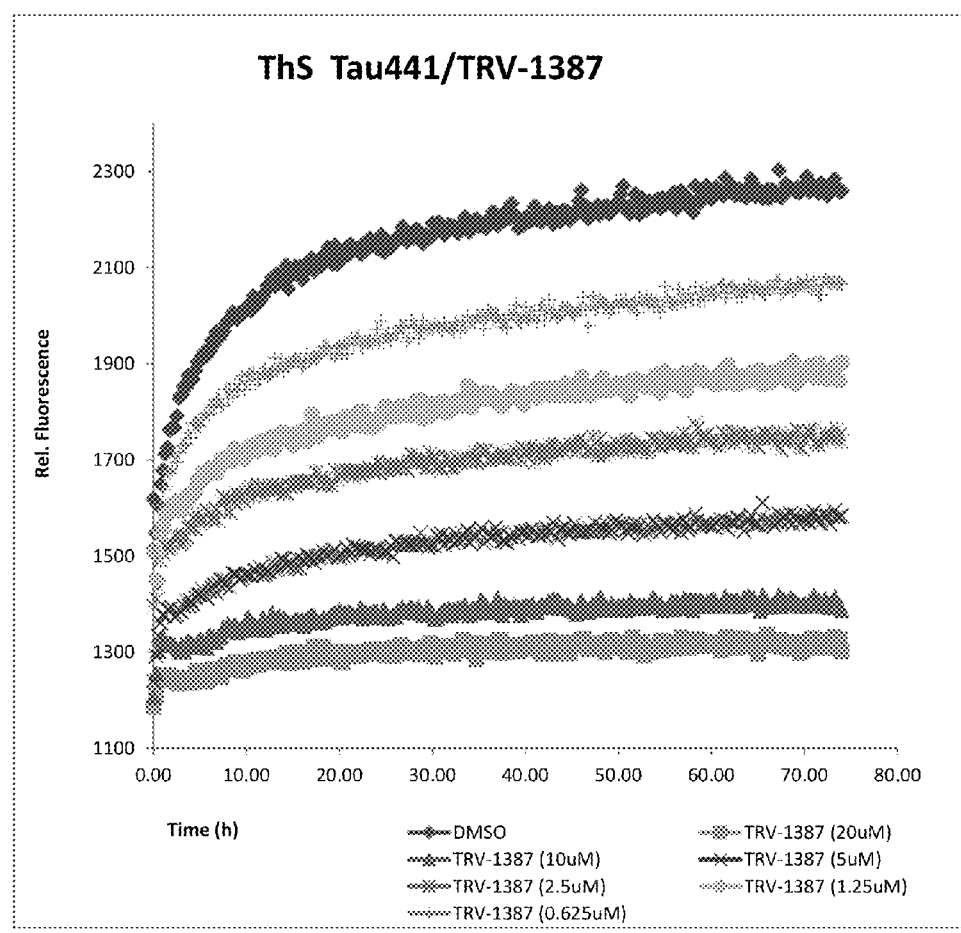
FIG. 7 shows a tau aggregation assay for a compound described herein.
Figure 8:
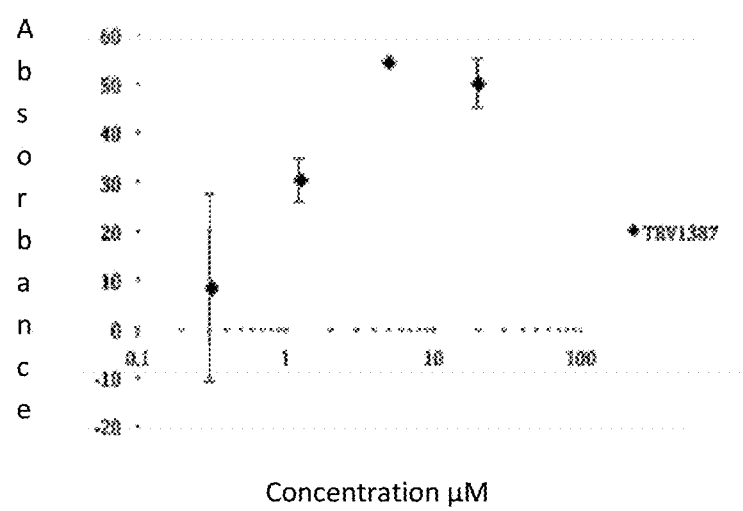
FIG. 8 shows a biotinylated beta-amyloid oligomerization assay for a compound described herein.

Fluorescence readings (λex=450 nm, λem=480 nm) were taken every 15 min., after first shaking at high intensity for 15 s and allowing to settle for 10 s before each reading. Active compounds attenuated the increase in fluorescence over time that occurred in controls. In FIGS. 1-7, the time this procedure was performed extended to 80 hours (rightmost part of X-axis), at which point fluorescence increase generally reached an asymptote. Applying a definition of DMSO control at 80 hr as 100% aggregation (0% inhibition) and DMSO control at 0 hr as 0% aggregation (100% inhibition), a % inhibition score where higher is better can be calculated for a given concentration of compound. By repeating this procedure over several concentrations, a mean inhibitory concentration (IC$_{50}$) can be measured, as is given in the table below for some compounds.

Aβ42 Biotinylated Assay

Terminally biotinylated beta-amyloid (biotin-AB) was dissolved in HFIP at the concentration of 1 mg/ml and aliquoted to 50 μl/tube in 0.65 ml colored microfuge tubes (Fisher 02-681-248). The aliquots were diluted immediately by adding 450 μl of HFIP to 0.1 mg/ml. Approximately 46 ul (containing approximately 4.6 ug of biotin-AB) were taken from a tube, 100 ul of HFIP added, vortexed, and dried to a thin film under an N$_2$ stream. 100 μl of trifluoroacetic acid (TFA) was added and vortexed. After 10 minute incubation at room temperature in a hood, resulting in disaggregation of seeds, the sample was vortexed again and dried again to a thin film under an N$_2$ stream. 100 μl of HFIP was added, mixed, and the biotin-AB sample was dried for a third time under an N$_2$ stream to remove residual TFA. The treated biotin-AB was dissolved in DMSO to a final peptide concentration of 2.3 μg/ml (SOX).

An ELISA "capture" plate (Costar 9018) was coated with 50 μl of 1 μg/ml NeutrAvidin™ (NA) in 10 mM sodium phosphate buffer, pH 7.5. (NeutrAvidin can be prepared as 1 mg/ml (1000×) in milliQ water/10% glycerol and stored at −80° C. before use.) The plate was sealed plate with adhesive film and stored at 4° C. overnight, then blocked for 2 hours (unsealed) at room temperature with 200 μl/well OFB+0.1% v/v Tween 20. The "capture" plate was allowed to come to room temperature.

Several dilutions of test compound were prepared with 100% DMSO, according to the desired concentration to be tested. 2.5 μl of diluted test compound was pipetted into the bottom of each well of a 96-well "dilution" polypropylene plate (Costar 3365), to which was added 250 ul of Oligomer Formation Buffer (OFB: 20 mM sodium phosphate, pH 7.5-150 mM NaCl). To begin oligomerization, 2 μl/well of the biotin-AB was added to the bottom of each well of a 96-well "reaction" polypropylene plate (Costar 3365) and 100 ul of each well of the "dilution" plate was transferred to the "reaction" plate (final concentration of DMSO being up to 1%). The reaction plate was sealed and incubated for 1 hr at room temperature without shaking. The reaction was then stopped by the addition of 50 ul of 0.3% Tween 20 in water. The "capture" plate blocking solution was removed, and 50 ul of each well of the "reaction" plate was transferred to each well of the "capture" plate. The "capture" plate was sealed and incubated for 2 hours at room temperature with shaking at 150 rpm. The "capture" plate was then washed on a plate washer (3×) with 200 ul/well TBST (20 mM Tris-HCL, pH 7.5/150 mM NaCl/0.1% Tween 20). 50 ul of Streptavidin-horseradish protein (1:20,000 dilution) in OFB+0.1% Tween 20 was added to each well, the "capture" plate was sealed and incubated for 1 hr with shaking at 150 rpm. As before, the plate was washed, then 100 ul of TMB/H2O2 substrate solution was added to each well. After 5-10 minutes, 100 ul of 1% v/v sulfuric acid was added and the absorbance of each well was read at 450 nm using a standard plate reader. Data is summarized in the table below; numbers given in parenthesis for the Aβ 40 Thioflavin T assays are the values in that particular experiment for compound ID 1027, given as the first entry in this table for structural comparison. "IC50 Aβ42-bio" column refers to the approximate value of the Aβ42 biotinylated assay IC$_{50}$ in micromoles/L.

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1027 | 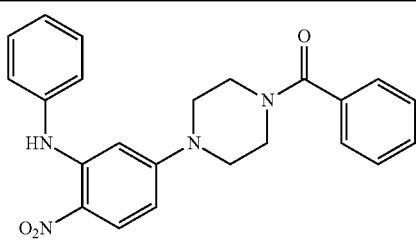 | | | | | | |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1259 | 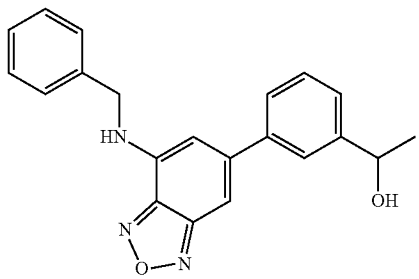 [SMILES: CC(O)c1cccc(-c2cc(NCc3ccccc3)c3nonc3c2)c1] | | | 66.34 (66.24) | | | |
| 1310 | 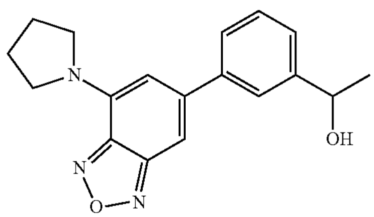 [SMILES: CC(O)c1cccc(-c2cc(N3CCCC3)c3nonc3c2)c1] | | | 81.54 (64.67) | | | |
| 1358 | 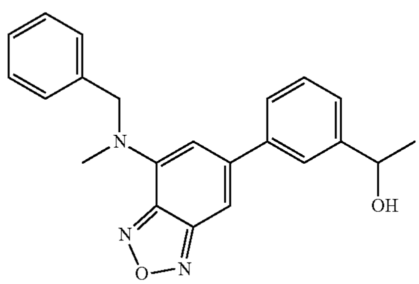 [SMILES: CC(O)c1cccc(-c2cc(N(C)Cc3ccccc3)c3nonc3c2)c1] | | | 72.72 (67.72) | | | |
| 1359 | 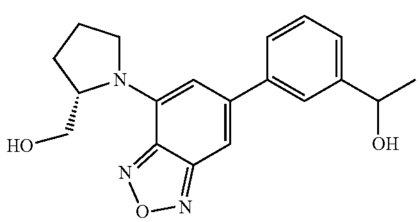 [SMILES: CC(O)c1cccc(-c2cc(N3CCC[C@H]3CO)c3nonc3c2)c1] | | | 75.19 (67.72) | | | |
| 1360 | 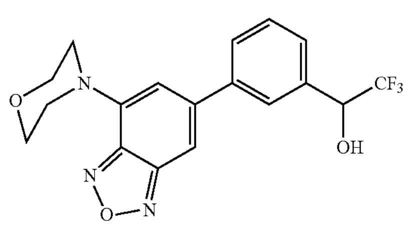 [SMILES: OC(c1cccc(-c2cc(N3CCOCC3)c3nonc3c2)c1)C(F)(F)F] | | | 58.91 (67.72) | | | |
| 1361 | 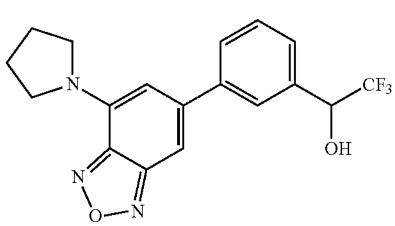 [SMILES: OC(c1cccc(-c2cc(N3CCCC3)c3nonc3c2)c1)C(F)(F)F] | | | 88.94 (67.72) | | | |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1362 | 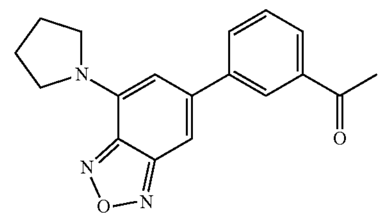 [SMILES: CC(=O)c1cccc(-c2cc(N3CCCC3)c3nonc3c2)c1] | | | 41.36 (65.29) | | | |
| 1364 | 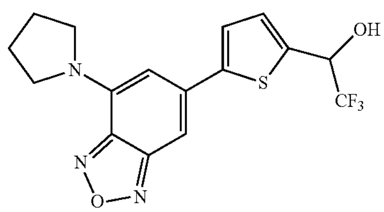 [SMILES: OC(c1ccc(-c2cc(N3CCCC3)c3nonc3c2)s1)C(F)(F)F] | 1.00 (10.47) | | | | | |
| 1365 | 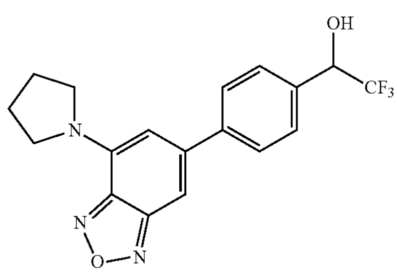 [SMILES: OC(c1ccc(-c2cc(N3CCCC3)c3nonc3c2)cc1)C(F)(F)F] | 0.92 (10.47) | | | | | |
| 1366 | 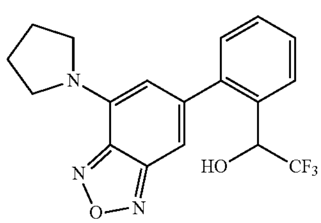 [SMILES: OC(c1ccccc1-c1cc(N2CCCC2)c2nonc2c1)C(F)(F)F] | 3.03 (10.47) | | | | | |
| 1368 | 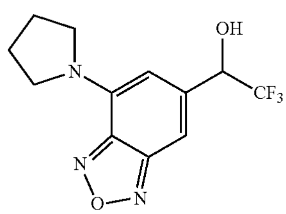 [SMILES: OC(c1cc(N2CCCC2)c2nonc2c1)C(F)(F)F] | | | 61.43 (53.47) | | | |
| 1376 | 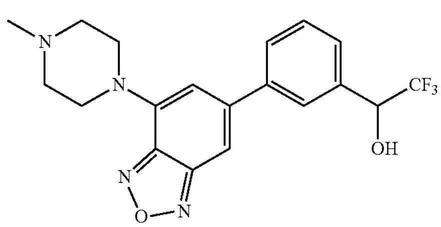 [SMILES: CN1CCN(c2cc(-c3cccc(C(O)C(F)(F)F)c3)cc3nonc23)CC1] | 51.7 (14.7) | | | | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1377 | 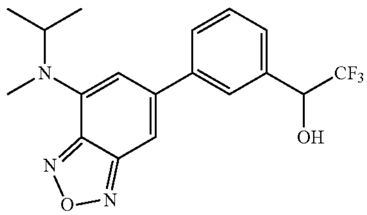 [SMILES: CC(C)N(C)c1cc(-c2cccc(C(O)C(F)(F)F)c2)cc2nonc12] | 1.86 (22.1) | | | | | |
| 1378 | 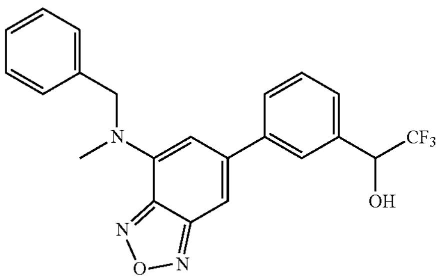 [SMILES: CN(Cc1ccccc1)c1cc(-c2cccc(C(O)C(F)(F)F)c2)cc2nonc12] | 2.38 (22.1) | | | | | |
| 1379 | 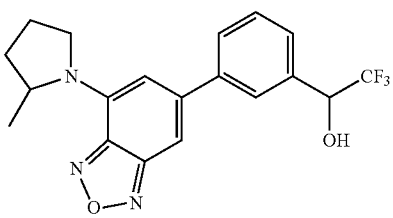 [SMILES: CC1CCCN1c1cc(-c2cccc(C(O)C(F)(F)F)c2)cc2nonc12] | 1.65 (22.1) | | | | | |
| 1380 | 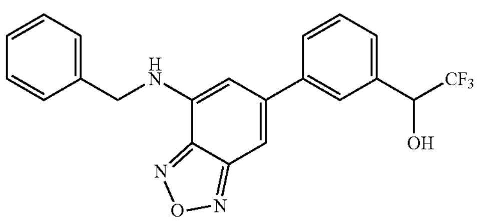 [SMILES: OC(c1cccc(-c2cc(NCc3ccccc3)c3nonc3c2)c1)C(F)(F)F] | | | | 57.10 (55.8) | | |
| 1381 | 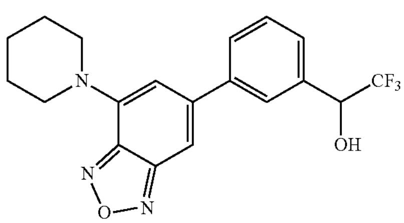 [SMILES: OC(c1cccc(-c2cc(N3CCCCC3)c3nonc3c2)c1)C(F)(F)F] | | | | 70.36 (55.78) | | |
| 1382 | 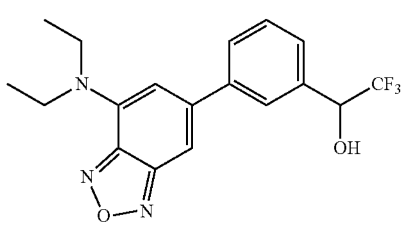 [SMILES: CCN(CC)c1cc(-c2cccc(C(O)C(F)(F)F)c2)cc2nonc12] | | | | 60.02 (55.78) | | |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42- bio |
|---|---|---|---|---|---|---|---|
| 1383 | 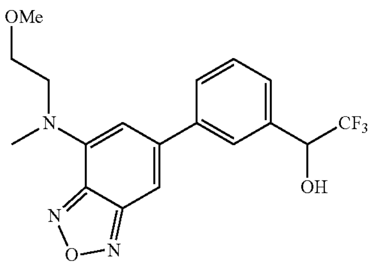 [SMILES: COCCN(C)c1cc(-c2cccc(C(O)C(F)(F)F)c2)cc2nonc12] | | | | 54.94 (55.78) | | |
| 1384 | 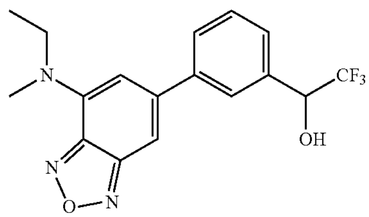 [SMILES: CCN(C)c1cc(-c2cccc(C(O)C(F)(F)F)c2)cc2nonc12] | | | | 72.39 (55.78) | | |
| 1385 | 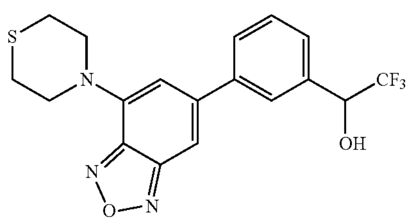 [SMILES: OC(c1cccc(-c2cc(N3CCSCC3)c3nonc3c2)c1)C(F)(F)F] | | | | 65.63 (55.78) | | |
| 1387 | 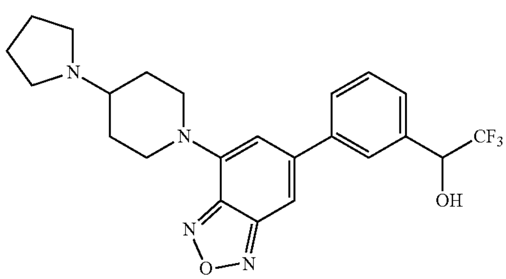 [SMILES: OC(c1cccc(-c2cc(N3CCC(N4CCCC4)CC3)c3nonc3c2)c1)C(F)(F)F] | 5.76 | 78 (69) | 52 (56) | 40 (38) | | |
| 1390 | 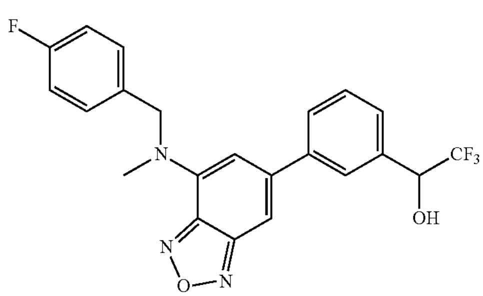 [SMILES: CN(Cc1ccc(F)cc1)c1cc(-c2cccc(C(O)C(F)(F)F)c2)cc2nonc12] | | 75 (69) | | 51 (48) | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1392 | 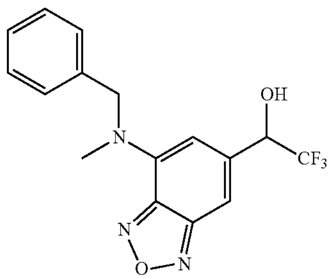 [SMILES: CN(Cc1ccccc1)c1cc(C(O)C(F)(F)F)cc2nonc12] | | 69(53) | | 36 (28) | | |
| 1397 | 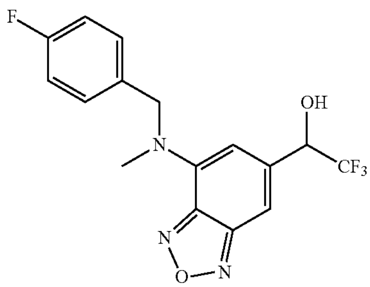 [SMILES: CN(Cc1ccc(F)cc1)c1cc(C(O)C(F)(F)F)cc2nonc12] | | 61(53) | | 38(28) | | |
| 1400 | 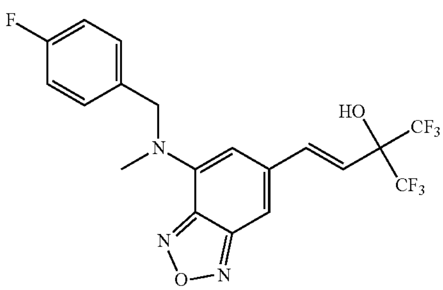 [SMILES: CN(Cc1ccc(F)cc1)c1cc(/C=C/C(O)(C(F)(F)F)C(F)(F)F)cc2nonc12] | | 80 (58) | | 48 (34) | | |
| 1401 | 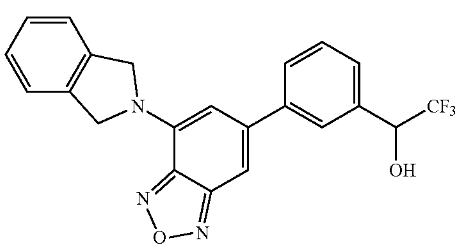 [SMILES: OC(c1cccc(-c2cc(N3Cc4ccccc4C3)c3nonc3c2)c1)C(F)(F)F] | | 58 (58) | | 39 (34) | | |
| 1403 | 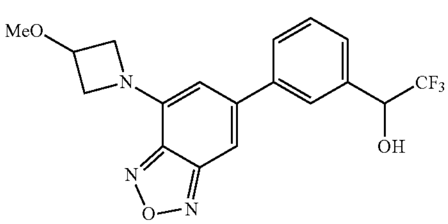 [SMILES: COC1CN(c2cc(-c3cccc(C(O)C(F)(F)F)c3)cc3nonc23)C1] | | 81 (58) | | 51 (34) | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1404 | 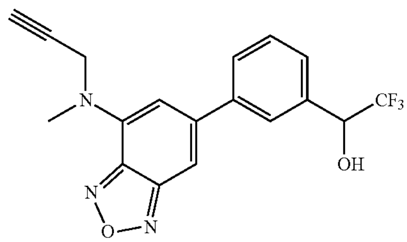 [SMILES: C#CCN(C)c1cc(-c2cccc(C(O)C(F)(F)F)c2)cc2nonc12] | | 69 (52) | | 39 (28) | | |
| 1405 | 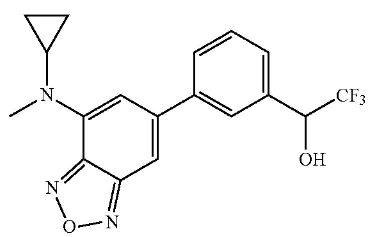 [SMILES: CN(c1cc(-c2cccc(C(O)C(F)(F)F)c2)cc2nonc12)C1CC1] | | 76 (52) | | 46 (28) | | |
| 1406 | 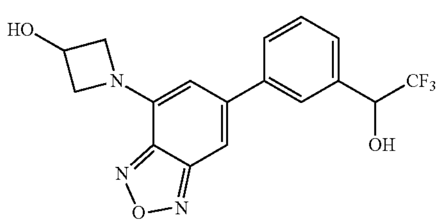 [SMILES: OC1CN(c2cc(-c3cccc(C(O)C(F)(F)F)c3)cc3nonc23)C1] | | 83 (52) | | 53 (28) | | |
| 1409 | 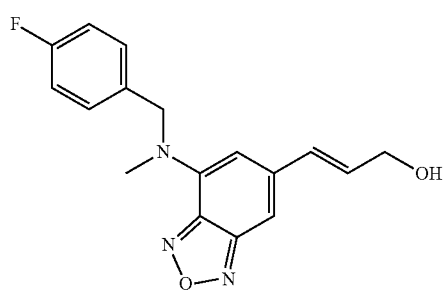 [SMILES: CN(Cc1ccc(F)cc1)c1cc(/C=C/CO)cc2nonc12] | | 69 (52) | | 50 (28) | | |
| 1411 | 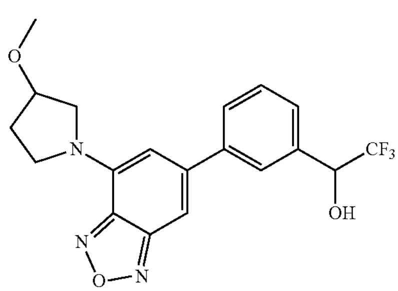 [SMILES: COC1CCN(c2cc(-c3cccc(C(O)C(F)(F)F)c3)cc3nonc23)C1] | | 81 (53) | | 56(28) | | |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1412 | 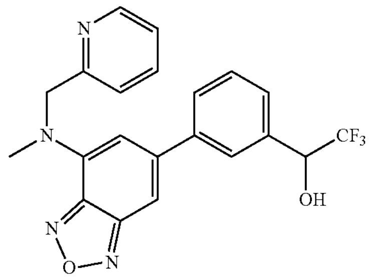 [SMILES: CN(Cc1ccccn1)c1cc(-c2cccc(C(O)C(F)(F)F)c2)cc2nonc12] | | 64(53) | | 51(28) | | |
| 1413 | 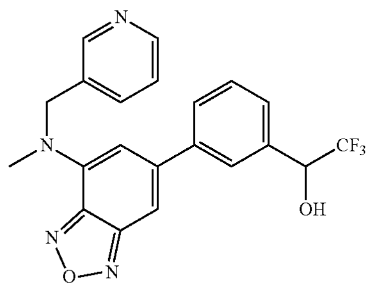 [SMILES: CN(Cc1cccnc1)c1cc(-c2cccc(C(O)C(F)(F)F)c2)cc2nonc12] | | 61.3(53) | | 53(28) | | |
| 1414 | 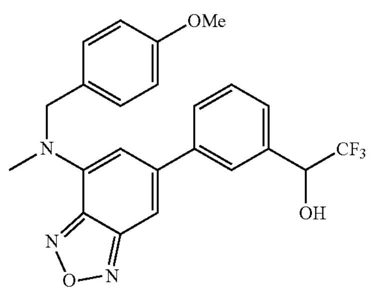 [SMILES: COc1ccc(CN(C)c2cc(-c3cccc(C(O)C(F)(F)F)c3)cc3nonc23)cc1] | | 69(53) | | 53(28) | | |
| 1415 | 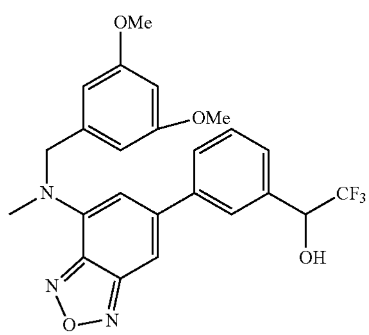 [SMILES: COc1cc(CN(C)c2cc(-c3cccc(C(O)C(F)(F)F)c3)cc3nonc23)cc(OC)c1] | | 53 (51) | | 52 (33) | | |
| 1417 | 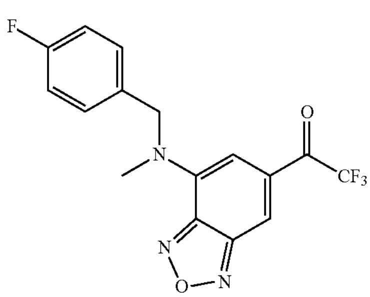 [SMILES: CN(Cc1ccc(F)cc1)c1cc(C(=O)C(F)(F)F)cc2nonc12] | | 75 (51) | | 52 (33) | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1418 | 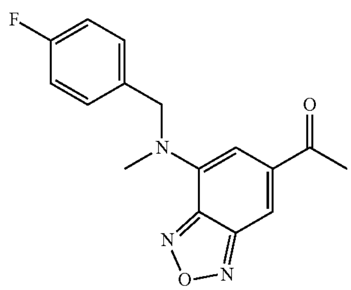 [SMILES: CC(=O)c1cc(N(C)Cc2ccc(F)cc2)c2nonc2c1] | | | 55 (51) | 34 (33) | | |
| 1419 | 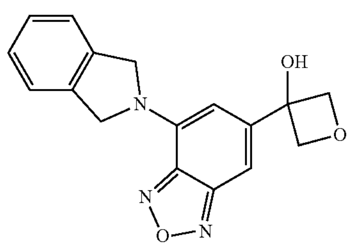 [SMILES: OC1(c2cc(N3Cc4ccccc4C3)c3nonc3c2)COC1] | | | 55 (51) | 48 (33) | | |
| 1420 | 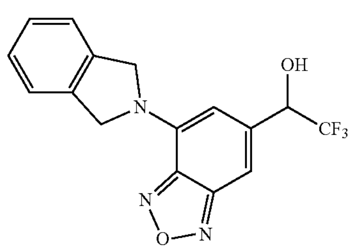 [SMILES: OC(c1cc(N2Cc3ccccc3C2)c2nonc2c1)C(F)(F)F] | | | 48 (51) | 44 (33) | | |
| 1427 | 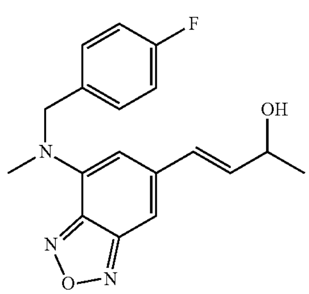 [SMILES: CC(O)/C=C/c1cc(N(C)Cc2ccc(F)cc2)c2nonc2c1] | | | 41 (38) | 18 (18) | | |
| 1428 | 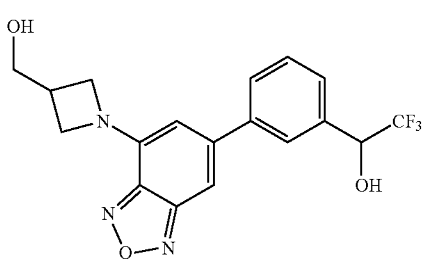 [SMILES: OCC1CN(c2cc(-c3cccc(C(O)C(F)(F)F)c3)cc3nonc23)C1] | | | 78 (47) | 52 (26) | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1432 | 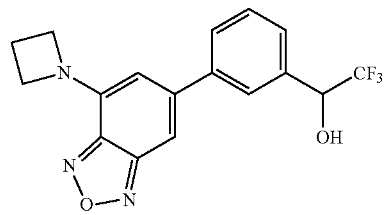 [SMILES: OC(c1cccc(-c2cc(N3CCC3)c3nonc3c2)c1)C(F)(F)F] | | | 51 (47) | | 23 (26) | |
| 1435 | 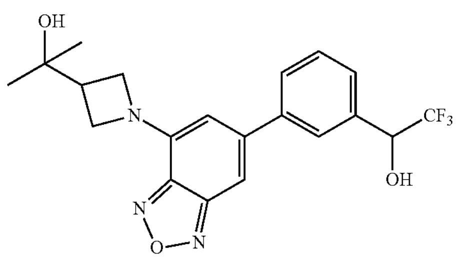 [SMILES: CC(C)(O)C1CN(c2cc(-c3cccc(C(O)C(F)(F)F)c3)cc3nonc23)C1] | | | 66 (50) | 52 (34) | | |
| 1436 | 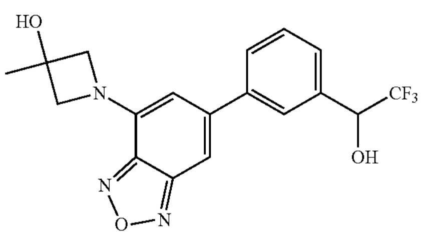 [SMILES: CC1(O)CN(c2cc(-c3cccc(C(O)C(F)(F)F)c3)cc3nonc23)C1] | | | 67 (50) | 48 (33) | | |
| 1437 | 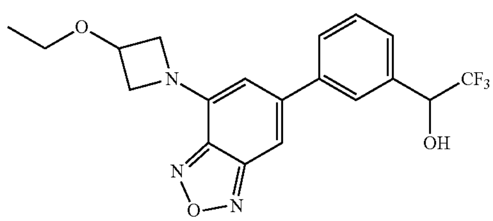 [SMILES: CCOC1CN(c2cc(-c3cccc(C(O)C(F)(F)F)c3)cc3nonc23)C1] | | | 50 (50) | 44 (33) | | |
| 1440 | 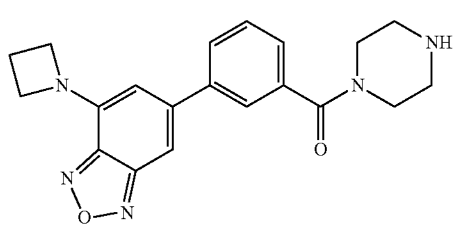 [SMILES: O=C(c1cccc(-c2cc(N3CCC3)c3nonc3c2)c1)N1CCNCC1] | | | 60 (50) | 52 (33) | | |
| 1441 | 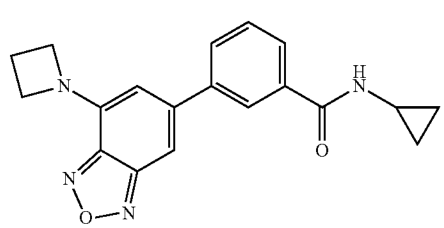 [SMILES: O=C(NC1CC1)c1cccc(-c2cc(N3CCC3)c3nonc3c2)c1] | | | 64 (50) | 47 (33) | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1442 | 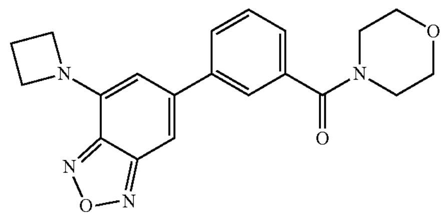 [SMILES: O=C(c1cccc(-c2cc(N3CCC3)c3nonc3c2)c1)N1CCOCC1] | | | | 43 (50) | 29 (33) | |
| 1446 | 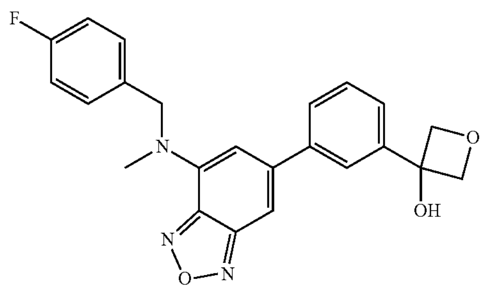 [SMILES: CN(Cc1ccc(F)cc1)c1cc(-c2cccc(C3(O)COC3)c2)cc2nonc12] | | | | 50 (50) | 29 (36) | |
| 1447 | 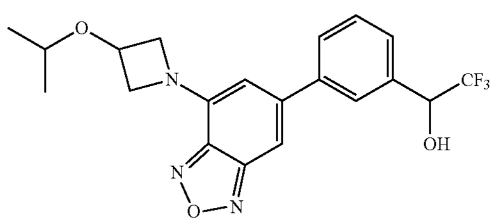 [SMILES: CC(C)OC1CN(c2cc(-c3cccc(C(O)C(F)(F)F)c3)cc3nonc23)C1] | | | | 70 (50) | 54 (36) | |
| 1448 | 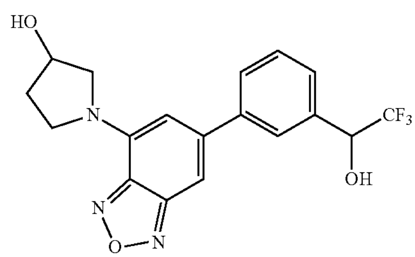 [SMILES: OC1CCN(c2cc(-c3cccc(C(O)C(F)(F)F)c3)cc3nonc23)C1] | | | | 55 (50) | 45 (36) | |
| 1449 | 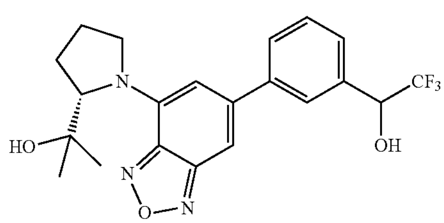 [SMILES: CC(C)(O)[C@@H]1CCCN1c1cc(-c2cccc(C(O)C(F)(F)F)c2)cc2nonc12] | | | | 72 (50) | 55 (36) | |
| 1450 | 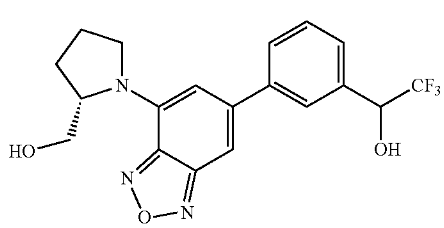 [SMILES: OC[C@@H]1CCCN1c1cc(-c2cccc(C(O)C(F)(F)F)c2)cc2nonc12] | | | | 79 (50) | 57 (36) | |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1451 | 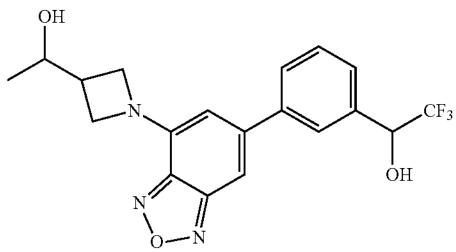 [SMILES: CC(O)C1CN(c2cc(-c3cccc(C(O)C(F)(F)F)c3)cc3nonc23)C1] | | | 73 (56) | 54 (38) | | |
| 1452 | 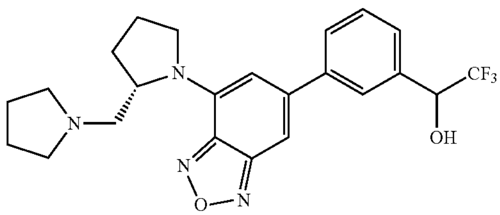 [SMILES: OC(c1cccc(-c2cc(N3CCC[C@H]3CN3CCCC3)c3nonc3c2)c1)C(F)(F)F] | | | 63(47) | 50(23) | | |
| 1455 | 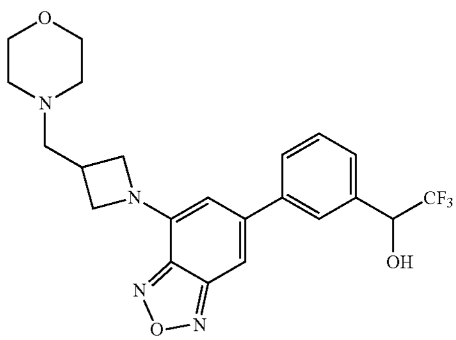 [SMILES: OC(c1cccc(-c2cc(N3CC(CN4CCOCC4)C3)c3nonc3c2)c1)C(F)(F)F] | | | 60(47) | 41(23) | | |
| 1456 | 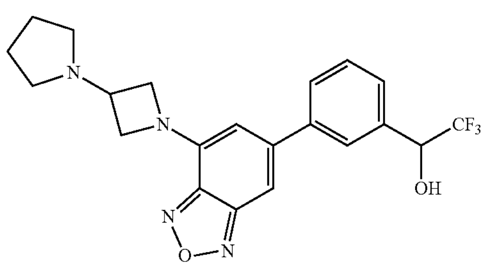 [SMILES: OC(c1cccc(-c2cc(N3CC(N4CCCC4)C3)c3nonc3c2)c1)C(F)(F)F] | | | 64(47) | 36(23) | | |
| 1457 | 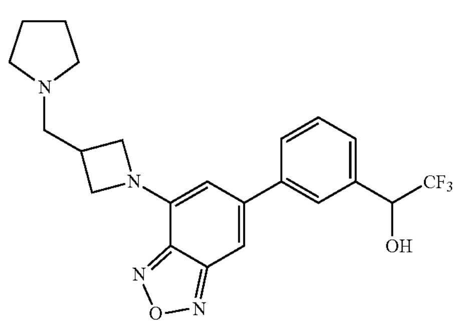 [SMILES: OC(c1cccc(-c2cc(N3CC(CN4CCCC4)C3)c3nonc3c2)c1)C(F)(F)F] | | | 65(47) | 51(23) | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1459 | 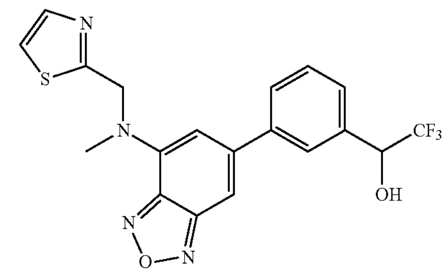 [SMILES: CN(Cc1nccs1)c1cc(-c2cccc(C(O)C(F)(F)F)c2)cc2nonc12] | | | 62 (56) | 47 (38) | | |
| 1460 | 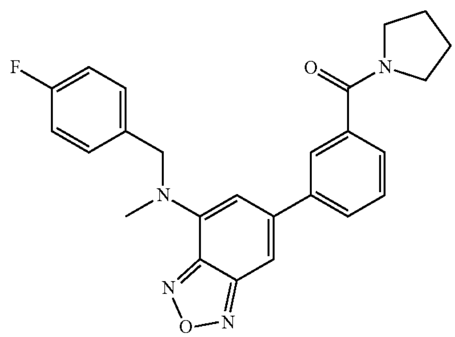 [SMILES: CN(Cc1ccc(F)cc1)c1cc(-c2cccc(C(=O)N3CCCC3)c2)cc2nonc12] | | | 44 (56) | 36 (38) | | |
| 1461 | 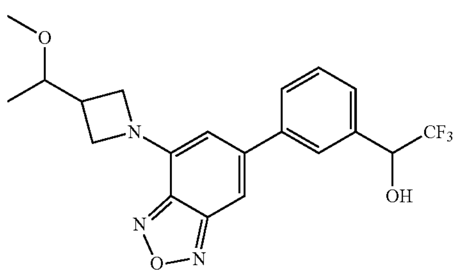 [SMILES: COC(C)C1CN(c2cc(-c3cccc(C(O)C(F)(F)F)c3)cc3nonc23)C1] | | | 71.7 (46.8) | 58.9 22.9 | | |
| 1462 | 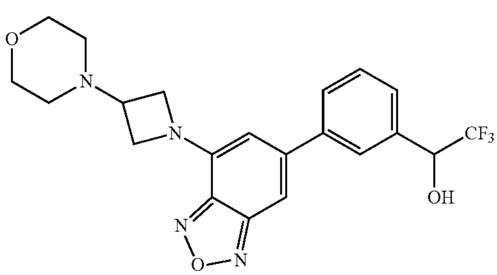 [SMILES: OC(c1cccc(-c2cc(N3CC(N4CCOCC4)C3)c3nonc3c2)c1)C(F)(F)F] | | | 48 (56) | 53 (38) | | |
| 1463 | 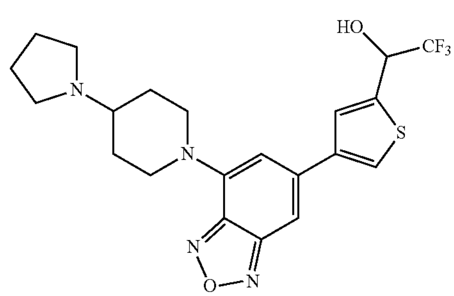 [SMILES: OC(c1cc(-c2cc(N3CCC(N4CCCC4)CC3)c3nonc3c2)cs1)C(F)(F)F] | | | 61 (51) | 37 (50) | | |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1464 | 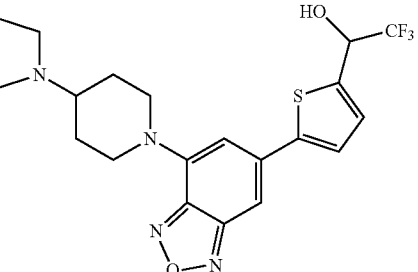 | | | 35 (51) | | | >20 |
| 1465 | 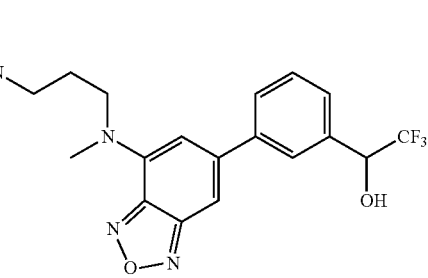 | | | 62 (64) | 44 (42) | | >20 |
| 1466 | 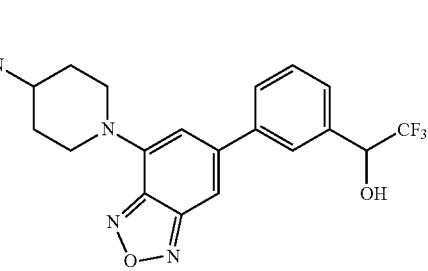 | | | 49 (64) | 37 (42) | | 4.1 |
| 1467 | 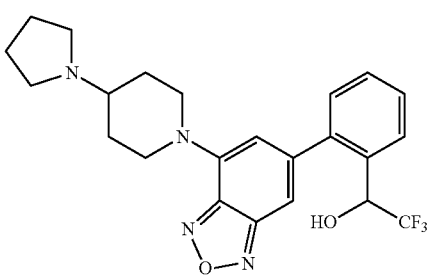 [SMILES: OC(c1ccccc1-c1cc(N2CCC(N3CCCC3)CC2)c2nonc2c1)C(F)(F)F] | | | 43 (64) | 28 (42) | | 5.1 |
| 1468 | 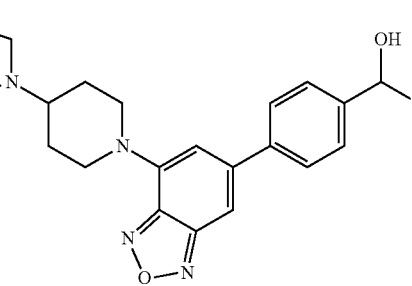 | | | 65 (64) | 44 (42) | | 2.4 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1469 | 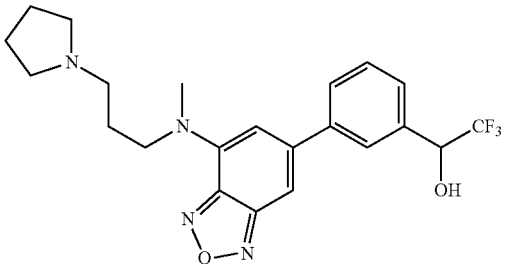 [SMILES: CN(CCCN1CCCC1)c1cc(-c2cccc(C(O)C(F)(F)F)c2)cc2nonc12] | | | 75 (55) | 70 (50) | | 2.4 |
| 1470 | 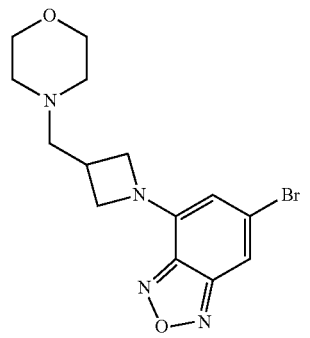 [SMILES: Brc1cc(N2CC(CN3CCOCC3)C2)c2nonc2c1] | | | 62 (55) | | | >20 |
| 1471 | 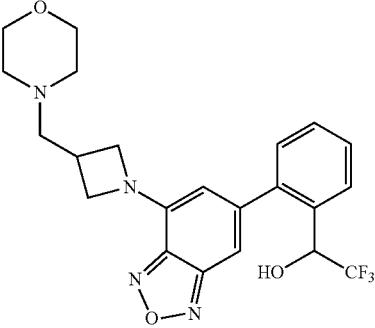 [SMILES: OC(c1ccccc1-c1cc(N2CC(CN3CCOCC3)C2)c2nonc2c1)C(F)(F)F] | | | 29 (55) | | | 4.4 |
| 1472 | 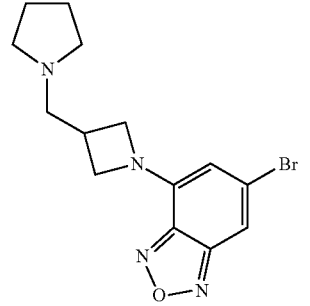 [SMILES: Brc1cc(N2CC(CN3CCCC3)C2)c2nonc2c1] | | | 65 (55) | | | 3.6 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1473 | 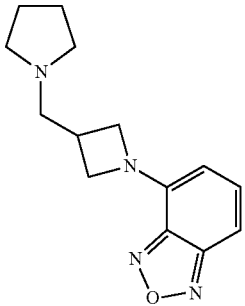 [SMILES: c1cc(N2CC(CN3CCCC3)C2)c2nonc2c1] | | | | 31 (55) | | 18.1 |
| 1474 | 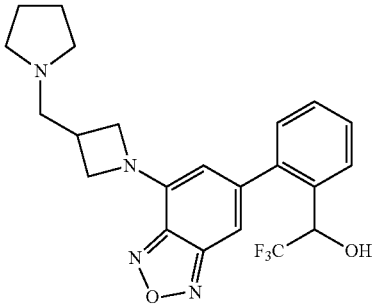 [SMILES: OC(c1ccccc1-c1cc(N2CC(CN3CCCC3)C2)c2nonc2c1)C(F)(F)F] | | | | 77 (55) | | 3.1 |
| 1476 | 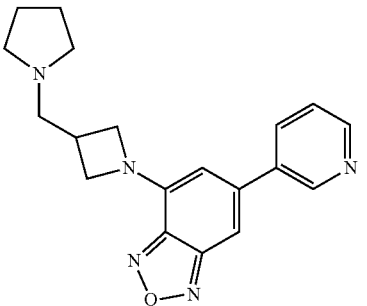 [SMILES: c1cncc(-c2cc(N3CC(CN4CCCC4)C3)c3nonc3c2)c1] | | | | 36 (55) | | 12.2 |
| 1477 | 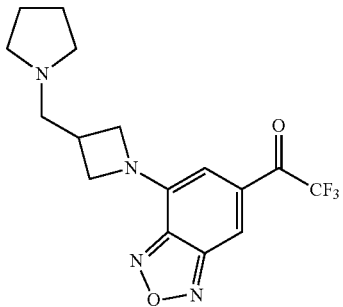 [SMILES: O=C(c1cc(N2CC(CN3CCCC3)C2)c2nonc2c1)C(F)(F)F] | | | | 30 (51) | | 1.83 |

| ID | Structure | IC50 Thioflavin T A β 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1478 | 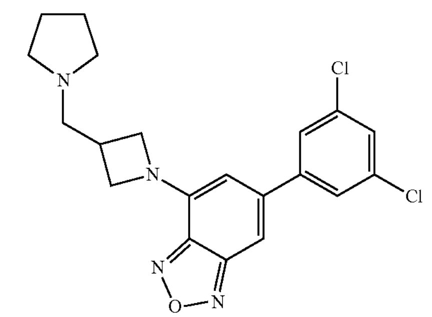 [SMILES: Clc1cc(Cl)cc(-c2cc(N3CC(CN4CCCC4)C3)c3nonc3c2)c1] | | | 63 (61) | | | 1.82 |
| 1479 | 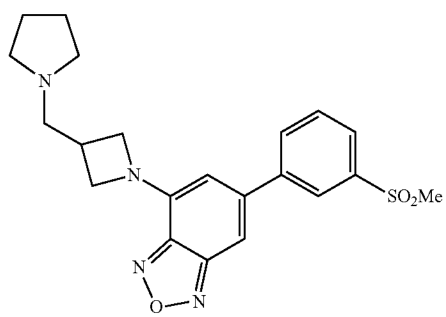 [SMILES: CS(=O)(=O)c1cccc(-c2cc(N3CC(CN4CCCC4)C3)c3nonc3c2)c1] | | | 24 (51) | | | 7.94 |
| 1480 | 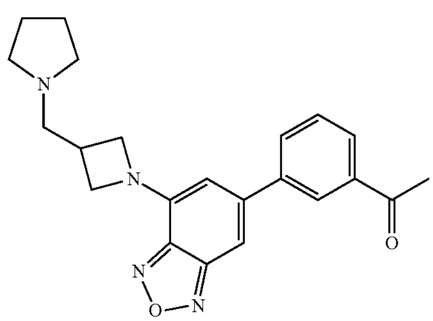 [SMILES: CC(=O)c1cccc(-c2cc(N3CC(CN4CCCC4)C3)c3nonc3c2)c1] | | | 31 (51) | | | 6.33 |
| 1481 | 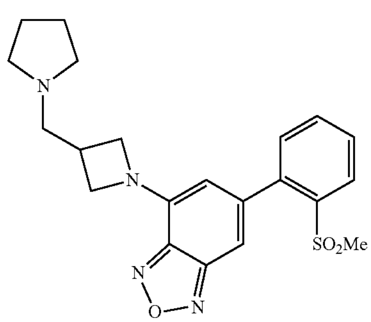 [SMILES: CS(=O)(=O)c1ccccc1-c1cc(N2CC(CN3CCCC3)C2)c2nonc2c1] | | | 11 (51) | | | 6.14 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1482 | 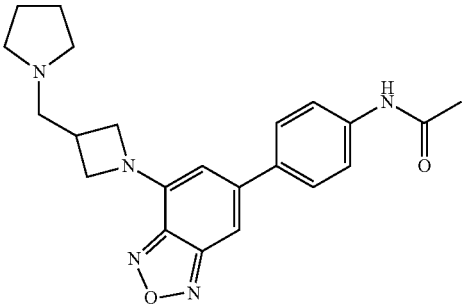 [SMILES: CC(=O)Nc1ccc(-c2cc(N3CC(CN4CCCC4)C3)c3nonc3c2)cc1] | | | 41 (51) | | | 5.52 |
| 1483 | 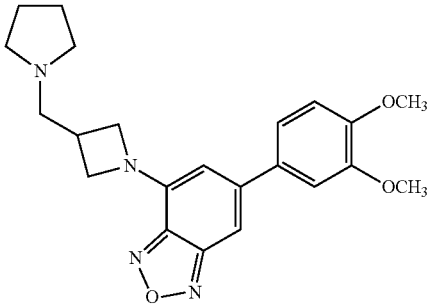 [SMILES: COc1ccc(-c2cc(N3CC(CN4CCCC4)C3)c3nonc3c2)cc1OC] | | | 36 (51) | | | 8.21 |
| 1484 | 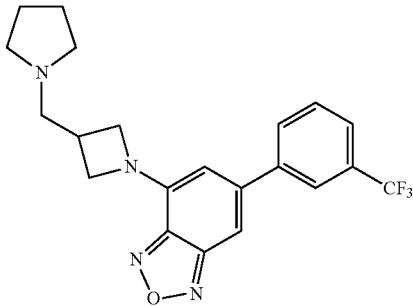 [SMILES: FC(F)(F)c1cccc(-c2cc(N3CC(CN4CCCC4)C3)c3nonc3c2)c1] | | | 56 (61) | | | 6.5 |
| 1485 | 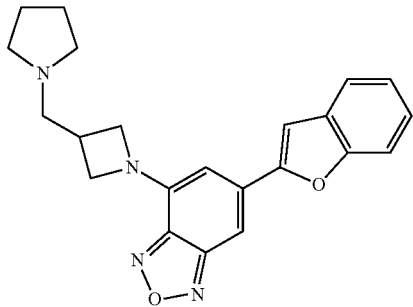 [SMILES: c1ccc2oc(-c3cc(N4CC(CN5CCCC5)C4)c4nonc4c3)cc2c1] | | | 26 (61) | | | 2.63 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1486 | 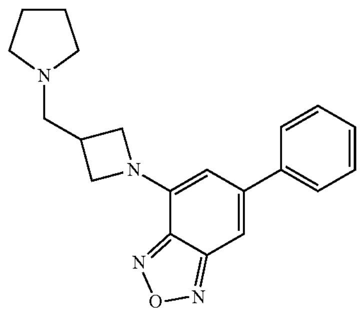 [SMILES: c1ccc(-c2cc(N3CC(CN4CCCC4)C3)c3nonc3c2)cc1] | | | 32 (61) | | | 19.7 |
| 1487 | 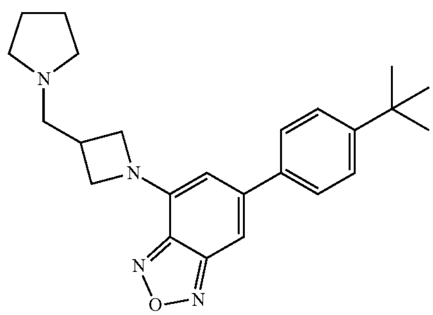 [SMILES: CC(C)(C)c1ccc(-c2cc(N3CC(CN4CCCC4)C3)c3nonc3c2)cc1] | | | 33 (61) | | | 0.62 |
| 1488 | 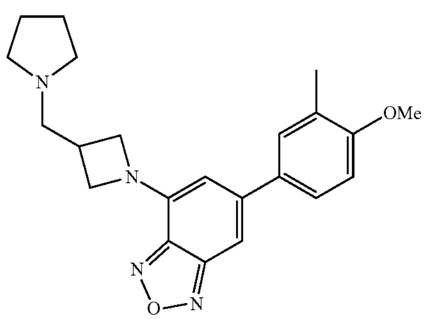 [SMILES: COc1ccc(-c2cc(N3CC(CN4CCCC4)C3)c3nonc3c2)cc1C] | | | 31 (61) | | | 8.69 |
| 1489 | 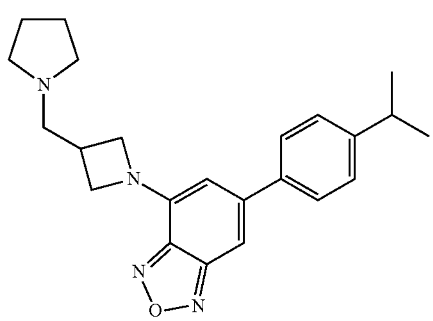 [SMILES: CC(C)c1ccc(-c2cc(N3CC(CN4CCCC4)C3)c3nonc3c2)cc1] | | | 34 (61) | | | 1.6 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1490 | 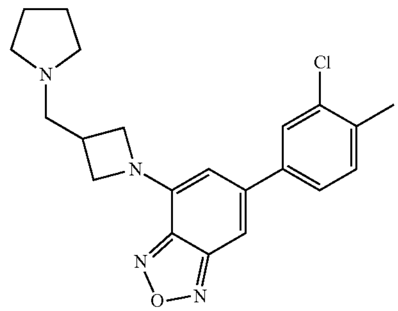 [SMILES: Cc1ccc(-c2cc(N3CC(CN4CCCC4)C3)c3nonc3c2)cc1Cl] | | | 27 (61) | | | 4.4 |
| 1491 | 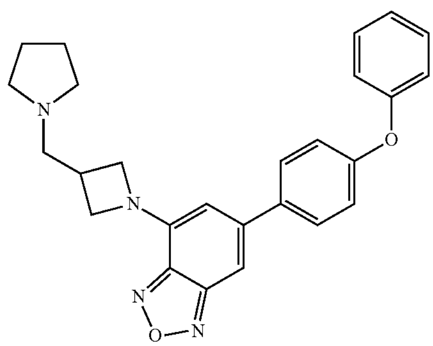 [SMILES: c1ccc(Oc2ccc(-c3cc(N4CC(CN5CCCC5)C4)c4nonc4c3)cc2)cc1] | | | 32 (61) | | | 0.52 |
| 1492 | 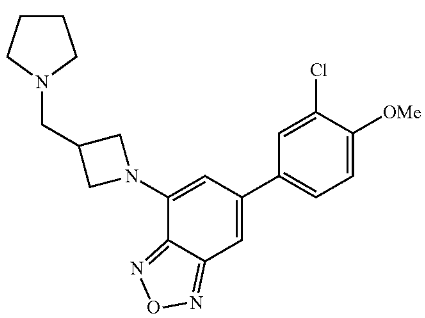 [SMILES: COc1ccc(-c2cc(N3CC(CN4CCCC4)C3)c3nonc3c2)cc1Cl] | | | 22 (61) | | | 4.8 |
| 1493 | 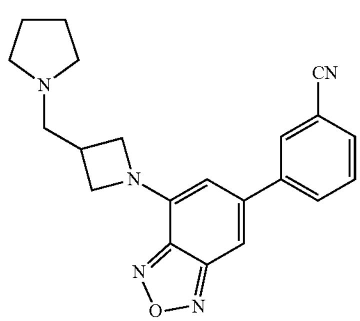 [SMILES: N#Cc1cccc(-c2cc(N3CC(CN4CCCC4)C3)c3nonc3c2)c1] | | | 57 (61) | | | 12.9 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1494 | 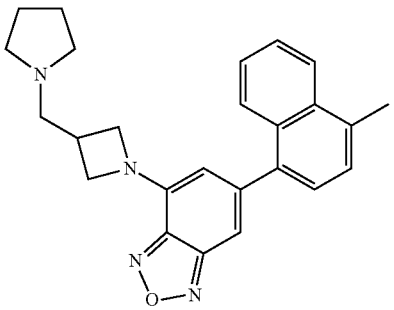 [SMILES: Cc1ccc(-c2cc(N3CC(CN4CCCC4)C3)c3nonc3c2)c2ccccc12] | | | 45 (62) | | | 2.01 |
| 1495 | 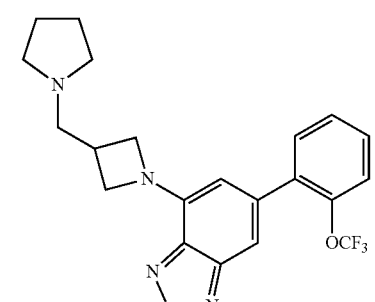 | | | 64 (61) | | | 5.91 |
| 1496 | 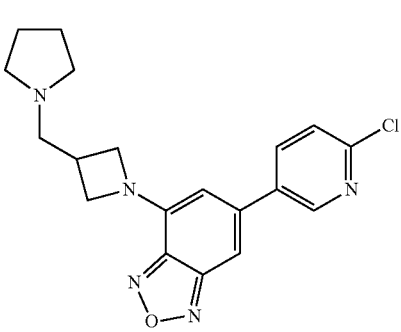 [SMILES: Clc1ccc(-c2cc(N3CC(CN4CCCC4)C3)c3nonc3c2)cn1] | | | 41 (61) | | | 13.5 |
| 1497 | 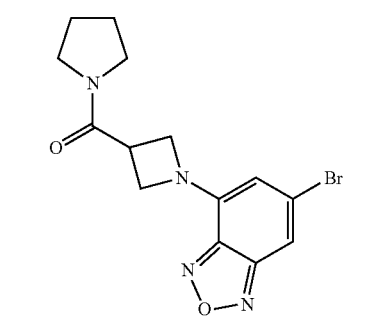 [SMILES: O=C(C1CN(c2cc(Br)cc3nonc23)C1)N1CCCC1] | | | 65 (61) | | | >20 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1498 | 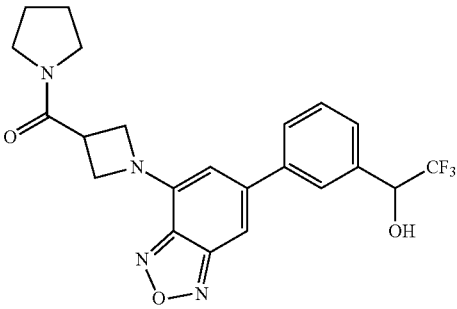 [SMILES: O=C(C1CN(c2cc(-c3cccc(C(O)C(F)(F)F)c3)cc3nonc23)C1)N1CCCC1] | | | 48 (61) | | | 10.8 |
| 1499 | 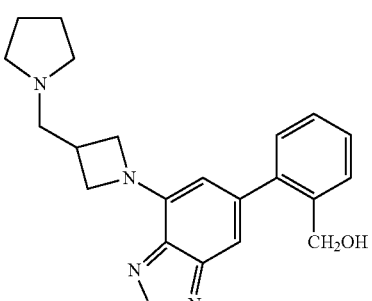 | | | 34 (57) | | | 23.3 |
| 1500 | 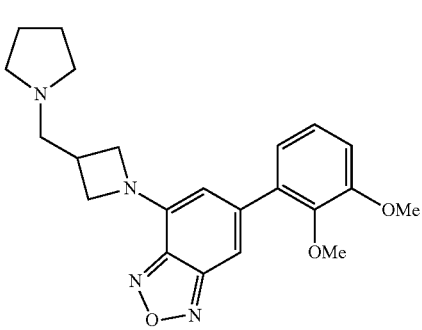 [SMILES: COc1cccc(-c2cc(N3CC(CN4CCCC4)C3)c3nonc3c2)c1OC] | | | 51 (57) | | | >20 |
| 1501 | 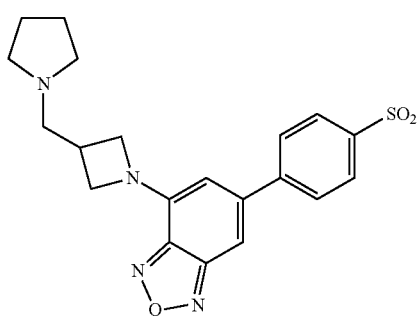 | | | 48 (57) | | | >20 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1502 | 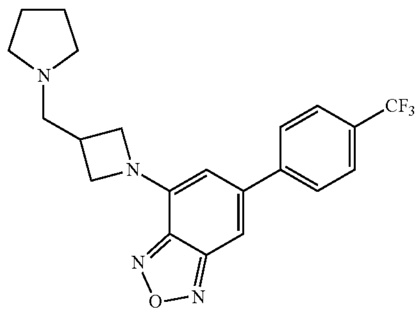 [SMILES: FC(F)(F)c1ccc(-c2cc(N3CC(CN4CCCC4)C3)c3nonc3c2)cc1] | | | 55 (57) | | | 4.78 |
| 1503 | 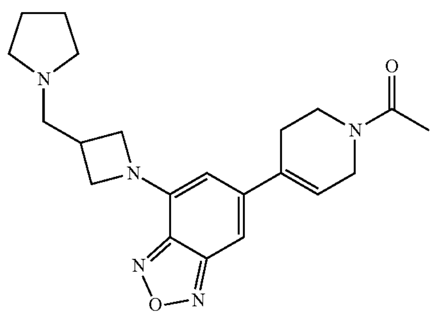 [SMILES: CC(=O)N1CC=C(c2cc(N3CC(CN4CCCC4)C3)c3nonc3c2)CC1] | | | 33 (57) | | | >20 |
| 1504 | 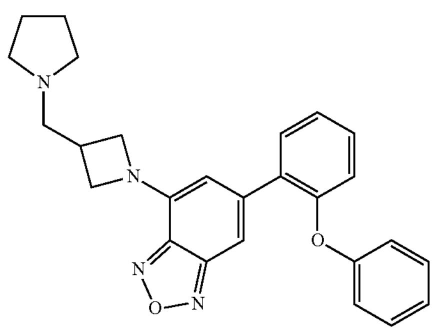 [SMILES: c1ccc(Oc2ccccc2-c2cc(N3CC(CN4CCCC4)C3)c3nonc3c2)cc1] | | | 72 (67) | | | 5.27 |
| 1505 | 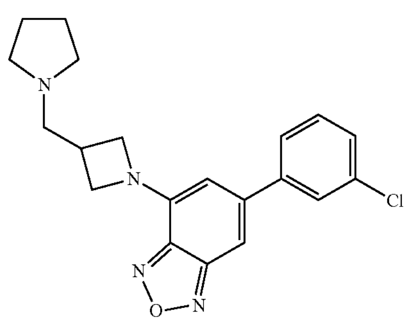 [SMILES: Clc1cccc(-c2cc(N3CC(CN4CCCC4)C3)c3nonc3c2)c1] | | | 62 (57) | | | 4.62 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1506 | 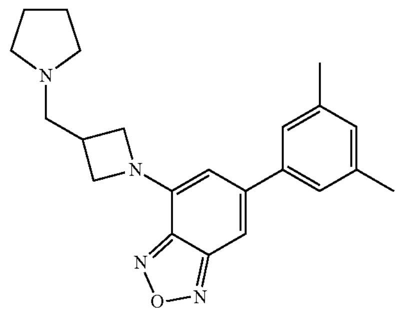 [SMILES: Cc1cc(C)cc(-c2cc(N3CC(CN4CCCC4)C3)c3nonc3c2)c1] | | | 44 (61) | | | 4.44 |
| 1507 | 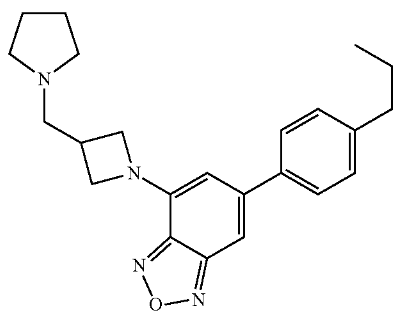 [SMILES: CCCc1ccc(-c2cc(N3CC(CN4CCCC4)C3)c3nonc3c2)cc1] | | | 83 (69) | | | 2.46 |
| 1509 | 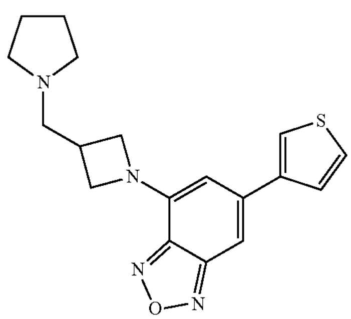 [SMILES: c1cc(-c2cc(N3CC(CN4CCCC4)C3)c3nonc3c2)cs1] | | | 71 (69) | | | >20 |
| 1510 | 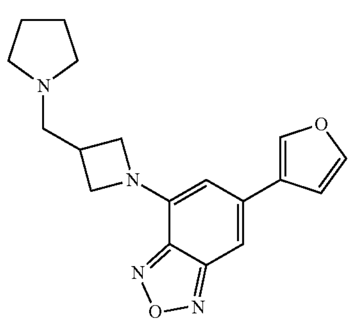 [SMILES: c1cc(-c2cc(N3CC(CN4CCCC4)C3)c3nonc3c2)co1] | | | 65 (69) | | | >20 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1511 | 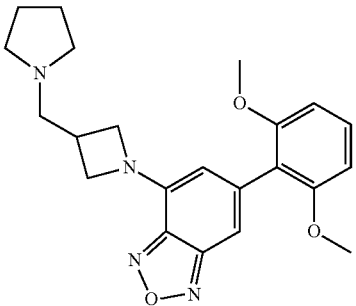 [SMILES: COc1cccc(OC)c1-c1cc(N2CC(CN3CCCC3)C2)c2nonc2c1] | | | 27 (69) | | | 21.3 |
| 1512 | 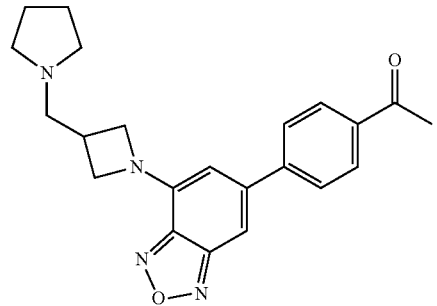 [SMILES: CC(=O)c1ccc(-c2cc(N3CC(CN4CCCC4)C3)c3nonc3c2)cc1] | | | 77 (69) | | | 12.0 |
| 1514 | 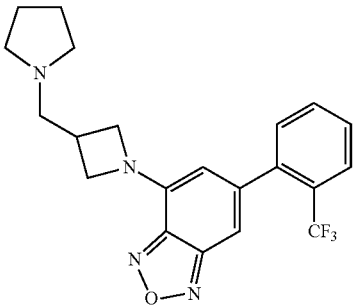 [SMILES: FC(F)(F)c1ccccc1-c1cc(N2CC(CN3CCCC3)C2)c2nonc2c1] | | | 57 (69) | | | 11.2 |
| 1515 | 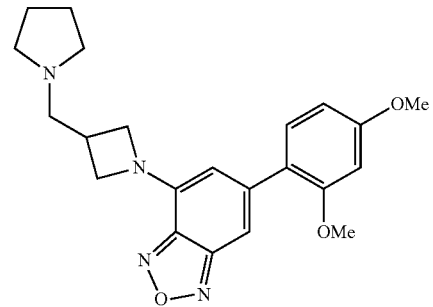 [SMILES: COc1ccc(-c2cc(N3CC(CN4CCCC4)C3)c3nonc3c2)c(OC)c1] | | | 61 (69) | | | 16.7 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1516 | 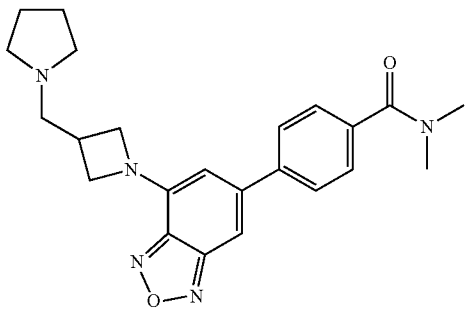 [SMILES: CN(C)C(=O)c1ccc(-c2cc(N3CC(CN4CCCC4)C3)c3nonc3c2)cc1] | | | 47 (69) | | | >20 |
| 1517 | 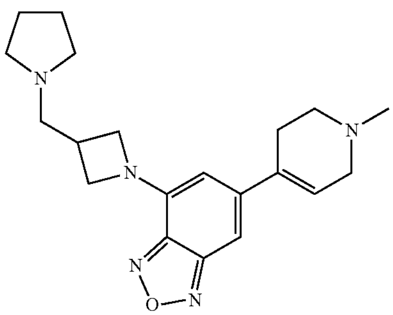 [SMILES: CN1CC=C(c2cc(N3CC(CN4CCCC4)C3)c3nonc3c2)CC1] | | | 33 (69) | | | 6.8 |
| 1518 | 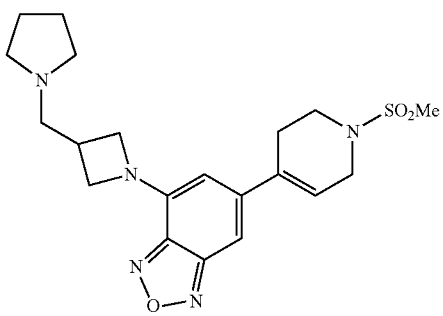 [SMILES: CS(=O)(=O)N1CC=C(c2cc(N3CC(CN4CCCC4)C3)c3nonc3c2)CC1] | | | 35 (69) | | | >20 |
| 1519 | 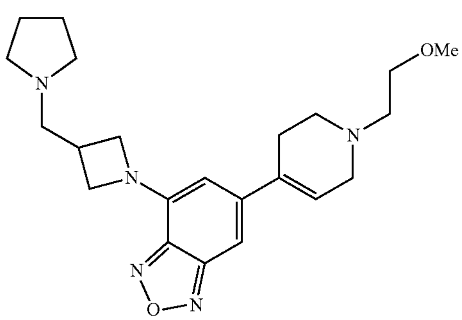 [SMILES: COCCN1CC=C(c2cc(N3CC(CN4CCCC4)C3)c3nonc3c2)CC1] | | | 53 (69) | | | 8.2 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1520 | 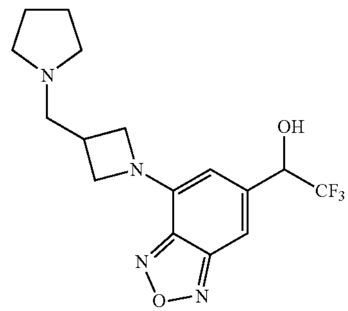 [SMILES: OC(c1cc(N2CC(CN3CCCC3)C2)c2nonc2c1)C(F)(F)F] | | | 46 (69) | | | 6.1 |
| 1521 | 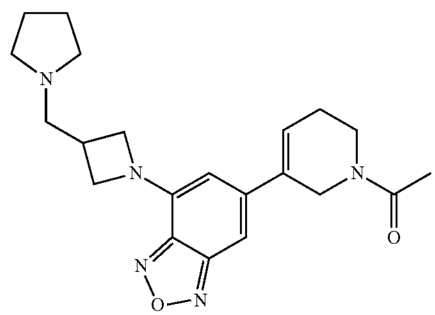 [SMILES: CC(=O)N1CCC=C(c2cc(N3CC(CN4CCCC4)C3)c3nonc3c2)C1] | | | 20 (70) | | | 30.1 |
| 1522 | 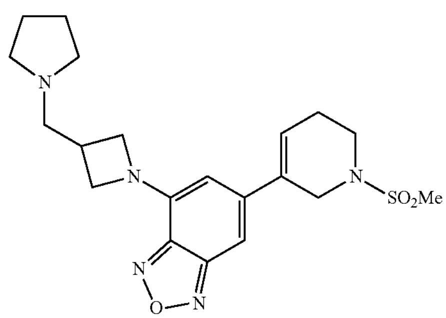 [SMILES: CS(=O)(=O)N1CCC=C(c2cc(N3CC(CN4CCCC4)C3)c3nonc3c2)C1] | | | 44 (70) | | | 10.1 |
| 1523 | 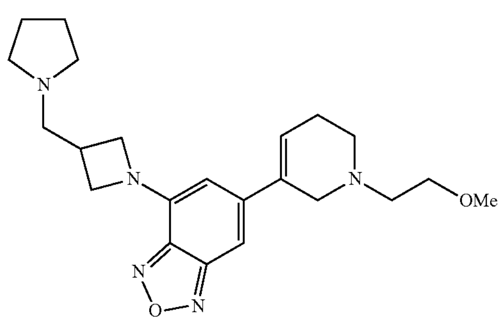 [SMILES: COCCN1CCC=C(c2cc(N3CC(CN4CCCC4)C3)c3nonc3c2)C1] | | | 55 (73) | | | 1.3 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1524 | 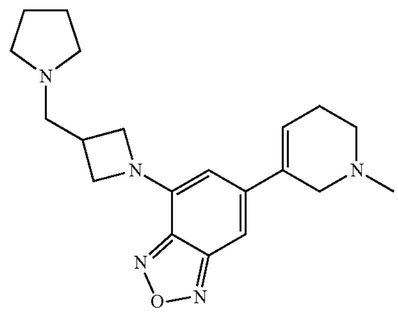 [SMILES: CN1CCC=C(c2cc(N3CC(CN4CCCC4)C3)c3nonc3c2)C1] | | | 61 (73) | | | 14.9 |
| 1525 | 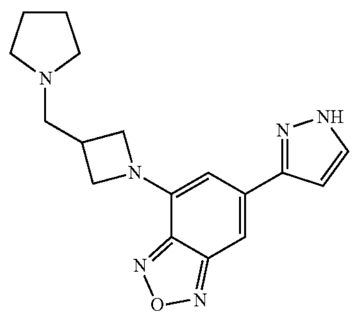 [SMILES: c1cc(-c2cc(N3CC(CN4CCCC4)C3)c3nonc3c2)n[nH]1] | | | 63 (73) | | | 13.2 |
| 1526 | 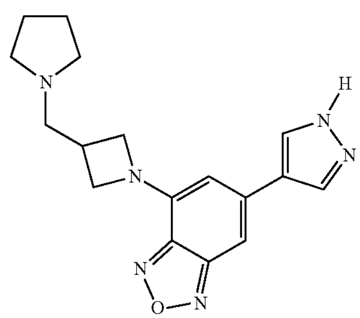 [SMILES: c1n[nH]cc1-c1cc(N2CC(CN3CCCC3)C2)c2nonc2c1] | | | 60 (73) | | | 5.8 |
| 1527 | 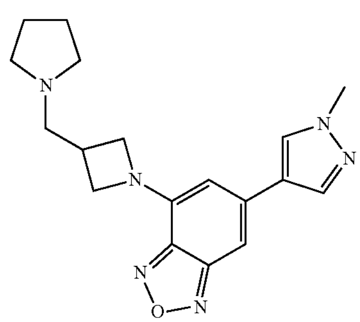 [SMILES: Cn1cc(-c2cc(N3CC(CN4CCCC4)C3)c3nonc3c2)cn1] | | | 49 (73) | | | 7.5 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1528 | 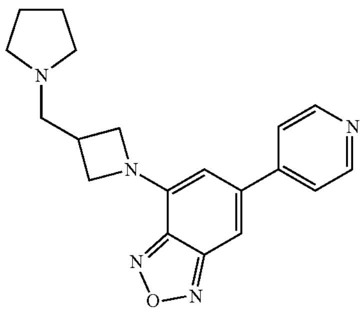 [SMILES: c1cc(-c2cc(N3CC(CN4CCCC4)C3)c3nonc3c2)ccn1] | | | 50 (73) | | | 7.8 |
| 1529 | 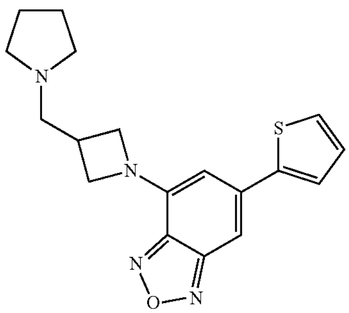 [SMILES: c1csc(-c2cc(N3CC(CN4CCCC4)C3)c3nonc3c2)c1] | | | 74 (73) | | | 9.0 |
| 1530 | 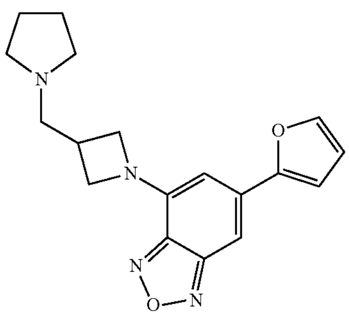 [SMILES: c1coc(-c2cc(N3CC(CN4CCCC4)C3)c3nonc3c2)c1] | | | 79 (73) | | | 10.5 |
| 1531 | 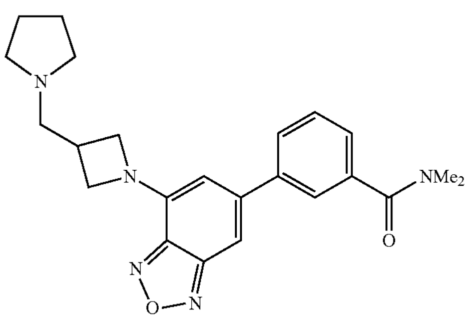 [SMILES: CN(C)C(=O)c1cccc(-c2cc(N3CC(CN4CCCC4)C3)c3nonc3c2)c1] | | | 45 (73) | | | 2.7 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1532 | 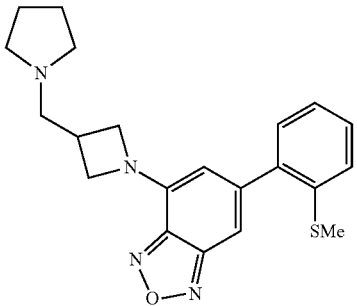 [SMILES: CSc1ccccc1-c1cc(N2CC(CN3CCCC3)C2)c2nonc2c1] |  |  | 68 (73) |  |  | 27.1 |
| 1533 | 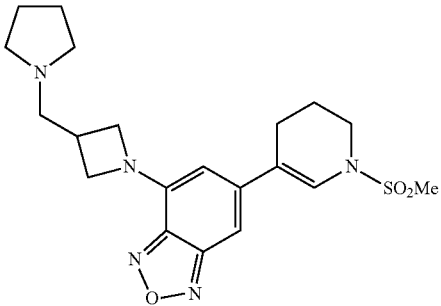 [SMILES: CS(=O)(=O)N1C=C(c2cc(N3CC(CN4CCCC4)C3)c3nonc3c2)CCC1] |  |  | 35 (73) |  |  | 5.6 |
| 1534 | 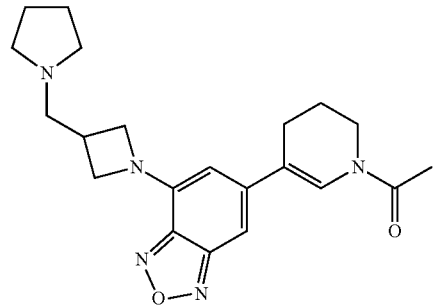 [SMILES: CC(=O)N1C=C(c2cc(N3CC(CN4CCCC4)C3)c3nonc3c2)CCC1] |  |  | 67 (77) |  |  | 3.5 |
| 1535 | 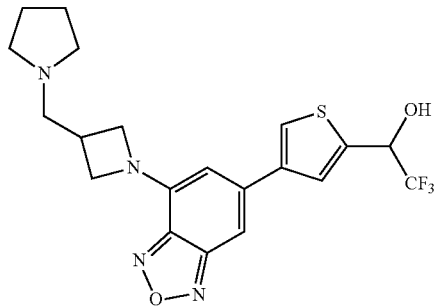 [SMILES: OC(c1cc(-c2cc(N3CC(CN4CCCC4)C3)c3nonc3c2)cs1)C(F)(F)F] |  |  | 77 (78) | 71 (59) |  | 2.9 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1536 | 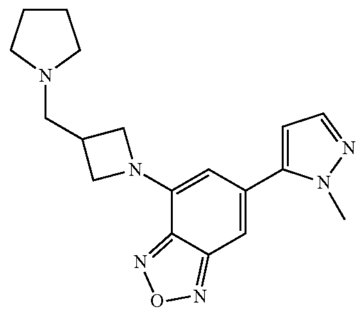 [SMILES: Cn1nccc1-c1cc(N2CC(CN3CCCC3)C2)c2nonc2c1] | | | 61 (78) | 43 (59) | | 4.2 |
| 1537 | 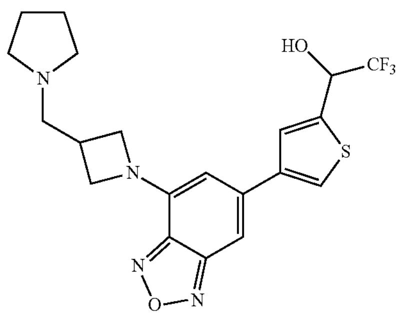 [SMILES: OC(c1cc(-c2cc(N3CC(CN4CCCC4)C3)c3nonc3c2)cs1)C(F)(F)F] | | | 74 (78) | 71 (59) | | 3.5 |
| 1538 | 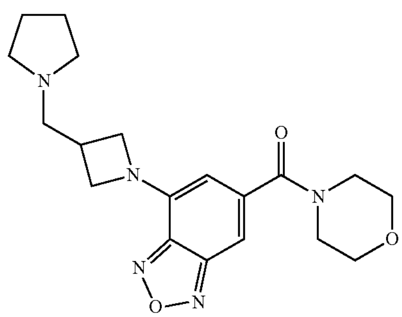 [SMILES: O=C(c1cc(N2CC(CN3CCCC3)C2)c2nonc2c1)N1CCOCC1] | | | 54 (78) | 47 (59) | | 2.9 |
| 1539 | 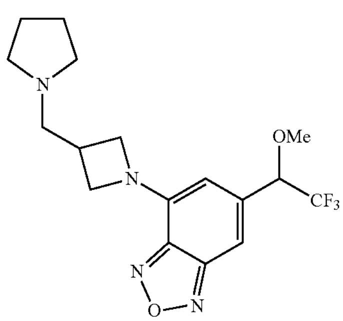 [SMILES: COC(c1cc(N2CC(CN3CCCC3)C2)c2nonc2c1)C(F)(F)F] | | | 55 (78) | 53 (59) | | 7.8 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1540 | 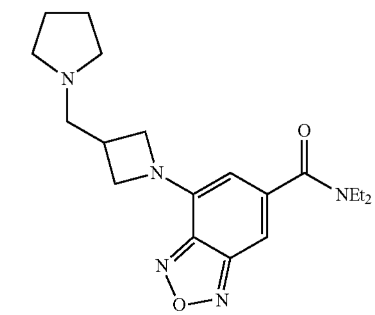 | | | 50 (78) | 41 (59) | | 1.8 |
| 1541 | 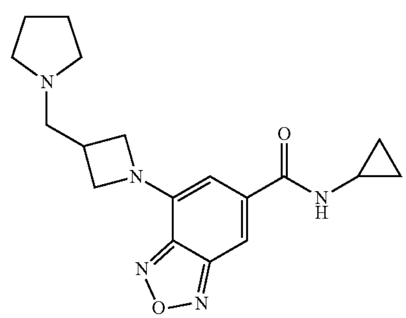 [SMILES: O=C(NC1CC1)c1cc(N2CC(CN3CCCC3)C2)c2nonc2c1] | | | 31 (68) | 19 (53) | | 4.0 |
| 1542 | 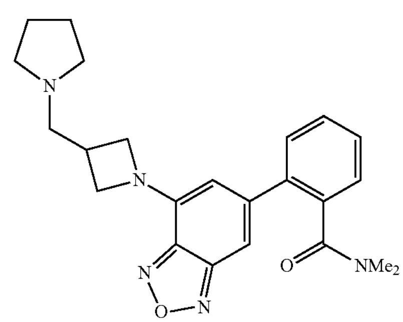 [SMILES: CN(C)C(=O)c1ccccc1-c1cc(N2CC(CN3CCCC3)C2)c2nonc2c1] | | | 36 (68) | 15 (53) | | >20 |
| 1543 | 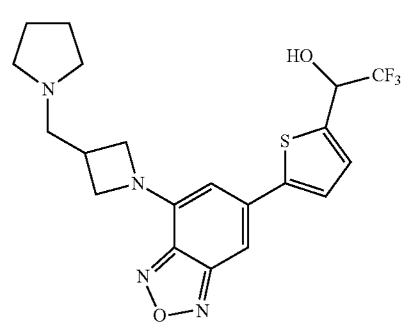 [SMILES: OC(c1ccc(-c2cc(N3CC(CN4CCCC4)C3)c3nonc3c2)s1)C(F)(F)F] | | | 84 (68) | 63 (53) | | 1.1 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1544 | 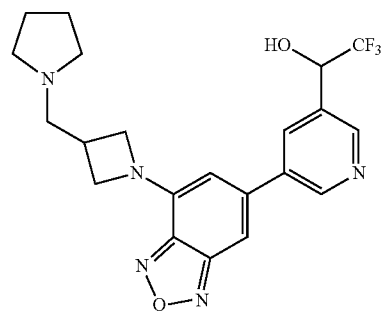 [SMILES: OC(c1cncc(-c2cc(N3CC(CN4CCCC4)C3)c3nonc3c2)c1)C(F)(F)F] | | | | NA | NA | 3.9 |
| 1545 | 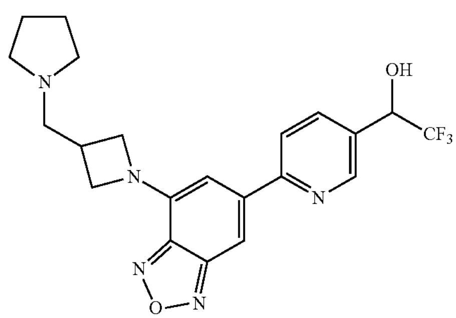 [SMILES: OC(c1ccc(-c2cc(N3CC(CN4CCCC4)C3)c3nonc3c2)nc1)C(F)(F)F] | | | | NA | NA | 8.4 |
| 1546 | 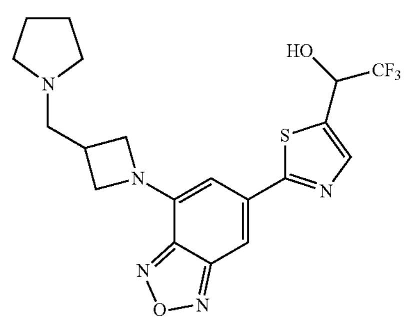 [SMILES: OC(c1cnc(-c2cc(N3CC(CN4CCCC4)C3)c3nonc3c2)s1)C(F)(F)F] | | | | NA | NA | 8.4 |
| 1547 | 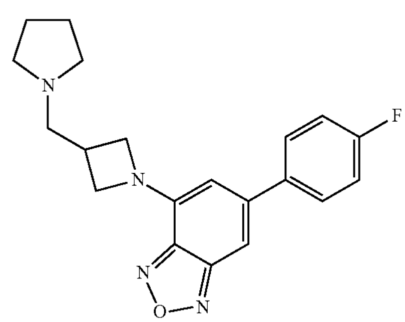 [SMILES: Fc1ccc(-c2cc(N3CC(CN4CCCC4)C3)c3nonc3c2)cc1] | | | | NA | NA | 12.0 |

| ID | Structure | IC50 Thioflavin T A β 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1548 | 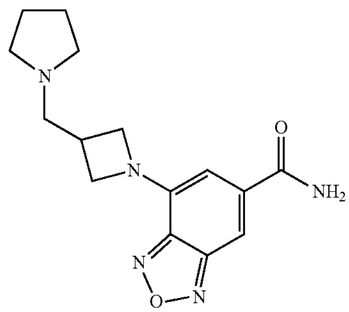 [SMILES: NC(=O)c1cc(N2CC(CN3CCCC3)C2)c2nonc2c1] | | | | NA | NA | 25.3 |
| 1549 | 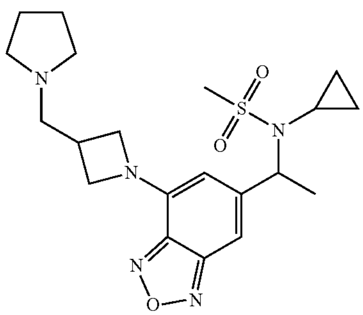 [SMILES: CC(c1cc(N2CC(CN3CCCC3)C2)c2nonc2c1)N(C1CC1)S(C)(=O)=O] | | | | NA | NA | 5.5 |
| 1550 | 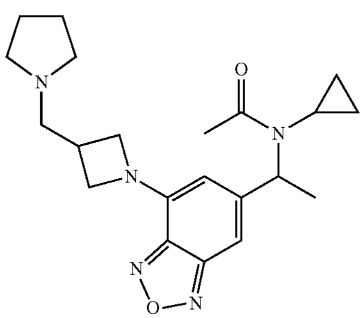 [SMILES: CC(=O)N(C1CC1)C(C)c1cc(N2CC(CN3CCCC3)C2)c2nonc2c1] | | | | NA | NA | 5.3 |
| 1551 | 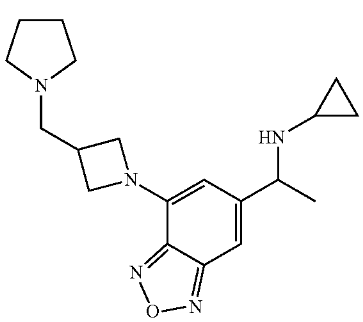 [SMILES: CC(NC1CC1)c1cc(N2CC(CN3CCCC3)C2)c2nonc2c1] | | | | NA | NA | 6.8 |

US 9,938,249 B2

333                                                                            334

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1552 | 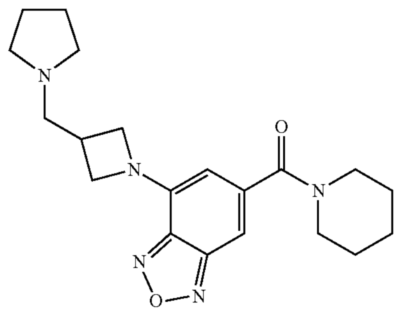 [SMILES: O=C(c1cc(N2CC(CN3CCCC3)C2)c2nonc2c1)N1CCCCC1] | | | | NA | NA | 5.7 |
| 1553 | 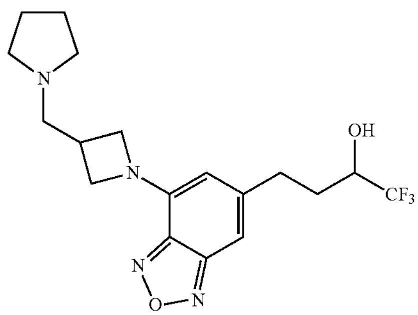 [SMILES: OC(CCc1cc(N2CC(CN3CCCC3)C2)c2nonc2c1)C(F)(F)F] | | | | NA | NA | 12.1 |
| 1554 | 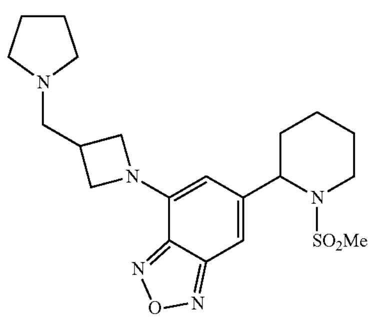 [SMILES: CS(=O)(=O)N1CCCCC1c1cc(N2CC(CN3CCCC3)C2)c2nonc2c1] | | | | NA | NA | 8.3 |
| 1555 | 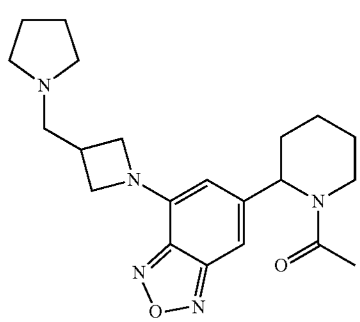 [SMILES: CC(=O)N1CCCCC1c1cc(N2CC(CN3CCCC3)C2)c2nonc2c1] | | | | NA | NA | 5.0 |

| ID | Structure | IC50 Thioflavin T A β 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1556 | 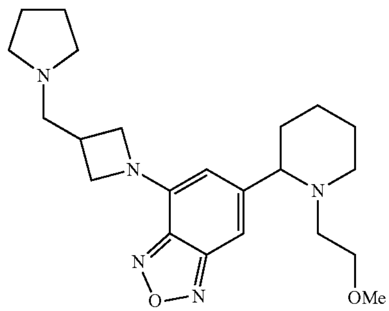 [SMILES: COCCN1CCCCC1c1cc(N2CC(CN3CCCC3)C2)c2nonc2c1] | | | | NA | NA | 6.6 |
| 1557 | 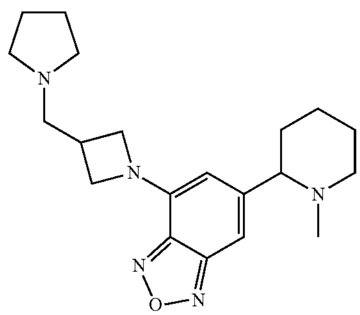 [SMILES: CN1CCCCC1c1cc(N2CC(CN3CCCC3)C2)c2nonc2c1] | | | | NA | NA | 18.7 |
| 1558 | 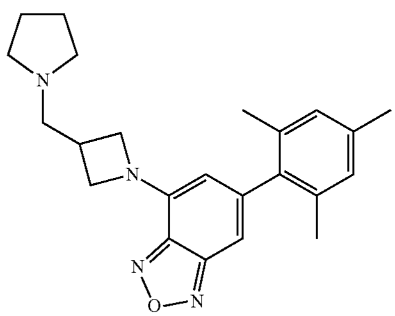 [SMILES: Cc1cc(C)c(-c2cc(N3CC(CN4CCCC4)C3)c3nonc3c2)c(C)c1] | | | | NA | NA | 5.9 |
| 1559 | 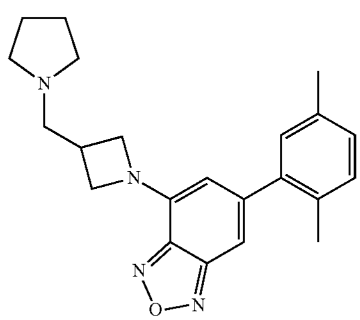 [SMILES: Cc1ccc(C)c(-c2cc(N3CC(CN4CCCC4)C3)c3nonc3c2)c1] | | | | NA | NA | 7.6 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1560 | 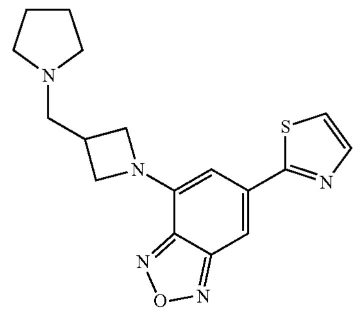 [SMILES: c1csc(-c2cc(N3CC(CN4CCCC4)C3)c3nonc3c2)n1] | | | | NA | NA | 6.7 |
| 1561 | 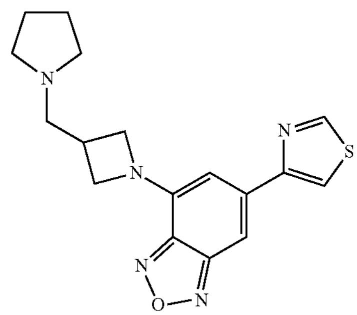 [SMILES: c1nc(-c2cc(N3CC(CN4CCCC4)C3)c3nonc3c2)cs1] | | | | NA | NA | 6.9 |
| 1562 | 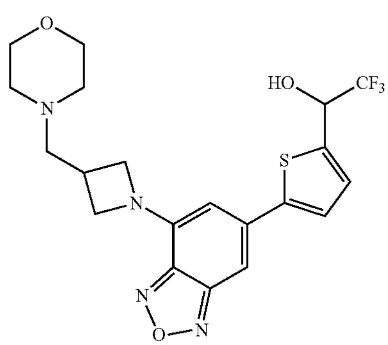 [SMILES: OC(c1ccc(-c2cc(N3CC(CN4CCOCC4)C3)c3nonc3c2)s1)C(F)(F)F] | | | | | | 2.7 |
| 1563 | 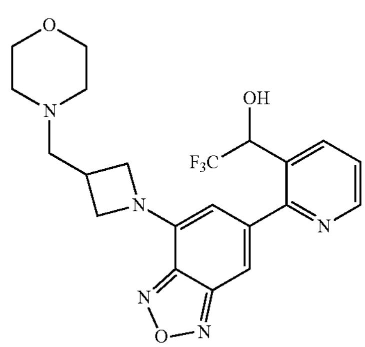 [SMILES: OC(c1cccnc1-c1cc(N2CC(CN3CCOCC3)C2)c2nonc2c1)C(F)(F)F] | | | | | | >20 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1564 | 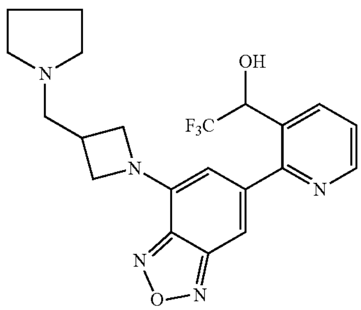 [SMILES: OC(c1cccnc1-c1cc(N2CC(CN3CCCC3)C2)c2nonc2c1)C(F)(F)F] | | | | | | 6.0 |
| 1565 | 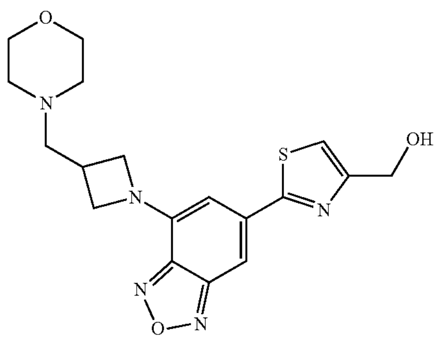 [SMILES: OCc1csc(-c2cc(N3CC(CN4CCOCC4)C3)c3nonc3c2)n1] | | | | | | >20 |
| 1566 | 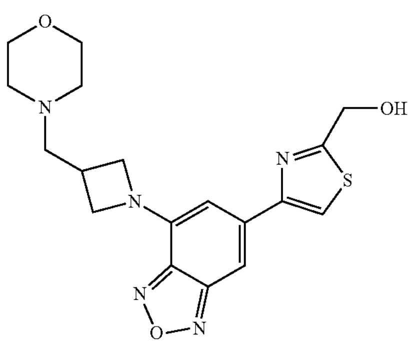 [SMILES: OCc1nc(-c2cc(N3CC(CN4CCOCC4)C3)c3nonc3c2)cs1] | | | | | | >20 |
| 1567 | 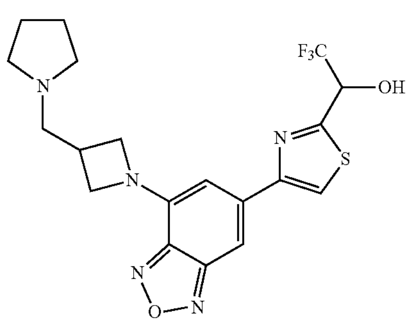 [SMILES: OC(c1nc(-c2cc(N3CC(CN4CCCC4)C3)c3nonc3c2)cs1)C(F)(F)F] | | | | | | 26.9 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1568 | 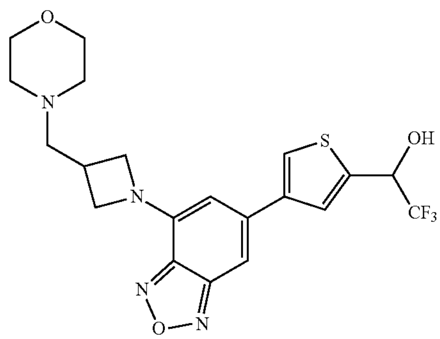 [SMILES: OC(c1cc(-c2cc(N3CC(CN4CCOCC4)C3)c3nonc3c2)cs1)C(F)(F)F] | | | | | | 5.5 |
| 1569 | 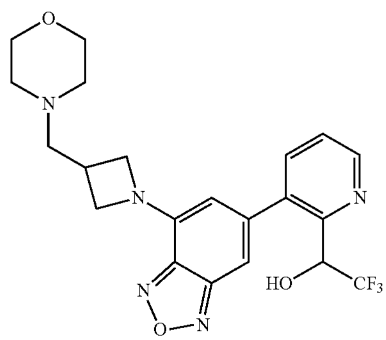 [SMILES: OC(c1ncccc1-c1cc(N2CC(CN3CCOCC3)C2)c2nonc2c1)C(F)(F)F] | | | | | | 11.5 |
| 1570 | 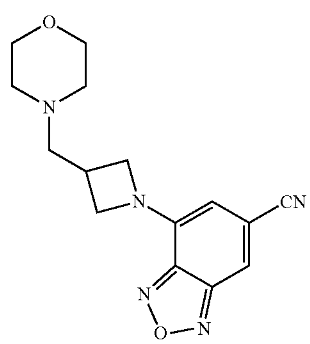 [SMILES: N#Cc1cc(N2CC(CN3CCOCC3)C2)c2nonc2c1] | | | | | | >20 |
| 1571 | 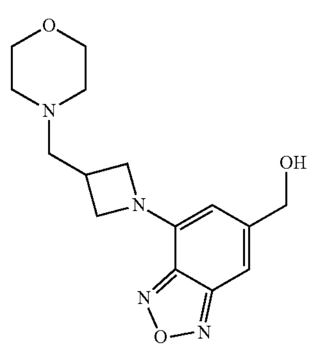 [SMILES: OCc1cc(N2CC(CN3CCOCC3)C2)c2nonc2c1] | | | | | | >20 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1572 | 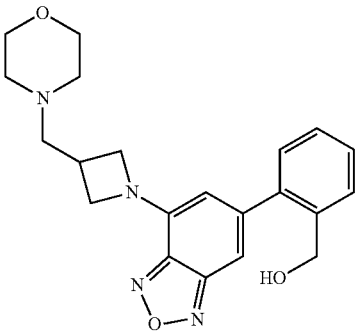 [SMILES: OCc1ccccc1-c1cc(N2CC(CN3CCOCC3)C2)c2nonc2c1] | | | | | | >20 |
| 1573 | 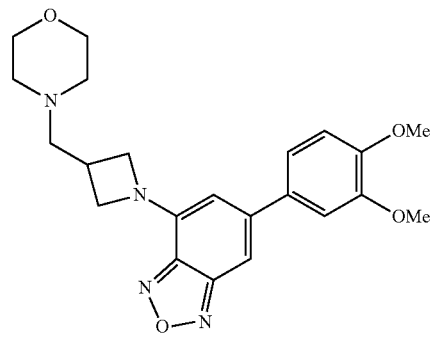 [SMILES: COc1ccc(-c2cc(N3CC(CN4CCOCC4)C3)c3nonc3c2)cc1OC] | | | | | | 12.9 |
| 1574 | 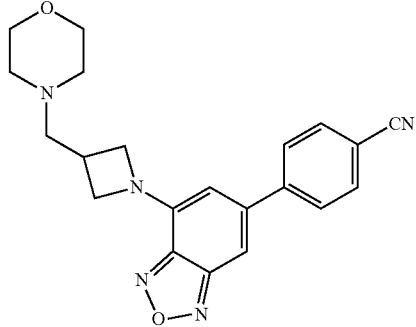 [SMILES: N#Cc1ccc(-c2cc(N3CC(CN4CCOCC4)C3)c3nonc3c2)cc1] | | | | | | 16.5 |
| 1575 | 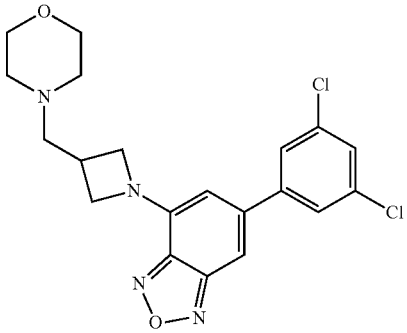 [SMILES: Clc1cc(Cl)cc(-c2cc(N3CC(CN4CCOCC4)C3)c3nonc3c2)c1] | | | | | | 4.0 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1576 | 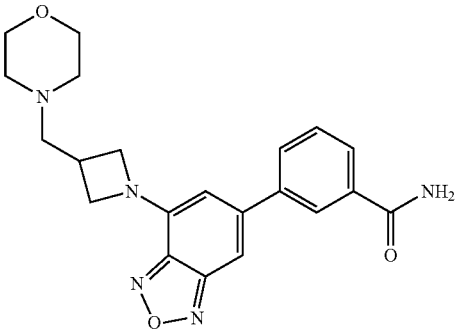 [SMILES: NC(=O)c1cccc(-c2cc(N3CC(CN4CCOCC4)C3)c3nonc3c2)c1] | | | | | | 46.0 |
| 1577 | 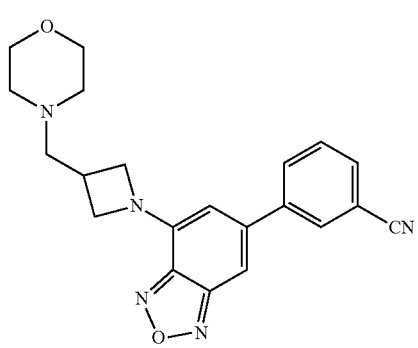 [SMILES: N#Cc1cccc(-c2cc(N3CC(CN4CCOCC4)C3)c3nonc3c2)c1] | | | | | | 14.8 |
| 1578 | 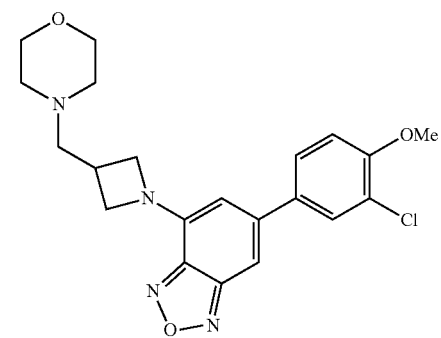 [SMILES: COc1ccc(-c2cc(N3CC(CN4CCOCC4)C3)c3nonc3c2)cc1Cl] | | | | | | 2.9 |
| 1579 | 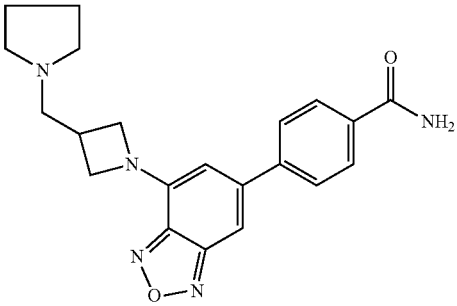 [SMILES: NC(=O)c1ccc(-c2cc(N3CC(CN4CCCC4)C3)c3nonc3c2)cc1] | | | | | | 96.0 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1580 | 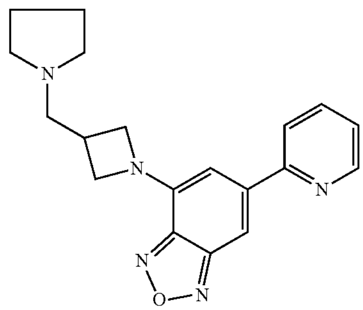 [SMILES: c1ccc(-c2cc(N3CC(CN4CCCC4)C3)c3nonc3c2)nc1] | | | | | | >20 |
| 1584 | 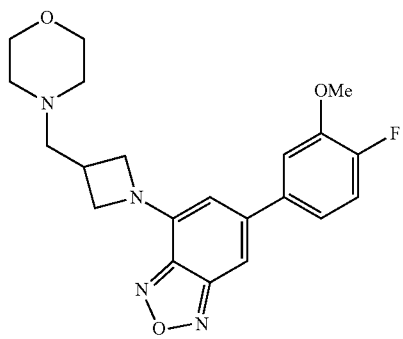 [SMILES: COc1cc(-c2cc(N3CC(CN4CCOCC4)C3)c3nonc3c2)ccc1F] | | | | | | 7.0 |
| 1585 | 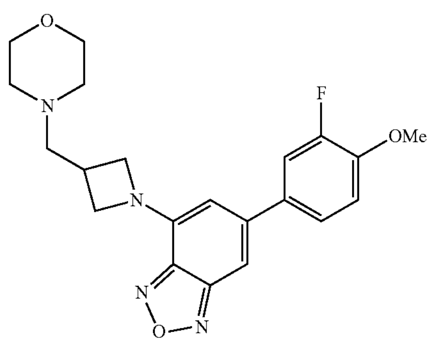 [SMILES: COc1ccc(-c2cc(N3CC(CN4CCOCC4)C3)c3nonc3c2)cc1F] | | | | | | 5.8 |
| 1586 | 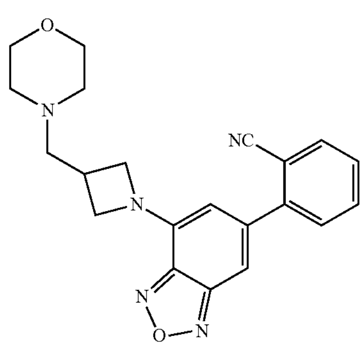 [SMILES: N#Cc1ccccc1-c1cc(N2CC(CN3CCOCC3)C2)c2nonc2c1] | | | | | | 41.9 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1587 | 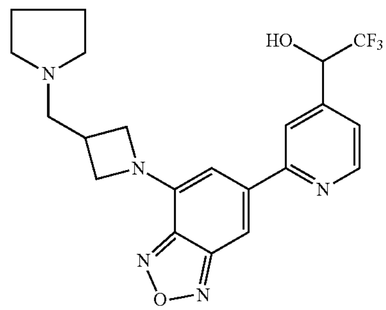 [SMILES: OC(c1ccnc(-c2cc(N3CC(CN4CCCC4)C3)c3nonc3c2)c1)C(F)(F)F] | | | | | | 12.3 |
| 1588 | 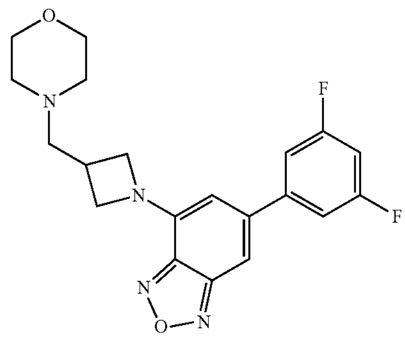 [SMILES: Fc1cc(F)cc(-c2cc(N3CC(CN4CCOCC4)C3)c3nonc3c2)c1] | | | | | | 30.2 |
| 1592 | 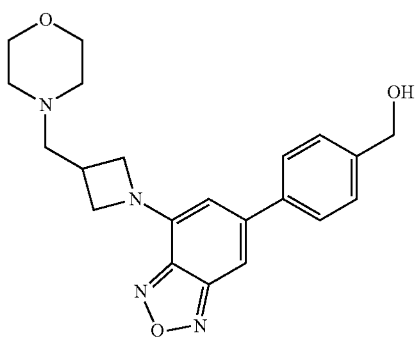 [SMILES: OCc1ccc(-c2cc(N3CC(CN4CCOCC4)C3)c3nonc3c2)cc1] | | | | | | 15.1 |
| 1594 | 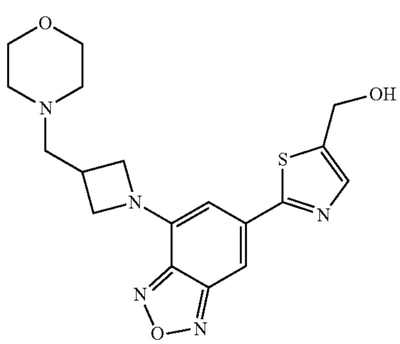 [SMILES: OCc1cnc(-c2cc(N3CC(CN4CCOCC4)C3)c3nonc3c2)s1] | | | | | | >20 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1597 | 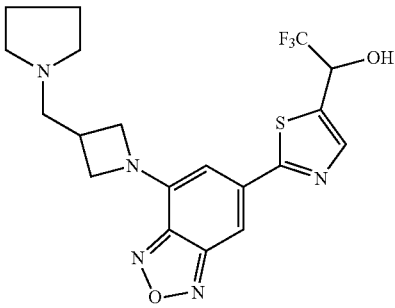 [SMILES: OC(c1cnc(-c2cc(N3CC(CN4CCCC4)C3)c3nonc3c2)s1)C(F)(F)F] | | | | | | 7.5 |
| 1598 | 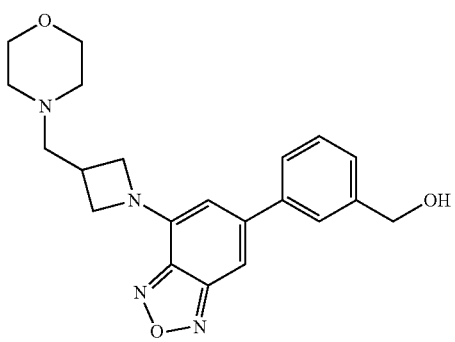 [SMILES: OCc1cccc(-c2cc(N3CC(CN4CCOCC4)C3)c3nonc3c2)c1] | | | | | | 9.9 |
| 1599 | 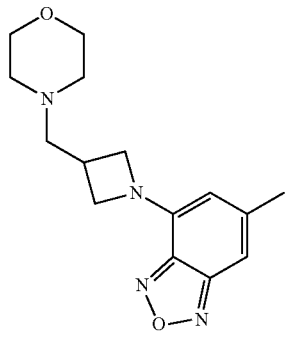 [SMILES: Cc1cc(N2CC(CN3CCOCC3)C2)c2nonc2c1] | | | | | | |
| 1600 | 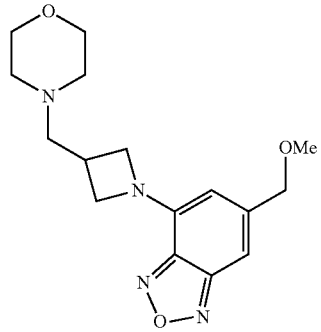 [SMILES: COCc1cc(N2CC(CN3CCOCC3)C2)c2nonc2c1] | | | | | | |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1606 | 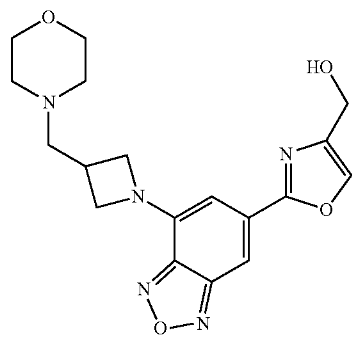 [SMILES: OCc1coc(-c2cc(N3CC(CN4CCOCC4)C3)c3nonc3c2)n1] | | | | | | >20 |
| 1607 | 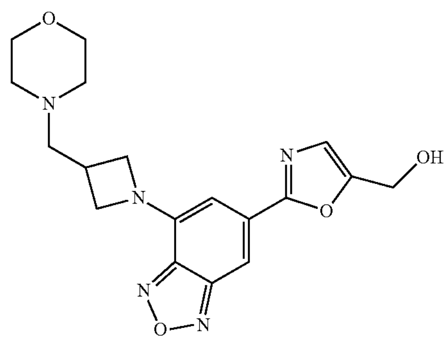 [SMILES: OCc1cnc(-c2cc(N3CC(CN4CCOCC4)C3)c3nonc3c2)o1] | | | | | | >20 |
| 1608 | 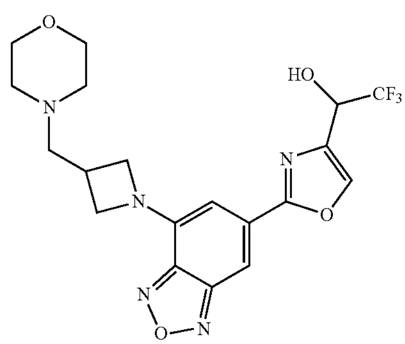 [SMILES: OC(c1coc(-c2cc(N3CC(CN4CCOCC4)C3)c3nonc3c2)n1)C(F)(F)F] | | | | | | 8.6 |
| 1609 | 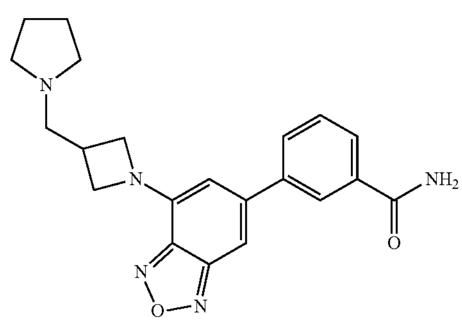 [SMILES: NC(=O)c1cccc(-c2cc(N3CC(CN4CCCC4)C3)c3nonc3c2)c1] | | | | | | 2.4 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1610 | 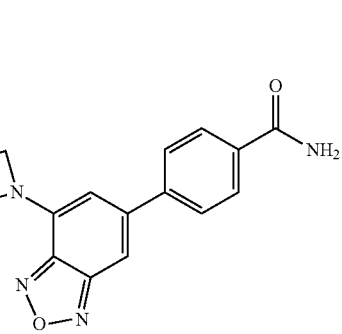 | | | | | | >20 |
| 1611 | 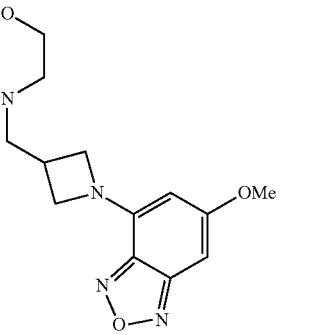 | | | | | | >20 |
| 1612 | 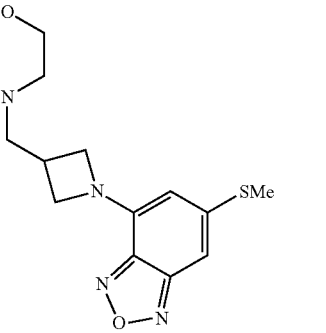 | | | | | | >20 |
| 1613 | 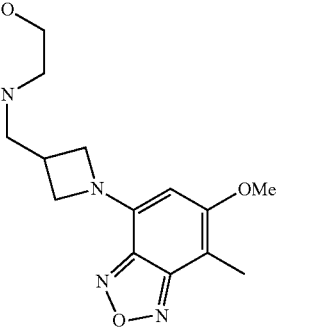 | | | | | | >20 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1615 | 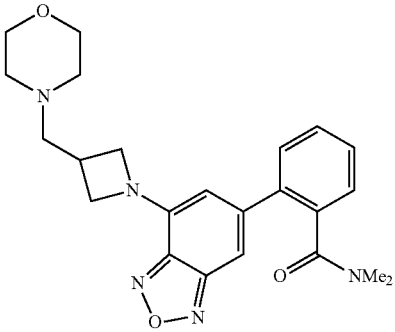 [SMILES: CN(C)C(=O)c1ccccc1-c1cc(N2CC(CN3CCOCC3)C2)c2nonc2c1] | | | | | | >20 |
| 1616 | 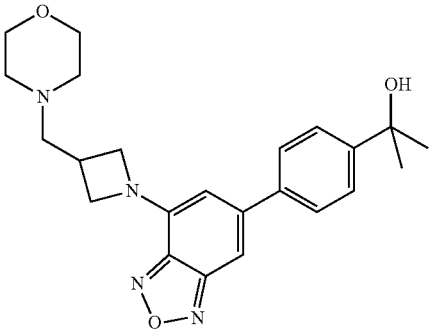 [SMILES: CC(C)(O)c1ccc(-c2cc(N3CC(CN4CCOCC4)C3)c3nonc3c2)cc1] | | | | | | 16.2 |
| 1617 | 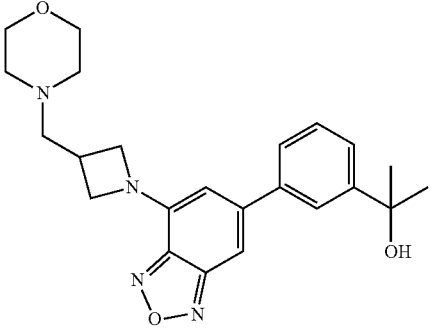 [SMILES: CC(C)(O)c1cccc(-c2cc(N3CC(CN4CCOCC4)C3)c3nonc3c2)c1] | | | | | | 14.6 |
| 1618 | 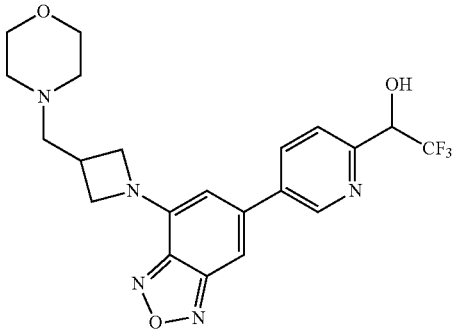 [SMILES: OC(c1ccc(-c2cc(N3CC(CN4CCOCC4)C3)c3nonc3c2)cn1)C(F)(F)F] | | | | | | 4.98 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1619 | 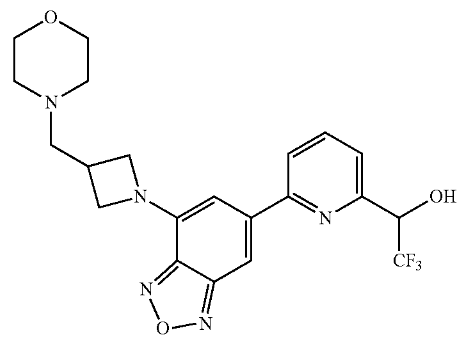 [SMILES: OC(c1cccc(-c2cc(N3CC(CN4CCOCC4)C3)c3nonc3c2)n1)C(F)(F)F] | | | | | | 11.3 |
| 1620 | 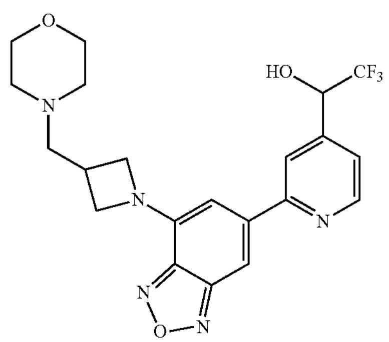 [SMILES: OC(c1ccnc(-c2cc(N3CC(CN4CCOCC4)C3)c3nonc3c2)c1)C(F)(F)F] | | | | | | 11.1 |
| 1621 | 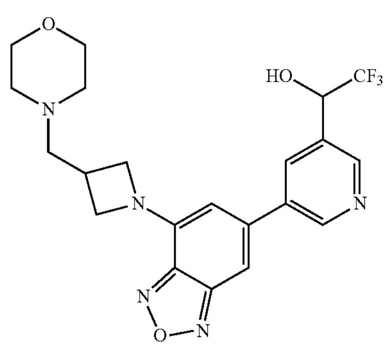 [SMILES: OC(c1cncc(-c2cc(N3CC(CN4CCOCC4)C3)c3nonc3c2)c1)C(F)(F)F] | | | | | | 16.7 |
| 1622 | 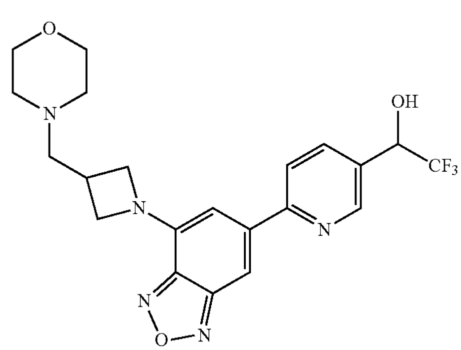 [SMILES: OC(c1ccc(-c2cc(N3CC(CN4CCOCC4)C3)c3nonc3c2)nc1)C(F)(F)F] | | | | | | 5.8 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1625 | 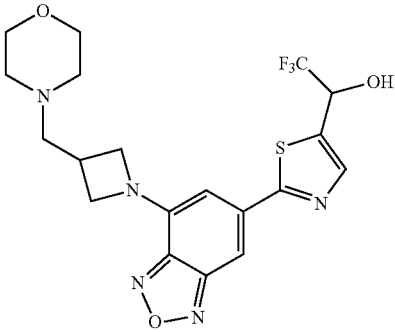 [SMILES: OC(c1cnc(-c2cc(N3CC(CN4CCOCC4)C3)c3nonc3c2)s1)C(F)(F)F] | | | | | | 4.2 |
| 1626 | 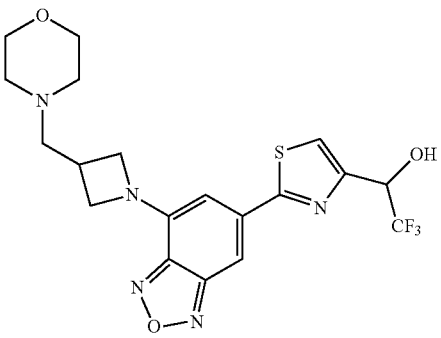 [SMILES: OC(c1csc(-c2cc(N3CC(CN4CCOCC4)C3)c3nonc3c2)n1)C(F)(F)F] | | | | | | 10.9 |
| 1627 | 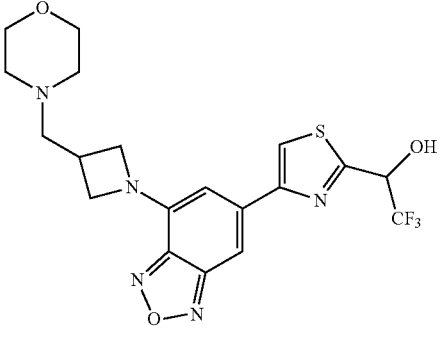 [SMILES: OC(c1nc(-c2cc(N3CC(CN4CCOCC4)C3)c3nonc3c2)cs1)C(F)(F)F] | | | | | | 10.4 |
| 1628 | 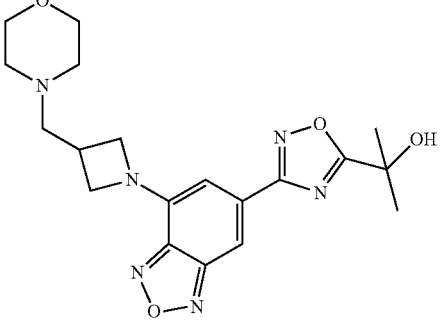 | | | | | | 33.1 |

-continued

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1629 | 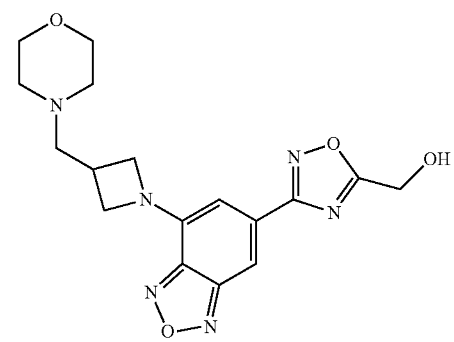 [SMILES: OCc1nc(-c2cc(N3CC(CN4CCOCC4)C3)c3nonc3c2)no1] | | | | | | 15.7 |
| 1636 | 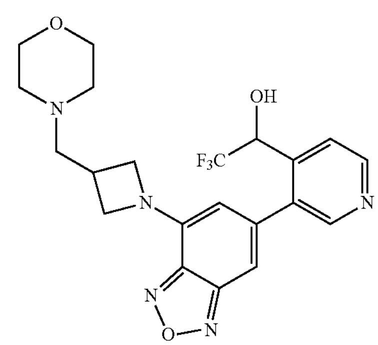 [SMILES: OC(c1ccncc1-c1cc(N2CC(CN3CCOCC3)C2)c2nonc2c1)C(F)(F)F] | | | | | | 10.3 |
| 1638 | 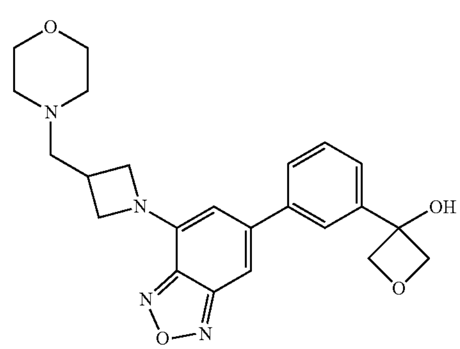 [SMILES: OC1(c2cccc(-c3cc(N4CC(CN5CCOCC5)C4)c4nonc4c3)c2)COC1] | | | | | | 3.0 |
| 1639 | 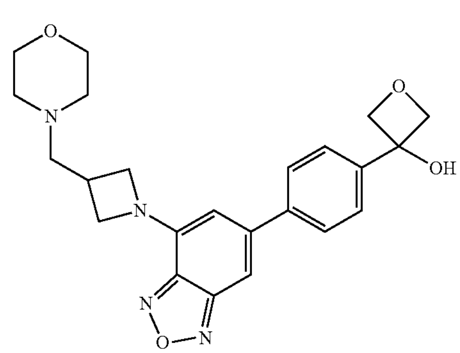 [SMILES: OC1(c2ccc(-c3cc(N4CC(CN5CCOCC5)C4)c4nonc4c3)cc2)COC1] | | | | | | 3.2 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1643 | 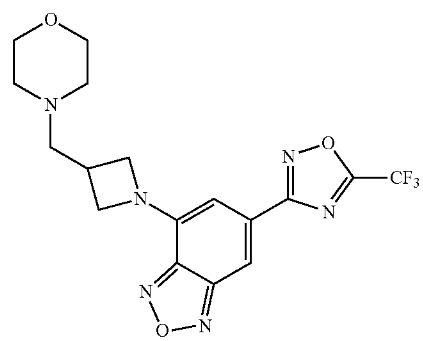 [SMILES: FC(F)(F)c1nc(-c2cc(N3CC(CN4CCOCC4)C3)c3nonc3c2)no1] | | | | | | 14.2 |
| 1645 | 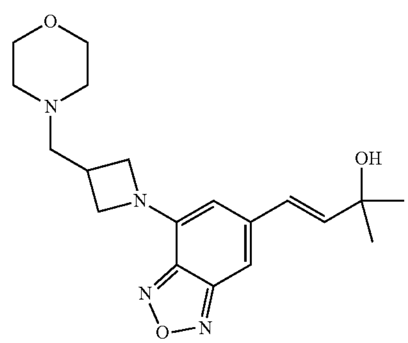 [SMILES: CC(C)(O)/C=C/c1cc(N2CC(CN3CCOCC3)C2)c2nonc2c1] | | | | | | >20 |
| 1647 | 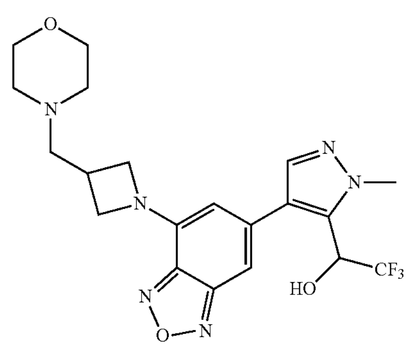 [SMILES: Cn1ncc(-c2cc(N3CC(CN4CCOCC4)C3)c3nonc3c2)c1C(O)C(F)(F)F] | | | | | | 14.7 |
| 1651 | 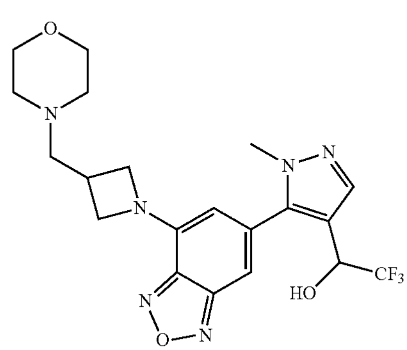 [SMILES: Cn1ncc(C(O)C(F)(F)F)c1-c1cc(N2CC(CN3CCOCC3)C2)c2nonc2c1] | | | | | | 30.1 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1658 | 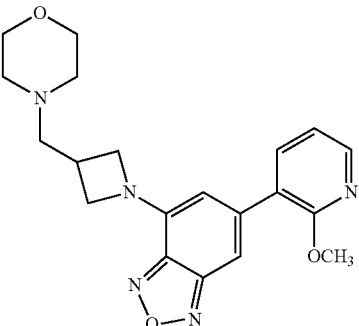 | | | | | | >20 |
| 1659 | 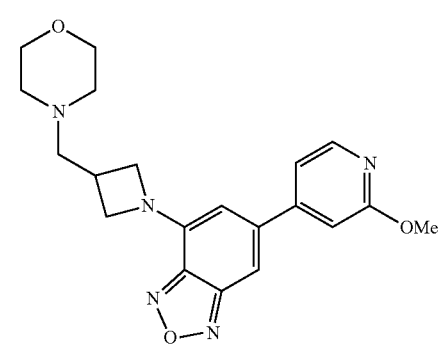 [SMILES: COc1cc(-c2cc(N3CC(CN4CCOCC4)C3)c3nonc3c2)ccn1] | | | | | | 12.4 |
| 1660 | 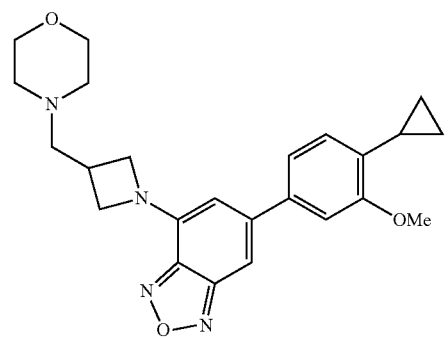 [SMILES: COc1cc(-c2cc(N3CC(CN4CCOCC4)C3)c3nonc3c2)ccc1C1CC1] | | | | | | 3.9 |
| 1663 | 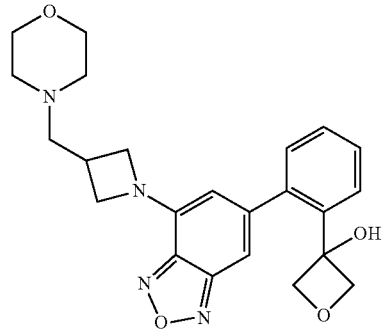 | | | | | | >20 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1665 | 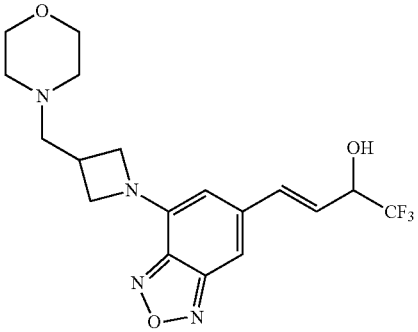 [SMILES: OC(/C=C/c1cc(N2CC(CN3CCOCC3)C2)c2nonc2c1)C(F)(F)F] | | | | | | 21.8 |
| 1666 | 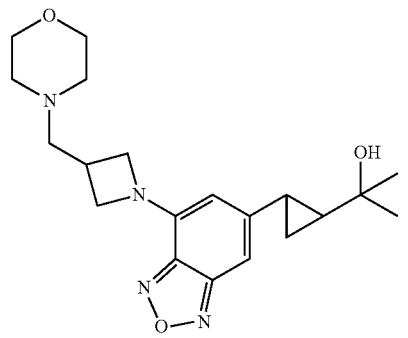 [SMILES: CC(C)(O)C1CC1c1cc(N2CC(CN3CCOCC3)C2)c2nonc2c1] | | | | | | >20 |
| 1667 | 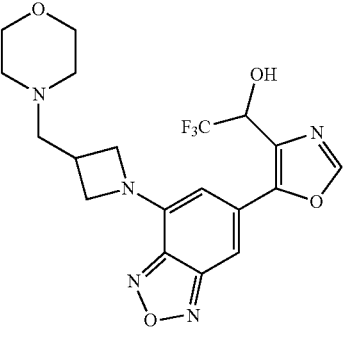 [SMILES: OC(c1ncoc1-c1cc(N2CC(CN3CCOCC3)C2)c2nonc2c1)C(F)(F)F] | | | | | | 17.5 |
| 1670 | 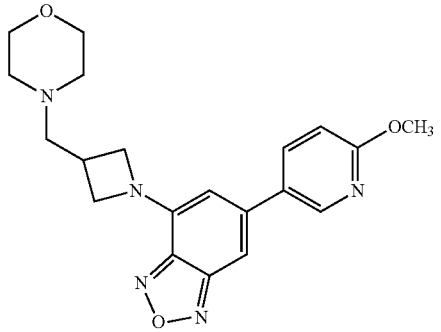 [SMILES: COc1ccc(-c2cc(N3CC(CN4CCOCC4)C3)c3nonc3c2)cn1] | | | | | | 11.2 |

-continued
| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Aβ 42-bio |
|---|---|---|---|---|---|---|---|
| 1677 | 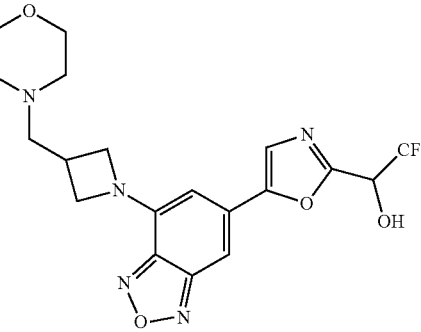 | | | | | | 26.1 |
| 1692 | 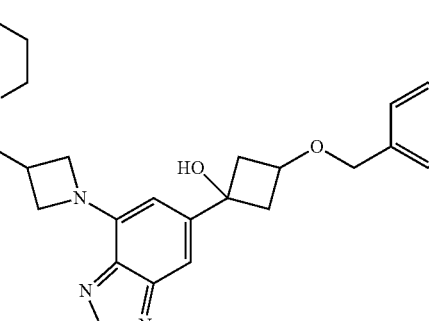 | | | | | | 5.6 |
| 1717 | 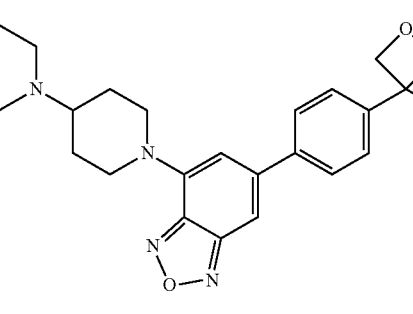 | | | | | | 22.6 |
| 1719 | 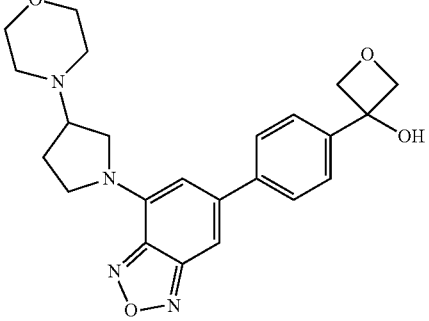 | | | | | | 13.0 |

| ID | Structure | IC50 Thioflavin T Aβ 1-40 | % inhib. Thioflavin T Aβ 40 (20 μM) | % inhib Thioflavin T Aβ 40 10 μM | % inhib Thioflavin T Aβ 40 (5 μm) | % inhib Thioflavin T Aβ 40 (3 μm) | IC50 Thioflavin T Aβ 42-bio |
|---|---|---|---|---|---|---|---|
| 1735 | 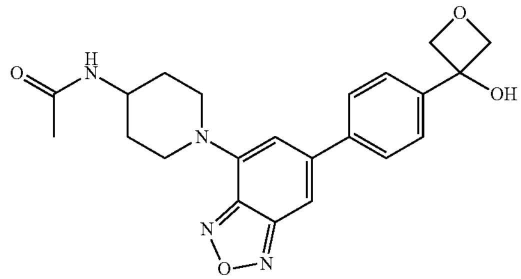 [SMILES: CC(=O)NC1CCN(c2cc(-c3ccc(C4(O)COC4)cc3)cc3nonc23)CC1] | | | | | | 2.4 |
| 1736 | 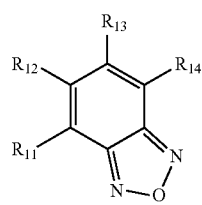 | | | | | | 9.7 |

The invention claimed is:

1. A compound of Formula I:

(I)

$$\text{R}_{13}, \text{R}_{12}, \text{R}_{14}, \text{R}_{11}$$

or a pharmaceutically acceptable salt thereof,
in which $R_{11}$ is selected from the group consisting of 4-(pyrrolidin-1-yl)piperidin-1-yl, N-methyl-3-(pyrrolidin-1-yl)propan-1-amino, $N^1,N^1,N^3$-trimethylpropane-1,3-diamino, N,N-dimethylpiperidin-4-amino, 3-(pyrrolidin-1-ylmethyl)azetidin-1-yl, 3-(pyrrolidin-1-ylmethanon)azetidin-1-yl, 3-(morpholin-4-ylmethyl)azetidin-1-yl, 3-(2-ethanolamino-N-methyl)azetidin-1-yl, 3-(morpholin-4-yl)pyrrolidin-1-yl, 3-(morpholin-4-ylmethyl)pyrrolidin-1-yl, 4-(ethylamido)piperidin-1-yl, 3-(aminomethyl)azetidin-1-yl, 4-(morpholin-4-yl)piperidin-1-yl, 4-(morpholin-4-ylmethyl)piperidin-1-yl, 3-amidoazetidin-1-yl, 3-(propan-2-ol-2-yl)azetidin-1-yl, 3-(methylsulfonamide-N-methyl)azetidin-1-yl, 3-(methylamido-N-methyl)azetidin-1-yl, and 3-(methylamino-N-methyl)azetidin-1-yl;

$R_{13}$ is selected from the group consisting of, oxazole optionally substituted with one or more of substituents A, oxadiazole optionally substituted with one or more of substituents A, phenyl optionally substituted with one or more of substituents A, thiophene optionally substituted with one or more of substituents A, thiazole optionally substituted with one or more of substituents A, furan optionally substituted with one or more of substituents A, pyrazole optionally substituted with one or more of substituents A, N-methylpyrazole optionally substituted with one or more of substituents A, and pyridine optionally substituted with one or more of substituents A, where A is selected from the group consisting of alkyl, alkoxy, alkthiolyl, isopropyl, t-butyl, trifluoromethyl, chloro, cyano, $CF_3O$—, methanonyl, methylsulfonyl, trifluoromethylsulfonyl, amide (connected in either direction) optionally substituted with one or more alkyl, —$CH_2OH$, 1-ol-2,2,2-trifluoroethan-1-yl, 2-ol-propan-2-yl, and cyclopropyl;

and $R_{12}$ and $R_{14}$ are each independently hydrogen or alkyl;

with the proviso that if A is 1-ol-2,2,2-trifluoroethan-1-yl, then it cannot be connected to phenyl or thiophene; and with the proviso that if A is methanonyl, then it cannot be connected to phenyl.

2. The compound of claim 1 or a pharmaceutically acceptable salt thereof, in which $R_{11}$ is selected from the group consisting of 4-(pyrrolidin-1-yl)piperidin-1-yl, N-methyl-3-(pyrrolidin-1-yl)propan-1-amino, $N^1,N^1,N^3$-trimethylpropane-1,3-diamino, N,N-dimethylpiperidin-4-amino, 3-(pyrrolidin-1-ylmethyl)azetidin-1-yl, 3-(pyrrolidin-1-ylmethanon)azetidin-1-yl, 3-(morpholin-1ylmethyl)pyrrolidin-1-yl, and 3-(morpholin-4-ylmethyl)azetidin-1-yl; and $R_{13}$ is selected from the group consisting of phenyl optionally substituted with one or more of substituents A, thiophene optionally substituted with one or more of substituents A, thiazole optionally substituted with one or more of substituents A, furan optionally substituted with one or more of substituents A, pyrazole optionally substituted with one or more of substituents A, N-methylpyrazole optionally substituted with one or more of substituents A, and pyridine optionally substituted with one or more of substituents A, where A is selected from the group consisting of alkyl, alkoxy, alkthiolyl, isopropyl, t-butyl, trifluoromethyl, chloro, cyano, $CF_3O$—, methanonyl, methylsulfonyl, trifluoromethylsulfonyl, amide (connected in either direction) optionally substituted with one or more alkyl, and —$CH_2OH$; with the proviso that if A is methanonyl, then it cannot be connected to phenyl.

3. The compound of claim 1 or a pharmaceutically acceptable salt thereof, in which $R_{11}$ is selected from the group consisting of 3-(morpholin-4-ylmethyl)azetidin-1-yl, 3-(2-ethanolamino-N-methyl)azetidin-1-yl, 3-(morpholin-4-yl)pyrrolidin-1-yl, 4-(ethylamido)piperidin-1-yl, 3-(aminomethyl)azetidin-1-yl, 4-(morpholin-4-yl)piperidin-1-yl, 4-(morpholin-4-ylmethyl)piperidin-1-yl, 3-amidoazetidin-1-yl, 3-(propan-2-ol-2-yl)azetidin-1-yl, 3-(methylsulfonamide-N-methyl)azetidin-1-yl, 3-(methylamido-N-methyl)azetidin-1-yl, and 3-(methylamino-N-methyl)azetidin-1-yl; and $R_{13}$ is selected from the group consisting of oxazole optionally substituted with one or more of substituents A, oxadiazole optionally substituted with one or more of substituents A, thiazole optionally substituted with one or more of substituents A, furan optionally substituted with one or more of substituents A, and pyridine optionally substituted with one or more of substituents A, where A is selected from the group consisting of 1-ol-2,2,2-trifluoroethan-1-yl, 2-ol-propan-2-yl, and cyclopropyl.

4. The compound of claim 3 or a pharmaceutically acceptable salt thereof, in which $R_{13}$ is selected from the group consisting of 5-(2-ol-propan-2-yl)oxadizol-3-yl, 4-(1-ol-2,2,2-trifluoroethan-1-yl)oxazol-5-yl, 4-(1-ol-2,2,2-trifluoroethan-1-yl)pyridin-2-yl, 4-(1-ol-2,2,2-trifluoroethan-1-yl)pyridin-3-yl, 4-(1-ol-2,2,2-trifluoroethan-1-yl)thiazol-2-yl, 4-(1-ol-2,2,2-trifluoroethan-1-yl)pyridin-6-yl, 2-(1-ol-2,2,2-trifluoroethan-1-yl)-pyridin-6-yl, 5-(1-ol-2,2,2-trifluoroethan-1-yl)oxazol-2-yl, 5-(1-ol-2,2,2-trifluoroethan-1-yl)oxazol-3-yl, 2-(1-ol-2,2,2-trifluoroethan-1-yl)pyridin-5-yl, 3-(1-ol-2,2,2-trifluoroethan-1-yl)pyridin-2-yl, 3-(1-ol-2,2,2-trifluoroethan-1-yl)pyridin-6-yl, and 2-(1-ol-2,2,2-trifluoroethan-1-yl)pyridin-3-yl.

5. The compound of claim 4 or a pharmaceutically acceptable salt thereof, in which $R_{11}$ is 3-(morpholin-4-ylmethyl)azetidin-1-yl and $R_{13}$ is selected from the group consisting of 2-(1-ol-2,2,2-trifluoroethan-1-yl)pyridin-3-yl and 5-(2-ol-propan-2-yl)oxadizol-3-yl.

6. A method of treatment of an amyloid disease in a subject comprising administering a therapeutically effective amount of a compound of any of claims 1-5 to the subject.

7. The method of claim 6 in which the amyloid disease is Alzheimer's disease.

8. The method of claim 6 in which the amyloid disease is Parkinson's disease.

9. The method of claim 6 in which the amyloid disease is frontotemporal dementia.

10. The method of claim 6 in which the amyloid disease is progressive supranuclear palsy.

11. The method of claim 6 in which the amyloid disease is type 2 diabetes mellitus.

12. A pharmaceutical composition comprising a compound of claim 1 and a pharmaceutically acceptable carrier.

13. A method for treating a condition which is a member selected from loss of memory, loss of cognition and a combination thereof, said method comprising administering to a subject in need thereof a therapeutically effective amount of a compound of claim 1.

14. The method according to claim 13, wherein said condition is associated with Alzheimer's disease.

15. The method according to claim 13, wherein a total daily dose of from about 0.0003 to about 50 mg/kg of body weight is administered.

16. A pharmaceutical composition comprising a compound of claim 2 and a pharmaceutically acceptable carrier.

17. A pharmaceutical composition comprising a compound of claim 3 and a pharmaceutically acceptable carrier.

18. A pharmaceutical composition comprising a compound of claim 4 and a pharmaceutically acceptable carrier.

19. A pharmaceutical composition comprising a compound of claim 5 and a pharmaceutically acceptable carrier.

20. A method for treating a condition which is a member selected from loss of memory, loss of cognition and a combination thereof, said method comprising administering to a subject in need thereof a therapeutically effective amount of a compound of claim 4.

* * * * *